(12) United States Patent  (10) Patent No.: US 12,391,663 B2
Fasching et al.  (45) Date of Patent: *Aug. 19, 2025

(54) ISOINDOLINONE COMPOUNDS

(71) Applicant: Monte Rosa Therapeutics AG, Basel (CH)

(72) Inventors: Bernhard Fasching, Basel (CH); Thomas Ryckmans, Basel (CH); Alexander Flohr, Basel (CH); Andreas Ritzén, Basel (CH); Freya Harvey, Basel (CH); Laura McAllister, Basel (CH)

(73) Assignee: Monte Rosa Therapeutics AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/496,504

(22) Filed: Oct. 27, 2023

(65) Prior Publication Data

US 2024/0083869 A1  Mar. 14, 2024

Related U.S. Application Data

(63) Continuation of application No. 18/349,634, filed on Jul. 10, 2023, now Pat. No. 11,912,682, which is a continuation of application No. PCT/EP2022/050699, filed on Jan. 13, 2022.

(60) Provisional application No. 63/281,049, filed on Nov. 18, 2021.

(51) Int. Cl.
C07D 401/04 (2006.01)

(52) U.S. Cl.
CPC .................. *C07D 401/04* (2013.01)

(58) Field of Classification Search
CPC .................................... C07D 401/04
USPC ........................................ 514/323
See application file for complete search history.

(56) References Cited

U.S. PATENT DOCUMENTS

| 8,445,198 B2 | 5/2013 | Knudsen |
| 9,662,319 B2 | 5/2017 | Stewart et al. |

(Continued)

FOREIGN PATENT DOCUMENTS

| CN | 105175285 A | 12/2015 |
| CN | 107698575 A | 2/2018 |

(Continued)

OTHER PUBLICATIONS

"UNIPROTKB", Database accession No. Q13542 (One extra 4 removed).

Akinjiyan, F. A., et al. "A Novel Luminescence-Based High-Throughput Approach for Cellular Resolution of Protein Ubiquitination Using Tandem Ubiquitin Binding Entities (TUBEs)", SLAS Discovery, 25(4):350-360, (2020).

Asatsuma-Okumura, T., et al. "Molecular mechanisms of cereblon-based drugs," Pharmacology & Therapeutics, 202:132-139, (2019).

(Continued)

*Primary Examiner* — Kahsay Habte
(74) *Attorney, Agent, or Firm* — Goodwin Procter LLP

(57) ABSTRACT

Disclosed herein are compound or pharmaceutically acceptable salts or stereoisomers thereof of formula I:

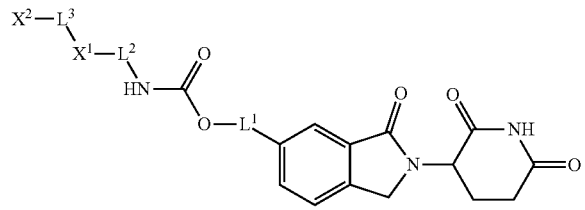

$X^1$ is linear or branched $C_{1-6}$ alkyl, $C_{3-8}$ cycloalkyl, $C_{6-10}$ aryl, 5-10 membered heteroaryl, 4-8 membered heterocycloalkyl, wherein $X^1$ is unsubstituted or substituted with one or more of halogen, linear or branched $C_{1-6}$ alkyl, linear or branched $C_{1-6}$ heteroalkyl, $CF_3$, $CHF_2$, $CMeF_2$, —O—$CHF_2$, —O—$(CH_2)_2$—OMe, $OCF_3$, $C_{1-6}$ alkylamino, —CN, —N(H)C(O)—$C_{1-6}$alkyl, —OC(O)—$C_{1-6}$alkyl, —OC(O)—$C_{1-4}$alkylamino, —C(O)O—$C_{1-6}$alkyl, —COOH, —$C_{1-6}$alkylC(O)OH, —$C_{1-6}$alkylC(O)O—$C_{1-6}$ alkyl, $NH_2$, $C_{1-4}$ alkoxy, $C_{1-4}$ alkylhydroxy, —$CH_2F$, —N(H)C(O)—O—$C_{1-6}$ alkyl, and $C(OH)(CF_3)$; or $X^1$ together with the N atom of the carbamate forms a 4-8 membered heterocycloalkyl, which is unsubstituted or substituted with one or more of halogen, linear or branched —$C_{1-6}$ alkyl, $CF_3$, $CHF_2$, $CMeF_2$, —O—$(CH_2)_2$—OMe, $OCF_3$, $OCHF_2$, $C_{1-6}$ alkylamino, —CN, —N(H)C(O)—$C_{1-6}$ alkyl, —OC(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, $NH_2$, $C_{1-4}$ alkylhydroxy, and $C_{1-4}$ alkoxy; $X^2$ is H, $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and $C_{1-4}$ alkylhydroxy; $L^1$ is a covalent bond, linear or branched $C_{1-6}$ alkyl; $L^2$ is a covalent bond, linear or branched $C_{1-6}$ alkyl; and $L^3$ is a covalent bond, linear or branched $C_{1-6}$ alkyl, —O—, or —$C_{1-4}$ alkoxy, wherein linear or branched $C_{1-6}$ alkyl is unsubstituted or substituted with one or more of halogen. Disclosed herein is also their use as modulators of cereblon, methods of preparation of these compounds, compositions comprising these compounds, and methods of using them in the treatment of abnormal cell growth in mammals, especially humans.

20 Claims, 8 Drawing Sheets

(56) References Cited

U.S. PATENT DOCUMENTS

| | | | |
|---|---|---|---|
| 9,857,359 B2 | 1/2018 | Schafer et al. | |
| 11,912,682 B2 * | 2/2024 | Fasching | C07D 401/04 |
| 2007/0128636 A1 | 6/2007 | Baker et al. | |
| 2015/0374678 A1 | 12/2015 | Chamberlain et al. | |
| 2016/0176916 A1 | 6/2016 | Bradner et al. | |
| 2017/0199193 A1 | 7/2017 | Filvaroff et al. | |
| 2018/0170948 A1 | 6/2018 | Chan et al. | |
| 2018/0264000 A1 | 9/2018 | Chan et al. | |
| 2019/0233433 A1 | 8/2019 | Crews et al. | |
| 2020/0022966 A1 | 1/2020 | Tang et al. | |
| 2020/0369679 A1 | 11/2020 | Chan et al. | |
| 2021/0322398 A1 | 10/2021 | Tang et al. | |
| 2022/0242846 A1 | 8/2022 | Flohr et al. | |
| 2024/0051936 A1 | 2/2024 | Fasching et al. | |
| 2024/0051937 A1 | 2/2024 | Fasching et al. | |
| 2024/0216355 A1 | 7/2024 | Fasching et al. | |
| 2024/0261274 A1 | 8/2024 | Gavory et al. | |
| 2024/0294495 A1 | 9/2024 | Fasching et al. | |
| 2024/0308976 A1 | 9/2024 | Fasching et al. | |

FOREIGN PATENT DOCUMENTS

| | | |
|---|---|---|
| CN | 110204543 A | 9/2019 |
| CN | 110305126 A | 10/2019 |
| CN | 110372669 A | 10/2019 |
| CN | 110563703 A | 12/2019 |
| CN | 110684015 A | 1/2020 |
| CN | 110734426 A | 1/2020 |
| CN | 112812109 A | 5/2021 |
| EP | 3214081 A1 | 9/2017 |
| EP | 3329923 A1 | 6/2018 |
| JP | 2021020879 A | 2/2021 |
| WO | WO-1998003502 A1 | 1/1998 |
| WO | WO-1998054170 A1 | 12/1998 |
| WO | WO-1999047512 A1 | 9/1999 |
| WO | WO-2002059106 A1 | 8/2002 |
| WO | WO-2007027527 A2 | 3/2007 |
| WO | 2008028926 A2 | 3/2008 |
| WO | WO-2008027542 A2 | 3/2008 |
| WO | WO-2008033567 A1 | 3/2008 |
| WO | WO-2008115516 A2 | 9/2008 |
| WO | WO-2009145899 A1 | 12/2009 |
| WO | WO-2010053732 A1 | 5/2010 |
| WO | WO-201160042 A1 | 5/2011 |
| WO | WO-2011100380 A1 | 8/2011 |
| WO | 2012145309 A1 | 10/2012 |
| WO | 2012146259 A1 | 11/2012 |
| WO | WO-2014004990 A2 | 1/2014 |
| WO | WO-2014028445 A2 | 2/2014 |
| WO | WO-2014091446 A1 | 6/2014 |
| WO | WO-2014172429 A1 | 10/2014 |
| WO | WO-2014/190207 A1 | 11/2014 |
| WO | WO-2015006299 A1 | 1/2015 |
| WO | WO-2015085172 A2 | 6/2015 |
| WO | WO-2015123377 A1 | 8/2015 |
| WO | WO-2015134464 A2 | 9/2015 |
| WO | WO-2015143004 A1 | 9/2015 |
| WO | WO-2015160845 A2 | 10/2015 |
| WO | WO-2015200795 A1 | 12/2015 |
| WO | WO-2016007848 A1 | 1/2016 |
| WO | WO-2016029004 A1 | 2/2016 |
| WO | WO-2016057503 A1 | 4/2016 |
| WO | WO-2016065139 A1 | 4/2016 |
| WO | WO-2016105518 A1 | 6/2016 |
| WO | WO-2016118666 A1 | 7/2016 |
| WO | WO-2016/197114 A1 | 12/2016 |
| WO | WO-2016197032 A1 | 12/2016 |
| WO | WO-2017007612 A1 | 1/2017 |
| WO | WO-2017024317 A2 | 2/2017 |
| WO | WO-2017024318 A1 | 2/2017 |
| WO | WO-2017024319 A1 | 2/2017 |
| WO | WO-2017030814 A1 | 2/2017 |
| WO | WO-2017046036 A1 | 3/2017 |
| WO | 2017120422 A1 | 7/2017 |
| WO | WO-2017117118 A1 | 7/2017 |
| WO | WO-2017120437 A1 | 7/2017 |
| WO | WO-2017120446 A1 | 7/2017 |
| WO | WO-2017143059 A1 | 8/2017 |
| WO | WO-2017161119 A1 | 9/2017 |
| WO | WO-2017176958 A1 | 10/2017 |
| WO | WO-2017184995 A1 | 10/2017 |
| WO | WO-2017/197051 A1 | 11/2017 |
| WO | WO-2017197055 A1 | 11/2017 |
| WO | WO-2017197056 A1 | 11/2017 |
| WO | WO-2017223415 A1 | 12/2017 |
| WO | WO-2017223452 A1 | 12/2017 |
| WO | WO-2018052945 A1 | 3/2018 |
| WO | WO-2018052949 A1 | 3/2018 |
| WO | WO-2018071606 A1 | 4/2018 |
| WO | WO-2018085247 A1 | 5/2018 |
| WO | WO-2018098275 A1 | 5/2018 |
| WO | WO-2018098280 A1 | 5/2018 |
| WO | WO-2018098288 A1 | 5/2018 |
| WO | WO-2018/102067 A2 | 6/2018 |
| WO | WO-2018/106870 A1 | 6/2018 |
| WO | WO-2018102725 A1 | 6/2018 |
| WO | WO-2018118598 A1 | 6/2018 |
| WO | WO-2018119357 A1 | 6/2018 |
| WO | WO-2018119441 A1 | 6/2018 |
| WO | WO-2018119448 A1 | 6/2018 |
| WO | WO-2018140809 A1 | 8/2018 |
| WO | WO-2018144649 A1 | 8/2018 |
| WO | WO-2018148440 A1 | 8/2018 |
| WO | WO-2018148443 A1 | 8/2018 |
| WO | WO-2018214796 A1 | 11/2018 |
| WO | WO-201909478 A1 | 1/2019 |
| WO | WO-2019006299 A1 | 1/2019 |
| WO | WO-2019014100 A1 | 1/2019 |
| WO | WO-2019099868 A2 | 5/2019 |
| WO | WO-2019099926 A1 | 5/2019 |
| WO | WO-2019133531 A1 | 7/2019 |
| WO | WO-2019136016 A1 | 7/2019 |
| WO | WO-2019140387 A1 | 7/2019 |
| WO | WO-2019146773 A1 | 8/2019 |
| WO | WO-2019148055 A1 | 8/2019 |
| WO | WO-2019164891 A1 | 8/2019 |
| WO | WO-2019165189 A1 | 8/2019 |
| WO | WO-2019170150 A1 | 9/2019 |
| WO | WO-2019177902 A1 | 9/2019 |
| WO | 2019191451 A1 | 10/2019 |
| WO | WO-2019195201 A1 | 10/2019 |
| WO | WO-2019195609 A2 | 10/2019 |
| WO | WO-2019196812 A1 | 10/2019 |
| WO | WO-2019199816 A1 | 10/2019 |
| WO | WO-2019209692 A1 | 10/2019 |
| WO | 2019241271 A1 | 12/2019 |
| WO | WO-2019241274 A1 | 12/2019 |
| WO | WO-2020/023480 A1 | 1/2020 |
| WO | WO-2020006264 A1 | 1/2020 |
| WO | WO-2020014489 A2 | 1/2020 |
| WO | WO-2020023782 A1 | 1/2020 |
| WO | WO-2020023851 A1 | 1/2020 |
| WO | WO-2020038415 A1 | 2/2020 |
| WO | WO-2020041331 A1 | 2/2020 |
| WO | WO-2020051235 A1 | 3/2020 |
| WO | WO-2020051564 A1 | 3/2020 |
| WO | WO-2020064002 A1 | 4/2020 |
| WO | WO-2020069117 A1 | 4/2020 |
| WO | WO-2020079103 A1 | 4/2020 |
| WO | WO-2020081880 A1 | 4/2020 |
| WO | WO-2020097403 A1 | 5/2020 |
| WO | WO-2020102195 A1 | 5/2020 |
| WO | WO-2020103878 A1 | 5/2020 |
| WO | WO-2020114482 A1 | 6/2020 |
| WO | WO-2020118098 A1 | 6/2020 |
| WO | WO-2020146440 A1 | 7/2020 |
| WO | WO-2020152440 A1 | 7/2020 |
| WO | WO-2020162725 A1 | 8/2020 |
| WO | WO-2020167518 A1 | 8/2020 |
| WO | WO-2020173440 A1 | 9/2020 |
| WO | WO-2020200291 A1 | 10/2020 |
| WO | WO-2020206137 A1 | 10/2020 |
| WO | WO-2020227325 A1 | 11/2020 |
| WO | WO-2020242960 A1 | 12/2020 |

(56) References Cited

FOREIGN PATENT DOCUMENTS

| | | |
|---|---|---|
| WO | WO-2020243379 A1 | 12/2020 |
| WO | WO-2020251972 A1 | 12/2020 |
| WO | WO-2020257278 A2 | 12/2020 |
| WO | WO-2020264490 A1 | 12/2020 |
| WO | WO-2021011631 A1 | 1/2021 |
| WO | WO-2021011634 A1 | 1/2021 |
| WO | WO-2021011868 A1 | 1/2021 |
| WO | WO-2021011871 A1 | 1/2021 |
| WO | WO-2021011913 A1 | 1/2021 |
| WO | WO-2021022163 A2 | 2/2021 |
| WO | WO-2021026109 A1 | 2/2021 |
| WO | WO-2021041664 A1 | 3/2021 |
| WO | WO-2021041861 A1 | 3/2021 |
| WO | WO-2021051034 A1 | 3/2021 |
| WO | WO-2021053555 A1 | 3/2021 |
| WO | WO-2021067606 A1 | 4/2021 |
| WO | WO-2021069705 A1 | 4/2021 |
| WO | WO-2021086829 A1 | 5/2021 |
| WO | WO-2021086830 A1 | 5/2021 |
| WO | 2021126973 A1 | 6/2021 |
| WO | 2021126974 A1 | 6/2021 |
| WO | WO-2021188537 A1 | 9/2021 |
| WO | WO-2022073469 A1 | 4/2022 |
| WO | WO-2022093742 A1 | 5/2022 |
| WO | 2022152821 A1 | 7/2022 |
| WO | 2022152822 A1 | 7/2022 |
| WO | 2022200857 A1 | 9/2022 |
| WO | 2022219407 A1 | 10/2022 |
| WO | 2022219412 A1 | 10/2022 |
| WO | 2023069708 A1 | 4/2023 |
| WO | 2023069731 A1 | 4/2023 |
| WO | 2024015565 A1 | 1/2024 |

OTHER PUBLICATIONS

Berge, S. M., et al., "Pharmaceutical Salts," Journal of Pharmaceutical Sciences, American Chemical Society and American Pharmaceutical Association, US, 66(1):1-19, Jan. 1, 1977.

Bondeson, D.P et al., "Targeted Protein Degradation by Small Molecules," Annu Rev Pharmacol Toxicol, 57:107-123, Jan. 6, 2017.

Brito, M., et al., "Polyglycine expansions in eRF3/GSPT1 are associated with gastric cancer susceptibility," Carcinogenesis, 26(12):2046-2049, (2005).

Cancer Genome Atlas Network, "Comprehensive Molecular Portraits of Human Breast Tumours," Nature, 490(7418):61-70, Oct. 4, 2012.

Chamberlain, P.P. et al., "Cereblon modulators: Low molecular weight inducers of protein degradation," Drug Discov Today: Technologies, 31:29-34, Apr. 31, 2019.

Chauvin, C., et al., "Human Eukaryotic Release Factor 3a Depletion Causes Cell Cycle Arrest at $G_1$ Phase through Inhibition of the mTOR Pathway." Molecular and Cellular Biology, 27(16):5619-5629, (2007).

Collins, I. et al., "Chemical approaches to targeted protein degradation through modulation of the ubiquitin-proteasome pathway," Biochem J., 474(7):1127-1147, Mar. 15, 2017.

Gandhi, A.K. et al., "Immunomodulatory agents lenalidomide and pomalidomide co-stimulate T cells by inducing degradation of T cell repressors Ikaros and Aiolos via modulation of the E3 ubiquitin ligase complex CRL4CRBN," Br. J. Haematol., 164(6):811-21, Mar. 2014.

Gao, S. et al., "Novel immunomodulatory drugs and neo-substrates," Biomark Res., 8(2):1-8, Jan. 9, 2020.

Garrido-Castro, A.C. et al., "Insights into Molecular Classifications of Triple-Negative Breast Cancer: Improving Patient Selection for Treatment," Cancer Discov., 9(2):176-198, Feb. 2019.

GenBank Accession No. NP_001123478.2, "eukaryotic peptide chain release factor GTP-binding subunit ERF3A isoform 2 [*Homo sapiens*]," Jun. 6, 2022, 3 pages.

Gérald et al., "Abstract LBA004: Identification of GSPT1-directed molecular glue degrader (MGD) for the treatment of Myc-driven breast cancer," Molecular Cancer Therapeutics, American Association for Cancer Research, Dec. 1, 2021.

Ghoreishi, K., "The effects of GSPT1 degradation on serum calcium, parathyroid hormone, and fibroblast growth factor 23 concentrations in human Cereblon knock-in mice.", VCU Scholars Compass, https://doi.org/10.25772/6RMR-9298, (2020).

Hansen, J. D., et al. "CC-90009: A Cereblon E3 Ligase Modulating Drug That Promotes Selective Degradation of GSPT1 for the Treatment of Acute Myeloid Leukemia", J. Med. Chem., 64(4):1835-1843, Feb. 25, 2021.

Hansen, J.D. et al., "Protein Degradation via $CRL4^{CRBN}$ Ubiquitin Ligase: Discovery and Structure-Activity Relationships of Novel Glutarimide Analogs That Promote Degradation of Aiolos and/or GSPT1," J. Med Chem., 61(2):492-503, Jan. 25, 2018, 2018.

Hashimoto, Y., et al., "Translation termination factor eRF3 is targeted for caspase-mediated proteolytic cleavage and degradation during DNA damage-induced apoptosis" Apoptosis, 17:1287-1299, (2012).

Heim, C., et al. "On the correlation of cereblon binding, fluorination and antiangiogenic properties of immunomodulatory drugs", Biochemical and Biophysical Research Communications, 534:67-72, Jan. 1, 2021.

Huang, L. et al., "Targeting Translation Termination Machinery with Antisense Oligonucleotides for Diseases Caused by Nonsense Mutations," Nucleic Acid Ther., 29(4):175-186, Aug. 2019.

International Search Report and Written Opinion for International Patent Application No. PCT/EP2020/078483, mailed Jan. 12, 2021.

International Search Report and Written Opinion for International Patent Application No. PCT/EP2022/050699, mailed Apr. 4, 2022.

International Search Report and Written Opinion for International Patent Application No. PCT/EP2022/050702, mailed Apr. 12, 2022.

Ishii, T. et al., "A Novel Rac1-GSPT1 Signaling Pathway Controls Astrogliosis Following Central Nervous System Injury", J. Biol. Chem., 292(4):1240-1250, Jan. 27, 2017.

Ito, T. et al., "Identification of a Primary Target of Thalidomide Teratogenicity," Science, 327(5971):1345-1350, Mar. 10, 2010.

Ito, T., et al. "Cereblon and its downstream substrates as molecular targets of immunomodulatory drugs", Int. J. Hematol., 104:293-299, (2016).

Klauber-DeMore, N. et al., "Targeting MYC for triple-negative breast cancer treatment," Oncoscience, 5(5-6):120-121, Jun. 23, 2018.

Krönke, J. et al., "Lenalidomide Causes Selective Degradation of IKZF1 and IKZF3 in Multiple Myeloma Cells," Science, 343(6168):301-305, Jan. 17, 2014.

Krönke, J. et al., "Lenalidomide induces ubiquitination and degradation of CK1α in del(5q) MDS," Nature, 523(7559):183-188, Jul. 9, 2015.

Leissing, T. M., et al. "Structure driven compound optimization in targeted protein degradation", Drug Discovery Today: Technologies, 37:73-82, (2020).

Li, M., et al., "eRF3b, a Biomarker for Hepatocellular Carcinoma, Influences Cell Cycle and Phosphoralation Status of 4E-BP1" PLoS ONE, 9(1): e86371, (2004).

Lindner, S., et al. "The molecular mechanism of thalidomide analogs in hematologic malignancies", J. Mol. Med., 94:1327-1334, (2016).

Lu, G. et al., "The Myeloma Drug Lenalidomide Promotes the Cereblon-Dependent Destruction of Ikaros Proteins," Science, 343(6168):305-309, Jan. 17, 2014.

Malta-Vacas, J., et al., "Differential expression of GSPT1 GGCn alleles in cancer" Canc. Genet. Cyto., 195,(2):132-142, (2009).

Matyskiela, A. et al., "A Cereblon Modulator (CC-220) with Improved Degradation of Ikaros and Aiolos," J. Med. Chem., 61(2):535-542, Jan. 25, 2018.

Matyskiela, M. E., et al. "A novel cereblon modulator recruits GSPT1 to the CRL4CRBN ubiquitin ligase", Nature, 535:252-257, (2016).

Matyskiela, M.E. et al., "A novel cereblon modulator recruits GSPT1 to the $CRL4^{CRBN}$ ubiquitin ligase," Nature, 535(7611):252-257, Jul. 14, 2016.

(56) References Cited

OTHER PUBLICATIONS

Mertz, J. A., et al., "Targeting MYC dependence in cancer by inhibiting BET bromodomains," Proceedings of the National Academy of Sciences, 108(40):16669-16674, Oct. 4, 2011.

Miri, M., et al., "GGCn polymorphism of eRF3a/GSPT1 gene and breast cancer susceptibility," Med. Oncol., 29:1581-1585, Nov. 19, 2011.

Nishiguchi, G., et al., "Identification of Potent, Selective, and Orally Bioavailable Small-Molecule GSPT1/2 Degraders from a Focused Library of Cereblon Modulators", J. Med. Chem., 64(11):7296-7311, Jun. 10, 2021.

Pierce, D. W., et al., "Synergistic combination activity of the novel GSPT1 in acute myeloid leukemia models", Presented at the 63rd American Society of Hematology (ASH) Annual Meeting, Atlanta, GA, USA, Dec. 11-14, 2021.

Pourdehnad, M., et al., "Myc and mTOR converge on a common node in protein synthesis control that confers synthetic lethality in Myc-driven cancers," Proceedings of the National Academy of Sciences, National Academy of Sciences, 110(29):11988-11993, Jul. 16, 2013.

Powell, C. E., et al., "Selective Degradation of GSPT1 by Cereblon Modulators Identified via a Focused Combinatorial Library", ACS Chemical Biology, 15((10):2722-2730, Oct. 16, 2020.

Slabicki, M., et al., "The CDK inhibitor CR8 acts as a molecular glue degrader that depletes cyclin K," Nature, Nature Publishing Group UK, London, 585(7824):293-297, Jun. 3, 2020.

Surka, C., et al., "CC-90009, a novel cereblon E3 ligase modulator, targets acute myeloid leukemia blasts and leukemia stem cells", Blood, 137(5):661-677, Feb. 4, 2021.

Tian, Q-G., et al., "Expressions and correlation analysis of HIF-a, survivin and VEGF in patients with hepatocarcinoma" Eur. Rev. Med. Pharmacol. Sci., 22, pp. 3378-3385, (2018).

Wang, S., et al., "Gene expression in triple-negative breast cancer in relation to survival," Breast Cancer Res Treat, 171:199-207, May 10, 2018.

Wei, Y., et al., "Discovery of new Lenalidomide derivatives as potent and selective GSPT1 degraders" European Journal of Medicinal Chemistry, vol. 258, (2023).

Wright, J. L., et al., "Newer Potential Biomarkers in Prostate Cancer", Rev. Urol., 9(4): 207-213, (2003).

Xiao, D., et al. "Design, synthesis and biological evaluation of the thioether-containing lenalidomide analogs with anti-proliferative activities", European Journal of Medicinal Chemistry, vol. 176:419-430, (2019).

Xiao, R. et al., "miRNA-144 suppresses proliferation and migration of colorectal cancer cells through GSPT1," Biomed Pharmacother, 74:138-144, Aug. 3, 2015.

Yamamoto, J., et al. "Discovery of CRBN as a target of thalidomide: a breakthrough for progress in the development of protein degraders", Chem. Soc. Rev., 51:6234-6250, (2022).

Yang, J., et al., "Simple Structural Modifications Converting a Bona fide MDM2 PROTAC Degrader into a Molecular Glue Molecule: A Cautionary Tale in the Design of PROTAC Degraders", J. Med. Chem., 62(21):9471-9487, Nov. 14, 2019.

Yao, T-W. S., et al., "Discovery of induction and release of IL-1b are unique and on-target effects of GSPT1 degradation that provide potention mitigation strategies to hypotension in the CC-90009-AML-001 phase 1 trial", Presented on Jun. 22-24, 2020, at American Association for Cancer Research (AACR) Virtual Annual Meeting II.

Zeidan, A. M., et al., "Clinical activity of CC-90009, a cereblon E3 ligase modulator and first-in-class GSPT1 degrader, as a single agent in patients with relapsed or refractory acute myeloid leukemia: First results from phase 1 dose-finding study", Presented at the 25th Congress of the European Hematology Association (EHA), Jun. 11-14, 2020.

Zhang, C et al., "Downregulation of microRNA-27b-3p via aberrant DNA methylation contributes to malignant behavior of gastric cancer cells by targeting GSPT1," Biomed & Pharmacother, 119:109417, Nov. 2019.

Zou, J. et al., "The novel protein homeostatic modulator BTX306 is active in myeloma and overcomes bortezomib and lenalidomide resistance," J Mol Med, 98(8):1161-1173, Jul. 6, 2020.

Gang, L., et al., "A novel cereblon modulator recruits GSPT1 to the CRL4CRBN ubiquitin ligase." Nature, 535:252-257, Jul. 14, 2016.

Baradaran-Heravi, A., et al. "Effect of small molecule eRF3 degraders on premature termination codon readthrough." Nucleic Acids Research, 49(7):3692-3708, Mar. 25, 2021.

International Search Report and Written Opinion for International Patent Application No. PCT/IB2022/000150, mailed Jun. 9, 2022.

International Search Report and Written Opinion for International Patent Application No. PCT/IB2022/000215, mailed Sep. 15, 2022.

International Search Report and Written Opinion for International Patent Application No. PCT/IB2022/000223, mailed Aug. 17, 2022.

Ishoey, M., et al. "Translation Termination Factor GSPT1 Is a Phenotypically Relevant Off-Target of Heterobifunctional Phthalimide Degraders." ACS Chemical Biology, 13(3):553-560, (2018).

Ishoey, M., et al. "Translation Termination Factor GSPT1 Is a Phenotypically Relevant Off-Target of Heterobifunctional Phthalimide Degraders." Supporting Information. ACS Chemical Biology, 13(3):553-560, (2018).

Keeling, K. M., et al. "Suppression of Premature Termination Codons as a Therapeutic Approach." Critical Reviews in Biochemistry and Molecular Biology, 47(5):444-463, (2012).

Min, J., et al. "Phenyl-Glutarimides: Alternative Cereblon Binders for the Design of PROTACs." Angewandte Chemie International Edition, 60(51):26663-26670, Oct. 6, 2021.

Wong, E., et al. "Pharmacological depletion of ERF1 or ERF3A enhances effect of aminoglycosides on CFTR premature termination codon readthrough." Pediatric Pulmonology, vol. 55, (Suppl. 2), p. 61, Poster Session Abstract, Oct. 1, 2020.

U.S. Appl. No. 18/349,634, Isoindolinone Compounds, filed Jul. 10, 2023, Granted U.S. Pat. No. 11,912,682.

U.S. Appl. No. 17/716,169, Isoindolinone Compounds, filed Apr. 8, 2022, Published US20220242846A1.

U.S. Appl. No. 18/485,766, Isoindolinone Compounds, filed Oct. 12, 2023, Published US20240051936A1.

U.S. Appl. No. 18/485,780, Isoindolinone Compounds Amide Compounds Useful to Treat Diseases Associated With GSPT1, filed Oct. 12, 2023, Published US20240051937A1.

U.S. Appl. No. 18/271,954, Treatment of Myc Driven Cancers With GSPT1 Degraders, filed Jul. 12, 2023, Published US20240261274A1.

U.S. Appl. No. 18/471,563, Pharmaceutical Compositions for Use in the Prevention and Treatment of a Disease or Disorder caused by or Associated With One or More Premature Termination Codons, filed Sep. 21, 2023, Published US20240216355A1.

U.S. Appl. No. 18/640,889, Compounds That Mediate Protein Degradation and Uses Thereof, Apr. 19, 2024, Published US20240308976A1.

U.S. Appl. No. 18/640,909, Compounds That Mediate Protein Degradation and Methods of Uses Thereof, Apr. 19, 2024, Published US20240294495A1.

Monte Rosa Therapeutics et al.: "NCT05546268—Study of Oral MRT-2359 in Selected Cancer Patients," National Library of Medicine, posted Aug. 31, 2023. Retrieved from https://clinicaltrials.gov/study/NCT05546268?tab=history&a=10#version-content-panel on Nov. 7, 2024.

Butreddy, A., "Hydroxypropyl methylcellulose acetate succinate as an exceptional polymer for amorphous solid dispersion formulations: A review from bench to clinic," European Journal of Pharmaceutics and Biopharmaceutics, 177:289-307, Aug. 1, 2022.

Greijer, A. E., et al.: "Up-regulation of gene 1-15 expression by hypoxia is mediated predominantly by hypoxia-inducible factor 1 (HIF-1)," The Journal of Pathology, 206(3):291-304, May 19, 2005.

Zhang, J., et al.: "Human differentiation-related gene NDRG1 is a Myc downstream-regulated gene that is repressed by Myc on the core promoter region," Gene, 417(1-2):1-5, Jul. 1, 2008.

\* cited by examiner

○ Vehicle, PO, QD
▦ Compound 10, 1 mg/kg PO, QD
▲ Compound 10, 3 mg/kg PO, QD
▼ Compound 10, 6 mg/kg PO, 5 ON – 9 OFF
✦ Gemcitabine, 40 mg/kg IP, Q4Dx5

○ Vehicle, PO, QD
▲ Compound 10, 3 mg/kg PO, QD
▼ Compound 10, 6 mg/kg PO, 5 ON – 9 OFF
✧ Cisplatin, 6 mg/kg IP, QWx3

○   Vehicle, PO, QD
▲   Compound 10, 3 mg/kg PO, QD
▼   Compound 10, 6 mg/kg PO, 5 ON – 9 OFF
✳   Cisplatin, 6 mg/kg IP, QWx3

ISOINDOLINONE COMPOUNDS

CROSS-REFERENCE

This application is a continuation of U.S. Non-provisional application Ser. No. 18/349,634, filed Jul. 10, 2023, which is a continuation of International Patent Application No. PCT/EP2022/050699, filed Jan. 13, 2022, which claims priority to Swiss Patent Application No. 00025/21 filed Jan. 13, 2021, Swiss Patent Application No. 00386/21 filed Apr. 14, 2021, Swiss Patent Application No. 00655/21 filed Jun. 4, 2021, and U.S. Provisional Application No. 63/281,049 filed Nov. 18, 2021, the contents of each of which are incorporated herein by reference in their entireties.

FIELD OF DISCLOSURE

The present disclosure relates to new compounds as modulators of cereblon. The disclosure also relates to methods of preparation of these compounds, compositions comprising these compounds, and methods of using them in the treatment of abnormal cell growth in mammals, especially humans.

BACKGROUND

The ubiquitin proteasome system can be manipulated with different small molecules to trigger targeted degradation of specific proteins of interest. Promoting the targeted degradation of pathogenic proteins using small molecule degraders is emerging as a new modality in the treatment of diseases. One such modality relies on redirecting the activity of E3 ligases such as cereblon (a phenomenon known as E3 reprogramming) using low molecular weight compounds, which have been termed molecular glues to promote the poly-ubiquitination and ultimately proteasomal degradation of new protein substrates involved in the development of diseases. The molecular glues bind to both the E3 ligase and the target protein, thereby mediating an alteration of the ligase surface and enabling an interaction with the target protein. Particularly relevant compounds for the E3 ligase cereblon are the IMiD (immunomodulatory imide drugs) class including Thalidomide, Lenalidomide and Pomalidomide. These IMiDs have been approved by the FDA for use in hematological cancers. However, compounds for efficiently targeting other diseases, in particular other types of cancers, are still required.

SUMMARY OF DISCLOSURE

It is therefore an object of the present disclosure to advance the state of the art of cereblon modulators and provide modulators for novel use in different diseases, in particular in different cancers.

In some embodiments, compounds are provided for use in therapy of solid tumors, such as for use in the therapy of lung cancer for example, non-small cell lung cancer (e.g., squamous cell lung cancer) and small cell lung cancer, breast cancer, and neuroendocrine cancer, e.g., neuroendocrine prostate cancer such as castration-resistant neuroendocrine prostate cancer (NEPC) and lung neuroendocrine tumors (Lu-NETs). In some embodiments, compounds are provided for use in therapy of blood-borne (or haematological) cancers such as for use in the therapy of leukemias (e.g. acute myelogenous leukemia (AML)) and myelomas (e.g. multiple myeloma (MM)).

The present disclosure is in a first aspect directed towards a compound or pharmaceutically acceptable salts or stereoisomers thereof formula I.

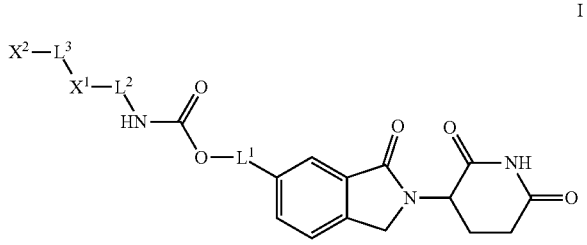

wherein
$X^1$ is linear or branched $C_{1-6}$ alkyl, $C_{3-8}$ cycloalkyl, $C_{6-10}$ aryl, 5-10 membered heteroaryl, 4-8 membered heterocycloalkyl, wherein $X^1$ is unsubstituted or substituted with one or more of halogen, linear or branched $C_{1-6}$ alkyl, linear or branched $C_{1-6}$ heteroalkyl, $CF_3$, $CHF_2$, $CMeF_2$, —O—$CHF_2$, —O—$(CH_2)_2$—OMe, $OCF_3$, $C_{1-6}$ alkylamino, —CN, —N(H)C(O)—$C_{1-6}$alkyl, —OC(O)—$C_{1-6}$alkyl, —OC(O)—$C_{1-4}$alkylamino, —C(O)O—$C_{1-6}$alkyl, —COOH, —$C_{1-6}$alkylC(O)OH, —$C_{1-6}$alkylC(O)O—$C_{1-6}$-alkyl, $NH_2$, $C_{1-4}$ alkoxy, $C_{1-4}$ alkylhydroxy, —$CH_2F$, —N(H)C(O)—O—$C_{1-6}$ alkyl, and $C(OH)(CF_3)$;
or $X^1$ together with the N atom of the carbamate forms a 4-8 membered heterocycloalkyl, which is unsubstituted or substituted with one or more of halogen, linear or branched —$C_{1-6}$ alkyl, $CF_3$, $CHF_2$, $CMeF_2$, —O—$(CH_2)_2$—OMe, $OCF_3$, $OCHF_2$, $C_{1-6}$ alkylamino, —CN, —N(H)C(O)—$C_{1-6}$alkyl, —OC(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$alkyl, $NH_2$, $C_{1-4}$ alkylhydroxy, and $C_{1-4}$ alkoxy;
$X^2$ is H, $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and $C_{1-4}$ alkylhydroxy;
$L^1$ is a covalent bond, linear or branched $C_{1-6}$ alkyl;
$L^2$ is a covalent bond, linear or branched $C_{1-6}$ alkyl; and
$L^3$ is a covalent bond, linear or branched $C_{1-6}$ alkyl, —O—, or —$C_{1-4}$ alkoxy, wherein linear or branched $C_{1-6}$ alkyl is unsubstituted or substituted with one or more of halogen.
In some embodiments,
$X^1$ is linear or branched $C_{1-6}$ alkyl, $C_{3-6}$ cycloalkyl, $C_{6-10}$ aryl, 5-10 membered heteroaryl, 4-8 membered heterocycloalkyl, wherein $X^1$ is unsubstituted or substituted with one or more of halogen, linear or branched $C_{1-6}$ alkyl, linear or branched $C_{1-6}$ heteroalkyl, $CF_3$, $CHF_2$, $CMeF_2$, —O—$CHF_2$, —O—$(CH_2)_2$—OMe, $OCF_3$, $C_{1-6}$ alkylamino, —CN, —N(H)C(O)—$C_{1-6}$alkyl, —OC(O)—$C_{1-6}$alkyl, —OC(O)—$C_{1-4}$alkylamino, —C(O)O—$C_{1-6}$alkyl, —COOH, —$C_{1-6}$alkylC(O)OH, —$C_{1-6}$alkylC(O)O—$C_{1-6}$-alkyl, $NH_2$, $C_{1-4}$ alkoxy and $C_{1-4}$ alkylhydroxy;
or $X^1$ together with the N atom of the carbamate forms a 4-8 membered heterocycloalkyl, which is unsubstituted or substituted with one or more of halogen, linear or branched —$C_{1-6}$ alkyl, $CF_3$, $CHF_2$, $CMeF_2$, —O—$(CH_2)_2$—OMe, $OCF_3$, $OCHF_2$, $C_{1-6}$ alkylamino, —CN, —N(H)C(O)—C$_{1-6}$alkyl, —OC(O)—C$_{1-6}$alkyl, —C(O)O—C$_{1-6}$alkyl, —COOH, —C$_{1-6}$alkylC(O)OH, —C$_{1-6}$alkylC(O)O—C$_{1-6}$alkyl, NH$_2$, C$_{1-4}$ alkylhydroxy, and C$_{1-4}$ alkoxy;

X$^2$ is H, C$_{3-6}$ cycloalkyl, C$_{6-10}$ aryl, 5-10 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and C$_{1-4}$ alkylhydroxy;

L$^1$ is a covalent bond, linear or branched C$_{1-6}$ alkyl;
L$^2$ is a covalent bond, linear or branched C$_{1-6}$ alkyl; and
L$^3$ is a covalent bond, linear or branched C$_{1-6}$ alkyl, —O—, —C$_{1-4}$ alkoxy.

In some embodiments of a compound of formula I, X$^1$ is linear or branched —C$_{1-6}$ alkyl, —C$_{3-6}$ cycloalkyl, —C$_{6-10}$ aryl, 5-10 membered heteroaryl, 5-6 membered heterocycloalkyl, wherein X$^1$ is unsubstituted or substituted with one or more of halogen, linear or branched —C$_{1-4}$ alkyl, CF$_3$, CHF$_2$, CMeF$_2$, —O—(CH$_2$)$_2$—OMe, OCF$_3$, OCHF$_2$, C$_{1-6}$ alkylamino, —CN, NH$_2$, C$_{1-4}$ alkylhydroxy, and C$_{1-4}$ alkoxy; or X$^1$ together with the N atom of the carbamate forms a 4-8 membered heterocycloalkyl, which is unsubstituted or substituted with one or more of halogen, linear or branched —C$_{1-4}$ alkyl, CF$_3$, CHF$_2$, CMeF$_2$, —O—(CH$_2$)$_2$—OMe, OCF$_3$, OCHF$_2$, C$_{1-6}$ alkylamino, —CN, NH$_2$, C$_{1-4}$ alkylhydroxy, and C$_{1-4}$ alkoxy.

In some embodiments of a compound of formula I, X$^2$ is H, C$_{3-6}$ cycloalkyl, C$_6$ aryl, 5-6 membered heteroaryl, 4-8 membered heterocycloalkyl, wherein X$^2$ is unsubstituted or substituted with one or more of linear or branched C$_{1-4}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy.

In some embodiments, the present disclosure is directed towards a compound or pharmaceutically acceptable salts or stereoisomers thereof formula II.

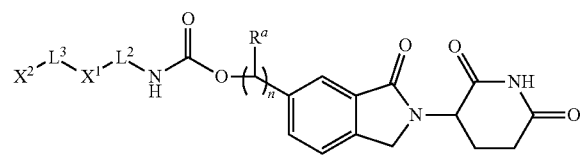

II wherein
X$^1$ is linear or branched C$_{1-6}$ alkyl, C$_{3-6}$ cycloalkyl, C$_{6-10}$ aryl, 5-10 membered heteroaryl, 4-8 membered heterocycloalkyl, wherein X$^1$ is unsubstituted or substituted with one or more of halogen, linear or branched C$_{1-6}$ alkyl, linear or branched C$_{1-6}$ heteroalkyl, CF$_3$, CHF$_2$, CMeF$_2$, —O—CHF$_2$, —O—(CH$_2$)$_2$—OMe, OCF$_3$, C$_{1-6}$ alkylamino, —CN, —N(H)C(O)—C$_{1-6}$alkyl, —OC(O)—C$_{1-6}$alkyl, —OC(O)—C$_{1-4}$alkylamino, —C(O)O—C$_{1-6}$alkyl, —COOH, —C$_{1-6}$alkylC(O)OH, —C$_{1-6}$alkylC(O)O—C$_{1-6}$-alkyl, NH$_2$, C$_{1-4}$ alkoxy and C$_{1-4}$ alkylhydroxy;

or X$^1$ together with the N atom of the carbamate forms a 4-8 membered heterocycloalkyl, which is unsubstituted or substituted with one or more of halogen, linear or branched —C$_{1-6}$ alkyl, CF$_3$, CHF$_2$, CMeF$_2$, —O—(CH$_2$)$_2$—OMe, OCF$_3$, OCHF$_2$, C$_{1-6}$ alkylamino, —CN, —N(H)C(O)—C$_{1-6}$alkyl, —OC(O)—C$_{1-6}$alkyl, —C(O)O—C$_{1-6}$alkyl, —COOH, —C$_{1-6}$alkylC(O)OH, —C$_{1-6}$alkylC(O)O—C$_{1-6}$alkyl, NH$_2$, C$_{1-4}$ alkylhydroxy, and C$_{1-4}$ alkoxy;

X$^2$ is H, C$_{3-6}$ cycloalkyl, C$_{6-10}$ aryl, 5-10 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and C$_{1-4}$ alkylhydroxy;

L$^2$ is a covalent bond, linear or branched C$_{1-6}$ alkyl; L$^3$ is a covalent bond, linear or branched C$_{1-6}$ alkyl, —O—, —C$_{1-4}$ alkoxy;

R$^a$ is H or linear or branched C$_{1-4}$ alkyl, such as methyl or ethyl; and n is 1 or 2.

In some embodiments of a compound of formula II, n is 1.

In some embodiments, the present disclosure is directed towards a compound or pharmaceutically acceptable salts or stereoisomers thereof formula III, such as IVa or IVb:

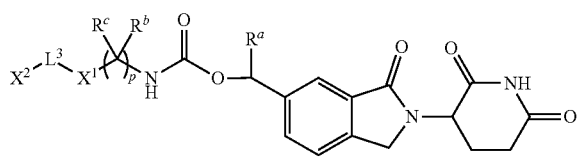

III

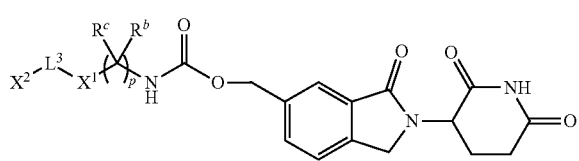

IVa

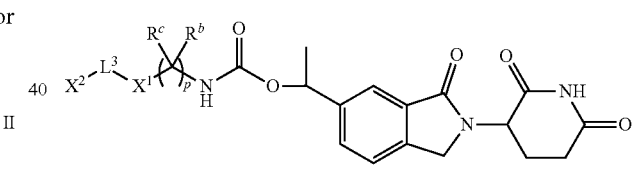

IVb wherein
X$^1$ is linear or branched C$_{1-6}$ alkyl, C$_{3-6}$ cycloalkyl, C$_{6-10}$ aryl, 5-10 membered heteroaryl, 4-8 membered heterocycloalkyl, wherein X$^1$ is unsubstituted or substituted with one or more of halogen, linear or branched C$_{1-6}$ alkyl, linear or branched C$_{1-6}$ heteroalkyl, CF$_3$, CHF$_2$, CMeF$_2$, —O—CHF$_2$, —O—(CH$_2$)$_2$—OMe, OCF$_3$, C$_{1-6}$ alkylamino, —CN, —N(H)C(O)—C$_{1-6}$alkyl, —OC(O)—C$_{1-6}$ alkyl, —OC(O)—C$_{1-4}$alkylamino, —C(O)O—C$_{1-6}$alkyl, —COOH, —C$_{1-6}$alkylC(O)OH, —C$_{1-6}$ alkylC(O)O—C$_{1-6}$alkyl, NH$_2$, C$_{1-4}$ alkoxy and C$_{1-4}$ alkylhydroxy;

or X$^1$ together with the N atom of the carbamate forms a 4-8 membered heterocycloalkyl, which is unsubstituted or substituted with one or more of halogen, linear or branched —C$_{1-6}$ alkyl, CF$_3$, CHF$_2$, CMeF$_2$, —O—(CH$_2$)$_2$—OMe, OCF$_3$, OCHF$_2$, C$_{1-6}$ alkylamino, —CN, —N(H)C(O)—C$_{1-6}$alkyl, —OC(O)—C$_{1-6}$alkyl, —C(O)O—C$_{1-6}$alkyl, —COOH, —C$_{1-6}$alkylC(O)OH, —C$_{1-6}$alkylC(O)O—C$_{1-6}$alkyl, NH$_2$, C$_{1-4}$ alkylhydroxy, and C$_{1-4}$ alkoxy;

X$^2$ is H, C$_{3-6}$ cycloalkyl, C$_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and $C_{1-4}$ alkylhydroxy;

$L^3$ is a covalent bond, linear or branched $C_{1-6}$ alkyl, —O—, —$C_{1-4}$ alkoxy;

$R^a$, $R^b$, $R^c$ are independently of each other H, linear or branched $C_{1-4}$ alkyl, such as methyl; and p is 0 or 1.

In some embodiments, a compound of formula I is a compound or pharmaceutically acceptable salts or stereoisomers thereof formula V, VI or VII:

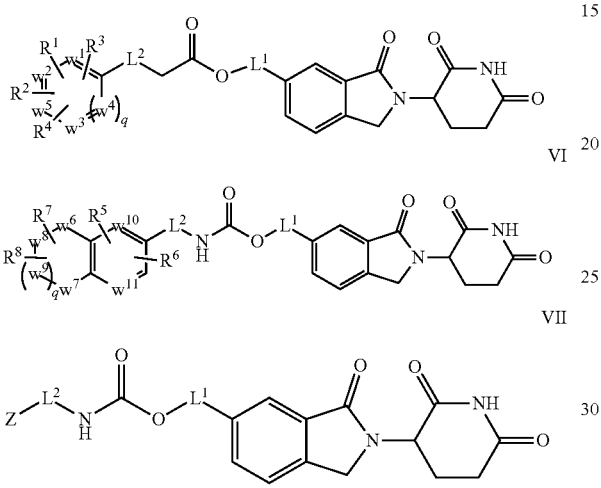

wherein
one or two of $w^1$, $w^2$, $w^3$, $w^4$ $w^5$ are independently of each other selected from C, N, S, and O, and the remaining of $w^1$, $w^2$, $w^3$, $w^4$, $w^5$ are C;
one or two of $w^6$, $w^7$, $w^8$, $w^9$ are selected from C and O and the remaining of $w^6$, $w^7$, $w^8$, $w^9$ are C; $w^{10}$, $w^{11}$ are independently of each other selected from C and N; and q is 0 or 1;
$L^1$ is a covalent bond, linear or branched $C_{1-6}$ alkyl; $L^2$ is a covalent bond, linear or branched $C_{1-6}$ alkyl;
$R^1$, $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl, or a group of formula -$L^3$-$X^2$, wherein $L^3$ is a covalent bond, linear or branched $C_{1-6}$ alkyl, —O—, —$C_{1-4}$ alkoxy and $X^2$ is $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and $C_{1-4}$ alkylhydroxy;

$R^5$, $R^6$, $R^7$ $R^8$ are independently of each other selected from H, linear or branched $C_{1-4}$ alkyl, such as methyl, and halogen, such as F or Cl, e.g. F;

Z is linear or branched —$C_{1-6}$ alkyl, —$C_{3-6}$ cycloalkyl, 4-8 membered heterocycloalkyl, wherein Z is unsubstituted or substituted with $C_{1-4}$ alkyl, $C_6$ aryl, $C_6$ aryloxy, 6 membered heteroaryl or $CF_3$; or Z together with the N atom of the carbamate forms a 4-8 membered heterocycloalkyl, which is unsubstituted or substituted with $C_{1-4}$ alkyl, $C_6$ aryl, $C_6$ aryloxy, 6 membered heteroaryl or $CF_3$; q is 0 or 1.

In some embodiments, the present disclosure is directed towards a compound or pharmaceutically acceptable salts or stereoisomers thereof formula VIII, e.g. VIIIa

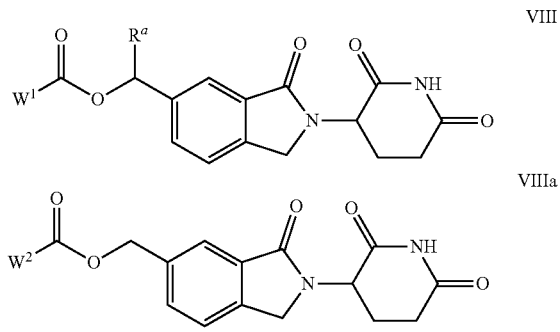

wherein $R^a$ is H or methyl and $w^1$ and $w^2$ are selected from

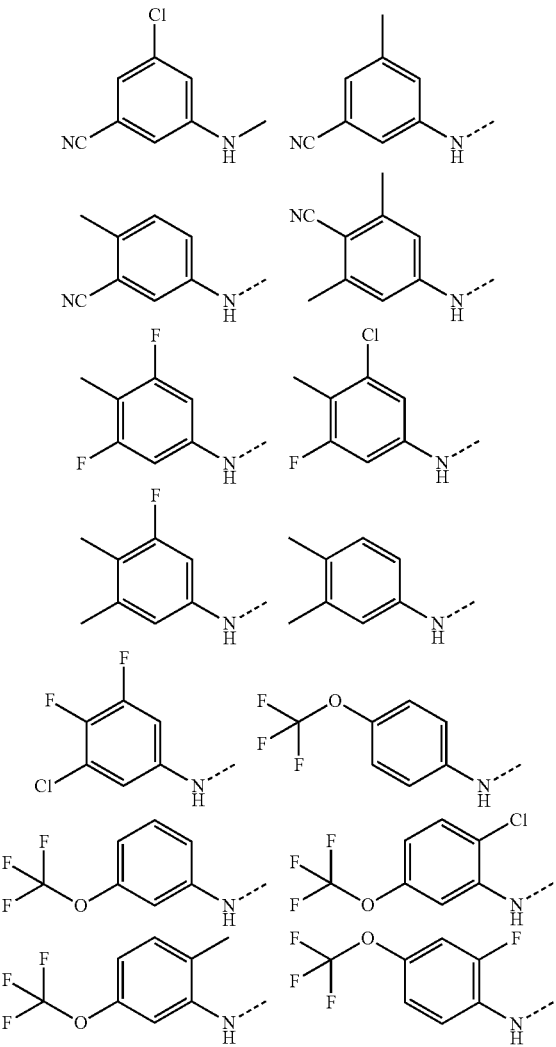

-continued
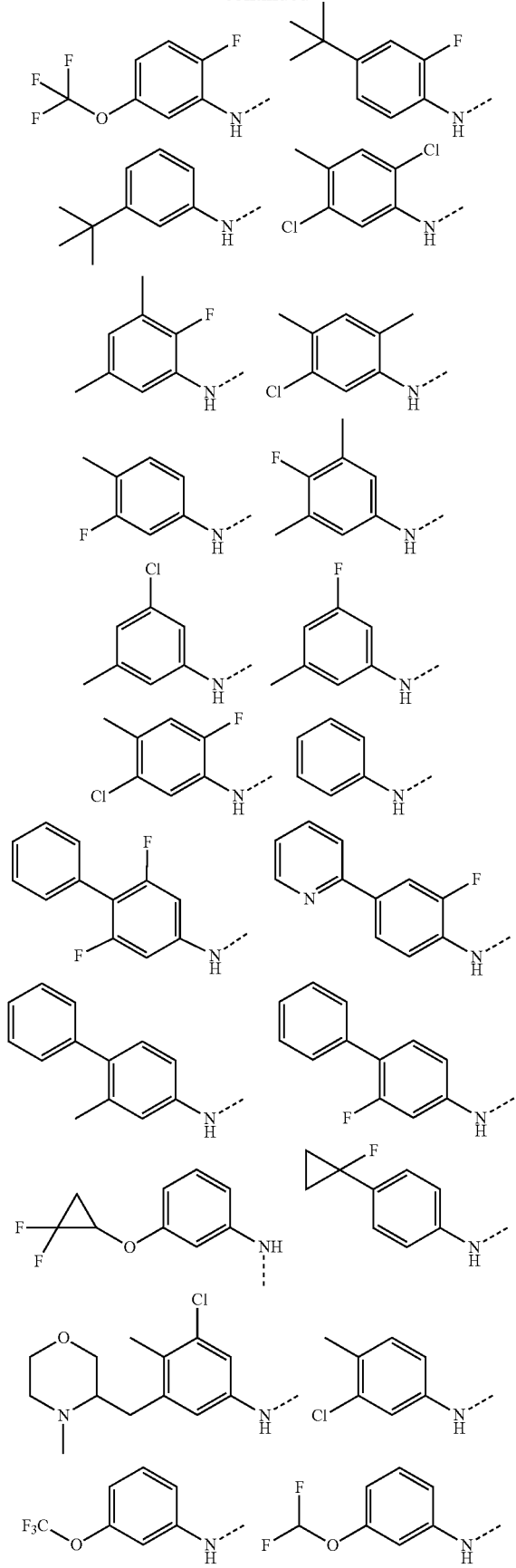
-continued
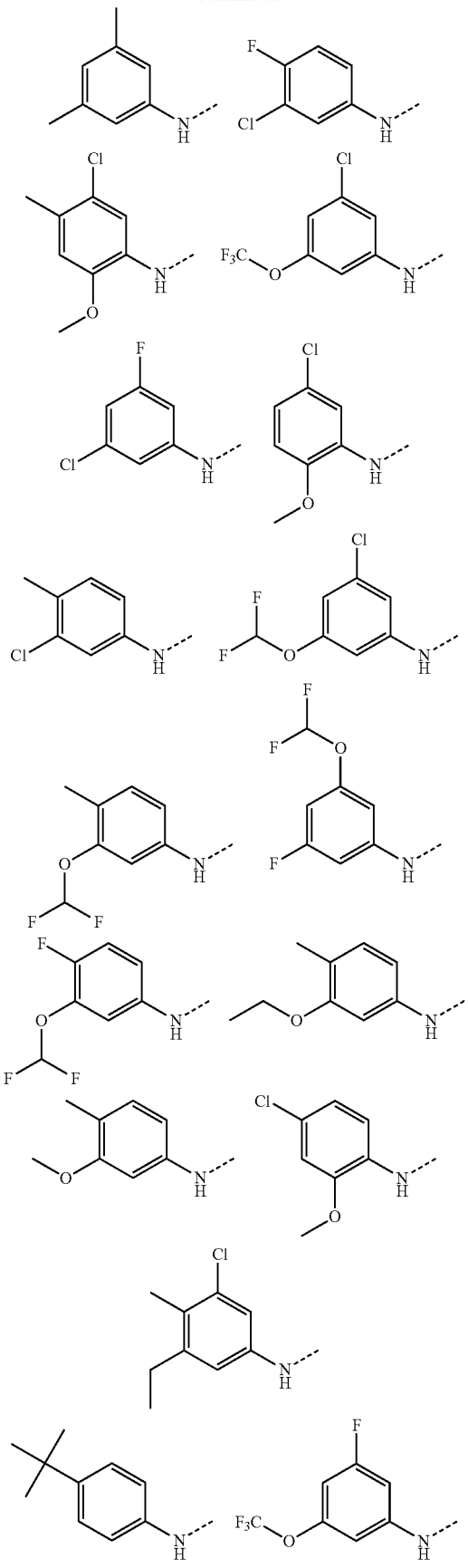

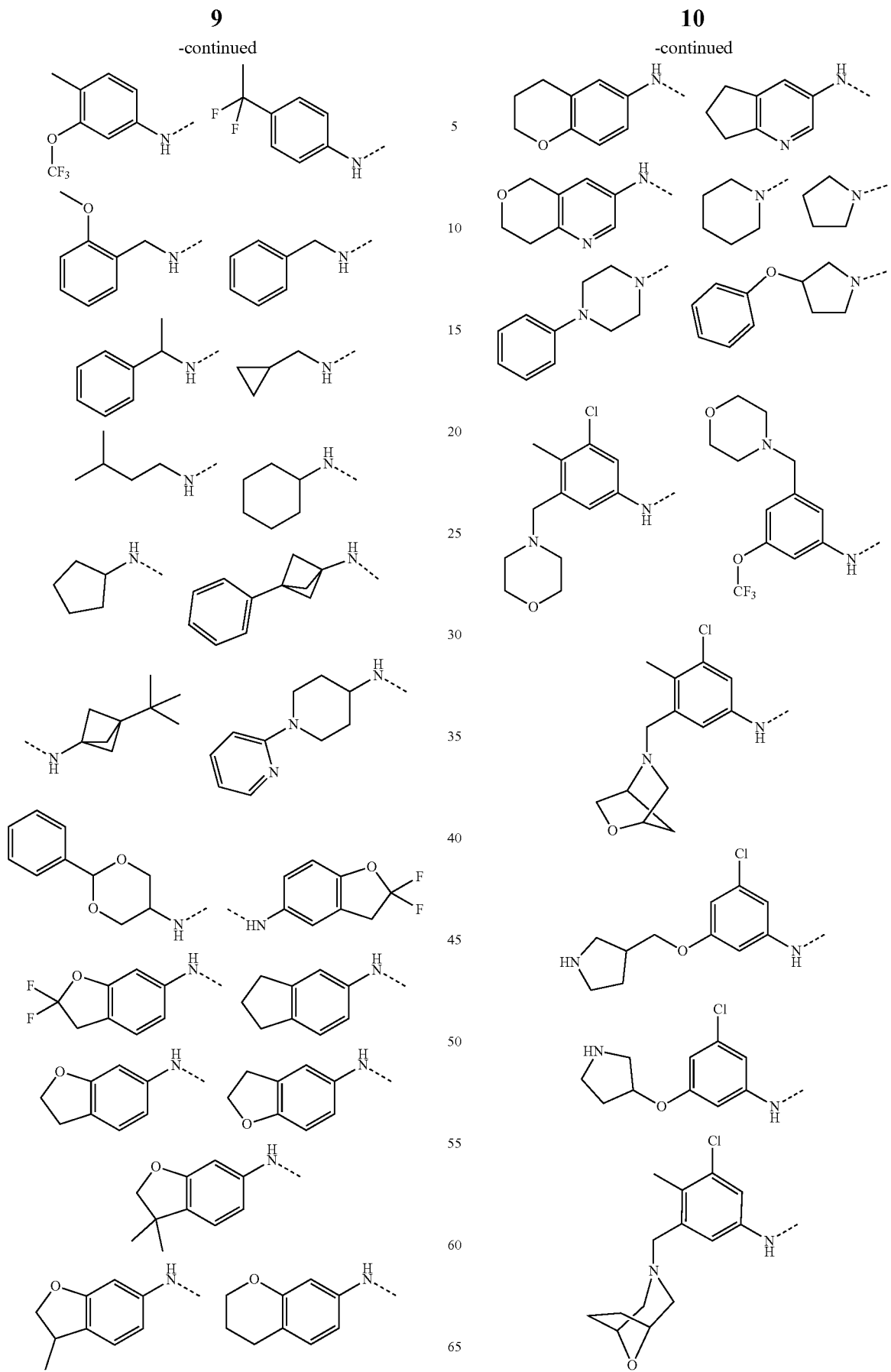

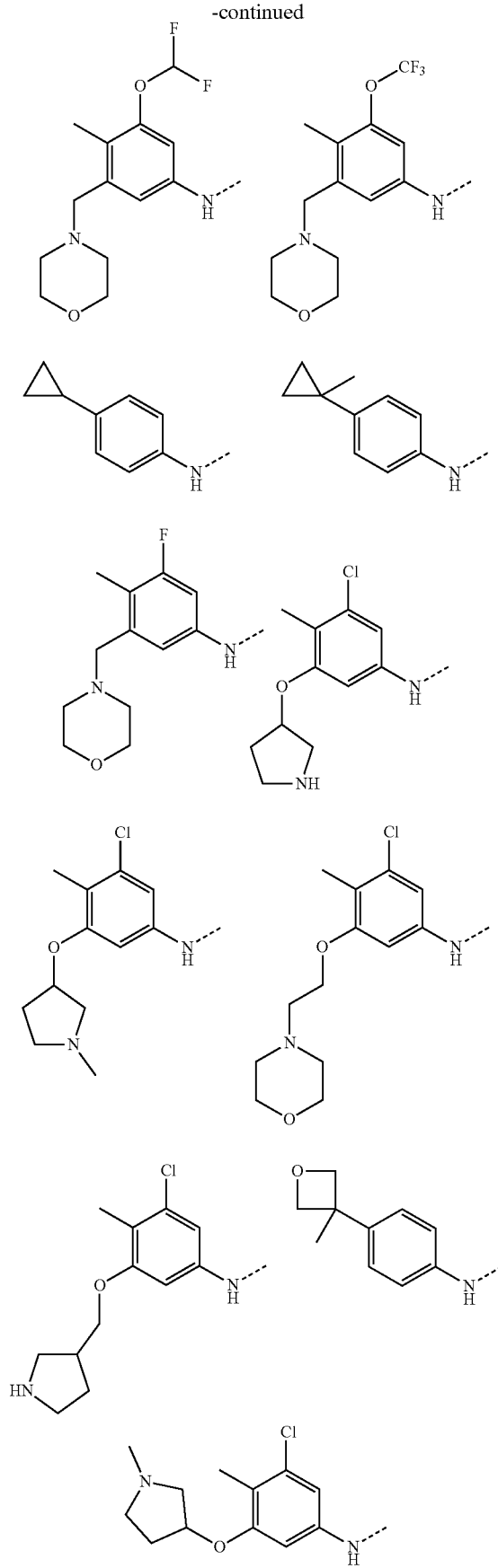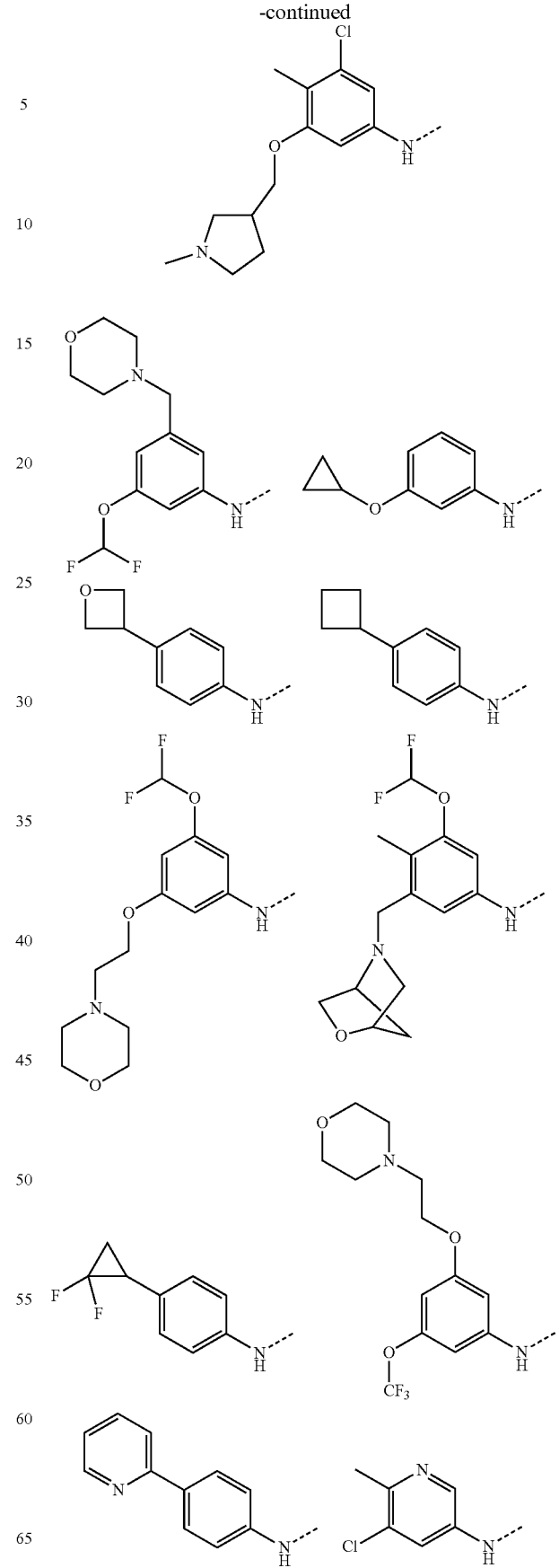

-continued
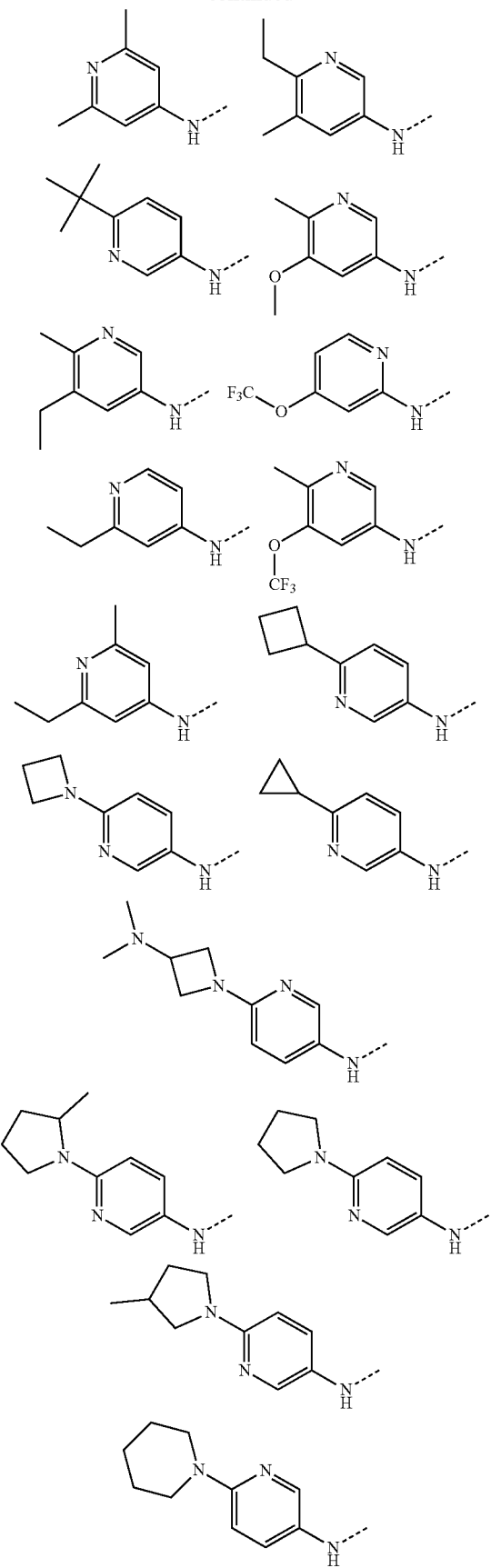
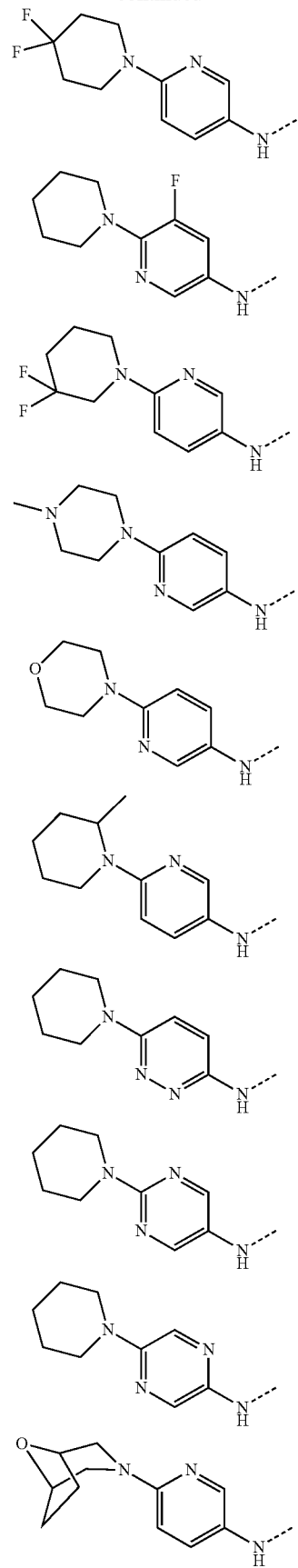

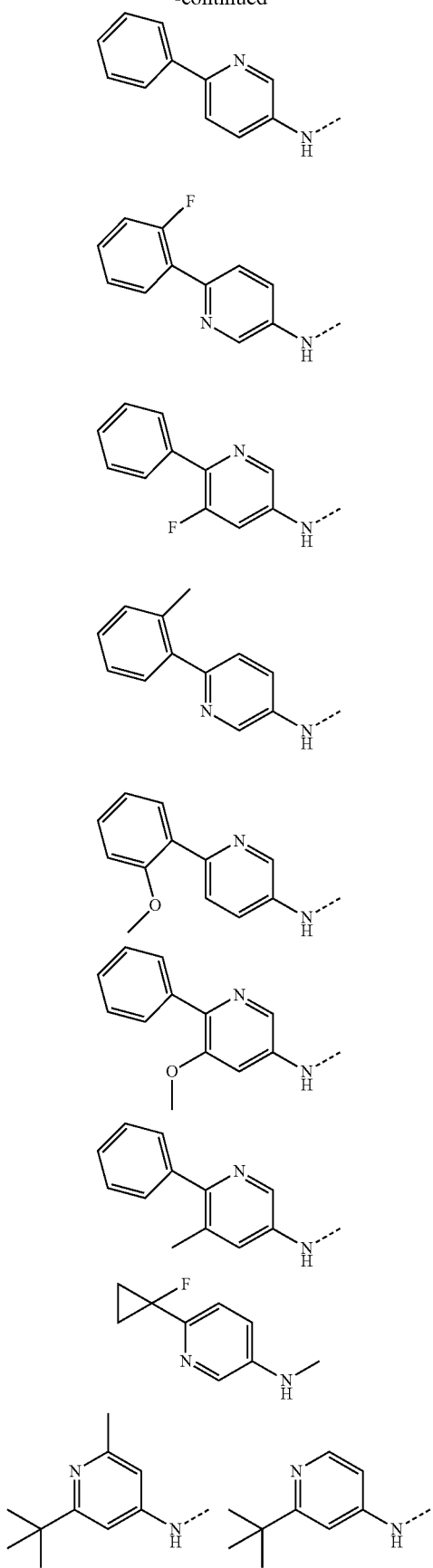
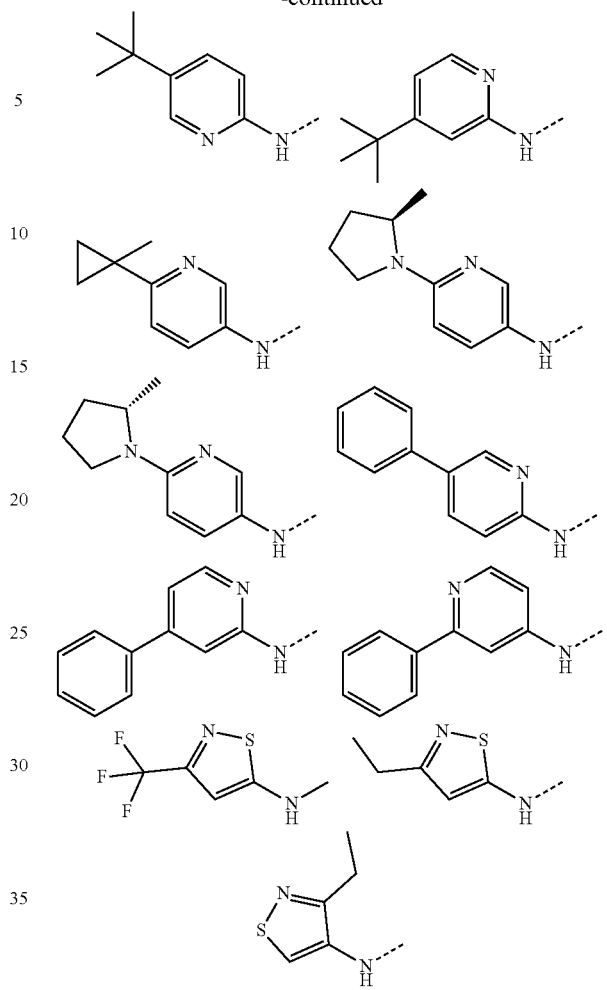

In a second aspect, the disclosure is directed to a composition comprising a compound according to any one of the embodiments or pharmaceutically acceptable salts or stereoisomers thereof described herein.

In some embodiments, the composition further comprises a pharmaceutically acceptable carrier.

In some embodiments, the composition further comprises a second therapeutically active agent.

In a third aspect, the disclosure is directed to a composition according to any of the embodiments described herein, for use in therapy.

In a fourth aspect, some embodiments comprise a compound or pharmaceutically acceptable salts or stereoisomers thereof formula I-VIII, a pharmaceutical acceptable salt thereof or a composition described herein for use in the treatment of diseases associated or caused by GSPT1, in particular the treatment of cancer associated with GSPT1, such as solid cancers including but not limited to cancers of the bladder, bone, brain, breast, cervix, chest, colon, endometrium, esophagus, eye, head, kidney, liver, lymph nodes, lung, upper aerodigestive tract (including nasal cavity and paranasal sinuses, nasopharynx or cavum, oral cavity, oropharynx, larynx, hypopharynx and salivary glands), neck, ovaries, pancreas, prostate, rectum, skin, stomach, testis, throat, uterus, amyloidosis, neuroblastoma, meningioma, hemangiopericytoma, multiple brain metastase, glioma, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, e.g., neuroendocrine prostate cancer such as castration-resistant neuroendocrine prostate cancer (NEPC) and lung neuroendocrine tumors (Lu-NETs), rectal adenocarcinoma, colorectal cancer, including stage 3 and stage 4 colorectal cancer, unresectable colorectal carcinoma, metastatic hepatocellular carcinoma, Kaposi's sarcoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma; and blood bourne (liquid) or hematological cancers, including but not limited to leukemias, lymphomas, and myelomas, such as diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, peripheral T-cell lymphoma (PTCL), cutaneous T-cell lymphoma (CTCL), mantle cell lymphoma (MCL), Hodgkin's lymphoma (HL), non-Hodgkin's lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, ALK-positive large B-cell lymphoma, indolent lymphoma (for example, DLBCL, follicular lymphoma, or marginal zone lymphoma), acute myelogenous leukemia (AML), acute lymphocytic leukemia (ALL), adult T-cell leukemia, chronic lymphocytic leukemia (CLL), small lymphocytic lymphoma (SLL), hairy cell leukemia, myelodysplasia, myeloproliferative disorders, chronic myelogenous leukemia (CMIL), acute monocytic leukemia (AMoL), myelodysplastic syndrome (MDS), human lymphotropic virus-type 1 (HTLV-1) leukemia, mastocytosis, B-cell acute lymphoblastic leukemia, Non-Hodgkin's Lymphoma, Hodgkin's Lymphoma, and multiple myeloma (MM).

Some embodiments comprise the compound or the composition according to any of the embodiments described herein for use in the treatment of breast cancer.

Some embodiments comprise the compound or the composition according to any of the embodiments described herein for use in the treatment of lung cancer, for example, non-small cell lung cancer (e.g., squamous cell lung cancer) and small cell lung cancer.

Some embodiments comprise the use of a compound or a composition according to any of the embodiments described herein for treating neuroendocrine prostate cancer, for example, castration-resistant neuroendocrine prostate cancer (NEPC).

Some embodiments comprise the use of a compound or a composition according to any of the embodiments described herein for treating lung neuroendocrine tumors (Lu-NETs).

Some embodiments comprise the compound or the composition according to any of the embodiments described herein for use in the treatment of acute myelogenous leukemia (AML) and multiple myeloma (MM).

In a fifth aspect, the disclosure is directed to a use of a compound or the composition according to any of the embodiments described herein for binding to cereblon comprising administering to a subject a therapeutically-effective amount of the composition.

Some embodiments comprise the use of a composition according to any of the embodiments described herein for treating cancer associated with GSPT1, such as solid cancers including but not limited to cancers of the bladder, bone, brain, breast, cervix, chest, colon, endrometrium, esophagus, eye, head, kidney, liver, lymph nodes, lung, upper aerodigestive tract (including nasal cavity and paranasal sinuses, nasopharynx or cavum, oral cavity, oropharynx, larynx, hypopharynx and salivary glands), neck, ovaries, pancreas, prostate, rectum, skin, stomach, testis, throat, uterus, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, e.g., neuroendocrine prostate cancer such as castration-resistant neuroendocrine prostate cancer (NEPC) and lung neuroendocrine tumors (Lu-NETs), rectal adenocarcinoma, colorectal cancer, including stage 3 and stage 4 colorectal cancer, unresectable colorectal carcinoma, metastatic hepatocellular carcinoma, Kaposi's sarcoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma, and blood bourne (liquid) or hematological cancers, including but not limited to leukemias, lymphomas, and myelomas, such as diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, peripheral T-cell lymphoma (PTCL), cutaneous T-cell lymphoma (CTCL), mantle cell lymphoma (MCL), Hodgkin's lymphoma (HL), non-Hodgkin's lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, ALK-positive large B-cell lymphoma, indolent lymphoma (for example, DLBCL, follicular lymphoma, or marginal zone lymphoma), acute myelogenous leukemia (AML), acute lymphocytic leukemia (ALL), adult T-cell leukemia, chronic lymphocytic leukemia (CLL), small lymphocytic lymphoma (SLL), hairy cell leukemia, myelodysplasia, myeloproliferative disorders, chronic myelogenous leukemia (CMIL), acute monocytic leukemia (AMoL), myelodysplastic syndrome (MDS), human lymphotropic virus-type 1 (HTLV-1) leukemia, mastocytosis, B-cell acute lymphoblastic leukemia, Non-Hodgkin's Lymphoma, Hodgkin's Lymphoma, and multiple myeloma (MM).

Some embodiments comprise the use of a compound or a composition according to any of the embodiments described herein for treating breast cancer.

Some embodiments comprise the use of a compound or a composition according to any of the embodiments described herein for treating lung cancer, for example, non-small cell lung cancer (e.g., squamous cell lung cancer) and small cell lung cancer.

Some embodiments comprise the use of a compound or a composition according to any of the embodiments described herein for treating neuroendocrine prostate cancer, for example, castration-resistant neuroendocrine prostate cancer (NEPC).

Some embodiments comprise the use of a compound or a composition according to any of the embodiments described herein for treating lung neuroendocrine tumors (Lu-NETs).

Some embodiments comprise the use of a compound or a composition according to any of the embodiments described herein for treating acute myelogenous leukemia (AIL) and multiple myeloma (MM).

In a sixth aspect, the disclosure is directed to a method of treating cancer in a subject, comprising administering to a subject a therapeutically effective amount of the compound or the composition of any of the embodiments as described herein.

In some embodiments, the method comprises a compound according to any of the embodiments as described herein or pharmaceutically acceptable salts or stereoisomers thereof that binds to cereblon.

In a seventh aspect, the disclosure is directed to a method of treating a Myc-driven cancer in a subject in need thereof, comprising administering the subject a therapeutically effective amount of the compound or a composition as described herein. In an eighth aspect, the disclosure is directed to a method of degrading GSPT1 in a subject suffering from cancer, comprising administering the subject a therapeutically effective amount of a compound or a composition as described herein.

In a ninth aspect, the disclosure is directed to a method of reducing the level of GSPT1 in a subject suffering from cancer, comprising administering the subject a therapeutically effective amount of a compound or a composition as described herein.

BRIEF DESCRIPTION OF THE FIGURES

FIG. 1.

FIG. 2.

FIG. 3.

DETAILED DESCRIPTION OF THE DISCLOSURE

Figure 1A:
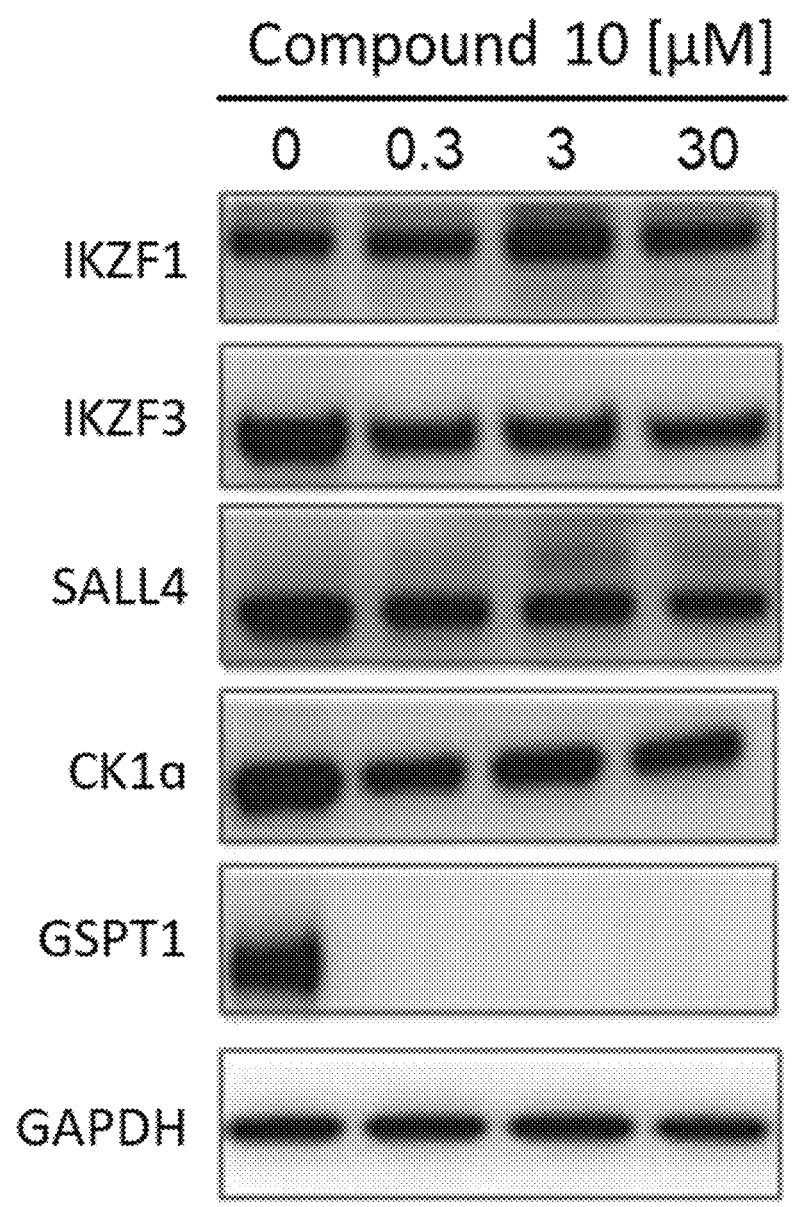
FIG. 1A shows that cells treated with 0.3 □M compound 10 induces complete degradation of GSPT1, while no induction of degradation of IKZF1, IKZF3, SALL4, CK1alpha was observed at concentrations up to 30 □M.

Unless specified otherwise the following general definitions apply to all compounds of the disclosure according to the description.

The term "compound of the disclosure" as used herein, refers to compounds represented by formulae I to VIII (including pharmaceutically acceptable salts and stereoisomers thereof) and any of the specific examples disclosed herein. References to any compound of any formula herein includes also pharmaceutically acceptable salts or stereoisomers thereof.

A "subject" to which administration is contemplated includes, but is not limited to, humans (e.g., a pediatric subject (e.g, infant, child, adolescent) or adult subject (e.g., a young adult, a middle-aged adult, or a senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "patient" and "subject" are used interchangeably herein.

It is understood that "independently of each other" means that when a group is occurring more than one time in any compound, its definition on each occurrence is independent from any other occurrence.

It is further understood that a dashed line (or a wave being transverse to a bond) or a solid line without attachment, such as —$C_{1-4}$ alkyl, depicts the site of attachment of a residue (i.e. a partial formula).

It is further understood that the abbreviations "C" and "N" are representative for all possible degrees of saturation, which typically do not result in radicals, nitrenes or carbenes, i.e. N includes —NH— and —N=, C includes —$CH_2$— and =CH—. In addition, "C" as an atom in an aromatic or heteroaromatic ring which has a substituent $R^x$ at any suitable position, includes =CH— as well as =$CR^x$—.

The term "saturated" in reference to ring systems refers to a ring having no double or triple bonds. The term "partially unsaturated" in reference to ring systems refers to a ring that includes at least one double or triple bond, but does not include aromatic systems.

The term "aromatic" refers to monocyclic or multicyclic (e.g. bicyclic) ring systems, which show some or complete conjugation or delocalization of their electrons. Aromatic monocyclic rings, such as aryl or heteroaryl rings as defined herein, include phenyl, pyridinyl, furyl and the like.

Aromatic multicyclic rings, such as aryl or heteroaryl rings as defined herein, refer to ring systems, wherein at least one ring is an aromatic ring, and thus include (i) aromatic ring systems, wherein an aromatic ring is fused to one or more aromatic rings, such as in e.g. naphthyl, indolyl, benzimidazolyl, and the like (also referred to as fully aromatic ring systems), and (ii) aromatic ring systems, wherein an aromatic ring is fused to one or more non-aromatic rings, such as in e.g. indanyl, indenyl, phthalimidyl, naphthimidyl, phenanthridinyl, tetrahydronaphthyl, 1,4-dihydronapthyl, and the like (also referred to as partially aromatic ring systems).

The term "non-aromatic" refers to (i) fully saturated rings such as monocyclic rings, e.g. cyclohexyl, and bicyclic rings, e.g. tetrahydronaphthyl, and (ii) partially unsaturated rings such as monocyclic rings, e.g. cyclohexenyl, and bicyclic rings, e.g. 1,4-dihydronapthyl.

The term "$C_{6-10}$ aryl" includes both fully aromatic $C_{6-10}$ aryl and partially aromatic $C_{6-10}$ aryl having 6, 7, 8, 9, or 10 ring atoms and includes monocycles and fused bicycles. Examples of fully aromatic $C_{6-10}$ aryl include e.g. phenyl (fully aromatic $C_6$ aryl), naphthyl (fully aromatic $C_{10}$ aryl). Examples of partially aromatic $C_{6-10}$ aryl include e.g. indenyl (partially aromatic $C_9$ aryl), 2,3-dihydroindenyl (partially aromatic $C_9$ aryl), 1, 2, 3, 4-tetrahydronaphthyl (partially aromatic $C_{10}$ aryl). In some embodiments for group $X^1$, $C_{6-10}$ aryl is phenyl, 2,3-dihydroindenyl. In some embodiments for group $X^2$, $C_{6-10}$ aryl is phenyl. The term "—$C_{1-6}$ alkyl-$C_{6-10}$ aryl" refers to -$L^2$-$X^1$- or $L^3$-$X^2$- with $L^2$, $L^3$ being a $C_{1-6}$ alkyl group and $X^1$, $X^2$ being a $C_{6-10}$ aryl, and thus refers to a $C_{6-10}$ aryl, which is linked through a $C_{1-6}$ alkyl group as defined herein to its neighbouring group. The term "—$C_{1-6}$ alkoxy-$C_{6-10}$ aryl" refers to -$L^2$-$X^1$- or $L^3$-$X^2$- with $L^2$, $L^3$ being a $C_{1-6}$ alkoxy group and $X^1$, $X^2$ being a $C_{6-10}$ aryl, and thus refers to a $C_{6-10}$ aryl, which is linked through a $C_{1-6}$ alkoxy group as defined herein to its neighbouring group. The term "—O—$C_{6-10}$ aryl" or "$C_{6-10}$ aryloxy" refers to -$L^2$-$X^1$- or $L^3$-$X^2$- with $L^2$, $L^3$ being —O— and $X^1$, $X^2$ being a $C_{6-10}$ aryl, and thus refers to a $C_{6-10}$ aryl, which is linked through a —O— group to its neighbouring group. The $C_{6-10}$ aryl group may be unsubstituted or substituted with $C_{1-4}$ alkyl, such as methyl, ethyl, t-butyl, fluorinated $C_{1-4}$ alkyl, such as —$CF_3$, —$C(CH_3)F_2$, $C_{1-4}$ alkoxy, such as methoxy, ethoxy, fluorinated $C_{1-4}$ alkoxy, such as —$OCF_3$, —$OCHF_2$, CN, —$N(Me)_2$, halogen, such as F, Cl, or Br, such as F or Cl.

In some embodiments for $X^1$, a $C_{6-10}$ aryl group refers to a fully aromatic ring system, e.g. phenyl, which is unsubstituted or substituted with $C_{1-4}$ alkyl, such as methyl, ethyl, t-butyl, fluorinated $C_{1-4}$ alkyl, such as —$C(CH_3)F_2$, $C_{1-4}$ alkoxy, such as methoxy, ethoxy, fluorinated $C_{1-4}$ alkoxy, such as —$OCF_3$, —$OCHF_2$, CN, halogen, such as F or Cl, In some embodiments for $X^1$, a $C_{6-10}$ aryl group refers to a partially aromatic ring system, e.g. 2,3-dihydroindenyl, which is unsubstituted or substituted with $C_{1-4}$ alkyl, such as methyl, ethyl, t-butyl, or halogen, such as F or Cl, In some embodiments for $X^2$, a $C_{6-10}$ aryl group refers to a fully aromatic ring system, e.g. phenyl, which is unsubstituted or substituted with $C_{1-4}$ alkyl, such as methyl, ethyl, $C_{1-4}$ alkoxy, such as methoxy, ethoxy, halogen, such as F, Cl, or Br, such as F or Cl, e.g. F.

The term "5-10 membered heteroaryl" refers to a fully or partially aromatic ring system in form of monocycles or fused bicycles having 5, 6, 7, 8, 9, 10 ring atoms selected from C, N, O, and S, such as C, N, and O, or C, N, and S, with the number of N atoms being e.g. 0, 1, 2 or 3 and the number of O and S atoms each being 0, 1 or 2. In some embodiments a 5-10 membered heteroaryl refers to a fully aromatic ring system having 5, 6, 7, 8, 9, 10, such as 5 or 6, e.g. 6 ring atoms selected from C and N, with the number of N atoms being 1, 2 or 3, such as 1 or 2. In some embodiments a 5-10 membered heteroaryl refers to a fully aromatic ring system having 5, 6, 7, 8, 9, 10, such as 5 or 6, e.g. 5 ring atoms selected from C, N, O, S with the number of N, S and O atoms each being independently 0, 1 or 2. In some embodiments the total number of N, S and O atoms is 2. In some embodiments a 5-10 membered heteroaryl refers to a fully aromatic ring system having 5 ring atoms selected from C, N, S with the number of N and S atoms each being independently 0 or 1. In some embodiments the total number of N and S atoms is 2. In some embodiments a 5-10 membered heteroaryl refers to a fully aromatic ring system having 6 ring atoms selected from C and N, with the number of N atoms being 1 or 2. In other embodiments a 5-10 membered heteroaryl refers to a partially aromatic ring system having 9 or 10 ring atoms selected from C, N and O, with the number of O atoms being 1, 2 or 3, such as 1 or 2, and the number of N atoms being 1 or 2, such as 1. In some embodiments, examples of "5-10 membered heteroaryl" include furyl, imidazolyl, isoxazolyl, oxazolyl, pyrazinyl, pyrazolyl (pyrazyl), pyridazinyl, pyridinyl, pyrimidinyl, pyrrolyl, thiophenyl, thiazolyl, thienyl, indolyl, quinazolinyl, oxazolinyl, isoxazolinyl, indazolinyl, isothiazolyl, 1,3-benzodioxolyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, benzodihydropyrane, 1,2,3,4-tetrahydronaphthyl, 2,3-dihydroindenyl and the like. In some embodiments, examples of "5-10 membered heteroaryl" include 5-membered heteroaryl, such as isothiazole, 6-membered heteroaryl, such as pyridinyl, pyrimidinyl, pyridazinyl, pyrazinyl, 9-membered heteroaryl, such as 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, and 10-membered heteroaryl, such as benzodihydropyrane (chromane), dihydropyrano-pyridine. The term "—$C_{1-6}$ alkyl 5-10 membered heteroaryl" refers to -$L^2$-$X^1$- or $L^3$-$X^2$- with $L^2$, $L^3$ being a $C_{1-6}$ alkyl group and $X^1$, $X^2$ being a 5-10 membered heteroaryl, and thus refers to a 5-10 membered heteroaryl, which is linked through a $C_{1-6}$ alkyl group as defined herein to its neighbouring group. The term "—$C_{1-6}$ alkoxy 5-10 membered heteroaryl" refers to -$L^2$-$X^1$- or $L^3$-$X^2$- with $L^2$, $L^3$ being a $C_{1-6}$ alkoxy group and $X^1$, $X^2$ being a 5-10 membered heteroaryl, and thus refers to a 5-10 membered heteroaryl, which is linked through a $C_{1-6}$ alkoxy group as defined herein to its neighbouring group. The term "—O-5-10 membered heteroaryl" refers to -$L^2$-$X^1$- or $L^3$-$X^2$- with $L^2$, $L^3$ being —O— and $X^1$, $X^2$ being a 5-10 membered heteroaryl, and thus refers to a 5-10 membered heteroaryl, which is linked through a —O— group to its neighbouring group. The 5-10 membered heteroaryl group may be unsubstituted or substituted with $C_{1-4}$ alkyl, such as methyl, ethyl, t-butyl, fluorinated $C_{1-4}$ alkyl, such as —$CF_3$, —$C(CH_3)F_2$, $C_{1-4}$ alkoxy, such as methoxy, ethoxy, fluorinated $C_{1-4}$ alkoxy, such as —$OCF_3$, —$OCHF_2$, CN, —$N(Me)_2$, halogen, such as F, Cl, or Br, such as F or Cl. In some embodiments, the 5-10 membered heteroaryl group may be unsubstituted or substituted with $C_{1-4}$ alkyl, such as methyl, ethyl, t-butyl, fluorinated $C_{1-4}$ alkyl, such as —$CF_3$, $C_{1-4}$ alkoxy, such as methoxy, ethoxy, halogen, such as F or Cl.

In some embodiments for $X^1$, a 5-10 membered heteroaryl refers to a fully aromatic ring system having 5 ring atoms selected from C, N and S with the number of N and S atoms being independently of each other 0 or 1, e.g. 1 or a fully aromatic ring system having 6 ring atoms selected from C and N, with the number of N atoms being 1 or 2 or a partially aromatic ring system having 9 or 10 ring atoms selected from C, N and O, with the number of 0 atoms being 1 or 2 and the number of N atoms being 1. In some embodiments for $X^1$, a 5-10 membered heteroaryl refers to isothiazole, phenyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine.

In some embodiments for $X^2$ a 5-10 membered heteroaryl refers to a fully aromatic ring system having 6 ring atoms selected from C and N, with the number of N atoms being 1 or 2, such as 1. In some embodiments for $X^2$ a 5-10 membered heteroaryl refers to pyridinyl.

The term "$C_{3-8}$ cycloalkyl" refers to a non-aromatic, i.e. saturated or partially unsaturated alkyl ring system, such as monocycles, fused bicycles, bridged bicycles or spirobicycles, containing 3, 4, 5 6, 7, or 8 carbon atoms. The term "$C_{3-6}$ cycloalkyl" refers to a non-aromatic, i.e. saturated or partially unsaturated alkyl ring system, such as monocycles, fused bicycles, bridged bicycles or spirobicycles, containing 3, 4, 5, or 6 carbon atoms. Examples of "$C_{3-8}$ cycloalkyl" include monocycles, such as cyclopropyl, cyclobutyl, cyclopentyl, cyclohexyl, bridged bicycles, such as bicyclo[1.1.1]pentyl, bicyclo[2.1.1]hexyl, fused bicycles, such as bicyclo[3.1.0]hexyl. The $C_{3-6}$ cycloalkyl group may be unsubstituted or substituted with $C_{1-4}$ alkyl, such as methyl, ethyl, t-butyl, fluorinated $C_{1-4}$ alkyl, such as —$CF_3$, —$C(CH_3)F_2$, $C_{1-4}$ alkoxy, such as methoxy, ethoxy, fluorinated $C_{1-4}$ alkoxy, such as —$OCF_3$, —$OCHF_2$, CN, —$N(Me)_2$, halogen, such as F, Cl, or Br, such as F or Cl.

In some embodiments the $C_{3-6}$ cycloalkyl group may be unsubstituted or substituted by e.g. one or more of $C_{1-4}$ alkyl, such as methyl and halogen, such as F. The term "—$C_{1-4}$ alkyl-$C_{3-6}$ cycloalkyl" refers to -$L^2$-$X^1$- or $L^3$-$X^2$- with $L^2$, $L^3$ being a $C_{1-4}$ alkyl group and $X^1$, $X^2$ being $C_{3-6}$ cycloalkyl as defined herein and refers to a $C_{3-6}$ cycloalkyl, which is linked through a $C_{1-6}$ alkyl group as defined herein to its neighbouring group. The term "—O—$C_{3-6}$ cycloalkyl" refers to -$L^2$- $X^1$- or $L^3$-$X^2$- with $L^2$, $L^3$ being —O— and $X^1$, $X^2$ being $C_{3-6}$ cycloalkyl as defined herein and refers to a $C_{3-6}$ cycloalkyl, which is linked through —O— to its neighbouring group. The term "—$C_{1-4}$ alkoxy-$C_{3-6}$ cycloalkyl" refers to -$L^2$-$X^1$- or $L^3$-$X^2$- with $L^2$, $L^3$ being a $C_{1-4}$ alkoxy group and $X^1$, $X^2$ being $C_3$. 6 cycloalkyl as defined herein and refers to a $C_{3-6}$ cycloalkyl, which is linked through a $C_{1-6}$ alkoxy group as defined herein to its neighbouring group. In some embodiments for $X^1$, a $C_{3-6}$ cycloalkyl refers to cyclopropyl, cyclopentyl, cyclohexyl. In some embodiments for $X^2$, a $C_{3-6}$ cycloalkyl refers to cyclopropyl, cyclobutyl.

The term "4-8 membered heterocycloalkyl" refers to a non-aromatic, i.e. saturated or partially unsaturated ring system having 4, 5, 6, 7 or 8 ring atoms (of which at least one is a heteroatom), which ring atoms are selected from C, N, O, and S, such as C, N, and O, the number of N atoms being 0, 1, or 2 and the number of O and S atoms each being 0, 1, or 2. In some embodiments the term "4-8 membered heterocycloalkyl" comprises saturated or partially unsaturated monocycles, fused bicycles, bridged bicycles or spirobicycles. In some embodiments the term "4-8 membered heterocycloalkyl" comprises fully saturated or partially unsaturated monocycles and bridged bicycles. Examples of 4-8 membered heterocycloalkyl groups include azetidinyl, oxetanyl, pyrrolidinyl, tetrahydrofuranyl, tetrahydrothiopyranyl, dihydropyranyl, tetrahydropyranyl, 1,3-dioxolanyl, 1,4-dioxanyl, 1,4-oxathianyl 1,4-dithianyl, 1,3-dioxanyl, 1,3-dithianyl, piperazinyl, thiomorpholinyl, piperidinyl, morpholinyl, azabicyclo[2.2.1]heptan-5-yl, 8-oxa-3-azabicyclo[3.2.1]octan-3-yl and the like. The 4-8 membered heterocycloalkyl group may be unsubstituted or substituted with $C_{1-4}$ alkyl, such as methyl, ethyl, $C_{1-4}$ alkoxy, such as methoxy, ethoxy, halogen, such as F, Cl or Br, e.g. F or Cl.

In some embodiments, the 4-8 membered heterocycloalkyl representing group $X^1$ is a non-aromatic ring system having 5 or 6 ring atoms of which at least one is a heteroatom selected from N and O, the number of N atoms being 1 or 2 and the number of O being 0, 1, or 2, such as a non-aromatic 6 membered ring system having 1 or 2 N-atoms, such as piperidine. In some embodiments, the 4-8 membered heterocycloalkyl formed by groups $X^1$ together with the N atom of the carbamate forms is a non-aromatic ring system having 5 or 6 ring atoms of which at least one is a heteroatom selected from N and O, the number of N atoms being 1 or 2 and the number of O being 0, 1, or 2, e.g. a non-aromatic ring system having 5 or 6 ring atoms comprising one or two N-atoms. Examples include pyrrolidinyl, piperdinyl, morpholinyl, piperazinyl, N-methyl piperazinyl. In some embodiments, the 4-8 membered heterocycloalkyl representing $X^2$ is a non-aromatic ring system having 4, 5, 6, 7 or 8 ring atoms of which at least one is a heteroatom selected from N and O, the number of N atoms being 1 or 2 and the number of O being 0, 1, or 2. In some embodiments, 4-8 membered heterocycloalkyl include 4-membered heterocycloalkyl having at least one heteroatom selected from N and O, the number of N atoms being 1 or 2 and the number of O being 0 or 1, such as azetidinyl, oxetanyl, unsubstituted or substituted by e.g. $C_{1-4}$alkyl, such as methyl; 5-membered heterocycloalkyl having 1 or 2 N-atoms, such as pyrrolidinyl, unsubstituted or substituted by e.g. one or more of $C_{1-4}$alkyl, such as methyl; 6-membered heterocycloalkyl having N and O-atoms, such as morpholinyl, piperazinyl, piperidinyl, dioxanyl, unsubstituted or substituted by e.g. one or more of $C_{1-4}$alkyl, such as methyl, halogen, e.g. F; 7-membered heterocycloalkyl having N and O-atoms, such as 1 N- and 1 O-atom, such as 2-oxa-5-azabicyclo[2.2.1]heptan-5-yl, 1,4-diazabicyclo [3.2.1]octan-4-yl, 3-methyl-3-azabicyclo[3.1.0]hexan-1-yl; 8-membered heterocycloalkyl having N and O-atoms, such as 1 N- and 1 O-atom, such as 8-oxa-3-azabicyclo[3.2.1] octan-3-yl.

The term "$C_{1-4}$ alkyl 4-8 membered heterocycloalkyl" refers to -L²-X¹- or L³-X²- with L², L³ being $C_{1-4}$ alkyl and X¹, X² being 4-8 membered heterocycloalkyl as defined herein. Thus, the 4-8 membered hetereocycloalkyl is linked through a $C_{1-4}$ alkyl group as defined to the neighbouring group. In some embodiments, the alkyl may be $C_1$, resulting in —(CH₂)-(4-8 membered heterocycloalkyl) or $C_2$, resulting in —(CH₂)₂-(4-8 membered heterocycloalkyl) or $C_3$, resulting in —(CH₂)₃-(4-8 membered heterocycloalkyl) or $C_4$, resulting in —(CH₂)₄-(4-8 membered heterocycloalkyl). Examples include —(CH₂)-morpholinyl, —(CH₂)₂-morpholinyl, —(CH₂)₃-morpholinyl, —(CH₂)₄-morpholinyl, —(CH₂)-piperazinyl, —(CH₂)₂—N-methyl-piperazinyl, —(CH₂)₃-piperazinyl or —(CH₂)₄-piperazinyl.

The term "—$C_{1-4}$ alkoxy 4-8 membered heterocycloalkyl" refers to -L²-X¹- or L³-X²- with L², L³ being $C_{1-4}$ alkoxy and X¹, X² being 4-8 membered heterocycloalkyl as defined herein. Thus, the 4-8 membered hetereocycloalkyl is linked via a $C_{1-4}$ alkoxy group as defined herein to its neighbouring group. In some embodiments, the $C_{1-4}$ alkoxy may be $C_1$, resulting in —(O—CH₂)-(4-8 membered heterocycloalkyl) or $C_2$, resulting in —(O—CH₂)₂-(4-8 membered heterocycloalkyl) or $C_3$, resulting in —(O—CH₂)₃-(4-8 membered heterocycloalkyl). Examples include —(O—CH₂)—(N-morpholinyl), —(O—CH₂)₂—(N-morpholinyl).

The term "—O-(4-8 membered heterocycloalkyl)" refers to -L²-X¹- or L³-X²- with L², L³ being —O— and X¹, X² being 4-8 membered heterocycloalkyl as defined herein. Thus, the 4-8 membered hetereocycloalkyl is linked through an —O-atom to the neighbouring group. Examples include —O— morpholinyl, —O-piperazinyl, —O-pyrrolidinyl and the like.

The term "halogen" or "hal" as used herein may be fluoro, chloro, bromo or iodo such as fluoro, chloro or bromo, e.g. fluoro or chloro.

The term "$C_{1-4}$ alkyl" and "$C_{1-6}$alkyl" refer to a fully saturated branched or unbranched hydrocarbon moiety having 1, 2, 3 or 4 and 1, 2, 3, 4, 5 or 6 carbon atoms, respectively. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, iso-hexyl or neohexyl.

The term "$C_{1-6}$ heteroalkyl" refers to an alkyl as defined with 1, 2, 3, 4, 5 or 6 carbon atoms in which at least one carbon atom is replaced with a heteroatom, such as N, O, or S, e.g. N, O. It is understood that the heteroatom may further be substituted with one or two $C_{1-6}$ alkyl. Examples include —(CH₂)₂—O-Me, —(CH₂)₃—O-Me, —(CH₂)₂O—CH₂Me, —(CH₂)₂—NMe₂, —(CH₂)—NMe₂, —(CH₂)₂—NEt₂, —(CH₂)—NEt₂ and the like.

The term "$C_{1-4}$alkylamino" refers to a fully saturated branched or unbranched $C_{1-4}$ alkyl, which is substituted with at least one, such as only one, amino group, alkylamino group or dialkylaminogroup, such as NH₂, HN($C_{1-4}$alkyl) or N($C_{1-4}$alkyl)₂. Thus, a $C_{1-4}$alkylamino refers to $C_{1-4}$alkylamino, $C_{1-4}$alkyl-($C_{1-4}$alkyl)amino, $C_{1-4}$alkyl-($C_{1-4}$dialkyl) amino. Examples include but are not limited to methylaminomethyl, dimethylamonimethyl, aminomethyl, dimethylaminoethyl, aminoethyl, methylaminoethyl, n-propylamino, iso-propylamino, n-butylamino, sec-butylamino, iso-butylamino, tert-butylamino.

The term "$C_{1-4}$ alkoxy" refers to an unsubstituted or substituted alkyl chain linked to the remainder of the molecule through an oxygen atom, and in particular to methoxy, ethoxy, n-propoxy, isopropoxy, n-butoxy, iso-butoxy, and t-butoxy.

Based on the definitions given throughout the application the skilled person knows which combinations are synthetically feasible and realistic, e.g. typically combinations of groups leading to some heteroatoms directly linked to each other, e.g. —O—O—, are not contemplated, however synthetically feasible combinations, such as —S—N= in aisothiazole are contemplated.

In a first aspect the disclosure provides a compound or pharmaceutically acceptable salts or stereoisomers thereof formula I.

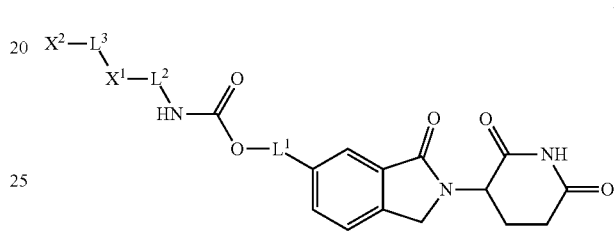

I wherein

X¹ is linear or branched $C_{1-6}$ alkyl, $C_{3-8}$ cycloalkyl, $C_{6-10}$ aryl, 5-10 membered heteroaryl, 4-8 membered heterocycloalkyl, wherein X¹ is unsubstituted or substituted with one or more of halogen, linear or branched $C_{1-6}$ alkyl, linear or branched $C_{1-6}$ heteroalkyl, CF₃, CHF₂, CMeF₂, —O—CHF₂, —O—(CH₂)₂—OMe, OCF₃, $C_{1-6}$ alkylamino, —CN, —N(H)C(O)—$C_{1-6}$alkyl, —OC(O)—$C_{1-6}$alkyl, —OC(O)—$C_{1-4}$alkylamino, —C(O)O—$C_{1-6}$alkyl, —COOH, —$C_{1-6}$alkylC(O)OH, —$C_{1-6}$alkylC(O)O—$C_{1-6}$ alkyl, NH₂, $C_{1-4}$ alkoxy, $C_{1-4}$ alkylhydroxy, —CH₂F, —N(H)C(O)—O—$C_{1-6}$ alkyl, and C(OH)(CF₃);

or X¹ together with the N atom of the carbamate forms a 4-8 membered heterocycloalkyl, which is unsubstituted or substituted with one or more of halogen, linear or branched —$C_{1-6}$ alkyl, CF₃, CHF₂, CMeF₂, —O—(CH₂)₂—OMe, OCF₃, OCHF₂, $C_{1-6}$ alkylamino, —CN, —N(H)C(O)—$C_{1-6}$alkyl, —OC(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$alkyl, NH₂, $C_{1-4}$ alkylhydroxy, and $C_{1-4}$ alkoxy;

X² is H, $C_{3-6}$ cycloalkyl, $C_{6-10}$ aryl, 5-10 membered heteroaryl, 4-8 membered heterocycloalkyl, wherein X² is unsubstituted or substituted with one or more of linear or branched $C_{1-6}$ alkyl, —$C_{1-4}$ alkoxy, NH₂, NMe₂, halogen, CF₃, CHF₂, CMeF₂, —O—(CH₂)₂—OMe, OCF₃, OCHF₂, and $C_{1-4}$ alkylhydroxy;

L¹ is a covalent bond, linear or branched $C_{1-6}$ alkyl;

L² is a covalent bond, linear or branched $C_{1-6}$ alkyl; and

L³ is a covalent bond, linear or branched $C_{1-6}$ alkyl, —O—, or —$C_{1-4}$ alkoxy, wherein linear or branched $C_{1-6}$ alkyl is unsubstituted or substituted with one or more of halogen.

In some embodiments, X¹ is linear or branched $C_{1-6}$ alkyl, $C_{3-6}$ cycloalkyl, $C_{6-10}$ aryl, 5-10 membered heteroaryl, 4-8 membered heterocycloalkyl, wherein X¹ is unsubstituted or substituted with one or more of halogen, linear or branched $C_{1-6}$ alkyl, linear or branched $C_{1-6}$ heteroalkyl, CF₃, CHF₂, CMeF$_2$, —O—CHF$_2$, —O—(CH$_2$)$_2$—OMe, OCF$_3$, C$_{1-6}$ alkylamino, —CN, —N(H)C(O)—C$_{1-6}$ alkyl, —OC(O)—C$_{1-6}$alkyl, —OC(O)—C$_{1-4}$alkylamino, —C(O)O—C$_{1-6}$alkyl, —COOH, —C$_{1-6}$alkylC(O)OH, —C$_{1-6}$alkylC(O)O—C$_{1-6}$alkyl, NH$_2$, C$_{1-4}$ alkoxy and C$_{1-4}$ alkylhydroxy;

or X$^1$ together with the N atom of the carbamate forms a 4-8 membered heterocycloalkyl, which is unsubstituted or substituted with one or more of halogen, linear or branched —C$_{1-6}$ alkyl, CF$_3$, CHF$_2$, CMeF$_2$, —O—(CH$_2$)$_2$—OMe, OCF$_3$, OCHF$_2$, C$_{1-6}$ alkylamino, —CN, —N(H)C(O)—C$_{1-6}$alkyl, —OC(O)—C$_{1-6}$alkyl, —C(O)O—C$_{1-6}$alkyl, —COOH, —C$_{1-6}$alkylC(O)OH, —C$_{1-6}$alkylC(O)O—C$_{1-6}$alkyl, NH$_2$, C$_{1-4}$ alkylhydroxy, and C$_{1-4}$ alkoxy;

X$^2$ is H, C$_{3-6}$ cycloalkyl, C$_{6-10}$ aryl, 5-10 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and C$_{1-4}$ alkylhydroxy;

L$^1$ is a covalent bond, linear or branched C$_{1-6}$ alkyl;

L$^2$ is a covalent bond, linear or branched C$_{1-6}$ alkyl;

L$^3$ is a covalent bond, linear or branched C$_{1-6}$ alkyl, —O—, —C$_{1-4}$ alkoxy.

In some embodiments of a compound of formula I, L$^1$ is a linear or branched C$_{1-6}$ alkyl. In some embodiments of a compound of formula I, L$^1$ is linear or branched C$_{1-4}$ alkyl, such as —CH$_2$— or —CH(CH$_3$)—.

In some embodiments of a compound of formula I, L$^2$ is a covalent bond. In some embodiments of a compound of formula I, L$^2$ is linear or branched C$_{1-6}$ alkyl, such as linear or branched C$_{1-4}$ alkyl, e.g. —CH$_2$— or —CH(CH$_3$)—.

In some embodiments of a compound of formula I, L$^3$ is a covalent bond. In some embodiments L$^3$ is linear or branched C$_{1-4}$ alkyl. In some embodiments of a compound of formula I, L$^3$ is —O—.

In some embodiments of a compound of formula I, L$^3$ is linear or branched C$_{1-4}$ alkoxy, such as —O—CH$_2$—, —O—CH$_2$—CH$_2$—.

In some embodiments of a compound of formula I, L$^1$ is —CH$_2$— and L$^2$ is a covalent bond. In some embodiments of a compound of formula I, L$^1$ is —CH$_2$— and L$^2$ is —CH$_2$—. In some embodiments of a compound of formula I, L$^1$ is —CH$_2$— and L$^2$ is —CH(CH$_2$)—.

In some embodiments of a compound of formula I, L$^1$ is —CH$_2$—, L$^2$ is a covalent bond and L$^3$ is a covalent bond. In some embodiments of a compound of formula I, L$^1$ is —CH$_2$—, L$^2$ is a covalent bond and L$^3$ is —CH$_2$—. In some embodiments of a compound of formula I, L$^1$ is —CH$_2$—, L$^2$ is a covalent bond and L$^3$ is —O—. In some embodiments of a compound of formula I, L$^1$ is —CH$_2$—, L$^2$ is a covalent bond and L$^3$ is —O—CH$_2$—. In some embodiments of a compound of formula I, L$^1$ is —CH$_2$—, L$^2$ is a covalent bond and L$^3$ is —O—CH$_2$—CH$_2$—.

In some embodiments of a compound of formula I, X$^1$ is linear or branched —C$_{1-6}$ alkyl, —C$_{3-6}$ cycloalkyl, —C$_{6-10}$ aryl, 5-10 membered heteroaryl, 5-6 membered heterocycloalkyl, wherein X$^1$ is unsubstituted or substituted with one or more of halogen, linear or branched —C$_{1-4}$ alkyl, CF$_3$, CHF$_2$, CMeF$_2$, —O—(CH$_2$)$_2$—OMe, OCF$_3$, OCHF$_2$, C$_{1-6}$ alkylamino, —CN, NH$_2$, C$_{1-4}$ alkylhydroxy, and C$_{1-4}$ alkoxy; or X$^1$ together with the N atom of the carbamate forms a 5-6 membered heterocycloalkyl, which is unsubstituted or substituted with one or more of halogen, linear or branched —C$_{1-4}$ alkyl, CF$_3$, CHF$_2$, CMeF$_2$, —O—(CH$_2$)$_2$—OMe, OCF$_3$, OCHF$_2$, C$_{1-6}$ alkylamino, —CN, NH$_2$, C$_{1-4}$ alkylhydroxy, and C$_{1-4}$ alkoxy.

In some embodiments of a compound of formula I, X$^1$ is linear or branched —C$_{1-6}$ alkyl, —C$_{3-6}$ cycloalkyl, —C$_{6-10}$ aryl, 5-10 membered heteroaryl, 6 membered heterocycloalkyl, wherein X$^1$ is unsubstituted or substituted with one or more of halogen, linear or branched —C$_{1-4}$ alkyl, CF$_3$, CHF$_2$, CMeF$_2$, OCHF$_2$, CN and C$_{1-4}$ alkoxy; or X$^1$ together with the N atom of the carbamate forms a 6 membered heterocycloalkyl, which is unsubstituted or substituted with one or more of halogen, linear or branched —C$_{1-4}$ alkyl, CF$_3$, CHF$_2$, CMeF$_2$, OCF$_3$, OCHF$_2$, and C$_{1-4}$ alkoxy.

In some embodiments of a compound of formula I, X$^1$ is linear or branched —C$_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein X$^1$ is unsubstituted or substituted with one or more of halogen, such as Cl, F, linear or branched —C$_{1-4}$ alkyl, CF$_3$, CHF$_2$, CMeF$_2$, —O—(CH$_2$)$_2$—OMe, OCF$_3$, OCHF$_2$, C$_{1-6}$ alkylamino, —CN, NH$_2$, C$_{1-4}$ alkylhydroxy, and C$_{1-4}$ alkoxy; or X$^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —C$_{1-4}$ alkyl, CF$_3$, CHF$_2$, CMeF$_2$, —O—(CH$_2$)$_2$—OMe, OCF$_3$, OCHF$_2$, C$_{1-6}$ alkylamino, —CN, NH$_2$, C$_{1-4}$ alkylhydroxy, or C$_{1-4}$ alkoxy.

In some embodiments of a compound of formula I, X$^1$ is linear or branched —C$_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein X$^1$ is unsubstituted or substituted with one or more of halogen, such as Cl, F, linear or branched —C$_{1-4}$ alkyl, CF$_3$, CHF$_2$, CMeF$_2$, —OCF$_3$, OCHF$_2$, CN, and C$_{1-4}$ alkoxy; or X$^1$ together with the N atom of the carbamate forms a pyrrolidinyl, piperdinyl, piperazinyl, which is unsubstituted or substituted with one or more of halogen, linear or branched —C$_{1-4}$ alkyl, CF$_3$, CHF$_2$, CMeF$_2$, OCF$_3$, OCHF$_2$, CN, and C$_{1-4}$ alkoxy.

In some embodiments of a compound of formula I, X$^2$ is H, C$_{3-6}$ cycloalkyl, C$_6$ aryl, 5-6 membered heteroaryl, 4-8 membered heterocycloalkyl, wherein X$^2$ is unsubstituted or substituted with one or more of linear or branched C$_{1-4}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy.

In some embodiments of a compound of formula I, X$^2$ is H, C$_{3-6}$ cycloalkyl, C$_6$ aryl, 6 membered heteroaryl, 4-8 membered heterocycloalkyl, wherein X$^2$ is unsubstituted or substituted with one or more of linear or branched C$_{1-4}$ alkyl, —C$_{1-4}$ alkoxy, NH$_2$, NMe$_2$, and halogen, e.g. F.

In some embodiments of a compound of formula I, X$^2$ is H, cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein X$^2$ is unsubstituted or substituted with one or more of linear or branched $C_{1-4}$ alkyl, $—C_{1-4}$ alkoxy, $NMe_2$ and halogen, e.g. F.

In some embodiments of a compound of formula I, $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula I $L^1$ is a linear or branched $C_{1-4}$ alkyl and $X^1$ is linear or branched $—C_{1-6}$ alkyl, $—C_{3-6}$ cycloalkyl, $—C_{6-10}$ aryl, 5-10 membered heteroaryl, 5-6 membered heterocycloalkyl, wherein $X^1$ is unsubstituted or substituted with one or more of halogen, linear or branched $—C_{1-4}$ alkyl, $CF_3$, $CHF_2$, $CMeF_2$, $—O—(CH_2)_2—OMe$, $OCF_3$, $OCHF_2$, $C_{1-6}$ alkylamino, $—CN$, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched $—C_{1-4}$ alkyl, $CF_3$, $CHF_2$, $CMeF_2$, $—O—(CH_2)_2—OMe$, $OCF_3$, $OCHF_2$, $C_{1-6}$ alkylamino, $—CN$, $NH_2$, $C_{1-4}$ alkylhydroxy, and $C_{1-4}$ alkoxy.

In some embodiments of a compound of formula I $L^1$ is a linear or branched $C_{1-4}$ alkyl and $X^1$ is linear or branched $—C_{1-6}$ alkyl, $—C_{3-6}$ cycloalkyl, $—C_{6-10}$ aryl, 5-10 membered heteroaryl, 6 membered heterocycloalkyl, wherein $X^1$ is unsubstituted or substituted with one or more of halogen, linear or branched $—C_{1-4}$ alkyl, $CF_3$, $CHF_2$, $CMeF_2$, $OCF_3$, $OCHF_2$, $CN$ and $C_{1-4}$ alkoxy; or $X^1$ together with the N atom of the carbamate forms a 6 membered heterocycloalkyl, which is unsubstituted or substituted with one or more of halogen, linear or branched $—C_{1-4}$ alkyl, $CF_3$, $CHF_2$, $CMeF_2$, $OCF_3$, $OCHF_2$, $CN$ and $C_{1-4}$ alkoxy.

In some embodiments of a compound of formula I $L^1$ is a linear or branched $C_{1-4}$ alkyl and $X^1$ is linear or branched $—C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched $—C_{1-4}$ alkyl, $CF_3$, $CHF_2$, $CMeF_2$, $—O—(CH_2)_2—OMe$, $OCF_3$, $OCHF_2$, $C_{1-6}$ alkylamino, $—CN$, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched $—C_{1-4}$ alkyl, $CF_3$, $CHF_2$, $CMeF_2$, $—O—(CH_2)_2$ $—OMe$, $OCF_3$, $OCHF_2$, $C_{1-6}$ alkylamino, $—CN$, $NH_2$, alkylhydroxy, or $C_{1-4}$ alkoxy.

In some embodiments of a compound of formula I $L^1$ is a linear or branched $C_{1-4}$ alkyl and $X^1$ is linear or branched $—C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched $—C_{1-4}$ alkyl, $CF_3$, $CHF_2$, $CMeF_2$, $—OCF_3$, $OCHF_2$, $CN$, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched $—C_{1-4}$ alkyl, $CF_3$, $CHF_2$, $CMeF_2$, $OCF_3$, $OCHF_2$, $CN$, and $C_{1-4}$ alkoxy.

In some embodiments of a compound of formula I $L^1$ is $—CH_2—$ and $X^1$ is linear or branched $—C_{1-6}$ alkyl, $—C_{3-6}$ cycloalkyl, $—C_{6-10}$ aryl, 5-10 membered heteroaryl, 5-6 membered heterocycloalkyl, wherein $X^1$ is unsubstituted or substituted with one or more of halogen, linear or branched $—C_{1-4}$ alkyl, $CF_3$, $CHF_2$, $CMeF_2$, $—O—(CH_2)_2—OMe$, $OCF_3$, $OCHF_2$, $C_{1-6}$ alkylamino, $—CN$, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched $—C_{1-4}$ alkyl, $CF_3$, $CHF_2$, $CMeF_2$, $—O—(CH_2)_2—OMe$, $OCF_3$, $OCHF_2$, $C_{1-6}$ alkylamino, $—CN$, $NH_2$, $C_{1-4}$ alkylhydroxy, and $C_{1-4}$ alkoxy.

In some embodiments of a compound of formula I $L^1$ is $—CH_2—$ and $X^1$ is linear or branched $—C_{1-6}$ alkyl, $—C_{3-6}$ cycloalkyl, $—C_{6-10}$ aryl, 5-10 membered heteroaryl, 6 membered heterocycloalkyl, wherein $X^1$ is unsubstituted or substituted with one or more of halogen, linear or branched $—C_{1-4}$ alkyl, $CF_3$, $CHF_2$, $CMeF_2$, $OCF_3$, $OCHF_2$, $CN$ and $C_{1-4}$ alkoxy; or $X^1$ together with the N atom of the carbamate forms a 6 membered heterocycloalkyl, which is unsubstituted or substituted with one or more of halogen, linear or branched $—C_{1-4}$ alkyl, $CF_3$, $CHF_2$, $CMeF_2$, $OCF_3$, $OCHF_2$, $CN$ and $C_{1-4}$ alkoxy.

In some embodiments of a compound of formula I $L^1$ is $—CH_2—$ and $X^1$ is linear or branched $—C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched $—C_{1-4}$ alkyl, $CF_3$, $CHF_2$, $CMeF_2$, $—O—(CH_2)_2—OMe$, $OCF_3$, $OCHF_2$, $C_{1-6}$ alkylamino, $—CN$, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched $—C_{1-4}$ alkyl, $CF_3$, $CHF_2$, $CMeF_2$, $—O—(CH_2)_2—OMe$, $OCF_3$, $OCHF_2$, $C_{1-6}$ alkylamino, $—CN$, $NH_2$, $C_{1-4}$ alkylhydroxy, or $C_{1-4}$ alkoxy.

In some embodiments of a compound of formula I $L^1$ is $—CH_2—$ and $X^1$ is linear or branched $—C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched $—C_{1-4}$ alkyl, $CF_3$, $CHF_2$, $CMeF_2$, $—OCF_3$, $OCHF_2$, $CN$, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula I $L^1$ is —$CH(CH_3)$— and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula I $L^1$ is —$CH(CH_3)$— and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula I $L^1$ is —$CH(CH_3)$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula I $L^1$ is —$CH(CH_3)$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula I $L^1$ is —$CH(CH_3)$— and $X^1$ is phenyl, which is unsubstituted or substituted with one or more of halogen, such as Cl, F, linear or branched —$C_{1-4}$ alkyl, such as methyl, fluorinated $C_{1-4}$ alkoxy, such as —$OCF_3$.

In some embodiments of a compound of formula I $L^2$ is a covalent bond and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula I $L^2$ is a covalent bond and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula I $L^2$ is a covalent bond and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula I $L^2$ is a covalent bond and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula I $L^2$ is linear or branched $C_{1-4}$ alkyl and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula I $L^2$ is linear or branched $C_{1-4}$ alkyl and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula I $L^2$ is linear or branched $C_{1-4}$ alkyl and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula I $L^2$ is linear or branched $C_{1-4}$ alkyl and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula I $L^2$ is —$CH_2$— and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula I $L^2$ is —$CH_2$— and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula I $L^2$ is —$CH_2$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula I $L^2$ is —$CH_2$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula I, $L^2$ is —$CH_2$— and $X^1$ is phenyl, which is unsubstituted or substituted with one or more of halogen, linear or branched —$C_{1-4}$ alkyl, and $C_{1-4}$ alkoxy, preferably unsubstituted or substituted —OMe.

In some embodiments of a compound of formula I $L^2$ is —CH($CH_3$)— and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula I $L^2$ is —CH($CH_3$)— and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula I $L^2$ is —CH($CH_3$)— and $X^1$ is linear or branched —$C_{1-6}$ alkyl, cyclopropyl, cyclobutyl, cyclopentyl, cyclohexyl, piperidinyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydro benzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula I $L^2$ is —CH($CH_3$)— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula II n is 1, $R^a$ is H, $L^2$ is —CH($CH_3$)— and $X^1$ is phenyl.

In some embodiments of a compound of formula I $L^1$ is —$CH_2$—, $L^2$ is a covalent bond and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula I $L^1$ is —$CH_2$—, $L^2$ is a covalent bond and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula I $L^1$ is —$CH_2$—, $L^2$ is a covalent bond and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula I $L^1$ is —$CH_2$—, $L^2$ is a covalent bond and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula I $L^1$ is —$CH_2$—, $L^2$ is a linear or branched $C_{1-4}$ alkyl and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula I $L^1$ is —$CH_2$—, $L^2$ is a linear or branched $C_{1-4}$ alkyl and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula I $L^1$ is —$CH_2$—, $L^2$ is a linear or branched $C_{1-4}$ alkyl and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula I $L^1$ is —$CH_2$—, $L^2$ is a linear or branched $C_{1-4}$ alkyl and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula I $L^1$ is —$CH_2$—, $L^2$ is —$CH_2$— and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula I $L^1$ is —$CH_2$—, $L^2$ is —$CH_2$— and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula I $L^1$ is —$CH_2$—, $L^2$ is —$CH_2$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula I $L^1$ is —$CH_2$—, $L^2$ is —$CH_2$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula I $L^1$ is —$CH_2$—, $L^2$ is —$CH_2$— and $X^1$ is phenyl, which is unsubstituted or substituted with one or more of halogen, linear or branched —$C_{1-4}$ alkyl, and $C_{1-4}$ alkoxy, preferably unsubstituted or substituted —OMe.

In some embodiments of a compound of formula I $L^1$ is —$CH_2$—, $L^2$ is —$CH(CH_3)$— and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula I $L^1$ is —$CH_2$—, $L^2$ is —$CH(CH_3)$— and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula I $L^1$ is —$CH_2$—, $L^2$ is —$CH(CH_3)$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula I $L^1$ is —$CH_2$—, $L^2$ is —$CH(CH_3)$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula I $L^1$ is —$CH_2$—, $L^2$ is —$CH(CH_3)$— and $X^1$ is phenyl.

In some embodiments of a compound of formula I $L^1$ is —$CH(CH_3)$—, $L^2$ is a covalent bond and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula I $L^1$ is —$CH(CH_3)$—, $L^2$ is a covalent bond and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula I $L^1$ is —$CH(CH_3)$—, $L^2$ is a covalent bond and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula I $L^1$ is —$CH(CH_3)$—, $L^2$ is a covalent bond and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula I $L^1$ is —CH(CH$_3$)—, $L^2$ is a covalent bond and $X^1$ is phenyl, which is unsubstituted or substituted with one or more of halogen, such as Cl, F, linear or branched —C$_{1-4}$ alkyl, such as methyl, fluorinated C$_{1-4}$ alkoxy, such as —OCF$_3$ In some embodiments of a compound of formula I $L^1$ is —CH(CH$_3$)—, $L^2$ is a linear or branched C$_{1-4}$ alkyl and $X^1$ is linear or branched —C$_{1-6}$ alkyl, —C$_{3-6}$ cycloalkyl, —C$_{6-10}$ aryl, 5-10 membered heteroaryl, 5-6 membered heterocycloalkyl, wherein $X^1$ is unsubstituted or substituted with one or more of halogen, linear or branched —C$_{1-4}$ alkyl, CF$_3$, CHF$_2$, CMeF$_2$, —O—(CH$_2$)$_2$—OMe, OCF$_3$, OCHF$_2$, C$_{1-6}$ alkylamino, —CN, NH$_2$, C$_{1-4}$ alkylhydroxy, and C$_{1-4}$ alkoxy; or $X^1$ together with the N atom of the carbamate forms a 5-6 membered heterocycloalkyl, which is unsubstituted or substituted with one or more of halogen, linear or branched —C$_{1-4}$ alkyl, CF$_3$, CHF$_2$, CMeF$_2$, —O—(CH$_2$)$_2$ —OMe, OCF$_3$, OCHF$_2$, C$_{1-6}$ alkylamino, —CN, NH$_2$, C$_{1-4}$ alkylhydroxy, and C$_{1-4}$ alkoxy.

In some embodiments of a compound of formula I $L^1$ is —CH(CH$_3$)—, $L^2$ is a linear or branched C$_{1-4}$ alkyl and $X^1$ is linear or branched —C$_{1-6}$ alkyl, —C$_{3-6}$ cycloalkyl, —C$_{6-10}$ aryl, 5-10 membered heteroaryl, 6 membered heterocycloalkyl, wherein $X^1$ is unsubstituted or substituted with one or more of halogen, linear or branched —C$_{1-4}$ alkyl, CF$_3$, CHF$_2$, CMeF$_2$, OCF$_3$, OCHF$_2$, CN and C$_{1-4}$ alkoxy; or $X^1$ together with the N atom of the carbamate forms a 6 membered heterocycloalkyl, which is unsubstituted or substituted with one or more of halogen, linear or branched —C$_{1-4}$ alkyl, CF$_3$, CHF$_2$, CMeF$_2$, OCF$_3$, OCHF$_2$, CN and C$_{1-4}$ alkoxy.

In some embodiments of a compound of formula I $L^1$ is —CH(CH$_3$)—, $L^2$ is a linear or branched C$_{1-4}$ alkyl and $X^1$ is linear or branched —C$_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —C$_{1-4}$ alkyl, CF$_3$, CHF$_2$, CMeF$_2$, —O—(CH$_2$)$_2$—OMe, OCF$_3$, OCHF$_2$, C$_{1-6}$ alkylamino, —CN, NH$_2$, C$_{1-4}$ alkylhydroxy, and C$_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —C$_{1-4}$ alkyl, CF$_3$, CHF$_2$, CMeF$_2$, —O—(CH$_2$)$_2$—OMe, OCF$_3$, OCHF$_2$, C$_{1-6}$ alkylamino, —CN, NH$_2$, C$_{1-4}$ alkylhydroxy, or C$_{1-4}$ alkoxy.

In some embodiments of a compound of formula I $L^1$ is —CH(CH$_3$)—, $L^2$ is a linear or branched C$_{1-4}$ alkyl and $X^1$ is linear or branched —C$_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —C$_{1-4}$ alkyl, CF$_3$, CHF$_2$, CMeF$_2$, —OCF$_3$, OCHF$_2$, CN, and C$_{1-4}$ alkoxy; or $X^1$ together with the N atom of the carbamate forms a pyrrolidinyl, piperdinyl, piperazinyl, which is unsubstituted or substituted with one or more of halogen, linear or branched —C$_{1-4}$ alkyl, CF$_3$, CHF$_2$, CMeF$_2$, OCF$_3$, OCHF$_2$, CN, and C$_{1-4}$ alkoxy.

In some embodiments of a compound of formula I $L^1$ is —CH(CH$_3$)—, $L^2$ is —CH$_2$— and $X^1$ is linear or branched —C$_{1-6}$ alkyl, —C$_{3-6}$ cycloalkyl, —C$_{6-10}$ aryl, 5-10 membered heteroaryl, 5-6 membered heterocycloalkyl, wherein $X^1$ is unsubstituted or substituted with one or more of halogen, linear or branched —C$_{1-4}$ alkyl, CF$_3$, CHF$_2$, CMeF$_2$, —O—(CH$_2$)$_2$—OMe, OCF$_3$, OCHF$_2$, C$_{1-6}$ alkylamino, —CN, NH$_2$, C$_{1-4}$ alkylhydroxy, and C$_{1-4}$ alkoxy; or $X^1$ together with the N atom of the carbamate forms a 5-6 membered heterocycloalkyl, which is unsubstituted or substituted with one or more of halogen, linear or branched —C$_{1-4}$ alkyl, CF$_3$, CHF$_2$, CMeF$_2$, —O—(CH$_2$)$_2$—OMe, OCF$_3$, OCHF$_2$, C$_{1-6}$ alkylamino, —CN, NH$_2$, C$_{1-4}$ alkylhydroxy, and C$_{1-4}$ alkoxy.

In some embodiments of a compound of formula I $L^1$ is —CH(CH$_3$)—, $L^2$ is —CH$_2$— and $X^1$ is linear or branched —C$_{1-6}$ alkyl, —C$_{3-6}$ cycloalkyl, —C$_{6-10}$ aryl, 5-10 membered heteroaryl, 6 membered heterocycloalkyl, wherein $X^1$ is unsubstituted or substituted with one or more of halogen, linear or branched —C$_{1-4}$ alkyl, CF$_3$, CHF$_2$, CMeF$_2$, OCF$_3$, OCHF$_2$, CN and C$_{1-4}$ alkoxy; or $X^1$ together with the N atom of the carbamate forms a 6 membered heterocycloalkyl, which is unsubstituted or substituted with one or more of halogen, linear or branched —C$_{1-4}$ alkyl, CF$_3$, CHF$_2$, CMeF$_2$, OCF$_3$, OCHF$_2$, CN and C$_{1-4}$ alkoxy.

In some embodiments of a compound of formula I $L^1$ is —CH(CH$_3$)—, $L^2$ is —CH$_2$— and $X^1$ is linear or branched —C$_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —C$_{1-4}$ alkyl, CF$_3$, CHF$_2$, CMeF$_2$, —O—(CH$_2$)$_2$—OMe, OCF$_3$, OCHF$_2$, C$_{1-6}$ alkylamino, —CN, NH$_2$, C$_{1-4}$ alkylhydroxy, and C$_{1-4}$ alkoxy; or $X^1$ together with the N atom of the carbamate forms a pyrrolidinyl, piperidinyl, morpholinyl, piperazinyl, N-methyl piperazinyl, which is unsubstituted or substituted with one or more of halogen, such as Cl, F, linear or branched —C$_{1-4}$ alkyl, CF$_3$, CHF$_2$, CMeF$_2$, —O—(CH$_2$)$_2$—OMe, OCF$_3$, OCHF$_2$, C$_{1-6}$ alkylamino, —CN, NH$_2$, C$_{1-4}$ alkylhydroxy, or C$_{1-4}$ alkoxy.

In some embodiments of a compound of formula I $L^1$ is —CH(CH$_3$)—, $L^2$ is —CH$_2$— and $X^1$ is linear or branched —C$_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —C$_{1-4}$ alkyl, CF$_3$, CHF$_2$, CMeF$_2$, —OCF$_3$, OCHF$_2$, CN, and C$_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula I $L^1$ is —$CH(CH_3)$—, $L^2$ is —$CH(CH_3)$— and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula I $L^1$ is —$CH(CH_3)$—, $L^2$ is —$CH(CH_3)$— and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula I $L^1$ is —$CH(CH_3)$—, $L^2$ is —$CH(CH_3)$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperidinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula I $L^1$ is —$CH(CH_3)$—, $L^2$ is —$CH(CH_3)$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperidinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula I, $L^2$ is a covalent bond and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula I, $L^2$ is a covalent bond and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula I, $L^2$ is a covalent bond and $X^2$ is H, cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula I, $L^2$ is a covalent bond and $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula I, $L^2$ is —$CH_2$— and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula I, $L^2$ is —$CH_2$— and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula I, $L^2$ is —$CH_2$— and $X^2$ is $C_6$ aryl, which is unsubstituted or substituted with one or more of linear or branched $C_{1-4}$ alkyl, —$C_{1-4}$ alkoxy, such as unsubstituted or substituted with —OMe.

In some embodiments of a compound of formula I, $L^2$ is —$CH(CH_3)$— and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula I, $L^2$ is —$CH(CH_3)$— and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula I, $L^2$ is —$CH(CH_3)$— and $X^2$ is $C_6$ aryl, which is unsubstituted or substituted with one or more of linear or branched $C_{1-4}$ alkyl, —$C_{1-4}$ alkoxy, e.g. unsubstituted.

In some embodiments of a compound of formula I, $L^3$ is a covalent bond and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula I, $L^3$ is a covalent bond and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula I, $L^3$ is a covalent bond and $X^2$ is H, cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula I, $L^3$ is a covalent bond and $X^2$ is cyclopropyl, cyclobutyl, azetidinyl, oxetanyl, pyrrolidinyl, piperidinyl, piperazinyl, morpholinyl, 8-oxa-3-azabicyclo[3.2.1]octan-3-yl, $C_6$ aryl, pyridinyl, wherein $X^2$ is unsubstituted or substituted with one or more of linear or branched $C_{1-6}$ alkyl, e.g. methyl, —$C_{1-4}$ alkoxy, e.g. —OMe, $NMe_2$ and halogen, e.g. F.

In some embodiments of a compound of formula I, $L^3$ is a covalent bond and $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula I, $L^3$ is a covalent bond and $X^2$ is cyclopropyl, methyl-cyclopropyl, fluoro-cyclopropyl, difluoro-cyclopropyl, cyclobutyl, azetidinyl, $NMe_2$-azetidinyl, oxetanyl, methyl-oxetanyl, pyrrolidinyl, methyl-pyrrolidinyl, piperidinyl, Me-piperidinyl, Di-F-piperidinyl, N-Me-piperazinyl, morpholinyl, 8-oxa-3-azabicyclo[3.2.1]octan-3-yl, $C_6$ aryl, methoxy-$C_6$ aryl, pyridinyl.

In some embodiments of a compound of formula I, $L^3$ is a linear or branched $C_{1-4}$ alkyl, such as —$CH_2$—, and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula I, $L^3$ is a linear or branched $C_{1-4}$ alkyl, such as —$CH_2$—, and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula I, $L^3$ is a linear or branched $C_{1-4}$ alkyl, such as —$CH_2$—, and $X^2$ is H, cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula I, $L^3$ is a linear or branched $C_{1-4}$ alkyl, such as —$CH_2$—, and $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula I, $L^3$ is linear or branched $C_{1-4}$ alkyl, such as —$CH_2$—, and $X^2$ is morpholinyl, N-methyl-morpholinyl, 2-oxa-5-azabicyclo[2.2.1]heptanyl, 8-oxa-3-azabicyclo[3.2.1]octan-3-yl.

In some embodiments of a compound of formula I, $L^3$ is —O— and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula I, $L^3$ is —O— and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula I, $L^3$ is —O— and $X^2$ is H, cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula I, $L^3$ is —O— and $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula I, $L^3$ is —O— and $X^2$ is cyclopropyl, pyrrolidinyl, N-methyl-pyrrolidinyl, In some embodiments of a compound of formula I, $L^3$ is —O—$CH_2$— and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula I, $L^3$ is —O—$CH_2$— and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula I, $L^3$ is —O—$CH_2$— and $X^2$ is H, cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula I, $L^3$ is —O—$CH_2$— and $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula I, $L^3$ is —O—$CH_2$— and $X^2$ is pyrrolidinyl, N-methyl-pyrrolidinyl.

In some embodiments of a compound of formula I, $L^3$ is —O—$CH_2$—$CH_2$— and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula I, $L^3$ is —O—$CH_2$—$CH_2$— and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula I, $L^3$ is —O—$CH_2$—$CH_2$— and $X^2$ is H, cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula I, $L^3$ is —O—$CH_2$—$CH_2$— and $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula I, $L^3$ is —O—$CH_2$—$CH_2$— and $X^2$ is morpholinyl.

In specific embodiments the compound of formula I is a compound or pharmaceutically acceptable salts or stereoisomers thereof formula II.

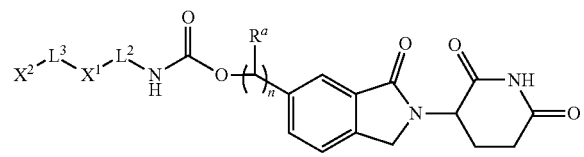

wherein $X^1$ is linear or branched $C_{1-6}$ alkyl, $C_{3-6}$ cycloalkyl, $C_{6-10}$ aryl, 5-10 membered heteroaryl, 4-8 membered heterocycloalkyl, wherein $X^1$ is unsubstituted or substituted with one or more of halogen, linear or branched $C_{1-6}$ alkyl, linear or branched $C_{1-6}$ heteroalkyl, $CF_3$, $CHF_2$, $CMeF_2$, —O—$CHF_2$, —O—$(CH_2)_2$—OMe, $OCF_3$, $C_{1-6}$ alkylamino, —CN, —N(H)C(O)—$C_{1-6}$alkyl, —OC(O)—$C_{1-6}$ alkyl, —OC(O)—$C_{1-4}$alkylamino, —C(O)O—$C_{1-6}$alkyl, —COOH, —$C_{1-6}$alkylC(O)OH, —$C_{1-6}$ alkylC(O)O—$C_{1-6}$alkyl, $NH_2$, $C_{1-4}$ alkoxy and $C_{1-4}$ alkylhydroxy;

or $X^1$ together with the N atom of the carbamate forms a 4-8 membered heterocycloalkyl, which is unsubstituted or substituted with one or more of halogen, linear or branched —$C_{1-6}$ alkyl, $CF_3$, $CHF_2$, $CMeF_2$, —O—$(CH_2)_2$—OMe, $OCF_3$, $OCHF_2$, $C_{1-6}$ alkylamino, —CN, —N(H)C(O)—$C_{1-6}$alkyl, —OC(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, $C_{1-4}$ alkylhydroxy, and $C_{1-4}$ alkoxy;

$X^2$ is H, $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and $C_{1-4}$ alkylhydroxy;

$L^2$ is a covalent bond, linear or branched $C_{1-6}$ alkyl; $L^3$ is a covalent bond, linear or branched $C_{1-6}$ alkyl, —O—, —$C_{1-4}$ alkoxy;

$R^a$ is H or linear or branched $C_{1-4}$ alkyl, such as methyl or ethyl; and n is 1 or 2.

In some embodiments of a compound of formula II, $R^a$ is H. In some embodiments of a compound of formula II, $R^a$ is linear or branched $C_{1-4}$ alkyl, such as methyl.

In some embodiments of a compound of formula II, n is 1.

In some embodiments of a compound of formula II, $L^2$ is a covalent bond. In some embodiments of a compound of formula II, $L^2$ is linear or branched $C_{1-6}$ alkyl. In some embodiments of a compound of formula II, $L^2$ is linear or branched $C_{1-4}$ alkyl, such as —$CH_2$— or —$CH(CH_3)$—.

In some embodiments of a compound of formula II, $L^3$ is a covalent bond. In some embodiments of a compound of formula II, $L^3$ is linear or branched $C_{1-4}$ alkyl. In some embodiments of a compound of formula II, $L^3$ is —O—. In some embodiments $L^3$ is linear or branched $C_{1-4}$ alkoxy, such as —O—$CH_2$—, —O—$CH_2$—$CH_2$—, O—$CH_2$—$CH_2$—$CH_2$—.

In some embodiments of a compound of formula II, $L^1$ is —$CH_2$— and $L^2$ is a covalent bond. In some embodiments of a compound of formula II, $L^1$ is —$CH_2$— and $L^2$ is —$CH_2$—. In some embodiments $L^1$ is —$CH_2$— and $L^2$ is —$CH(CH_3)$—.

In some embodiments of a compound of formula II, $L^1$ is —$CH_2$—, $L^2$ is a covalent bond and $L^3$ is a covalent bond. In some embodiments of a compound of formula II, $L^1$ is —$CH_2$—, $L^2$ is a covalent bond and $L^3$ is —$CH_2$—. In some embodiments of a compound of formula II, $L^1$ is —$CH_2$—, $L^2$ is a covalent bond and $L^3$ is —O—. In some embodiments of a compound of formula II, $L^1$ is —$CH_2$—, $L^2$ is a covalent bond and $L^3$ is —O—$CH_2$—. In some embodiments of a compound of formula II, $L^1$ is —$CH_2$—, $L^2$ is a covalent bond and $L^3$ is —O—$CH_2$—$CH_2$—.

In some embodiments of a compound of formula II, $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula II, $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula II, $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula II, $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula II, $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula II, $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula II, $X^2$ is H, cyclopropyl, cyclobutyl, $C_6$ aryl, pyridinyl, pyrrolidinyl, piperdinyl, morpholinyl, oxetanyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula II, $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula II n is 1, $R^a$ is H and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula II n is 1, $R^a$ is H and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula II n is 1, $R^a$ is H and $X^1$ is linear or branched —$C_{1-6}$ alkyl, cyclopropyl, cyclobutyl, cyclopentyl, cyclohexyl, bicyclo[1.1.1] pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula II n is 1, $R^a$ is H and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula II n is 1, $R^a$ is —$CH_3$ and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula II n is 1, $R^a$ is —$CH_3$ and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula II n is 1, $R^a$ is —$CH_3$ and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula II n is 1, $R^a$ is —$CH_3$ and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula II n is 1, $R^a$ is —$CH_3$ and $X^1$ is phenyl, which is unsubstituted or substituted with one or more of halogen, such as Cl, F, linear or branched —$C_{1-4}$ alkyl, such as methyl, fluorinated $C_{1-4}$ alkoxy, such as —$OCF_3$.

In some embodiments of a compound of formula II $L^2$ is a covalent bond and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula II $L^2$ is a covalent bond and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula II $L^2$ is a covalent bond and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula II $L^2$ is a covalent bond and $X^1$ is linear or branched —$C_{1-6}$ alkyl, cyclopropyl, cyclobutyl, cyclopentyl, cyclohexyl, bicyclo

[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula II $L^2$ is linear or branched $C_{1-4}$ alkyl and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula II $L^2$ is linear or branched $C_{1-4}$ alkyl and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula II $L^2$ is linear or branched $C_{1-4}$ alkyl and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula II $L^2$ is linear or branched $C_{1-4}$ alkyl and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula II $L^2$ is —$CH_2$— and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula II $L^2$ is —$CH_2$— and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula II $L^2$ is —$CH_2$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula II $L^2$ is —$CH_2$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula II, $L^2$ is —$CH_2$— and $X^1$ is phenyl, which is unsubstituted or substituted with one or more of halogen, linear or branched —$C_{1-4}$ alkyl, and $C_{1-4}$ alkoxy, preferably —OMe.

In some embodiments of a compound of formula II $L^2$ is —$CH(CH_3)$— and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula II $L^2$ is —$CH(CH_3)$— and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula II $L^2$ is —$CH(CH_3)$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula II $L^2$ is —$CH(CH_3)$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula II, $L^2$ is —$CH(CH_3)$— and $X^1$ is phenyl.

In some embodiments of a compound of formula II n is 1, $R^a$ is H, $L^2$ is a covalent bond and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula II n is 1, $R^a$ is H, $L^2$ is a covalent bond and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula II n is 1, $R^a$ is H, $L^2$ is a covalent bond and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula II n is 1, $R^a$ is H, $L^2$ is a covalent bond and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula II n is 1, $R^a$ is H, $L^2$ is a linear or branched $C_{1-4}$ alkyl and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula II n is 1, $R^a$ is H, $L^2$ is a linear or branched $C_{1-4}$ alkyl and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula II n is 1, $R^a$ is H, $L^2$ is a linear or branched $C_{1-4}$ alkyl and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula II n is 1, $R^a$ is H, $L^2$ is a linear or branched $C_{1-4}$ alkyl and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula II n is 1, $R^a$ is H, $L^2$ is —$CH_2$— and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula II n is 1, $R^a$ is H, $L^2$ is —$CH_2$— and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula II n is 1, $R^a$ is H, $L^2$ is —$CH_2$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula II n is 1, $R^a$ is H, $L^2$ is —$CH_2$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula II n is 1, $R^a$ is H, $L^2$ is —$CH_2$— and $X^1$ is phenyl, which is unsubstituted or substituted with one or more of halogen, linear or branched —$C_{1-4}$ alkyl, and $C_{1-4}$ alkoxy, preferably unsubstituted or substituted —OMe.

In some embodiments of a compound of formula II n is 1, $R^a$ is H, $L^2$ is —$CH(CH_3)$— and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula II n is 1, $R^a$ is H, $L^2$ is —$CH(CH_3)$— and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula II n is 1, $R^a$ is H, $L^2$ is —$CH(CH_3)$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula II n is 1, $R^a$ is H, $L^2$ is —$CH(CH_3)$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula II n is 1, $R^a$ is H, $L^2$ is —$CH(CH_3)$— and $X^1$ is phenyl.

In some embodiments of a compound of formula II n is 1, $R^a$ is —$CH_3$, $L^2$ is a covalent bond and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula II n is 1, $R^a$ is —$CH_3$, $L^2$ is a covalent bond and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula II n is 1, $R^a$ is —$CH_3$, $L^2$ is a covalent bond and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula II n is 1, $R^a$ is —$CH_3$, $L^2$ is a covalent bond and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula II, n is 1, $R^a$ is —$CH_3$, $L^2$ is a covalent bond and $X^1$ is phenyl, which is unsubstituted or substituted with one or more of halogen, linear or branched —$C_{1-4}$ alkyl, and $C_{1-4}$ alkoxy, fluorinated $C_{1-4}$ alkyl, such as —$CF_3$.

In some embodiments of a compound of formula II n is 1, $R^a$ is —$CH_3$, $L^2$ is a linear or branched $C_{1-4}$ alkyl and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula II n is 1, $R^a$ is —$CH_3$, $L^2$ is a linear or branched $C_{1-4}$ alkyl and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula II n is 1, $R^a$ is —$CH_3$, $L^2$ is a linear or branched $C_{1-4}$ alkyl and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula II n is 1, $R^a$ is —$CH_3$, $L^2$ is a linear or branched $C_{1-4}$ alkyl and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula II n is 1, $R^a$ is —$CH_3$, $L^2$ is —$CH_2$— and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula II n is 1, $R^a$ is —$CH_3$, $L^2$ is —$CH_2$— and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula II n is 1, $R^a$ is —$CH_3$, $L^2$ is —$CH_2$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula II n is 1, $R^a$ is —$CH_3$, $L^2$ is —$CH_2$— and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula II n is 1, $R^a$ is —$CH_3$, $L^2$ is —$CH(CH_3)$— and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula II n is 1, $R^a$ is —$CH_3$, $L^2$ is —$CH(CH_3)$— and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula II n is 1, $R^a$ is —$CH_3$, $L^2$ is —$CH(CH_3)$— and $X^1$ is linear or branched—$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$ —OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula II n is 1, $R^a$ is —$CH_3$, $L^2$ is —$CH(CH_3)$— and $X^1$ is linear or branched—$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula II, $L^3$ is a covalent bond and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula II, $L^3$ is a covalent bond and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula II, $L^3$ is a covalent bond and $X^2$ is H, cyclopropyl, cyclobutyl, azetidinyl, oxetanyl, pyrrolidinyl, piperidinyl, piperazinyl, morpholinyl, 2-oxa-5-azabicyclo[2.2.1]heptanyl, 8-oxa-3-azabicyclo[3.2.1]octan-3-yl, $C_6$ aryl, pyridinyl, wherein $X^2$ is unsubstituted or substituted with one or more of linear or branched $C_{1-4}$ alkyl, e.g. methyl, —$C_{1-4}$ alkoxy, e.g. —OMe, $NMe_2$ and halogen, e.g. F.

In some embodiments of a compound of formula II, $L^3$ is a covalent bond and $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula II, $L^3$ is a covalent bond and $X^2$ is H, cyclopropyl, methyl-cyclopropyl, fluoro-cyclopropyl, difluoro-cyclopropyl, cyclobutyl, azetidinyl, $NMe_2$-azetidinyl, oxetanyl, methyl-oxetanyl, pyrrolidinyl, methyl-pyrrolidinyl, piperidinyl, Me-piperidinyl, Di-F-piperidinyl, N-Me-piperazinyl, morpholinyl, 8-oxa-3-azabicyclo[3.2.1]octan-3-yl, $C_6$ aryl, methoxy-$C_6$ aryl, pyridinyl.

In some embodiments of a compound of formula II, $L^3$ is a linear or branched $C_{1-4}$ alkyl, such as —$CH_2$—, and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula II, $L^3$ is a linear or branched $C_{1-4}$ alkyl, such as —$CH_2$—, and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula II, $L^3$ is a linear or branched $C_{1-4}$ alkyl, such as —$CH_2$—, and $X^2$ is H, cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula II, $L^3$ is a linear or branched $C_{1-4}$ alkyl, such as —$CH_2$—, and $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula II, $L^3$ is linear or branched $C_{1-4}$ alkyl, such as —$CH_2$—, and $X^2$ is morpholinyl, N-methyl-morpholinyl, 2-oxa-5-azabicyclo[2.2.1]heptanyl, 8-oxa-3-azabicyclo[3.2.1]octan-3-yl.

In some embodiments of a compound of formula II, $L^3$ is —O— and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula II, $L^3$ is —O— and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula II, $L^3$ is —O— and $X^2$ is H, cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula II, $L^3$ is —O— and $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula II, $L^3$ is —O— and $X^2$ is cyclopropyl, pyrrolidinyl, N-methyl-pyrrolidinyl, In some embodiments of a compound of formula II, $L^3$ is —O—$CH_2$— and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula II, $L^3$ is —O—$CH_2$— and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula II, $L^3$ is —O—$CH_2$— and $X^2$ is H, cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula II, $L^3$ is —O—$CH_2$— and $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula II, $L^3$ is —O—$CH_2$— and $X^2$ is pyrrolidinyl, N-methyl-pyrrolidinyl.

In some embodiments of a compound of formula II, $L^3$ is —O—$CH_2$—$CH_2$— and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula II, $L^3$ is —O—$CH_2$—$CH_2$— and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula II, $L^3$ is —O—$CH_2$—$CH_2$— and $X^2$ is H, cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula II, $L^3$ is —O—$CH_2$—$CH_2$— and $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula II, $L^3$ is —O—$CH_2$—$CH_2$— and $X^2$ is morpholinyl.

In specific embodiments the compound of formula I or II is a compound or pharmaceutically acceptable salts or stereoisomers thereof formula III, such as IVa or IVb:

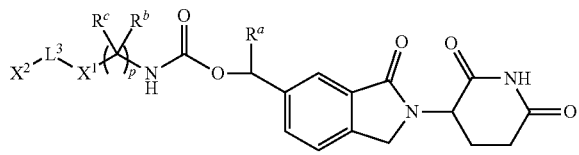

III

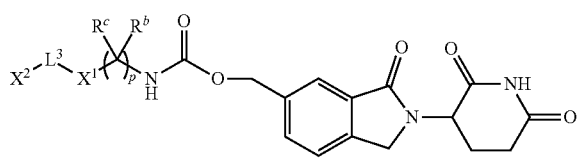

IVa

-continued

IVb

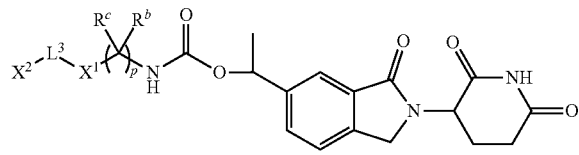

wherein
$X^1$ is linear or branched $C_{1-6}$ alkyl, $C_{3-6}$ cycloalkyl, $C_{6-10}$ aryl, 5-10 membered heteroaryl, 4-8 membered heterocycloalkyl, wherein $X^1$ is unsubstituted or substituted with one or more of halogen, linear or branched $C_{1-6}$ alkyl, linear or branched $C_{1-6}$ heteroalkyl, $CF_3$, $CHF_2$, $CMeF_2$, —O—$CHF_2$, —O—$(CH_2)_2$—OMe, $OCF_3$, $C_{1-6}$ alkylamino, —CN, —N(H)C(O)—$C_{1-6}$alkyl, —OC(O)—$C_{1-6}$ alkyl, —OC(O)—$C_{1-4}$alkylamino, —C(O)O—$C_{1-6}$alkyl, —COOH, —$C_{1-6}$alkylC(O)OH, —$C_{1-6}$ alkylC(O)O—$C_{1-6}$alkyl, $NH_2$, $C_{1-4}$ alkoxy and $C_{1-4}$ alkylhydroxy;
or $X^1$ together with the N atom of the carbamate forms a 4-8 membered heterocycloalkyl, which is unsubstituted or substituted with one or more of halogen, linear or branched —$C_{1-6}$ alkyl, $CF_3$, $CHF_2$, $CMeF_2$, —O—$(CH_2)_2$—OMe, $OCF_3$, $OCHF_2$, $C_{1-6}$ alkylamino, —CN, —N(H)C(O)—$C_{1-6}$alkyl, —OC(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, $C_{1-4}$ alkylhydroxy, and $C_{1-4}$ alkoxy;
$X^2$ is H, $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and $C_{1-4}$ alkylhydroxy;
$L^3$ is a covalent bond, linear or branched $C_{1-6}$ alkyl, —O—, —$C_{1-4}$ alkoxy;
$R^a$, $R^b$, $R^c$ are independently of each other H, linear or branched $C_{1-4}$ alkyl, such as methyl;
p is 0 or 1.

In some embodiments of a compound of formula III, $R^a$ is H. In some embodiments of a compound of formula III, $R^a$ is linear or branched $C_{1-4}$ alkyl, such as methyl.

In some embodiments of a compound of formula III, IVa or IVb, p is 0. In some embodiments of a compound of formula III, IVa or IVb, p is 1. In some embodiments of a compound of formula III, IVa or IVb, p is 1 and $R^b$ and $R^c$ are H. In some embodiments of a compound of formula III, IVa or IVb, p is 1, $R^b$ is linear or branched $C_{1-4}$ alkyl, such as methyl and $R^c$ is H.

In some embodiments of a compound of formula III, IVa or IVb, $L^3$ is a covalent bond. In some embodiments of a compound of formula III, IVa or IVb, $L^3$ is linear or branched $C_{1-4}$ alkyl, such as —$CH_2$—. In some embodiments of a compound of formula III, IVa or IVb, $L^3$ is —O—. In some embodiments $L^3$ is linear or branched $C_{1-4}$ alkoxy, such as —O—$CH_2$—, —O—$(CH_2)_2$—.

In some embodiments of a compound of formula III, IVa or IVb, $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula III, IVa or IVb, $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula III, IVa or IVb, $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula III, IVa or IVb, $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula III, IVa or IVb, $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula III, IVa or IVb, $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula II, $L^3$ is —O—$CH_2$—$CH_2$— and $X^2$ is H, cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula III, IVa or IVb, $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula III, $R^a$ is H and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula III, $R^a$ is H and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula III, $R^a$ is H and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula III, $R^a$ is H and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula III, $R^a$ is —$CH_3$ and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula III, $R^a$ is —$CH_3$ and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula III, $R^a$ is —$CH_3$ and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula III, $R^a$ is —$CH_3$ and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula III, $R^a$ is —$CH_3$ and $X^1$ is phenyl, which is unsubstituted or substituted with one or more of halogen, such as Cl, F, linear or branched —$C_{1-4}$ alkyl, such as methyl, fluorinated $C_{1-4}$ alkoxy, such as —$OCF_3$.

In some embodiments of a compound of formula III, IVa, or IVb, p is 0 and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula III, IVa, or IVb, p is 0 and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula III, IVa, or IVb, p is 0 and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula III, IVa, or IVb, p is 0 and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula III, IVa or IVb, p is 1, $R^b$, $R^c$ are H and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula III, IVa or IVb, p is 1, $R^b$, $R^c$ are H and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula III, IVa or IVb, p is 1, $R^b$, $R^c$ are H and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula III, IVa or IVb, p is 1, $R^b$, $R^c$ are H and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula III, IVa or IVb, p is 1, $R^b$, $R^c$ are H and $X^1$ is phenyl, which is unsubstituted or substituted with one or more of halogen, linear or branched —$C_{1-4}$ alkyl, and $C_{1-4}$ alkoxy, preferably unsubstituted or substituted with —OMe.

In some embodiments of a compound of formula III, IVa or IVb, p is 1, $R^b$ is —$CH_3$, $R^c$ is H and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula III, IVa or IVb, p is 1, $R^b$ is —$CH_3$, $R^c$ is H and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula III, IVa or IVb, p is 1, $R^b$ is —$CH_3$, $R^c$ is H and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula III, IVa or IVb, p is 1, $R^b$ is —$CH_3$, $R^c$ is H and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula III, IVa or IVb, p is 1, $R^b$ is —$CH_3$, $R^c$ is H and $X^1$ is phenyl, which is unsubstituted or substituted with one or more of halogen, linear or branched —$C_{1-4}$ alkyl, and $C_{1-4}$ alkoxy preferably unsubstituted or substituted —OMe.

In some embodiments of a compound of formula III, IVa or IVb, p is 0 and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula III, IVa or IVb, p is 0 and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula III, IVa or IVb, p is 0 and $X^2$ is H, cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, e.g. Me, —$C_{1-4}$ alkoxy, e.g. —OMe, $NH_2$, $NMe_2$ and halogen, e.g. F.

In some embodiments of a compound of formula III, IVa or IVb, p is 0 and $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula III, IVa or IVb, p is 0 and $X^2$ is H, cyclopropyl, methyl-cyclopropyl, fluoro-cyclopropyl, difluoro-cyclopropyl, cyclobutyl, azetidinyl, $NMe_2$-azetidinyl, oxetanyl, methyl-oxetanyl, pyrrolidinyl, methyl-pyrrolidinyl, piperidinyl, Me-piperidinyl, Di-F-piperidinyl, N-Me-piperazinyl, morpholinyl, 8-oxa-3-azabicyclo[3.2.1]octan-3-yl, $C_6$ aryl, methoxy-$C_6$ aryl, pyridinyl In some embodiments of a compound of formula III, IVa or IVb, p is 1, $R^b$ and $R^c$ are H, and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula III, IVa or IVb, p is 1, $R^b$ and $R^c$ are H, and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula III, IVa or IVb, p is 1, $R^b$ and $R^c$ are H, and $X^2$ is H, cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula III, IVa or IVb, p is 1, $R^b$ and $R^c$ are H, and $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula III, IVa or IVb, p is 1, $R^b$ and $R^c$ are H, and $X^2$ is phenyl, which is unsubstituted or substituted with one or more of halogen, linear or branched —$C_{1-4}$ alkyl, and $C_{1-4}$ alkoxy, preferably unsubstituted or substituted —OMe.

In some embodiments of a compound of formula III, IVa or IVb, p is 1, $R^b$ is $CH_3$, $R^c$ are H, and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula III, IVa or IVb, p is 1, $R^b$ is $CH_3$, $R^c$ are H, and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula II, $L^3$ is —O—$CH_2$—$CH_2$— and $X^2$ is H, cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula III, IVa or IVb, p is 1, $R^b$ is $CH_3$, $R^c$ are H, and $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula III, IVa or IVb, p is 1, $R^b$ is $CH_3$, $R^c$ are H, and $X^2$ is phenyl.

In some embodiments of a compound of formula III, $R^a$ is H, p is 0 and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula III, $R^a$ is H, p is 0 and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula III, $R^a$ is H, p is 0 and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$ —OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula III, $R^a$ is H, p is 0 and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula III, $R^a$ is H, p is 1, $R^b$ and $R^c$ are H, and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula III, $R^a$ is H, p is 1, $R^b$ and $R^c$ are H, and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula III, $R^a$ is H, p is 1, $R^b$ and $R^c$ are H, and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula III, $R^a$ is H, p is 1, $R^b$ and $R^c$ are H, and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula III, $R^a$ is H, p is 1, $R^b$ and $R^c$ are H, and $X^1$ is phenyl, which is unsubstituted or substituted with one or more of halogen, linear or branched —$C_{1-4}$ alkyl, and $C_{1-4}$ alkoxy, preferably unsubstituted or substituted —OMe.

In some embodiments of a compound of formula III, $R^a$ is H, p is 1, $R^b$ is $CH_3$, $R^c$ are H, and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula III, $R^a$ is H, p is 1, $R^b$ is $CH_3$, $R^c$ are H, and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula III, $R^a$ is H, p is 1, $R^b$ is $CH_3$, $R^c$ are H, and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula III, $R^a$ is H, p is 1, $R^b$ is $CH_3$, $R^c$ are H, and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula III, $R^a$ is H, p is 1, $R^b$ is $CH_3$, $R^c$ are H, and $X^1$ is phenyl.

In some embodiments of a compound of formula III, $R^a$ is $CH_3$, p is 0 and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula III, $R^a$ is $CH_3$, p is 0 and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula III, $R^a$ is $CH_3$, p is 0 and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula III, $R^a$ is $CH_3$, p is 0 and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula III, $R^a$ is —$CH_3$, p is 0 and $X^1$ is phenyl, which is unsubstituted or substituted with one or more of halogen, such as Cl, F, linear or branched —$C_{1-4}$ alkyl, such as methyl, fluorinated $C_{1-4}$ alkoxy, such as —$OCF_3$.

In some embodiments of a compound of formula III, $R^a$ is $CH_3$, p is 1, $R^b$ and $R^c$ are H, and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

In some embodiments of a compound of formula III, $R^a$ is $CH_3$, p is 1, $R^b$ and $R^c$ are H, and $X^1$ is linear or branched —$C_{1-6}$ alkyl, —$C_{3-6}$ cycloalkyl, —$C_{6-10}$ aryl, 5-10 membered heteroaryl, 6 membered heterocycloalkyl, wherein $X^1$ is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy; or $X^1$ together with the N atom of the carbamate forms a 6 membered heterocycloalkyl, which is unsubstituted or substituted with one or more of halogen, linear or branched —$C_{1-4}$ alkyl, $CF_3$, $CHF_2$, $CMeF_2$, $OCF_3$, $OCHF_2$, CN and $C_{1-4}$ alkoxy.

In some embodiments of a compound of formula III, $R^a$ is $CH_3$, p is 1, $R^b$ and $R^c$ are H, and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, or $C_{1-4}$ alkoxy.

In some embodiments of a compound of formula III, $R^a$ is $CH_3$, p is 1, $R^b$ and $R^c$ are H, and $X^1$ is linear or branched —$C_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein $X^1$ is unsubstituted or substituted with one or more of halogen, such as Cl, F, linear or branched —$C_{1-4}$ alkyl, $CF_3$, $CHF_2$, $CMeF_2$, —$OCF_3$, $OCHF_2$, CN, and $C_{1-4}$ alkoxy; or $X^1$ together with the N atom of the carbamate forms a pyrrolidinyl, piperdinyl, piperazinyl, which is unsubstituted or substituted with one or more of halogen, linear or branched —$C_{1-4}$ alkyl, $CF_3$, $CHF_2$, $CMeF_2$, $OCF_3$, $OCHF_2$, CN, and $C_{1-4}$ alkoxy.

In some embodiments of a compound of formula III, $R^a$ is $CH_3$, p is 1, $R^b$ is $CH_3$, $R^c$ are H, and $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, NH$_2$, C$_{1-4}$ alkylhydroxy, and C$_{1-4}$ alkoxy; or X$^1$ together with the N atom of the carbamate forms a 5-6 membered heterocycloalkyl, which is unsubstituted or substituted with one or more of halogen, linear or branched —C$_{1-4}$ alkyl, CF$_3$, CHF$_2$, CMeF$_2$, —O—(CH$_2$)$_2$—OMe, OCF$_3$, OCHF$_2$, C$_{1-6}$ alkylamino, —CN, NH$_2$, C$_{1-4}$ alkylhydroxy, and C$_{1-4}$ alkoxy.

In some embodiments of a compound of formula III, R$^a$ is CH$_3$, p is 1, R$^b$ is CH$_3$, R$^c$ are H, and X$^1$ is linear or branched —C$_{1-6}$ alkyl, —C$_{3-6}$ cycloalkyl, —C$_{6-10}$ aryl, 5-10 membered heteroaryl, 6 membered heterocycloalkyl, wherein X$^1$ is unsubstituted or substituted with one or more of halogen, linear or branched —C$_{1-4}$ alkyl, CF$_3$, CHF$_2$, CMeF$_2$, OCF$_3$, OCHF$_2$, CN and C$_{1-4}$ alkoxy; or X$^1$ together with the N atom of the carbamate forms a 6 membered heterocycloalkyl, which is unsubstituted or substituted with one or more of halogen, linear or branched —C$_{1-4}$ alkyl, CF$_3$, CHF$_2$, CMeF$_2$, OCF$_3$, OCHF$_2$, CN and C$_{1-4}$ alkoxy.

In some embodiments of a compound of formula III, R$^a$ is CH$_3$, p is 1, R$^b$ is CH$_3$, R$^c$ are H, and X$^1$ is linear or branched —C$_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein X$^1$ is unsubstituted or substituted with one or more of halogen, such as Cl, F, linear or branched —C$_{1-4}$ alkyl, CF$_3$, CHF$_2$, CMeF$_2$, —O—(CH$_2$)$_2$—OMe, OCF$_3$, OCHF$_2$, C$_{1-6}$ alkylamino, —CN, NH$_2$, C$_{1-4}$ alkylhydroxy, and C$_{1-4}$ alkoxy; or X$^1$ together with the N atom of the carbamate forms a pyrrolidinyl, piperdinyl, morpholinyl, piperazinyl, N-methyl piperazinyl, which is unsubstituted or substituted with one or more of halogen, such as Cl, F, linear or branched —C$_{1-4}$ alkyl, CF$_3$, CHF$_2$, CMeF$_2$, —O—(CH$_2$)$_2$—OMe, OCF$_3$, OCHF$_2$, C$_{1-6}$ alkylamino, —CN, NH$_2$, C$_{1-4}$ alkylhydroxy, or C$_{1-4}$ alkoxy.

In some embodiments of a compound of formula III, R$^a$ is CH$_3$, p is 1, R$^b$ is CH$_3$, R$^c$ are H, and X$^1$ is linear or branched —C$_{1-6}$ alkyl, cyclopropyl, cyclobutyl, cyclopentyl, cyclohexyl, bicyclo[1.1.1]pentyl, piperidinyl, 1,3-dioxanyl, phenyl, dihydroindenyl, isothiazolyl, pyridinyl, pyrazinyl, pyridazinyl, pyrimidinyl, 2,2-difluoro-1,3-benzodioxolyl, 2,3-dihydrobenzofuryl, 2-methyl-2,3-dihydrobenzofuryl, 3-methyl-2,3-dihydrobenzofuryl, 3,3-dimethyl-2,3-dihydrobenzofuryl, 2,3-dimethyl-2,3-dihydrobenzofuryl, cyclopentenopyridine, benzodihydropyrane, dihydropyrano-pyridine, wherein X$^1$ is unsubstituted or substituted with one or more of halogen, such as Cl, F, linear or branched —C$_{1-4}$ alkyl, CF$_3$, CHF$_2$, CMeF$_2$, —OCF$_3$, OCHF$_2$, CN, and C$_{1-4}$ alkoxy; or X$^1$ together with the N atom of the carbamate forms a pyrrolidinyl, piperdinyl, piperazinyl, which is unsubstituted or substituted with one or more of halogen, linear or branched —C$_{1-4}$ alkyl, CF$_3$, CHF$_2$, CMeF$_2$, OCF$_3$, OCHF$_2$, CN, and C$_{1-4}$ alkoxy.

In some embodiments of a compound of formula III, IVa or IVb, L$^3$ is a covalent bond and X$^2$ is H, C$_{3-6}$ cycloalkyl, C$_6$ aryl, 5-6 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy.

In some embodiments of a compound of formula III, IVa or IVb, L$^3$ is a covalent bond and X$^2$ is H, C$_{3-6}$ cycloalkyl, C$_6$ aryl, 6 membered heteroaryl, 4-8 membered heterocycloalkyl, wherein X$^2$ is unsubstituted or substituted with one or more of linear or branched C$_{1-4}$ alkyl, —C$_{1-4}$ alkoxy, NH$_2$, NMe$_2$, and halogen, e.g. F.

In some embodiments of a compound of formula III, IVa or IVb, L$^3$ is a covalent bond and X$^2$ is H, cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein X$^2$ is unsubstituted or substituted with one or more of linear or branched C$_{1-4}$ alkyl, —C$_{1-4}$ alkoxy, NH$_2$, NMe$_2$ and halogen.

In some embodiments of a compound of formula III, IVa or IVb, L$^3$ is a covalent bond and X$^2$ is H, cyclopropyl, cyclobutyl, azetidinyl, oxetanyl, pyrrolidinyl, piperidinyl, piperazinyl, morpholinyl, 8-oxa-3-azabicyclo[3.2.1]octan-3-yl, C$_6$ aryl, pyridinyl, wherein X$^2$ is unsubstituted or substituted with one or more of linear or branched C$_{1-6}$ alkyl, e.g. methyl, —C$_{1-4}$ alkoxy, e.g. —OMe, NMe$_2$ and halogen, e.g. F.

In some embodiments of a compound of formula III, IVa or IVb, p is 1, L$^3$ is a covalent bond and X$^2$ is H, cyclopropyl, methyl-cyclopropyl, fluoro-cyclopropyl, difluoro-cyclopropyl, cyclobutyl, C$_6$ aryl, methyl-C$_6$ aryl, fluoro-C$_6$ aryl, methoxy-C$_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 8-oxa-3-azabicyclo[3.2.1]octan-3-yl.

In some embodiments of a compound of formula III, IVa or IVb, L$^3$ is a covalent bond and X$^2$ is H, cyclopropyl, methyl-cyclopropyl, fluoro-cyclopropyl, difluoro-cyclopropyl, cyclobutyl, azetidinyl, NMe$_2$-azetidinyl, oxetanyl, methyl-oxetanyl, pyrrolidinyl, methyl-pyrrolidinyl, piperidinyl, Me-piperidinyl, Di-F-piperidinyl, N-Me-piperazinyl, morpholinyl, 8-oxa-3-azabicyclo[3.2.1]octan-3-yl, C$_6$ aryl, methoxy-C$_6$ aryl, pyridinyl.

In some embodiments of a compound of formula III, IVa or IVb, L$^3$ is a linear or branched C$_{1-4}$ alkyl, such as —CH$_2$—, and X$^2$ is H, C$_{3-6}$ cycloalkyl, C$_6$ aryl, 5-6 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy.

In some embodiments of a compound of formula III, IVa or IVb, L$^3$ is a linear or branched C$_{1-4}$ alkyl, such as —CH$_2$—, and X$^2$ is H, C$_{3-6}$ cycloalkyl, C$_6$ aryl, 6 membered heteroaryl, 4-8 membered heterocycloalkyl, wherein X$^2$ is unsubstituted or substituted with one or more of linear or branched C$_{1-4}$ alkyl, —C$_{1-4}$ alkoxy, NH$_2$, NMe$_2$, and halogen, e.g. F.

In some embodiments of a compound of formula III, IVa or IVb, L$^3$ is a linear or branched C$_{1-4}$ alkyl, such as —CH$_2$—, and X$^2$ is H, cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein X$^2$ is unsubstituted or substituted with one or more of linear or branched C$_{1-4}$ alkyl, —C$_{1-4}$ alkoxy, NH$_2$, NMe$_2$ and halogen.

In some embodiments of a compound of formula III, IVa or IVb, L$^3$ is a linear or branched C$_{1-4}$ alkyl, such as —CH$_2$—, and X$^2$ is H, cyclopropyl, methyl-cyclopropyl, fluoro-cyclopropyl, difluoro-cyclopropyl, cyclobutyl, C$_6$ aryl, methyl-C$_6$ aryl, fluoro-C$_6$ aryl, methoxy-C$_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula III, IVa or IVb, $L^3$ is linear or branched $C_{1-4}$ alkyl, such as —$CH_2$—, and $X^2$ is morpholinyl, N-methyl-morpholinyl, 2-oxa-5-azabicyclo[2.2.1]heptanyl, 8-oxa-3-azabicyclo[3.2.1]octan-3-yl.

In some embodiments of a compound of formula III, IVa or IVb, $L^3$ is —O— and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula III, IVa or IVb $L^3$ is —O— and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula III, IVa or IVb $L^3$ is —O— and $X^2$ is H, cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula III, IVa or IVb, $L^3$ is —O— and $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula III, IVa or IVb, $L^3$ is —O— and $X^2$ is cyclopropyl, pyrrolidinyl, N-methyl-pyrrolidinyl, In some embodiments of a compound of formula III, IVa or IVb, $L^3$ is —O—$CH_2$— and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula III, IVa or IVb, $L^3$ is —O—$CH_2$— and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula III, IVa or IVb, $L^3$ is —O—$CH_2$— and $X^2$ is H, cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula III, IVa or IVb, $L^3$ is —O—$CH_2$— and $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula III, IVa or IVb, $L^3$ is —O—$CH_2$— and $X^2$ is pyrrolidinyl, N-methyl-pyrrolidinyl.

In some embodiments of a compound of formula III, IVa or IVb, $L^3$ is —O—$CH_2$—$CH_2$— and $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula III, IVa or IVb, $L^3$ is —O—$CH_2$—$CH_2$— and $X^2$ is H, $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula III, IVa or IVb, $L^3$ is —O—$CH_2$—$CH_2$— and $X^2$ is H, cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula III, IVa or IVb, $L^3$ is —O—$CH_2$—$CH_2$— and $X^2$ is H, cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula III, IVa or IVb, $L^3$ is —O—$CH_2$—$CH_2$— and $X^2$ is morpholinyl.

In some embodiments of a compound of formula III, IVa or IVb, $X^1$ is a $C_6$ aryl or 6-membered heteroaryl, such as a pyridine, pyridazine, pyrimidine or pyrazine. In some embodiments of a compound of formula III, IVa or IVb, $X^1$ is a partially aromatic 6 to 10 membered aryl or heteroaryl, such as a 5-6 or 6-6 fused ring system with a 6 membered ring being a phenyl or pyridyl group. In some embodiments of a compound of formula III, IVa or IVb, $X^1$ is $C_{1-6}$ alkyl, $C_{3-6}$ cycloalkyl, 4-8 membered heterocycloalkyl. In some embodiments of a compound of formula III, IVa or IVb, $X^1$ together with the N atom of the carbamate forms a 4-8 membered heterocycloalkyl. Thus, in some embodiments a compound of formula I is a compound or pharmaceutically acceptable salts or stereoisomers thereof formula V, VI or VII:

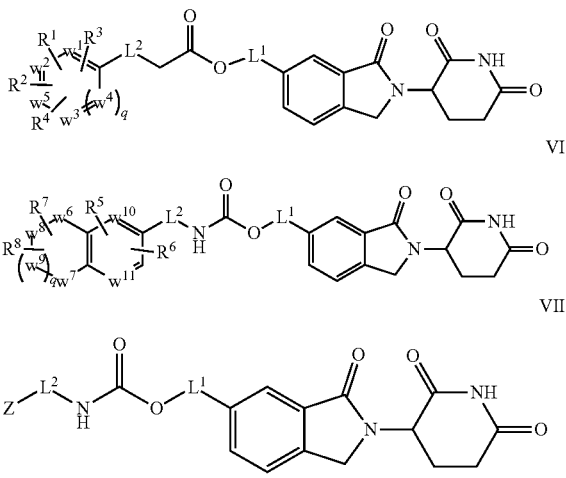

wherein one or two of $w^1$, $w^2$, $w^3$, $w^4$, $w^5$ are independently of each other selected from C, N, S, and O, and the remaining of $w^1$, $w^2$, $w^3$, $w^4$, $w^5$ are C;

one or two of $w^6$, $w^7$, $w^8$, $w^9$ are selected from C and O and the remaining of $w^6$, $w^7$, $w^8$, $w^9$ are C; $w^{10}$, $w^{11}$ are independently of each other selected from C and N;

$L^1$ is a covalent bond, linear or branched $C_{1-6}$ alkyl; $L^2$ is a covalent bond, linear or branched $C_{1-6}$ alkyl;

$R^1$, $R^2$, $R^3$, $R^4$ are independently of each other selected from H, linear or branched $-C_{1-6}$ alkyl, linear or branched $C_{1-6}$ heteroalkyl, $-C_{1-4}$ alkoxy, $CF_3$, $CHF_2$, $CMeF_2$, $-O-(CH_2)_2-OMe$, $OCF_3$, $OCHF_2$, $-C_{1-6}$ alkylamino, $-CN$, $-OC(O)-C_{1-6}$alkyl, $-N(H)C(O)-C_{1-6}$alkyl, $-C(O)O-C_{1-6}$alkyl, $-COOH$, $-C_{1-6}$alkylC(O)OH, $-C_{1-6}$alkylC(O)O$-C_{1-6}$alkyl, $NH_2$, $-C_{1-4}$ alkylhydroxy, and halogen, such as F, Cl or Br, e.g. F or Cl, or a group of formula $-L^3-X^2$, wherein $L^3$ is a covalent bond, linear or branched $C_{1-6}$ alkyl, $-O-$, $-C_{1-4}$ alkoxy; and $X^2$ is $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, $-C_{1-4}$ alkoxy, $NH_2$, $NMe_2$, halogen, $CF_3$, $CHF_2$, $CMeF_2$, $-O-(CH_2)_2-OMe$, $OCF_3$, $OCHF_2$, and $-C_{1-4}$ alkylhydroxy;

$R^5$, $R^6$, $R^7$ $R^8$ are independently of each other selected from H, linear or branched $C_{1-4}$ alkyl, such as methyl, and halogen, such as F or Cl, e.g. F;

Z is linear or branched $-C_{1-6}$ alkyl, $-C_{3-6}$ cycloalkyl, 4-8 membered heterocycloalkyl, wherein Z is unsubstituted or substituted with $C_{1-4}$ alkyl, $C_6$ aryl, $C_6$ aryloxy, 6 membered heteroaryl or $CF_3$; or Z together with the N atom of the carbamate forms a 4-8 membered heterocycloalkyl, which is unsubstituted or substituted with $C_{1-4}$ alkyl, $C_6$ aryl, $C_6$ aryloxy, 6 membered heteroaryl or $CF_3$;

q is 0, 1.

In some embodiments of a compound of formula V, VI or VII, $L^1$ is a linear or branched $C_{1-4}$ alkyl.

In some embodiments of a compound of formula V, VI or VII, $L^1$ is $-CH_2-$. In some embodiments of a compound of formula V, VI or VII, $L^1$ is $-CH(CH_3)-$.

In some embodiments of a compound of formula V, VI or VII, $L^2$ is a covalent bond. In some embodiments of a compound of formula V, VI or VII, $L^2$ is linear or branched $C_{1-4}$ alkyl. In some embodiments of a compound of formula V, VI or VII, $L^2$ is $-CH_2-$. In some embodiments of a compound of formula V, VI or VII, $L^2$ is $-CH(CH_3)-$.

In some embodiments of a compound of formula V, VI or VII, $L^3$ is a covalent bond. In some embodiments of a compound of formula V, VI or VII, $L^3$ is linear or branched $C_{1-4}$ alkyl, such as $-CH_2-$. In some embodiments of a compound of formula V, VI or VII, $L^3$ is $-O-$. In some embodiments of a compound of formula V, VI or VII, $L^3$ is linear or branched $C_{1-4}$ alkoxy, such as $-O-CH_2-$, $-O-(CH_2)_2-$.

In some embodiments of a compound of formula VI one of $w^{10}$ and $w^{11}$ is C and the other is N. In some embodiments of a compound of formula VI, q is 1, one of $w^{10}$ and $w^{11}$ is C and the other is N. In some embodiments of a compound of formula VI, q is 0, one of $w^{10}$ and $w^{11}$ is C and the other is N.

In some embodiments of a compound of formula VI, q is 0 and $w^8$ is C. In some embodiments of a compound of formula VI, q is 0, $w^8$ is C and $w^6$, $w^7$ are selected from C and O. In some embodiments of a compound of formula VI, q is 0, $w^8$ is C and $w^6$, $w^7$ are O. In some embodiments of a compound of formula VI, q is 0, $w^8$ is C and one of $w^6$, $w^7$ is C and the other of $w^6$, $w^7$ is O.

In some embodiments of a compound of formula VI, q is 1, and $w^6$, $w^7$, $w^8$, $w^9$ are C. In some embodiments of a compound of formula VI, q is 1, and $w^6$ is O and $w^7$, $w^8$, $w^9$ are C. In some embodiments of a compound of formula VI, q is 1, and $w^7$ is O and $w^6$, $w^8$, $w^9$ are C. In some embodiments of a compound of formula VI, q is 1, and $w^8$ is O and $w^6$, $w^7$, $w^9$ are C. In some embodiments of a compound of formula VI, q is 1, and $w^9$ is O and $w^6$, $w^7$, $w^8$ are C.

In some embodiments of a compound of formula V, q is 1 and $w^1$, $w^2$, $w^3$, $w^4$, $w^5$ are C. In some embodiments of a compound of formula V, q is 1 and either $w^1$ or $w^2$ or $w^3$ or $w^4$ or $w^5$ is N and the remaining 4 of $w^1$, $w^2$, $w^3$, $w^4$, $w^5$ are C. In some embodiments of a compound of formula V, q is 1 and $w^1$, $w^2$ or $w^1$, $w^3$ or $w^1$, $w^4$ or $w^1$, $w^5$ or $w^2$, $w^3$ are N and the remaining 3 of $w^1$, $w^2$, $w^3$, $w^4$, $w^5$ are C.

In some embodiments of a compound of formula V, q is 0 and $w^1$, $w^2$, $w^3$, $w^5$ are C. In some embodiments of a compound of formula V, q is 0 and either $w^1$ or $w^2$ or $w^3$ or $w^5$ is selected from N, S and O and the remaining 4 of $w^1$, $w^2$, $w^3$, $w^5$ are C. In some embodiments of a compound of formula V, q is 0 and $w^1$, $w^2$ or $w^1$, $w^3$ or $w^1$, $w^5$ are selected from N, S and O and the remaining 2 of $w^1$, $w^2$, $w^3$, $w^5$ are C.

In some embodiments of a compound of formula V, $R^1$, $R^2$, $R^3$, and $R^4$ are independently of each other selected from H, linear or branched $-C_{1-6}$ alkyl, linear or branched $C_{1-6}$ heteroalkyl, $-C_{1-4}$ alkoxy, $CF_3$, $CHF_2$, $CMeF_2$, $-O-(CH_2)_2-OMe$, $OCF_3$, $OCHF_2$, $-C_{1-6}$ alkylamino, $-CN$, $-OC(O)-C_{1-6}$alkyl, $-N(H)C(O)-C_{1-6}$alkyl, $-C(O)O-C_{1-6}$alkyl, $-COOH$, $-C_{1-6}$alkylC(O)OH, $-C_{1-6}$alkylC(O)O$-C_{1-6}$-alkyl, $NH_2$, $-C_{1-4}$ alkylhydroxy, and halogen, such as F, Cl or Br, e.g. F or Cl.

In some embodiments of a compound of formula V, $R^1$, $R^2$, $R^3$, and $R^4$ are independently of each other selected from H, linear or branched $-C_{1-6}$ alkyl, $-C_{1-4}$ alkoxy, $CF_3$, $CHF_2$, $CMeF_2$, $OCF_3$, $OCHF_2$, $-CN$, and halogen, such as F, Cl or Br, e.g. F or Cl.

In some embodiments of a compound of formula V, $R^1$ is H and $R^2$, $R^3$, $R^4$ are independently of each other selected from H, linear or branched $-C_{1-6}$ alkyl, linear or branched $C_{1-6}$ heteroalkyl, $-C_{1-4}$ alkoxy, $CF_3$, $CHF_2$, $CMeF_2$, $-O-(CH_2)_2-OMe$, $OCF_3$, $OCHF_2$, $-C_{1-6}$ alkylamino, $-CN$, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$-alkyl, $NH_2$, —$C_{1-4}$ alkylhydroxy, and halogen, such as F, Cl or Br, e.g. F or Cl.

In some embodiments of a compound of formula V, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula V, $L^1$ is —$CH_2$— and $R^1$, $R^2$, $R^3$, and $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula V, $L^1$ is —$CH_2$— and $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula V, $L^1$ is —$CH(CH_3)$— and $R^1$, $R^2$, $R^3$, and $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula V, $L^1$ is —$CH(CH_3)$— and $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula V, $L^1$ is —$CH_2$—, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula V, $L^1$ is —$CH_2$—, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula V, $L^1$ is —$CH(CH_3)$—, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula V, $L^1$ is —$CH(CH_3)$—, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula V, $L^2$ is a covalent bond and $R^1$, $R^2$, $R^3$, and $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula V, $L^2$ is a covalent bond and $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula V, $L^2$ is a covalent bond, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula V, $L^2$ is a covalent bond, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula V, $L^2$ is —$CH_2$—, and $R^1$, $R^2$, $R^3$, and $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula V, $L^2$ is —$CH_2$—, and $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula V, $L^2$ is —$CH(CH_3)$—, and $R^1$, $R^2$, $R^3$, and $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula V, $L^2$ is —$CH(CH_3)$—, and $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula V, $L^2$ is —$CH_2$—, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula V, $L^2$ is —$CH_2$—, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula V, $L^2$ is —$CH(CH_3)$—, $R^c$ is H, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula V, $L^2$ is —$CH(CH_3)$—, $R^c$ is H, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula V, one of $R^1$, $R^2$, $R^3$, and $R^4$ is a group of formula -$L^3$-$X^2$, wherein $L^3$ is a covalent bond and $X^2$ is $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula V, one of $R^1$, $R^2$, $R^3$, and $R^4$ is a group of formula -$L^3$-$X^2$, wherein $L^3$ is a covalent bond and $X^2$ is $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula V, one of $R^1$, $R^2$, $R^3$, and $R^4$ is a group of formula -$L^3$-$X^2$, wherein $L^3$ is a covalent bond and $X^2$ is cyclopropyl, cyclobutyl, azetidinyl, oxetanyl, pyrrolidinyl, piperidinyl, piperazinyl, morpholinyl, 8-oxa-3-azabicyclo[3.2.1]octan-3-yl, $C_6$ aryl, pyridinyl, wherein $X^2$ is unsubstituted or substituted with one or more of linear or branched $C_{1-4}$ alkyl, e.g. methyl, —$C_{1-4}$ alkoxy, e.g. —OMe, $NMe_2$ and halogen, e.g. F.

In some embodiments of a compound of formula V, one of $R^1$, $R^2$, $R^3$, and $R^4$ is a group of formula -$L^3$-$X^2$, wherein $L^3$ is a covalent bond and $X^2$ is cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula V, one of $R^1$, $R^2$, $R^3$, and $R^4$ is a group of formula -$L^3$-$X^2$, wherein $L^3$ is a covalent bond and $X^2$ is H, cyclopropyl, methyl-cyclopropyl, fluoro-cyclopropyl, difluoro-cyclopropyl, cyclobutyl, azetidinyl, $NMe_2$-azetidinyl, oxetanyl, methyl-oxetanyl, pyrrolidinyl, methyl-pyrrolidinyl, piperidinyl, Me-piperidinyl, Di-F-piperidinyl, N-Me-piperazinyl, morpholinyl, 8-oxa-3-azabicyclo[3.2.1]octan-3-yl, $C_6$ aryl, methoxy-$C_6$ aryl, pyridinyl.

In some embodiments of a compound of formula V, one of $R^1$, $R^2$, $R^3$, and $R^4$ is a group of formula -$L^3$-$X^2$, wherein $L^3$ is a linear or branched $C_{1-4}$ alkyl, such as —$CH_2$—, and $X^2$ is $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula V, one of $R^1$, $R^2$, $R^3$, and $R^4$ is a group of formula -$L^3$-$X^2$, wherein $L^3$ is a linear or branched $C_{1-4}$ alkyl, such as —$CH_2$—, and $X^2$ is $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula V, one of $R^1$, $R^2$, $R^3$, and $R^4$ is a group of formula -$L^3$-$X^2$, wherein $L^3$ is a linear or branched $C_{1-4}$ alkyl, such as —$CH_2$—, and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula V, one of $R^1$, $R^2$, $R^3$, and $R^4$ is a group of formula -$L^3$-$X^2$, wherein $L^3$ is a linear or branched $C_{1-4}$ alkyl, such as —$CH_2$—, and $X^2$ is cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula V, one of $R^1$, $R^2$, $R^3$, and $R^4$ is a group of formula -$L^3$-$X^2$, wherein $L^3$ is linear or branched $C_{1-4}$ alkyl, such as —$CH_2$—, and $X^2$ is morpholinyl, N-methyl-morpholinyl, 2-oxa-5-azabicyclo[2.2.1]heptanyl, 8-oxa-3-azabicyclo[3.2.1]octan-3-yl.

In some embodiments of a compound of formula V, one of $R^1$, $R^2$, $R^3$, and $R^4$ is a group of formula -$L^3$-$X^2$, wherein $L^3$ is —O— and $X^2$ is $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula V, one of $R^1$, $R^2$, $R^3$, and $R^4$ is a group of formula -$L^3$-$X^2$, wherein $L^3$ is —O— and $X^2$ is $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula V, one of $R^1$, $R^2$, $R^3$, and $R^4$ is a group of formula -$L^3$-$X^2$, wherein $L^3$ is —O— and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula V, one of $R^1$, $R^2$, $R^3$, and $R^4$ is a group of formula -$L^3$-$X^2$, wherein $L^3$ is —O— and $X^2$ is cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula V, one of $R^1$, $R^2$, $R^3$, and $R^4$ is a group of formula -$L^3$-$X^2$, wherein $L^3$ is —O— and $X^2$ is cyclopropyl, pyrrolidinyl, N-methyl-pyrrolidinyl, In some embodiments of a compound of formula V, one of $R^1$, $R^2$, $R^3$, and $R^4$ is a group of formula -$L^3$-$X^2$, wherein $L^3$ is —O—$CH_2$— and $X^2$ is $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula V, one of $R^1$, $R^2$, $R^3$, and $R^4$ is a group of formula -$L^3$-$X^2$, wherein $L^3$ is —O—$CH_2$— and $X^2$ is $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula V, one of $R^1$, $R^2$, $R^3$, and $R^4$ is a group of formula -$L^3$-$X^2$, wherein $L^3$ is —O—$CH_2$— and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula V, one of $R^1$, $R^2$, $R^3$, and $R^4$ is a group of formula -$L^3$-$X^2$, wherein $L^3$ is —O—$CH_2$— and $X^2$ is cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula V, one of $R^1$, $R^2$, $R^3$, and $R^4$ is a group of formula -$L^3$-$X^2$, wherein $L^3$ is —O—$CH_2$— and $X^2$ is pyrrolidinyl, N-methyl-pyrrolidinyl.

In some embodiments of a compound of formula V, one of $R^1$, $R^2$, $R^3$, and $R^4$ is a group of formula -$L^3$-$X^2$, wherein $L^3$ is —O—$CH_2$—$CH_2$— and $X^2$ is $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula V, one of $R^1$, $R^2$, $R^3$, and $R^4$ is a group of formula -$L^3$-$X^2$, wherein $L^3$ is —O—$CH_2$—$CH_2$— and $X^2$ is $C_{3-6}$ cycloalkyl, $C_6$ aryl, 6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, and halogen, e.g. F.

In some embodiments of a compound of formula V, one of $R^1$, $R^2$, $R^3$, and $R^4$ is a group of formula -$L^3$-$X^2$, wherein $L^3$ is —O—$CH_2$—$CH_2$—, and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, $NH_2$, $NMe_2$ and halogen.

In some embodiments of a compound of formula V, one of $R^1$, $R^2$, $R^3$, and $R^4$ is a group of formula -$L^3$-$X^2$, wherein $L^3$ is —O—$CH_2$—$CH_2$— and $X^2$ is cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula V, one of $R^1$, $R^2$, $R^3$, and $R^4$ is a group of formula -$L^3$-$X^2$, wherein $L^3$ is —O—$CH_2$—$CH_2$— and $X^2$ is morpholinyl.

In some embodiments, a compound of formula I is a compound or pharmaceutically acceptable salts or stereoisomers thereof formula Va:

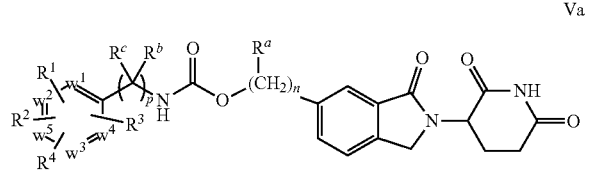

Va wherein
one or two of $w^1$, $w^2$, $w^3$, $w^4$ $w^5$ are independently of each other selected from C, N, S, and O, and the remaining of $w^1$, $w^2$, $w^3$, $w^4$, $w^5$ are C;

$R^1$, $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl, or a group of formula -$L^3$-$X^2$, wherein $L^3$ is a covalent bond, linear or branched $C_{1-6}$ alkyl, —O—, —$C_{1-4}$ alkoxy and $X^2$ is $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy;

$R^a$ is H, linear or branched $C_{1-4}$ alkyl, $R^b$, $R^c$ are independently of each other H, linear or branched $C_{1-4}$ alkyl; n is 1, or 2; and p is 0 or 1.

In some embodiments of a compound of formula Va, n is 1. In some embodiments n is 1 and $R^a$ is H. In some embodiments of a compound of formula Va, n is 1 and $R^a$ is methyl. In some embodiments of a compound of formula Va, n is 1, p is 0 and $R^a$ is H. In some embodiments of a compound of formula Va, n is 1, p is 0 and $R^a$ is methyl In some embodiments of a compound of formula Va, p is 0. In some embodiments of a compound of formula Va, p is 1. In some embodiments of a compound of formula Va, p is 1, and $R^b$ and $R^c$ are H. In some embodiments of a compound of formula Va, p is 1, $R^b$ is methyl and $R^c$ is H.

In some embodiments of a compound of formula Va, $w^1$, $w^2$, $w^3$, $w^4$, $w^5$ are C. In some embodiments of a compound of formula Va, either $w^1$ or $w^2$ or $w^3$ or $w^4$ or $w^5$ is N and the remaining 4 of $w^1$, $w^2$, $w^3$, $w^4$, $w^5$ are C. In some embodiments of a compound of formula Va, $w^1$, $w^2$ or $w^1$, $w^3$ or $w^1$, $w^4$ or $w^2$, $w^3$ are N and the remaining 3 of $w^1$, $w^2$, $w^3$, $w^4$, $w^5$ are C.

In some embodiments of a compound of formula Va, $L^3$ is a covalent bond. In some embodiments of a compound of formula Va, $L^3$ is linear or branched $C_{1-4}$ alkyl, such as —$CH_2$—. In some embodiments of a compound of formula Va, $L^3$ is —O—. In some embodiments of a compound of formula Va, $L^3$ is linear or branched $C_{1-4}$ alkoxy, such as —O—$CH_2$—, —O—$(CH_2)_2$—.

In some embodiments of a compound of formula Va, $R^1$, $R^2$, $R^3$, and $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$-alkyl, $NH_2$, —$C_{1-4}$ alkylhydroxy, and halogen, such as F, Cl or Br, e.g. F or Cl.

In some embodiments of a compound of formula Va, $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$-alkyl, $NH_2$, —$C_{1-4}$ alkylhydroxy, and halogen, such as F, Cl or Br, e.g. F or Cl.

In some embodiments of a compound of formula Va, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va, n is 1, $R^a$ is H and $R^1$, $R^2$, $R^3$, and $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va, n is 1, $R^a$ is H and $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va, n is 1, $R^a$ is $CH_3$ and $R^1$, $R^2$, $R^3$, and $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va, n is 1, $R^a$ is $CH_3$ and $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va, n is 1, $R^a$ is H, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va, n is 1, $R^a$ is H, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va, n is 1, $R^a$ is $CH_3$, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va, n is 1, $R^a$ is $CH_3$, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va, p is 0 and $R^1$, $R^2$, $R^3$, and $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va, p is 0 and $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va, p is 0, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va, p is 0, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va, p is 1, $R^b$, $R^c$ are H, and $R^1$, $R^2$, $R^3$, and $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va, p is 1, $R^b$, $R^c$ are H, and $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va, p is 1, $R^b$ is $CH_3$, $R^c$ is H, and $R^1$, $R^2$, $R^3$, and $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va, p is 1, $R^b$ is $CH_3$, R is H, and $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va, p is 1, $R^b$, $R^c$ are H, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va, p is 1, $R^b$, $R^c$ are H, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va, p is 1, $R^b$ is $CH_3$, $R^c$ is H, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va, p is 1, $R^b$ is $CH_3$, $R^c$ is H, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va, $R^1$ is $C_{3-6}$ cycloalkyl, —$C_{1-4}$ alkyl-$C_{3-6}$ cycloalkyl, —O—$C_{3-6}$ cycloalkyl, —$C_{1-4}$ alkoxy-$C_{3-6}$ cycloalkyl, $C_{6-10}$ aryl, —$C_{1-4}$ alkyl-$C_{6-10}$ aryl, —O—$C_{6-10}$ aryl, —$C_{1-4}$ alkoxy-$C_{6-10}$ aryl, 5-10 membered heteroaryl, —$C_{1-4}$ alkyl-(5-10 membered heteroaryl), —O-(5-10 membered heteroaryl), —$C_{1-4}$ alkoxy-(5-10 membered heteroaryl), 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl.

In some embodiments of a compound of formula Va, $R^1$ is $C_{3-6}$ cycloalkyl, $C_{6-10}$ aryl, 5-10 membered heteroaryl, 4-8 membered heterocycloalkyl, wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CH_1F_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl.

In some embodiments of a compound of formula Va, $R^1$ is —$C_{1-4}$ alkyl-$C_{3-6}$ cycloalkyl, —$C_{1-4}$ alkyl-$C_{6-10}$ aryl, —$C_{1-4}$ alkyl-(5-10 membered heteroaryl), —$C_{1-4}$ alkyl-(4-8 membered heterocycloalkyl), wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl.

In some embodiments of a compound of formula Va, $R^1$ is —O—$C_{3-6}$ cycloalkyl, —O—$C_{6-10}$ aryl, —O— (5-10 membered heteroaryl), —O-(4-8 membered heterocycloalkyl), wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl.

In some embodiments of a compound of formula Va, $R^1$ is —$C_{1-4}$ alkoxy-$C_{3-6}$ cycloalkyl, —$C_{1-4}$ alkoxy-$C_{6-10}$ aryl, —$C_{1-4}$ alkoxy-(5-10 membered heteroaryl), —$C_{1-4}$ alkoxy-(4-8 membered heterocycloalkyl), wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl.

In some embodiments of a compound of formula Va, $R^1$ is $C_{3-6}$ cycloalkyl, —O—$C_{3-6}$ cycloalkyl, $C_{6-10}$ aryl, 5-10 membered heteroaryl, 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy;

and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl.

In some embodiments of a compound of formula Va, $R^1$ is a group of formula -$L^3$-$X^2$, wherein $L^3$ is a covalent bond, linear or branched $C_{1-4}$ alkyl, —O—, —$C_{1-4}$ alkoxy and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl.

In some embodiments of a compound of formula Va, $R^1$ is a group of formula -$L^3$-$X^2$, wherein $L^3$ is a covalent bond, —$CH_2$—, —O—, —$OCH_2$—, —$O(CH_2)_2$— and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, e.g. —OMe, $NMe_2$, halogen, e.g. F; and $R^2$, $R^3$, $R^4$ are independently of each other selected from H, halogen, e.g. Cl, F, linear or branched —$C_{1-4}$ alkyl, e.g., Me, Et, t-But, $CF_3$, $CHF_2$, $CMeF_2$, —$OCF_3$, $OCHF_2$, CN, and $C_{1-4}$ alkoxy, e.g. —OMe.

In some embodiments of a compound of formula Va, $R^1$ is a group of formula -$L^3$-$X^2$, wherein $L^3$ is a covalent bond, —$CH_2$—, —O—, —$OCH_2$—, —$O(CH_2)_2$— and $X^2$ is cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl; and $R^2$, $R^3$, $R^4$ are independently of each other selected from H, halogen, e.g. Cl, F, linear or branched —$C_{1-4}$ alkyl, e.g., Me, Et, t-But, $CF_3$, $CHF_2$, $CMeF_2$, —$OCF_3$, $OCHF_2$, CN, and $C_{1-4}$ alkoxy, e.g. —OMe.

In some embodiments of a compound of formula Va, $R^1$ is $C_{3-6}$ cycloalkyl, —$C_{1-4}$ alkyl-$C_{3-6}$ cycloalkyl, —O—$C_{3-6}$ cycloalkyl, —$C_{1-4}$ alkoxy-$C_{3-6}$ cycloalkyl, $C_{6-10}$ aryl, —$C_{1-4}$ alkyl-$C_{6-10}$ aryl, —O—$C_{6-10}$ aryl, —$C_{1-4}$ alkoxy-$C_{6-10}$ aryl, 5-10 membered heteroaryl, —$C_{1-4}$ alkyl-(5-10 membered heteroaryl), —O-(5-10 membered heteroaryl), —$C_{1-4}$ alkoxy-(5-10 membered heteroaryl), 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl; and n is 1, $R^a$ is H; and p is 0.

In some embodiments of a compound of formula Va, $R^1$ is $C_{3-6}$ cycloalkyl, $C_{6-10}$ aryl, 5-10 membered heteroaryl, 4-8 membered heterocycloalkyl, wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CH_1F_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl; and n is 1, $R^a$ is H; and p is 0.

In some embodiments of a compound of formula Va, $R^1$ is —$C_{1-4}$ alkyl-$C_{3-6}$ cycloalkyl, —$C_{1-4}$ alkyl-$C_{6-10}$ aryl, —$C_{1-4}$ alkyl-(5-10 membered heteroaryl), —$C_{1-4}$ alkyl-(4-8 membered heterocycloalkyl), wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl; and n is 1, $R^a$ is H; and p is 0.

In some embodiments of a compound of formula Va, $R^1$ is —O—$C_{3-6}$ cycloalkyl, —O—$C_{6-10}$ aryl, —O— (5-10 membered heteroaryl), —O-(4-8 membered heterocycloalkyl), wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl; and n is 1, $R^a$ is H; and p is 0.

In some embodiments of a compound of formula Va, $R^1$ is —$C_{1-4}$ alkoxy-$C_{3-6}$ cycloalkyl, —$C_{1-4}$ alkoxy-$C_{6-10}$ aryl, —$C_{1-4}$ alkoxy-(5-10 membered heteroaryl), —$C_{1-4}$ alkoxy-(4-8 membered heterocycloalkyl), wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl; and n is 1, $R^a$ is H; and p is 0.

In some embodiments of a compound of formula Va, $R^1$ is $C_{3-6}$ cycloalkyl, —O—$C_{3-6}$ cycloalkyl, $C_{6-10}$ aryl, 5-10 membered heteroaryl, 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy;

and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl; and n is 1, $R^a$ is H; and p is 0.

In some embodiments of a compound of formula Va, $R^1$ is a group of formula -$L^3$-$X^2$, wherein $L^3$ is a covalent bond, linear or branched $C_{1-4}$ alkyl, —O—, —$C_{1-4}$ alkoxy and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl; and n is 1, $R^a$ is H; and p is 0.

In some embodiments of a compound of formula Va, $R^1$ is a group of formula -$L^3$-$X^2$, wherein $L^3$ is a covalent bond, —$CH_2$—, —O—, —$OCH_2$—, —$O(CH_2)_2$— and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, e.g. —OMe, $NMe_2$, halogen, e.g. F; and $R^2$, $R^3$, $R^4$ are independently of each other selected from H, halogen, e.g. Cl, F, linear or branched —$C_{1-4}$ alkyl, e.g., Me, Et, t-But, $CF_3$, $CHF_2$, $CMeF_2$, —$OCF_3$, $OCHF_2$, CN, and $C_{1-4}$ alkoxy, e.g. —OMe; and n is 1, $R^a$ is H; and p is 0.

In some embodiments of a compound of formula Va, $R^1$ is a group of formula -$L^3$-$X^2$, wherein $L^3$ is a covalent bond, —$CH_2$—, —O—, —$OCH_2$—, —$O(CH_2)_2$— and $X^2$ is cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl; and $R^2$, $R^3$, $R^4$ are independently of each other selected from H, halogen, e.g. Cl, F, linear or branched —$C_{1-4}$ alkyl, e.g., Me, Et, t-But, $CF_3$, $CHF_2$, $CMeF_2$, —$OCF_3$, $OCHF_2$, CN, and $C_{1-4}$ alkoxy, e.g. —OMe; and n is 1, $R^a$ is H; and p is 0.

In some embodiments of a compound of formula Va, $R^1$ is $C_{3-6}$ cycloalkyl, —$C_{1-4}$ alkyl-$C_{3-6}$ cycloalkyl, —O—$C_{3-6}$ cycloalkyl, —$C_{1-4}$ alkoxy-$C_{3-6}$ cycloalkyl, $C_{6-10}$ aryl, —$C_{1-4}$ alkyl-$C_{6-10}$ aryl, —O—$C_{6-10}$ aryl, —$C_{1-4}$ alkoxy-$C_{6-10}$ aryl, 5-10 membered heteroaryl, —$C_{1-4}$ alkyl-(5-10 membered heteroaryl), —O-(5-10 membered heteroaryl), —$C_{1-4}$ alkoxy-(5-10 membered heteroaryl), 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl; and n is 1, $R^a$ is $CH_3$; and p is 0.

In some embodiments of a compound of formula Va, $R^1$ is $C_{6-10}$ aryl, wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl; and n is 1, $R^a$ is $CH_3$; and p is 0.

In some embodiments of a compound of formula Va, $R^1$ is $C_{6-10}$ aryl, wherein $R^1$ is unsubstituted or substituted with linear or branched —$C_{1-4}$ alkyl, e.g. methyl, —$C_{1-4}$ alkoxy, e.g. —OMe, and halogen, such as F, Cl, e.g. Cl; and n is 1, $R^a$ is $CH_3$; and p is 0.

In some embodiments of a compound of formula Va, $R^1$ is $C_{3-6}$ cycloalkyl, —$C_{1-4}$ alkyl-$C_{3-6}$ cycloalkyl, —O—$C_{3-6}$ cycloalkyl, —$C_{1-4}$ alkoxy-$C_{3-6}$ cycloalkyl, $C_{6-10}$ aryl, —$C_{1-4}$ alkyl-$C_{6-10}$ aryl, —O—$C_{6-10}$ aryl, —$C_{1-4}$ alkoxy-$C_{6-10}$ aryl, 5-10 membered heteroaryl, —$C_{1-4}$ alkyl-(5-10 membered heteroaryl), —O-(5-10 membered heteroaryl), —$C_{1-4}$ alkoxy-(5-10 membered heteroaryl), 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl; and n, p are 1, $R^a$, $R^b$, $R^C$ are H.

In some embodiments of a compound of formula Va, $R^1$ is $C_{6-10}$ aryl, wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl; and n, p are 1, $R^a$, $R^b$, $R^c$ are H.

In some embodiments of a compound of formula Va, $R^1$ is $C_{6-10}$ aryl, wherein $R^1$ is unsubstituted or substituted with —$C_{1-4}$ alkoxy, e.g. —OMe; and n, p are 1, $R^a$, $R^b$, $R^c$ are H.

In some embodiments of a compound of formula Va, $R^1$ is $C_{3-6}$ cycloalkyl, —$C_{1-4}$ alkyl-$C_{3-6}$ cycloalkyl, —O—$C_{3-6}$ cycloalkyl, —$C_{1-4}$ alkoxy-$C_{3-6}$ cycloalkyl, $C_{6-10}$ aryl, —$C_{1-4}$ alkyl-$C_{6-10}$ aryl, —O—$C_{6-10}$ aryl, —$C_{1-4}$ alkoxy-$C_{6-10}$ aryl, 5-10 membered heteroaryl, —$C_{1-4}$ alkyl-(5-10 membered heteroaryl), —O-(5-10 membered heteroaryl), —$C_{1-4}$ alkoxy-(5-10 membered heteroaryl), 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—(CH$_2$)$_2$—OMe, OCF$_3$, OCHF$_2$, and —C$_{1-4}$ alkylhydroxy; and R$^2$, R$^3$, R$^4$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, NH$_2$, —C$_{1-4}$ alkylhydroxy, and halogen, such as F, Cl or Br, e.g. F or Cl; and n, p are 1, R$^a$, R$^c$ are H, R$^b$ is CH$_3$.

In some embodiments of a compound of formula Va, R$^1$ is C$_{6-10}$ aryl, wherein R$^1$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and R$^2$, R$^3$, R$^4$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, NH$_2$, —C$_{1-4}$ alkylhydroxy, and halogen, such as F, Cl or Br, e.g. F or Cl; and n, p are 1, R$^a$, R$^c$ are H, R$^b$ is CH$_3$.

In some embodiments of a compound of formula Va, R$^1$ is C$_{6-10}$ aryl; and n, p are 1, R$^a$, R$^c$ are H, R$^b$ is CH$_3$.

More specific embodiments of the compound of formula Va are provided by formula Va-1, wherein w$^1$ to w$^5$ are C, and by formula Va-2, Va-3, Va-4, wherein one of w$^1$ to w$^5$ is N, more specifically, wherein w$^1$ is N, w$^2$ to w$^5$ are C; or w$^2$ is N, w$^1$ and w$^3$ to w$^5$ are C; or w$^3$ is N, w$^1$, w$^2$ and w$^4$, w$^5$ are C

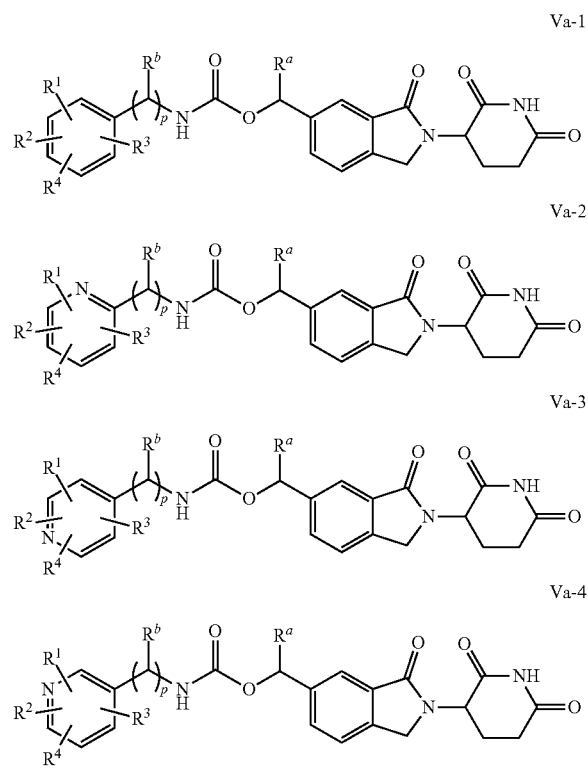

wherein
R$^1$, R$^2$, R$^3$, R$^4$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —OC(O)—C$_{1-6}$alkyl, —N(H)C(O)—C$_{1-6}$alkyl, —C(O)O—C$_{1-6}$alkyl, —COOH, —C$_{1-6}$alkylC(O)OH, —C$_{1-6}$alkylC(O)O—C$_{1-6}$alkyl, NH$_2$, —C$_{1-4}$ alkylhydroxy, and halogen, such as F, Cl or Br, e.g. F or Cl, or a group of formula -L$^3$-X$^2$, wherein L$^3$ is a covalent bond, linear or branched C$_{1-6}$ alkyl, —O—, or —C$_{1-4}$ alkoxy and X$^2$ is C$_{3-6}$ cycloalkyl, C$_{6-10}$ aryl, 5-10 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CH$_1$F$_2$, CMeF$_2$, —O—(CH$_2$)$_2$—OMe, OCF$_3$, OCHF$_2$, and —C$_{1-4}$ alkylhydroxy;

R$^a$, R$^b$ are independently of each other H or methyl; and p is 0 or 1.

In some embodiments of a compound of formula Va-1, Va-2, Va-3, Va-4, p is 0. In some embodiments of a compound of formula Va-1, Va-2, Va-3, Va-4, p is 1. In some embodiments of a compound of formula Va-1, Va-2, Va-3, Va-4, p is 1 and R$^b$ is H. In some embodiments of a compound of formula Va-1, Va-2, Va-3, Va-4, p is 1 and R$^b$ is methyl.

In some embodiments of a compound of formula Va-1, Va-2, Va-3, Va-4, p is 0 and R$^a$ is H. In some embodiments of a compound of formula Va-1, Va-2, Va-3, Va-4, p is 0 and R$^a$ is methyl. In some embodiments of a compound of formula Va-1, Va-2, Va-3, Va-4, p is 1, R$^b$ is H and R$^a$ is H. In some embodiments of a compound of formula Va-1, Va-2, Va-3, Va-4, p is 1, R$^b$ is methyl and R$^a$ is H.

In some embodiments of a compound of formula Va-1, Va-2, Va-3, Va-4, L$^3$ is a covalent bond. In some embodiments of a compound of formula Va-1, Va-2, Va-3, Va-4, L$^3$ is linear or branched C$_{1-4}$ alkyl, such as —CH$_2$—. In some embodiments of a compound of formula Va-1, Va-2, Va-3, Va-4, L$^3$ is —O—. In some embodiments L$^3$ is linear or branched C$_{1-4}$ alkoxy, such as —O—CH$_2$—, —O—(CH$_2$)$_2$—.

In some embodiments of a compound of formula Va-1, Va-2, Va-3, Va-4, R$^1$, R$^2$, R$^3$, and R$^4$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —OC(O)—C$_{1-6}$alkyl, —N(H)C(O)—C$_{1-6}$alkyl, —C(O)O—C$_{1-6}$alkyl, —COOH, —C$_{1-6}$alkylC(O)OH, —C$_{1-6}$ alkylC(O)O—C$_{1-6}$alkyl, NH$_2$, —C$_{1-4}$ alkylhydroxy, and halogen, such as F, Cl or Br, e.g. F or Cl.

In some embodiments of a compound of formula Va-1, Va-2, Va-3, Va-4, R$^1$, R$^2$, R$^3$, and R$^4$ are independently of each other selected from H, linear or branched —C$_{1-6}$ alkyl, —C$_{1-4}$ alkoxy, CF$_3$, CHF$_2$, CMeF$_2$, OCF$_3$, OCHF$_2$, —CN, and halogen, such as F, Cl or Br, e.g. F or Cl.

In some embodiments of a compound of formula Va-1, Va-2, Va-3, Va-4, R$^1$ is H and R$^2$, R$^3$, R$^4$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —OC(O)—C$_{1-6}$alkyl, —N(H)C(O)—C$_{1-6}$alkyl, —C(O)O—C$_{1-6}$alkyl, —COOH, —C$_{1-6}$ alkylC(O)OH, —C$_{1-6}$alkylC(O)O—C$_{1-6}$alkyl, NH$_2$, —C$_{1-4}$ alkylhydroxy, and halogen, such as F, Cl or Br, e.g. F or Cl.

In some embodiments of a compound of formula Va-1, Va-2, Va-3, Va-4, R$^1$ is H and R$^2$, R$^3$, R$^4$ are independently of each other selected from H, linear or branched —C$_{1-6}$ alkyl, —C$_{1-4}$ alkoxy, CF$_3$, CHF$_2$, CMeF$_2$, OCF$_3$, OCHF$_2$, —CN, and halogen, such as F, Cl or Br, e.g. F or Cl.

In some embodiments of a compound of formula Va-1, Va-2, Va-3, Va-4, R$^a$ is H and R$^1$, R$^2$, R$^3$, and R$^4$ are independently of each other selected from H, linear or branched —C$_{1-6}$ alkyl, linear or branched C$_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-1, Va-2, Va-3, Va-4, $R^a$ is H and $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1, Va-2, Va-3, Va-4, $R^a$ is $CH_3$ and $R^1$, $R^2$, $R^3$, and $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1, Va-2, Va-3, Va-4, $R^a$ is $CH_3$ and $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1, Va-2, Va-3, Va-4, $R^a$ is $CH_3$, and $R^1$, $R^2$, $R^3$, $R^4$ are independently of each other selected from H, halogen, such as Cl, F, linear or branched —$C_{1-4}$ alkyl, such as methyl, fluorinated $C_{1-4}$ alkoxy, such as —$OCF_3$.

In some embodiments of a compound of formula Va-1, Va-2, Va-3, Va-4, $R^a$ is H, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-1, Va-2, Va-3, Va-4, $R^a$ is H, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1, Va-2, Va-3, Va-4, $R^a$ is $CH_3$, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-1, Va-2, Va-3, Va-4, $R^a$ is $CH_3$, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1, $R^a$ is $CH_3$, $R^1$ is H and $R^2$, $R^3$, $R^4$ are independently of each other selected from H, halogen, such as Cl, F, linear or branched —$C_{1-4}$ alkyl, such as methyl, fluorinated $C_{1-4}$ alkoxy, such as —$OCF_3$.

In some embodiments of a compound of formula Va-1, Va-2, Va-3, Va-4, p is 0 and $R^1$, $R^2$, $R^3$, and $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-1, Va-2, Va-3, Va-4, p is 0 and $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1, Va-2, Va-3, Va-4, p is 0, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-1, Va-2, Va-3, Va-4, p is 0, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1, Va-2, Va-3, Va-4, p is 0, $R^a$ is H and $R^1$, $R^2$, $R^3$, and $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-1, Va-2, Va-3, Va-4, p is 0, $R^a$ is H and $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1, Va-2, Va-3, Va-4, p is 0, $R^a$ is $CH_3$ and $R^1$, $R^2$, $R^3$, and $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-1, Va-2, Va-3, Va-4, p is 0, $R^a$ is $CH_3$ and $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1, Va-2, Va-3, Va-4, p is 0, $R^a$ is $CH_3$, and $R^1$, $R^2$, $R^3$, $R^4$ are independently of each other selected from H, halogen, such as Cl, F, linear or branched —$C_{1-4}$ alkyl, such as methyl, fluorinated $C_{1-4}$ alkoxy, such as —$OCF_3$.

In some embodiments of a compound of formula Va-1, Va-2, Va-3, Va-4, p is 0, $R^a$ is H, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-1, Va-2, Va-3, Va-4, p is 0, $R^a$ is H, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1, Va-2, Va-3, Va-4, p is 0, $R^a$ is $CH_3$, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-1, Va-2, Va-3, Va-4, p is 0, $R^a$ is $CH_3$, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1, $w^a$ is $CH_3$, p is 0, $R^1$ is H and $R^2$, $R^3$, $R^4$ are independently of each other selected from H, halogen, such as Cl, F, linear or branched —$C_{1-4}$ alkyl, such as methyl, fluorinated $C_{1-4}$ alkoxy, such as —$OCF_3$.

In some embodiments of a compound of formula Va-1, Va-2, Va-3, Va-4, p is 1, $R^b$ and $R^c$ are H, and $R^1$, $R^2$, $R^3$, and $R^4$ are independently of each other selected from H, linear or branched —$C_{1-6}$ alkyl, linear or branched $C_{1-6}$ heteroalkyl, —$C_{1-4}$ alkoxy, $CF_3$, $CH_1F_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-1, Va-2, Va-3, Va-4, p is 1, $R^b$ and $R^c$ are H, and $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1, p is 1, $R^b$ and $R^c$ are H, and $R^1$, $R^2$, $R^3$, and $R^4$ are independently of each other selected from H and $C_{1-4}$ alkoxy, e.g. —OMe.

In some embodiments of a compound of formula Va-1, Va-2, Va-3, Va-4, p is 1, $R^b$ is $CH_3$, $R^c$ is H, and $R^1$, $R^2$, $R^3$, and $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1, Va-2, Va-3, Va-4, p is 1, $R^b$ is $CH_3$, $R^c$ is H, and $R^1$, $R^2$, $R^3$, and $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1, Va-2, Va-3, Va-4, p is 1, $R^b$ and $R^c$ are H, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-1, Va-2, Va-3, Va-4, p is 1, $R^b$ and $R^c$ are H, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1, p is 1, $R^b$ and $R^c$ are H, $R^1$ is H and $R^2$, $R^3$, and $R^4$ are independently of each other selected from H and $C_{1-4}$ alkoxy, e.g. —OMe.

In some embodiments of a compound of formula Va-1, Va-2, Va-3, Va-4, p is 1, $R^b$ is $CH_3$, $R^c$ is H, $R^1$ is H and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1, Va-2, Va-3, Va-4, p is 1, $R^b$ is $CH_3$, $R^c$ is H, $R^1$ is H and $R^2$, $R^3$, $R^4$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1, p is 1, $R^b$ is $CH_3$, $R^c$ is H, and $R^1$, $R^2$, $R^3$, $R^4$ are H.

In some embodiments of a compound of formula, Va-1, Va-2, Va-3, Va-4, $R^1$ is $C_{3-6}$ cycloalkyl, —$C_{1-4}$ alkyl-$C_{3-6}$ cycloalkyl, —O—$C_{3-6}$ cycloalkyl, —$C_{1-4}$ alkoxy-$C_{3-6}$ cycloalkyl, $C_{6-10}$ aryl, —$C_{1-4}$ alkyl-$C_{6-10}$ aryl, —O—$C_{6-10}$ aryl, —$C_{1-4}$ alkoxy-$C_{6-10}$ aryl, 5-10 membered heteroaryl, —$C_{1-4}$ alkyl-(5-10 membered heteroaryl), —O-(5-10 membered heteroaryl), —$C_{1-4}$ alkoxy-(5-10 membered heteroaryl), 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-1, Va-2, Va-3, Va-4, $R^1$ is $C_{3-6}$ cycloalkyl, —O—$C_{3-6}$ cycloalkyl, $C_{6-10}$ aryl, 5-10 membered heteroaryl, 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1, Va-2, Va-3, Va-4, $R^1$ is a group of formula -$L^3$-$X^2$, wherein $L^3$ is a covalent bond, linear or branched $C_{1-4}$ alkyl, —O—, —$C_{1-4}$ alkoxy and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1, Va-2, Va-3, Va-4, $R^1$ is a group of formula -$L^3$-$X^2$, wherein $L^3$ is a covalent bond, —$CH_2$—, —O—, —$OCH_2$—, —$O(CH_2)_2$— and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, e.g. —OMe, $NMe_2$, halogen, e.g. F; and $R^2$, $R^3$, $R^4$ are independently of each other selected from H, halogen, e.g. Cl, F, linear or branched —$C_{1-4}$ alkyl, e.g., Me, Et, t-But, $CF_3$, $CHF_2$, $CMeF_2$, —$OCF_3$, $OCHF_2$, CN, and $C_{1-4}$ alkoxy, e.g. —OMe.

In some embodiments of a compound of formula Va-1, Va-2, Va-3, Va-4, $R^1$ is a group of formula -$L^3$-$X^2$, wherein $L^3$ is a covalent bond, —$CH_2$—, —O—, —$OCH_2$—, —$O(CH_2)_2$— and $X^2$ is cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl; and $R^2$, $R^3$, $R^4$ are independently of each other selected from H, halogen, e.g. Cl, F, linear or branched —$C_{1-4}$ alkyl, e.g., Me, Et, t-But, $CF_3$, $CHF_2$, $CMeF_2$, —$OCF_3$, $OCHF_2$, CN, and $C_{1-4}$ alkoxy, e.g. —OMe.

In some embodiments of a compound of formula Va-1, Va-2, Va-3, Va-4, $R^1$ is $C_{3-6}$ cycloalkyl, —$C_{1-4}$ alkyl-$C_{3-6}$ cycloalkyl, —O—$C_{3-6}$ cycloalkyl, —$C_{1-4}$ alkoxy-$C_{3-6}$ cycloalkyl, $C_{6-10}$ aryl, —$C_{1-4}$ alkyl-$C_{6-10}$ aryl, —O—$C_{6-10}$ aryl, —$C_{1-4}$ alkoxy-$C_{6-10}$ aryl, 5-10 membered heteroaryl, —$C_{1-4}$ alkyl-(5-10 membered heteroaryl), —O-(5-10 membered heteroaryl), —$C_{1-4}$ alkoxy-(5-10 membered heteroaryl), 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl; and n is 1, $R^a$ is H; and p is 0.

In some embodiments of a compound of formula Va-1, Va-2, Va-3, Va-4, $R^1$ is $C_{3-6}$ cycloalkyl, —O—$C_{3-6}$ cycloalkyl, $C_{6-10}$ aryl, 5-10 membered heteroaryl, 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), wherein $R^1$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl; and n is 1, $R^a$ is H; and p is 0.

In some embodiments of a compound of formula Va-1, Va-2, Va-3, Va-4, $R^1$ is a group of formula -$L^3$-$X^2$, wherein $L^3$ is a covalent bond, linear or branched $C_{1-4}$ alkyl, —O—, —$C_{1-4}$ alkoxy and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl; and n is 1, $R^a$ is H; and p is 0.

In some embodiments of a compound of formula Va-1, Va-2, Va-3, Va-4, $R^1$ is a group of formula -$L^3$-$X^2$, wherein $L^3$ is a covalent bond, —$CH_2$—, —O—, —$OCH_2$—, —$O(CH_2)_2$— and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, e.g. —OMe, NMe$_2$, halogen, e.g. F; and $R^2$, $R^3$, $R^4$ are independently of each other selected from H, halogen, e.g. Cl, F, linear or branched —$C_{1-4}$ alkyl, e.g., Me, Et, t-But, CF$_3$, CHF$_2$, CMeF$_2$, —OCF$_3$, OCHF$_2$, CN, and $C_{1-4}$ alkoxy, e.g. —OMe; and n is 1, $R^a$ is H; and p is 0.

In some embodiments of a compound of formula Va-1, Va-2, Va-3, Va-4, $R^1$ is a group of formula -$L^3$-$X^2$, wherein $L^3$ is a covalent bond, —CH$_2$—, —O—, —OCH$_2$—, —O(CH$_2$)$_2$— and $X^2$ is cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl; and $R^2$, $R^3$, $R^4$ are independently of each other selected from H, halogen, e.g. Cl, F, linear or branched —$C_{1-4}$ alkyl, e.g., Me, Et, t-But, CF$_3$, CHF$_2$, CMeF$_2$, —OCF$_3$, OCHF$_2$, CN, and $C_{1-4}$ alkoxy, e.g. —OMe; and n is 1, $R^a$ is H; and p is 0.

In some embodiments of a compound of formula Va-1, Va-2, Va-3, Va-4, $R^1$ is $C_{3-6}$ cycloalkyl, —$C_{1-4}$ alkyl-$C_{3-6}$ cycloalkyl, —O—$C_{3-6}$ cycloalkyl, —$C_{1-4}$ alkoxy-$C_{3-6}$ cycloalkyl, $C_{6-10}$ aryl, —$C_{1-4}$ alkyl-$C_{6-10}$ aryl, —O—$C_{6-10}$ aryl, —$C_{1-4}$ alkoxy-$C_{6-10}$ aryl, 5-10 membered heteroaryl, —$C_{1-4}$ alkyl-(5-10 membered heteroaryl), —O-(5-10 membered heteroaryl), —$C_{1-4}$ alkoxy-(5-10 membered heteroaryl), 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), wherein $R^1$ is unsubstituted or substituted with one or more of linear or branched $C_{1-6}$ alkyl, —$C_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, CF$_3$, CHF$_2$, CMeF$_2$, —O—(CH$_2$)$_2$—OMe, OCF$_3$, OCHF$_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$ alkyl, NH$_2$, —$C_{1-4}$ alkylhydroxy, and halogen, such as F, Cl or Br, e.g. F or Cl; and n is 1, $R^a$ is CH$_3$; and p is 0.

In some embodiments of a compound of formula Va-1, Va-2, Va-3, Va-4, $R^1$ is a group of formula -$L^3$-$X^2$, wherein $L^3$ is a covalent bond, —CH$_2$—, —O—, —OCH$_2$—, —O(CH$_2$)$_2$— and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, e.g. —OMe, NMe$_2$, halogen, e.g. F; and $R^2$, $R^3$, $R^4$ are independently of each other selected from H, halogen, e.g. Cl, F, linear or branched —$C_{1-4}$ alkyl, e.g., Me, Et, t-But, CF$_3$, CHF$_2$, CMeF$_2$, —OCF$_3$, OCHF$_2$, CN, and $C_{1-4}$ alkoxy, e.g. —OMe; and n is 1, $R^a$ is CH$_3$; and p is 0.

In some embodiments of a compound of formula Va-1, Va-2, Va-3, Va-4, $R^1$ is a group of formula -$L^3$-$X^2$, wherein $L^3$ is a covalent bond, —CH$_2$—, —O—, —OCH$_2$—, —O(CH$_2$)$_2$— and $X^2$ is cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl; and $R^2$, $R^3$, $R^4$ are independently of each other selected from H, halogen, e.g. Cl, F, linear or branched —$C_{1-4}$ alkyl, e.g., Me, Et, t-But, CF$_3$, CHF$_2$, CMeF$_2$, —OCF$_3$, OCHF$_2$, CN, and $C_{1-4}$ alkoxy, e.g. —OMe; and n is 1, $R^a$ is CH$_3$; and p is 0.

In some embodiments of a compound of formula Va-1, Va-2, Va-3, Va-4, $R^1$ is $C_{3-6}$ cycloalkyl, —$C_{1-4}$ alkyl-$C_{3-6}$ cycloalkyl, —O—$C_{3-6}$ cycloalkyl, —$C_{1-4}$ alkoxy-$C_{3-6}$ cycloalkyl, $C_{6-10}$ aryl, —$C_{1-4}$ alkyl-$C_{6-10}$ aryl, —O—$C_{6-10}$ aryl, —$C_{1-4}$ alkoxy-$C_{6-10}$ aryl, 5-10 membered heteroaryl, —$C_{1-4}$ alkyl-(5-10 membered heteroaryl), —O-(5-10 membered heteroaryl), —$C_{1-4}$ alkoxy-(5-10 membered heteroaryl), 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), wherein $R^1$ is unsubstituted or substituted with one or more of linear or branched $C_{1-6}$ alkyl, —$C_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —$C_{1-4}$ alkylhydroxy; and $R^2$, $R^3$, $R^4$ are independently of each other selected from H, linear or branched —$C_{1-6}$ alkyl, linear or branched $C_{1-6}$ heteroalkyl, —$C_{1-4}$ alkoxy, CF$_3$, CHF$_2$, CMeF$_2$, —O—(CH$_2$)$_2$—OMe, OCF$_3$, OCHF$_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$ alkyl, NH$_2$, —$C_{1-4}$ alkylhydroxy, and halogen, such as F, Cl or Br, e.g. F or Cl; and n, p are 1, $R^a$, $R^b$, $R^c$ are H.

In some embodiments of a compound of formula Va-1, Va-2, Va-3, Va-4, $R^1$ is a group of formula -$L^3$-$X^2$, wherein $L^3$ is a covalent bond, —CH$_2$—, —O—, —OCH$_2$—, —O(CH$_2$)$_2$— and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, e.g. —OMe, NMe$_2$, halogen, e.g. F; and $R^2$, $R^3$, $R^4$ are independently of each other selected from H, halogen, e.g. Cl, F, linear or branched —$C_{1-4}$ alkyl, e.g., Me, Et, t-But, CF$_3$, CHF$_2$, CMeF$_2$, —OCF$_3$, OCHF$_2$, CN, and $C_{1-4}$ alkoxy, e.g. —OMe; and n, p are 1, $R^a$, $R^b$, $R^c$ are H.

In some embodiments of a compound of formula Va-1, Va-2, Va-3, Va-4, $R^1$ is $C_{3-6}$ cycloalkyl, —$C_{1-4}$ alkyl-$C_{3-6}$ cycloalkyl, —O—C$_{3-6}$ cycloalkyl, —C$_{1-4}$ alkoxy-C$_{3-6}$ cycloalkyl, C$_{6-10}$ aryl, —C$_{1-4}$ alkyl-C$_{6-10}$ aryl, —O—C$_{6-10}$ aryl, —C$_{1-4}$ alkoxy-C$_{6-10}$ aryl, 5-10 membered heteroaryl, —C$_{1-4}$ alkyl-(5-10 membered heteroaryl), —O-(5-10 membered heteroaryl), —C$_{1-4}$ alkoxy-(5-10 membered heteroaryl), 4-8 membered heterocycloalkyl, —C$_{1-4}$ alkyl-(4-8 membered heterocycloalkyl), —O-(4-8 membered heterocycloalkyl), —C$_{1-4}$ alkoxy-(4-8 membered heterocycloalkyl), wherein R$^1$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and R$^2$, R$^3$, R$^4$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —OC(O)—C$_{1-6}$ alkyl, —N(H)C(O)—C$_{1-6}$alkyl, —C(O)O—C$_{1-6}$alkyl, —COOH, —C$_{1-6}$alkylC(O)OH, —C$_{1-6}$ alkylC(O)O—C$_{1-6}$ alkyl, NH$_2$, —C$_{1-4}$ alkylhydroxy, and halogen, such as F, Cl or Br, e.g. F or Cl; and n, p are 1, R$^a$, R$^c$ are H, R$^b$ is CH$_3$.

In some embodiments of a compound of formula Va-1, Va-2, Va-3, Va-4, R$^1$ is a group of formula -L$^3$-X$^2$, wherein L$^3$ is a covalent bond, —CH$_2$—, —O—, —OCH$_2$—, —O(CH$_2$)$_2$— and X$^2$ is cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein X$^2$ is unsubstituted or substituted with one or more of linear or branched C$_{1-4}$ alkyl, —C$_{1-4}$ alkoxy, e.g. —OMe, NMe$_2$, halogen, e.g. F; and R$^2$, R$^3$, R$^4$ are independently of each other selected from H, halogen, e.g. Cl, F, linear or branched —C$_{1-4}$ alkyl, e.g., Me, Et, t-But, CF$_3$, CHF$_2$, CMeF$_2$, —OCF$_3$, OCHF$_2$, CN, and C$_{1-4}$ alkoxy, e.g. —OMe; and n, p are 1, R$^a$, R$^c$ are H, R$^b$ is CH$_3$.

In some embodiments of a compound of formula Va-1, Va-2, Va-3, Va-4, R$^1$ is a group of formula -L$^3$-X$^2$, wherein L$^3$ is a covalent bond, —CH$_2$—, —O—, —OCH$_2$—, —O(CH$_2$)$_2$— and X$^2$ is cyclopropyl, methyl-cyclopropyl, fluoro-cyclopropyl, difluoro-cyclopropyl, cyclobutyl, C$_6$ aryl, methyl-C$_6$ aryl, fluoro-C$_6$ aryl, methoxy-C$_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl; and R$^2$, R$^3$, R$^4$ are independently of each other selected from H, halogen, e.g. Cl, F, linear or branched —C$_{1-4}$ alkyl, e.g., Me, Et, t-But, CF$_3$, CHF$_2$, CMeF$_2$, —OCF$_3$, OCHF$_2$, CN, and C$_{1-4}$ alkoxy, e.g. —OMe; and n, p are 1, R$^a$, R$^c$ are H, R$^b$ is CH$_3$.

More specific embodiments of the compound of formula V are also provided by formula Va-5, Va-6, Va-7, Va-8, Va-9, Va-10, wherein two of w$^1$ to w$^5$ are N, e.g., wherein w$^1$, w$^2$ are N, w$^3$ to w$^5$ are C; or w$^1$, w$^5$ are N, w$^2$ to w$^4$ are C; or w$^2$, w$^4$ are N, w$^1$, w$^3$, w$^5$ are C; or w$^1$, w$^3$ are N, w$^2$ w$^4$, w$^5$ are C or w$^2$ w$^3$ are N, w$^1$, w$^4$ w$^5$ are C; or w$^1$, w$^4$ are N, w$^2$, w$^3$, w$^5$ are C

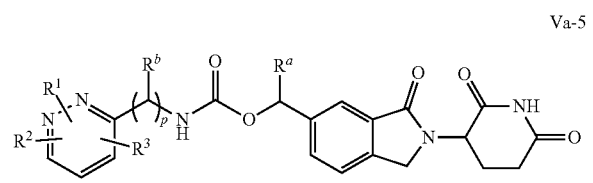

Va-5

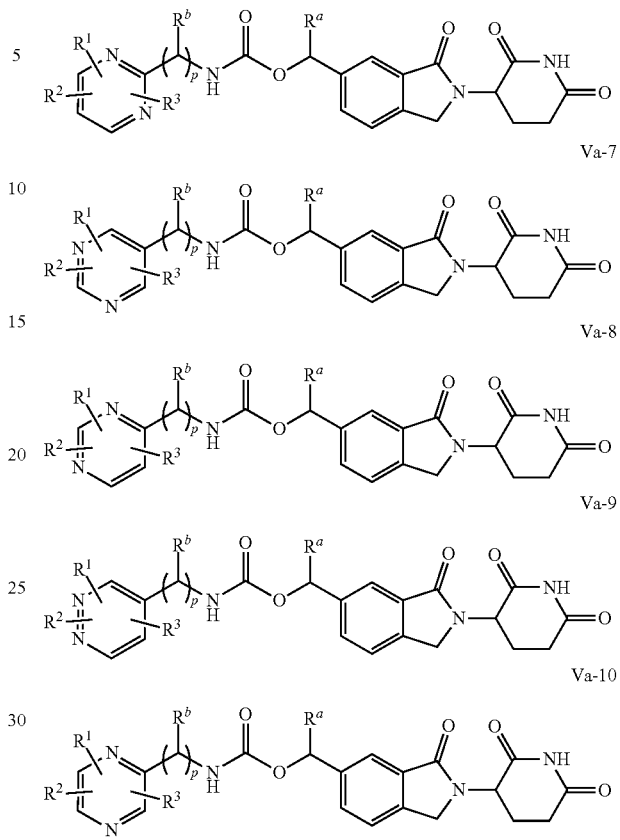

wherein
R$^1$, R$^2$, R$^3$, R$^4$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, NH$_2$, —C$_{1-4}$ alkylhydroxy, and halogen, such as F, Cl or Br, e.g. F or Cl, or a group of formula -L$^3$-X$^2$, wherein L$^3$ is a covalent bond, linear or branched C$_{1-6}$ alkyl, —O—, or —C$_{1-4}$ alkoxy and X$^2$ is C$_{3-6}$ cycloalkyl, C$_{6-10}$ aryl, 5-10 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; R$^a$, R$^b$ are independently of each other H or methyl; and p is 0 or 1.

In some embodiments of a compound of formula Va-5, Va-6, Va-7, Va-8, Va-9, Va-10, p is 0. In some embodiments of a compound of formula Va-5, Va-6, Va-7, Va-8, Va-9, Va-10, p is 1.

In some embodiments of a compound of formula Va-5, Va-6, Va-7, Va-8, Va-9, Va-10, R$^a$ is H. In some embodiments of a compound of formula Va-5, Va-6, Va-7, Va-8, Va-9, Va-10, R$^a$ is methyl. In some embodiments of a compound of formula Va-5, Va-6, Va-7, Va-8, Va-9, Va-10, p is 0 and R$^a$ is H. In some embodiments of a compound of formula Va-5, Va-6, Va-7, Va-8, Va-9, Va-10, p is 0 and R$^a$ is methyl.

In some embodiments of a compound of formula Va-5, Va-6, Va-7, Va-8, Va-9, Va-10, p is 1 and R$^b$ is H. In some embodiments of a compound of formula Va-5, Va-6, Va-7, Va-8, Va-9, Va-10, p is 1 and $R^b$ is methyl. In some embodiments of a compound of formula Va-5, Va-6, Va-7, Va-8, Va-9, Va-10, p is 1, $R^b$ is H and $R^a$ is H. In some embodiments of a compound of formula Va-5, Va-6, Va-7, Va-8, Va-9, Va-10, p is 1, $R^b$ is methyl and $R^a$ is H.

In some embodiments of a compound of formula Va-5, Va-6, Va-7, Va-8, Va-9, Va-10, $R^1$ is 4-8 membered heterocycloalkyl, which is unsubstituted or substituted with one or more of linear or branched $C_{1-6}$ alkyl, halogen, $CF_3$, $CHF_2$, $CMeF_2$, $OCF_3$, $OCHF_2$.

In some embodiments of a compound of formula Va-5, Va-6, Va-7, Va-8, Va-9, Va-10, $R^1$ is selected from pyrrolidinyl, piperidinyl, piperazinyl, morpholinyl and $R^2$, $R^3$ each are independently selected from H, linear or branched $C_{1-4}$ alkyl, $CF_3$, $CHF_2$, $CMeF_2$, $OCF_3$, $OCHF_2$, and halogen, such as F, Cl or Br, e.g. F or Cl.

In some embodiments of a compound of formula Va-5, Va-6, Va-7, Va-8, Va-9, Va-10, $R^1$ is piperidinyl.

In some embodiments the compound of formula V and Va-1 is defined by formula, Va-1a, Va-1b, Va-1c, Va-1d, Va-1e, Va-1f

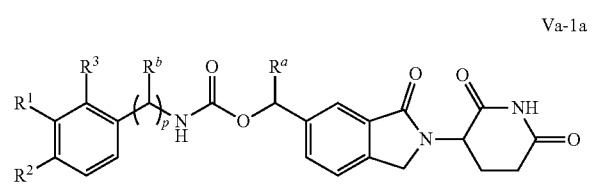

Va-1a

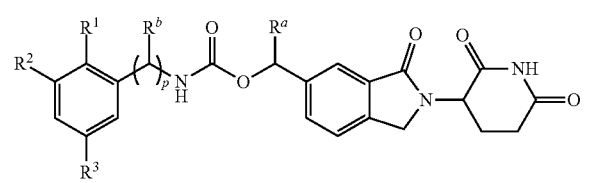

Va-1b

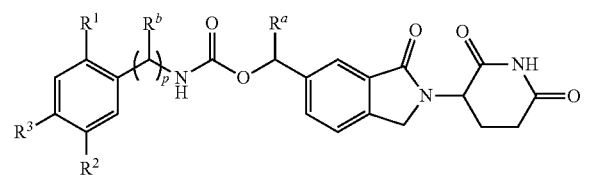

Va-1c

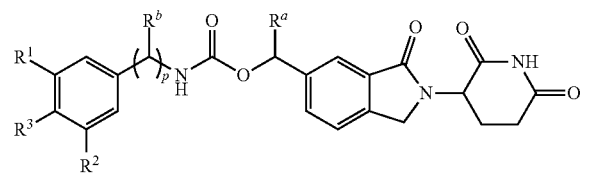

Va-1d

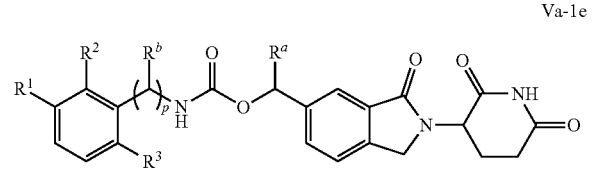

Va-1e

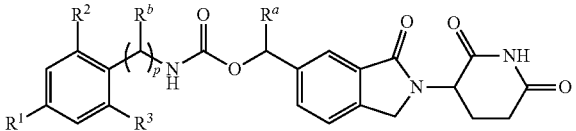

Va-1f wherein
$R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl, or a group of formula -$L^3$-$X^2$, wherein $L^3$ is a covalent bond, linear or branched $C_{1-6}$ alkyl, —O—, or —$C_{1-4}$ alkoxy and $X^2$ is $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; p is 0 or 1 and $R^a$, $R^b$ are independently of each other H or methyl.

In some embodiments of a compound of formula Va-1a, Va-1b, Va-1c, Va-1d, Va-1e or Va-1f, p is 0. In some embodiments of a compound of formula Va-1a, Va-1b, Va-1c, Va-1d, Va-1e or Va-1f, p is 1.

In some embodiments of a compound of formula Va-1a, Va-1b, Va-1c, Va-1d, Va-1e or Va-1f, $R^a$ is H. In some embodiments of a compound of formula Va-1a, Va-1b, Va-1c, Va-1d, Va-1e or Va-1f, $R^a$ is methyl. In some embodiments of a compound of formula Va-1a, Va-1b, Va-1c, Va-1d, Va-1e or Va-1f, p is 0 and $R^a$ is H. In some embodiments of a compound of formula Va-1a, Va-1b, Va-1c, Va-1d, Va-1e or Va-1f, p is 0 and $R^a$ is methyl.

In some embodiments of a compound of formula Va-1a, Va-1b, Va-1c, Va-1d, Va-1e or Va-1f, p is 1 and $R^b$ is H. In some embodiments of a compound of formula Va-1a, Va-1b, Va-1c, Va-1d, Va-1e or Va-1f, p is 1 and $R^b$ is methyl. In some embodiments of a compound of formula Va-1a, Va-1b, Va-1c, Va-1d, Va-1e, Va-1f, p is 1, $R^b$ is H and $R^a$ is H. In some embodiments of a compound of formula Va-1a, Va-1b, Va-1c, Va-1d, Va-1e, Va-1f, p is 1, $R^b$ is methyl and $R^a$ is H.

In some embodiments of a compound of formula Va-1a, Va-1b, Va-1c, Va-1d, Va-1e or Va-1f, $L^3$ is a covalent bond. In some embodiments of a compound of formula Va-1a, Va-1b, Va-1c, Va-1d, Va-1e or Va-1f, $L^3$ is linear or branched $C_{1-4}$ alkyl, such as —$CH_2$—. In some embodiments of a compound of formula Va-1a, Va-1b, Va-1c, Va-1d, Va-1e or Va-1f, $L^3$ is —O—. In some embodiments $L^3$ is linear or branched $C_{1-4}$ alkoxy, such as —O—$CH_2$—, —O—$(CH_2)_2$—

In some embodiments of a compound of formula Va-1a, Va-1b, Va-1c, Va-1d, Va-1e or Va-1f, $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e or Va-1f, $R^1$, $R^2$, $R^3$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1a, Va-1b, Va-1c, Va-1d, Va-1e or Va-1f, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e or Va-1f, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1a, Va-1b, Va-1c, Va-1d, Va-1e or Va-1f, $R^a$ is H and $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e or Va-1f, $R^a$ is H and $R^1$, $R^2$, $R^3$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1a, Va-1b, Va-1c, Va-1d, Va-1e or Va-1f, $R^a$ is $CH_3$ and $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e or Va-1f, $R^a$ is $CH_3$ and $R^1$, $R^2$, $R^3$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1a, Va-1b, Va-1c, Va-1d, Va-1e or Va-1f, $R^a$ is $CH_3$, and $R^1$, $R^2$, $R^3$ are independently of each other selected from H, halogen, such as Cl, F, linear or branched —$C_{1-4}$ alkyl, such as methyl, fluorinated $C_{1-4}$ alkoxy, such as —$OCF_3$.

In some embodiments of a compound of formula Va-1a, Va-1b, Va-1c, Va-1d, Va-1e or Va-1f, $R^a$ is H, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e or Va-1f, $R^a$ is H, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1a, Va-1b, Va-1c, Va-1d, Va-1e or Va-1f, $R^a$ is $CH_3$, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e or Va-1f, $R^a$ is $CH_3$, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1a, Va-1b, Va-1c, Va-1d, Va-1e or Va-1f, $R^a$ is $CH_3$, one of $R^1$, $R^2$, $R^3$ is H and the other two of $R^1$, $R^2$, $R^3$ are independently of each other selected from H, halogen, such as Cl, F, linear or branched —$C_{1-4}$ alkyl, such as methyl, fluorinated $C_{1-4}$ alkoxy, such as —$OCF_3$.

In some embodiments of a compound of formula Va-1a, Va-1b, Va-1c, Va-1d, Va-1e or Va-1f, p is 0 and $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e or Va-1f, p is 0 and $R^1$, $R^2$, $R^3$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1a, Va-1b, Va-1c, Va-1d, Va-1e or Va-1f, p is 0, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e or Va-1f, p is 0, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1a, Va-1b, Va-1c, Va-1d, Va-1e or Va-1f, p is 0, $R^a$ is H and $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)

O—$C_{1-6}$alkyl, —COOH, —$C_{1-6}$alkylC(O)OH, —$C_{1-6}$alkylC(O)O—$C_{1-6}$alkyl, NH$_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e or Va-1f, p is 0, $R^a$ is H and $R^1$, $R^2$, $R^3$ are independently of each other selected from H, linear or branched —$C_{1-6}$ alkyl, —$C_{1-4}$ alkoxy, CF$_3$, CHF$_2$, CMeF$_2$, OCF$_3$, OCHF$_2$, —CN, and halogen, such as F, Cl or Br, e.g. F or Cl.

In some embodiments of a compound of formula Va-1a, Va-1b, Va-1c, Va-1d, Va-1e or Va-1f, p is 0, $R^a$ is CH$_3$ and $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, CF$_3$, CHF$_2$, CMeF$_2$, —O—(CH$_2$)$_2$—OMe, OCF$_3$, OCHF$_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, NH$_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e or Va-1f, p is 0, $R^a$ is CH$_3$ and $R^1$, $R^2$, $R^3$ are independently of each other selected from H, linear or branched —$C_{1-6}$ alkyl, —$C_{1-4}$ alkoxy, CF$_3$, CHF$_2$, CMeF$_2$, OCF$_3$, OCHF$_2$, —CN, and halogen, such as F, Cl or Br, e.g. F or Cl.

In some embodiments of a compound of formula Va-1a, Va-1b, Va-1c, Va-1d, Va-1e or Va-1f, p is 0, $R^a$ is CH$_3$, and $R^1$, $R^2$, $R^3$ are independently of each other selected from H, halogen, such as Cl, F, linear or branched —$C_{1-4}$ alkyl, such as methyl, fluorinated $C_{1-4}$ alkoxy, such as —OCF$_3$.

In some embodiments of a compound of formula Va-1a, Va-1b, Va-1c, Va-1d, Va-1e or Va-1f, p is 0, $R^a$ is H, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, CF$_3$, CHF$_2$, CMeF$_2$, —O—(CH$_2$)$_2$—OMe, OCF$_3$, OCHF$_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, NH$_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e or Va-1f, p is 0, $R^a$ is H, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, CF$_3$, CH$_1$F$_2$, CMeF$_2$, OCF$_3$, OCHF$_2$, —CN, and halogen, such as F, Cl or Br, e.g. F or Cl.

In some embodiments of a compound of formula Va-1a, Va-1b, Va-1c, Va-1d, Va-1e or Va-1f, p is 0, $R^a$ is CH$_3$, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, CF$_3$, CHF$_2$, CMeF$_2$, —O—(CH$_2$)$_2$—OMe, OCF$_3$, OCHF$_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, NH$_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e or Va-1f, p is 0, $R^a$ is CH$_3$, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, CF$_3$, CHF$_2$, CMeF$_2$, OCF$_3$, OCHF$_2$, —CN, and halogen, such as F, Cl or Br, e.g. F or Cl.

In some embodiments of a compound of formula Va-1a, Va-1b, Va-1c, Va-1d, Va-1e or Va-1f, $R^a$ is CH$_3$, p is 0, one of $R^1$, $R^2$, $R^3$ is H and the other two of $R^1$, $R^2$, $R^3$ are independently of each other selected from H, halogen, such as Cl, F, linear or branched —$C_{1-4}$ alkyl, such as methyl, fluorinated $C_{1-4}$ alkoxy, such as —OCF$_3$.

In some embodiments of a compound of formula Va-1a, Va-1b, Va-1c, Va-1d, Va-1e or Va-1f, p is 1, $R^b$ and $R^c$ are H, and $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, CF$_3$, CHF$_2$, CMeF$_2$, —O—(CH$_2$)$_2$—OMe, OCF$_3$, OCHF$_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, NH$_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e or Va-1f, p is 1, $R^b$ and $R^c$ are H, and $R^1$, $R^2$, $R^3$ are independently of each other selected from H, linear or branched —$C_{1-6}$ alkyl, —$C_{1-4}$ alkoxy, CF$_3$, CHF$_2$, CMeF$_2$, OCF$_3$, OCHF$_2$, —CN, and halogen, such as F, Cl or Br, e.g. F or Cl.

In some embodiments of a compound of formula Va-1a, Va-1b, Va-1c, Va-1d, Va-1e or Va-1f, p is 1, $R^b$ and $R^c$ are H, and $R^1$, $R^2$, $R^3$ are independently of each other selected from H and $C_{1-4}$ alkoxy, e.g. —OMe.

In some embodiments of a compound of formula Va-1a, Va-1b, Va-1c, Va-1d, Va-1e or Va-1f, p is 1, $R^b$ is CH$_3$, $R^c$ is H, and $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, CF$_3$, CHF$_2$, CMeF$_2$, —O—(CH$_2$)$_2$—OMe, OCF$_3$, OCHF$_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, NH$_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e or Va-1f, p is 1, $R^b$ is CH$_3$, $R^c$ is H, and $R^1$, $R^2$, $R^3$ are independently of each other selected from H, linear or branched —$C_{1-6}$ alkyl, —$C_{1-4}$ alkoxy, CF$_3$, CHF$_2$, CMeF$_2$, OCF$_3$, OCHF$_2$, —CN, and halogen, such as F, Cl or Br, e.g. F or Cl.

In some embodiments of a compound of formula Va-1a, Va-1b, Va-1c, Va-1d, Va-1e or Va-1f, p is 1, $R^b$ and $R^c$ are H, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, CF$_3$, CHF$_2$, CMeF$_2$, —O—(CH$_2$)$_2$—OMe, OCF$_3$, OCHF$_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$-alkyl, NH$_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e or Va-1f, p is 1, $R^b$ and $R^c$ are H, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, CF$_3$, CHF$_2$, CMeF$_2$, OCF$_3$, OCHF$_2$, —CN, and halogen, such as F, Cl or Br, e.g. F or Cl.

In some embodiments of a compound of formula Va-1a, Va-1b, Va-1c, Va-1d, Va-1e or Va-1f, p is 1, $R^b$ and $R^c$ are H, one of $R^1$, $R^2$, $R^3$ is H and the other two of $R^1$, $R^2$, $R^3$ are independently of each other selected from H and $C_{1-4}$ alkoxy, e.g. —OMe.

In some embodiments of a compound of formula Va-1a, Va-1b, Va-1c, Va-1d, Va-1e or Va-1f, p is 1, $R^b$ is CH$_3$, $R^c$ is H, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$-alkyl, $NH_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e or Va-1f, p is 1, $R^b$ is $CH_3$, $R^c$ is H, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1a, Va-1b, Va-1c, Va-1d, Va-1e or Va-1f, p is 1, $R^b$ is $CH_3$, $R^c$ is H, and $R^1$, $R^2$, $R^3$ are H.

In some embodiments of a compound of formula Va-1a, Va-1b, Va-1c, Va-1d, Va-1e or Va-1f, one of $R^1$, $R^2$, $R^3$ is a group of formula -$L^3$-$X^2$, wherein $L^3$ is a covalent bond, —$CH_2$—, —O—, —$OCH_2$—, —$O(CH_2)_2$— and $X^2$ is $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e, Va-1f, one of $R^1$, $R^2$, $R^3$ is $C_{3-6}$ cycloalkyl, —$C_{1-4}$ alkyl-$C_{3-6}$ cycloalkyl, —O—$C_{3-6}$ cycloalkyl, —$C_{1-4}$ alkoxy-$C_{3-6}$ cycloalkyl, $C_{6-10}$ aryl, —$C_{1-4}$ alkyl-$C_{6-10}$ aryl, —O—$C_{6-10}$ aryl, —$C_{1-4}$ alkoxy-$C_{6-10}$ aryl, 5-10 membered heteroaryl, —$C_{1-4}$ alkyl-(5-10 membered heteroaryl), —O-(5-10 membered heteroaryl), —$C_{1-4}$ alkoxy-(5-10 membered heteroaryl), 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), wherein the $C_{3-6}$ cycloalkyl, $C_{6-10}$ aryl, 5-10 membered heteroaryl, and 4-8 membered heterocycloalkyl are unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy, and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e, Va-1f, one of $R^1$, $R^2$, $R^3$ is $C_{3-6}$ cycloalkyl, —O—$C_{3-6}$ cycloalkyl, $C_{6-10}$ aryl, 5-10 membered heteroaryl, 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), wherein the $C_{3-6}$ cycloalkyl, $C_{6-10}$ aryl, 5-10 membered heteroaryl, and 4-8 membered heterocycloalkyl are unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e, Va-1f, one of $R^1$, $R^2$, $R^3$ is a group of formula -$L^3$-$X^2$, wherein $L^3$ is a covalent bond, linear or branched $C_{1-4}$ alkyl, —O—, —$C_{1-4}$ alkoxy and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, and halogen, such as F, Cl or Br, e.g. F or Cl In some embodiments of a compound of formula Va-1a, Va-1b, Va-1c, Va-1d, Va-1e, Va-1f, one of $R^1$, $R^2$, $R^3$ is a group of formula -$L^3$-$X^2$, wherein $L^3$ is a covalent bond, —$CH_2$—, —O—, —$OCH_2$—, —$O(CH_2)_2$— and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, e.g. —OMe, $NMe_2$, halogen, e.g. F; and the other two of $R^1$, $R^2$, $R^3$ are independently of each other selected from H, halogen, e.g. Cl, F, linear or branched —$C_{1-4}$ alkyl, e.g., Me, Et, t-But, $CF_3$, $CHF_2$, $CMeF_2$, —$OCF_3$, $OCHF_2$, CN, and $C_{1-4}$ alkoxy, e.g. —OMe.

In some embodiments of a compound of formula Va-1a, Va-1b, Va-1c, Va-1d, Va-1e, Va-1f, one of $R^1$, $R^2$, $R^3$ is a group of formula -$L^3$-$X^2$, wherein $L^3$ is a covalent bond, —$CH_2$—, —O—, —$OCH_2$—, —$O(CH_2)_2$— and $X^2$ is cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl; and the other two of $R^1$, $R^2$, $R^3$ are independently of each other selected from H, halogen, e.g. Cl, F, linear or branched —$C_{1-4}$ alkyl, e.g., Me, Et, t-But, $CF_3$, $CHF_2$, $CMeF_2$, —$OCF_3$, $OCHF_2$, CN, and $C_{1-4}$ alkoxy, e.g. —OMe.

In some embodiments of a compound of formula Va-1a, Va-1b, Va-1c, Va-1d, Va-1e or Va-1f, $R^a$ is H, one of $R^1$, $R^2$, $R^3$ is a group of formula -$L^3$-$X^2$, wherein $L^3$ is a covalent bond, —$CH_2$—, —O—, —$OCH_2$—, —$O(CH_2)_2$— and $X^2$ is $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C (O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e, Va-1f, $R^a$ is H, one of $R^1$, $R^2$, $R^3$ is $C_{3-6}$ cycloalkyl, —$C_{1-4}$ alkyl-$C_{3-6}$ cycloalkyl, —O—$C_{3-6}$ cycloalkyl, —$C_{1-4}$ alkoxy-$C_{3-6}$ cycloalkyl, $C_{6-10}$ aryl, —$C_{1-4}$ alkyl-$C_{6-10}$ aryl, —O—$C_{6-10}$ aryl, —$C_{1-4}$ alkoxy-$C_{6-10}$ aryl, 5-10 membered heteroaryl, —$C_{1-4}$ alkyl-(5-10 membered heteroaryl), —O-(5-10 membered heteroaryl), —$C_{1-4}$ alkoxy-(5-10 membered heteroaryl), 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), wherein the $C_{3-6}$ cycloalkyl, $C_{6-10}$ aryl, 5-10 membered heteroaryl, and 4-8 membered heterocycloalkyl are unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e, Va-1f, $R^a$ is H, one of $R^1$, $R^2$, $R^3$ is $C_{3-6}$ cycloalkyl, —O—$C_{3-6}$ cycloalkyl, $C_{6-10}$ aryl, 5-10 membered heteroaryl, 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), wherein the $C_{3-6}$ cycloalkyl, $C_{6-10}$ aryl, 5-10 membered heteroaryl, and 4-8 membered heterocycloalkyl are unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e, Va-1f, $R^a$ is H, one of $R^1$, $R^2$, $R^3$ is a group of formula -$L^3$-$X^2$, wherein $L^3$ is a covalent bond, linear or branched $C_{1-4}$ alkyl, —O—, —$C_{1-4}$ alkoxy and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e, Va-1f, $R^a$ is H, one of $R^1$, $R^2$, $R^3$ is a group of formula -$L^3$-$X^2$, wherein $L^3$ is a covalent bond, —$CH_2$—, —O—, —$OCH_2$—, —$O(CH_2)_2$— and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, e.g. —OMe, $NMe_2$, halogen, e.g. F; and the other two of $R^1$, $R^2$, $R^3$ are independently of each other selected from H, halogen, e.g. Cl, F, linear or branched —$C_{1-4}$ alkyl, e.g., Me, Et, t-But, $CF_3$, $CHF_2$, $CMeF_2$, —$OCF_3$, $OCHF_2$, CN, and $C_{1-4}$ alkoxy, e.g. —OMe.

In some embodiments of a compound of formula Va-1a, Va-1b, Va-1c, Va-1d, Va-1e, Va-1f, $R^a$ is H, one of $R^1$, $R^2$, $R^3$ is a group of formula -$L^3$-$X^2$, wherein $L^3$ is a covalent bond, —$CH_2$—, —O—, —$OCH_2$—, —$O(CH_2)_2$— and $X^2$ is cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl; and the other two of $R^1$, $R^2$, $R^3$ are independently of each other selected from H, halogen, e.g. Cl, F, linear or branched —$C_{1-4}$ alkyl, e.g., Me, Et, t-But, $CF_3$, $CHF_2$, $CMeF_2$, —$OCF_3$, $OCHF_2$, CN, and $C_{1-4}$ alkoxy, e.g. —OMe.

In some embodiments of a compound of formula Va-1a, Va-1b, Va-1c, Va-1d, Va-1e or Va-1f, p is 0, one of $R^1$, $R^2$, $R^3$ is a group of formula -$L^3$-$X^2$, wherein $L^3$ is a covalent bond, —$CH_2$—, —O—, —$OCH_2$—, —$O(CH_2)_2$— and $X^2$ is $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e, Va-1f, p is 0, one of $R^1$, $R^2$, $R^3$ is a group selected from $C_{3-6}$ cycloalkyl, —$C_{1-4}$ alkyl-$C_{3-6}$ cycloalkyl, —O—$C_{3-6}$ cycloalkyl, —$C_{1-4}$ alkoxy-$C_{3-6}$ cycloalkyl, $C_{6-10}$ aryl, —$C_{1-4}$ alkyl-$C_{6-10}$ aryl, —O—$C_{6-10}$ aryl, —$C_{1-4}$ alkoxy-$C_{6-10}$ aryl, 5-10 membered heteroaryl, —$C_{1-4}$ alkyl-(5-10 membered heteroaryl), —O-(5-10 membered heteroaryl), —$C_{1-4}$ alkoxy-(5-10 membered heteroaryl), 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), which group is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and the other two of $R^1$, $R^2$, $R^3$ are independently of each other selected from H, linear or branched —$C_{1-6}$ alkyl, linear or branched $C_{1-6}$ heteroalkyl, —$C_1$. 4 alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, and halogen, such as F, Cl or Br, e.g. F or Cl.

In some embodiments of a compound of formula Va-1a, Va-1b, Va-1c, Va-1d, Va-1e, Va-1f, p is 0, one of $R^1$, $R^2$, $R^3$ is a group selected from $C_{3-6}$ cycloalkyl, —O—$C_{3-6}$ cycloalkyl, $C_{6-10}$ aryl, 5-10 membered heteroaryl, 4-8 membered heterocycloalkyl, —$C_{1-4}$ alkyl-(4-8 membered heterocycloalkyl), —O-(4-8 membered heterocycloalkyl), —C$_{1-4}$ alkoxy-(4-8 membered heterocycloalkyl), which group is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and the other two of R$^1$, R$^2$, R$^3$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —C$_{1-4}$ alkylhydroxy, and halogen, such as F, Cl or Br, e.g. F or Cl.

In some embodiments of a compound of formula Va-1a, Va-1b, Va-1c, Va-1d, Va-1e, Va-1f, p is 0, one of R$^1$, R$^2$, R$^3$ is a group of formula -L$^3$-X$^2$, wherein L$^3$ is a covalent bond, linear or branched C$_{1-4}$ alkyl, —O—, —C$_{1-4}$ alkoxy and X$^2$ is cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and the other two of R$^1$, R$^2$, R$^3$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —C$_{1-4}$ alkylhydroxy, and halogen, such as F, Cl or Br, e.g. F or Cl.

In some embodiments of a compound of formula Va-1a, Va-1b, Va-1c, Va-1d, Va-1e, Va-1f, p is 0, one of R$^1$, R$^2$, R$^3$ is a group of formula -L$^3$-X$^2$, wherein L$^3$ is a covalent bond, —CH$_2$—, —O—, —OCH$_2$—, —O(CH$_2$)$_2$— and X$^2$ is cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein X$^2$ is unsubstituted or substituted with one or more of linear or branched C$_{1-4}$ alkyl, —C$_{1-4}$ alkoxy, e.g. —OMe, NMe$_2$, halogen, e.g. F; and the other two of R$^1$, R$^2$, R$^3$ are independently of each other selected from H, halogen, e.g. Cl, F, linear or branched —C$_{1-4}$ alkyl, e.g., Me, Et, t-But, CF$_3$, CHF$_2$, CMeF$_2$, —OCF$_3$, OCHF$_2$, CN, and C$_{1-4}$ alkoxy, e.g. —OMe.

In some embodiments of a compound of formula Va-1a, Va-1b, Va-1c, Va-1d, Va-1e, Va-1f, p is 0, one of R$^1$, R$^2$, R$^3$ is a group of formula -L$^3$-X$^2$, wherein L$^3$ is a covalent bond, —CH$_2$—, —O—, —OCH$_2$—, —O(CH$_2$)$_2$— and X$^2$ is cyclopropyl, methyl-cyclopropyl, fluoro-cyclopropyl, difluoro-cyclopropyl, cyclobutyl, C$_6$ aryl, methyl-C$_6$ aryl, fluoro-C$_6$ aryl, methoxy-C$_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl; and the other two of R$^1$, R$^2$, R$^3$ are independently of each other selected from H, halogen, e.g. Cl, F, linear or branched —C$_{1-4}$ alkyl, e.g., Me, Et, t-But, CF$_3$, CHF$_2$, CMeF$_2$, —OCF$_3$, OCHF$_2$, CN, and C$_{1-4}$ alkoxy, e.g. —OMe.

In some embodiments, the compound of formula Va and Va-1a is a compound of formula Va-1g, Va-1h, Va-1i, Va-1j, Va-1k or Va-1l,

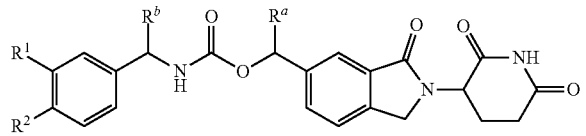

Va-1g

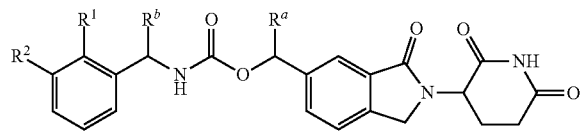

Va-1h

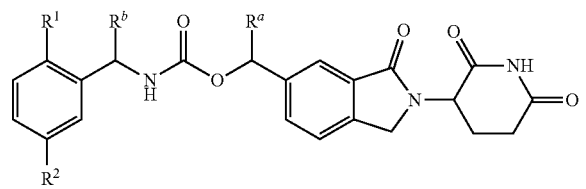

Va-1i

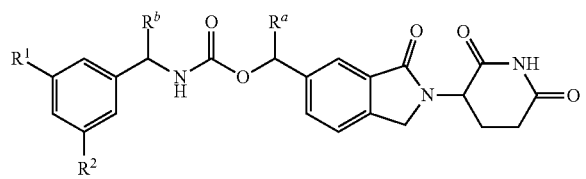

Va-1j

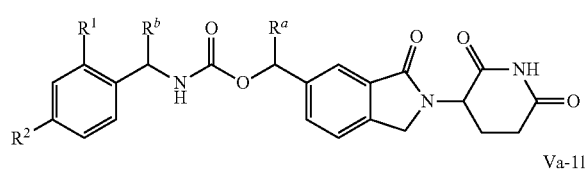

Va-1k

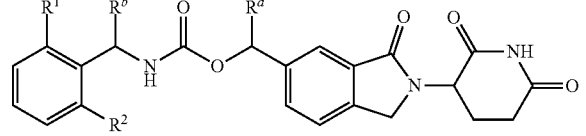

Va-1l wherein
R$^1$, R$^2$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, NH$_2$, —C$_{1-4}$ alkylhydroxy, and halogen, such as F, Cl or Br, e.g. F or Cl, or a group of formula -L$^3$-X$^2$, wherein L$^3$ is a covalent bond, linear or branched C$_{1-6}$ alkyl, —O—, or —C$_{1-4}$ alkoxy and X$^2$ is C$_{3-6}$ cycloalkyl, C$_{6-10}$ aryl, 5-10 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and R$^a$, R$^b$ are independently of each other H or methyl.

In some embodiments of a compound of formula Va-1g, Va-1h, Va-1i, Va-1j, Va-1k or Va-1l, R$^a$ is H. In some embodiments of a compound of formula Va-1g, Va-1h, Va-1i, Va-1j, Va-1k or Va-1l, R$^a$ is methyl.

In some embodiments of a compound of formula Va-1g, Va-1h, Va-1i, Va-1j, Va-1k or Va-1l, R$^b$ is H. In some embodiments of a compound of formula Va-1g, Va-1h, Va-1i, Va-1j, Va-1k or Va-1, $R^b$ is methyl.

In some embodiments of a compound of formula Va-1g, Va-1h, Va-1i, Va-1j, Va-1k or Va-1l, $L^3$ is a covalent bond. In some embodiments of a compound of formula Va-1g, Va-1h, Va-1i, Va-1j, Va-1k or Va-1l, $L^3$ is linear or branched $C_{1-4}$ alkyl, such as —$CH_2$—. In some embodiments of a compound of formula Va-1g, Va-1h, Va-1i, Va-1j, Va-1k or Va-1l, $L^3$ is —O—. In some embodiments $L^3$ is linear or branched $C_{1-4}$ alkoxy, such as —O—$CH_2$—, —O—$(CH_2)_2$—

In some embodiments of a compound of formula Va-1g, Va-1h, Va-1i, Va-1j, Va-1k or Va-1l, $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1g, Va-1h, Va-1i, Va-1j, Va-1k or Va-1l, $R^1$, $R^2$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1g, Va-1h, Va-1i, Va-1j, Va-1k or Va-1l, $R^a$ is H and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1g, Va-1h, Va-1i, Va-1j, Va-1k or Va-1l, $R^a$ is H and $R^1$, $R^2$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1g, Va-1h, Va-1i, Va-1j, Va-1k or Va-1l, $R^a$ is $CH_3$ and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1g, Va-1h, Va-1i, Va-1j, Va-1k or Va-1l, $R^a$ is $CH_3$ and $R^1$, $R^2$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1g, Va-1h, Va-1i, Va-1j, Va-1k or Va-1l, $R^a$ is $CH_3$, and $R^1$, $R^2$ are independently of each other selected from H, halogen, such as Cl, F, linear or branched —$C_{1-4}$ alkyl, such as methyl, fluorinated $C_{1-4}$ alkoxy, such as —$OCF_3$.

In some embodiments of a compound of formula Va-1g, Va-1h, Va-1i, Va-1j, Va-1k or Va-1l, $R^b$ is H and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-1g, Va-1h, Va-1i, Va-1j, Va-1k or Va-1i, $R^b$ is H and $R^1$, $R^2$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1g, Va-1h, Va-1i, Va-1j, Va-1k or Va-1l, $R^b$ is $CH_3$ and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-1g, Va-1h, Va-1i, Va-1j, Va-1k or Va-1l, $R^b$ is $CH_3$ and $R^1$, $R^2$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1g, Va-1h, Va-1i, Va-1j, Va-1k or Va-1l, $R^b$ is H, $R^a$ is H and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1g, Va-1h, Va-1i, Va-1j, Va-1k or Va-1l, $R^b$ is H, $R^a$ is H and $R^1$, $R^2$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1g, Va-1h, Va-1i, Va-1j, Va-1k or Va-1l, $R^b$ is H, $R^a$ is $CH_3$ and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O) O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1g, Va-1h, Va-1i, Va-1j, Va-1k or Va-1l, $R^b$ is H, $R^a$ is $CH_3$ and $R^1$, $R^2$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1g, Va-1h, Va-1i, Va-1j, Va-1k or Va-1l, $R^b$ is H, $R^a$ is $CH_3$, and $R^1$, $R^2$ are independently of each other selected from H, halogen, such as Cl, F, linear or branched —$C_{1-4}$ alkyl, such as methyl, fluorinated $C_{1-4}$ alkoxy, such as —$OCF_3$.

In some embodiments of a compound of formula Va-1g, Va-1h, Va-1i, Va-1j, Va-1k or Va-1l, $R^b$ is $CH_3$, $R^a$ is H, and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-1g, Va-1h, Va-1i, Va-1j, Va-1k or Va-1l, $R^b$ is $CH_3$, $R^a$ is H, and $R^1$, $R^2$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, —CN, and halogen, such as F, Cl or Br, e.g. F or Cl.

In some embodiments of a compound of formula Va-1g, Va-1h, Va-1i, Va-1j, Va-1k or Va-1l, $R^b$ is $CH_3$, $R^a$ is H, and $R^1$, $R^2$ are independently of each other selected from H and $C_{1-4}$ alkoxy, e.g. —OMe.

In some embodiments of a compound of formula Va-1g, Va-1h, Va-1i, Va-1j, Va-1k or Va-1l, one of $R^1$, $R^2$ is selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl; the other of $R^1$, $R^2$ is a group of formula -$L^3$-$X^2$, wherein $L^3$ is a covalent bond, —$CH_2$—, —O—, —$OCH_2$—, —$O(CH_2)_2$— and $X^2$ is $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula Va-1g, Va-1h, Va-1i, Va-1j, Va-1k or Va-1l, one of $R^1$, $R^2$ is selected from a group consisting of $C_{3-6}$ cycloalkyl, —$C_{1-4}$ alkyl-$C_{3-6}$ cycloalkyl, —O—$C_{3-6}$ cycloalkyl, —$C_{1-4}$ alkoxy-$C_{3-6}$ cycloalkyl, $C_{6-10}$ aryl, —$C_{1-4}$ alkyl-$C_{6-10}$ aryl, —O—$C_{6-10}$ aryl, —$C_{1-4}$ alkoxy-$C_{6-10}$ aryl, 5-10 membered heteroaryl, —$C_{1-4}$ alkyl-(5-10 membered heteroaryl), —O-(5-10 membered heteroaryl), —$C_{1-4}$ alkoxy-(5-10 membered heteroaryl), 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), which group is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and the other of $R^1$, $R^2$ is selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, and halogen, such as F, Cl or Br, e.g. F or Cl.

In some embodiments of a compound of formula Va-1g, Va-1h, Va-1i, Va-1j, Va-1k or Va-1l, one of $R^1$, $R^2$ is selected from a group consisting of $C_{3-6}$ cycloalkyl, —O—$C_{3-6}$ cycloalkyl, $C_{6-10}$ aryl, 5-10 membered heteroaryl, 4-8 membered heterocycloalkyl, —$C_{1-4}$ alkyl-(4-8 membered heterocycloalkyl), —O-(4-8 membered heterocycloalkyl), —$C_{1-4}$ alkoxy-(4-8 membered heterocycloalkyl), which group is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and the other of $R^1$, $R^2$ is selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, and halogen, such as F, Cl or Br, e.g. F or Cl.

In some embodiments of a compound of formula Va-1g, Va-1h, Va-1i, Va-1j, Va-1k or Va-1l, one of $R^1$, $R^2$ is selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, and halogen, such as F, Cl or Br, e.g. F or Cl; the other of $R^1$, $R^2$ is a group of formula -$L^3$-$X^2$, wherein $L^3$ is a covalent bond, linear or branched $C_{1-4}$ alkyl, —O—, —$C_{1-4}$ alkoxy and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and In some embodiments of a compound of formula Va-1g, Va-1h, Va-1i, Va-1j, Va-1k or Va-1l, one of $R^1$, $R^2$ is selected from H, halogen, e.g. Cl, F, linear or branched —$C_{1-4}$ alkyl, e.g., Me, Et, t-But, $CF_3$, $CHF_2$, $CMeF_2$, —$OCF_3$, $OCHF_2$, CN, and $C_{1-4}$ alkoxy, e.g. —OMe, the other of $R^1$, $R^2$ is a group of formula -$L^3$-$X^2$, wherein $L^3$ is a covalent bond, —$CH_2$—, —O—, —$OCH_2$—, —$O(CH_2)_2$— and $X^2$ is cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein $X^2$ is unsubstituted or substituted with one or more of linear or branched $C_{1-4}$ alkyl, —$C_{1-4}$ alkoxy, e.g. —OMe, $NMe_2$, halogen, e.g. F.

In some embodiments of a compound of formula Va-1g, Va-1h, Va-1i, Va-1j, Va-1k or Va-1l, one of $R^1$, $R^2$ is selected from H, halogen, e.g. Cl, F, linear or branched —$C_{1-4}$ alkyl, e.g., Me, Et, t-But, $CF_3$, $CHF_2$, $CMeF_2$, —$OCF_3$, $OCHF_2$, CN, and $C_{1-4}$ alkoxy, e.g. —OMe; the other of $R^1$, $R^2$ is a group of formula -$L^3$-$X^2$, wherein $L^3$ is a covalent bond, —$CH_2$—, —O—, —$OCH_2$—, —$O(CH_2)_2$— and $X^2$ is cyclopropyl, methyl-cyclopropyl, fluoro-cyclopropyl, difluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula Va-1g, Va-1h, Va-1i, Va-1j, Va-1k or Va-1l, $R^a$ is H, one of $R^1$, $R^2$ is selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, $NH_2$, —$C_{1-4}$ alkylhydroxy, and halogen, such as F, Cl or Br, e.g. F or Cl; the other of $R^1$, $R^2$ is a group of formula -$L^3$-$X^2$, wherein $L^3$ is a covalent bond, —$CH_2$—, —O—, —$OCH_2$—, —$O(CH_2)_2$— and $X^2$ is $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

In some embodiments of a compound of formula Va-1h, Va-1i, Va-1j, Va-1k or Va-1l, $R^a$ is H, one of $R^1$, $R^2$ is selected from a group consisting of $C_{3-6}$ cycloalkyl, —$C_{1-4}$ alkyl-$C_{3-6}$ cycloalkyl, —O—$C_{3-6}$ cycloalkyl, —$C_{1-4}$ alkoxy-$C_{3-6}$ cycloalkyl, $C_{6-10}$ aryl, —$C_{1-4}$ alkyl-$C_{6-10}$ aryl, —O—C$_{6-10}$ aryl, —C$_{1-4}$ alkoxy-C$_{6-10}$ aryl, 5-10 membered heteroaryl, —C$_{1-4}$ alkyl-(5-10 membered heteroaryl), —O-(5-10 membered heteroaryl), —C$_{1-4}$ alkoxy-(5-10 membered heteroaryl), 4-8 membered heterocycloalkyl, —C$_{1-4}$ alkyl-(4-8 membered heterocycloalkyl), —O-(4-8 membered heterocycloalkyl), —C$_{1-4}$ alkoxy-(4-8 membered heterocycloalkyl), which group is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and the other of R$^1$, R$^2$ is selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —C$_{1-4}$ alkylhydroxy, and halogen, such as F, Cl or Br, e.g. F or Cl.

In some embodiments of a compound of formula Va-1g, Va-1h, Va-1i, Va-1j, Va-1k or Va-1l, R$^a$ is H, one of R$^1$, R$^2$ is selected from a group consisting of C$_{3-6}$ cycloalkyl, —O—C$_{3-6}$ cycloalkyl, C$_{6-10}$ aryl, 5-10 membered heteroaryl, 4-8 membered heterocycloalkyl, —C$_{1-4}$ alkyl-(4-8 membered heterocycloalkyl), —O-(4-8 membered heterocycloalkyl), —C$_{1-4}$ alkoxy-(4-8 membered heterocycloalkyl), which group is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and the other of R$^1$, R$^2$ is selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —C$_{1-4}$ alkylhydroxy, and halogen, such as F, Cl or Br, e.g. F or Cl.

In some embodiments of a compound of formula Va-1g, Va-1h, Va-1i, Va-1j, Va-1k or Va-1l, R$^a$ is H, one of R$^1$, R$^2$ is selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —C$_{1-4}$ alkylhydroxy, and halogen, such as F, Cl or Br, e.g. F or Cl; the other of R$^1$, R$^2$ is a group of formula -L$^3$-X$^2$, wherein L$^3$ is a covalent bond, linear or branched C$_{1-4}$ alkyl, —O—, —C$_{1-4}$ alkoxy and X$^2$ is cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and In some embodiments of a compound of formula Va-1g, Va-1h, Va-1i, Va-1j, Va-1k or Va-1l, R$^a$ is H, one of R$^1$, R$^2$ is selected from H, halogen, e.g. Cl, F, linear or branched —C$_{1-4}$ alkyl, e.g., Me, Et, t-But, CF$_3$, CHF$_2$, CMeF$_2$, —OCF$_3$, OCHF$_2$, CN, and C$_{1-4}$ alkoxy, e.g. —OMe, the other of R$^1$, R$^2$ is a group of formula -L$^3$-X$^2$, wherein L$^3$ is a covalent bond, —CH$_2$—, —O—, —OCH$_2$—, —O(CH$_2$)$_2$— and X$^2$ is cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein X$^2$ is unsubstituted or substituted with one or more of linear or branched C$_{1-4}$ alkyl, —C$_{1-4}$ alkoxy, e.g. —OMe, NMe$_2$, halogen, e.g. F.

In some embodiments of a compound of formula Va-1g, Va-1h, Va-1i, Va-1j, Va-1k or Va-1l, R$^a$ is H, one of R$^1$, R$^2$ is selected from H, halogen, e.g. Cl, F, linear or branched —C$_{1-4}$ alkyl, e.g., Me, Et, t-But, CF$_3$, CHF$_2$, CMeF$_2$, —OCF$_3$, OCHF$_2$, CN, and C$_{1-4}$ alkoxy, e.g. —OMe; the other of R$^1$, R$^2$ is a group of formula -L$^3$-X$^2$, wherein L$^3$ is a covalent bond, —CH$_2$—, —O—, —OCH$_2$—, —O(CH$_2$)$_2$—

— and X$^2$ is cyclopropyl, methyl-cyclopropyl, fluoro-cyclopropyl, difluoro-cyclopropyl, cyclobutyl, C$_6$ aryl, methyl-C$_6$ aryl, fluoro-C$_6$ aryl, methoxy-C$_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments, the compound of formula Va and Va-1a is a compound of formula Va-1m, Va-1n, Va-1o, Va-1p, Va-1q or Va-1r, Va-1m
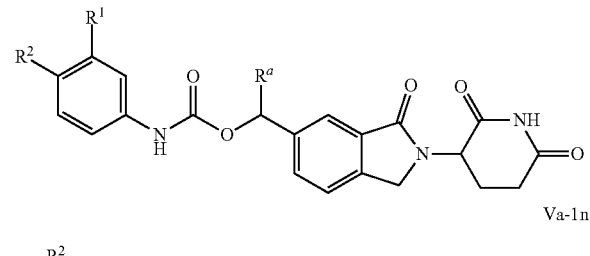

Va-1n
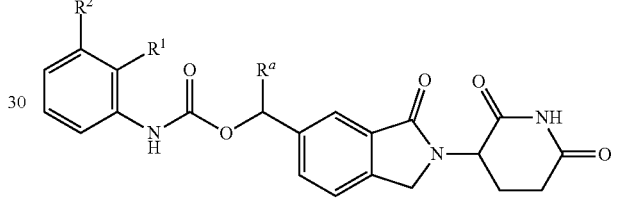

Va-1o
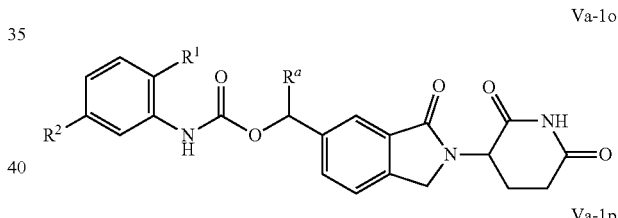

Va-1p
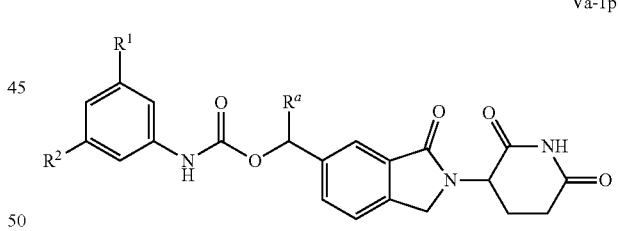

Va-1q
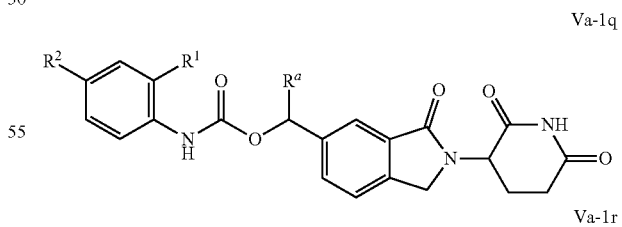

Va-1r
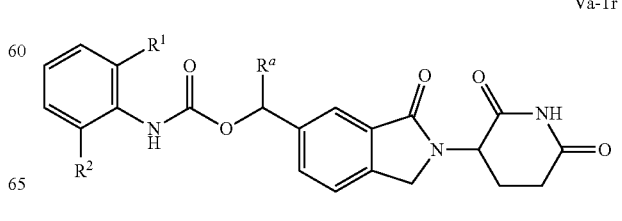

wherein

R$^1$, R$^2$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, NH$_2$, —C$_{1-4}$ alkylhydroxy, and halogen, such as F, Cl or Br, e.g. F or Cl, or a group of formula -L$^3$-X$^2$, wherein L$^3$ is a covalent bond, linear or branched C$_{1-6}$ alkyl, —O—, or —C$_{1-4}$ alkoxy and X$^2$ is C$_{3-6}$ cycloalkyl, C$_{6-10}$ aryl, 5-10 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and R$^a$ is H or methyl.

In some embodiments of a compound of formula Va-1m, Va-1n, Va-1o, Va-1p, Va-1q or Va-1r, R$^a$ is H. In some embodiments of a compound of formula Va-1m, Va-1n, Va-1o, Va-1p, Va-1q or Va-1r, R$^a$ is methyl.

In some embodiments of a compound of formula Va-1m, Va-1n, Va-1o, Va-1p, Va-1q or Va-1r, L$^3$ is a covalent bond. In some embodiments of a compound of formula Va-1m, Va-1n, Va-1o, Va-1p, Va-1q or Va-1r, L$^3$ is linear or branched C$_{1-4}$ alkyl, such as —CH$_2$—. In some embodiments of a compound of formula Va-1m, Va-1n, Va-1o, Va-1p, Va-1q or Va-1r, L$^3$ is —O—. In some embodiments L$^3$ is linear or branched C$_{1-4}$ alkoxy, such as —O—CH$_2$—, —O—(CH$_2$)$_2$—

In some embodiments of a compound of formula Va-1m, Va-1n, Va-1o, Va-1p, Va-1q or Va-1r, R$^1$, R$^2$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —OC(O)—C$_{1-6}$alkyl, —N(H)C(O)—C$_{1-6}$alkyl, —C(O)O—C$_{1-6}$alkyl, —COOH, —C$_{1-6}$alkylC(O)OH, —C$_{1-6}$alkylC(O)O—C$_{1-6}$alkyl, NH$_2$, —C$_{1-4}$ alkylhydroxy, and halogen, such as F, Cl or Br, e.g. F or Cl.

In some embodiments of a compound of formula Va-1m, Va-1n, Va-1o, Va-1p, Va-1q or Va-1r, R$^1$, R$^2$ are independently of each other selected from H, linear or branched —C$_{1-6}$ alkyl, —C$_{1-4}$ alkoxy, CF$_3$, CHF$_2$, CMeF$_2$, OCF$_3$, OCHF$_2$, —CN, and halogen, such as F, Cl or Br, e.g. F or Cl.

In some embodiments of a compound of formula Va-1m, Va-1n, Va-1o, Va-1p, Va-1q or Va-1r, R$^a$ is H and R$^1$, R$^2$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —OC(O)—C$_{1-6}$ alkyl, —N(H)C(O)—C$_{1-6}$alkyl, —C(O)O—C$_{1-6}$alkyl, —COOH, —C$_{1-6}$alkylC(O)OH, —C$_{1-6}$alkylC(O)O—C$_{1-6}$ alkyl, NH$_2$, —C$_{1-4}$ alkylhydroxy, and halogen, such as F, Cl or Br, e.g. F or Cl.

In some embodiments of a compound of formula Va-1m, Va-1n, Va-1o, Va-1p, Va-1q or Va-1r, R$^a$ is H and R$^1$, R$^2$ are independently of each other selected from H, linear or branched —C$_{1-6}$ alkyl, —C$_{1-4}$ alkoxy, CF$_3$, CHF$_2$, CMeF$_2$, OCF$_3$, OCHF$_2$, —CN, and halogen, such as F, Cl or Br, e.g. F or Cl.

In some embodiments of a compound of formula Va-1m, Va-1n, Va-1o, Va-1p, Va-1q or Va-1r, R$^a$ is CH$_3$ and R$^1$, R$^2$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —OC(O)—C$_{1-6}$ alkyl, —N(H)C(O)—C$_{1-6}$alkyl, —C(O)O—C$_{1-6}$alkyl, —COOH, —C$_{1-6}$alkylC(O)OH, —C$_{1-6}$alkylC(O)O—C$_{1-6}$ alkyl, NH$_2$, —C$_{1-4}$ alkylhydroxy, and halogen, such as F, Cl or Br, e.g. F or Cl.

In some embodiments of a compound of formula Va-1m, Va-1n, Va-1o, Va-1p, Va-1q or Va-1r, R$^a$ is CH$_3$ and R$^1$, R$^2$ are independently of each other selected from H, linear or branched —C$_{1-6}$ alkyl, —C$_{1-4}$ alkoxy, CF$_3$, CHF$_2$, CMeF$_2$, OCF$_3$, OCHF$_2$, —CN, and halogen, such as F, Cl or Br, e.g. F or Cl.

In some embodiments of a compound of formula Va-1m, Va-1n, Va-1o, Va-1p, Va-1q or Va-1r, R$^a$ is CH$_3$, and R$^1$, R$^2$ are independently of each other selected from H, halogen, such as Cl, F, linear or branched —C$_{1-4}$ alkyl, such as methyl, fluorinated C$_{1-4}$ alkoxy, such as —OCF$_3$.

In some embodiments of a compound of formula Va-1m, Va-1n, Va-1o, Va-1p, Va-1q or Va-1r, one of R$^1$, R$^2$ is selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, NH$_2$, —C$_{1-4}$ alkylhydroxy, and halogen, such as F, Cl or Br, e.g. F or Cl; the other of R$^1$, R$^2$ is a group of formula -L$^3$-X$^2$, wherein L$^3$ is a covalent bond, —CH$_2$—, —O—, —OCH$_2$—, —O(CH$_2$)$_2$— and X$^2$ is C$_{3-6}$ cycloalkyl, C$_{6-10}$ aryl, 5-10 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy.

In some embodiments of a compound of formula Va-1m, Va-1n, Va-1o, Va-1p, Va-1q or Va-1r, one of R$^1$, R$^2$ is selected from a group consisting of C$_{3-6}$ cycloalkyl, —C$_{1-4}$ alkyl-C$_{3-6}$ cycloalkyl, —O—C$_{3-6}$ cycloalkyl, —C$_{1-4}$ alkoxy-C$_{3-6}$ cycloalkyl, C$_{6-10}$ aryl, —C$_{1-4}$ alkyl-C$_{6-10}$ aryl, —O—C$_{6-10}$ aryl, —C$_{1-4}$ alkoxy-C$_{6-10}$ aryl, 5-10 membered heteroaryl, —C$_{1-4}$ alkyl-(5-10 membered heteroaryl), —O-(5-membered heteroaryl), —C$_{1-4}$ alkoxy-(5-10 membered heteroaryl), 4-8 membered heterocycloalkyl, —C$_{1-4}$ alkyl-(4-8 membered heterocycloalkyl), —O-(4-8 membered heterocycloalkyl), —C$_{1-4}$ alkoxy-(4-8 membered heterocycloalkyl), which group is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and the other of R$^1$, R$^2$ is selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —C$_{1-4}$ alkylhydroxy, and halogen, such as F, Cl or Br, e.g. F or Cl.

In some embodiments of a compound of formula Va-1m, Va-1n, Va-1o, Va-1p, Va-1q or Va-1r, one of R$^1$, R$^2$ is selected from a group consisting of C$_{3-6}$ cycloalkyl, —O—C$_{3-6}$ cycloalkyl, C$_{6-10}$ aryl, 5-10 membered heteroaryl, 4-8 membered heterocycloalkyl, —C$_{1-4}$ alkyl-(4-8 membered heterocycloalkyl), —O-(4-8 membered heterocycloalkyl), —C$_{1-4}$ alkoxy-(4-8 membered heterocycloalkyl), which group is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and the other of R$^1$, R$^2$ is selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —C$_{1-4}$ alkylhydroxy, and halogen, such as F, Cl or Br, e.g. F or Cl.

In some embodiments of a compound of formula Va-1m, Va-1n, Va-1o, Va-1p, Va-1q or Va-1r, one of R$^1$, R$^2$ is selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —C$_{1-4}$ alkylhydroxy, and halogen, such as F, Cl or Br, e.g. F or Cl; the other of R$^1$, R$^2$ is a group of formula -L$^3$-X$^2$, wherein L$^3$ is a covalent bond, linear or branched C$_{1-4}$ alkyl, —O—, —C$_{1-4}$ alkoxy and X$^2$ is cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy.

In some embodiments of a compound of formula Va-1m, Va-1n, Va-1o, Va-1p, Va-1q or Va-1r, one of R$^1$, R$^2$ is selected from H, halogen, e.g. Cl, F, linear or branched —C$_{1-4}$ alkyl, e.g., Me, Et, t-But, CF$_3$, CHF$_2$, CMeF$_2$, —OCF$_3$, OCHF$_2$, CN, and C$_{1-4}$ alkoxy, e.g. —OMe, the other of R$^1$, R$^2$ is a group of formula -L$^3$-X$^2$, wherein L$^3$ is a covalent bond, —CH$_2$—, —O—, —OCH$_2$—, —O(CH$_2$)$_2$— and X$^2$ is cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein X$^2$ is unsubstituted or substituted with one or more of linear or branched C$_{1-4}$ alkyl, —C$_{1-4}$ alkoxy, e.g. —OMe, NMe$_2$, halogen, e.g. F.

In some embodiments of a compound of formula Va-1m, Va-1n, Va-1o, Va-1p, Va-1q or Va-1r, one of R$^1$, R$^2$ is selected from H, halogen, e.g. Cl, F, linear or branched —C$_{1-4}$ alkyl, e.g., Me, Et, t-But, CF$_3$, CHF$_2$, CMeF$_2$, —OCF$_3$, OCHF$_2$, CN, and C$_{1-4}$ alkoxy, e.g. —OMe; the other of R$^1$, R$^2$ is a group of formula -L$^3$-X$^2$, wherein L$^3$ is a covalent bond, —CH$_2$—, —O—, —OCH$_2$—, —O(CH$_2$)$_2$— and X$^2$ is cyclopropyl, methyl-cyclopropyl, fluoro-cyclopropyl, difluoro-cyclopropyl, cyclobutyl, C$_6$ aryl, methyl-C$_6$ aryl, fluoro-C$_6$ aryl, methoxy-C$_6$ aryl, pyridinyl, pyrrolidinyl, N-methyl-pyrrolidinyl, methyl-pyrrolidinyl, piperdinyl, N-methyl piperdinyl, methyl-piperdinyl, difluoro-piperidinyl, morpholinyl, N-methyl-morpholinyl, oxetanyl, methyl-oxetanyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl.

In some embodiments of a compound of formula Va-1m, Va-1n, Va-1o, Va-1p, Va-1q or Va-1r, R$^a$ is H and In some embodiments of a compound of formula Va-1m, Va-1n, Va-1o, Va-1p, Va-1q or Va-1r, R$^a$ is H and In some embodiments of a compound of formula Va-1m, Va-1n, Va-1o, Va-1p, Va-1q or Va-1r, R$^a$ is H and In some embodiments of a compound of formula Va-1m, Va-1n, Va-1o, Va-1p, Va-1q or Va-1r, R$^a$ is H and In some embodiments of a compound of formula Va-1m, Va-1n, Va-1o, Va-1p, Va-1q or Va-1r, R$^a$ is H and In some embodiments of a compound of formula Va-1m, Va-1n, Va-1o, Va-1p, Va-1q or Va-1r, R$^a$ is H and In some embodiments the compound of formula V and Va-2 is defined by formula Va-2a, Va-2b, Va-2c, Va-2d:

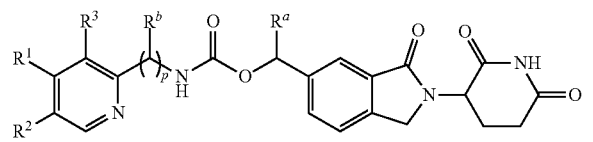

Va-2a

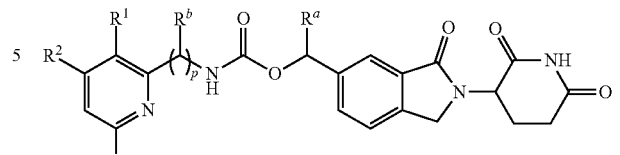

Va-2b

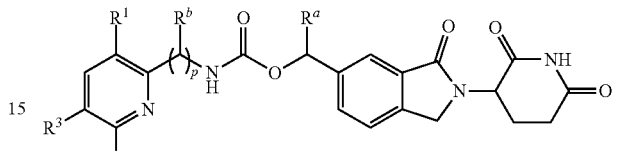

Va-2c

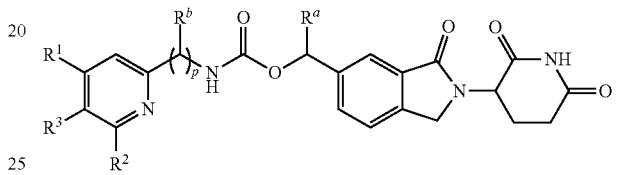

Va-2d wherein
R$^1$, R$^2$, R$^3$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —OC(O)—C$_{1-6}$alkyl, —N(H)C(O)—C$_{1-6}$alkyl, —C(O)O—C$_{1-6}$alkyl, —COOH, —C$_{1-6}$alkylC(O)OH, —C$_{1-6}$alkylC(O)O—C$_{1-6}$alkyl, NH$_2$, —C$_{1-4}$ alkylhydroxy, and halogen, such as F, Cl or Br, e.g. F or Cl, or a group of formula -L$^3$-X$^2$, wherein L$^3$ is a covalent bond, linear or branched C$_{1-6}$ alkyl, —O—, —C$_{1-4}$ alkoxy and X$^2$ is C$_{3-6}$ cycloalkyl, C$_{6-10}$ aryl, 5-10 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; p is 0 or 1 and R$^a$, R$^b$ are independently of each other H or methyl.

In some embodiments of a compound of formula Va-2a, Va-2b, Va-2c, Va-2d, p is 0. In some embodiments of a compound of formula Va-2a, Va-2b, Va-2c, Va-2d, p is 1.

In some embodiments of a compound of formula Va-2a, Va-2b, Va-2c, Va-2d, R$^a$ is H. In some embodiments of a compound of formula Va-2a, Va-2b, Va-2c, Va-2d, R$^a$ is methyl. In some embodiments of a compound of formula Va-2a, Va-2b, Va-2c, Va-2d, p is 0 and R$^a$ is H. In some embodiments of a compound of formula Va-2a, Va-2b, Va-2c, Va-2d, p is 0 and R$^a$ is methyl.

In some embodiments of a compound of formula Va-2a, Va-2b, Va-2c, Va-2d, p is 1 and R$^b$ is H. In some embodiments of a compound of formula Va-2a, Va-2b, Va-2c, Va-2d, p is 1 and R$^b$ is methyl. In some embodiments of a compound of formula Va-2a, Va-2b, Va-2c, Va-2d, p is 1, R$^b$ is H and R$^a$ is H. In some embodiments of a compound of formula, p is 1, R$^b$ is methyl and R$^a$ is H.

In some embodiments of a compound of formula Va-2a, Va-2b, Va-2c, Va-2d, L$^3$ is a covalent bond.

In some embodiments of a compound of formula Va-2a, Va-2b, Va-2c, Va-2d, R$^1$, R$^2$, R$^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-2a, Va-2b, Va-2c, Va-2d, $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-2a, Va-2b, Va-2c, Va-2d, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-2a, Va-2b, Va-2c, Va-2d, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-2a, Va-2b, Va-2c, Va-2d, $R^a$ is H and $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-2a, Va-2b, Va-2c, Va-2d, $R^a$ is H and $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-2a, Va-2b, Va-2c, Va-2d, $R^a$ is H, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-2a, Va-2b, Va-2c, Va-2d, $R^a$ is H, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-2a, Va-2b, Va-2c, Va-2d, p is 0 and $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-2a, Va-2b, Va-2c, Va-2d, p is 0, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-2a, Va-2b, Va-2c, Va-2d, p is 0, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-2a, Va-2b, Va-2c, Va-2d, p is 0, $R^a$ is H and $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-2a, Va-2b, Va-2c, Va-2d p is 0, $R^a$ is H and $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-2a, Va-2b, Va-2c, Va-2d, p is 0, $R^a$ is H, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-2a, Va-2b, Va-2c, Va-2d, p is 0, $R^a$ is H, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-2a, Va-2b, Va-2c, Va-2d, one of $R^1$, $R^2$, $R^3$ is a group of formula -$L^3$-$X^2$, wherein $L^3$ is a covalent bond, —$CH_2$—, —O—, —$OCH_2$—, —$O(CH_2)_2$— and $X^2$ is $C_{3-6}$ cycloalkyl, $C_{6-10}$ aryl, 5-10 membered heteroaryl, 4-8 membered heterocycloalkyl, which group is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —C$_{1-6}$alkylC(O)O—C$_{1-6}$alkyl, NH$_2$, —C$_{1-4}$ alkylhydroxy, and halogen, such as F, Cl or Br, e.g. F or Cl; p is 0 and R$^a$ is H.

In some embodiments of a compound of formula Va-2a, Va-2b, Va-2c, Va-2d, one of R$^1$, R$^2$, R$^3$ is selected from a group consisting of C$_{3-6}$ cycloalkyl, C$_{6-10}$ aryl, 5-10 membered heteroaryl, 4-8 membered heterocycloalkyl, which group is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and the other two of R$^1$, R$^2$, R$^3$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —C$_{1-4}$ alkylhydroxy, and halogen, such as F, Cl or Br, e.g. F or Cl; p is 0 and R$^a$ is H.

In some embodiments of a compound of formula Va-2a, Va-2b, Va-2c, Va-2d, one of R$^1$, R$^2$, R$^3$ is selected from a group consisting of cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, which group is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and the other two of R$^1$, R$^2$, R$^3$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —C$_{1-4}$ alkylhydroxy, halogen, such as F, Cl or Br, e.g. F or Cl; p is 0 and R$^a$ is H.

In some embodiments of a compound of formula Va-2a, Va-2b, Va-2c, Va-2d, one of R$^1$, R$^2$, R$^3$ is selected from a group consisting of cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, which group is unsubstituted or substituted with one or more of linear or branched C$_{1-4}$ alkyl, e.g. methyl, —C$_{1-4}$ alkoxy, e.g. —OMe, NMe$_2$, halogen, e.g. F; and the other two of R$^1$, R$^2$, R$^3$ are independently of each other selected from H, halogen, e.g. Cl, F, linear or branched —C$_{1-4}$ alkyl, e.g., Me, Et, t-But, CF$_3$, CHF$_2$, CMeF$_2$, —OCF$_3$, OCHF$_2$, CN, C$_{1-4}$ alkoxy, e.g. —OMe; p is 0 and R$^a$ is H.

In some embodiments of a compound of formula Va-2a, Va-2b, Va-2c, Va-2d, one of R$^1$, R$^2$, R$^3$ is selected from a group consisting of cyclopropyl, methyl-cyclopropyl, fluoro-cyclopropyl, cyclobutyl, C$_6$ aryl, methyl-C$_6$ aryl, fluoro-C$_6$ aryl, methoxy-C$_6$ aryl, pyridinyl, pyrrolidinyl, methyl-pyrrolidinyl, piperdinyl, N-methyl piperdinyl, methyl-piperdinyl, difluoro-piperidinyl, morpholinyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl; and the other two of R$^1$, R$^2$, R$^3$ are independently of each other selected from H, halogen, e.g. Cl, F, linear or branched —C$_{1-4}$ alkyl, e.g., Me, Et, t-But, CF$_3$, CHF$_2$, CMeF$_2$, —OCF$_3$, OCHF$_2$, CN, and C$_{1-4}$ alkoxy, e.g. —OMe; p is 0 and R$^a$ is H.

In some embodiments the compound of formula Va and Va-2 is defined by formula Va-2e, Va-2f, Va-2g, Va-2h, Va-2i, Va-2j:

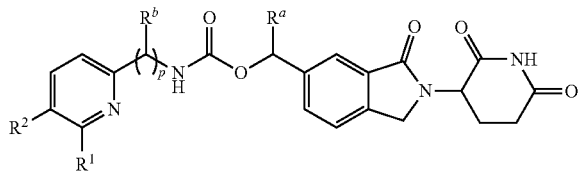

Va-2e

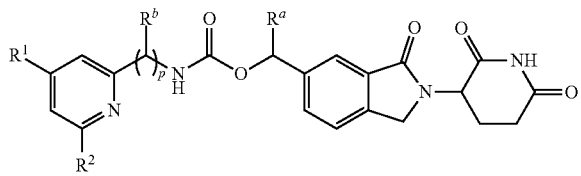

Va-2f

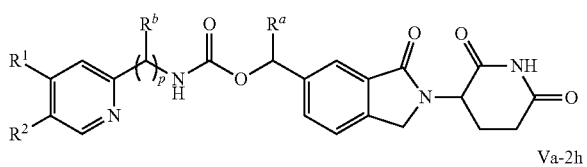

Va-2g

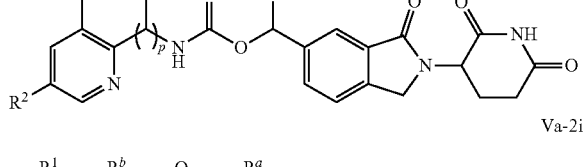

Va-2h

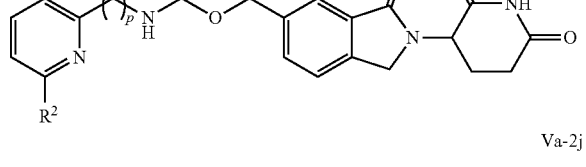

Va-2i

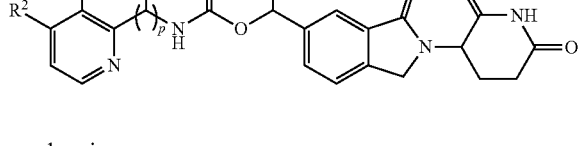

Va-2j wherein

R$^1$, R$^2$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —OC(O)—C$_{1-6}$alkyl, —N(H)C(O)—C$_{1-6}$alkyl, —C(O)O—C$_{1-6}$alkyl, —COOH, —C$_{1-6}$ alkylC(O)OH, —C$_{1-6}$alkylC(O)O—C$_{1-6}$alkyl, NH$_2$, —C$_{1-4}$ alkylhydroxy, and halogen, such as F, Cl or Br, e.g. F or Cl, or a group of formula -L$^3$-X$^2$, wherein L$^3$ is a covalent bond, linear or branched C$_{1-6}$ alkyl, —O—, —C$_{1-4}$ alkoxy and X$^2$ is C$_{3-6}$ cycloalkyl, C$_{6-10}$ aryl, 5-10 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; p is 0 or 1 and R$^a$, R$^b$ are independently of each other H or methyl.

In some embodiments of a compound of formula Va-2e, Va-2f, Va-2g, Va-2h, Va-2i, Va-2j, p is 0. In some embodiments of a compound of formula Va-2e, Va-2f, Va-2g, Va-2h, Va-2i, Va-2j, p is 1.

In some embodiments of a compound of formula Va-2e, Va-2f, Va-2g, Va-2h, Va-2i, Va-2j, $R^a$ is H. In some embodiments of a compound of formula Va-2e, Va-2f, Va-2g, Va-2h, Va-2i, Va-2j, $R^a$ is methyl. In some embodiments of a compound of formula Va-2e, Va-2f, Va-2g, Va-2h, Va-2i, Va-2j, p is 0 and $R^a$ is H. In some embodiments of a compound of formula Va-2e, Va-2f, Va-2g, Va-2h, Va-2i, Va-2j, p is 0 and $R^a$ is methyl.

In some embodiments of a compound of formula Va-2e, Va-2f, Va-2g, Va-2h, Va-2i, Va-2j, p is 1 and $R^b$ is H. In some embodiments of a compound of formula Va-2e, Va-2f, Va-2g, Va-2h, Va-2i, Va-2j, p is 1 and $R^b$ is methyl. In some embodiments of a compound of formula Va-2e, Va-2f, Va-2g, Va-2h, Va-2i, Va-2j, p is 1, $R^b$ is H and $R^a$ is H. In some embodiments of a compound of formula Va-2e, Va-2f, Va-2g, Va-2h, Va-2i, Va-2j, p is 1, $R^b$ is methyl and $R^a$ is H.

In some embodiments of a compound of formula Va-2e, Va-2f, Va-2g, Va-2h, Va-2i, Va-2j, $L^3$ is a covalent bond.

In some embodiments of a compound of formula Va-2e, Va-2f, Va-2g, Va-2h, Va-2i, Va-2j, $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-2e, Va-2f, Va-2g, Va-2h, Va-2i, Va-2j, $R^1$, $R^2$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-2e, Va-2f, Va-2g, Va-2h, Va-2i, Va-2j, $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-2e, Va-2f, Va-2g, Va-2h, Va-2i, Va-2j, $R^1$, $R^2$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-2e, Va-2f, Va-2g, Va-2h, Va-2i, Va-2j, $R^a$ is H and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-2e, Va-2f, Va-2g, Va-2h, Va-2i, Va-2j, $R^a$ is H and $R^1$, $R^2$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-2e, Va-2f, Va-2g, Va-2h, Va-2i, Va-2j, $R^a$ is H, and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-2e, Va-2f, Va-2g, Va-2h, Va-2i, Va-2j, $R^a$ is H, and $R^1$, $R^2$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-2e, Va-2f, Va-2g, Va-2h, Va-2i, Va-2j, p is 0 and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-2e, Va-2f, Va-2g, Va-2h, Va-2i, Va-2j, p is 0 and $R^1$, $R^2$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-2e, Va-2f, Va-2g, Va-2h, Va-2i, Va-2j, p is 0, and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-2e, Va-2f, Va-2g, Va-2h, Va-2i, Va-2j, p is 0, and $R^1$, $R^2$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-2e, Va-2f, Va-2g, Va-2h, Va-2i, Va-2j, p is 0, $R^a$ is H and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-2e, Va-2f, Va-2g, Va-2h, Va-2i, Va-2j, p is 0, $R^a$ is H and $R^1$, $R^2$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-2e, Va-2f, Va-2g, Va-2h, Va-2i, Va-2j, p is 0, $R^a$ is H, and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —C$_{1-6}$alkylC(O)OH, —C$_{1-6}$alkylC(O)O—C$_{1-6}$ alkyl, NH$_2$, —C$_{1-4}$ alkylhydroxy, and halogen, such as F, Cl or Br, e.g. F or Cl.

In some embodiments of a compound of formula Va-2e, Va-2f, Va-2g, Va-2h, Va-2i, Va-2j, p is 0, R$^a$ is H, and R$^1$, R$^2$ are independently of each other selected from H, linear or branched —C$_{1-6}$ alkyl, —C$_{1-4}$ alkoxy, such as —OMe, OCF$_3$, and halogen, such as F, Cl or Br, e.g. F or Cl.

In some embodiments of a compound of formula Va-2e, Va-2f, Va-2g, Va-2h, Va-2i, Va-2j, one of R$^1$, R$^2$ is a group of formula -L$^3$-X$^2$, wherein L$^3$ is a covalent bond, —CH$_2$—, —O—, —OCH$_2$—, —O(CH$_2$)$_2$— and X$^2$ is C$_{3-6}$ cycloalkyl, C$_{6-10}$ aryl, 5-10 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and the other of R$^1$, R$^2$ is selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —OC(O)—C$_{1-6}$alkyl, —N(H)C(O)—C$_{1-6}$alkyl, —C(O)O—C$_{1-6}$alkyl, —COOH, —C$_{1-6}$alkylC(O)OH, —C$_{1-6}$alkylC(O)O—C$_{1-6}$alkyl, NH$_2$, —C$_{1-4}$ alkylhydroxy, and halogen, such as F, Cl or Br, e.g. F or Cl; p is 0 and R$^a$ is H.

In some embodiments of a compound of formula Va-2e, Va-2f, Va-2g, Va-2h, Va-2i, Va-2j, one of R$^1$, R$^2$ is a group selected from C$_{3-6}$ cycloalkyl, C$_{6-10}$ aryl, 5-10 membered heteroaryl, 4-8 membered heterocycloalkyl, which group is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy and the other of R$^1$, R$^2$ is selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —C$_{1-4}$ alkylhydroxy, and halogen, such as F, Cl or Br, e.g. F or Cl; p is 0 and R$^a$ is H.

In some embodiments of a compound of formula Va-2e, Va-2f, Va-2g, Va-2h, Va-2i, Va-2j, one of R$^1$, R$^2$ is a group selected from cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and the other of R$^1$, R$^2$ is selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —C$_{1-4}$ alkylhydroxy, halogen, such as F, Cl or Br, e.g. F or Cl; p is 0 and R$^a$ is H.

In some embodiments of a compound of formula Va-2e, Va-2f, Va-2g, Va-2h, Va-2i, Va-2j, one of R$^1$, R$^2$ is a group selected from cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, which group is unsubstituted or substituted with one or more of linear or branched C$_{1-4}$ alkyl, e.g. methyl, —C$_{1-4}$ alkoxy, e.g. —OMe, NMe$_2$, halogen, e.g. F; and the other of R$^1$, R$^2$ is selected from H, halogen, e.g. Cl, F, linear or branched —C$_{1-4}$ alkyl, e.g., Me, Et, t-But, CF$_3$, CHF$_2$, CMeF$_2$, —OCF$_3$, OCHF$_2$, CN, C$_{1-4}$ alkoxy, e.g. —OMe; p is 0 and R$^a$ is H.

In some embodiments of a compound of formula Va-2e, Va-2f, Va-2g, Va-2h, Va-2i, Va-2j, one of R$^1$, R$^2$ is a group selected from; and the other of R$^1$, R$^2$ are independently of each other selected from H, halogen, e.g. Cl, F, linear or branched —C$_{1-4}$ alkyl, e.g., Me, Et, t-But, CF$_3$, CHF$_2$, CMeF$_2$, —OCF$_3$, OCHF$_2$, CN, and C$_{1-4}$ alkoxy, e.g. —OMe, cyclopropyl, methyl-cyclopropyl, fluoro-cyclopropyl, cyclobutyl, C$_6$ aryl, methyl-C$_6$ aryl, fluoro-C$_6$ aryl, methoxy-C$_6$ aryl, pyridinyl, pyrrolidinyl, methyl-pyrrolidinyl, piperdinyl, N-methyl piperdinyl, methyl-piperdinyl, difluoro-piperidinyl, morpholinyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl; p is 0 and R$^a$ is H.

In some embodiments the compound of formula Va and Va-3 is defined by formula Va-3a or Va-3b:

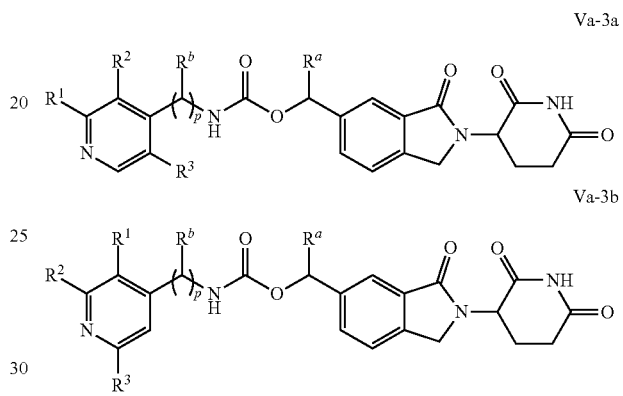

wherein
R$^1$, R$^2$, R$^3$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —OC(O)—C$_{1-6}$alkyl, —N(H)C(O)—C$_{1-6}$alkyl, —C(O)O—C$_{1-6}$alkyl, —COOH, —C$_{1-6}$alkylC(O)OH, —C$_{1-6}$alkylC(O)O—C$_{1-6}$alkyl, NH$_2$, —C$_{1-4}$ alkylhydroxy, and halogen, such as F, Cl or Br, e.g. F or Cl, or a group of formula -L$^3$-X$^2$, wherein L$^3$ is a covalent bond, linear or branched C$_{1-6}$ alkyl, —O—, —C$_{1-4}$ alkoxy and X$^2$ is C$_{3-6}$ cycloalkyl, C$_{6-10}$ aryl, 5-10 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; p is 0 or 1 and R$^a$, R$^b$ are independently of each other H or methyl.

In some embodiments of a compound of formula Va-3a, Va-3b, p is 0. In some embodiments of a compound of formula Va-3a, Va-3b, p is 1.

In some embodiments of a compound of formula Va-3a, Va-3b, R$^a$ is H. In some embodiments of a compound of formula Va-3a, Va-3b, R$^a$ is methyl. In some embodiments of a compound of formula Va-3a, Va-3b, p is 0 and R$^a$ is H. In some embodiments of a compound of formula Va-3a, Va-3b, p is 0 and R$^a$ is methyl.

In some embodiments of a compound of formula Va-3a, Va-3b, p is 1 and R$^b$ is H. In some embodiments of a compound of formula Va-3a, Va-3b, p is 1 and R$^b$ is methyl. In some embodiments of a compound of formula Va-3a, Va-3b, p is 1, R$^b$ is H and R$^a$ is H. In some embodiments of a compound of formula Va-3a, Va-3b, p is 1, R$^b$ is methyl and R$^a$ is H.

In some embodiments of a compound of formula Va-3a, Va-3b, $L^3$ is a covalent bond.

In some embodiments of a compound of formula Va-3a, Va-3b, $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$-alkyl, $NH_2$, —$C_{1-4}$ alkylhydroxy, and halogen, such as F, Cl or Br, e.g. F or Cl.

In some embodiments of a compound of formula Va-3a, Va-3b, $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-3a, Va-3b, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-3a, Va-3b, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-3a, Va-3b, $R^a$ is H and $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-3a, Va-3b, $R^a$ is H and $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-3a, Va-3b, $R^a$ is H, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-3a, Va-3b, $R^a$ is H, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-3a, Va-3b, p is 0 and $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$ alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-3a, Va-3b, p is 0 and $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-3a, Va-3b, p is 0, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-3a, Va-3b, p is 0, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-3a, Va-3b, p is 0, $R^a$ is H and $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-3a, Va-3b, p is 0, $R^a$ is H and $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-3a, Va-3b, p is 0, $R^a$ is H, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-3a, Va-3b, p is 0, $R^a$ is H, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-3a, Va-3b, one of $R^1$, $R^2$, $R^3$ is a group of formula -$L^3$-$X^2$, wherein $L^3$ is a covalent bond, —$CH_2$—, —O—, —$OCH_2$—, —$O(CH_2)_2$— and $X^2$ is $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —C$_{1-6}$alkylC(O)O—C$_{1-6}$alkyl, NH$_2$, —C$_{1-4}$ alkylhydroxy, and halogen, such as F, Cl or Br, e.g. F or Cl; p is 0 and R$^a$ is H.

In some embodiments of a compound of formula Va-3a, Va-3b, one of R$^1$, R$^2$, R$^3$ is a group selected from C$_{3-6}$ cycloalkyl, C$_{6-10}$ aryl, 5-10 membered heteroaryl, 4-8 membered heterocycloalkyl, which group is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and the other two of R$^1$, R$^2$, R$^3$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —C$_{1-4}$ alkylhydroxy, and halogen, such as F, Cl or Br, e.g. F or Cl; p is 0 and R$^a$ is H.

In some embodiments of a compound of formula Va-3a, Va-3b, one of R$^1$, R$^2$, R$^3$ is a group selected from cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, which group is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and the other two of R$^1$, R$^2$, R$^3$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —C$_{1-4}$ alkylhydroxy, halogen, such as F, Cl or Br, e.g. F or Cl; p is 0 and R$^a$ is H.

In some embodiments of a compound of formula Va-3a, Va-3b, one of R$^1$, R$^2$, R$^3$ is a group selected from cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, which group is unsubstituted or substituted with one or more of linear or branched C$_{1-4}$ alkyl, e.g. methyl, —C$_{1-4}$ alkoxy, e.g. —OMe, NMe$_2$, halogen, e.g. F; and the other two of R$^1$, R$^2$, R$^3$ are independently of each other selected from H, halogen, e.g. Cl, F, linear or branched —C$_{1-4}$ alkyl, e.g., Me, Et, t-But, CF$_3$, CHF$_2$, CMeF$_2$, —OCF$_3$, OCHF$_2$, CN, C$_{1-4}$ alkoxy, e.g. —OMe; p is 0 and R$^a$ is H.

In some embodiments of a compound of formula Va-3a, Va-3b, one of R$^1$, R$^2$, R$^3$ is a group selected from cyclopropyl, methyl-cyclopropyl, fluoro-cyclopropyl, cyclobutyl, C$_6$ aryl, methyl-C$_6$ aryl, fluoro-C$_6$ aryl, methoxy-C$_6$ aryl, pyridinyl, pyrrolidinyl, methyl-pyrrolidinyl, piperdinyl, N-methyl piperdinyl, methyl-piperdinyl, difluoro-piperidinyl, morpholinyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl; and the other two of R$^1$, R$^2$, R$^3$ are independently of each other selected from H, halogen, e.g. Cl, F, linear or branched —C$_{1-4}$ alkyl, e.g., Me, Et, t-But, CF$_3$, CHF$_2$, CMeF$_2$, —OCF$_3$, OCHF$_2$, CN, and C$_{1-4}$ alkoxy, e.g. —OMe; p is 0 and R$^a$ is H.

In some embodiments the compound of formula Va and Va-3 is defined by formula Va-3c, Va-3d, Va-3e:

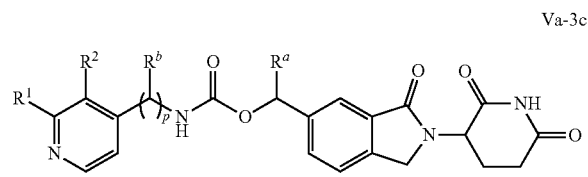

Va-3c

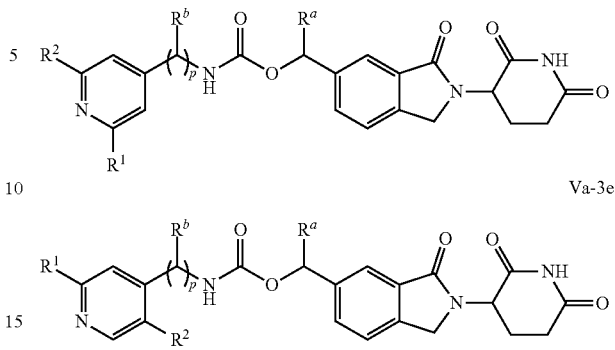

wherein
R$^1$, R$^2$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —OC(O)—C$_{1-6}$alkyl, —N(H)C(O)—C$_{1-6}$alkyl, —C(O)O—C$_{1-6}$alkyl, —COOH, —C$_{1-6}$ alkylC(O)OH, —C$_{1-6}$alkylC(O)O—C$_{1-6}$alkyl, NH$_2$, —C$_{1-4}$ alkylhydroxy, and halogen, such as F, Cl or Br, e.g. F or Cl, or a group of formula -L$^3$-X$^2$, wherein L$^3$ is a covalent bond, linear or branched C$_{1-6}$ alkyl, —O—, —C$_{1-4}$ alkoxy and X$^2$ is C$_{3-6}$ cycloalkyl, C$_{6-10}$ aryl, 5-10 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; p is 0 or 1 and R$^a$, R$^b$ are independently of each other H or methyl. In some embodiments of a compound of formula Va-3c, Va-3d, Va-3e, p is 0. In some embodiments of a compound of formula Va-3c, Va-3d, Va-3e, p is 1.

In some embodiments of a compound of formula Va-3c, Va-3d, Va-3e R$^a$ is H. In some embodiments of a compound of formula Va-3c, Va-3d, Va-3e R$^a$ is methyl. In some embodiments of a compound of formula Va-3c, Va-3d, Va-3e, p is 0 and R$^a$ is H. In some embodiments of a compound of formula Va-3c, Va-3d, Va-3e, p is 0 and R$^a$ is methyl.

In some embodiments of a compound of formula Va-3c, Va-3d, Va-3e, p is 1 and R$^b$ is H. In some embodiments of a compound of formula Va-3c, Va-3d, Va-3e, p is 1 and R$^b$ is methyl. In some embodiments of a compound of formula Va-3c, Va-3d, Va-3e, p is 1, R$^b$ is H and R$^a$ is H. In some embodiments of a compound of formula Va-3c, Va-3d, Va-3e, p is 1, R$^b$ is methyl and R$^a$ is H.

In some embodiments of a compound of formula Va-2e, Va-2f, Va-2g, Va-2h, Va-2i, Va-2j, L$^3$ is a covalent bond.

In some embodiments of a compound of formula Va-2e, Va-2f, Va-2g, Va-2h, Va-2i, Va-2j, R$^1$, R$^2$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —OC(O)—C$_{1-6}$alkyl, —N(H)C(O)—C$_{1-6}$alkyl, —C(O)O—C$_{1-6}$alkyl, —COOH, —C$_{1-6}$ alkylC(O)OH, —C$_{1-6}$alkylC(O)O—C$_{1-6}$alkyl, NH$_2$, —C$_{1-4}$ alkylhydroxy, and halogen, such as F, Cl or Br, e.g. F or Cl.

In some embodiments of a compound of formula Va-2e, Va-2f, Va-2g, Va-2h, Va-2i, Va-2j, R$^1$, R$^2$ are independently of each other selected from H, linear or branched —$C_{1-6}$ alkyl, —$C_{1-4}$ alkoxy, such as —OMe, OCF$_3$, and halogen, such as F, Cl or Br, e.g. F or Cl.

In some embodiments of a compound of formula Va-2e, Va-2f, Va-2g, Va-2h, Va-2i, Va-2j, $R^1$, $R^2$ are independently of each other selected from H, linear or branched —$C_{1-6}$ alkyl, linear or branched $C_{1-6}$ heteroalkyl, —$C_{1-4}$ alkoxy, CF$_3$, CHF$_2$, CMeF$_2$, —O—(CH$_2$)$_2$—OMe, OCF$_3$, OCHF$_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, NH$_2$, —$C_{1-4}$ alkylhydroxy, and halogen, such as F, Cl or Br, e.g. F or Cl.

In some embodiments of a compound of formula Va-2e, Va-2f, Va-2g, Va-2h, Va-2i, Va-2j, $R^1$, $R^2$ are independently of each other selected from H, linear or branched —$C_{1-6}$ alkyl, —$C_{1-4}$ alkoxy, such as —OMe, OCF$_3$, and halogen, such as F, Cl or Br, e.g. F or Cl.

In some embodiments of a compound of formula Va-2e, Va-2f, Va-2g, Va-2h, Va-2i, Va-2j, $R^a$ is H and $R^1$, $R^2$ are independently of each other selected from H, linear or branched —$C_{1-6}$ alkyl, linear or branched $C_{1-6}$ heteroalkyl, —$C_{1-4}$ alkoxy, CF$_3$, CHF$_2$, CMeF$_2$, —O—(CH$_2$)$_2$—OMe, OCF$_3$, OCHF$_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$ alkyl, NH$_2$, —$C_{1-4}$ alkylhydroxy, and halogen, such as F, Cl or Br, e.g. F or Cl.

In some embodiments of a compound of formula Va-2e, Va-2f, Va-2g, Va-2h, Va-2i, Va-2j, $R^a$ is H and $R^1$, $R^2$ are independently of each other selected from H, linear or branched —$C_{1-6}$ alkyl, —$C_{1-4}$ alkoxy, such as —OMe, OCF$_3$, and halogen, such as F, Cl or Br, e.g. F or Cl.

In some embodiments of a compound of formula Va-2e, Va-2f, Va-2g, Va-2h, Va-2i, Va-2j, $R^a$ is H, and $R^1$, $R^2$ are independently of each other selected from H, linear or branched —$C_{1-6}$ alkyl, linear or branched $C_{1-6}$ heteroalkyl, —$C_{1-4}$ alkoxy, CF$_3$, CHF$_2$, CMeF$_2$, —O—(CH$_2$)$_2$—OMe, OCF$_3$, OCHF$_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, NH$_2$, —$C_{1-4}$ alkylhydroxy, and halogen, such as F, Cl or Br, e.g. F or Cl.

In some embodiments of a compound of formula Va-2e, Va-2f, Va-2g, Va-2h, Va-2i, Va-2j, $R^a$ is H, and $R^1$, $R^2$ are independently of each other selected from H, linear or branched —$C_{1-6}$ alkyl, —$C_{1-4}$ alkoxy, such as —OMe, OCF$_3$, and halogen, such as F, Cl or Br, e.g. F or Cl.

In some embodiments of a compound of formula Va-2e, Va-2f, Va-2g, Va-2h, Va-2i, Va-2j, p is 0 and $R^1$, $R^2$ are independently of each other selected from H, linear or branched —$C_{1-6}$ alkyl, linear or branched $C_{1-6}$ heteroalkyl, —$C_{1-4}$ alkoxy, CF$_3$, CHF$_2$, CMeF$_2$, —O—(CH$_2$)$_2$—OMe, OCF$_3$, OCHF$_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$ alkyl, NH$_2$, —$C_{1-4}$ alkylhydroxy, and halogen, such as F, Cl or Br, e.g. F or Cl.

In some embodiments of a compound of formula Va-2e, Va-2f, Va-2g, Va-2h, Va-2i, Va-2j, p is 0 and $R^1$, $R^2$ are independently of each other selected from H, linear or branched —$C_{1-6}$ alkyl, —$C_{1-4}$ alkoxy, such as —OMe, OCF$_3$, and halogen, such as F, Cl or Br, e.g. F or Cl.

In some embodiments of a compound of formula Va-2e, Va-2f, Va-2g, Va-2h, Va-2i, Va-2j, p is 0, and $R^1$, $R^2$ are independently of each other selected from H, linear or branched —$C_{1-6}$ alkyl, linear or branched $C_{1-6}$ heteroalkyl, —$C_{1-4}$ alkoxy, CF$_3$, CHF$_2$, CMeF$_2$, —O—(CH$_2$)$_2$—OMe, OCF$_3$, OCHF$_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, NH$_2$, —$C_{1-4}$ alkylhydroxy, and halogen, such as F, Cl or Br, e.g. F or Cl.

In some embodiments of a compound of formula Va-2e, Va-2f, Va-2g, Va-2h, Va-2i, Va-2j, p is 0, and $R^1$, $R^2$ are independently of each other selected from H, linear or branched —$C_{1-6}$ alkyl, —$C_{1-4}$ alkoxy, such as —OMe, OCF$_3$, and halogen, such as F, Cl or Br, e.g. F or Cl.

In some embodiments of a compound of formula Va-2e, Va-2f, Va-2g, Va-2h, Va-2i, Va-2j, p is 0, $R^a$ is H and $R^1$, $R^2$ are independently of each other selected from H, linear or branched —$C_{1-6}$ alkyl, linear or branched $C_{1-6}$ heteroalkyl, —$C_{1-4}$ alkoxy, CF$_3$, CHF$_2$, CMeF$_2$, —O—(CH$_2$)$_2$—OMe, OCF$_3$, OCHF$_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, NH$_2$, —$C_{1-4}$ alkylhydroxy, and halogen, such as F, Cl or Br, e.g. F or Cl.

In some embodiments of a compound of formula Va-2e, Va-2f, Va-2g, Va-2h, Va-2i, Va-2j, p is 0, $R^a$ is H and $R^1$, $R^2$ are independently of each other selected from H, linear or branched —$C_{1-6}$ alkyl, —$C_{1-4}$ alkoxy, such as —OMe, OCF$_3$, and halogen, such as F, Cl or Br, e.g. F or Cl.

In some embodiments of a compound of formula Va-2e, Va-2f, Va-2g, Va-2h, Va-2i, Va-2j, p is 0, $R^a$ is H, and $R^1$, $R^2$ are independently of each other selected from H, linear or branched —$C_{1-6}$ alkyl, linear or branched $C_{1-6}$ heteroalkyl, —$C_{1-4}$ alkoxy, CF$_3$, CHF$_2$, CMeF$_2$, —O—(CH$_2$)$_2$—OMe, OCF$_3$, OCHF$_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, NH$_2$, —$C_{1-4}$ alkylhydroxy, and halogen, such as F, Cl or Br, e.g. F or Cl.

In some embodiments of a compound of formula Va-2e, Va-2f, Va-2g, Va-2h, Va-2i, Va-2j, p is 0, $R^a$ is H, and $R^1$, $R^2$ are independently of each other selected from H, linear or branched —$C_{1-6}$ alkyl, —$C_{1-4}$ alkoxy, such as —OMe, OCF$_3$, and halogen, such as F, Cl or Br, e.g. F or Cl.

In some embodiments of a compound of formula Va-3c, Va-3d, Va-3e, one of $R^1$, $R^2$ is a group selected from a group of formula -$L^3$-$X^2$, wherein $L^3$ is a covalent bond, —CH$_2$—, —O—, —OCH$_2$—, —O(CH$_2$)$_2$— and $X^2$ is $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —$C_{1-4}$ alkylhydroxy; and the other of $R^1$, $R^2$ are independently of each other selected from H, linear or branched —$C_{1-6}$ alkyl, linear or branched $C_{1-6}$ heteroalkyl, —$C_{1-4}$ alkoxy, CF$_3$, CHF$_2$, CMeF$_2$, —O—(CH$_2$)$_2$—OMe, OCF$_3$, OCHF$_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, NH$_2$, —$C_{1-4}$ alkylhydroxy, and halogen, such as F, Cl or Br, e.g. F or Cl; p is 0 and $R^a$ is H.

In some embodiments of a compound of formula Va-3c, Va-3d, Va-3e, one of $R^1$, $R^2$ is a group selected from $C_{3-6}$ cycloalkyl, $C_{6-10}$ aryl, 5-10 membered heteroaryl, 4-8 membered heterocycloalkyl, which group is unsubstituted or substituted with one or more of linear or branched $C_{1-6}$ alkyl, —$C_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —$C_{1-4}$ alkylhydroxy; and the other of $R^1$, $R^2$ is selected from H, linear or branched —$C_{1-6}$ alkyl, linear or branched $C_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —C$_{1-4}$ alkylhydroxy, and halogen, such as F, Cl or Br, e.g. F or Cl; p is 0 and R$^a$ is H.

In some embodiments of a compound of formula Va-3c, Va-3d, Va-3e, one of R$^1$, R$^2$ is a group selected from cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, which group is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; and the other of R$^1$, R$^2$ is selected from H, linear or branched —C$_{1-6}$ alkyl, linear or branched C$_{1-6}$ heteroalkyl, —C$_{1-4}$ alkyl, CF$_3$, CHF$_2$, CMeF$_2$, —O—(CH$_2$)$_2$—OMe, OCF$_3$, OCHF$_2$, —C$_{1-6}$ alkylamino, —CN, —C$_{1-4}$ alkylhydroxy, halogen, such as F, Cl or Br, e.g. F or Cl; p is 0 and R$^a$ is H.

In some embodiments of a compound of formula Va-3c, Va-3d, Va-3e, one of R$^1$, R$^2$ is a group selected from cyclopropyl, cyclobutyl, C$_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, which group is unsubstituted or substituted with one or more of linear or branched C$_{1-4}$ alkyl, e.g. methyl, —C$_{1-4}$ alkoxy, e.g. —OMe, NMe$_2$, halogen, e.g. F; and the other of R$^1$, R$^2$ is selected from H, halogen, e.g. Cl, F, linear or branched —C$_{1-4}$ alkyl, e.g., Me, Et, t-But, CF$_3$, CHF$_2$, CMeF$_2$, —OCF$_3$, OCHF$_2$, CN, C$_{1-4}$ alkoxy, e.g. —OMe; p is 0 and R$^a$ is H.

In some embodiments of a compound of formula Va-3c, Va-3d, Va-3e, one of R$^1$, R$^2$ is a group selected from cyclopropyl, methyl-cyclopropyl, fluoro-cyclopropyl, cyclobutyl, C$_6$ aryl, methyl-C$_6$ aryl, fluoro-C$_6$ aryl, methoxy-C$_6$ aryl, pyridinyl, pyrrolidinyl, methyl-pyrrolidinyl, piperdinyl, N-methyl piperdinyl, methyl-piperdinyl, difluoro-piperidinyl, morpholinyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl; and the other of R$^1$, R$^2$ is selected from H, halogen, e.g. Cl, F, linear or branched —C$_{1-4}$ alkyl, e.g., Me, Et, t-But, CF$_3$, CHF$_2$, CMeF$_2$, —OCF$_3$, OCHF$_2$, CN, and C$_{1-4}$ alkoxy, e.g. —OMe; p is 0 and R$^a$ is H.

In some embodiments the compound of formula Va and Va-4 is defined by formula Va-4a, Va-4b, Va-4c or Va-4d:

Va-4a

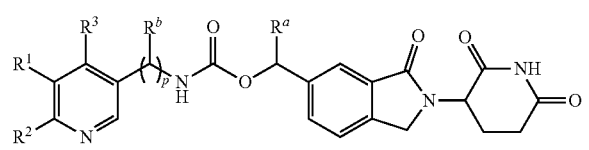

Va-4b

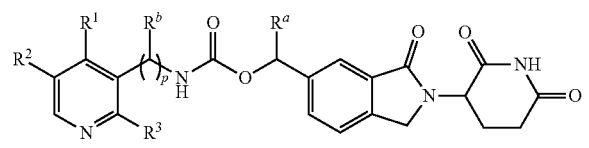

Va-4c

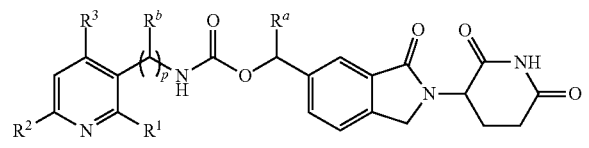

Va-4d

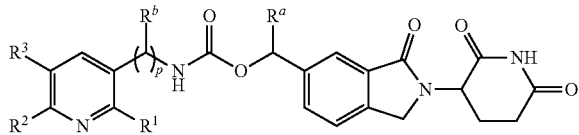

wherein
R$^1$, R$^2$, R$^3$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —OC(O)—C$_{1-6}$alkyl, —N(H)C(O)—C$_{1-6}$alkyl, —C(O)O—C$_{1-6}$alkyl, —COOH, —C$_{1-6}$alkylC(O)OH, —C$_{1-6}$alkylC(O)O—C$_{1-6}$alkyl, NH$_2$, —C$_{1-4}$ alkylhydroxy, and halogen, such as F, Cl or Br, e.g. F or Cl, or a group of formula -L$^3$-X$^2$, wherein L$^3$ is a covalent bond, linear or branched C$_{1-6}$ alkyl, —O—, —C$_{1-4}$ alkoxy and X$^2$ is C$_{3-6}$ cycloalkyl, C$_{6-10}$ aryl, 5-10 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy; p is 0 or 1 and R$^a$, R$^b$ are independently of each other H or methyl.

In some embodiments of a compound of formula Va-4a, Va-4b, Va-4c or Va-4d, p is 0. In some embodiments of a compound of formula Va-4a, Va-4b, Va-4c or Va-4d, p is 1.

In some embodiments of a compound of formula Va-4a, Va-4b, Va-4c or Va-4d, R$^a$ is H. In some embodiments of a compound of formula Va-4a, Va-4b, Va-4c or Va-4d, R$^a$ is methyl. In some embodiments of a compound of formula Va-4a, Va-4b, Va-4c or Va-4d, p is 0 and R$^a$ is H. In some embodiments of a compound of formula Va-4a, Va-4b, Va-4c or Va-4d, p is 0 and R$^a$ is methyl.

In some embodiments of a compound of formula Va-4a, Va-4b, Va-4c or Va-4d, p is 1 and R$^b$ is H. In some embodiments of a compound of formula Va-4a, Va-4b, Va-4c or Va-4d, p is 1 and R$^b$ is methyl. In some embodiments of a compound of formula Va-4a, Va-4b, Va-4c or Va-4d, p is 1, R$^b$ is H and R$^a$ is H. In some embodiments of a compound of formula Va-4a, Va-4b, Va-4c or Va-4d, p is 1, R$^b$ is methyl and R$^a$ is H.

In some embodiments of a compound of formula Va-4a, Va-4b, Va-4c or Va-4d, L$^3$ is a covalent bond.

In some embodiments of a compound of formula Va-4a, Va-4b, Va-4c or Va-4d, R$^1$, R$^2$, R$^3$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —OC(O)—C$_{1-6}$alkyl, —N(H)C(O)—C$_{1-6}$alkyl, —C(O)O—C$_{1-6}$alkyl, —COOH, —C$_{1-6}$alkylC(O)OH, —C$_{1-6}$ alkylC(O)O—C$_{1-6}$alkyl, NH$_2$, —C$_{1-4}$ alkylhydroxy, and halogen, such as F, Cl or Br, e.g. F or Cl.

In some embodiments of a compound of formula Va-4a, Va-4b, Va-4c or Va-4d, R$^1$, R$^2$, R$^3$ are independently of each other selected from H, linear or branched —C$_{1-6}$ alkyl, —C$_{1-4}$ alkoxy, such as —OMe, OCF$_3$, and halogen, such as F, Cl or Br, e.g. F or Cl.

In some embodiments of a compound of formula Va-4a, Va-4b, Va-4c or Va-4d, one of R$^1$, R$^2$, R$^3$ is H and the other two of R$^1$, R$^2$, R$^3$ are independently of each other selected from H, linear or branched —C$_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-4a, Va-4b, Va-4c or Va-4d, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-4a, Va-4b, Va-4c or Va-4d, $R^a$ is H and $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-4a, Va-4b, Va-4c or Va-4d, $R^a$ is H and $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-4a, Va-4b, Va-4c or Va-4d, $R^a$ is H, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-4a, Va-4b, Va-4c or Va-4d, $R^a$ is H, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-4a, Va-4b, Va-4c or Va-4d, p is 0 and $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-4a, Va-4b, Va-4c or Va-4d, p is 0 and $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-4a, Va-4b, Va-4c or Va-4d, p is 0, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-4a, Va-4b, Va-4c or Va-4d, p is 0, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-4a, Va-4b, Va-4c or Va-4d, p is 0, $R^a$ is H and $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-4a, Va-4b, Va-4c or Va-4d, p is 0, $R^a$ is H and $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-4a, Va-4b, Va-4c or Va-4d, p is 0, $R^a$ is H, one of $R^1$, $R^2$, $R^3$ is H and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-4a, Va-4b, Va-4c or Va-4d, p is 0, $R^a$ is H, one of $R^1$, $R^2$, $R^3$ is H and the other two of $R^1$, $R^2$, $R^3$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-4a, Va-4b, Va-4c or Va-4d, one of $R^1$, $R^2$ is a group of formula -$L^3$-$X^2$, wherein $L^3$ is a covalent bond, —$CH_2$—, —O—, —$OCH_2$—, —$O(CH_2)_2$— and $X^2$ is $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and the other two of $R^1$, $R^2$, $R^3$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl; p is 0 and $R^a$ is H.

In some embodiments of a compound of formula Va-4a, Va-4b, Va-4c or Va-4d, one of $R^1$, $R^2$ is a group selected from $C_{3-6}$ cycloalkyl, $C_{6-10}$ aryl, 5-10 membered heteroaryl, 4-8 membered heterocycloalkyl, which group is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and the other two of $R^1$, $R^2$, $R^3$ are independently of each other selected from H, linear or branched —$C_{1-6}$ alkyl, linear or branched C_{1-6} heteroalkyl, —C_{1-4} alkoxy, CF_3, CHF_2, CMeF_2, —O—(CH_2)_2—OMe, OCF_3, OCHF_2, —C_{1-6} alkylamino, —CN, —C_{1-4} alkylhydroxy, and halogen, such as F, Cl or Br, e.g. F or Cl; p is 0 and R^a is H.

In some embodiments of a compound of formula Va-4a, Va-4b, Va-4c or Va-4d, one of R^1, R^2 is a group selected from cyclopropyl, cyclobutyl, C_6 aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, which group is unsubstituted or substituted with one or more of linear or branched C_{1-6} alkyl, —C_{1-4} alkoxy, NH_2, NMe_2, halogen, CF_3, CHF_2, CMeF_2, —O—(CH_2)_2—OMe, OCF_3, OCHF_2, and —C_{1-4} alkylhydroxy; and the other two of R^1, R^2, R^3 are independently of each other selected from H, linear or branched —C_{1-6} alkyl, linear or branched C_{1-6} heteroalkyl, —C_{1-4} alkoxy, CF_3, CHF_2, CMeF_2, —O—(CH_2)_2—OMe, OCF_3, OCHF_2, —C_{1-6} alkylamino, —CN, —C_{1-4} alkylhydroxy, halogen, such as F, Cl or Br, e.g. F or Cl; p is 0 and R^a is H.

In some embodiments of a compound of formula Va-4a, Va-4b, Va-4c or Va-4d, one of R^1, R^2 is a group selected from cyclopropyl, cyclobutyl, C_6 aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, which group is unsubstituted or substituted with one or more of linear or branched C_{1-4} alkyl, e.g. methyl, —C_{1-4} alkoxy, e.g. —OMe, NMe_2, halogen, e.g. F; and the other two of R^1, R^2, R^3 are independently of each other selected from H, halogen, e.g. Cl, F, linear or branched —C_{1-4} alkyl, e.g., Me, Et, t-But, CF_3, CHF_2, CMeF_2, —OCF_3, OCHF_2, CN, C_{1-4} alkoxy, e.g. —OMe; p is 0 and R^a is H.

In some embodiments of a compound of formula Va-4a, Va-4b, Va-4c or Va-4d, one of R^1, R^2 is a group selected from cyclopropyl, methyl-cyclopropyl, fluoro-cyclopropyl, cyclobutyl, C_6 aryl, methyl-C_6 aryl, fluoro-C_6 aryl, methoxy-C_6 aryl, pyridinyl, pyrrolidinyl, methyl-pyrrolidinyl, piperdinyl, N-methyl piperdinyl, methyl-piperdinyl, difluoro-piperidinyl, morpholinyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl; and the other two of R^1, R^2, R^3 are independently of each other selected from H, halogen, e.g. Cl, F, linear or branched —C_{1-4} alkyl, e.g., Me, Et, t-But, CF_3, CHF_2, CMeF_2, —OCF_3, OCHF_2, CN, and C_{1-4} alkoxy, e.g. —OMe; p is 0 and R^a is H.

In some embodiments the compound of formula Va and Va-4 is defined by formula Va-4e, Va-4f, Va-4g, Va-4h, Va-4i or Va-4j:

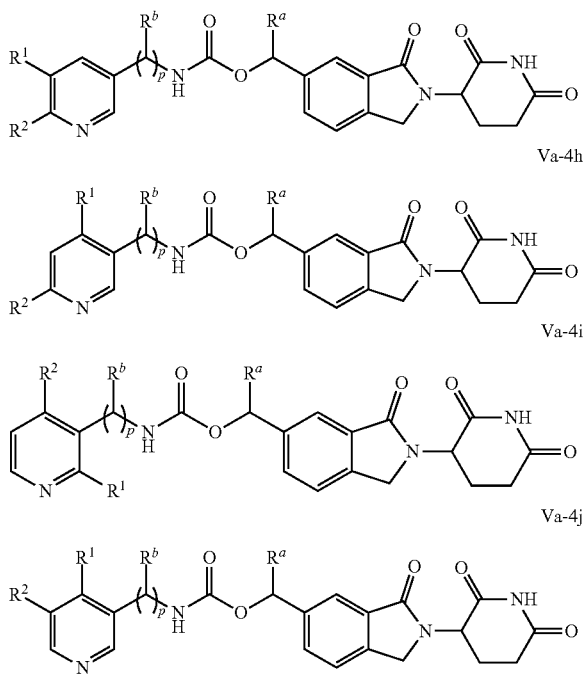

wherein
R^1, R^2 are independently of each other selected from H, linear or branched —C_{1-6} alkyl, linear or branched C_{1-6} heteroalkyl, —C_{1-4} alkoxy, CF_3, CHF_2, CMeF_2, —O—(CH_2)_2—OMe, OCF_3, OCHF_2, —C_{1-6} alkylamino, —CN, —OC(O)—C_{1-6}alkyl, —N(H)C(O)—C_{1-6}alkyl, —C(O)O—C_{1-6}alkyl, —COOH, —C_{1-6}alkylC(O)OH, —C_{1-6}alkylC(O)O—C_{1-6}alkyl, NH_2, —C_{1-4} alkylhydroxy, and halogen, such as F, Cl or Br, e.g. F or Cl, or a group of formula -L^3-X^2, wherein L^3 is a covalent bond, linear or branched C_{1-6} alkyl, —O—, —C_{1-4} alkoxy and X^2 is C_{3-6} cycloalkyl, C_{6-10} aryl, 5-10 membered heteroaryl, 4-8 membered heterocycloalkyl, wherein X^2 is unsubstituted or substituted with one or more of linear or branched C_{1-6} alkyl, —C_{1-4} alkoxy, NH_2, NMe_2, halogen, CF_3, CHF_2, CMeF_2, —O—(CH_2)_2—OMe, OCF_3, OCHF_2, and —C_{1-4} alkylhydroxy; p is 0 or 1 and R^a, R^b are independently of each other H or methyl.

In some embodiments of a compound of formula Va-4e, Va-4f, Va-4g, Va-4h, Va-4i or Va-4j, p is 0. In some embodiments of a compound of formula Va-4e, Va-4f, Va-4g, Va-4h, Va-4i or Va-4j, p is 1.

In some embodiments of a compound of formula Va-4e, Va-4f, Va-4g, Va-4h, Va-4i or Va-4j, R^a is H. In some embodiments of a compound of formula Va-4e, Va-4f, Va-4g, Va-4h, Va-4i or Va-4j, R^a is methyl. In some embodiments of a compound of formula Va-4e, Va-4f, Va-4g, Va-4h, Va-4i or Va-4j, p is 0 and R^a is H. In some embodiments of a compound of formula Va-4e, Va-4f, Va-4g, Va-4h, Va-4i or Va-4j, p is 0 and R^a is methyl.

In some embodiments of a compound of formula Va-4e, Va-4f, Va-4g, Va-4h, Va-4i or Va-4j, p is 1 and R^b is H. In some embodiments of a compound of formula Va-4e, Va-4f, Va-4g, Va-4h, Va-4i or Va-4j, p is 1 and R^b is methyl. In some embodiments of a compound of formula Va-4e, Va-4f, Va-4g, Va-4h, Va-4i or Va-4j, p is 1, R^b is H and R^a is H. In some embodiments of a compound of formula Va-4e, Va-4f, Va-4g, Va-4h, Va-4i or Va-4j, p is 1, $R^b$ is methyl and $R^a$ is H.

In some embodiments of a compound of formula Va-4e, Va-4f, Va-4g, Va-4h, Va-4i or Va-4j, $L^3$ is a covalent bond.

In some embodiments of a compound of formula Va-4e, Va-4f, Va-4g, Va-4h, Va-4i or Va-4j, $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-4e, Va-4f, Va-4g, Va-4h, Va-4i or Va-4j, $R^1$, $R^2$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-4e, Va-4f, Va-4g, Va-4h, Va-4i or Va-4j, $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$ alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl.

In some embodiments of a compound of formula Va-4e, Va-4f, Va-4g, Va-4h, Va-4i or Va-4j, $R^1$, $R^2$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-4e, Va-4f, Va-4g, Va-4h, Va-4i or Va-4j, $R^a$ is H and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-4e, Va-4f, Va-4g, Va-4h, Va-4i or Va-4j, $R^a$ is H and $R^1$, $R^2$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-4e, Va-4f, Va-4g, Va-4h, Va-4i or Va-4j, $R^a$ is H, and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-4e, Va-4f, Va-4g, Va-4h, Va-4i or Va-4j, $R^a$ is H, and $R^1$, $R^2$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-4e, Va-4f, Va-4g, Va-4h, Va-4i or Va-4j, p is 0 and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-4e, Va-4f, Va-4g, Va-4h, Va-4i or Va-4j, p is 0 and $R^1$, $R^2$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-4e, Va-4f, Va-4g, Va-4h, Va-4i or Va-4j, p is 0, and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-4e, Va-4f, Va-4g, Va-4h, Va-4i or Va-4j, p is 0, and $R^1$, $R^2$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-4e, Va-4f, Va-4g, Va-4h, Va-4i or Va-4j, p is 0, $R^a$ is H and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-4e, Va-4f, Va-4g, Va-4h, Va-4i or Va-4j, p is 0, $R^a$ is H and $R^1$, $R^2$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-4e, Va-4f, Va-4g, Va-4h, Va-4i or Va-4j, p is 0, $R^a$ is H, and $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$ alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$ alkyl, $NH_2$, —$C_{1-4}$ alkylhydroxy, and halogen, such as F, Cl or Br, e.g. F or Cl.

In some embodiments of a compound of formula Va-4e, Va-4f, Va-4g, Va-4h, Va-4i or Va-4j, p is 0, $R^a$ is H, and $R^1$, $R^2$ are independently of each other selected from H, linear or branched —$C_{1-6}$ alkyl, —$C_{1-4}$ alkoxy, such as —OMe, $OCF_3$, and halogen, such as F, Cl or Br, e.g. F or Cl.

In some embodiments of a compound of formula Va-4e, Va-4f, Va-4g, Va-4h, Va-4i or Va-4j, one of $R^1$, $R^2$ is a group of formula -$L^3$-$X^2$, wherein $L^3$ is a covalent bond, —$CH_2$—, —O—, —$OCH_2$—, —$O(CH_2)_2$— and $X^2$ is $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy;

and the other of $R^1$, $R^2$ is selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkylhydroxy, and halogen, such as F, Cl or Br, e.g. F or Cl; p is 0 and $R^a$ is H.

In some embodiments of a compound of formula Va-4e, Va-4f, Va-4g, Va-4h, Va-4i or Va-4j, one of $R^1$, $R^2$ is a group selected from $C_{3-6}$ cycloalkyl, $C_{6-10}$ aryl, 5-10 membered heteroaryl, 4-8 membered heterocycloalkyl, which group is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and the other of $R^1$, $R^2$ is selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, and halogen, such as F, Cl or Br, e.g. F or Cl; p is 0 and $R^a$ is H.

In some embodiments of a compound of formula Va-4e, Va-4f, Va-4g, Va-4h, Va-4i or Va-4j, one of $R^1$, $R^2$ is a group selected from cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, which group is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; and the other of $R^1$, $R^2$ is selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, halogen, such as F, Cl or Br, e.g. F or Cl; p is 0 and $R^a$ is H.

In some embodiments of a compound of formula Va-4e, Va-4f, Va-4g, Va-4h, Va-4i or Va-4j, one of $R^1$, $R^2$ is a group selected from cyclopropyl, cyclobutyl, $C_6$ aryl, pyridinyl, pyrrolidinyl, piperdinyl, morpholinyl, oxetanyl, piperazinyl, azetidinyl, 2-oxa-5-azabicyclo[2.2.1]heptanyl, 8-oxa-3-azabicyclo[3.2.1]octan-3-yl, which group is unsubstituted or substituted with one or more of linear or branched $C_{1-4}$ alkyl, e.g. methyl, —$C_{1-4}$ alkoxy, e.g. —OMe, $NMe_2$, halogen, e.g. F; and the other of $R^1$, $R^2$ is selected from H, halogen, e.g. Cl, F, linear or branched —$C_{1-4}$ alkyl, e.g., Me, Et, t-But, $CF_3$, $CHF_2$, $CMeF_2$, —$OCF_3$, $OCHF_2$, CN, $C_{1-4}$ alkoxy, e.g. —OMe; p is 0 and $R^a$ is H.

In some embodiments of a compound of formula Va-4e, Va-4f, Va-4g, Va-4h, Va-4i or Va-4j, one of $R^1$, $R^2$ is a group selected from cyclopropyl, methyl-cyclopropyl, fluoro-cyclopropyl, cyclobutyl, $C_6$ aryl, methyl-$C_6$ aryl, fluoro-$C_6$ aryl, methoxy-$C_6$ aryl, pyridinyl, pyrrolidinyl, methyl-pyrrolidinyl, piperdinyl, N-methyl piperdinyl, methyl-piperdinyl, difluoro-piperidinyl, morpholinyl, piperazinyl, N-methyl-piperazinyl, azetidinyl, methyl-azetidinyl, N-dimethyl-azetidinyl, 2-oxa-5-azabicyclo[2.2.1]heptanyl, 8-oxa-3-azabicyclo[3.2.1]octan-3-yl; and the other of $R^1$, $R^2$ is selected from H, halogen, e.g. Cl, F, linear or branched —$C_{1-4}$ alkyl, e.g., Me, Et, t-But, $CF_3$, $CHF_2$, $CMeF_2$, —$OCF_3$, $OCHF_2$, CN, and $C_{1-4}$ alkoxy, e.g. —OMe; p is 0 and $R^a$ is H.

In some embodiments the compound of formula Va and Va-5 is defined by formula Va-5a, Va-5b, Va-5c:

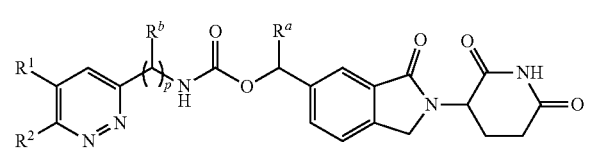

Va-5a

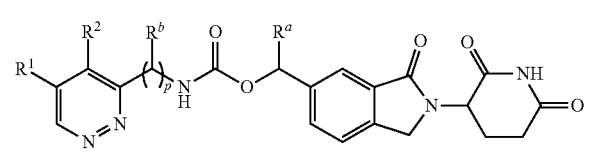

Va-5b

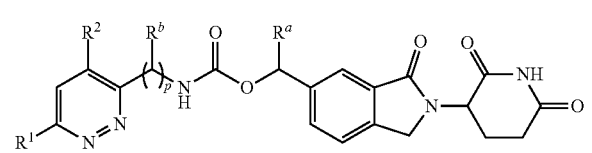

Va-5c wherein
$R^1$ and $R^2$ each are independently selected from H, linear or branched $C_{1-4}$ alkyl, $C_{1-4}$ alkoxy, 4-8 membered heterocycloalkyl, —$C_{1-4}$ alkyl 4-8 membered heterocycloalkyl, —$C_{1-4}$ alkoxy 4-8 membered heterocycloalkyl, —O-(4-8 membered heterocycloalkyl), $CF_3$, $CHF_2$, $CMeF_2$, —O—$(CH_2)_2$—OMe, $OCF_3$, $OCHF_2$, $C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkoxy, —$C_{1-4}$ alkylhydroxy, $C_6$ aryloxy and halogen, such as F, Cl or Br, e.g. F or Cl, and $C_6$ aryl, such as phenyl, wherein the 4-8 membered heterocycloalkyl may be unsubstituted or substituted with $C_{1-4}$ alkyl, such as methyl, ethyl, $C_{1-4}$ alkoxy, such as methoxy, ethoxy, halogen, such as F, Cl or Br, e.g. F or Cl; $R^a$, $R^b$ are independently of each other H or methyl and p is 0 or 1.

In some embodiments of a compound of formula Va-5a, Va-5b, Va-5c, p is 0. In some embodiments of a compound of formula Va-5a, Va-5b, Va-5c, p is 1.

In some embodiments of a compound of formula Va-5a, Va-5b, Va-5c, $R^a$ is H. In some embodiments of a compound of formula Va-5a, Va-5b, Va-5c, $R^a$ is methyl. In some embodiments of a compound of formula Va-5a, Va-5b, Va-5c, p is 0 and $R^a$ is H. In some embodiments of a compound of formula Va-5a, Va-5b, Va-5c, p is 0 and $R^a$ is methyl.

In some embodiments of a compound of formula Va-5a, Va-5b, Va-5c, p is 1 and $R^b$ is H. In some embodiments of a compound of formula Va-5a, Va-5b, Va-5c, p is 1 and $R^b$ is methyl. In some embodiments of a compound of formula Va-5a, Va-5b, Va-5c, p is 1, $R^b$ is H and $R^a$ is H. In some embodiments of a compound of formula Va-5a, Va-5b, Va-5c, p is 1, $R^b$ is methyl and $R^a$ is H.

In some embodiments of a compound of formula Va-5a, Va-5b, Va-5c, $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, and halogen, such as F, Cl or Br, e.g. F or Cl, or a 4-8 membered heterocycloalkyl, which is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; p is 0 and $R^a$ is H.

In some embodiments of a compound of formula Va-5a, Va-5b, Va-5c, $R^1$, $R^2$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, halogen, such as F, Cl or Br, e.g. F or Cl, or piperidinyl, which is unsubstituted or substituted with one or more of linear or branched $C_{1-4}$ alkyl, e.g. methyl, —$C_{1-4}$ alkoxy, e.g. —OMe, $NMe_2$, halogen, e.g. F; p is 0 and $R^a$ is H.

In some embodiments the compound of formula Va and Va-6 is defined by formula Va-6a, Va-6b:

Va-6a

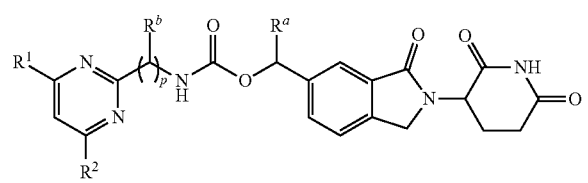

Va-6b

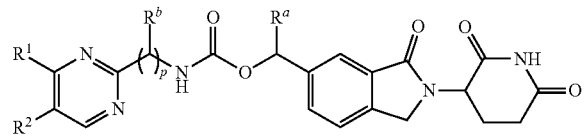

wherein $R^1$ and $R^2$ each are independently selected from H, linear or branched $C_{1-4}$ alkyl, $C_{1-4}$ alkoxy, 4-8 membered heterocycloalkyl, —$C_{1-4}$ alkyl 4-8 membered heterocycloalkyl, —$C_{1-4}$ alkoxy 4-8 membered heterocycloalkyl, —O-(4-8 membered heterocycloalkyl), $CF_3$, $CHF_2$, $CMeF_2$, —O—$(CH_2)_2$—OMe, $OCF_3$, $OCHF_2$, $C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkoxy, —$C_{1-4}$ alkylhydroxy, $C_6$ aryloxy and halogen, such as F, Cl or Br, e.g. F or Cl, and $C_6$ aryl, such as phenyl, wherein the 4-8 membered heterocycloalkyl may be unsubstituted or substituted with $C_{1-4}$ alkyl, such as methyl, ethyl, $C_{1-4}$ alkoxy, such as methoxy, ethoxy, halogen, such as F, Cl or Br, e.g. F, Cl;
$R^a$, $R^b$ are independently of each other H or methyl and p is 0 or 1.

In some embodiments of a compound of formula Va-6a, Va-6b, p is 0. In some embodiments of a compound of formula Va-6a, Va-6b, p is 1.

In some embodiments of a compound of formula Va-6a, Va-6b, $R^a$ is H. In some embodiments of a compound of formula Va-6a, Va-6b, $R^a$ is methyl. In some embodiments of a compound of formula Va-6a, Va-6b, p is 0 and $R^a$ is H. In some embodiments of a compound of formula Va-6a, Va-6b, p is 0 and $R^a$ is methyl.

In some embodiments of a compound of formula Va-6a, Va-6b, p is 1 and $R^b$ is H. In some embodiments of a compound of formula Va-6a, Va-6b, p is 1 and $R^b$ is methyl. In some embodiments of a compound of formula Va-6a, Va-6b, p is 1, $R^b$ is H and $R^a$ is H. In some embodiments of a compound of formula Va-6a, Va-6b, p is 1, $R^b$ is methyl and $R^a$ is H.

In some embodiments of a compound of formula Va-6a, Va-6b, $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, and halogen, such as F, Cl or Br, e.g. F or Cl, or a 4-8 membered heterocycloalkyl, which is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; p is 0 and $R^a$ is H.

In some embodiments of a compound of formula Va-6a, Va-6b, $R^1$, $R^2$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, halogen, such as F, Cl or Br, e.g. F or Cl, or piperidinyl, which is unsubstituted or substituted with one or more of linear or branched $C_{1-4}$ alkyl, e.g. methyl, —$C_{1-4}$ alkoxy, e.g. —OMe, $NMe_2$, halogen, e.g. F; p is 0 and $R^a$ is H.

In some embodiments the compound of formula Va and Va-7 is defined by formula Va-7a, Va-7b:

Va-7a

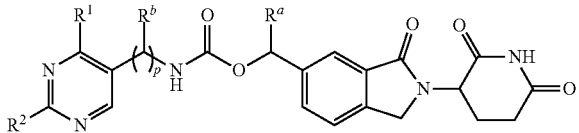

Va-7b

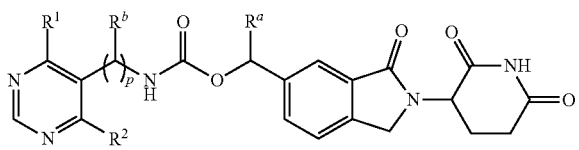

wherein $R^1$ and $R^2$ each are independently selected from H, linear or branched $C_{1-4}$ alkyl, $C_{1-4}$ alkoxy, 4-8 membered heterocycloalkyl, —$C_{1-4}$ alkyl 4-8 membered heterocycloalkyl, —$C_{1-4}$ alkoxy 4-8 membered heterocycloalkyl, —O-(4-8 membered heterocycloalkyl), $CF_3$, $CHF_2$, $CMeF_2$, —O—$(CH_2)_2$—OMe, $OCF_3$, $OCHF_2$, $C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkoxy, —$C_{1-4}$ alkylhydroxy, $C_6$ aryloxy and halogen, such as F, Cl or Br, e.g. F or Cl, and $C_6$ aryl, such as phenyl, wherein the 4-8 membered heterocycloalkyl may be unsubstituted or substituted with $C_{1-4}$ alkyl, such as methyl, ethyl, $C_{1-4}$ alkoxy, such as methoxy, ethoxy, halogen, such as F, Cl or Br, e.g. F, Cl;
$R^a$, $R^b$ are independently of each other H or methyl and p is 0 or 1.

In some embodiments of a compound of formula Va-7a, Va-7b, p is 0. In some embodiments of a compound of formula Va-7a, Va-7b, p is 1.

In some embodiments of a compound of formula Va-7a, Va-7b, and $R^a$ is H. In some embodiments of a compound of formula Va-7a, Va-7b, $R^a$ is methyl. In some embodiments of a compound of formula Va-7a, Va-7b, p is 0 and $R^a$ is H. In some embodiments of a compound of formula Va-7a, Va-7b, p is 0 and $R^a$ is methyl.

In some embodiments of a compound of formula Va-7a, Va-7b, p is 1 and $R^b$ is H. In some embodiments of a compound of formula Va-7a, Va-7b, p is 1 and $R^b$ is methyl. In some embodiments of a compound of formula Va-7a, Va-7b, p is 1, $R^b$ is H and $R^a$ is H. In some embodiments of a compound of formula Va-7a, Va-7b, p is 1, $R^b$ is methyl and $R^a$ is H.

In some embodiments of a compound of formula Va-7a, Va-7b, $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, and halogen, such as F, Cl or Br, e.g. F or Cl, or a 4-8 membered heterocycloalkyl, which is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; p is 0 and $R^a$ is H.

In some embodiments of a compound of formula Va-7a, Va-7b, $R^1$, $R^2$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, halogen, such as F, Cl or Br, e.g. F or Cl, or piperidinyl, which is unsubstituted or substituted with one or more of linear or branched $C_{1-4}$ alkyl, e.g. methyl, —$C_{1-4}$ alkoxy, e.g. —OMe, $NMe_2$, halogen, e.g. F; p is 0 and $R^a$ is H.

—C In some embodiments the compound of formula Va and Va-8 is defined by formula Va-8a, Va-8b, Va-8c:

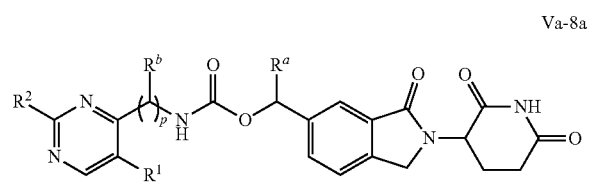

Va-8a

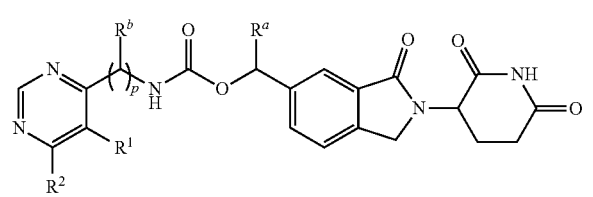

Va-8b

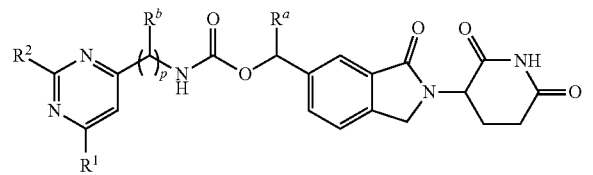

Va-8c wherein
$R^1$ and $R^2$ each are independently selected from H, linear or branched $C_{1-4}$ alkyl, $C_{1-4}$ alkoxy, 4-8 membered heterocycloalkyl, —$C_{1-4}$ alkyl 4-8 membered heterocycloalkyl, —$C_{1-4}$ alkoxy 4-8 membered heterocycloalkyl, —O-(4-8 membered heterocycloalkyl), $CF_3$, $CHF_2$, $CMeF_2$, —O—$(CH_2)_2$—OMe, $OCF_3$, $OCHF_2$, $C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkoxy, —$C_{1-4}$ alkylhydroxy, $C_6$ aryloxy and halogen, such as F, Cl or Br, e.g. F or Cl, and $C_6$ aryl, such as phenyl, wherein the 4-8 membered heterocycloalkyl may be unsubstituted or substituted with $C_{1-4}$ alkyl, such as methyl, ethyl, $C_{1-4}$ alkoxy, such as methoxy, ethoxy, halogen, such as F, Cl or Br, e.g. F, Cl;
$R^a$, $R^b$ are independently of each other H or methyl and p is 0 or 1.

In some embodiments of a compound of formula Va-8a, Va-8b, Va-8c, p is 0. In some embodiments of a compound of formula Va-8a, Va-8b, Va-8c, p is 1.

In some embodiments of a compound of formula Va-8a, Va-8b, Va-8c, $R^a$ is H. In some embodiments of a compound of formula Va-8a, Va-8b, Va-8c, $w^a$ is methyl. In some embodiments of a compound of formula Va-8a, Va-8b, Va-8c, p is 0 and $R^a$ is H. In some embodiments of a compound of formula Va-8a, Va-8b, Va-8c, p is 0 and $R^a$ is methyl.

In some embodiments of a compound of formula Va-8a, Va-8b, Va-8c, p is 1 and $R^b$ is H. In some embodiments of a compound of formula Va-8a, Va-8b, Va-8c, p is 1 and $R^b$ is methyl. In some embodiments of a compound of formula Va-8a, Va-8b, Va-8c, p is 1, $R^b$ is H and $R^a$ is H. In some embodiments of a compound of formula Va-8a, Va-8b, Va-8c, p is 1, $R^b$ is methyl and $R^a$ is H.

In some embodiments of a compound of formula Va-8a, Va-8b, Va-8c, $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, and halogen, such as F, Cl or Br, e.g. F or Cl, or a 4-8 membered heterocycloalkyl, which is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; p is 0 and $R^a$ is H.

In some embodiments of a compound of formula Va-8a, Va-8b, Va-8c, $R^1$, $R^2$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, halogen, such as F, Cl or Br, e.g. F or Cl, or piperidinyl, which is unsubstituted or substituted with one or more of linear or branched $C_{1-4}$ alkyl, e.g. methyl, —$C_{1-4}$ alkoxy, e.g. —OMe, $NMe_2$, halogen, e.g. F; p is 0 and $R^a$ is H.

—C In some embodiments the compound of formula Va and Va-9 is defined by formula Va-9a, Va-9b, Va-9c:

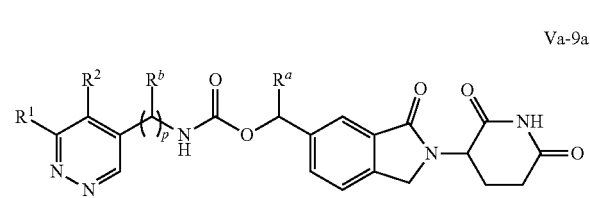

Va-9a

Va-9b

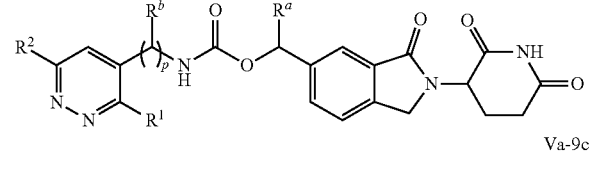

Va-9c

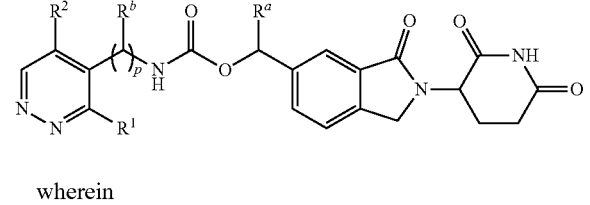

wherein $R^1$ and $R^2$ each are independently selected from H, linear or branched $C_{1-4}$ alkyl, $C_{1-4}$ alkoxy, 4-8 membered heterocycloalkyl, —$C_{1-4}$ alkyl 4-8 membered heterocycloalkyl, —$C_{1-4}$ alkoxy 4-8 membered heterocycloalkyl, —O-(4-8 membered heterocycloalkyl), $CF_3$, $CHF_2$, $CMeF_2$, —O—$(CH_2)_2$—OMe, $OCF_3$, $OCHF_2$, $C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkoxy, —$C_{1-4}$ alkylhydroxy, $C_6$ aryloxy and halogen, such as F, Cl or Br, e.g. F or Cl, and $C_6$ aryl, such as phenyl, wherein the 4-8 membered heterocycloalkyl may be unsubstituted or substituted with $C_{1-4}$ alkyl, such as methyl, ethyl, $C_{1-4}$ alkoxy, such as methoxy, ethoxy, halogen, such as F, Cl or Br, e.g. F, Cl; $R^a$, $R^b$ are independently of each other H or methyl and p is 0 or 1.

In some embodiments of a compound of formula Va-9a, Va-9b, Va-9c, p is 0. In some embodiments of a compound of formula Va-9a, Va-9b, Va-9c, p is 1.

In some embodiments of a compound of formula Va-9a, Va-9b, Va-9c, $R^a$ is H. In some embodiments of a compound of formula Va-9a, Va-9b, Va-9c, $R^a$ is methyl. In some embodiments of a compound of formula Va-9a, Va-9b, Va-9c, p is 0 and $R^a$ is H. In some embodiments of a compound of formula Va-9a, Va-9b, Va-9c, p is 0 and $R^a$ is methyl.

In some embodiments of a compound of formula Va-9a, Va-9b, Va-9c, p is 1 and $R^b$ is H. In some embodiments of a compound of formula Va-9a, Va-9b, Va-9c, p is 1 and $R^b$ is methyl. In some embodiments of a compound of formula Va-9a, Va-9b, Va-9c, p is 1, $R^b$ is H and $R^a$ is H. In some embodiments of a compound of formula Va-9a, Va-9b, Va-9c, p is 1, $R^b$ is methyl and $R^a$ is H.

In some embodiments of a compound of formula Va-9a, Va-9b, Va-9c, $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, and halogen, such as F, Cl or Br, e.g. F or Cl, or a 4-8 membered heterocycloalkyl, which is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; p is 0 and $R^a$ is H.

In some embodiments of a compound of formula Va-9a, Va-9b, Va-9c, $R^1$, $R^2$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, halogen, such as F, Cl or Br, e.g. F or Cl, or piperidinyl, which is unsubstituted or substituted with one or more of linear or branched $C_{1-4}$ alkyl, e.g. methyl, —$C_{1-4}$ alkoxy, e.g. —OMe, $NMe_2$, halogen, e.g. F; p is 0 and $R^a$ is H.

In some embodiments the compound of formula Va and Va-10 is defined by formula Va-10a, Va-10b, Va-10c Va-10a

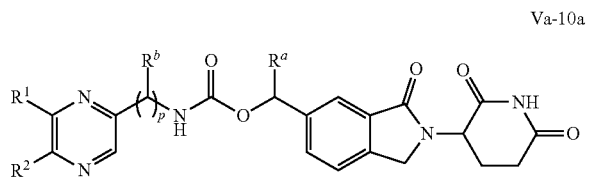

Va-10b

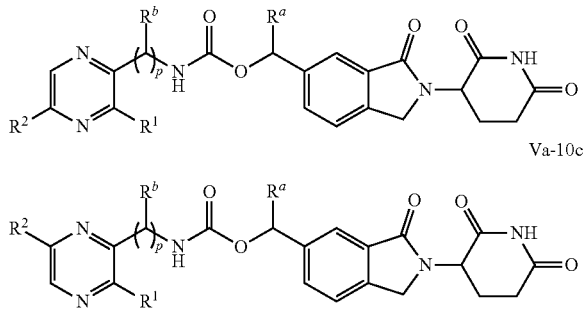

Va-10c

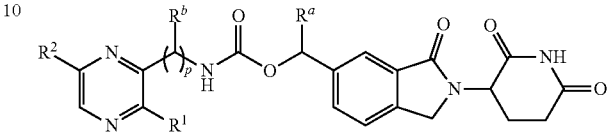

wherein
$R^1$ and $R^2$ each are independently selected from H, linear or branched $C_{1-4}$ alkyl, $C_{1-4}$ alkoxy, 4-8 membered heterocycloalkyl, —$C_{1-4}$ alkyl 4-8 membered heterocycloalkyl, —$C_{1-4}$ alkoxy 4-8 membered heterocycloalkyl, —O-(4-8 membered heterocycloalkyl), $CF_3$, $CHF_2$, $CMeF_2$, —O—$(CH_2)_2$—OMe, $OCF_3$, $OCHF_2$, $C_{1-6}$ alkylamino, —CN, —OC(O)—$C_{1-6}$alkyl, —N(H)C(O)—$C_{1-6}$alkyl, —C(O)O—$C_{1-6}$alkyl, —COOH, —$C_{1-6}$alkylC(O)OH, —$C_{1-6}$alkylC(O)O—$C_{1-6}$alkyl, $NH_2$, —$C_{1-4}$ alkoxy, —$C_{1-4}$ alkylhydroxy, $C_6$ aryloxy and halogen, such as F, Cl or Br, e.g. F or Cl, and $C_6$ aryl, such as phenyl, wherein the 4-8 membered heterocycloalkyl may be unsubstituted or substituted with $C_{1-4}$ alkyl, such as methyl, ethyl, $C_{1-4}$ alkoxy, such as methoxy, ethoxy, halogen, such as F, Cl or Br, e.g. F, Cl; $R^a$, $R^b$ are independently of each other H or methyl and p is 0 or 1.

In some embodiments of a compound of formula Va-10a, Va-10b, Va-10c, p is 0. In some embodiments of a compound of formula Va-10a, Va-10b, Va-10c, p is 1.

In some embodiments of a compound of formula Va-10a, Va-10b, Va-10c, $R^a$ is H. In some embodiments of a compound of formula Va-10a, Va-10b, Va-10c, $R^a$ is methyl. In some embodiments of a compound of formula Va-10a, Va-10b, Va-10c, p is 0 and $R^a$ is H. In some embodiments of a compound of formula Va-10a, Va-10b, Va-10c, p is 0 and $R^a$ is methyl.

In some embodiments of a compound of formula Va-10a, Va-10b, Va-10c, p is 1 and $R^b$ is H. In some embodiments of a compound of formula Va-10a, Va-10b, Va-10c, p is 1 and $R^b$ is methyl.

In some embodiments of a compound of formula Va-10a, Va-10b, Va-10c, p is 1, $R^b$ is H and $R^a$ is H. In some embodiments of a compound of formula Va-10a, Va-10b, Va-10c, p is 1, $R^b$ is methyl and $R^a$ is H.

In some embodiments of a compound of formula Va-10a, Va-10b, Va-10c, $R^1$, $R^2$ are independently of each other selected from H, linear or branched —$C_{1-6}$ alkyl, linear or branched $C_{1-6}$ heteroalkyl, —$C_{1-4}$ alkoxy, $CF_3$, $CHF_2$, $CMeF_2$, —O—$(CH_2)_2$—OMe, $OCF_3$, $OCHF_2$, —$C_{1-6}$ alkylamino, —CN, —$C_{1-4}$ alkylhydroxy, and halogen, such as F, Cl or Br, e.g. F or Cl, or a 4-8 membered heterocycloalkyl, which is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy; p is 0 and $R^a$ is H.

In some embodiments of a compound of formula Va-10a, Va-10b, Va-10c, $R^1$, $R^2$ are independently of each other selected from H, linear or branched —$C_{1-6}$ alkyl, —$C_{1-4}$ alkoxy, $CF_3$, $CHF_2$, $CMeF_2$, $OCF_3$, $OCHF_2$, halogen, such as as F, Cl or Br, e.g. F or Cl, or piperidinyl, which is unsubstituted or substituted with one or more of linear or branched $C_{1-4}$ alkyl, e.g. methyl, —$C_{1-4}$ alkoxy, e.g. —OMe, $NMe_2$, halogen, e.g. F; p is 0 and $R^a$ is H.

In some embodiments a compound of formula I is a compound or pharmaceutically acceptable salts or stereoisomers thereof formula Vb:

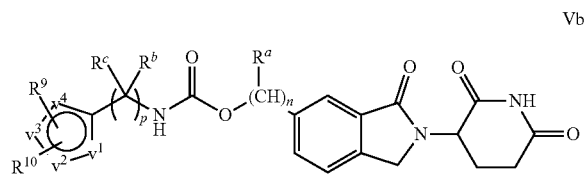

Vb wherein one or two of $v^1$, $v^2$, $v^3$, and $v^4$ are selected from O, N, NMe, NH, or S while two or three of $v^1$, $v^2$, $V^3$, and $v^4$ are C;

$R^9$, $R^{10}$ each are independently selected from H, linear or branched —$C_{1-4}$ alkyl, —$CF_3$, —$CHF_2$, halogen, preferably F, Cl, Br, more preferably F or Cl;

$R^a$ is H, linear or branched $C_{1-4}$ alkyl; $R^b$, $R^c$ are independently of each other H, linear or branched $C_{1-4}$ alkyl; n is 1, or 2; and p is 0 or 1.

In some embodiments of a compound of formula Vb, one or two of $v^1$, $v^2$, $V^3$, and $v^4$ are selected from N, NMe, NH, or S and the remaining of $v^1$, $v^2$, $V^3$, and $v^4$ are C. In some embodiments of compounds of formula Vb, one of $v^1$, $v^2$, $V^3$, $V^4$ is N, one of $v^1$, $v^2$, $V^3$, $V^4$ is S and the remaining of $v^1$, $v^2$, $v^3$, and $v^4$ are C.

In some embodiments of a compound of formula Vb, n is 1. In some embodiments of a compound of formula Vb, n is 1 and $R^a$ is H. In some embodiments of a compound of formula Vb, n is 1 and $R^a$ is methyl. In some embodiments n is 1, p is 0 and $R^a$ is H. In some embodiments of a compound of formula Vb, n is 1, p is 0 and $R^a$ is methyl.

In some embodiments of a compound of formula Vb, p is 0. In some embodiments of a compound of formula Vb, p is 1. In some embodiments of a compound of formula Vb, p is 1, and $R^b$ and $R^c$ are H. In some embodiments of a compound of formula Vb, p is 1, $R^b$ is methyl and $R^c$ is H.

In some embodiments of compounds of formula Vb, $R^9$, $R^{10}$ each are independently selected from H, methyl, ethyl and $CF_3$.

In some embodiments the compound of formula Vb is defined by formula Vb-1

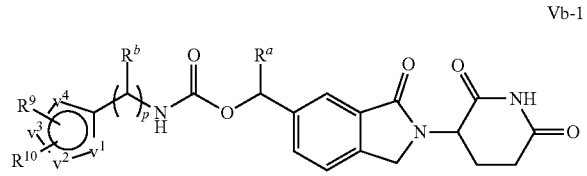

Vb-1 wherein one or two of $v^1$, $v^2$, $v^3$, and $v^4$ are selected from C, O, N, NMe, NH, or S while two or three of $v^1$, $v^2$, $v^3$, and $v^4$ are C;

$R^9$, $R^{10}$ each are independently selected from H, linear or branched —$C_{1-4}$ alkyl, —$CF_3$, —$CHF_2$, halogen, preferably F, Cl, Br, more preferably F or Cl;

$R^a$, $R^b$ are independently of each other H, linear or branched $C_{1-4}$ alkyl; and p is 0 or 1.

In some embodiments of a compound of formula Vb-1, one or two of $v^1$, $v^2$, $v^3$, and $v^4$ are selected from N, NMe, NH, or S and the remaining of $v^1$, $v^2$, $v^3$, and $v^4$ are C. In some embodiments of compounds of formula Vb-1, one of $v^1$, $v^2$, $v^3$, $V^4$ is N, one of $v^1$, $v^2$, $v^3$, $v^4$ is S and the remaining of $v^1$, $v^2$, $v^3$, and $v^4$ are C.

In some embodiments of a compound of formula Vb-1, $R^a$ is H. In some embodiments of a compound of formula Vb-1, $R^a$ is methyl. In some embodiments of a compound of formula Vb-1, p is 0 and $R^a$ is H. In some embodiments of a compound of formula Vb-1, p is 0 and $R^a$ is methyl.

In some embodiments of a compound of formula Vb-1, p is 1. In some embodiments of a compound of formula Vb-1, p is 1, $R^b$ is H and $R^a$ is H. In some embodiments of a compound of formula Vb-1a and Vb-1b, p is 1, $R^b$ is methyl and $R^a$ is H.

In some embodiments of compounds of formula Vb-1 or pharmaceutically acceptable salts or stereoisomers thereof, $R^9$, $R^{10}$ each are independently selected from H, methyl, ethyl and $CF_3$.

In some embodiments of compounds of formula Vb-1, one or two of $v^1$, $v^2$, $v^3$, $v^4$ are independently of each other selected from N and S (with the proviso that no —S—S— linkages are formed), while two or three of $v^1$, $v^2$, $v^3$, and $v^4$ are C.

In some embodiments the compound of formula Vb-1 is defined by formula Vb-1a or Vb-1b

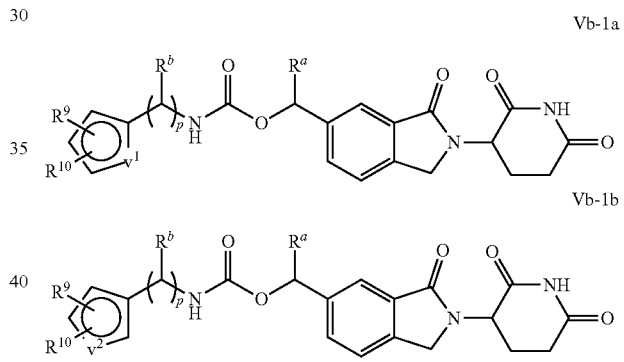

Vb-1a

Vb-1b wherein $v^1$ (in a compound of formula Vb-1a) and $v^2$ (in a compound of formula Vb-1b) are selected from O, N, NMe, NH, and S;

$R^9$, $R^{10}$ each are independently selected from H, linear or branched —$C_{1-4}$ alkyl, —$CF_3$, —$CHF_2$, halogen, preferably F, Cl, Br, more preferably F or Cl;

$R^a$, $R^b$ are independently of each other H, linear or branched $C_{1-4}$ alkyl; and p is 0 or 1.

In some embodiments of a compound of formula Vb-1a and Vb-1b, $R^a$ is H. In some embodiments of a compound of formula Vb-1a and Vb-1b, $R^a$ is methyl. In some embodiments of a compound of formula Vb-1a and Vb-1b, p is 0 and $R^a$ is H. In some embodiments of a compound of formula Vb-1a and Vb-1b, p is 0 and $R^a$ is methyl. In some embodiments of a compound of formula Vb-1a and Vb-1b, p is 1. In some embodiments of a compound of formula Vb-1a and Vb-1b, p is 1, $R^b$ is H and $R^a$ is H. In some embodiments of a compound of formula Vb-1a and Vb-1b, p is 1, $R^b$ is methyl and $R^a$ is H.

In some embodiments of compounds of formula Vb-1a, Vb-1b or pharmaceutically acceptable salts or stereoisomers thereof, $R^9$, $R^{10}$ each are independently selected from H, methyl, ethyl and $CF_3$.

In some embodiments the compound of formula Vb is defined by formula Vb-2a, Vb-2b, Vb-2c, or Vb-2d

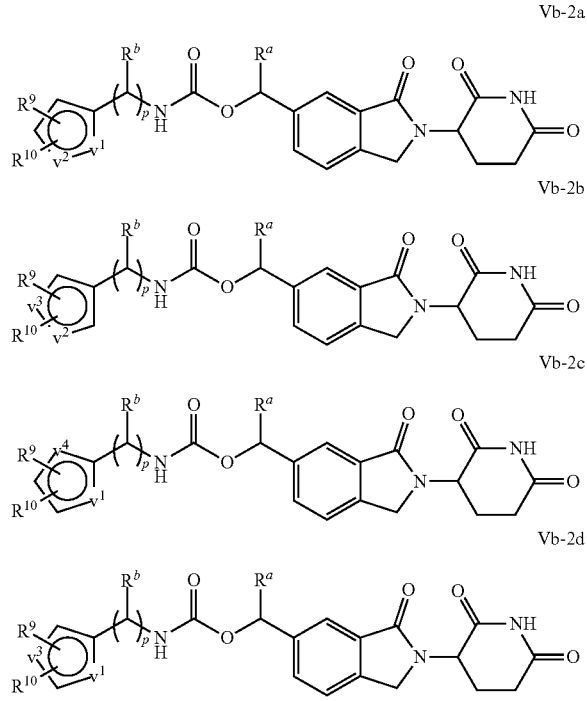

wherein $v^1$, $v^2$, $v^3$, $v^4$ are independently of each other selected from O, N, NMe, NH, and S, more specifically $v^1$, $v^2$ (in a compound of formula Vb-2a), $v^2$, $v^3$ (in a compound of formula Vb-2b), $v^1$, $v^4$ (in a compound of formula Vb-2c), and $v^1$, $v^3$ (in a compound of formula Vb-2d) are independently of each other selected from O, N, NMe, NH, and S;

$R^9$, $R^{10}$ each are independently selected from H, linear or branched —$C_{1-4}$ alkyl, —$CF_3$, —$CHF_2$, halogen, such as F, Cl;

$R^a$, $R^b$ are independently of each other H, linear or branched $C_{1-4}$ alkyl; and p is 0 or 1.

In some embodiments of a compound of formula Vb-2a, Vb-2b, Vb-2c, or Vb-2d, $R^a$ is H. In some embodiments of a compound of formula Vb-2a, Vb-2b, Vb-2c, or Vb-2d, $R^a$ is methyl. In some embodiments of a compound of formula Vb-2a, Vb-2b, Vb-2c, or Vb-2d, p is 0 and $R^a$ is H. In some embodiments of a compound of formula Vb-2a, Vb-2b, Vb-2c, or Vb-2d, p is 0 and $R^a$ is methyl. In some embodiments of a compound of formula Vb-2a, Vb-2b, Vb-2c, or Vb-2d, p is 1.

In some embodiments of a compound of formula Vb-2a, Vb-2b, Vb-2c, or Vb-2d, p is 1, $R^b$ is H and $R^a$ is H. In some embodiments of a compound of formula Vb-2a, Vb-2b, Vb-2c, or Vb-2d, p is 1, $R^b$ is methyl and $R^a$ is H.

In some embodiments of compounds of formula Vb-2a, Vb-2b, Vb-2c, or Vb-2d, $R^9$, $R^{10}$ each are independently selected from H, methyl, ethyl and $CF_3$.

In some embodiments of compounds of formula Vb-2a, Vb-2b, Vb-2c, or Vb-2d, $v^1$, $v^2$, $v^3$, $v^4$ are independently of each other selected from N and S, more specifically $v^1$, $v^2$ (in a compound of formula Vb-2a), $v^2$, $v^3$ (in a compound of formula Vb-2b), $v^1$, $v^4$ (in a compound of formula Vb-2c), and $v^1$, $v^3$ (in a compound of formula Vb-2d) are independently of each other selected from N and S.

In some embodiments of compounds of formula Vb-2a, $v^1$ is S and $v^2$ is N. In some embodiments of compounds of formula Vb-2a, $v^1$ is N and $v^2$ is S. In some embodiments of compounds of formula Vb-2b, $v^2$ is S and $v^3$ is N. In some embodiments of compounds of formula Vb-2c, $v^1$ is S and $v^4$ is N. In some embodiments of compounds of formula Vb-2d, $v^1$ is N and $v^3$ is S. In some embodiments of compounds of formula Vb-2d, $v^1$ is S and $v^3$ is N.

In some embodiments a compound of formula I is a fused 6(saturated)-6(aromatic) ring system or a fused 5(saturated)-6(aromatic) ring system, more specifically a compound or pharmaceutically acceptable salts or stereoisomers thereof formula VIa:

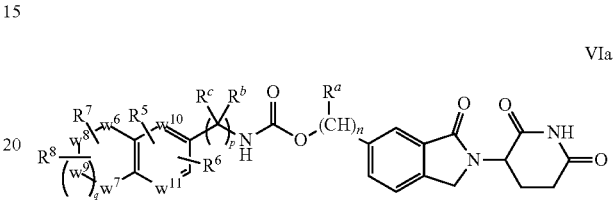

wherein one or two of $w^6$, $w^7$, $w^8$ $w^9$ are selected from C and O and the remaining of $w^6$, $w^7$, $w^8$, $w^9$ are C; $w^{10}$, $w^{11}$ are independently of each other selected from C and N;

$R^5$, $R^6$, $R^7$ $R^8$ are independently of each other selected from H, linear or branched $C_{1-4}$ alkyl, such as methyl, halogen, such as F or Cl, e.g. F;

$R^a$ is H, linear or branched $C_{1-4}$ alkyl; $R^b$, $R^c$ are independently of each other H, linear or branched $C_{1-4}$ alkyl; q is 0, 1; n is 1 or 2; and p is 0 or 1.

In some embodiments of a compound of formula VIa, $R^a$ is H. In some embodiments of a compound of formula VIa, $R^a$ is methyl. In some embodiments of a compound of formula VIa, n is 1. In some embodiments of a compound of formula VIa, n is 1 and $R^a$ is H. In some embodiments of a compound of formula VIa, n is 1 and $R^a$ is methyl.

In some embodiments of a compound of formula VIa, p is 0. In some embodiments of a compound of formula VIa, p is 0 and $R^a$ is H. In some embodiments of a compound of formula VIa, p is 0 and $R^a$ is methyl. In some embodiments of a compound of formula VIa, p is 1. In some embodiments of a compound of formula VIa, p is 1, and $R^b$ and $R^c$ are H. In some embodiments of a compound of formula VIa, p is 1, $R^b$ is methyl and $R^c$ is H.

In some embodiments of a compound of formula VIa, one of $w^{10}$ and $w^{11}$ is C. In some embodiments of a compound of formula VIa, one of $w^{10}$ and $w^{11}$ is C and the other is N.

In some embodiments of a compound of formula VIa, q is 0 and $w^8$ is C. In some embodiments of a compound of formula VIa, q is 0, $w^8$ is C and $w^6$, $w^7$ are selected from C and O. In some embodiments of a compound of formula VIa, q is 0, $w^8$ is C and $w^6$, $w^7$ are O. In some embodiments of a compound of formula VIa, q is 0, $w^8$ is C and one of $w^6$, $w^7$ is C and the other of $w^6$, $w^7$ is O.

In some embodiments of a compound of formula VIa, q is 1, and $w^6$, $w^7$, $w^8$, $w^9$ are C. In some embodiments of a compound of formula VIa, q is 1, and $w^6$ is O and $w^7$, $w^8$, $w^9$ are C. In some embodiments of a compound of formula VIa, q is 1, and $w^7$ is O and $w^6$, $w^8$, $w^9$ are C. In some embodiments of a compound of formula VIa, q is 1, and $w^8$ is O and $w^6$, $w^7$, $w^9$ are C. In some embodiments of a compound of formula VIa, q is 1, and $w^9$ is O and $w^6$, $w^7$, $w^8$ are C.

In some embodiments of a compound of formula VIa, $R^5$, $R^6$ are H.

In some embodiments of a compound of formula VIa, $R^7$ $R^8$ are independently of each other selected from H, linear or branched $C_{1-4}$ alkyl, such as methyl, halogen, such as F or Cl, e.g. F. $R^7$ $R^8$ may be attached to the same ring atom or to different ring atoms.

Some embodiments of a compound of formula VIa are provided by formula VIa-1

VIa-1

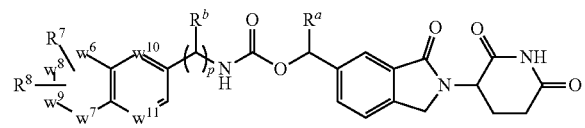

wherein one or two of $w^6$, $w^7$, $w^8$, $w^9$ are selected from C and O and the remaining of $w^6$, $w^7$, $w^8$, $w^9$ are C; $w^{10}$, $w^{11}$ are independently of each other selected from C and N;

$R^7$, $R^8$ are independently of each other selected from H, linear or branched $C_{1-4}$ alkyl, such as methyl, halogen, such as F or Cl, e.g. F; $R^a$, $R^b$ are independently of each other H, linear or branched $C_{1-4}$ alkyl; and p is 0 or 1.

In some embodiments of a compound of formula VIa-1, p is 0. In some embodiments of a compound of formula VIa-1, p is 1.

In some embodiments of a compound of formula VIa-1, $R^a$ is H. In some embodiments of a compound of formula VIa-1, $R^a$ is methyl. In some embodiments of a compound of formula VIa-1, p is 0 and $R^a$ is H. In some embodiments of a compound of formula VIa-1, p is 0 and $R^a$ is methyl. In some embodiments of a compound of formula VIa-1, p is 1 and $R^b$ is H. In some embodiments of a compound of formula VIa-1, p is 1 and $R^b$ is methyl.

In some embodiments of a compound of formula VIa-1, one of $w^{10}$ and $w^{11}$ are C. In some embodiments of a compound of formula VIa-1, one of $w^{10}$ and $w^{11}$ is C and the other is N.

In some embodiments of a compound of formula VIa-1, $w^6$, $w^7$, $w^8$, $w^9$ are C. In some embodiments of a compound of formula VIa-1, $w^6$ is O and $w^7$, $w^8$, $w^9$ are C. In some embodiments of a compound of formula VIa-1, $w^7$ is O and $w^6$, $w^8$, $w^9$ are C. In some embodiments of a compound of formula VIa-1, $w^8$ is O and $w^6$, $w^7$, $w^9$ are C. In some embodiments of a compound of formula VIa-1, $w^9$ is O and $w^6$, $w^7$, $w^8$ are C.

In some embodiments of a compound of formula VIa-1, $R^7$, $R^8$ are independently of each other selected from H, linear or branched $C_{1-4}$ alkyl, such as methyl, halogen, such as F or Cl, e.g. F. $R^7$, $R^8$ may be attached to the same ring atom or to different ring atoms.

Some embodiments of a compound of formula VIa-1 are provided by formula VIa-1a, VIa-1b, VIa-1c, VIa-1d VIa-1

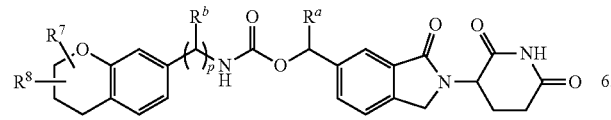

VIa-1b

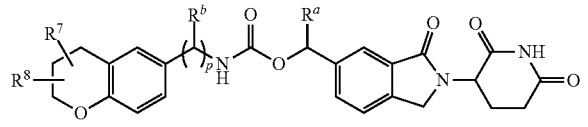

VIa-1c

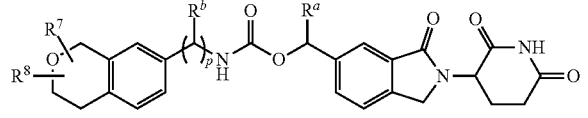

VIa-1d

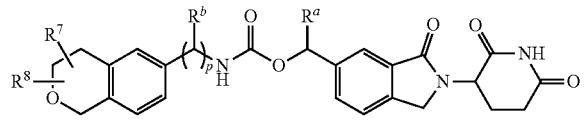

wherein
$R^7$ $R^8$ are independently of each other selected from H, linear or branched $C_{1-4}$ alkyl, such as methyl, halogen, such as F or Cl, e.g. F; $R^a$, $R^b$ are independently of each other H, linear or branched $C_{1-4}$ alkyl, and p is 0 or 1.

In some embodiments of a compound of formula VIa-1a, VIa-1b, VIa-1c, VIa-1d, p is 0. In some embodiments of a compound of formula VIa-1a, VIa-1b, VIa-1c, VIa-1d, p is 1.

In some embodiments of a compound of formula VIa-1a, VIa-1b, VIa-1c, VIa-1d, $R^a$ is H. In some embodiments of a compound of formula VIa-1a, VIa-1b, VIa-1c, VIa-1d, $R^a$ is methyl. In some embodiments of a compound of formula VIa-1a, VIa-1b, VIa-1c, VIa-1d, p is 0 and $R^a$ is H. In some embodiments of a compound of formula VIa-1a, VIa-1b, VIa-1c, VIa-1d, p is 0 and $R^a$ is methyl.

In some embodiments of a compound of formula VIa-1a, VIa-1b, VIa-1c, VIa-1d, p is 1 and $R^b$ is H. In some embodiments of a compound of formula VIa-1a, VIa-1b, VIa-1c, VIa-1d, p is 1 and $R^b$ is methyl. In some embodiments of a compound of formula VIa-1a, VIa-1b, VIa-1c, VIa-1d, p is 1, $R^b$ is H and $R^a$ is H. In some embodiments of a compound of formula VIa-1a, VIa-1b, VIa-1c, VIa-1d, p is 1, $R^b$ is methyl and $R^a$ is H.

In some embodiments of a compound of formula VIa-1a, VIa-1b, VIa-1c, VIa-1d, $R^7$, $R^8$ are independently of each other selected from H, linear or branched $C_{1-4}$ alkyl, such as methyl, halogen, such as F or Cl, e.g. F. $R^7$, $R^8$ may be attached to the same ring atom or to different ring atoms.

Some embodiments of a compound of formula VIa and VIa-1 are provided by formula VIa-2, VIa-3

VIa-2

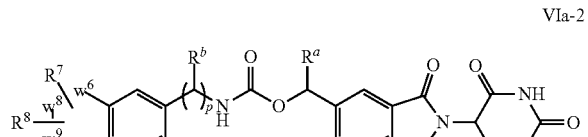

VIa-3

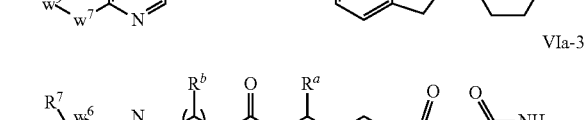

wherein one or two of $w^6$, $w^7$, $w^8$, $w^9$ are selected from C and O and the remaining of $w^6$, $w^7$, $w^8$, $w^9$ are C;

$R^7$ $R^8$ are independently of each other selected from H, linear or branched $C_{1-4}$ alkyl, such as methyl, halogen, such as F or Cl, e.g. F; $R^a$, $R^b$ are independently of each other H, linear or branched $C_{1-4}$ alkyl; and p is 0 or 1.

In some embodiments of a compound of formula VIa-2 or VIa-3, p is 0. In some embodiments of a compound of formula VIa-2 or VIa-3, p is 1.

In some embodiments of a compound of formula VIa-2 or VIa-3, $R^a$ is H. In some embodiments of a compound of formula VIa-2 or VIa-3, $R^a$ is methyl. In some embodiments of a compound of formula VIa-2 or VIa-3, p is 0 and $R^a$ is H. In some embodiments of a compound of formula VIa-2 or VIa-3, p is 0 and $R^a$ is methyl.

In some embodiments of a compound of formula VIa-2 or VIa-3, p is 1 and $R^b$ is H. In some embodiments of a compound of formula VIa-2 or VIa-3, p is 1 and $R^b$ is methyl. In some embodiments of a compound of formula VIa-2 or VIa-3, p is 1, $R^b$ is H and $R^a$ is H. In some embodiments of a compound of formula VIa-2 or VIa-3, p is 1, $R^b$ is methyl and $R^a$ is H.

In some embodiments of a compound of formula VIa-2 or VIa-3, $w^6$, $w^7$, $w^8$, $w^9$ are C. In some embodiments of a compound of formula VIa-2 or VIa-3, $w^6$ is O and $w^7$, $w^8$, $w^9$ are C. In some embodiments of a compound of formula VIa-2 or VIa-3, $w^7$ is O and $w^6$, $w^8$, $w^9$ are C. In some embodiments of a compound of formula VIa-2 or VIa-3, $w^8$ is O and $w^6$, $w^7$, $w^9$ are C. In some embodiments of a compound of formula VIa-2 or VIa-3, $w^9$ is O and $w^6$, $w^7$, $w^8$ are C.

In some embodiments of a compound of formula VIa-2 or VIa-3, $R^7$, $R^8$ are independently of each other selected from H, linear or branched $C_{1-4}$ alkyl, such as methyl, halogen, such as F or Cl, e.g. F. $R^7$, $R^8$ may be attached to the same ring atom or to different ring atoms.

Some embodiments of a compound of formula VIa-2 are provided by formula VIa-2a, VIa-2b, VIa-2c, VIa-2d

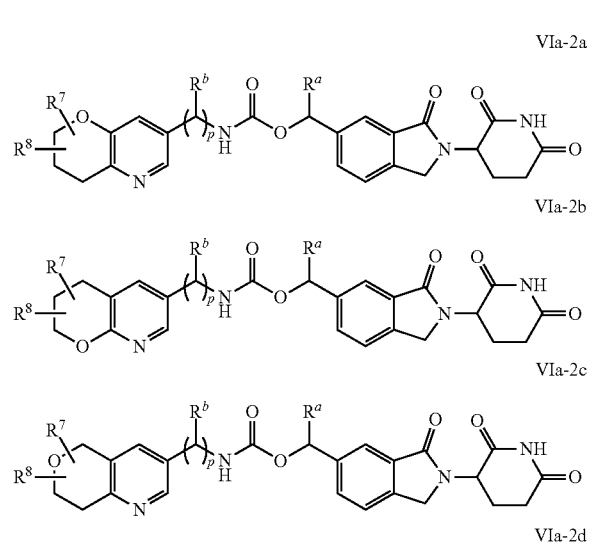

wherein $R^7$ $R^8$ are independently of each other selected from H, linear or branched $C_{1-4}$ alkyl, such as methyl, halogen, such as F or Cl, e.g. F; $R^a$, $R^b$ are independently of each other H, linear or branched $C_{1-4}$ alkyl, and p is 0 or 1.

In some embodiments of a compound of formula VIa-2a, VIa-2b, VIa-2c, VIa-2d, p is 0. In some embodiments of a compound of formula VIa-2a, VIa-2b, VIa-2c, VIa-2d, p is 1.

In some embodiments of a compound of formula VIa-2a, VIa-2b, VIa-2c, VIa-2d, $R^a$ is H. In some embodiments of a compound of formula VIa-2a, VIa-2b, VIa-2c, VIa-2d, $R^a$ is methyl. In some embodiments of a compound of formula VIa-2a, VIa-2b, VIa-2c, VIa-2d, p is 0 and $R^a$ is H. In some embodiments of a compound of formula VIa-2a, VIa-2b, VIa-2c, VIa-2d, p is 0 and $R^a$ is methyl.

In some embodiments of a compound of formula VIa-2a, VIa-2b, VIa-2c, VIa-2d, p is 1 and $R^b$ is H. In some embodiments of a compound of formula VIa-2a, VIa-2b, VIa-2c, VIa-2d, p is 1 and $R^b$ is methyl. In some embodiments of a compound of formula VIa-2a, VIa-2b, VIa-2c, VIa-2d, p is 1, $R^b$ is H and $R^a$ is H. In some embodiments of a compound of formula VIa-2a, VIa-2b, VIa-2c, VIa-2d, p is 1, $R^b$ is methyl and $R^a$ is H.

In some embodiments of a compound of formula VIa-2a, VIa-2b, VIa-2c, VIa-2d, $R^7$, $R^8$ are independently of each other selected from H, linear or branched $C_{1-4}$ alkyl, such as methyl, halogen, such as F or Cl, e.g. F. $R^7$, $R^8$ may be attached to the same ring atom or to different ring atoms.

Some embodiments of a compound of formula VIa-1 are provided by formula VIa-1a, VIa-1b, VIa-1c, VIa-1d

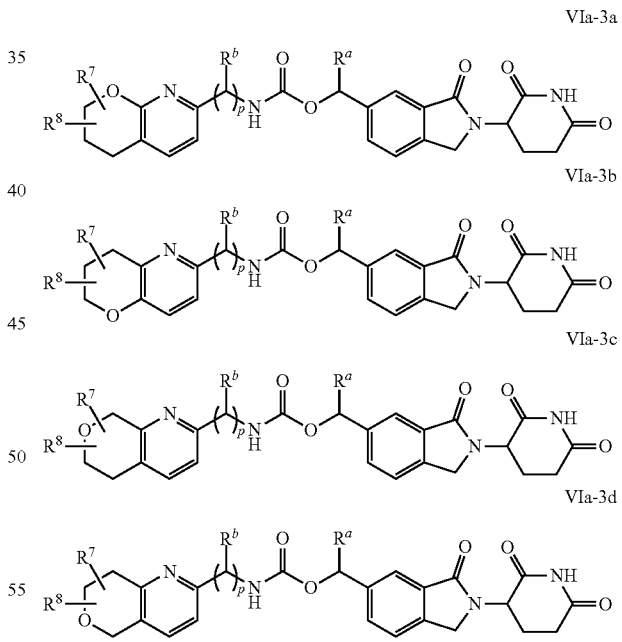

wherein $R^7$ $R^8$ are independently of each other selected from H, linear or branched $C_{1-4}$ alkyl, such as methyl, halogen, such as F or Cl, e.g. F; $R^a$, $R^b$ are independently of each other H, linear or branched $C_{1-4}$ alkyl, and p is 0 or 1.

In some embodiments of a compound of formula VIa-3a, VIa-3b, VIa-3c, VIa-3d, p is 0. In some embodiments of a compound of formula VIa-3a, VIa-3b, VIa-3c, VIa-3d, p is 1.

In some embodiments of a compound of formula VIa-3a, VIa-3b, VIa-3c, VIa-3d, $R^a$ is H. In some embodiments of a compound of formula VIa-3a, VIa-3b, VIa-3c, VIa-3d, $R^a$ is methyl. In some embodiments of a compound of formula VIa-3a, VIa-3b, VIa-3c, VIa-3d, p is 0 and $R^a$ is H. In some embodiments of a compound of formula VIa-3a, VIa-3b, VIa-3c, VIa-3d, p is 0 and $R^a$ is methyl.

In some embodiments of a compound of formula VIa-3a, VIa-3b, VIa-3c, VIa-3d, p is 1 and $R^b$ is H. In some embodiments of a compound of formula VIa-3a, VIa-3b, VIa-3c, VIa-3d, p is 1 and $R^b$ is methyl. In some embodiments of a compound of formula VIa-3a, VIa-3b, VIa-3c, VIa-3d, p is 1, $R^b$ is H and $R^a$ is H. In some embodiments of a compound of formula VIa-3a, VIa-3b, VIa-3c, VIa-3d, p is 1, $R^b$ is methyl and $R^a$ is H.

In some embodiments of a compound of formula VIa-3a, VIa-3b, VIa-3c, VIa-3d, $R^7$, $R^8$ are independently of each other selected from H, linear or branched $C_{1-4}$ alkyl, such as methyl, halogen, such as F or Cl, e.g. F. $R^7$, $R^8$ may be attached to the same ring atom or to different ring atoms.

In some embodiments the compound of formula Via, q is 0 and thus formula VIa is provided by formula VIb

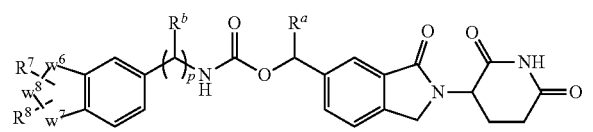

VIb wherein $w^6$, $w^7$, $w^8$ are independently of each other selected from C and O;

$R^7$ $R^8$ are independently of each other selected from H, linear or branched $C_{1-4}$ alkyl, such as methyl, halogen, such as F or Cl, e.g. F; $R^a$, $R^b$ are independently of each other H, linear or branched $C_{1-4}$ alkyl and p is 0 or 1.

In some embodiments of a compound of formula VIb, $w^6$, $w^7$, $w^8$ are independently of each other selected from C and O; with the proviso that neighbouring groups cannot be both O.

In some embodiments of a compound of formula VIb, p is 0. In some embodiments of a compound of formula VIb, p is 1.

In some embodiments of a compound of formula VIb, $R^a$ is H. In some embodiments of a compound of formula VIb, $R^a$ is methyl. In some embodiments of a compound of formula VIb, p is 0 and $R^a$ is H. In some embodiments of a compound of formula VIb, p is 0 and $R^a$ is methyl.

In some embodiments of a compound of formula VIb, p is 1 and $R^b$ is H. In some embodiments of a compound of formula VIb, p is 1 and $R^b$ is methyl. In some embodiments of a compound of formula VIb, p is 1, $R^b$ is H and $R^a$ is H. In some embodiments of a compound of formula VIb, p is 1, $R^b$ is methyl and $R^a$ is H.

In some embodiments of a compound of formula VIb, $w^8$ is C. In some embodiments of a compound of formula VIb, $w^8$ is C and $w^6$, $w^7$ are selected from C and O. In some embodiments of a compound of formula VIb, $w^8$ is C and $w^6$, $w^7$ are O. In some embodiments of a compound of formula VIb, $w^8$ is C and one of $w^6$, $w^7$ is C and the other of $w^6$, $w^7$ is O.

In some embodiments of a compound of formula VIb, $R^7$, $R^8$ are independently of each other selected from H, linear or branched $C_{1-4}$ alkyl, such as methyl, halogen, such as F or Cl, e.g. F. $R^7$, $R^8$ may be attached to the same ring atom or to different ring atoms.

In some embodiments the compound of formula VIb is provided by formula VIb-1, VIb-2, VIb-3, VIb-4

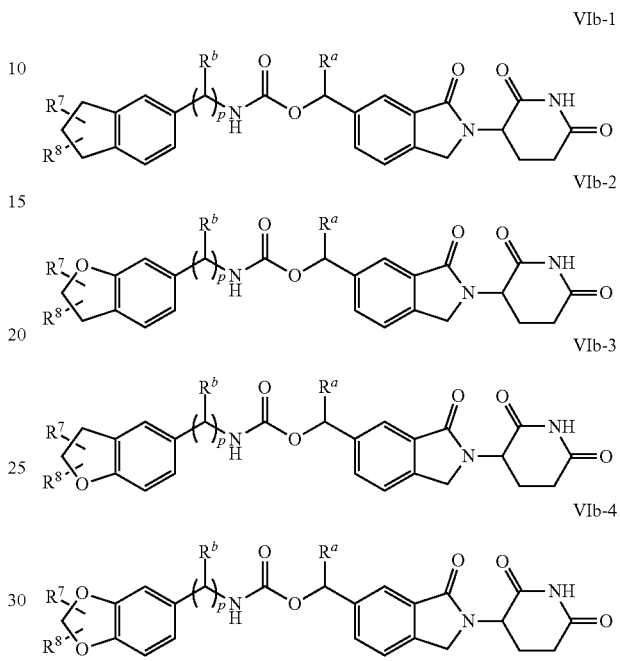

wherein
$R^7$ $R^8$ are independently of each other selected from H, linear or branched $C_{1-4}$ alkyl, such as methyl, halogen, such as F or Cl, e.g. F; $R^a$, $R^b$ are independently of each other H, linear or branched $C_{1-4}$ alkyl, and p is 0 or 1.

In some embodiments of a compound of formula VIb-1, VIb-2, VIb-3, or VIb-4, p is 0. In some embodiments of a compound of formula VIb-1, VIb-2, VIb-3, or VIb-4, p is 1.

In some embodiments of a compound of formula VIb-1, VIb-2, VIb-3, or VIb-4, $R^a$ is H. In some embodiments of a compound of formula VIb-1, VIb-2, VIb-3, or VIb-4, $R^a$ is methyl. In some embodiments of a compound of formula VIb-1, VIb-2, VIb-3, or VIb-4, p is 0 and $R^a$ is H. In some embodiments of a compound of formula VIb-1, VIb-2, VIb-3, or VIb-4, p is 0 and $R^a$ is methyl.

In some embodiments of a compound of formula VIb-1, VIb-2, VIb-3, or VIb-4, p is 1 and $R^b$ is H. In some embodiments of a compound of formula VIb-1, VIb-2, VIb-3, or VIb-4, p is 1 and $R^b$ is methyl. In some embodiments of a compound of formula VIb-1, VIb-2, VIb-3, or VIb-4, p is 1, $R^b$ is H and $R^a$ is H. In some embodiments of a compound of formula VIb-1, VIb-2, VIb-3, or VIb-4, p is 1, $R^b$ is methyl and $R^a$ is H.

In some embodiments of a compound of formula VIb-1, VIb-2, VIb-3, or VIb-4, $R^7$, $R^8$ are independently of each other selected from H, linear or branched $C_{1-4}$ alkyl, such as methyl, halogen, such as F or Cl, e.g. F. In some embodiments of a compound of formula VIb-1, VIb-2, VIb-3, or VIb-4, $R^7$, $R^8$ are H. In some embodiments of a compound of formula VIb-1, VIb-2, VIb-3, or VIb-4, $R^7$, $R^8$ are methyl. In some embodiments of a compound of formula VIb-1, VIb-2, VIb-3, or VIb-4, one of $R^7$, $R^8$ is H, the other is methyl.

R[7], R may be attached to the same ring atom or to different ring atoms.

In some embodiments a compound of formula I is a compound or pharmaceutically acceptable salts or stereoisomers thereof formula VIIa:

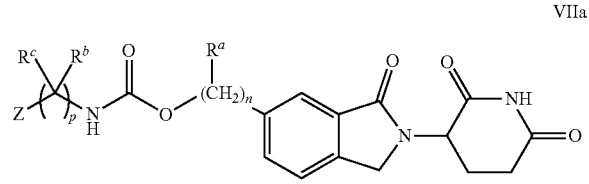

VIIa wherein

Z is H, linear or branched —$C_{1-6}$ alkyl, —$C_{3-6}$ cycloalkyl, 4-8 membered heterocycloalkyl, wherein Z is unsubstituted or substituted with linear or branched $C_{1-4}$ alkyl, $C_6$ aryl, $C_6$ aryloxy, 6 membered heteroaryl or $CF_3$; or Z together with the N atom of the carbamate forms a 4-8 membered heterocycloalkyl, which is unsubstituted or substituted with linear or branched $C_{1-4}$ alkyl, $C_6$ aryl, $C_6$ aryloxy, 6 membered heteroaryl or $CF_3$;

$R^a$ is H, linear or branched $C_{1-4}$ alkyl, such as methyl; $R^b$, $R^c$ are independently of each other H, linear or branched $C_{1-4}$ alkyl, such as methyl; n is 1, or 2; and p is 0 or 1.

In some embodiments of a compound of formula VIIa, $R^a$ is H. In some embodiments of a compound of formula VIIa, $R^a$ is methyl. In some embodiments of a compound of formula VIIa, n is 1. In some embodiments of a compound of formula VIIa, n is 1 and $R^a$ is H. In some embodiments of a compound of formula VIIa, n is 1 and $R^a$ is methyl.

In some embodiments of a compound of formula VIIa, p is 0. In some embodiments of a compound of formula VIIa, p is 1. In some embodiments of a compound of formula VIIa, p is 1, and $R^b$ and $R^c$ are H. In some embodiments of a compound of formula VIIa, p is 1, $R^b$ is methyl and $R^c$ is H.

In some embodiments of a compound of formula VIIa, n is 1 and p is 1. In some embodiments of a compound of formula VIIa, n is 1, p is 1, $R^a$ is H and $R^b$, $R^c$ are H. In some embodiments of a compound of formula VIIa, n is 1, p is 1, $R^a$ is methyl and $R^b$, $R^c$ are H.

In some embodiments of a compound of formula VIIa, n is 1 and p is 0. In some embodiments of a compound of formula VIIa, n is 1, p is 0 and $R^a$ is H. In some embodiments of a compound of formula VIIa, n is 1, p is 0 and $R^a$ is methyl.

In some embodiments of a compound of formula VIIa-1, Z is linear or branched —$C_{1-6}$ alkyl, —$C_{3-6}$ cycloalkyl, 4-6 membered heterocycloalkyl, wherein Z is unsubstituted or substituted with linear or branched $C_{1-4}$ alkyl, $C_6$ aryl, $C_6$ aryloxy, 6 membered heteroaryl; or Z together with the N atom of the carbamate forms a 4-6 membered heterocycloalkyl, which is unsubstituted or substituted with $C_{1-4}$ alkyl, $C_6$ aryl, $C_6$ aryloxy, 6 membered heteroaryl.

In some embodiments of a compound of formula VIIa-1, Z is linear or branched —$C_{1-6}$ alkyl, —$C_{3-6}$ cycloalkyl, 5-6 membered heterocycloalkyl, wherein Z is unsubstituted or substituted with linear or branched $C_{1-4}$ alkyl, $C_6$ aryl, $C_6$ aryloxy, 6 membered heteroaryl; or Z together with the N atom of the carbamate forms a pyrrolidinyl, piperdinyl, morpholinyl, piperazinyl, which is unsubstituted or substituted with $C_{1-4}$ alkyl, $C_6$ aryl, $C_6$ aryloxy, 6 membered heteroaryl.

In some embodiments of a compound of formula VIIa-1, Z is linear or branched $C_{1-4}$ alkyl, cyclopropyl, cyclopentyl, cyclohexyl, bicyclo[1.1.1]pentyl, piperidinyl, 1,3-dioxanyl, wherein Z is unsubstituted or substituted with $C_{1-4}$ alkyl, phenyl, pyridinyl; or Z together with the N atom of the carbamate forms a pyrrolidinyl, piperdinyl, piperazinyl, which is unsubstituted or substituted with $C_6$ aryl, $C_6$ aryloxy.

In some embodiments a compound of formula I is a compound or pharmaceutically acceptable salts or stereoisomers thereof formula VIIa-1, e.g. VIIa-1a:

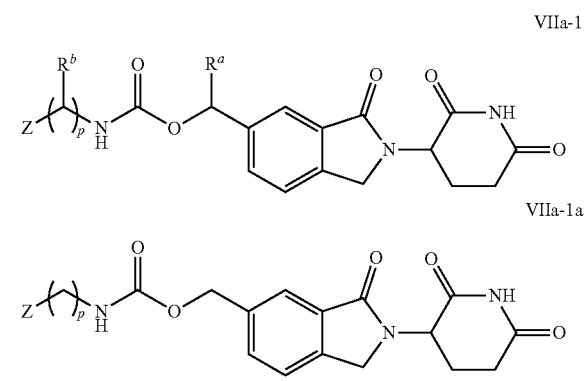

VIIa-1

VIIa-1a wherein Z is H, linear or branched —$C_{1-6}$ alkyl, —$C_{3-6}$ cycloalkyl, 4-8 membered heterocycloalkyl, wherein Z is unsubstituted or substituted with linear or branched $C_{1-4}$ alkyl, $C_6$ aryl, $C_6$ aryloxy, 6 membered heteroaryl or $CF_3$; or Z together with the N atom of the carbamate forms a 4-8 membered heterocycloalkyl, which is unsubstituted or substituted with linear or branched $C_{1-4}$ alkyl, $C_6$ aryl, $C_6$ aryloxy, 6 membered heteroaryl or $CF_3$;

$R^a$, $R^b$ are independently of each other H, linear or branched $C_{1-4}$ alkyl, such as methyl; and p is 0 or 1.

In some embodiments of a compound of formula VIIa-1, $R^a$ is H. In some embodiments of a compound of formula VIIa, $R^a$ is methyl.

In some embodiments of a compound of formula VIIa-1, p is 0. In some embodiments of a compound of formula VIIa-1, p is 0 and $R^a$ is H. In some embodiments of a compound of formula VIIa-1, p is 0 and $R^a$ is methyl.

In some embodiments of a compound of formula VIIa-1, p is 1. In some embodiments of a compound of formula VIIa-1, p is 1 and $R^b$ is H. In some embodiments of a compound of formula VIIa-1, p is 1 and $R^b$ is methyl. In some embodiments of a compound of formula VIIa-1, p is 1 and $R^a$ and $R^b$ are H. In some embodiments of a compound of formula VIIa-1, p is 1, $R^a$ is methyl and $R^b$ is H. In some embodiments of a compound of formula VIIa-1, p is 1, $R^a$ and $R^b$ are methyl.

In some embodiments of a compound of formula VIIa-1a, p is 0. In some embodiments of a compound of formula VIIa-1a, p is 1.

In some embodiments of a compound of formula VIIa-1, Z is linear or branched —$C_{1-6}$ alkyl, —$C_{3-6}$ cycloalkyl, 4-6 membered heterocycloalkyl, wherein Z is unsubstituted or substituted with linear or branched $C_{1-4}$ alkyl, $C_6$ aryl, $C_6$ aryloxy, 6 membered heteroaryl; or Z together with the N atom of the carbamate forms a 4-6 membered heterocycloalkyl, which is unsubstituted or substituted with $C_{1-4}$ alkyl, $C_6$ aryl, $C_6$ aryloxy, 6 membered heteroaryl.

In some embodiments of a compound of formula VIIa-1, Z is linear or branched —$C_{1-6}$ alkyl, —$C_{3-6}$ cycloalkyl, 5-6 membered heterocycloalkyl, wherein Z is unsubstituted or substituted with linear or branched $C_{1-4}$ alkyl, $C_6$ aryl, $C_6$ aryloxy, 6 membered heteroaryl; or Z together with the N atom of the carbamate forms a pyrrolidinyl, piperdinyl, morpholinyl, piperazinyl, which is unsubstituted or substituted with $C_{1-4}$ alkyl, $C_6$ aryl, $C_6$ aryloxy, 6 membered heteroaryl.

In some embodiments of a compound of formula VIIa-1, Z is linear or branched $C_{1-4}$ alkyl, cyclopropyl, cyclopentyl, cyclohexyl, bicyclo[1.1.1]pentyl, piperidinyl, 1,3-dioxanyl, wherein Z is unsubstituted or substituted with $C_{1-4}$ alkyl, phenyl, pyridinyl; or Z together with the N atom of the carbamate forms a pyrrolidinyl, piperdinyl, piperazinyl, which is unsubstituted or substituted with $C_6$ aryl, $C_6$ aryloxy.

In some embodiments of a compound of formula VIIa-1, p is 0 and Z is linear or branched —$C_{1-6}$ alkyl, —$C_{3-6}$ cycloalkyl, 4-6 membered heterocycloalkyl, wherein Z is unsubstituted or substituted with linear or branched $C_{1-4}$ alkyl, $C_6$ aryl, $C_6$ aryloxy, 6 membered heteroaryl.

In some embodiments of a compound of formula VIIa-1, p is 0 and Z is linear or branched —$C_{1-6}$ alkyl, —$C_{3-6}$ cycloalkyl, 5-6 membered heterocycloalkyl, wherein Z is unsubstituted or substituted with linear or branched $C_{1-4}$ alkyl, $C_6$ aryl, $C_6$ aryloxy, 6 membered heteroaryl.

In some embodiments of a compound of formula VIIa-1, p is 0 and Z is linear or branched $C_{1-4}$ alkyl, cyclopropyl, cyclopentyl, cyclohexyl, bicyclo[1.1.1]pentyl, piperidinyl, 1,3-dioxanyl, wherein Z is unsubstituted or substituted with $C_{1-4}$ alkyl, phenyl, pyridinyl.

In some embodiments of a compound of formula VIIa-1, p is 1 and Z is linear or branched —$C_{1-6}$ alkyl, —$C_{3-6}$ cycloalkyl, 4-6 membered heterocycloalkyl, wherein Z is unsubstituted or substituted with linear or branched $C_{1-4}$ alkyl, $C_6$ aryl, $C_6$ aryloxy, 6 membered heteroaryl; or Z together with the N atom of the carbamate forms a 4-6 membered heterocycloalkyl, which is unsubstituted or substituted with $C_{1-4}$ alkyl, $C_6$ aryl, $C_6$ aryloxy, 6 membered heteroaryl.

In some embodiments of a compound of formula VIIa-1, p is 1 and Z is linear or branched —$C_{1-6}$ alkyl, —$C_{3-6}$ cycloalkyl, wherein Z is unsubstituted or substituted with linear or branched $C_{1-4}$ alkyl, $C_6$ aryl; or Z together with the N atom of the carbamate forms a pyrrolidinyl, piperdinyl, morpholinyl, piperazinyl, which is unsubstituted or substituted with $C_{1-4}$ alkyl, $C_6$ aryl, $C_6$ aryloxy, 6 membered heteroaryl.

In some embodiments of a compound of formula VIIa-1, p is 1 and Z is linear or branched $C_{1-6}$ alkyl, cyclopropyl; or Z together with the N atom of the carbamate forms a pyrrolidinyl, piperdinyl, piperazinyl, which is unsubstituted or substituted with $C_6$ aryl, $C_6$ aryloxy.

In more specific embodiments, the present disclosure is directed towards a compound or pharmaceutically acceptable salts or stereoisomers thereof formula VIII, e.g. VIIIa

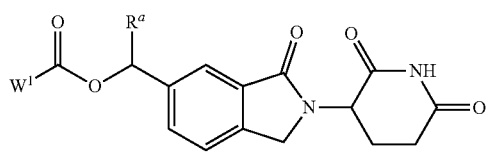

VIII

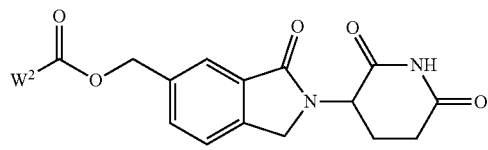

VIIIa wherein $R^a$ is H or methyl and $w^1$ and $w^2$ are selected from

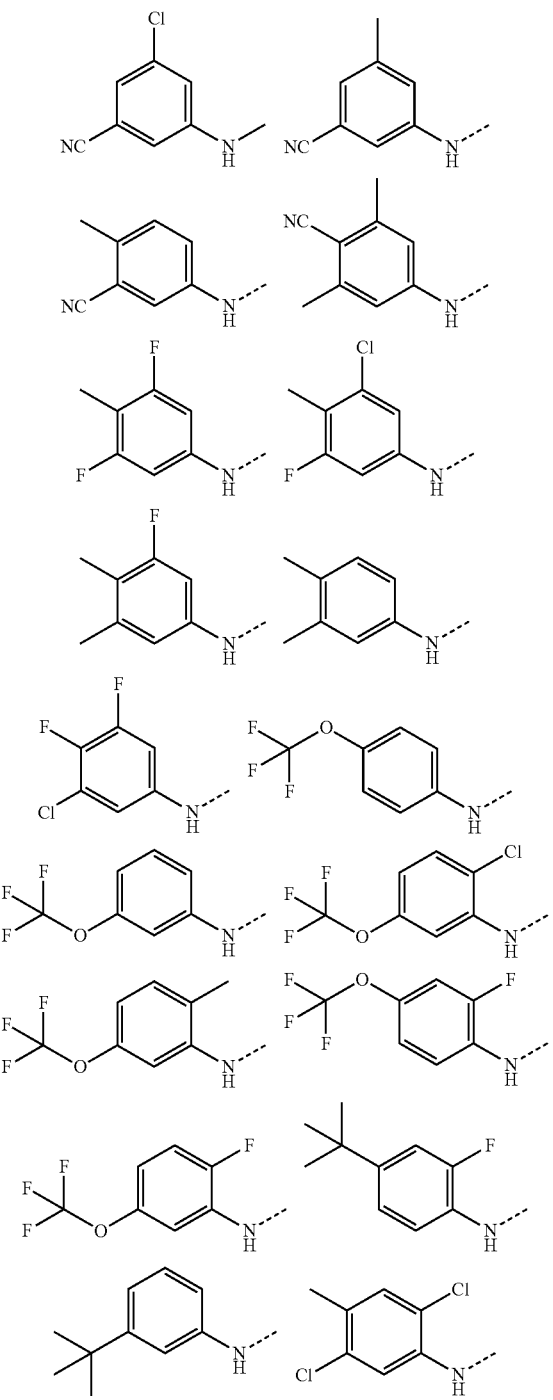

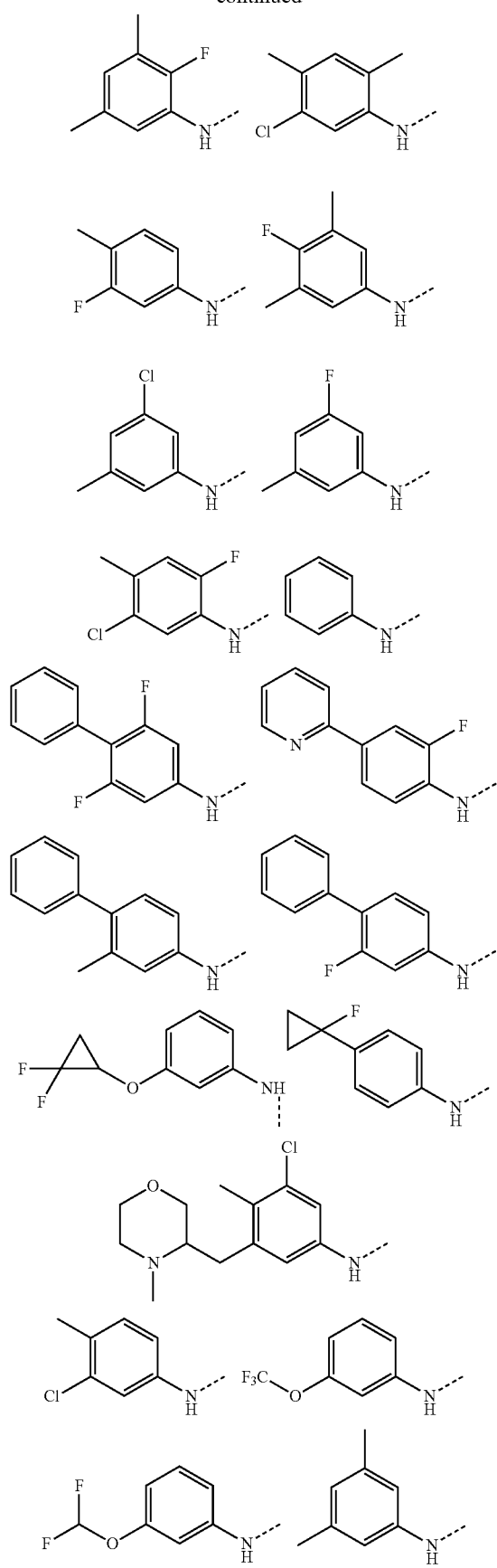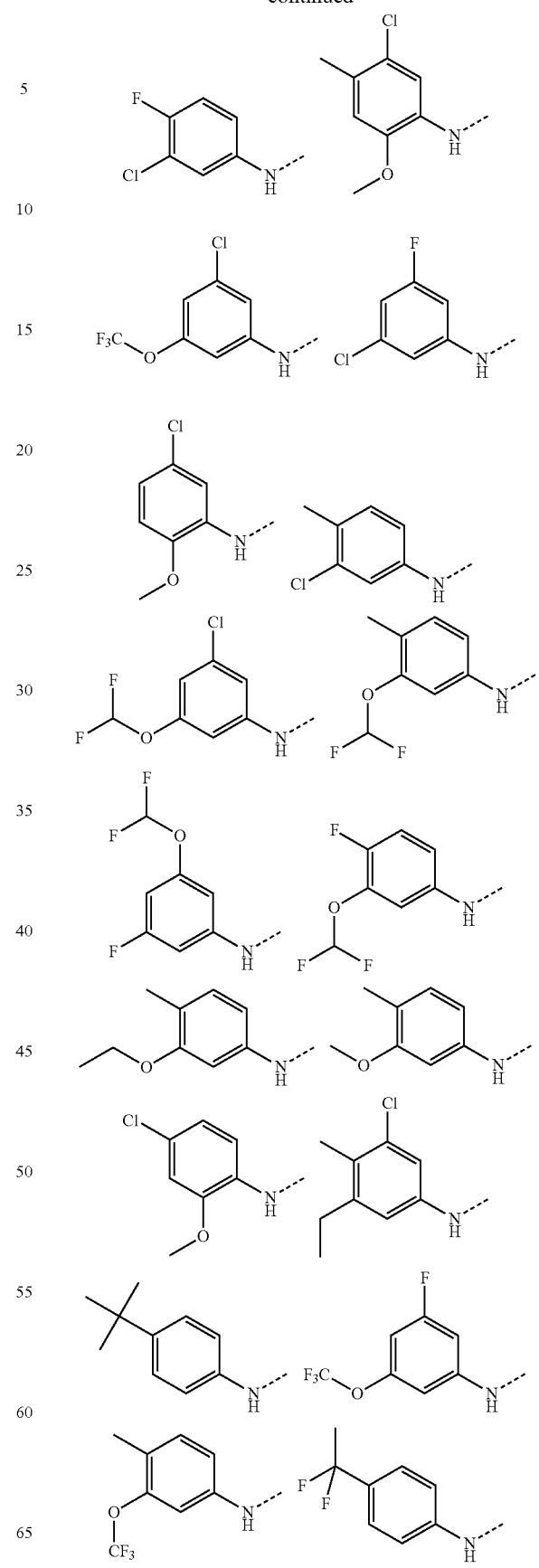

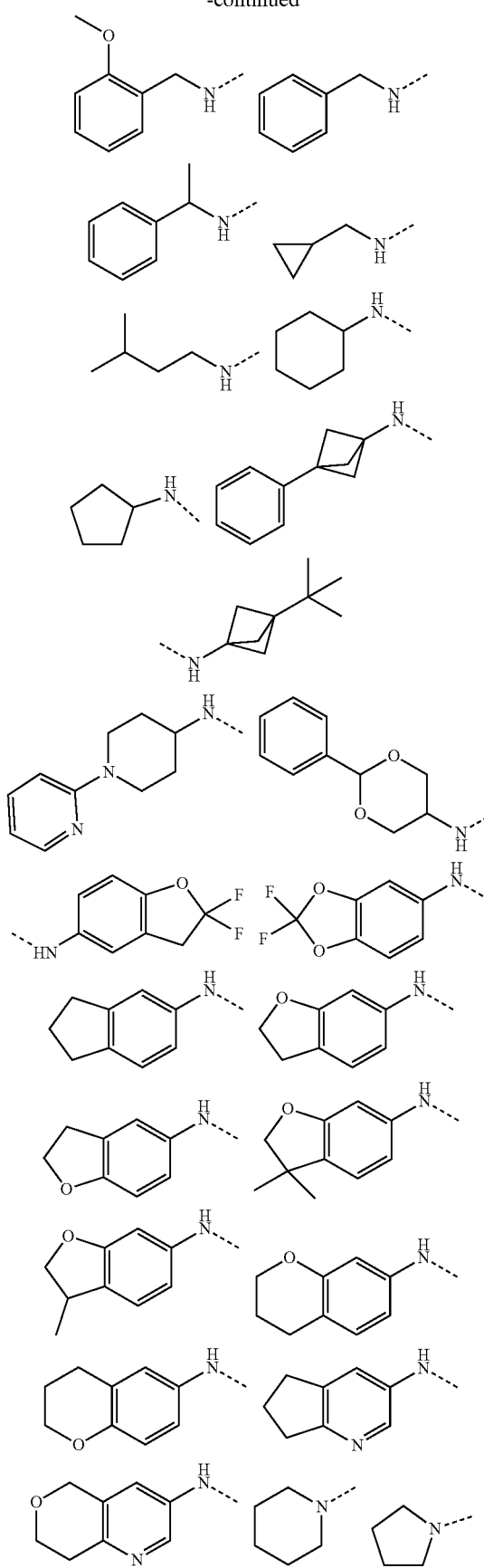
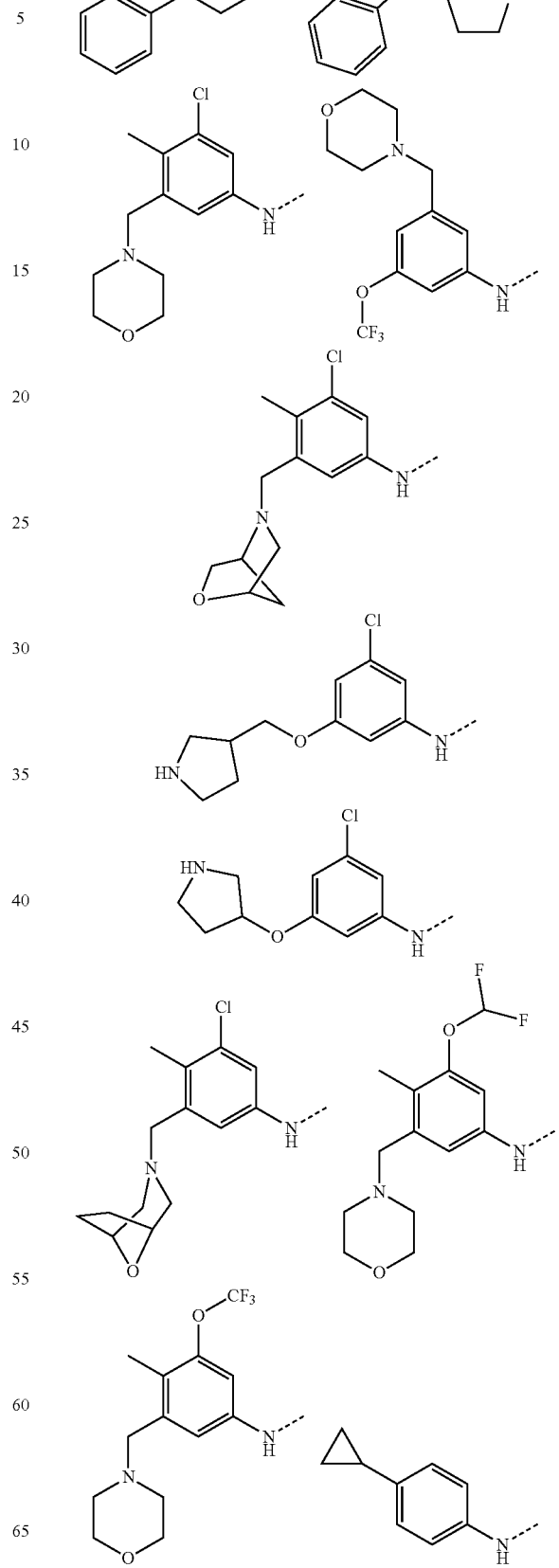

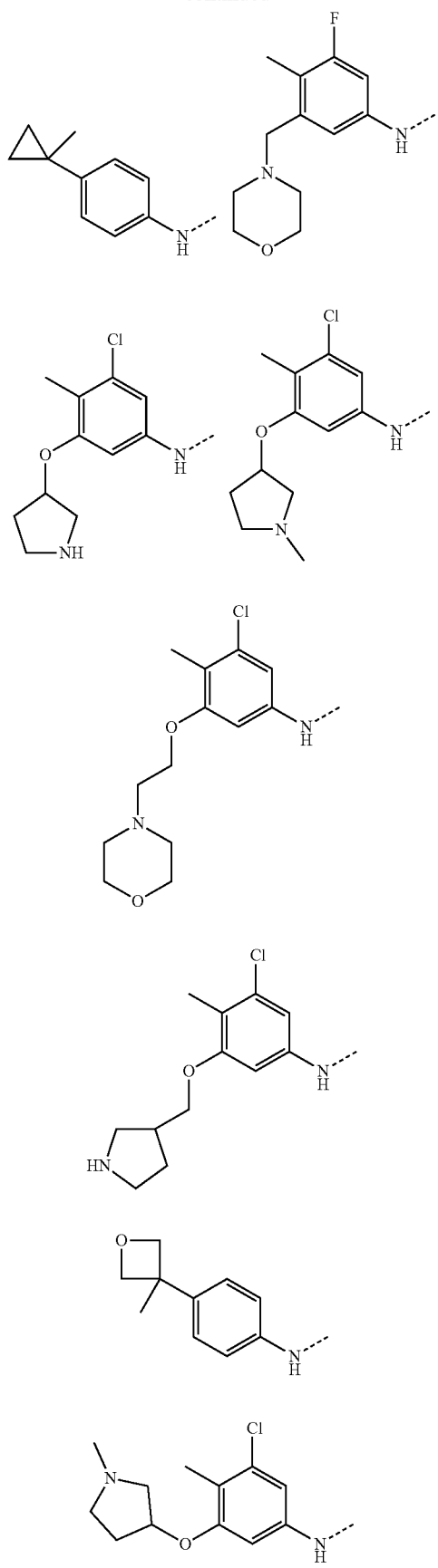
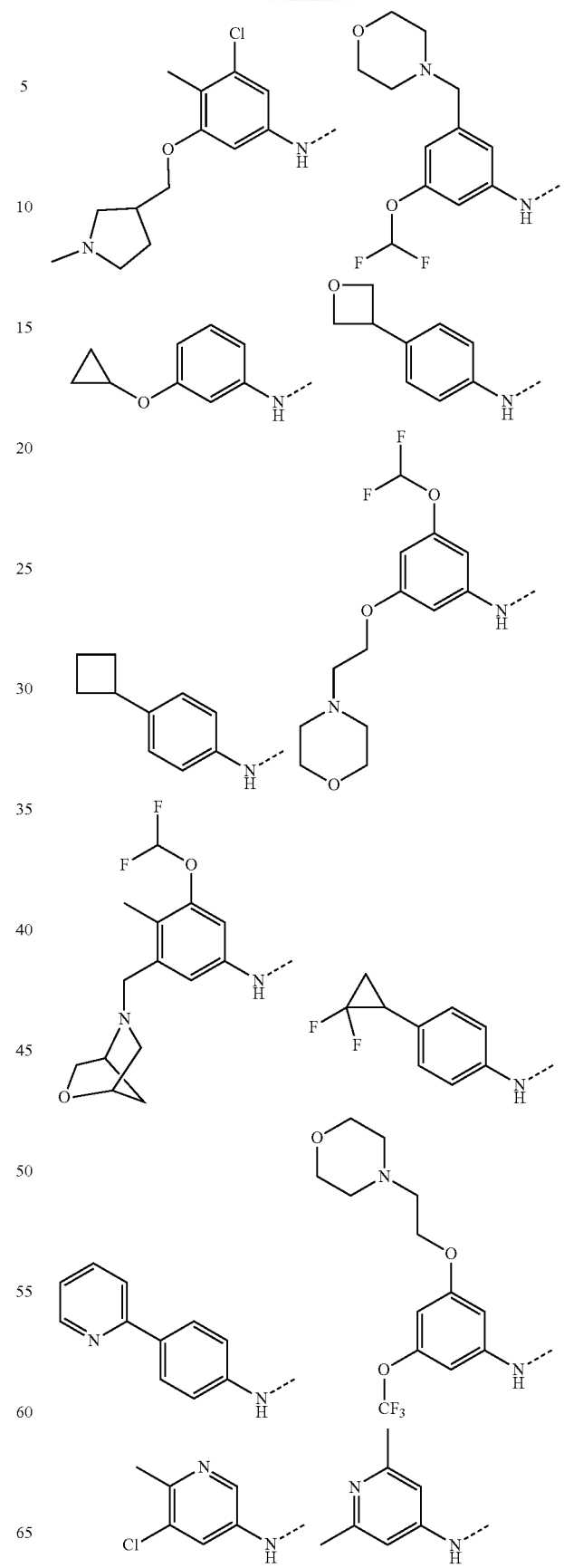

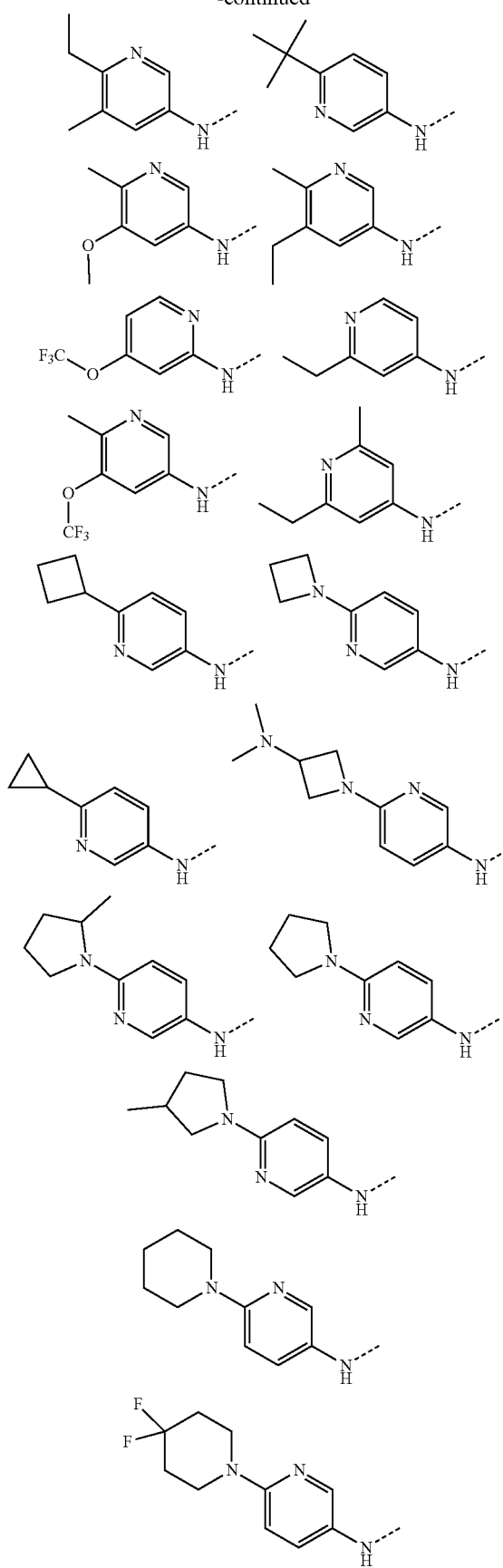
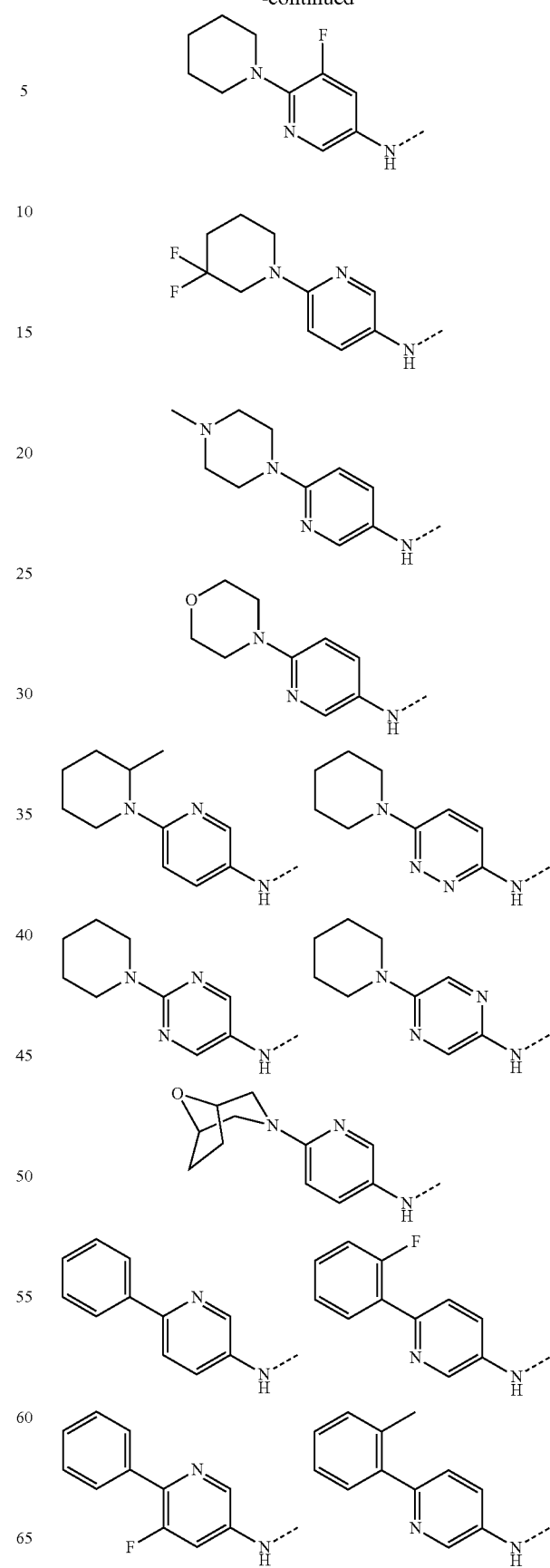

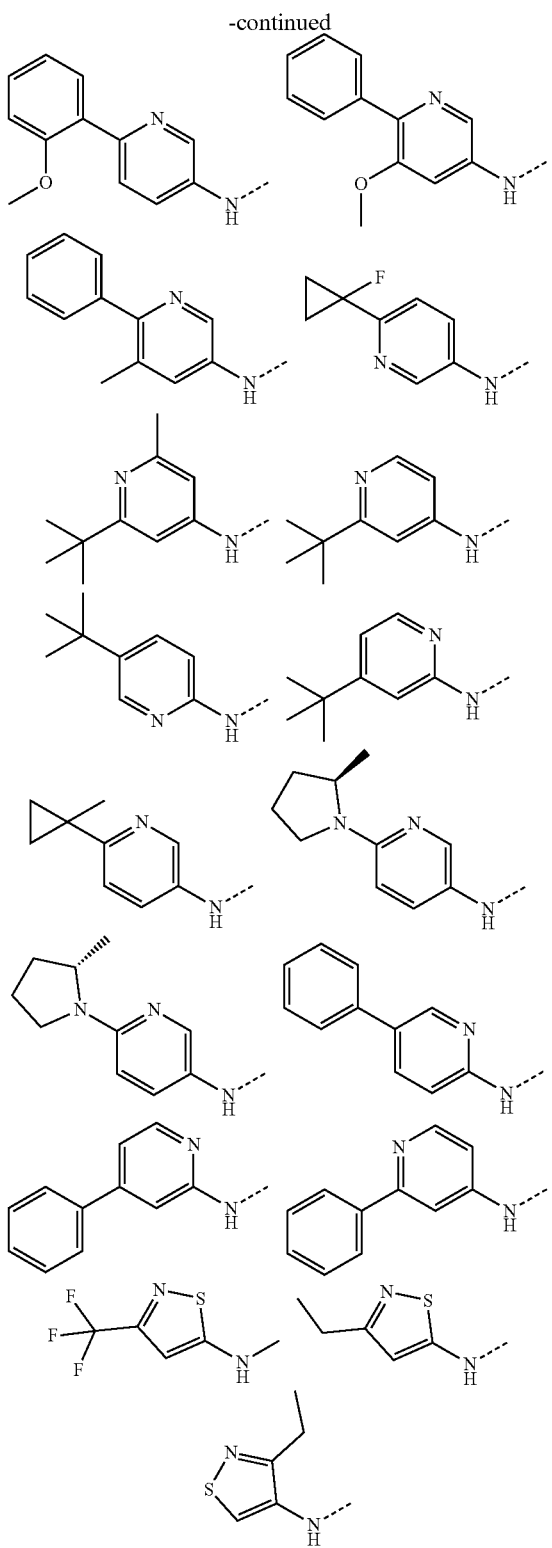

In more specific embodiments of a compound of formula VIII, $R^a$ is H.

In further specific embodiments, the disclosure is directed to the specific examples disclosed in Table 1.

In some embodiments, the disclosure is directed to the (S) enantiomer of the compounds of any of formula I-VIII. In some embodiments, the disclosure is directed to the (R) enantiomer of the compounds of any of formula I-VIII. In some embodiments, the disclosure is directed to the racemate of the compounds of any of formula I-VIII.

The compounds of the disclosure may contain one or more asymmetric centers in the molecule. A compound without designation of the stereochemistry is to be understood to include all the optical isomers (e.g., diastereomers, enantiomers, etc.) in pure or substantially pure form, as well as mixtures thereof (e.g. a racemic mixture, or an enantiomerically enriched mixture). It is well known in the art how to prepare such optically active forms (e.g. by resolution of the racemic form by recrystallization techniques, by synthesis from optically-active starting materials, by chiral synthesis, by chromatographic separation using a chiral stationary phase, and other methods).

The compounds may be isotopically-labeled compounds, for example, compounds including various isotopes of hydrogen, carbon, nitrogen, oxygen, phosphorous, fluorine, iodine, or chlorine. The disclosed compounds may exist in tautomeric forms and mixtures and separate individual tautomers are contemplated. In addition, some compounds may exhibit polymorphism.

The compounds of the disclosure include the free form as well as the pharmaceutically acceptable salts and stereoisomers thereof. The pharmaceutically acceptable salts include all the typical pharmaceutically acceptable salts. The pharmaceutically acceptable salts of the present compounds can be synthesized from the compounds of this disclosure which contain a basic or acidic moiety by conventional chemical methods, see e.g. Berge et al, "Pharmaceutical Salts," J. Pharm. ScL, 1977:66:1-19. Furthermore, the compounds of the disclosure also include lyophilized and polymorphs of the free form.

For example, conventional pharmaceutically acceptable salts for a basic compound include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. Conventional pharmaceutically acceptable salts for an acidic compound include those derived from inorganic bases include aluminum, ammonium, calcium, copper, ferric, ferrous, lithium, magnesium, manganic salts, manganous, potassium, sodium, zinc and the like. Salts derived from pharmaceutically acceptable organic bases include salts of primary, secondary and tertiary amines, substituted amines including naturally occurring substituted amines, cyclic amines and basic ion exchange resins, such as arginine, betaine caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The compounds of the disclosure may exist in solid, i.e. crystalline (e.g., polymorphs, i.e., different crystalline structures that have the same chemical composition but differ in packing, geometrical arrangement) or noncrystalline form (optionally as solvates) or liquid form. In the solid state, it may exist in, or as a mixture thereof. In crystalline solvates, solvent molecules are incorporated into the crystalline lattice during crystallization. The formation of solvates may include non-aqueous solvents such as, but not limited to, ethanol, isopropanol, DMSO, acetic acid, ethanolamine, or ethyl acetate, or aqueous solvents such as water (also called "hydrates"). Different polymorphs may be produced, for example, by changing or adjusting the reaction is conditions or reagents.

In a further aspect, the disclosure also provides methods of preparation of the compounds of formula I-VIII of the disclosure. In some embodiments, they are prepared according to the general procedure A.

In yet another aspect, the disclosure further provides a pharmaceutical composition comprising a therapeutically-effective amount of one or more of the compounds of the disclosure or pharmaceutically acceptable salt thereof and one or more pharmaceutically acceptable carriers and/or excipients (also referred to as diluents). The excipients are acceptable in the sense of being compatible with the other ingredients of the formulation and not deleterious to the recipient thereof (i.e., the patient). The term "therapeutically-effective amount", or "therapeutically effective amount" as used herein refers to the amount of a compound (as such or in form of a pharmaceutical composition) of the present disclosure which is effective for producing some desired therapeutic effect.

Pharmaceutical compositions may be in unit dose form containing a predetermined amount of a compound of the disclosure per unit dose. Such a unit may contain a therapeutically effective dose of a compound of the disclosure or salt thereof or a fraction of a therapeutically effective dose such that multiple unit dosage forms might be administered at a given time to achieve the desired therapeutically effective dose. Preferred unit dosage formulations are those containing a daily dose or sub-dose, or an appropriate fraction thereof, of a compound of the disclosure or salt thereof.

The compounds of the disclosure may be administered by any acceptable means in solid or liquid form, including (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical compositions.

Such compositions may contain further components conventional in pharmaceutical preparations, e.g. wetting agents, emulsifiers and lubricants, such as sodium lauryl sulfate and magnesium stearate, as well as coloring agents, release agents, coating agents, sweetening, flavoring and perfuming agents, preservatives and antioxidants, pH modifiers, bulking agents, and further active agents. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Such compositions may be prepared by any method known in the art, for example, by bringing into association the active ingredient with one or more carriers and/or excipients. Different compositions and examples of carriers and/or excipients are well known to the skilled person and are described in detail in, e.g., Remington: The Science and Practice of Pharmacy. Pharmaceutical Press, 2013; Rowe, Sheskey, Quinn: Handbook of Pharmaceutical Excipients. Pharmaceutical Press, 2009. Excipients that may be used in the preparation of the pharmaceutical compositions may include one or more of buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide a composition suitable for an administration of choice.

As indicated above, the compounds of the present disclosure may be in solid or liquid form and administered by various routes in any convenient administrative form, e.g., tablets, powders, capsules, solutions, dispersions, suspensions, syrups, sprays, suppositories, gels, emulsions, patches, etc.

In solid dosage forms of the disclosure for oral administration (capsules, tablets, pills, dragees, powders, granules, trouches and the like), a compound is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7)

wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof, (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like. A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent. The tablets, and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. An oral composition can also include adjuvants such as wetting agents, emulsifying and suspending agents, sweetening, flavoring, coloring, perfuming and preservative agents.

In form of suspensions, a compound may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for rectal or vaginal administration of a compound of the disclosure include a suppository, which may be prepared by mixing one or more compounds of the disclosure with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound. Other suitable forms include pessaries, tampons, creams, gels, pastes, foams or spray formulations containing such carriers as are known in the art to be appropriate.

Dosage forms for the topical or transdermal administration of a compound of the disclosure include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required. Such ointments, pastes, creams and gels may contain, in addition to a compound of the disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Dosage forms such as powders and sprays for administration of a compound of the disclosure, may contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Dosage forms such as transdermal patches for administration of a compound of the disclosure may include absorption enhancers or retarders to increase or decrease the flux of the compound across the skin. The rate of such flux can be controlled by either providing a rate controlling membrane or dispersing the compound in a polymer matrix or gel. Other dosage forms contemplated include ophthalmic formulations, eye ointments, powders, solutions and the like. It is understood that all contemplated compositions must be stable under the conditions of manufacture and storage, and preserved against the contaminating action of microorganisms, such as bacteria and fungi.

The dosage levels of a compound of the disclosure in the pharmaceutical compositions of the disclosure may be adjusted in order to obtain an amount of a compound of the disclosure which is effective to achieve the desired therapeutic response for a particular patient, composition, and mode of administration, without being deleterious to the patient. The dosage of choice will depend upon a variety of factors including the nature of the particular compound of the present disclosure used, the route of administration, the time of administration, the rate of excretion or metabolism of the particular compound used, the rate and extent of absorption, the duration of the treatment, other drugs, compounds and/or materials used in combination with the particular compound, the age, sex, weight, condition, general health and prior medical history of the patient being treated, and like factors well known in the medical arts. A medical practitioner having ordinary skill in the art can readily determine and prescribe the effective amount of the pharmaceutical composition required.

Typically, a suitable daily dose of a compound of the disclosure will be that amount of the compound, which is the lowest dose effective to produce a therapeutic effect. Such an effective dose will generally depend upon the factors described above. Generally, oral, intravenous, intracerebroventricular and subcutaneous doses of the compounds of this disclosure for a patient, when used for the indicated analgesic effects, will range from about 0.0001 to about 100 mg, more usual 0.1 to 100 mg/kg per kilogram of body weight of recipient (patient, mammal) per day. Acceptable daily dosages may be from about 1 to about 1000 mg/day, and for example, from about 1 to about 100 mg/day.

A compound of the disclosure, or a pharmaceutically acceptable salt, or stereoisomer, thereof, may be administered once daily (QD) or divided into multiple daily doses such as twice daily (BID), three times daily (TID), and four times daily (QID) or may be administered in regular intervals of more than one day, such as every two days (Q2D). Administration may be continuous (i.e., daily for consecutive days or every day) or intermittent, e.g., in cycles (i.e., including days, weeks, or months of rest without drug). In some embodiments, a compound of the disclosure, or a pharmaceutically acceptable salt, or stereoisomer thereof, is administered every day for at least 21 days. In some embodiments, a compound of the disclosure, or a pharmaceutically acceptable salt or stereoisomer thereof, is administered every two days for at least 21 days.

The term "intermittent" or "intermittently" as used herein is intended to mean stopping and starting at either regular or irregular intervals. For example, intermittent administration of a compound of the disclosure, or a pharmaceutically acceptable salt, or stereoisomer, thereof, is administration for one to six days per week, administration in cycles (e.g., daily administration for two to eight consecutive weeks, then a rest (or holiday) period with no administration for up to one week), or administration on alternate days. The term "cycling" as used herein is intended to mean that a compound of the disclosure, or a pharmaceutically acceptable salt, or stereoisomer, thereof, is administered daily or continuously but with a rest period. In some embodiments, the rest period is the same length as the treatment period. In other embodiments, the rest period has different length from the treatment period. In some embodiments, a compound of the disclosure, or a pharmaceutically acceptable salt, or stereoisomer, thereof, is administered intermittently once per day for 5 days followed by a rest of 3 days (i.e. 5 days on/3 days off). This intermittent administration is repeated for 3 to 4 cycles. In some embodiments, a compound of the disclosure, or a pharmaceutically acceptable salt, or stereoisomer thereof, is administered intermittently once per day for 5 days followed by a rest of 9 days (i.e. 5 days on/9 days off). This intermittent administration is repeated for 2 cycles. It is understood that dosing regimen also depend on factors as indicated above, e.g. on the administration, and can be readily arrived at by one skilled in medicine or the pharmacy art.

The compounds of the disclosure modulate the activity of cereblon. Thus, the compounds and compositions of the disclosure can be useful as a medicament, i.e. as a medicament in therapy, more specifically for the treatment of cancer, as detailed below. Therefore, in a further aspect, the present disclosure provides a method of treatment of a mammal, for example, a human, suffering from cancer, as detailed below. The term "treatment" is intended to encompass prophylaxis, therapy and cure. Such treatment comprises the step of administering a therapeutically effective amount of a compound of Formula I or salt thereof (or of a pharmaceutical composition containing a compound of Formula I or salt thereof) to said mammal, for example, a human.

Thus, the disclosure is directed towards the use of the compounds of the disclosure or pharmaceutically acceptable salts or stereoisomers thereof or a pharmaceutical composition thereof for the treatment of a disease associated or caused with GSPT1, in particular the treatment of cancer, as detailed below, in a mammal, for example a human.

Myc-Driven Cancers

Described herein, in some embodiments, are cancers exhibiting increased expression of one or more of c-Myc, L-Myc, N-Myc, EIF4EBP1, and EIF4EBP2 as well as ones with increase phosphorylation of one or both of EIF4EBP1 and EIF4EBP2.

Myc-driven cancers refer to cancers where there is abnormal activation of Myc oncogene, either due to transcriptional overexpression (e.g., caused by gene amplification, translocation, alterations in upstream signaling pathways) and/or protein stabilization. A myc-driven cancer cell includes a cancer cell that has an increased expression or overexpression (and/or increased activity) of at least one myc transcription factor such as N-myc and/or L-myc and/or C-myc, or a surrogate marker thereof, relative to a control cell such as a normal (e.g., non-cancerous) cell of the same or corresponding cell type. The term "cancerous" when referring to a sample such as a cell or tissue, generally refers to any sample, such as cells or tissues that exhibit, or are predisposed to exhibiting, unregulated growth, including, for example, a neoplastic cell/tissue such as a premalignant cell/tissue or a cancer cell (e.g., carcinoma cell or sarcoma cell).

In some embodiments the Myc-driven cancer or tumor as defined herein refers to a blood borne tumor cancer, such as a hematological cancer, preferably a cancer of hematopoietic and lymphoid tissues and lymphatic system, such as blood cancer, bone marrow cancer, lymph node cancer, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, non-Hodgkin's lymphomas and multiple myeloma (MM).

In some embodiments, the Myc-driven cancer or tumour is a solid tumor cancer, such as breast cancer, colorectal cancer, lung cancer, e.g. SCLC, NSCLC, neuroendocrine cancer, e.g., neuroendocrine prostate cancer (for example, NEPC (castration-resistant neuroendocrine prostate cancer)) and lung neuroendocrine tumors (Lu-NETs), liver cancer, stomach cancer, pancreatic cancer, gastric cancer, esophageal cancer, bladder cancer, skin cancer, brain cancer, cervical cancer, ovarian cancer, melanoma and head and neck cancer.

In some embodiments the Myc-driven cancer as used herein refers in particular to breast cancer and SCLC. In some embodiments the myc-driven cancer as used herein refers in particular to NSCLC. In some embodiments, the cancer is solid tumor cancer exhibiting amplification of the N-Myc gene and/or the L-Myc gene. In some embodiments the Myc-driven cancer as used herein refers to neuroendocrine cancer, for example, neuroendocrine prostate cancer (for example, NEPC (castration-resistant neuroendocrine prostate cancer)) and lung neuroendocrine tumors (Lu-NETs), acute myelogenous leukemia (AML), lymphoma, and multiple myeloma (MM).

Solid and Liquid Cancers

The term "solid cancer" or "solid tumor" refers to disease of tissues or organs, such as to malignant, neoplastic, or cancerous solid tumors, i.e. sarcomas, carcinomas. The tissue structure of solid tumors includes interdependent tissue compartments and usually does not contain cysts or fluid areas. A solid cancer or solid tumor includes cancers of the bladder, bone, brain, breast, cervix, chest, colon, endometrium, esophagus, eye, head, kidney, liver, lymph nodes, lung, upper aerodigestive tract (including nasal cavity and paranasal sinuses, nasopharynx or cavum, oral cavity, oropharynx, larynx, hypopharynx and salivary glands), neck, ovaries, pancreas, prostate, rectum, skin, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, e.g., neuroendocrine prostate cancer (for example, NEPC (castration-resistant neuroendocrine prostate cancer)) and lung neuroendocrine tumors (Lu-NETs), rectal adenocarcinoma, colorectal cancer, including stage 3 and stage 4 colorectal cancer, unresectable colorectal carcinoma, metastatic hepatocellular carcinoma, Kaposi's sarcoma, malignant melanoma, cervical cancer, ovarian cancer, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In some embodiments, a solid cancer or solid tumor is a cancer of the breast, lung, stomach, colon, bladder, brain, pancreas, liver, head and neck, prostate, ovaries, upper aerodigestive tract and the like.

The term "blood borne cancer" or "blood borne tumor" (also typically referred to as "hematological cancer") refers to cancer of the body's blood-forming and immune system—the bone marrow and lymphatic tissue. The tissue structure of blood-borne cancers or tumors includes an abnormal mass of cells that is fluid in nature. Such cancers include leukemias (malignant neoplasms of the blood-forming tissues), lymphomas (Non-Hodgkin's Lymphoma), Hodgkin's disease (Hodgkin's Lymphoma) and myeloma. In one embodiment, the myeloma is multiple myeloma (MM). In some embodiments, the leukemia is, for example, acute myelogenous leukemia (AML), acute lymphocytic leukemia (ALL), adult T-cell leukemia, chronic lymphocytic leukemia (CLL), small lymphocytic lymphoma (SLL), hairy cell leukemia, myelodysplasia, myeloproliferative disorders, chronic myelogenous leukemia (CML), acute monocytic leukemia (AMoL), myelodysplastic syndrome (MDS), human lymphotropic virus-type 1 (HTLV-1) leukemia, mastocytosis, or B-cell acute lymphoblastic leukemia. The leukemia can be relapsed, refractory or resistant to conventional therapy. In some embodiments, the lymphoma is, for example, diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, peripheral T-cell lymphoma (PTCL), cutaneous T-cell lymphoma (CTCL), mantle cell lymphoma (MCL), Hodgkin's lymphoma (HL), non-Hodgkin's lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, or ALK-positive large B-cell lymphoma. In one embodiment, the hematological cancer is indolent lymphoma including, for example, DLBCL, follicular lymphoma, or marginal zone lymphoma. In some embodiments blood-borne cancers or hematological cancers include acute lymphoblastic leukemia (ALL), chronic lymphocytic lymphoma (CLL), small lymphocytic lymphoma (SLL), acute myelogenous leukemia (AML), chronic myelogenous leukemia (CMIL), acute monocytic leukemia (AMoL), Hodgkin's lymphoma, non-Hodgkin's lymphomas and multiple myeloma (MM).

In particular embodiments, the compounds of the disclosure or pharmaceutically acceptable salts or stereoisomers thereof or a pharmaceutical composition thereof are used for the treatment of cancer associated with GSPT1, such as solid cancers including but not limited to cancers of the bladder, bone, brain, breast, cervix, chest, colon, endometrium, esophagus, eye, head, kidney, liver, lymph nodes, lung, upper aerodigestive tract (including nasal cavity and paranasal sinuses, nasopharynx or cavum, oral cavity, oropharynx, larynx, hypopharynx and salivary glands), neck, ovaries, pancreas, prostate, rectum, skin, stomach, testis, throat, uterus, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, e.g., neuroendocrine prostate cancer such as castration-resistant neuroendocrine prostate cancer (NEPC) and lung neuroendocrine tumors (Lu-NETs), rectal adenocarcinoma, colorectal cancer, including stage 3 and stage 4 colorectal cancer, unresectable colorectal carcinoma, metastatic hepatocellular carcinoma, Kaposi's sarcoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma; and blood bourne (liquid) or hematological cancers, including but not limited to leukemias, lymphomas, and myelomas, such as diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, peripheral T-cell lymphoma (PTCL), cutaneous T-cell lymphoma (CTCL), mantle cell lymphoma (MCL), Hodgkin's lymphoma (HL), non-Hodgkin's lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, ALK-positive large B-cell lymphoma, indolent lymphoma (for example, DLBCL, follicular lymphoma, or marginal zone lymphoma), acute myelogenous leukemia (AML), acute lymphocytic leukemia (ALL), adult T-cell leukemia, chronic lymphocytic leukemia (CLL), small lymphocytic lymphoma (SLL), hairy cell leukemia, myelodysplasia, myeloproliferative disorders, chronic myelogenous leukemia (CMIL), acute monocytic leukemia (AMoL), myelodysplastic syndrome (MDS), human lymphotropic virus-type 1 (HTLV-1) leukemia, mastocytosis, B-cell acute lymphoblastic leukemia, Non-Hodgkin's Lymphoma, Hodgkin's Lymphoma, and multiple myeloma (MM).

Such a use (or method of treatment) of a subject comprises administering to a subject in need of such treatment a therapeutically effective amount of a compound of the disclosure or pharmaceutically acceptable salts thereof or a pharmaceutical composition thereof by targeting cereblon.

Disclosed herein, in part, is a method of treating a Myc-driven cancer in a subject in need thereof, comprising administering the subject a therapeutically effective amount of a compound described herein or a composition as described herein.

In some embodiments, the Myc-driven cancer is a Myc-driven lung cancer.

In some embodiments, the Myc-driven cancer is characterized by high driven Myc tumor.

In some embodiments, the Myc-driven cancer is a Myc-driven small cell lung cancer.

In some embodiments, the Myc-driven small cell lung cancer is a high L-Myc small cell lung cancer.

In some embodiments, the Myc-driven cancer is a Myc-driven non-small cell lung cancer.

In some embodiments, the Myc-driven non-small cell lung cancer is a high N-Myc non-small cell lung cancer.

In some embodiments, the compound or the composition is administered to the subject via oral administration.

In another aspect, provided herein is a method of degrading GSPT1 in a subject suffering from cancer, comprising administering to the subject a therapeutically effective amount of a compound described herein or a composition described herein.

In some embodiments, the cancer is a Myc-driven cancer.

In some embodiments, the Myc-driven cancer is a Myc-driven lung cancer.

In some embodiments, the Myc-driven cancer is a Myc-driven small cell lung cancer.

In some embodiments, the Myc-driven small cell lung cancer is a high L-Myc small cell lung cancer.

In some embodiments, the Myc-driven cancer is a Myc-driven non-small cell lung cancer.

In some embodiments, the Myc-driven non-small cell lung cancer is a high N-Myc non-small cell lung cancer.

In some embodiments, the compound or the composition is administered to the subject via oral administration.

In another aspect, the disclosure is directed to a method of reducing the level of GSPT1 in a subject suffering from cancer, comprising administering the subject a therapeutically effective amount of a compound or a composition as described herein.

In some embodiments, the cancer is a Myc-driven cancer.

In some embodiments, the Myc-driven cancer is a Myc-driven lung cancer.

In some embodiments, the Myc-driven cancer is a Myc-driven small cell lung cancer.

In some embodiments, the Myc-driven small cell lung cancer is a high L-Myc small cell lung cancer.

In some embodiments, the Myc-driven cancer is a Myc-driven non-small cell lung cancer.

In some embodiments, the Myc-driven non-small cell lung cancer is a high N-Myc non-small cell lung cancer.

In some embodiments, the compound or the composition is administered to the subject via oral administration.

The present disclosure contemplates administration of a compound of the disclosure alone or in combination with one or more additional therapeutic agents, such as other Tyrosine kinase inhibitors: Erlotinib hydrochloride (e.g. Tarceva® by Genentech/Roche), Linifanib (or ABT 869, by Genentech), sunitinib malate (e.g. Sutent® by Pfizer), bosutinib (or SKI-606, described in U.S. Pat. No. 6,780,996), dasatinib (e.g. Sprycel® by Bristol-Myers Squibb), armala (e.g. pazopanib, e.g. Votrient® by GlaxoSmithKline), imatinib and imatinib mesylate (e.g. Gilvec® and Gleevec® by Novartis); Vascular Endothelial Growth Factor (VEG) receptor inhibitors (Bevacizumab, or Avastin® by Genentech/Roche), axitinib, (or AG013736, described in WO 01/002369), Brivanib Alaninate (or BMS-582664), motesanib (or AMG-706, described in PCT WO 02/066470), pasireotide (e.g. SOM230, described in WO 02/010192), sorafenib (e.g. Nexavar®); HER2 receptor inhibitors: Trastuzumab (e.g. Herceptin® by Genentech/Roche), neratinib (or HKI-272, described WO 05/028443), lapatinib or lapatinib ditosylate (e.g. Tykerb® by GlaxoSmithKline); CD20 antibodies: Rituximab (e.g. Riuxan® and MabThera® by Genentech/Roche), tositumomab (e.g. Bexxar® by GlaxoSmithKline), ofatumumab (e.g. Arzerra® by GlaxoSmithKline); Ber/Abl kinase inhibitors: nilotinib hydrochloride (e.g. Tasigna® by Novartis); DNA Synthesis inhibitors: Capecitabine (e.g. Xeloda® by Roche), gemcitabine hydrochloride (e.g. Gemzar® by Eli Lilly and Company), nelarabine (or Arranon® and Atriance® by GlaxoSmithKline); Antineoplastic agents: oxaliplatin (e.g. Eloxatin® ay Sanofi-Aventis described in U.S. Pat. No. 4,169,846); Epidermal growth factor receptor (EGFR) inhibitors: Gefitinib (or Iressa®), Afatinib (or Tovok® by Boehringer Ingelheim), cetuximab (e.g. Erbitux® by Bristol-Myers Squibb), panitumumab (e.g. Vectibix® by Amgen); HER dimerization inhibitors: Pertuzumab (e.g. Omnitarg®, by Genentech); Human Granulocyte colony-stimulating factor (G-CSF) modulators: Filgrastim (e.g. Neupogen® by Amgen); Immunomodulators: Afutuzumab (by Roche®), pegfilgrastim (e.g. Neulasta® by Amgen), lenalidomide (e.g. CC-5013, e.g. Revlimid®), thalidomide (e.g. Thalomid®); CD40 inhibitors: Dacetuzumab (e.g. SGN-40 or huS2C6, by Seattle Genetics, Inc); Pro-apoptotic receptor agonists (PARAs): Dulanermin (e.g. AMG-951, by Amgen/Genentech); Hedgehog antagonists: Vismodegib (or GDC-0449, described in WO 06/028958); Phospholipase A2 inhibitors: Anagrelide (e.g. Agrylin®); BCL-2 inhibitors: Navitoclax (or ABT-263, described in WO 09/155386); Mitogen-activated protein kinase kinase (MEK) inhibitors: XL-518 (Cas No. 1029872-29-4, by ACC Corp.); Aromatase inhibitors: Exemestane (e.g. Aromasin® by Pfizer), letrozole (e.g. Femara® by Novartis), anastrozole (e.g. Arimidex®); Topoisomerase I inhibitors: Irinotecan (e.g. Camptosar® by Pfizer), topotecan hydrochloride (e.g. Hycamtin® by GlaxoSmithKline); Topoisomerase II inhibitors: etoposide (e.g. VP-16 and Etoposide phosphate, e.g. Toposar®, VePesid® and Etopophos®), teniposide (e.g. VM-26, e.g. Vumon®); mTOR inhibitors: Temsirolimus (e.g. Torisel® by Pfizer), ridaforolimus (formally known as deferolimus, (or AP23573 and MK8669, described in WO 03/064383), everolimus (e.g. Afinitor® by Novartis); Osteoclastic bone resorption inhibitors: zoledronic acid (or Zometa® by Novartis); CD33 Antibody Drug Conjugates: Gemtuzumab ozogamicin (e.g. Mylotarg® by Pfizer/Wyeth); CD22 Antibody Drug Conjugates: Inotuzumab ozogamicin (also referred to as CMC-544 and WAY-207294, by Hangzhou Sage Chemical Co., Ltd.); CD20 Antibody Drug Conjugates: Ibritumomab tiuxetan (e.g. Zevalin®); Somatostain analogs: octreotide (e.g. octreotide acetate, e.g. Sandostatin® and Sandostatin LAR®); Synthetic Interleukin-11 (IL-11): oprelvekin (e.g. Neumega® by Pfizer/Wyeth); Synthetic erythropoietin: Darbepoetin alfa (e.g. Aranesp® by Amgen); Receptor Activator for Nuclear Factor kappa B (RANK) inhibitors: Denosumab (e.g. Prolia® by Amgen); Thrombopoietin mimetic peptibodies: Romiplostim (e.g. Nplate® by Amgen; Cell growth stimulators: Palifermin (e.g. Kepivance® by Amgen); Anti-Insulin-like Growth Factor-1 receptor (IGF-1R) antibodies: Figitumumab (e.g. CP-751,871, by ACC Corp), robatumumab (CAS No. 934235-44-6); Anti-CS1 antibodies: Elotuzumab (HuLuc63, CAS No. 915296-00-3); CD52 antibodies: Alemtuzumab (e.g. Campath®); CTLA-4 inhibitors: Tremelimumab (IgG2 monoclonal antibody by Pfizer, formerly known as ticilimumab, CP-675,206), ipilimumab (CTLA-4 antibody, e.g. MDX-010, CAS No. 477202-00-9); Histone deacetylase inhibitors (HDI): Voninostat (e.g. Zolinza® by Merck); Alkylating agents: Temozolomide (e.g. Temodar® and Temodal® by Schering-Plough/Merck), dactinomycin (e.g. actinomycin-D and e.g. Cosmegen®), melphalan (e.g. L-PAM, L-sarcolysin, and phenylalanine mustard, e.g. Alkeran®), altretamine (e.g. hexamethylmelamine (HMM), e.g. Hexalen®, carmustine (e.g. BiCNU®, bendamustine (e.g. Treanda®, busulfan (e.g. Busulfex® and Myleran®, carboplatin (e.g. Paraplatin®, lomustine (e.g. CCNU, e.g. CeeNU®, cisplatin (e.g. CDDP, e.g. Platinol® and Platinol®-AQ), chlorambucil (e.g. Leukeran®, cyclophosphamide (e.g. Cytoxan® and Neosar®, dacarbazine (e.g. DTIC, DIC and imidazole carboxamide, e.g. DTIC-Dome®, altretamine (e.g. hexamethylmelamine (HMM) e.g. Hexalen®, ifosfamide (e.g. Ifex®, procarbazine (e.g. Matulane®, mechlorethamine (e.g. nitrogen mustard, mustine and mechloroethamine hydrochloride, e.g. Mustargen®, streptozocin (e.g. Zanosar®, thiotepa (e.g. thiophosphoamide, TESPA and TSPA, e.g. Thioplex®; Biologic response modifiers: *Bacillus* calmette-guerin (e.g. theraCys® and TICE® BCG), denileukin diftitox (e.g. Ontak®)); Anti-tumor antibiotics: doxorubicin (e.g. Adriamycin® and Rubex®, bleomycin (e.g. Lenoxane®, daunorubicin (e.g. dauorubicin hydrochloride, daunomycin, and rubidomycin hydrochloride, e.g. Cerubidine®, daunorubicin liposomal (daunorubicin citrate liposome, e.g. DaunoXome®, mitoxantrone (e.g. DHAD, e.g. Novantrone®, epirubicin (e.g. Ellence™), idarubicin (e.g. Idamycin®, Idamycin PFS®, mitomycin C (e.g. Mutamycin®)); Anti-microtubule agents: Estramustine (e.g. Emcyl®)); Cathepsin K inhibitors: Odanacatib (or MK-0822, by Lanzhou Chon Chemicals, ACC Corp., and ChemieTek, described in WO 03/075836); Epothilone B analogs: Ixabepilone (e.g. Lxempra® by Bristol-Myers Squibb); Heat Shock Protein (HSP) inhibitors: Tanespimycin (17-allylamino-17-demethoxygeldanamycin, e.g. KOS-953 and 17-AAG, by SIGMA, described in U.S. Pat. No. 4,261,989); TpoR agonists: Eltrombopag (e.g. Promacta® and Revolade® by GlaxoSmithKline); Anti-mitotic agents: Docetaxel (e.g. Taxotere® by Sanofi-Aventis); Adrenal steroid inhibitors: aminoglutethimide (e.g. Cytadren®)); Anti-androgens: Nilutamide (e.g. Nilandron® and Anandron®, bicalutamide (sold under tradename Casodex®, flutamide (e.g. Fulexin™); Androgens: Fluoxymesterone (e.g. Halotestin®)); Proteasome inhibitors: Bortezomib (e.g. Velcade®)); CDK1 inhibitors: Alvocidib (e.g. flovopirdol or HMR-1275, described in U.S. Pat. No. 5,621, 002); Gonadotropin-releasing hormone (GnRH) receptor agonists: Leuprolide or leuprolide acetate (e.g. Viadure® by Bayer AG, Eligard® by Sanofi-Aventis and Lupron® by Abbott Lab); Taxane anti-neoplastic agents: Cabazitaxel, larotaxel; 5HT1a receptor agonists: Xaliproden (or SR57746, described in U.S. Pat. No. 5,266,573); HPC vaccines: Cervarix® sold by GlaxoSmithKline, Gardasil® sold by Merck; Iron Chelating agents: Deferasinox (e.g. Exjade® by Novartis); Anti-metabolites: Claribine (2-chlorodeoxyadenosine, e.g. Leustatin®, 5-fluorouracil (e.g. Adrucil®, 6-thioguanine (e.g. Purinethol®, pemetrexed (e.g. Alimta®, cytarabine (e.g. arabinosylcytosine (Ara-C), e.g. Cytosar-U®, cytarabine liposomal (e.g. Liposomal Ara-C, e.g. DepoCyt™), decitabine (e.g. Dacogen®, hydroxyurea (e.g. Hydrea®, Droxia™ and Mylocel™), fludarabine (e.g. Fludara®, floxuridine (e.g. FUDR®, cladribine (e.g. 2-chlorodeoxyadenosine (2-CdA) e.g. Leustatin™), methotrexate (e.g. amethopterin, methotrexate sodim (MTX), e.g. Rheumatrex® and Trexall™), pentostatin (e.g. Nipent®)); Bisphosphonates: Pamidronate (e.g. Aredia®, zoledronic acid (e.g. Zometa®)); Demethylating agents: 5-azacitidine (e.g. Vidaza®, decitabine (e.g. Dacogen®)); Plant Alkaloids: Paclitaxel protein-bound (e.g. Abraxane®, vinblastine (e.g. vinblastine sulfate, vincaleukoblastine and VLB, e.g. Alkaban-AQ® and Velban®, vincristine (e.g. vincristine sulfate, LCR, and VCR, e.g. Oncovin® and Vincasar Pfs®, vinorelbine (e.g. Navelbine®, paclitaxel (e.g. Taxol and Onxal™); Retinoids: Alitretinoin (e.g. Panretin®, tretinoin (all-trans retinoic acid, e.g. ATRA, e.g. Vesanoid®, Isotretinoin (13-cis-retinoic acid, e.g. Accutane®, Amnesteem®, Claravis®, Clarus®, Decutan®, Isotane®, Izotech®, Oratane®, Isotret®, and Sotret®, bexarotene (e.g. Targretin®)); Glucocorticosteroids: Hydrocortisone (e.g. cortisone, hydrocortisone sodium succinate, hydrocortisone sodium phosphate, and e.g. Ala-Cort®, Hydrocortisone Phosphate, Solu-Cortef®, Hydrocort Acetate® and Lanacort®, dexamethasone, prednisolone (e.g. Delta-Cortel®, Orapred®, Pediapred® and Prelone®, prednisone (e.g. Deltasone®, Liquid Red®, Meticorten® and Orasone®, methylprednisolone (e.g. 6-Methylprednisolone, Methylprednisolone Acetate, Methylprednisolone Sodium Succinate, e.g. Duralone®, Medralone®, Medrol®, M-Prednisol® and Solu-Medrol®)); Cytokines: interleukin-2 (e.g. aldesleukin and IL-2, e.g. Proleukin®, interleukin-11 (e.g. oprevelkin, e.g. Neumega®, alpha interferon alfa (e.g. IFN-alpha, e.g. Intron® A, and Roferon-A®)); Lutinizing hormone releasing hormone (LHRH) agonists: Goserelin (e.g. Zoladex®)); Progesterones: megestrol (e.g. megestrol acetate, e.g. Megace®)); Miscellaneous cytotoxic agents: Arsenic trioxide (e.g. Trisenox®, asparaginase (e.g. L-asparaginase, *Erwinia* L-asparaginase, e.g. Elspar® and Kidrolase®)); Anti-nausea drugs: NK-1 receptor antagonists: Casopitant (e.g. Rezonic® and Zunrisa® by GlaxoSmithKline); and Cytoprotective agents: Amifostine (e.g. Ethyol®, leucovorin (e.g. calcium leucovorin, citrovorum factor and folinic acid).

EXAMPLES

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Example 1: General Procedure A

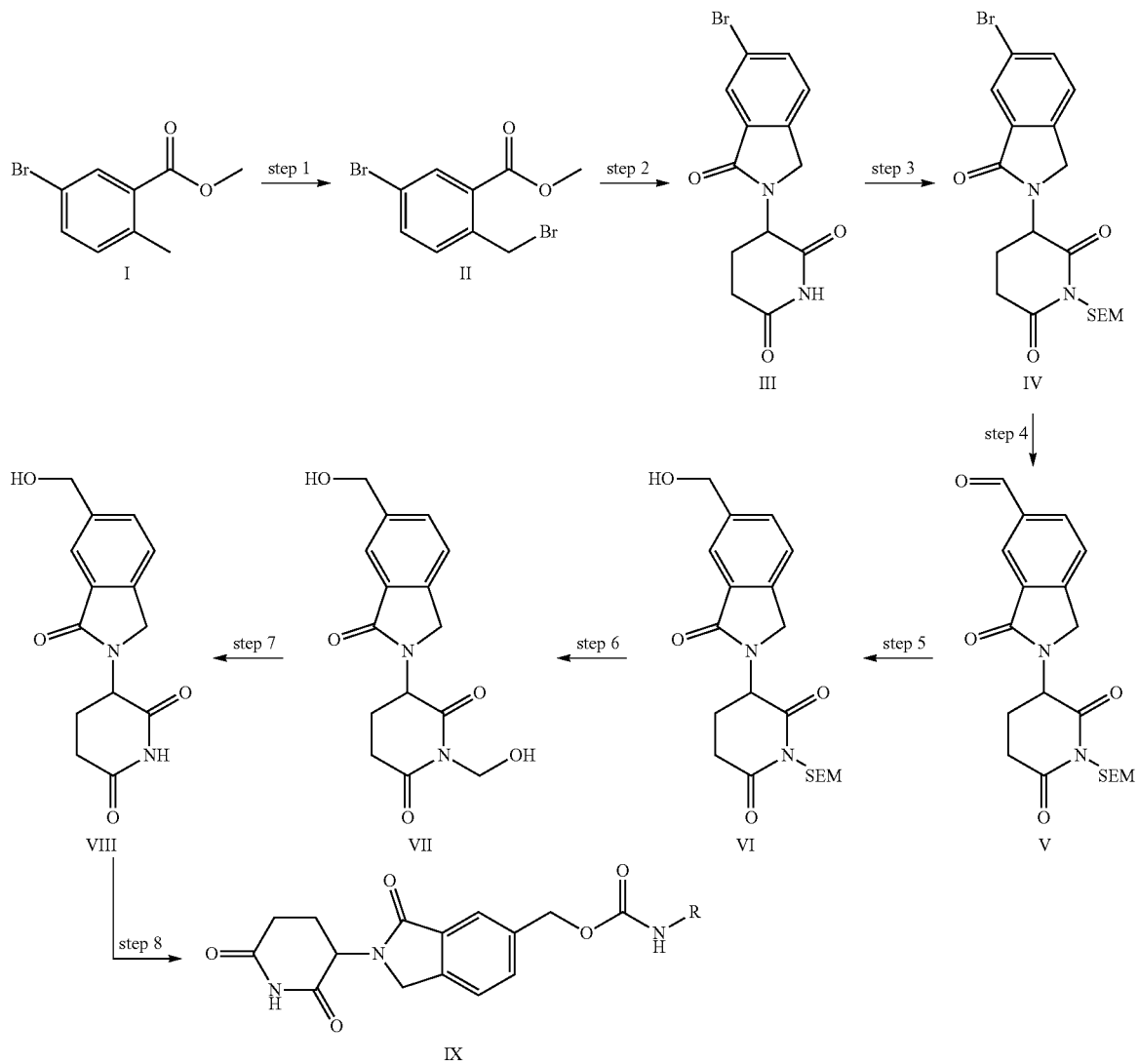

II: To a solution of methyl 5-bromo-2-methylbenzoate I (100 g, 436 mmol, 1.00 eq) in trichloromethane (800 mL) was added N-bromosuccinimide (77.6 g, 436 mmol, 1.00 eq) and (E)-2,2'-(diazene-1,2-diyl)bis(2-methylpropanenitrile) (10.5 g, 43.3 mmol, 0.10 eq). The solution was degassed by purging with nitrogen, and the reaction was stirred at 80° C. for 12 h under nitrogen atmosphere. The mixture was concentrated under reduced pressure to give a residue. The residue was purified by silica gel column chromatography (petroleum ether/ethyl acetate=1/0 to 20/1) to afford methyl 5-bromo-2-(bromomethyl)benzoate II. $^1$H NMR (400 MHz, DMSO-$d_6$) δ=7.98 (d, J=2.0 Hz, 1H), 7.81-7.79 (m, 1H), 7.57-7.55 (m, 1H), 4.97 (s, 2H), 3.87 (m, 3H).

III: To a solution of methyl 5-bromo-2-(bromomethyl) benzoate II (72.5 g, 235 mmol 1.00 eq) and 3-aminopiperidine-2,6-dione hydrochloride (46.6 g, 283 mmol, 1.20 eq, hydrochloride) in acetonitrile (600 mL) was added diisopropylethylamine (123 mL, 706 mmol, 3.00 eq) in one portion under nitrogen. The reaction was stirred at 80° C. for 4 h. After cooling to room temperature, the mixture was concentrated under reduced pressure to give a residue. The residue was triturated with hydrochloric acid (1 M)/ethyl acetate (300 mL/200 mL) at 25° C. for 30 min. The mixture was filtered, and the filter cake was washed with ethyl acetate (100 mL) and dried under reduced pressure to afford 3-(6-bromo-1-oxoisoindolin-2-yl)piperidine-2,6-dione III. $^1$H NMR (400 MHz, DMSO-$d_6$) δ=11.04 (s, 1H), 7.86 (d, J=1.6 Hz, 1H), 7.82 (dd, J=1.8, 8.1 Hz, 1H), 7.60 (d, J=8.1 Hz, 1H), 5.12 (dd, J=5.1, 13.3 Hz, 1H), 4.49-4.28 (m, 2H), 2.99-2.84 (m, 1H), 2.60 (br d, J=17.5 Hz, 1H), 2.39 (dq, J=4.4, 13.2 Hz, 1H), 2.13-1.91 (m, 1H).

IV: To a solution of 3-(6-bromo-1-oxoisoindolin-2-yl) piperidine-2,6-dione III (40.0 g, 123 mmol, 1.00 eq) in dimethylformamide (200 mL) was added 1,8-Diazabicyclo [5.4.0]-7-undecene (48.0 mL, 318 mmol, 2.57 eq) and 2-(chloromethoxy)ethyltrimethylsilane (stabilized with diisopropylethylamine) (40.0 mL, 226 mmol, 1.83 eq) dropwise at 0° C. The reaction was stirred at 25° C. for 6 h. The mixture was diluted with water (500 mL) and ethyl acetate (800 mL). The organic phase was washed with brine (200 mL), dried over anhydrous sodium sulfate, filtered, and concentrated under reduced pressure. The residue was purified by silica gel column chromatography (petroleum ether/ethyl acetate=4/1 to 1/1) to afford 3-(6-bromo-1-oxoisoindolin-2-yl)-1-((2-(trimethylsilyl)ethoxy)methyl)piperidine-2,6-dione IV $^1$H NMR (400 MHz, DMSO-$d_6$) δ=7.90 (d, J=1.6 Hz, 1H), 7.86 (dd, J=2.0, 8.1 Hz, 1H), 7.63 (d, J=8.1 Hz, 1H), 5.26 (dd, J=5.1, 13.4 Hz, 1H), 5.07 (q, J=9.8 Hz, 2H), 4.50 (d, J=17.6 Hz, 1H), 4.36-4.28 (m, 1H), 3.60-3.49 (m, 2H), 3.13-3.01 (m, 1H), 2.86-2.78 (m, 1H), 2.48-2.36 (m, 1H), 2.12-2.05 (m, 1H), 0.90-0.83 (m, 2H), 0.02--0.01 (m, 9H).

V: To a solution of 3-(6-bromo-1-oxoisoindolin-2-yl)-1-((2-(trimethylsilyl)ethoxy)methyl)piperidine-2,6-dione IV (53.0 g, 117 mmol, 1 eq) in dimethylformamide (300 mL) was added diisopropylethylamine (100 mL, 574 mmol, 4.91 eq), [1,1'-bis(diphenylphosphino)ferrocene]dichloropalladium(II) (8.48 g, 11.6 mmol, 0.10 eq) and triethylsilane (150 mL, 939 mmol, 8.00 eq). The reaction was stirred at 80° C. for 12 h under carbon monoxide atmosphere (50 Psi). The mixture was diluted with ethyl acetate (1.00 L) and water (1.00 L). The organic layer was separated and concentrated under reduced pressure to give a residue. The residue was purified by silica gel column chromatography (petroleum ether/ethyl acetate=1/1) to afford 2-(2,6-dioxo-1-((2-(trimethylsilyl)ethoxy)methyl)piperidin-3-yl)-3-oxoisoindoline-5-carbaldehyde V. $^1$H NMR (400 MHz, DMSO-$d_6$) δ=10.16 (s, 1H), 8.29 (s, 1H), 8.19 (d, J=7.8 Hz, 1H), 7.87 (d, J=7.8 Hz, 1H), 5.30 (br dd, J=4.9, 13.4 Hz, 1H), 5.13-5.03 (m, 2H), 4.65 (br d, J=18.4 Hz, 1H), 4.50-4.40 (m, 1H), 3.62-3.51 (m, 2H), 3.17-3.06 (m, 1H), 2.83 (br d, J=15.8 Hz, 1H), 2.44 (br dd, J=4.1, 13.1 Hz, 1H), 2.15-2.07 (m, 1H), 0.86 (br t, J=7.6 Hz, 2H), 0.00 (s, 9H)

VI: To a solution of 2-(2,6-dioxo-1-((2-(trimethylsilyl)ethoxy)methyl)piperidin-3-yl)-3-oxoisoindoline-5-carbaldehyde V (38.0 g, 94.4 mmol, 1.00 eq) in dimethylformamide (100 mL) and dichloromethane (500 mL) was added sodium triacetoxyborohydride (64.0 g, 302 mmol, 3.20 eq) and acetic acid (27.9 g, 465 mmol, 4.93 eq). The reaction was stirred at 50° C. for 2 h. The mixture was diluted with water (500 mL) and dichloromethane (500 mL). The organic layer was separated and concentrated under reduced pressure to give a residue. The residue was purified by silica gel column chromatography (petroleum ether/ethyl acetate=5/1 to 0/1) to give 3-(6-(hydroxymethyl)-1-oxoisoindolin-2-yl)-1-((2-(trimethylsilyl)ethoxy)methyl) piperidine-2,6-dione VI. $^1$H NMR (400 MHz, DMSO-$d_6$) δ=7.70 (s, 1H), 7.62-7.52 (m, 2H), 5.35 (t, J=5.8 Hz, 1H), 5.29-5.20 (m, 1H), 5.06 (q, J=9.8 Hz, 2H), 4.61 (d, J=5.8 Hz, 2H), 4.47 (br d, J=17.1 Hz, 1H), 4.28 (d, J=16.9 Hz, 1H), 3.61-3.49 (m, 2H), 3.11-3.02 (m, 1H), 2.84-2.77 (m, 1H), 2.40 (br d, J=8.7 Hz, 1H), 2.11-2.03 (m, 1H), 0.89-0.81 (m, 2H), 0.01--0.03 (m, 9H).

VII: A solution of 3-(6-(hydroxymethyl)-1-oxoisoindolin-2-yl)-1-((2-(trimethylsilyl)ethoxy)methyl)piperidine-2,6-dione VI (17.0 g, 42.0 mmol, 1.00 eq) in hydrochloric acid/dioxane (150 mL) (6 M) was stirred at 50° C. for 2 h. The mixture was concentrated under reduced pressure to afford 1-(hydroxymethyl)-3-(6-(hydroxymethyl)-1-oxoisoindolin-2-yl)piperidine-2,6-dione VII.

VIII: To a solution of 1-(hydroxymethyl)-3-(6-(hydroxymethyl)-1-oxoisoindolin-2-yl)piperidine-2,6-dione VII (13.0 g, 42.7 mmol, 1 eq) in acetonitrile (50.0 mL) was added ammonium hydroxide 30% (0.500 mL, 0.09 eq). The reaction was stirred at 25° C. for 1 h. The pH was adjusted to pH=5 by addition of 0.5 M hydrochloric acid, and the mixture was concentrated under reduced pressure to give a residue. The residue was purified by reversed phase preparative HPLC to afford 3-(6-(hydroxymethyl)-1-oxoisoindolin-2-yl)piperidine-2,6-dione VIII. $^1$H NMR (400 MHz, DMSO-$d_6$) δ=11.24-10.78 (m, 1H), 7.69 (s, 1H), 7.60-7.53 (m, 2H), 5.35 (t, J=5.8 Hz, 1H), 5.12 (dd, J=5.1, 13.4 Hz, 1H), 4.61 (d, J=5.5 Hz, 2H), 4.49-4.40 (m, 1H), 4.35-4.26 (m, 1H), 2.98-2.86 (m, 1H), 2.66-2.57 (m, 1H), 2.40 (dd, J=4.4, 13.1 Hz, 1H), 2.01 (dtd, J=2.2, 5.2, 12.6 Hz, 1H).

IX: Variant i): To a solution of 3-(6-(hydroxymethyl)-1-oxoisoindolin-2-yl)piperidine-2,6-dione VIII (1.00 eq) in dimethylformamide or acetonitrile (0.04-0.73 M reaction) was added the phenyl carbamate (0.66-1.70 eq) and sodium hydride (60% dispersion in mineral oil) (1.70-3.00 eq) at 0° C. The reaction was stirred at a temperature range of 0 to 25° C. for 0.5-4 h. If necessary, upon completion the reaction was acidified with HCl. If the product precipitated, it was collected by filtration to afford the final carbamate compounds. Otherwise, the mixture was either concentrated to give a residue, or it was extracted and the organic layers were combined, dried over sodium sulfate, filtered, and concentrated to give a residue. The residue was purified by standard methods to afford the final carbamate compounds.

IX: Variant ii): To a solution of 3-(6-(hydroxymethyl)-1-oxoisoindolin-2-yl)piperidine-2,6-dione VIII (1.50 g, 5.47 mmol, 1.00 eq) in dimethylformamide (15.0 mL) was added pyridine (2.21 mL, 27.3 mmol, 5.00 eq) and phenyl chloroformate (1.37 mL, 10.9 mmol, 2.00 eq) at 0° C. The reaction was stirred at 25° C. for 12 h. The mixture was concentrated under reduced pressure to give a residue. The residue was purified by reversed phase preparative HPLC to afford (2-(2,6-dioxopiperidin-3-yl)-3-oxoisoindolin-5-yl) methyl phenyl carbonate. To a solution of (2-(2,6-dioxopiperidin-3-yl)-3-oxoisoindolin-5-yl)methyl phenyl carbonate (1.00 eq) in dimethylformamide (0.1-0.14 M reaction) was added the amine (1.50-5.00 eq). The reaction was stirred at 25° C. for 1-36 h. The mixture was either: diluted to 0.07 M with dimethylformamide and purified by a standard method, or: diluted to 0.10 M with formic acid to give a precipitate which was filtered and dried, or: diluted to 0.10 M with formic acid and purified by a standard method, to afford the final carbamate compounds.

Example 2: Synthesis of Specific Examples

TABLE 1

| Specific examples | |
|---|---|
| Compound | No. |
| (structure) | 1 |
| (structure) | 2 |
| (structure) | 3 |
| (structure) | 4 |
| (structure) | 5 |
| (structure) | 6 |

TABLE 1-continued

Specific examples

| Compound | No. |
|---|---|
| (2,6-dimethylpyridin-4-yl)carbamate-CH2-isoindolinone-glutarimide | 7 |
| (3,5-dimethylphenyl)carbamate-CH2-isoindolinone-glutarimide | 8 |
| (3-chloro-4-fluorophenyl)carbamate-CH2-isoindolinone-glutarimide | 9 |
| (3-chloro-4-methylphenyl)carbamate-CH2-isoindolinone-glutarimide | 10 |
| (3-chloro-5-trifluoromethoxyphenyl)carbamate-CH2-isoindolinone-glutarimide | 11 |
| (3-chloro-5-fluorophenyl)carbamate-CH2-isoindolinone-glutarimide | 12 |

TABLE 1-continued

Specific examples

| Compound | No. |
|---|---|
| (structure) | 13 |
| (structure) | 14 |
| (structure) | 15 |
| (structure) | 16 |
| (structure) | 17 |
| (structure) | 18 |

TABLE 1-continued
| Specific examples | |
|---|---|
| Compound | No. |
| 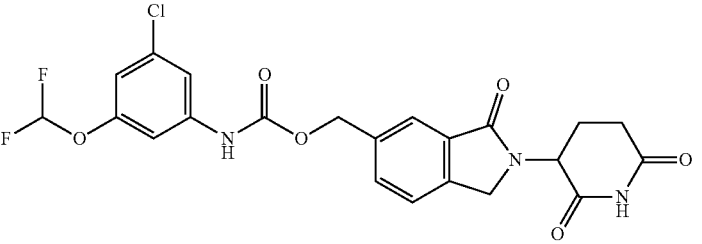 [SMILES: O=C1CCC(N2Cc3ccc(COC(=O)Nc4cc(Cl)cc(OC(F)F)c4)cc3C2=O)C(=O)N1] | 19 |
| 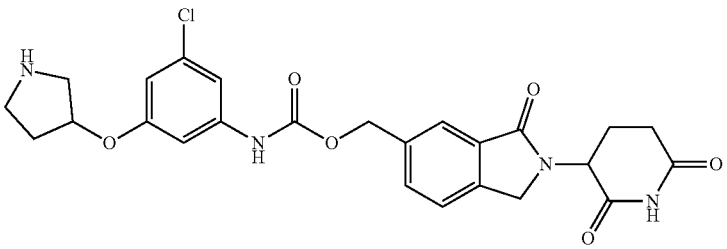 [SMILES: O=C1CCC(N2Cc3ccc(COC(=O)Nc4cc(Cl)cc(OC5CCNC5)c4)cc3C2=O)C(=O)N1] | 20 |
| 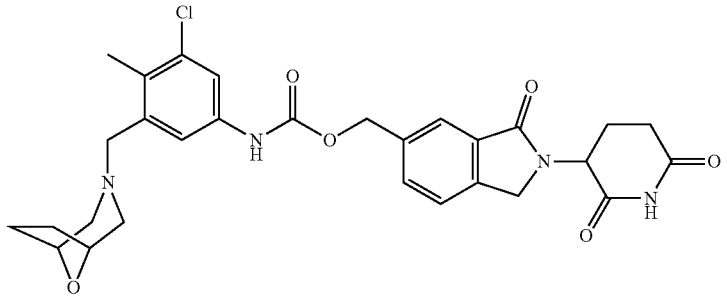 [SMILES: Cc1c(Cl)cc(NC(=O)OCc2ccc3c(c2)C(=O)N(C2CCC(=O)NC2=O)C3)cc1CN1CC2CCC(C1)O2] | 21 |
| 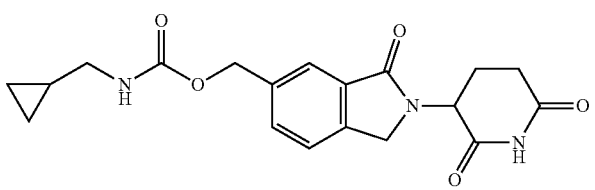 [SMILES: O=C1CCC(N2Cc3ccc(COC(=O)NCC4CC4)cc3C2=O)C(=O)N1] | 22 |
| 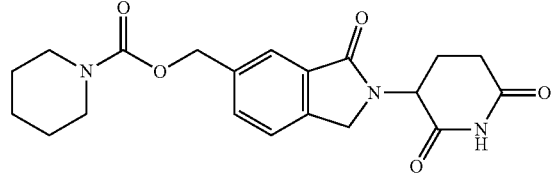 [SMILES: O=C1CCC(N2Cc3ccc(COC(=O)N4CCCCC4)cc3C2=O)C(=O)N1] | 23 |
| 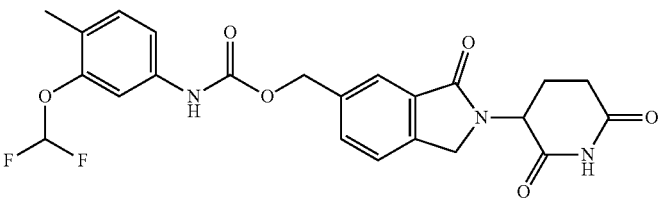 [SMILES: Cc1ccc(NC(=O)OCc2ccc3c(c2)C(=O)N(C2CCC(=O)NC2=O)C3)cc1OC(F)F] | 24 |

TABLE 1-continued
| Specific examples | |
|---|---|
| Compound | No. |
| 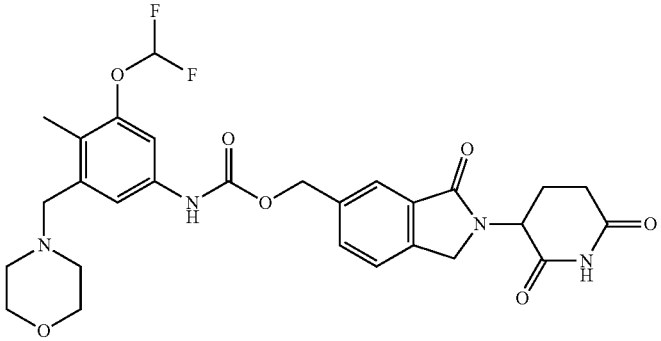 [SMILES: Cc1c(CN2CCOCC2)cc(NC(=O)OCc2ccc3c(c2)C(=O)N(C2CCC(=O)NC2=O)C3)cc1OC(F)F] | 25 |
| 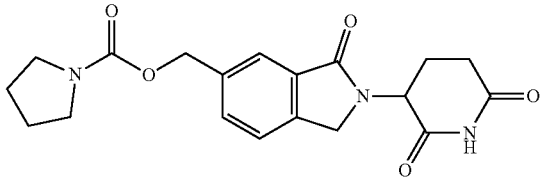 [SMILES: O=C1CCC(N2Cc3ccc(COC(=O)N4CCCC4)cc3C2=O)C(=O)N1] | 26 |
| 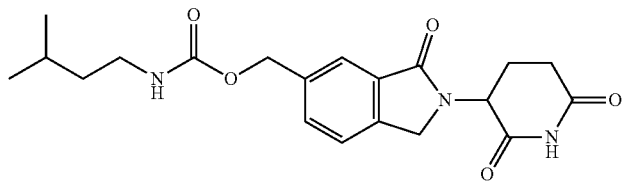 [SMILES: CC(C)CCNC(=O)OCc1ccc2c(c1)C(=O)N(C1CCC(=O)NC1=O)C2] | 27 |
| 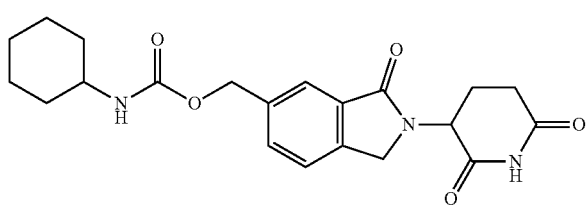 [SMILES: O=C1CCC(N2Cc3ccc(COC(=O)NC4CCCCC4)cc3C2=O)C(=O)N1] | 28 |
| 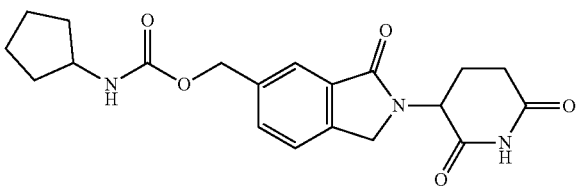 [SMILES: O=C1CCC(N2Cc3ccc(COC(=O)NC4CCCC4)cc3C2=O)C(=O)N1] | 29 |
| 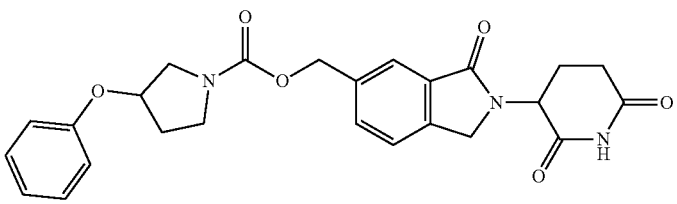 [SMILES: O=C1CCC(N2Cc3ccc(COC(=O)N4CCC(Oc5ccccc5)C4)cc3C2=O)C(=O)N1] | 30 |

TABLE 1-continued

Specific examples

| Compound | No. |
|---|---|
| | 31 |
| | 32 |
| | 33 |
| | 34 |
| | 35 |
| | 36 |

TABLE 1-continued

| Specific examples | |
|---|---|
| Compound | No. |
| | 37 |
| | 38 |
| | 39 |
| | 40 |
| | 41 |
| | 42 |

TABLE 1-continued

| Specific examples | |
|---|---|
| Compound | No. |
| | 43 |
| | 44 |
| | 45 |
| | 46 |
| | 47 |
| | 48 |

TABLE 1-continued

Specific examples

| Compound | No. |
|---|---|
| | 49 |
| | 50 |
| | 51 |
| | 52 |
| | 53 |
| | 54 |

TABLE 1-continued

Specific examples

| Compound | No. |
|---|---|
| (structure) | 55 |
| (structure) | 56 |
| (structure) | 57 |
| (structure) | 58 |
| (structure) | 59 |
| (structure) | 60 |

TABLE 1-continued
Specific examples
| Compound | No. |
|---|---|
| 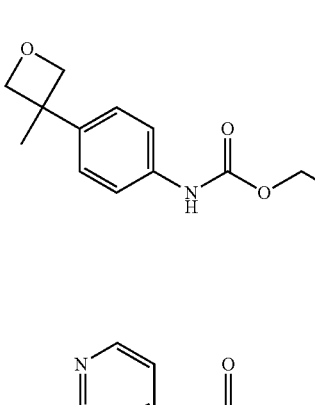 | 61 |
| | 62 |
| | 63 |
| 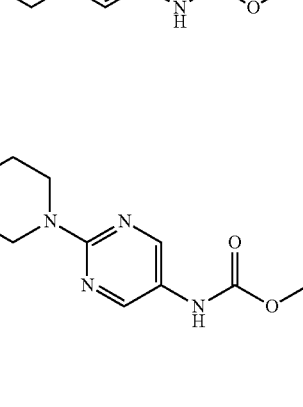 | 64 |
| 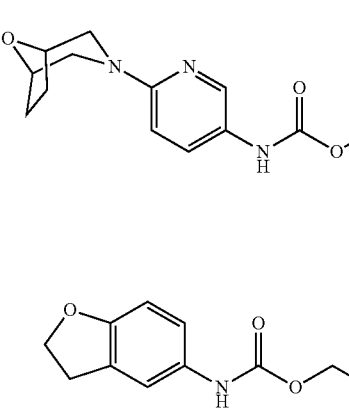 | 65 |
|  | 66 |

TABLE 1-continued

Specific examples

| Compound | No. |
|---|---|
| | 67 |
| | 68 |
| | 69 |
| | 70 |
| | 71 |

TABLE 1-continued

Specific examples

| Compound | No. |
|---|---|
| (structure) | 72 |
| (structure) | 73 |
| (structure) | 74 |
| (structure) | 75 |
| (structure) | 76 |

TABLE 1-continued

Specific examples

| Compound | No. |
|---|---|
| | 77 |
| | 78 |
| | 79 |
| | 80 |
| | 81 |
| | 82 |

TABLE 1-continued

| Specific examples | |
|---|---|
| Compound | No. |
| | 83 |
| | 84 |
| | 85 |
| | 86 |
| | 87 |

TABLE 1-continued

Specific examples

| Compound | No. |
|---|---|
| | 88 |
| | 89 |
| | 90 |
| | 91 |
| | 92 |
| | 93 |

TABLE 1-continued
| Specific examples | |
|---|---|
| Compound | No. |
| 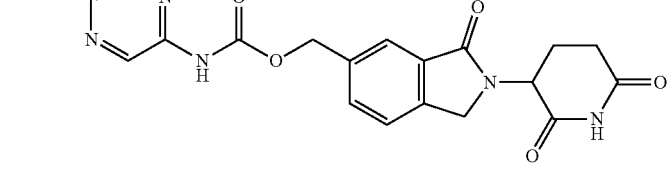 | 94 |
| 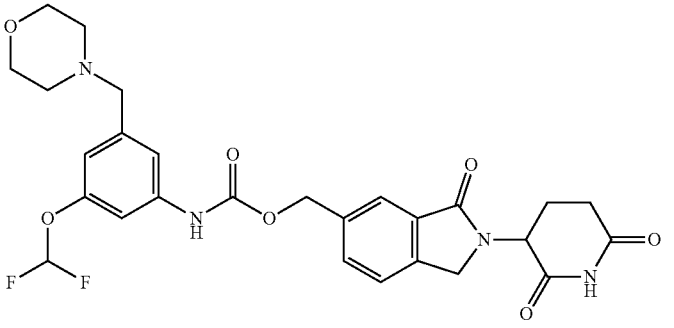 [SMILES: O=C1CCC(N2Cc3ccc(COC(=O)Nc4cc(CN5CCOCC5)cc(OC(F)F)c4)cc3C2=O)C(=O)N1] | 95 |
| 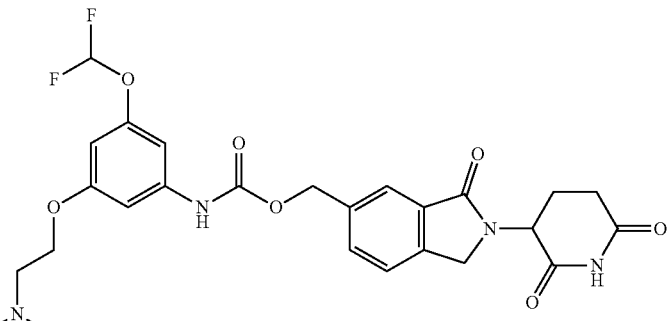 | 96 |
| 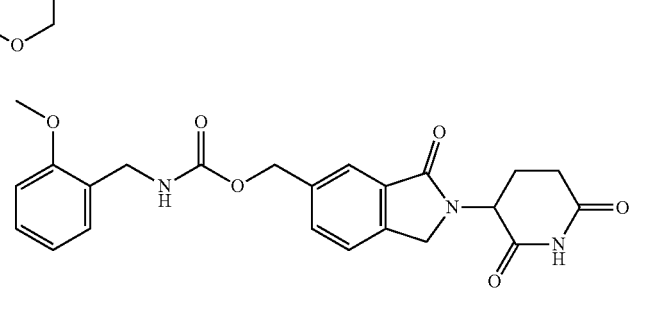 | 97 |
| 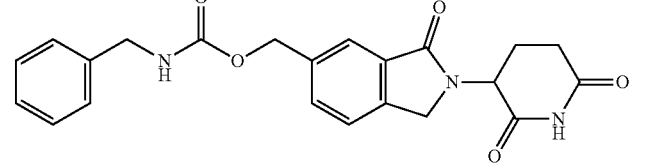 | 98 |

TABLE 1-continued

Specific examples

| Compound | No. |
|---|---|
| | 99 |
| | 100 |
| | 101 |
| | 102 |
| | 103 |
| | 104 |

TABLE 1-continued
Specific examples
| Compound | No. |
|---|---|
|  | 105 |
| 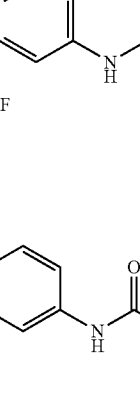 | 106 |
| 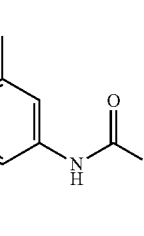 | 107 |
|  | 108 |
|  | 109 |

TABLE 1-continued

| Specific examples | |
|---|---|
| Compound | No. |
| | 110 |
| | 111 |
| | 112 |
| | 113 |
| | 114 |
| | 115 |

TABLE 1-continued

| Specific examples | |
|---|---|
| Compound | No. |
| | 116 |
| | 117 |
| | 118 |
| | 119 |
| | 120 |
| | 121 |

TABLE 1-continued

Specific examples

| Compound | No. |
|---|---|
| (structure) | 122 |
| (structure) | 123 |
| (structure) | 124 |
| (structure) | 125 |
| (structure) | 126 |
| (structure) | 127 |

TABLE 1-continued

Specific examples

| Compound | No. |
|---|---|
| | 128 |
| | 129 |
| | 130 |
| | 131 |
| | 132 |
| | 133 |

TABLE 1-continued

Specific examples

| Compound | No. |
|---|---|
| (structure) | 134 |
| (structure) | 135 |
| (structure) | 136 |
| (structure) | 137 |
| (structure) | 138 |
| (structure) | 139 |

TABLE 1-continued

| Specific examples | |
|---|---|
| Compound | No. |
| | 140 |
| | 141 |
| | 142 |
| | 143 |
| | 144 |
| | 145 |

TABLE 1-continued

| Specific examples | |
|---|---|
| Compound | No. |
| | 146 |
| | 147 |
| | 148 |
| | 149 |
| | 150 |
| | 151 |

TABLE 1-continued

| Specific examples | |
|---|---|
| Compound | No. |
| | 152 |
| | 153 |
| | 154 |
| | 155 |
| | 156 |
| | 157 |

TABLE 1-continued

Specific examples

| Compound | No. |
|---|---|
| | 158 |
| | 159 |
| | 160 |
| | 161 |

TABLE 1-continued
Specific examples
| Compound | No. |
|---|---|
| 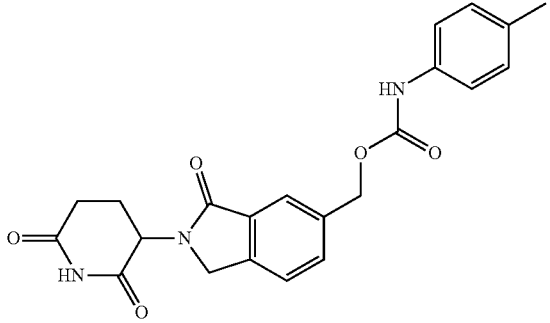 [SMILES: Cc1ccc(NC(=O)OCc2ccc3c(c2)C(=O)N(C2CCC(=O)NC2=O)C3)cc1] | 162 |
| 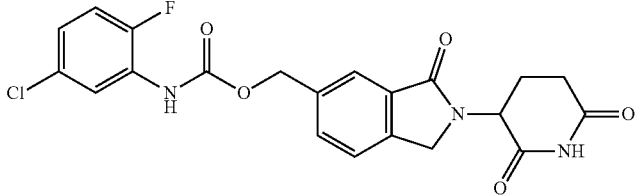 [SMILES: O=C1CCC(N2Cc3ccc(COC(=O)Nc4cc(Cl)ccc4F)cc3C2=O)C(=O)N1] | 163 |
| 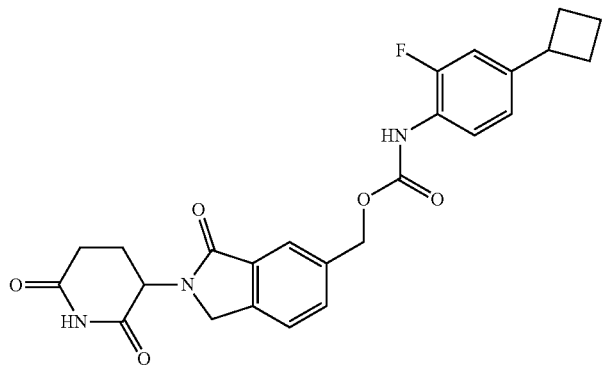 [SMILES: O=C1CCC(N2Cc3ccc(COC(=O)Nc4ccc(C5CCC5)cc4F)cc3C2=O)C(=O)N1] | 164 |
| 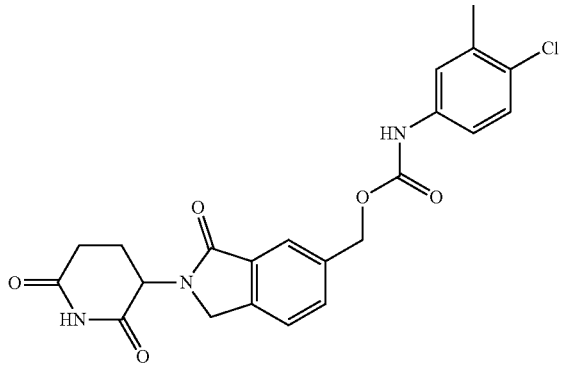 [SMILES: Cc1cc(NC(=O)OCc2ccc3c(c2)C(=O)N(C2CCC(=O)NC2=O)C3)ccc1Cl] | 165 |

TABLE 1-continued

Specific examples

| Compound | No. |
|---|---|
| | 166 |
| | 167 |
| | 168 |
| | 169 |

TABLE 1-continued
Specific examples
| Compound | No. |
|---|---|
| 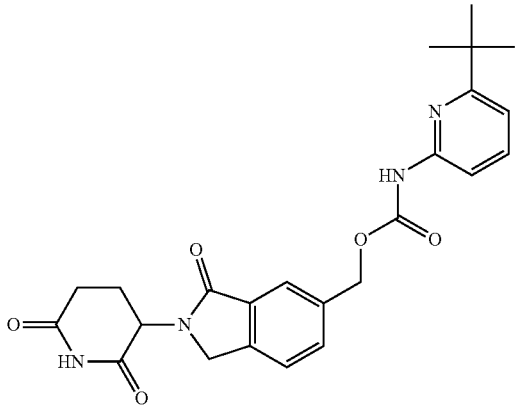 [SMILES: CC(C)(C)c1cccc(NC(=O)OCc2ccc3c(c2)C(=O)N(C2CCC(=O)NC2=O)C3)n1] | 170 |
| 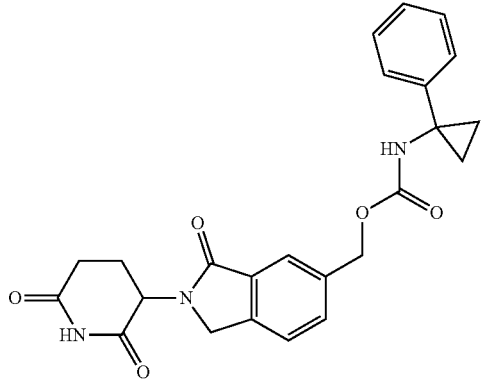 [SMILES: O=C1CCC(N2Cc3ccc(COC(=O)NC4(c5ccccc5)CC4)cc3C2=O)C(=O)N1] | 171 |
| 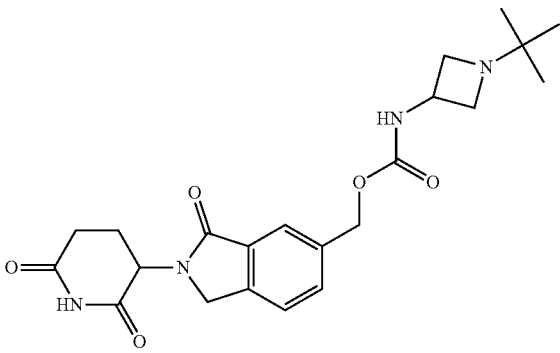 [SMILES: CC(C)(C)N1CC(NC(=O)OCc2ccc3c(c2)C(=O)N(C2CCC(=O)NC2=O)C3)C1] | 172 |

TABLE 1-continued

| Specific examples | |
|---|---|
| Compound | No. |
| | 173 |
| | 174 |
| | 175 |

TABLE 1-continued

| Specific examples | |
|---|---|
| Compound | No. |
| | 176 |
| | 177 |
| | 178 |
| | 179 |

TABLE 1-continued
Specific examples
| Compound | No. |
|---|---|
| 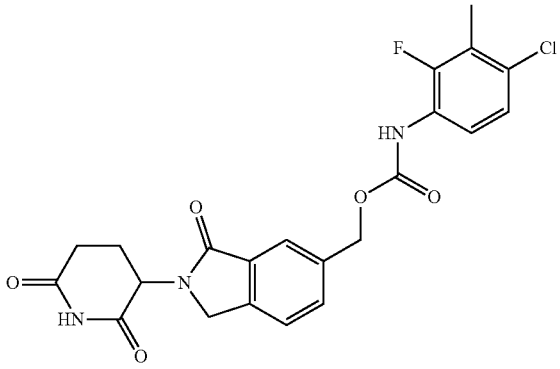 [SMILES: Cc1c(Cl)ccc(NC(=O)OCc2ccc3c(c2)C(=O)N(C2CCC(=O)NC2=O)C3)c1F] | 180 |
| 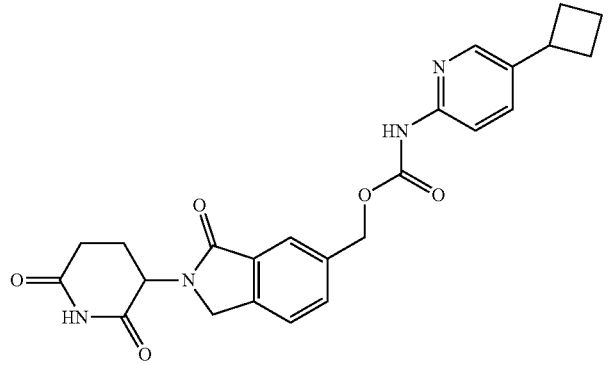 [SMILES: O=C1CCC(N2Cc3ccc(COC(=O)Nc4ccc(C5CCC5)cn4)cc3C2=O)C(=O)N1] | 181 |
| 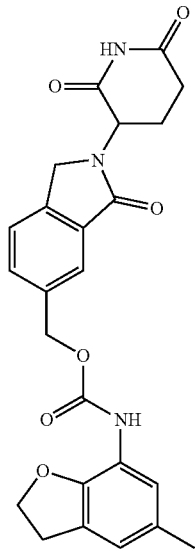 [SMILES: Cc1cc2c(c(NC(=O)OCc3ccc4c(c3)C(=O)N(C3CCC(=O)NC3=O)C4)c1)OCC2] | 182 |

TABLE 1-continued
| Specific examples | |
|---|---|
| Compound | No. |
| 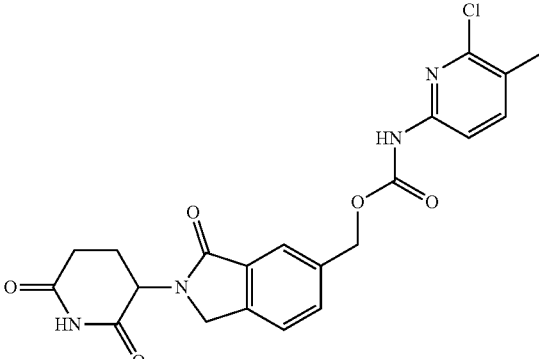 | 183 |
| 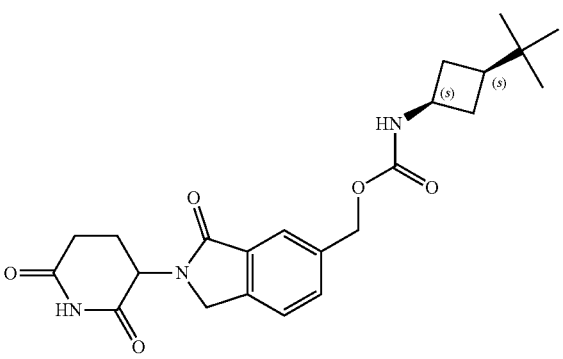 | 184 |
| 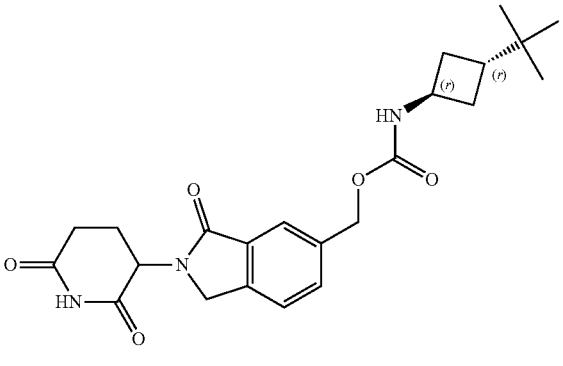 | 185 |
| 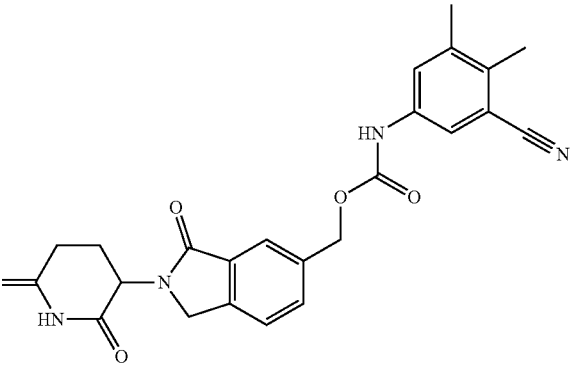 | 186 |

TABLE 1-continued

Specific examples

| Compound | No. |
|----------|-----|
| | 187 |
| | 188 |
| | 189 |

TABLE 1-continued

| Specific examples | |
|---|---|
| Compound | No. |
| | 190 |
| | 191 |
| | 192 |

TABLE 1-continued
Specific examples
| Compound | No. |
|---|---|
| 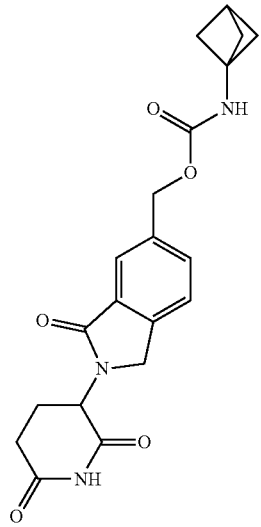 [SMILES: O=C1CCC(N2Cc3ccc(COC(=O)NC45CC(C4)C5)cc3C2=O)C(=O)N1] | 193 |
| 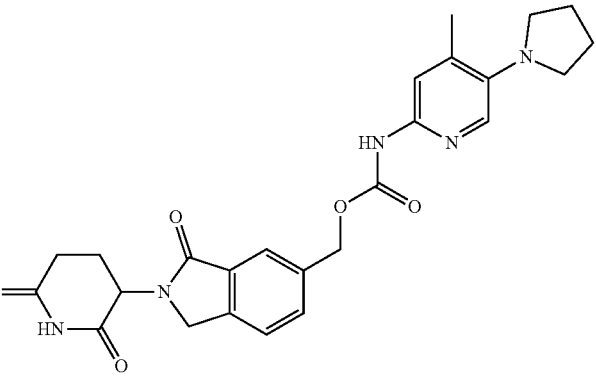 | 194 |
| 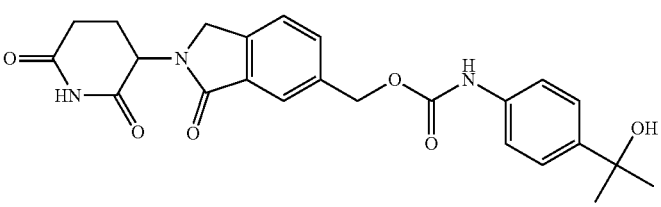 | 195 |

TABLE 1-continued

| Specific examples | |
|---|---|
| Compound | No. |
| | 196 |
| | 197 |
| | 198 |

TABLE 1-continued
| Specific examples | |
|---|---|
| Compound | No. |
| 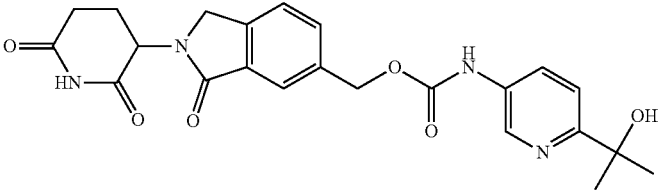 [SMILES: CC(C)(O)c1ccc(NC(=O)OCc2ccc3c(c2)C(=O)N(C2CCC(=O)NC2=O)C3)cc1] | 199 |
| 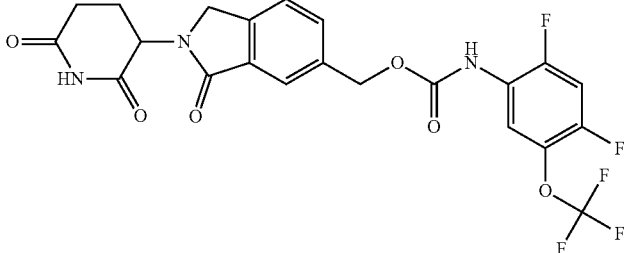 [SMILES: O=C1CCC(N2Cc3ccc(COC(=O)Nc4cc(OC(F)(F)F)c(F)cc4F)cc3C2=O)C(=O)N1] | 200 |
| 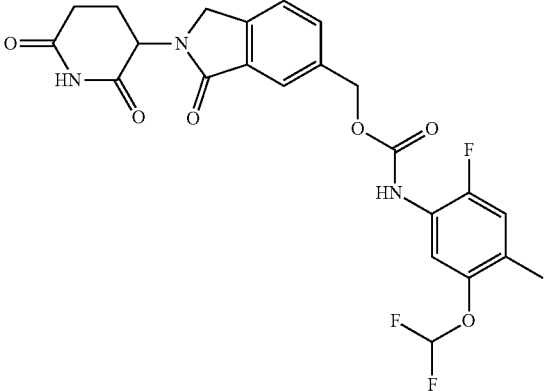 [SMILES: Cc1cc(F)c(NC(=O)OCc2ccc3c(c2)C(=O)N(C2CCC(=O)NC2=O)C3)cc1OC(F)F] | 201 |
| 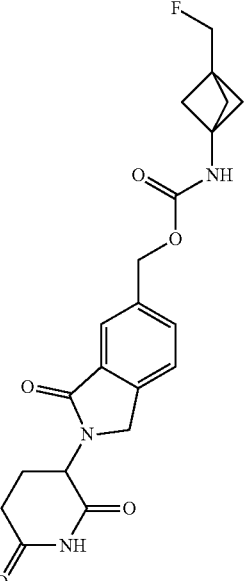 | 202 |

TABLE 1-continued
Specific examples
| Compound | No. |
|---|---|
| 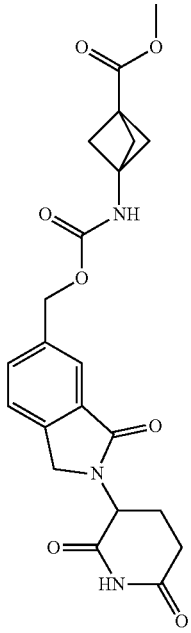 [SMILES: COC(=O)C12CC(NC(=O)OCc3ccc4c(c3)C(=O)N(C3CCC(=O)NC3=O)C4)(C1)C2] | 203 |
| 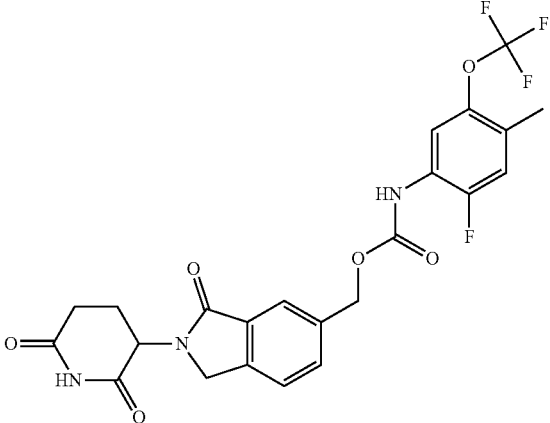 [SMILES: Cc1cc(F)c(NC(=O)OCc2ccc3c(c2)C(=O)N(C2CCC(=O)NC2=O)C3)cc1OC(F)(F)F] | 204 |
| 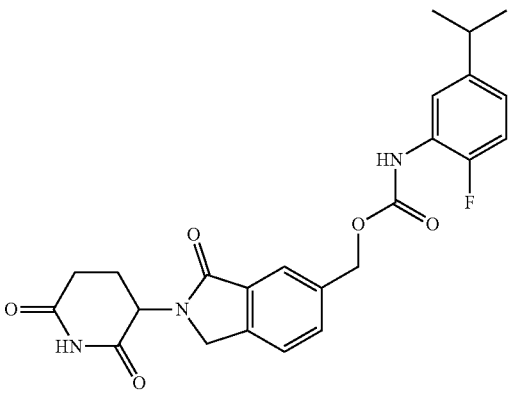 [SMILES: CC(C)c1ccc(F)c(NC(=O)OCc2ccc3c(c2)C(=O)N(C2CCC(=O)NC2=O)C3)c1] | 205 |

TABLE 1-continued

Specific examples

| Compound | No. |
|---|---|
| (structure) | 206 |
| (structure) | 207 |
| (structure) | 208 |
| (structure) | 209 |

TABLE 1-continued

Specific examples

| Compound | No. |
|---|---|
| | 210 |
| | 211 |
| | 212 |
| | 213 |

TABLE 1-continued

Specific examples

| Compound | No. |
|---|---|
| | 214 |
| | 215 |
| | 216 |

TABLE 1-continued
Specific examples
| Compound | No. |
|---|---|
| 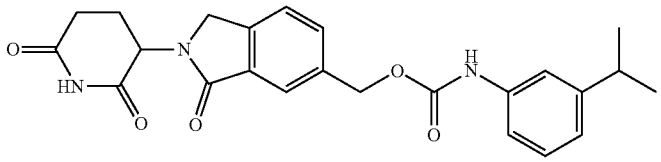 [SMILES: CC(C)c1cccc(NC(=O)OCc2ccc3c(c2)C(=O)N(C2CCC(=O)NC2=O)C3)c1] | 217 |
| 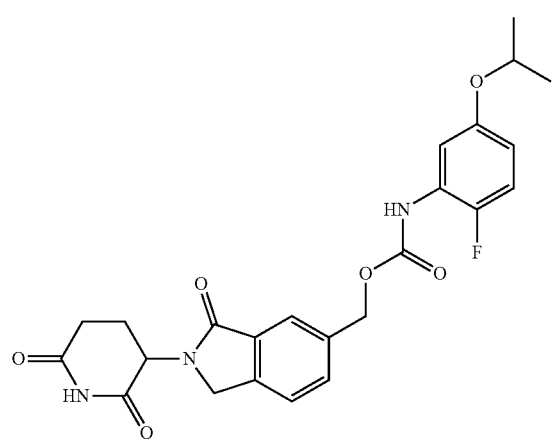 [SMILES: CC(C)Oc1ccc(F)c(NC(=O)OCc2ccc3c(c2)C(=O)N(C2CCC(=O)NC2=O)C3)c1] | 218 |
| 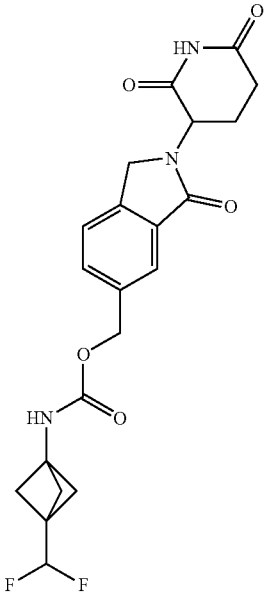 [SMILES: O=C1CCC(N2Cc3ccc(COC(=O)NC45CC(C(F)F)(C4)C5)cc3C2=O)C(=O)N1] | 219 |
| 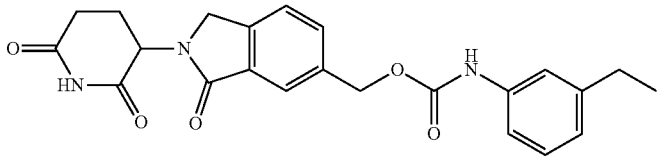 [SMILES: CCc1cccc(NC(=O)OCc2ccc3c(c2)C(=O)N(C2CCC(=O)NC2=O)C3)c1] | 220 |

TABLE 1-continued

Specific examples

| Compound | No. |
|---|---|
| | 221 |
| | 222 |
| | 223 |

TABLE 1-continued
Specific examples
| Compound | No. |
|---|---|
| 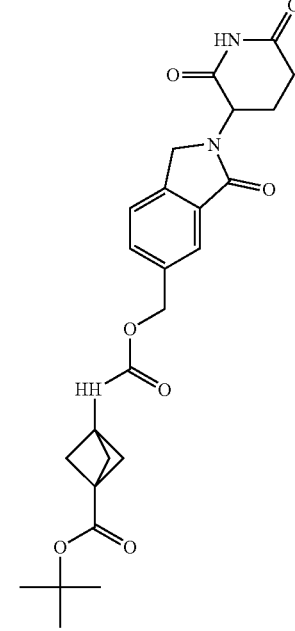 | 224 |
| 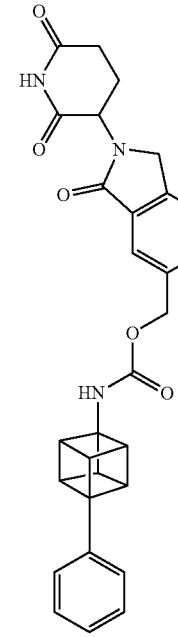 | 225 |
| 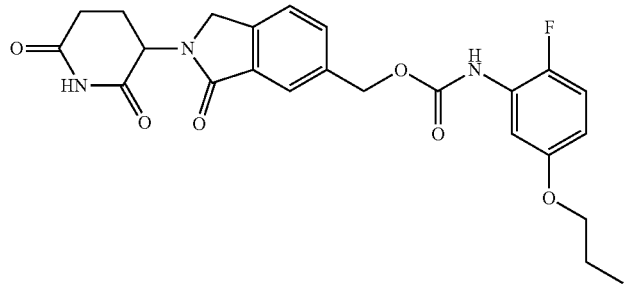 [SMILES: CCCOc1ccc(F)c(NC(=O)OCc2ccc3c(c2)C(=O)N(C2CCC(=O)NC2=O)C3)c1] | 226 |

TABLE 1-continued

Specific examples

| Compound | No. |
|---|---|
| | 227 |
| | 228 |
| | 229 |
| | 230 |

TABLE 1-continued

| Specific examples | |
|---|---|
| Compound | No. |
| | 231 |
| | 232 |
| | 233 |
| | 234 |
| | 235 |

TABLE 1-continued
Specific examples
| Compound | No. |
|---|---|
| 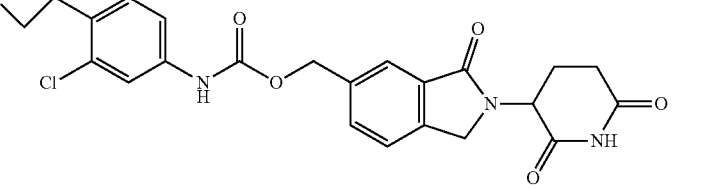 | 236 |
| 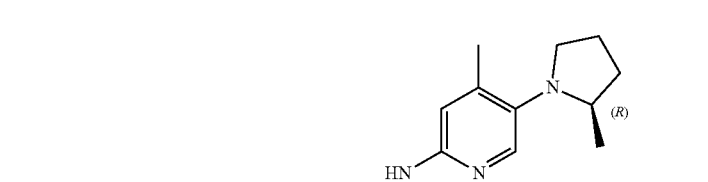 | 237 |
| 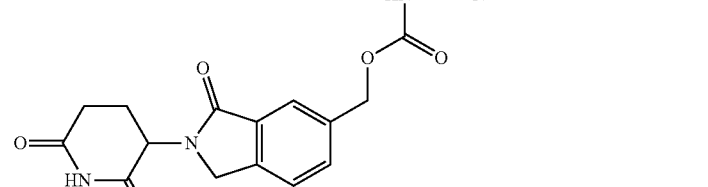 | 238 |
|  | 239 |

TABLE 1-continued

Specific examples

| Compound | No. |
|---|---|
| (structure) | 240 |

Compound 1: General procedure A with variant i) was used for the preparation from compound VIII employing phenyl (5-chloro-2-methoxy-4-methylphenyl)carbamate. $^1$H NMR (400 MHz, DMSO-d$_6$) δ=11.17-10.81 (m, 1H), 8.87 (s, 1H), 7.82 (s, 1H), 7.75-7.57 (m, 3H), 7.03 (s, 1H), 5.26 (s, 2H), 5.14 (br dd, J=5.1, 13.2 Hz, 1H), 4.53-4.40 (m, 1H), 4.39-4.29 (m, 1H), 3.80 (s, 3H), 2.92 (br s, 1H), 2.65-2.57 (m, 1H), 2.44-2.38 (m, 1H), 2.29 (s, 3H), 2.07-1.97 (m, 1H). MS (ESI) m/z 472.1 [M+H]$^+$ Step 1: To a solution of 4-chloro-5-methyl-2-nitrophenol (500 mg, 2.67 mmol, 1.00 eq) in dimethylformamide (3.00 mL) were added potassium carbonate (740 mg, 5.35 mmol, 2.01 eq) and methyl iodide (0.17 mL, 2.73 mmol, 1.02 eq). The reaction was stirred at 25° C. for 2 h. The mixture was extracted with water/ethyl acetate (2.00 mL/2.00 mL). The organic layer was collected and concentrated to afford 1-chloro-4-methoxy-2-methyl-5-nitrobenzene (490 mg, crude) as a yellow solid.

Step 2: To a solution of 1-chloro-4-methoxy-2-methyl-5-nitrobenzene (490 mg, 2.43 mmol, 1.00 eq) in methanol (9.00 mL) and water (3.00 mL) were added iron power (680 mg, 12.1 mmol, 5.01 eq) and ammonium chloride (1.04 g, 19.4 mmol, 8.00 eq). The reaction was stirred at 80° C. for 2 h. The mixture was filtered, and the filtrate was concentrated under reduced pressure to give a concentrated aqueous solution. The solution was extracted with water/ethyl acetate. The organic layers were collected and concentrated under reduced pressure to afford 5-chloro-2-methoxy-4-methylaniline.

Step 3: To a solution of 5-chloro-2-methoxy-4-methylaniline (200 mg, 1.17 mmol, 1.00 eq) in acetonitrile (3.00 mL) was added pyridine (0.47 mL, 5.82 mmol, 4.99 eq), phenyl chloroformate (0.22 mL, 1.75 mmol, 1.50 eq) at 0° C. The reaction was stirred at 0° C. for 2 h. The mixture was concentrated and the obtained residue was purified by standard methods to afford phenyl (5-chloro-2-methoxy-4-methylphenyl)carbamate (690 mg, crude) as an off-white solid.

Compound 2: General procedure A with variant i) was used for the preparation from compound VIII employing phenyl (3-chloro-4-methyl-5-(morpholinomethyl) phenyl) carbamate. $^1$H NMR (400 MHz, DMSO-d$_6$) δ=11.00 (s, 1H), 9.90 (br s, 1H), 8.14 (s, 1H), 7.80 (s, 1H), 7.70-7.62 (m, 2H), 7.55 (s, 1H), 7.43-7.28 (m, 1H), 5.28 (s, 2H), 5.13 (dd, J=5.1, 13.3 Hz, 1H), 4.51-4.44 (m, 1H), 4.39-4.31 (m, 1H), 3.57 (br s, 4H), 3.41 (br s, 2H), 2.96-2.87 (m, 1H), 2.63 (br s, 1H), 2.46-2.32 (m, 5H), 2.29 (s, 3H), 2.06-1.98 (m, 1H). MS (ESI) m/z 541.2 [M+H]$^+$ Step 1: To a solution of 2-methyl-5-nitro-benzoic acid (10.0 g, 55.2 mmol, 1.00 eq) in concentrated sulfuric acid (30.0 mL, 98% purity) was added 1,3-dichloro-5,5-dimethyl-imidazolidine-2,4-dione (13.0 g, 66.0 mmol, 1.20 eq). The mixture was stirred at 80° C. for 12 h. After cooling to room temperature, the mixture was poured into ice-water. The resulting white precipitate was collected by filtration and dried under reduced pressure to afford 3-chloro-2-methyl-5-nitro-benzoic acid.

Step 2: To a solution of 3-chloro-2-methyl-5-nitro-benzoic acid (15.0 g, 69.6 mmol, 1.00 eq) in tetrahydrofuran (100 mL) was added borane dimethyl sulfide complex (10 M, 14.0 mL, 140.0 mmol, 2.01 eq). The mixture was stirred at 20° C. for 12 h. The mixture was quenched with methanol (10.0 mL) at 0° C. and then concentrated under reduced pressure to give a residue. The residue was diluted with ethyl acetate (200 mL) and adjusted pH=8 with aqueous sodium bicarbonate (10%, 200 mL). The organic layer was separated and concentrated under reduced pressure to afford (3-chloro-2-methyl-5-nitrophenyl)methanol.

Step 3: To a solution of (3-chloro-2-methyl-5-nitro-phenyl)methanol (11.0 g, 54.5 mmol, 1 eq) (crude) in dichloromethane (200 mL) was added carbon tetrabromide (21 g, 63.32 mmol, 1.16 eq) and triphenylphosphine (18.6 g, 70.9 mmol, 1.30 eq) at 0° C. The mixture was stirred at 20° C. for 1 h. The mixture was concentrated under reduced pressure to give a residue. The residue was triturated with petroleum ether/ethyl acetate=1/1 (200 mL) and filtered. The filtrate was concentrated under reduced pressure to give a residue. The residue was purified by silica gel column chromatography (petroleum ether/ethyl acetate=8/1) to afford 1-(bromomethyl)-3-chloro-2-methyl-5-nitrobenzene.

Step 4: To a solution of 1-(bromomethyl)-3-chloro-2-methyl-5-nitro-benzene (16.0 g, 60.5 mmol, 1.00 eq) in acetonitrile (150 mL) was added morpholine (7.98 mL, 90.7 mmol, 1.50 eq), potassium carbonate (25.0 g, 181 mmol, 2.99 eq) and potassium iodide (1.00 g, 6.05 mmol, 0.100 eq). The reaction was stirred at 80° C. for 12 h. After cooling to room temperature, the mixture was filtered, and the filtrate was concentrated under reduced pressure to give a residue. The residue was purified by silica gel column chromatography (petroleum ether/ethyl acetate=8/1) to give 4-(3-chloro-2-methyl-5-nitrobenzyl)morpholine.

Step 5: To a solution of 4-(3-chloro-2-methyl-5-nitrobenzyl)morpholine (9.70 g, 35.8 mmol, 1.00 eq) in methanol (100 mL) and water (30.0 mL) was added ammonium chloride (15.0 g, 280 mmol, 7.83 eq) and ferrous powder (10.0 g, 179 mmol, 5.00 eq). The reaction was stirred at 80° C. for 2 h. The mixture was filtered, and methanol was removed under reduced pressure. The remaining aqueous solution was extracted with ethyl acetate (2×100 mL). The combined organic layers were washed with brine (20.0 mL), dried over sodium sulfate, filtered, and concentrated under reduced pressure to afford 3-chloro-4-methyl-5-(morpholinomethyl)aniline.

Step 6: To a solution of 3-chloro-4-methyl-5-(morpholinomethyl)aniline (1.00 g, 4.15 mmol, 1.00 eq) and pyridine (1.01 mL, 12.4 mmol, 3.00 eq) in acetonitrile (20.0 mL) was added phenyl chloroformate (0.52 mL, 4.15 mmol, 1.00 eq) at 0° C. The reaction was stirred at 20° C. for 2 h. The mixture was diluted with water (20.0 mL). The resulting precipitate was collected by filtration and dried to afford phenyl (3-chloro-4-methyl-5-(morpholinomethyl)phenyl) carbamate.

Compound 3: General procedure A with variant i) was used for the preparation from compound VIII employing phenyl (3-(trifluoromethoxy)phenyl)carbamate. $^1$H NMR (400 MHz, DMSO-$d_6$) δ=11.00 (s, 1H), 10.15 (s, 1H), 7.81 (s, 1H), 7.72-7.68 (m, 1H), 7.67-7.62 (m, 1H), 7.59 (s, 1H), 7.45-7.39 (m, 2H), 7.03-6.96 (m, 1H), 5.30 (s, 2H), 5.13 (dd, J=5.2, 13.3 Hz, 1H), 4.52-4.44 (m, 1H), 4.39-4.31 (m, 1H), 2.97-2.87 (m, 1H), 2.63 (br d, J=2.4 Hz, 1H), 2.47-2.35 (m, 1H), 2.02 (dtd, J=2.0, 5.1, 12.5 Hz, 1H). MS (ESI) m/z 478.1 [M+H]$^+$ Step 1: To a solution of 1-nitro-3-(trifluoromethoxy) benzene (1.00 g, 4.83 mmol, 1.00 eq) in methanol (15.0 mL) and water (5.00 mL) was added ammonium chloride (2.07 g, 38.6 mmol, 8.00 eq) and iron power (1.35 g, 24.1 mmol, 5.00 eq). The reaction was stirred at 80° C. for 2 h. The mixture was filtered, and the solvents were mostly removed under reduced pressure to give a concentrated solution. The solution was triturated with ethyl acetate/water (20.0 ml/10.0 ml), and a drop of saturated sodium bicarbonate solution was added. The organic layer was collected and concentrated under reduced pressure to afford 3-(trifluoromethoxy)aniline.

Step 2: To a solution of 3-(trifluoromethoxy)aniline (0.15 mL, 1.10 mmol, 1.00 eq) in acetonitrile (5.00 mL) was added pyridine (0.44 mL, 5.50 mmol, 5.00 eq). The reaction was stirred for 0.5 h, then phenyl chloroformate (0.16 mL, 1.32 mmol, 1.20 eq) was added at 0° C. The reaction was stirred for 1.5 h at 0° C. The mixture was concentrated under reduced pressure to give a residue. The residue was diluted with water (10.0 ml) and ethyl acetate (30.0 mL). The organic layer was collected and concentrated and the obtained residue was purified by standard methods to afford phenyl (3-(trifluoromethoxy)phenyl)carbamate.

Compound 4: General procedure A with variant i) was used for the preparation from compound VIII employing phenyl (3-(morpholinomethyl)-5-(trifluoromethoxy)phenyl) carbamate. $^1$H NMR (400 MHz, DMSO-$d_6$) δ=10.99 (s, 1H), 10.11 (s, 1H), 7.80 (s, 1H), 7.71-7.60 (m, 2H), 7.52-7.37 (m, 2H), 6.91 (s, 1H), 5.29 (s, 2H), 5.18-5.07 (m, 1H), 4.53-4.29 (m, 2H), 3.62-3.52 (m, 4H), 3.45 (s, 2H), 2.98-2.85 (m, 1H), 2.60 (br d, J=18.1 Hz, 1H), 2.43-2.38 (m, 1H), 2.34 (br s, 4H), 2.05-1.96 (m, 1H). MS (ESI) m/z 577.1 [M+H]$^+$ Step 1: To a solution of 3-hydroxy-5-nitro-benzoic acid (4.50 g, 24.6 mmol, 1.00 eq) and morpholine (2.57 g, 29.5 mmol, 2.60 mL, 1.2 eq) in dichloromethane (100 mL) was added O-(7-azabenzotriazol-1-yl)-N,N,N,N-tetramethyluronium hexafluorophosphate (11.2 g, 29.5 mmol, 1.20 eq) and triethylamine (5.06 mL, 49.2 mmol, 2.00 eq). The reaction was stirred at 20° C. for 12 h. The mixture was diluted with water (150 mL) and extracted with ethyl acetate (3×100 mL). The combined organic layers were washed with brine (100 mL), dried over sodium sulfate, filtered, and concentrated under reduced pressure to give a residue. The residue was purified by silica gel column chromatography (petroleum ether/ethyl acetate=0/1) to afford (3-hydroxy-5-nitrophenyl)(morpholino) methanone.

Step 2: To a solution of (3-hydroxy-5-nitro-phenyl)-morpholino-methanone (2.40 g, 9.52 mmol, 1.00 eq) in toluene (200 mL) were added trimethyl(trifluoromethyl)silane (6.77 g, 47.6 mmol, 5.00 eq), silver trifluoromethanesulfonate (12.2 g, 47.6 mmol, 5.00 eq), 2-fluoropyridine (4.09 mL, 47.6 mmol, 5.00 eq), caesium fluoride (2.10 mL, 57.1 mmol, 6.00 eq), N-fluorobenzenesulfonimide (6.00 g, 19.0 mmol, 2.00 eq) and 1-(chloromethyl)-4-fluoro-1,4-diazoniabicyclo (2.2.2)octane bis(tetrafluoroborate) (6.74 g, 19.0 mmol, 2.00 eq). The reaction was stirred at 25° C. under a nitrogen atmosphere for 12 h. The mixture was filtered, and the filtrate was concentrated under reduced pressure to give a residue. The residue was diluted with water (100 mL) and extracted with ethyl acetate (3×100 mL). The combined organic layers were washed with brine (100 mL), dried over anhydrous sodium sulfate, filtered, and the filtrate was concentrated to give a residue. The residue was purified by silica gel column chromatography (petroleum ether/ethyl acetate=1/1) to afford morpholino(3-nitro-5-(trifluoromethoxy) phenyl)methanone.

Step 3: To a solution of morpholino(3-nitro-5-(trifluoromethoxy)phenyl)methanone (2.60 g, 8.12 mmol, 1.00 eq) in tetrahydrofuran (30.0 mL) was added borane dimethyl sulfide complex (10.0 M, 1.62 mL, 2.00 eq) dropwise at 0° C. under nitrogen atmosphere. The reaction was stirred at 60° C. for 4 h. The mixture was quenched with methanol (9.00 mL) and concentrated to give a residue. The residue was purified by reversed phase preparative HPLC to afford 4-(3-nitro-5-(trifluoromethoxy)benzyl)morpholine.

Step 4: To a solution of 4-(3-nitro-5-(trifluoromethoxy) benzyl)morpholine (1.10 g, 3.59 mmol, 1.00 eq) in methanol (50.0 mL) and water (50.0 mL) were added iron powder (1.40 g, 25.14 mmol, 7.00 eq) and ammonium chloride (1.34 g, 25.14 mmol, 7.00 eq). The reaction was stirred at 80° C. for 3 h. The mixture was filtered over Celite, and the filtrate was concentrated under reduced pressure to afford 3-(morpholinomethyl)-5-(trifluoromethoxy)aniline.

Step 5: To a solution of 3-(morpholinomethyl)-5-(trifluoromethoxy)aniline (580 mg, 2.10 mmol, 1.00 eq) in acetonitrile (3.00 mL) was added phenyl chloroformate (0.39 mL, 3.15 mmol, 1.50 eq) and pyridine (0.5 mL, 6.30 mmol, 3.00 eq) at 0° C. The reaction was stirred at 25° C. for 12 h. The mixture was diluted with water (100 mL) and extracted with ethyl acetate (3×30.0 mL). The combined organic layers were washed with brine (30 mL), dried over anhydrous sodium sulfate, filtered, and the filtrate was concentrated and the obtained residue was purified by standard methods to afford phenyl (3-(morpholinomethyl)-5-(trifluoromethoxy) phenyl)carbamate.

Compound 5: General procedure A with variant i) was used for the preparation from compound VIII employing phenyl (3-(difluoromethoxy)phenyl)carbamate. $^1$H NMR (400 MHz, DMSO-$d_6$) δ=11.00 (br s, 1H), 10.05 (s, 1H), 7.80 (s, 1H), 7.71-7.67 (m, 1H), 7.67-7.62 (m, 1H), 7.40 (br s, 1H), 7.37 (s, 1H), 7.36-7.28 (m, 2H), 7.19 (t, J=76 Hz, 1H), 6.81 (br d, J=7.5 Hz, 1H), 5.29 (s, 2H), 5.13 (dd, J=5.1, 13.3 Hz, 1H), 4.52-4.44 (m, 1H), 4.39-4.30 (m, 1H), 2.97-2.87 (m, 1H), 2.64-2.58 (m, 1H), 2.48-2.37 (m, 1H), 2.07-1.98 (m, 1H). MS (ESI) m/z 460.1 [M+H]$^+$ Step 1: To a solution of 1-(difluoromethoxy)-3-nitrobenzene (2.00 g, 10.6 mmol, 1.00 eq) in methanol (15.0 mL) and water (5.00 mL) was added iron powder (2.95 g, 52.9 mmol, 5.00 eq) and ammonium chloride (4.53 g, 84.6 mmol, 8.00 eq). The reaction was stirred at 80° C. for 2 h. The reaction solution was filtered, and the filtrate was extracted with ethyl acetate. The combined organic layers were washed with brine, dried with anhydrous sodium sulfate, filtered, and concentrated under reduced pressure to afford 3-(difluoromethoxy)aniline.

Step 2: To a solution of 3-(difluoromethoxy)aniline (1.00 g, 6.28 mmol, 1.00 eq) and pyridine (2.54 mL, 31.4 mmol, 5.00 eq) in acetonitrile (5.00 mL) was added phenyl chloroformate (0.94 mL, 7.54 mmol, 1.20 eq). The mixture was stirred at 25° C. for 3 h. The mixture was concentrated and the obtained residue was purified by standard methods to afford phenyl (3-(difluoromethoxy)phenyl)carbamate.

Compound 6: General procedure A with variant i) was used for the preparation from compound VIII employing phenyl(5-chloro-6-methylpyridin-3-yl)carbamate. $^1$H NMR (400 MHz, DMSO-d$_6$) δ=11.00 (s, 1H), 10.18 (br s, 1H), 8.50-8.42 (m, 1H), 7.99 (s, 1H), 7.80 (s, 1H), 7.72-7.66 (m, 1H), 7.66-7.62 (m, 1H), 5.30 (s, 2H), 5.17-5.08 (m, 1H), 4.52-4.43 (m, 1H), 4.38-4.30 (m, 1H), 2.98-2.85 (m, 1H), 2.65-2.56 (m, 1H), 2.46 (s, 3H), 2.44-2.34 (m, 1H), 2.05-1.95 (m, 1H). MS (ESI) m/z 443.2 [M+H]$^+$ Step 1: To a solution of 3-chloro-2-methyl-5-nitropyridine (500 mg, 2.90 mmol, 1.00 eq) in methanol (5.00 mL) and water (5.00 mL) were added iron powder (1.13 g, 20.3 mmol, 7.00 eq) and ammonium chloride (1.08 g, 20.3 mmol, 7.00 eq). The reaction was stirred at 80° C. for 2 h. The mixture was filtered over Celite, and the filtrate was concentrated under reduced pressure to afford 5-chloro-6-methylpyridin-3-amine.

Step 2: To a solution of 5-chloro-6-methylpyridin-3-amine (200 mg, 1.40 mmol, 1.00 eq) in acetonitrile (2.00 mL) were added phenyl chloroformate (0.26 mL, 2.10 mmol, 1.50 eq) and pyridine (0.34 mL, 4.21 mmol, 3.00 eq). The reaction was stirred at 25° C. for 12 h. The mixture was diluted with ethyl acetate (30.0 mL) and water (50.0 mL). The organic layer was separated, and the aqueous phase was extracted with ethyl acetate (3×100 mL). The combined organic layers were dried over sodium sulfate, filtered, and concentrated and the obtained residue was purified by standard methods to afford phenyl (5-chloro-6-methylpyridin-3-yl)carbamate.

Compound 7: General procedure A with variant i) was used for the preparation from compound VIII employing phenyl (2,6-dimethylpyridin-4-yl)carbamate. $^1$H NMR (400 MHz, DMSO-d$_6$) δ=10.99 (s, 1H), 10.10 (s, 1H), 8.18 (s, 1H), 7.80 (s, 1H), 7.71-7.60 (m, 2H), 7.12 (s, 2H), 5.29 (s, 2H), 5.12 (dd, J=5.1, 13.3 Hz, 1H), 4.51-4.43 (m, 1H), 4.39-4.30 (m, 1H), 2.91 (ddd, J=5.4, 13.7, 17.4 Hz, 1H), 2.64-2.57 (m, 1H), 2.40 (br dd, J=4.6, 13.1 Hz, 1H), 2.33 (s, 6H), 2.07-1.97 (m, 1H). MS (ESI) m/z 423.1 [M+H]$^+$ To a solution of 2,6-dimethylpyridin-4-amine (1.00 g, 8.19 mmol, 1.00 eq) in acetonitrile (20.0 mL) was added pyridine (3.30 mL, 40.9 mmol, 5.00 eq) and phenyl chloroformate (1.54 mL, 12.2 mmol, 1.50 eq) at 0° C. The reaction was stirred at 25° C. for 0.5 h. The mixture was concentrated and the obtained residue was purified by standard methods to afford phenyl (2,6-dimethylpyridin-4-yl)carbamate.

Compound 8: General procedure A with variant i) was used for the preparation from compound VIII employing phenyl (3,5-dimethylphenyl)carbamate. $^1$H NMR (400 MHz, DMSO-d$_6$) δ=10.9 (br s, 1H), 9.65 (s, 1H), 7.78 (s, 1H), 7.70-7.59 (m, 2H), 7.09 (s, 2H), 6.64 (s, 1H), 5.25 (s, 2H), 5.13 (dd, J=5.1, 13.4 Hz, 1H), 4.52-4.42 (m, 1H), 4.39-4.28 (m, 1H), 2.99-2.84 (m, 1H), 2.60 (td, J=2.1, 15.3 Hz, 1H), 2.40 (br dd, J=4.4, 13.1 Hz, 1H), 2.21 (s, 6H), 2.06-1.98 (m, 1H). MS (ESI) m/z 422.1 [M+H]$^+$ To a solution of 3,5-dimethylaniline (0.51 mL, 4.13 mmol, 1.00 eq) in acetonitrile (10.00 mL) was added pyridine (1.67 mL, 20.6 mmol, 5.00 eq) and phenyl chloroformate (1.03 mL, 8.25 mmol, 2.00 eq) at 0° C. in portions. The reaction was stirred at 25° C. for 1 h. The mixture was concentrated under reduced pressure to give a residue, which was purified by silica gel column chromatography (petroleum ether/ethyl acetate=1/0 to 3/1) to afford phenyl (3,5-dimethylphenyl) carbamate.

Compound 9: General procedure A with variant i) was used for the preparation from compound VIII employing phenyl (3-chloro-4-fluorophenyl)carbamate. $^1$H NMR (400 MHz, DMSO-d$_6$) δ=10.99 (br s, 1H), 10.05 (br s, 1H), 7.79 (s, 1H), 7.74-7.61 (m, 3H), 7.44-7.31 (m, 2H), 5.28 (s, 2H), 5.12 (dd, J=5.1, 13.3 Hz, 1H), 4.52-4.41 (m, 1H), 4.39-4.29 (m, 1H), 2.98-2.85 (m, 1H), 2.60 (br dd, J=2.1, 15.4 Hz, 1H), 2.42 (dt, J=4.4, 13.3 Hz, 1H), 2.05-1.96 (m, 1H). MS (ESI) m/z 446.1 [M+H]$^+$ To a solution of 3-chloro-4-fluoroaniline (1.00 g, 6.87 mmol, 1.00 eq) in acetonitrile (10.0 mL) was added pyridine (2.77 mL, 34.4 mmol, 5.00 eq) and phenyl chloroformate (1.72 mL, 13.7 mmol, 2.00 eq) in portions at 0° C. The reaction was stirred at 25° C. for 0.5 h. The mixture was concentrated and the obtained residue was purified by standard methods to afford phenyl (3-chloro-4-fluorophenyl) carbamate.

Compound 10: General procedure A with variant i) was used for the preparation from compound VIII employing phenyl (3-chloro-4-methylphenyl)carbamate. $^1$H NMR (400 MHz, DMSO-d$_6$) δ=11.00 (s, 1H), 9.93 (s, 1H), 7.80 (s, 1H), 7.74-7.54 (m, 3H), 7.37-7.19 (m, 2H), 5.28 (s, 2H), 5.13 (dd, J=5.1, 13.2 Hz, 1H), 4.53-4.44 (m, 1H), 4.38-4.31 (m, 1H), 2.98-2.87 (m, 1H), 2.61 (br d, J=17.6 Hz, 1H), 2.41 (br dd, J=4.4, 13.2 Hz, 1H), 2.26 (s, 3H), 2.06-1.97 (m, 1H). MS (ESI) m/z 442.1 [M+H]$^+$ Preparation of phenyl (3-chloro-4-methylphenyl)carbamate: To a solution of 3-chloro-4-methylaniline (5.00 g, 35.3 mmol, 1.00 eq) in acetonitrile (50.0 mL) was added pyridine (5.70 mL, 70.6 mmol, 2.00 eq) and phenyl chloroformate (4.87 mL, 38.8 mmol, 1.10 eq) at 0° C. The mixture was stirred at 30° C. for 2 h. The mixture was concentrated and the obtained residue was purified by standard methods to afford phenyl (3-chloro-4-methylphenyl)carbamate.

Compound 11: General procedure A with variant i) was used for the preparation from compound VIII employing phenyl (3-chloro-5-(trifluoromethoxy)phenyl)carbamate. $^1$H NMR (400 MHz, DMSO-d$_6$) δ=11.00 (s, 1H), 10.35 (s, 1H), 7.81 (s, 1H), 7.73-7.68 (m, 1H), 7.67-7.62 (m, 1H), 7.60-7.49 (m, 2H), 7.17 (s, 1H), 5.31 (s, 2H), 5.13 (dd, J=5.1, 13.3 Hz, 1H), 4.53-4.44 (m, 1H), 4.39-4.31 (m, 1H), 2.99-2.85 (m, 1H), 2.64-2.58 (m, 1H), 2.41 (dd, J=4.4, 13.0 Hz, 1H), 2.07-1.95 (m, 1H). MS (ESI) m/z 332.0 [M+H]$^+$ To a solution of 3-chloro-5-(trifluoromethoxy)aniline (150 mg, 708 μmol, 1.00 eq) in acetonitrile (1.00 mL) were added pyridine (0.29 mL, 3.54 mmol, 5.00 eq) and phenyl chloroformate (0.11 mL, 850 µmol, 1.20 eq) at 0° C. The reaction was stirred at 0° C. for 2 h. The mixture was filtered to give a solution, which was purified by standard methods to afford phenyl (3-chloro-5-(trifluoromethoxy)phenyl)carbamate.

Compound 12: General procedure A with variant i) was used for the preparation from compound VIII employing phenyl (3-chloro-5-fluorophenyl)carbamate. $^1$H NMR (400 MHz, DMSO-d$_6$) δ=10.99 (s, 1H), 10.25 (s, 1H), 7.80 (s, 1H), 7.74-7.56 (m, 2H), 7.44-7.28 (m, 2H), 7.10-6.96 (m, 1H), 5.30 (s, 2H), 5.18-5.06 (m, 1H), 4.54-4.42 (m, 1H), 4.40-4.31 (m, 1H), 2.98-2.86 (m, 1H), 2.62 (br d, J=2.6 Hz, 1H), 2.46-2.37 (m, 1H), 2.05-1.96 (m, 1H). MS (ESI) m/z 446.0 [M+H]$^+$ To a solution of 3-chloro-5-fluoroaniline (1.00 g, 6.87 mmol, 1.00 eq) in acetonitrile (20.0 mL) were added pyridine (2.77 mL, 34.3 mmol, 5.00 eq) and phenyl chloroformate (1.29 mL, 10.3 mmol, 1.50 eq) at 0° C. The reaction was stirred at 25° C. for 1 h. The mixture was concentrated and the obtained residue was purified by standard methods to afford phenyl (3-chloro-5-fluorophenyl)carbamate.

Compound 13: General procedure A with variant i) was used for the preparation from compound VIII employing phenyl (3-(2-oxa-5-azabicyclo[2.2.1]heptan-5-ylmethyl)-5-chloro-4-methylphenyl)carbamate.

$^1$H NMR (400 MHz, DMSO-d$_6$) δ=11.00 (s, 1H), 9.89 (br s, 1H), 8.14 (s, 1H), 7.80 (s, 1H), 7.71-7.62 (m, 2H), 7.54 (br s, 1H), 7.41 (d, J=1.5 Hz, 1H), 5.27 (s, 2H), 5.13 (dd, J=5.0, 13.3 Hz, 1H), 4.46 (s, 1H), 4.37 (s, 2H), 3.91 (s, 1H), 3.72-3.64 (m, 2H), 3.54 (dd, J=1.6, 7.4 Hz, 1H), 3.46 (br s, 1H), 2.97-2.87 (m, 1H), 2.75 (br d, J=9.0 Hz, 1H), 2.61 (br d, J=17.0 Hz, 1H), 2.47 (br d, J=10.3 Hz, 1H), 2.41 (br dd, J=4.6, 13.0 Hz, 1H), 2.26 (s, 3H), 2.07-1.97 (m, 1H), 1.80 (br s, 1H), 1.61 (br d, J=9.3 Hz, 1H). MS (ESI) m/z 553.2 [M+H]$^+$

To a solution of 3-(2-oxa-5-azabicyclo[2.2.1]heptan-5-ylmethyl)-5-chloro-4-methylaniline (350 mg, 1.38 mmol, 1.00 eq) in acetonitrile (2.00 mL) were added pyridine (0.56 mL, 6.92 mmol, 5.00 eq) and phenyl chloroformate (0.21 mL, 1.66 mmol, 1.20 eq) at 0° C. The reaction was stirred at 0° C. for 2 h. The mixture was concentrated and the obtained residue was purified by standard methods to afford phenyl (3-(2-oxa-5-azabicyclo[2.2.1]heptan-5-ylmethyl)-5-chloro-4-methylphenyl)carbamate.

Compound 14: General procedure A with variant i) was used for the preparation from compound VIII employing phenyl(5-chloro-2-methoxyphenyl)carbamate.

$^1$H NMR (400 MHz, DMSO-d$_6$) δ=10.99 (br s, 1H), 8.95 (s, 1H), 7.82 (s, 1H), 7.77 (br d, J=1.5 Hz, 1H), 7.72-7.66 (m, 1H), 7.65-7.60 (m, 1H), 7.13-7.08 (m, 1H), 7.06-7.01 (m, 1H), 5.27 (s, 2H), 5.13 (dd, J=5.1, 13.3 Hz, 1H), 4.51-4.43 (m, 1H), 4.37-4.30 (m, 1H), 3.80 (s, 3H), 2.97-2.86 (m, 1H), 2.60 (td, J=2.1, 15.3 Hz, 1H), 2.40 (br dd, J=4.5, 13.1 Hz, 1H), 2.05-1.97 (m, 1H). MS (ESI) m/z 458.1 [M+H]$^+$

To a solution of 5-chloro-2-methoxyaniline (1.00 g, 6.35 mmol, 1.00 eq) in acetonitrile (10.0 mL) were added pyridine (2.56 mL, 31.7 mmol, 5.00 eq) and phenyl chloroformate (1.59 mL, 12.7 mmol, 2.00 eq) in portions at 0° C. The reaction was stirred at 25° C. for 1 h. The mixture was concentrated under reduced pressure to give a residue, which was diluted with water (50.0 mL) and exacted with ethyl acetate (3×30.0 mL). The combined organic layers were washed with water, dried over anhydrous sodium sulfate, filtered, and concentrated under reduced pressure to give a residue. The residue was purified by reversed phase preparative HPLC. The desired fraction was collected, and acetonitrile was removed under reduced pressure. The residual aqueous solution was exacted with ethyl acetate (3×50.0 mL). The combined organic layers were washed with brine, dried over anhydrous sodium sulfate, filtered, and concentrated to afford phenyl(5-chloro-2-methoxyphenyl)carbamate.

Compound 15: General procedure A with variant i) was used for the preparation from compound VIII employing phenyl(6-(piperidin-1-yl)pyridin-3-yl)carbamate.

$^1$H NMR (400 MHz, DMSO-d$_6$) δ=10.99 (s, 1H), 10.12 (br s, 1H), 8.19 (br s, 1H), 7.95-7.89 (m, 1H), 7.79 (s, 1H), 7.70-7.62 (m, 2H), 7.41 (br d, J=9.3 Hz, 1H), 5.29 (s, 2H), 5.12 (dd, J=5.1, 13.3 Hz, 1H), 4.52-4.44 (m, 1H), 4.39-4.31 (m, 1H), 3.64 (br s, 4H), 2.91 (ddd, J=5.4, 13.6, 17.5 Hz, 1H), 2.63-2.58 (m, 1H), 2.45-2.35 (m, 1H), 2.06-1.96 (m, 1H), 1.63 (br s, 6H). MS (ESI) m/z 478.1[M+H]$^+$ Step 1: To a solution of 2-fluoro-5-nitro-pyridine (5.00 g, 35.2 mmol, 1.00 eq) in acetonitrile (50.0 mL) were added potassium carbonate (9.73 g, 70.4 mmol, 2.00 eq) and piperidine (4.17 mL, 42.2 mmol, 1.20 eq). The reaction was stirred at 25° C. for 1 h. The mixture was filtered and concentrated under reduced pressure to afford 5-nitro-2-(1-piperidyl)pyridine.

Step 2: To a solution of 5-nitro-2-(piperidin-1-yl)pyridine (5.20 g, 25.1 mmol, 1.00 eq) and ammonium chloride (6.71 g, 125 mmol, 5.00 eq) in methanol (40.0 mL) and water (10.0 mL) was added iron powder (7.01 g, 126 mmol, 5.00 eq) in portions. The reaction was stirred at 80° C. for 2 h. The mixture was filtered, and the filtrate was concentrated under reduced pressure to give a residue. The residue was diluted with water (150 mL) and extracted with ethyl acetate (3×60.0 mL). The combined organic layers were washed with brine (60.0 mL), dried over sodium sulfate, filtered, and concentrated under reduced pressure to give a residue. The residue was purified by reversed phase preparative HPLC. The desired fraction was collected, diluted with saturated sodium bicarbonate (150 mL), and extracted with ethyl acetate (3×60.0 mL). The combined organic layers were washed with brine (60.0 mL), dried over sodium sulfate, filtered, and concentrated under reduced pressure to afford 6-(piperidin-1-yl)pyridin-3-amine.

Step 3: To a solution of 6-(piperidin-1-yl)pyridin-3-amine (300 mg, 1.69 mmol, 1.00 eq) and pyridine (0.41 mL, 5.08 mmol, 3.00 eq) in acetonitrile (3.00 mL) was added phenyl chloroformate (0.32 mL, 2.54 mmol, 1.50 eq) dropwise at 0° C. The reaction was stirred at 25° C. for 12 h. The mixture was diluted with water (50.0 mL) and extracted with ethyl acetate (3×40.0 mL). The combined organic layers were washed with brine (20.0 mL), dried over sodium sulfate, filtered, and concentrated under reduced pressure to give a residue. The residue was purified by reversed phase preparative HPLC. The desired fraction was collected, diluted with saturated sodium bicarbonate (30 mL), and extracted with ethyl acetate (3×40.0 mL). The combined organic layers were washed with brine (20.0 mL), dried over sodium sulfate, filtered, and concentrated to afford phenyl (6-(piperidin-1-yl)pyridin-3-yl)carbamate.

Compound 16:

Step 1: To a solution of tert-butyl 3-(hydroxymethyl)pyrrolidine-1-carboxylate (3.00 g, 14.9 mmol, 1.00 eq) and triethylamine (5.19 mL, 37.3 mmol, 2.50 eq) in dichloromethane (30.0 mL) at 0° C. was added methylsulfamoyl chloride (1.50 mL, 19.4 mmol, 1.30 eq) dropwise over 2 min under nitrogen atmosphere. The reaction was then stirred at 25° C. for 2 h. The mixture was diluted with ethyl acetate (100 mL) and water (150 mL). The organic layer was separated, and the aqueous phase was extracted with ethyl acetate (3×100 mL). The combined organic layers were dried over sodium sulfate, filtered, and concentrated under reduced pressure to afford tert-butyl 3-(((methylsulfonyl)oxy)methyl)pyrrolidine-1-carboxylate.

Step 2: A solution of tert-butyl 3-(((methylsulfonyl)oxy) methyl) pyrrolidine-1-carboxylate (3.00 g, 10.8 mmol, 1.00 eq), 3-chloro-5-nitrophenol (2.05 g, 11.8 mmol, 1.10 eq) and caesium carbonate (10.5 g, 32.2 mmol, 3.00 eq) in dimethylformamide (30.0 mL) was stirred at 80° C. for 12 h. The mixture was diluted with ethyl acetate (100 mL) and water (100 mL). The organic layer was separated, and the aqueous phase was extracted with ethyl acetate (3×80.0 mL). The combined organic layers were dried over sodium sulfate, filtered, and concentrated under reduced pressure to give a residue. The residue was purified by silica gel column chromatography (petroleum ether/ethyl acetate=3/1) to afford tert-butyl 3-((3-chloro-5-nitrophenoxy)methyl)pyrrolidine-1-carboxylate.

Step 3: A solution of tert-butyl 3-((3-chloro-5-nitrophenoxy)methyl)pyrrolidine-1-carboxylate (2.00 g, 5.61 mmol, 1.00 eq), iron powder (2.19 g, 39.2 mmol, 7.00 eq) and ammonium chloride (2.10 g, 39.2 mmol, 7.00 eq) in methanol (30.0 mL) and water (30.0 mL) was stirred at 80° C. for 2 h. The mixture was filtered over Celite, and the filtrate was concentrated under reduced pressure to afford tert-butyl 3-((3-amino-5-chlorophenoxy) methyl)pyrrolidine-1-carboxylate.

Step 4: A solution of phenyl chloroformate (0.11 mL, 918 µmol, 1.50 eq), tert-butyl 3-((3-amino-5-chlorophenoxy)methyl)pyrrolidine-1-carboxylate (200 mg, 612 µmol, 1.00 eq) and pyridine (0.15 mL, 1.84 mmol, 3.00 eq) in acetonitrile (2.00 mL) was stirred at 25° C. for 12 h. The mixture was diluted with ethyl acetate (80.0 mL) and water (80.0 mL). The organic layer was separated, and the aqueous phase was extracted with ethyl acetate (3×50.0 mL). The combined organic layers were dried over sodium sulfate, filtered, and concentrated under reduced pressure to give a residue. The residue was purified by silica gel column chromatography (petroleum ether/ethyl acetate=3/1) to afford tert-butyl 3-((3-chloro-5-((phenoxycarbonyl)amino) phenoxy) methyl)pyrrolidine-1-carboxylate.

Step 5: A solution of 3-(6-(hydroxymethyl)-1-oxoisoindolin-2-yl)piperidine-2,6-dione VIII (80.0 mg, 292 µmol, 1.00 eq), tert-butyl 3-((3-chloro-5-((phenoxycarbonyl) amino)phenoxy)methyl) pyrrolidine-1-carboxylate (156 mg, 350 µmol, 1.20 eq) and sodium hydride (60% dispersion in mineral oil) (23.3 mg, 583 µmol, 2.00 eq) in dimethylformamide (2.00 mL) was stirred at 0° C. for 4 h. The mixture was quenched by addition by hydrochloric acid (1M, 5.00 mL) and the filtrate was concentrated under reduced pressure to afford tert-butyl 3-((3-chloro-5-((((2-(2,6-dioxopiperidin-3-yl)-3-oxoisoindolin-5-yl)methoxy)carbonyl) amino)phenoxy)methyl)pyrrolidine-1-carboxylate.

Step 6: A solution of tert-butyl 3-((3-chloro-5-((((2-(2,6-dioxopiperidin-3-yl)-3-oxoisoindolin-5-yl)methoxy)carbonyl)amino)phenoxy)methyl)pyrrolidine-1-carboxylate (200 mg, 319 µmol, 1.00 eq) and hydrochloric acid (12 M, 26.6 µL, 1.00 eq) in water (2.00 mL) was stirred at 25° C. for 12 h. The mixture was diluted with acetonitrile (2.00 mL) and filtered. The filtrate was purified by a standard method to afford Compound 16. $^1$H NMR (400 MHz, DMSO-$d_6$) δ=10.99 (s, 1H), 10.04 (s, 1H), 9.12 (br d, J=2.7 Hz, 2H), 7.79 (s, 1H), 7.71-7.61 (m, 2H), 7.15-7.09 (m, 2H), 6.70 (t, J=2.0 Hz, 1H), 5.28 (s, 2H), 5.16-5.08 (m, 1H), 4.52-4.43 (m, 1H), 4.38-4.31 (m, 1H), 4.03-3.93 (m, 2H), 3.30-3.10 (m, 3H), 3.05-2.84 (m, 2H), 2.78-2.65 (m, 1H), 2.60 (br d, J=16.8 Hz, 1H), 2.47-2.35 (m, 1H), 2.13-1.96 (m, 2H), 1.80-1.68 (m, 1H). MS (ESI) m/z 527.3 [M+H]$^+$ Compound 17:

Step 1: To a solution of 2-(2,6-dioxo-1-((2-(trimethylsilyl)ethoxy)methyl)piperidin-3-yl)-3-oxoisoindoline-5-Carbaldehyde V (750 mg, 1.86 mmol, 1.00 eq) in dichloromethane (10.0 mL) was added methylmagnesium bromide 3.00 M in diethyl ether (3.00 M, 0.75 mL, 1.20 eq) dropwise at –78° C. The reaction was stirred at –78° C. for 2 h. The reaction was quenched with ammonium chloride (50.0 mL) to reach pH=7, and the mixture was extracted with ethyl acetate (3×30.0 mL). The combined organic layers were washed with brine (20.0 mL), dried over anhydrous sodium sulfate, filtered, and concentrated under reduces pressure to give a residue. The residue was purified by silica gel column chromatography (petroleum ether/ethyl acetate=10/1 to 2/3) to afford 3-(6-(1-hydroxyethyl)-1-oxoisoindolin-2-yl)-1-((2-(trimethylsilyl) ethoxy)methyl)piperidine-2,6-dione.

Step 2: A solution of 3-(6-(1-hydroxyethyl)-1-oxoisoindolin-2-yl)-1-((2-(trimethylsilyl)ethoxy) methyl)piperidine-2,6-dione (600 mg, 1.43 mmol, 1.00 eq) in hydrochloric acid/dioxane (6 M, 6.67 mL, 27.9 eq) was stirred at 50° C. for 1 h. The mixture was concentrated under reduced pressure to afford 3-(6-(1-hydroxyethyl)-1-oxoisoindolin-2-yl)-1-(hydroxymethyl)piperidine-2,6-dione.

Step 3: To a solution of 3-(6-(1-hydroxyethyl)-1-oxoisoindolin-2-yl)-1-(hydroxymethyl) piperidine-2,6-dione (450 mg, 1.41 mmol, 1.00 eq) in acetonitrile (10.0 mL) was added ammonium hydroxide 30% (0.20 mL, 1.56 mmol, 1.10 eq) dropwise. The reaction was stirred at 25° C. for 0.5 h. The reaction was quenched with 1M HCl to reach pH=3 and concentrated under reduced pressure to give a residue. The residue was purified by reversed phase preparative HPLC to afford 3-(6-(1-hydroxyethyl)-1-oxoisoindolin-2-yl)piperidine-2,6-dione.

Step 4: To a solution of 3-(6-(1-hydroxyethyl)-1-oxoisoindolin-2-yl)piperidine-2,6-dione (85.0 mg, 295 µmol, 1.00 eq) and phenyl (3-chloro-4-methylphenyl)carbamate (described in example 1) (84.9 mg, 324 µmol, 1.10 eq) in dimethylformamide (3.00 mL) was added sodium hydride (60% dispersion in mineral oil) (23.6 mg, 590 µmol, 2.00 eq) in portions at 0° C. The reaction was stirred at 0° C. for 0.5 h. The reaction was quenched with 1M hydrochloric acid (2.00 mL), filtered, and concentrated to give a residue. The residue was purified by a standard method to afford Compound 17. $^1$H NMR (400 MHz, DMSO-$d_6$) δ=11.00 (br s, 1H), 9.93 (br s, 1H), 7.77 (s, 1H), 7.71-7.60 (m, 2H), 7.58 (d, J=1.6 Hz, 1H), 7.35-7.18 (m, 2H), 5.91 (q, J=6.4 Hz, 1H), 5.13 (dd, J=5.0, 13.3 Hz, 1H), 4.56-4.26 (m, 2H), 2.98-2.86 (m, 1H), 2.65-2.56 (m, 1H), 2.45-2.35 (m, 1H), 2.24 (s, 3H), 2.06-1.96 (m, 1H), 1.58 (d, J=6.6 Hz, 3H). MS (ESI) m/z 456.1 [M+H]$^+$ Compound 18: General procedure A with variant i) was used for the preparation from compound VIII employing phenyl (2,3-dihydrobenzofuran-6-yl)carbamate.

$^1$H NMR (400 MHz, DMSO-$d_6$) δ=10.99 (s, 1H), 9.72 (br s, 1H), 7.79 (s, 1H), 7.69-7.61 (m, 2H), 7.09 (d, J=8.0 Hz, 1H), 6.98 (s, 1H), 6.88 (br d, J=7.9 Hz, 1H), 5.25 (s, 2H), 5.13 (dd, J=5.1, 13.2 Hz, 1H), 4.54-4.43 (m, 3H), 4.38-4.30 (m, 1H), 3.08 (t, J=8.6 Hz, 2H), 2.98-2.85 (m, 1H), 2.63-2.57 (m, 1H), 2.43-2.33 (m, 1H), 2.06-1.96 (m, 1H). MS (ESI) m/z 436.2 [M+H]$^+$

To a solution of 2,3-dihydrobenzofuran-6-amine (200 mg, 1.48 mmol, 1.00 eq) in acetonitrile (8.00 mL) were added pyridine (0.60 mL, 7.40 mmol, 5.00 eq) and phenyl chloroformate (0.37 mL, 2.96 mmol, 2.00 eq) at 0° C. in portions. The reaction was stirred at 25° C. for 1 h. The mixture was concentrated and the obtained residue was purified by standard methods to afford phenyl (2,3-dihydrobenzofuran-6-yl)carbamate.

Compound 19: General procedure A with variant i) was used for the preparation from compound VIII employing phenyl (3-chloro-5-(difluoromethoxy)phenyl)carbamate.

$^{1}$H NMR (400 MHz, DMSO-d$_6$) δ=10.99 (s, 1H), 10.23 (s, 1H), 7.79 (s, 1H), 7.72-7.61 (m, 2H), 7.42 (t, J=1.8 Hz, 1H), 7.31 (s, 1H), 7.06 (t, J=44 Hz, 1H), 6.94 (t, J=2.0 Hz, 1H), 5.29 (s, 2H), 5.12 (dd, J=5.1, 13.3 Hz, 1H), 4.51-4.43 (m, 1H), 4.38-4.30 (m, 1H), 2.97-2.85 (m, 1H), 2.60 (br d, J=17.5 Hz, 1H), 2.40 (dd, J=4.4, 13.1 Hz, 1H), 2.06-1.96 (m, 1H). MS (ESI) m/z 494.1 [M+H]$^+$

Step 1: To a solution of 3-chloro-5-nitro-phenol (1.50 g, 8.64 mmol, 1.00 eq) and sodium 2-chloro-2,2-difluoroacetate (5.27 g, 34.6 mmol, 4.00 eq) in dimethylformamide (17.0 mL) and water (2.00 mL) was added potassium carbonate (2.39 g, 17.3 mmol, 2.00 eq). The reaction was stirred at 100° C. for 12 h. The mixture was filtered and concentrated under reduced pressure to give a residue.

The residue was diluted with water (100 mL) and extracted with ethyl acetate (3×20.0 mL). The combined organic layers were washed with saturated sodium carbonate solution (50.0 mL) and brine (20.0 mL), dried over anhydrous sodium sulfate, filtered, and concentrated under reduced pressure to afford 1-chloro-3-(difluoromethoxy)-5-nitrobenzene.

Step 2: To a solution of 1-chloro-3-(difluoromethoxy)-5-nitro-benzene (1.70 g, 7.60 mmol, 1.00 eq) in methanol (10.0 mL) and water (10.0 mL) were added iron powder (2.12 g, 38.0 mmol, 5.00 eq) and ammonium chloride (2.03 g, 38.0 mmol, 5.00 eq). The reaction was stirred at 80° C. for 2 h. The mixture was concentrated under reduced pressure to give a residue. The residue was diluted with saturated sodium bicarbonate solution (20.0 mL) and extracted with ethyl acetate (3×20.0 mL). The combined organic layers were washed with brine (20.0 mL), dried over anhydrous sodium sulfate, filtered, and concentrated under reduced pressure to afford 3-chloro-5-(difluoromethoxy)aniline.

Step 3: To a solution 3-chloro-5-(difluoromethoxy)aniline (400 mg, 2.07 mmol, 1.00 eq) in acetonitrile (10.0 mL) were added pyridine (0.83 mL, 10.3 mmol, 5.00 eq) and phenyl chloroformate (0.39 mL, 3.10 mmol, 1.50 eq). The reaction was stirred at 25° C. for 1 h. The mixture was concentrated and the obtained residue was purified by standard methods to afford phenyl (3-chloro-5-(difluoromethoxy)phenyl)carbamate.

Compound 20:

Step 1: To a solution of 3-(6-(hydroxymethyl)-1-oxoisoindolin-2-yl)piperidine-2,6-dione (120 mg, 437 µmol, 1.00 eq) and tert-butyl 3-(3-chloro-5-((phenoxycarbonyl)amino) phenoxy)pyrrolidine-1-carboxylate (284 mg, 656 µmol, 1.50 eq) in dimethylformamide (2.00 mL) was added sodium hydride (60% dispersion in mineral oil) (35.0 mg, 875 µmol, 2.00 eq). The reaction was stirred at 25° C. for 1 h.

Step 2: A solution of tert-butyl 3-(3-chloro-5-((((2-(2,6-dioxopiperidin-3-yl)-3-oxoisoindolin-5-yl)methoxy)carbonyl)amino)phenoxy)pyrrolidine-1-carboxylate (250 mg, 407 µmol, 1.00 eq) in hydrochloric acid (4 M, 5.00 mL, 49.0 eq) was stirred at 25° C. for 12 h. The mixture was concentrated under reduced pressure to give a residue. The residue was purified by a standard method to afford Compound 20. $^{1}$H NMR (400 MHz, DMSO-d$_6$) δ=11.00 (s, 1H), 10.07 (s, 1H), 9.32-9.13 (m, 2H), 7.80 (s, 1H), 7.75-7.60 (m, 2H), 7.23-7.09 (m, 2H), 6.75 (t, J=2.0 Hz, 1H), 5.29 (s, 2H), 5.18-5.08 (m, 2H), 4.56-4.41 (m, 1H), 4.41-4.31 (m, 1H), 3.32-3.21 (m, 2H), 3.00-2.87 (m, 1H), 2.63 (br d, J=2.8 Hz, 2H), 2.43 (dt, J=4.5, 13.1 Hz, 2H), 2.25-2.10 (m, 2H), 2.06-1.97 (m, 1H). MS (ESI) m/z 513.0 [M+H]$^+$ Preparation of tert-butyl 3-(3-chloro-5-((phenoxycarbonyl)amino) phenoxy)pyrrolidine-1-carboxylate Step 1: To a solution of 3-chloro-5-nitro-phenol (5.00 g, 28.8 mmol, 1.00 eq), tert-butyl 3-hydroxypyrrolidine-1-carboxylate (5.93 g, 31.7 mmol, 1.10 eq) and triphenylphosphine (8.31 g, 31.7 mmol, 1.10 eq) in tetrahydrofuran (2.00 mL) was added diisopropyl azodiformate (6.16 mL, 31.7 mmol, 1.10 eq) at 0° C. The reaction was stirred at 25° C. for 12 h. The mixture was concentrated under reduced pressure to give a residue. The residue was purified by reversed phase preparative HPLC to afford tert-butyl 3-(3-chloro-5-nitrophenoxy)pyrrolidine-1-carboxylate.

Step 2: A mixture of tert-butyl 3-(3-chloro-5-nitro-phenoxy)pyrrolidine-1-carboxylate (3.00 g, 8.75 mmol, 100 eq), iron powder (1.47 g, 26.2 mmol, 3.00 eq) and ammonium chloride (2.34 g, 43.8 mmol, 5.00 eq) in methanol (20.0 mL) and water (10.0 mL) was stirred at 80° C. for 2 h. The mixture was filtered, and the filtrate was concentrated under reduced pressure to give a residue. It was added to water (80.0 mL) and saturated sodium bicarbonate (40.0 mL) and stirred for 10 min.

The aqueous layer was extracted with ethyl acetate (3×60.0 mL). The combined organic layers were washed with brine (100 mL), dried over anhydrous sodium sulfate, filtered, and concentrated under reduced pressure to afford tert-butyl 3-(3-amino-5-chlorophenoxy)pyrrolidine-1-carboxylate.

Compound 21: General procedure A with variant i) was used for the preparation from compound VIII employing phenyl (3-(8-oxa-3-azabicyclo[3.2.1]octan-3-ylmethyl)-5-chloro-4-methylphenyl)carbamate. $^{1}$H NMR (400 MHz, DMSO-d$_6$) δ=11.05-10.93 (m, 1H), 9.95-9.84 (m, 1H), 7.79 (s, 1H), 7.71-7.61 (m, 2H), 7.51 (s, 1H), 7.33 (d, J=1.7 Hz, 1H), 5.27 (s, 2H), 5.12 (dd, J=5.2, 13.4 Hz, 1H), 4.51-4.42 (m, 1H), 4.39-4.29 (m, 1H), 4.21-4.15 (m, 2H), 2.95-2.86 (m, 1H), 2.60 (br dd, J=1.7, 16.8 Hz, 1H), 2.45 (br d, J=10.3 Hz, 4H), 2.41-2.36 (m, 1H), 2.29-2.25 (m, 3H), 2.19 (br d, J=9.8 Hz, 2H), 2.04-1.98 (m, 1H), 1.88-1.79 (m, 2H), 1.68 (br dd, J=4.1, 7.0 Hz, 2H). MS (ESI) m/z 567.2 [M+H]$^+$ Step 1: To a solution of (3-chloro-2-methyl-5-nitro-phenyl)methanol (2.00 g, 9.92 mmol, 1.00 eq) in dichloromethane (30.0 mL) was added thionyl chloride (3.60 mL, 49.6 mmol, 5.00 eq) at 25° C. The reaction was stirred at 25° C. for 12 h. The reaction was quenched by addition of ice water (20.0 mL) at 0° C., and the aqueous layer was extracted with ethyl acetate (3×20.0 mL). The combined organic layers were washed with brine (30.0 mL), dried over anhydrous sodium sulfate, filtered, and concentrated under reduced pressure to afford 1-chloro-3-(chloromethyl)-2-methyl-5-nitrobenzene.

Step 2: To a solution of 1-chloro-3-(chloromethyl)-2-methyl-5-nitro-benzene (1.40 g, 6.36 mmol, 1.00 eq), 8-oxa-3-azabicyclo[3.2.1]octane (1.14 g, 7.63 mmol, 1.20 eq, HCl) and potassium carbonate (2.64 g, 19.1 mmol, 3.00 eq) in acetonitrile (20.0 mL) was added potassium iodide (106 mg, 0.64 mmol, 0.10 eq) at 25° C. The reaction was stirred at 80° C. for 12 h. The mixture was filtered and concentrated under reduced pressure to give a residue. The residue was purified by silica gel column chromatography (petroleum ether/ethyl acetate=10/1 to 2/1) to afford 3-(3-chloro-2-methyl-5-nitrobenzyl)-8-oxa-3-azabicyclo[3.2.1]octane.

Step 3: To a solution of 3-(3-chloro-2-methyl-5-nitrobenzyl)-8-oxa-3-azabicyclo[3.2.1]octane (1.00 g, 3.37 mmol, 1.00 eq) in methanol (20.0 mL) were added iron powder (941 mg, 16.9 mmol, 5.00 eq), ammonium chloride (901 mg, 16.9 mmol, 5.00 eq) and water (5.00 mL) at 25° C. The reaction was stirred at 80° C. for 2 h. The mixture was concentrated under reduced pressure to give a residue. Sodium bicarbonate (20.0 mL) was added, and the aqueous layer was extracted with ethyl acetate (3×20.0 mL). The combined organic layers were washed with brine (20.0 mL), dried over anhydrous sodium sulfate, filtered, and concentrated under reduced pressure to afford 3-(8-oxa-3-azabicyclo[3.2.1]octan-3-ylmethyl)-5-chloro-4-methylaniline.

Step 4: To a solution of 3-(8-oxa-3-azabicyclo[3.2.1]octan-3-ylmethyl)-5-chloro-4-methylaniline (200 mg, 749 µmol, 1.00 eq) in acetonitrile (5.00 mL) were added pyridine (0.30 mL, 3.75 mmol, 5.00 eq) and phenyl chloroformate (0.14 mL, 1.12 mmol, 1.50 eq). The reaction was stirred at 25° C. for 1 h. The mixture was concentrated and the obtained residue was purified by standard methods to afford phenyl (3-(8-oxa-3-azabicyclo[3.2.1]octan-3-ylmethyl)-5-chloro-4-methylphenyl)carbamate.

Compound 22: General procedure A with variant ii) was used for the preparation from compound VIII employing cyclopropylmethanamine. $^1$H NMR (400 MHz, DMSO-$d_6$) δ=10.99 (s, 1H), 7.71 (s, 1H), 7.60 (s, 2H), 7.40 (br t, J=5.6 Hz, 1H), 5.16-5.06 (m, 3H), 4.49-4.42 (m, 1H), 4.36-4.29 (m, 1H), 2.96-2.85 (m, 3H), 2.65-2.56 (m, 1H), 2.43-2.37 (m, 1H), 2.06-1.96 (m, 1H), 0.96-0.85 (m, 1H), 0.43-0.35 (m, 2H), 0.19-0.09 (m, 2H). MS (ESI) m/z 372.1 [M+H]$^+$ Compound 23: General procedure A with variant ii) was used for the preparation from compound VIII employing piperidine. $^1$H NMR (400 MHz, DMSO-$d_6$) δ=11.06-10.92 (m, 1H), 7.69 (s, 1H), 7.64-7.54 (m, 2H), 5.17 (s, 2H), 5.11 (dd, J=5.1, 13.3 Hz, 1H), 4.51-4.41 (m, 1H), 4.38-4.28 (m, 1H), 3.37 (br s, 4H), 2.97-2.85 (m, 1H), 2.60 (br d, J=17.6 Hz, 1H), 2.40 (br dd, J=4.3, 13.0 Hz, 1H), 2.06-1.95 (m, 1H), 1.59-1.50 (m, 2H), 1.48-1.39 (m, 4H). MS (ESI) m/z 386.1 [M+H]$^+$ Compound 24: General procedure A with variant i) was used for the preparation from compound VIII employing phenyl (3-(difluoromethoxy)-4-methylphenyl)carbamate. $^1$H NMR (400 MHz, DMSO-$d_6$) δ=10.99 (br s, 1H), 9.92 (br s, 1H), 7.79 (s, 1H), 7.70-7.61 (m, 2H), 7.41 (s, 1H), 7.19 (s, 2H), 7.09 (t, J=74 Hz, 1H), 5.27 (s, 2H), 5.12 (dd, J=5.1, 13.2 Hz, 1H), 4.52-4.43 (m, 1H), 4.38-4.30 (m, 1H), 2.96-2.85 (m, 1H), 2.63-2.57 (m, 1H), 2.40 (br dd, J=4.3, 13.1 Hz, 1H), 2.15 (s, 3H), 2.04-1.96 (m, 1H). MS (ESI) m/z 474.1 [M+H]$^+$ Step 1: To a solution of 2-methyl-5-nitrophenol (5.00 g, 32.7 mmol, 1.00 eq) and sodium 2-chloro-2,2-difluoroacetate (12.4 g, 81.6 mmol, 2.50 eq) in dimethylformamide (50.0 mL) was added caesium carbonate (21.3 g, 65.3 mmol, 2.00 eq) in portions. The reaction was stirred at 100° C. for 2 h. The mixture was diluted with water (800 mL) and extracted with ethyl acetate (3×100 mL). The combined organic layers were washed with brine (80.0 mL), dried over anhydrous sodium sulfate, filtered, and concentrated under reduced pressure to give a residue. The residue was purified by silica gel column chromatography (petroleum ether/ethyl acetate=1/0 to 10/1) to afford 2-(difluoromethoxy)-1-methyl-4-nitrobenzene.

Step 2: To a solution of 2-(difluoromethoxy)-1-methyl-4-nitrobenzene (4.85 g, 23.8 mmol, 1.00 eq) and ammonium chloride (6.39 g, 119 mmol, 5.00 eq) in methanol (40.0 mL) and water (40.0 mL) was added iron powder (4.00 g, 71.6 mmol, 3.00 eq) in portions. The reaction was stirred at 80° C. for 2 h. The mixture was filtered, and the filtrate was concentrated under reduced pressure to give a residue. Water (100 mL) was added, and the mixture was extracted with ethyl acetate (3×50.0 mL). The combined organic layers were washed with brine (20 mL), dried over anhydrous sodium sulfate, filtered, and concentrated to afford 3-(difluoromethoxy)-4-methylaniline.

Step 3: To a solution of 3-(difluoromethoxy)-4-methylaniline (1.00 g, 5.78 mmol, 1.00 eq) and pyridine (1.40 mL, 17.3 mmol, 3.00 eq) in acetonitrile (10.0 mL) was added phenyl chloroformate (1.09 mL, 8.66 mmol, 1.50 eq) dropwise. The reaction was stirred at 25° C. for 12 h. The mixture was diluted with water (150 mL) and extracted with ethyl acetate (3×50.0 mL). The combined organic layers were washed with brine (20.0 mL), dried over anhydrous sodium sulfate, filtered, and concentrated and the obtained residue was purified by standard methods to afford phenyl (3-(difluoromethoxy)-4-methylphenyl)carbamate.

Compound 25: General procedure A with variant i) was used for the preparation from compound VIII employing phenyl (3-(difluoromethoxy)-4-methyl-5-(morpholinomethyl)phenyl)carbamate. $^1$H NMR (400 MHz, DMSO-$d_6$) δ=10.99 (s, 1H), 9.89 (s, 1H), 8.21 (s, 1H), 7.78 (s, 1H), 7.70-7.60 (m, 2H), 7.35 (br s, 1H), 7.26 (d, J=1.8 Hz, 1H), 7.25-6.85 (m, 1H), 5.27 (s, 2H), 5.16-5.08 (m, 1H), 4.51-4.28 (m, 2H), 3.55 (br t, J=4.3 Hz, 4H), 3.39 (s, 2H), 2.98-2.84 (m, 1H), 2.65-2.56 (m, 1H), 2.45-2.38 (m, 1H), 2.35 (br s, 4H), 2.14 (s, 3H), 2.06-1.96 (m, 1H). MS (ESI) m/z 573.4 [M+H]$^+$ Step 1: To a solution of 2-methyl-5-nitro-benzoic acid (10.0 g, 55.2 mmol, 1.00 eq) in sulfuric acid (20.0 mL) was added N-Iodosuccinimide (14.9 g, 66.3 mmol, 1.20 eq). The reaction was stirred at 60° C. for 2 h. The mixture was diluted with ice water (200 mL) and the resulting precipitate was collected by filtration. The filter cake was washed with water (100 mL) and dried under vacuum to afford 3-iodo-2-methyl-5-nitro-benzoic acid.

Step 2: To a solution of 3-iodo-2-methyl-5-nitro-benzoic acid (5.00 g, 16.3 mmol, 1.00 eq), copper iodide (310 mg, 1.63 mmol, 0.100 eq), and quinolin-8-ol (0.56 mL, 3.26 mmol, 0.200 eq) in water (3.00 mL) and dimethylsulfoxide (3.00 mL) was added potassium hydroxide (3.65 g, 65.1 mmol, 4.00 eq). The reaction was stirred at 100° C. for 12 h. The mixture was diluted with water (50.0 mL) and extracted with ethyl acetate (2×50.0 mL). The combined organic layers were washed with water (50.0 mL), dried over anhydrous sodium sulfate, filtered, and concentrated under reduced pressure to afford 3-hydroxy-2-methyl-5-nitro-benzoic acid.

Step 3: To a solution of 3-hydroxy-2-methyl-5-nitrobenzoic acid (3.20 g, 16.2 mmol, 1.00 eq) and morpholine (1.71 mL, 19.5 mmol, 1.20 eq) in dichloromethane (100 mL) were added triethylamine (2.26 mL, 16.2 mmol, 1.00 eq) and O-(7-azabenzotriazol-1-yl)-N,N,N,N-tetramethyluroniumhexafluorophosphate (7.41 g, 19.5 mmol, 1.20 eq) at 20° C. The reaction was stirred at 20° C. for 12 h. The mixture was concentrated under reduced pressure to afford a residue.

The residue was diluted with water (100 mL) and extracted with ethyl acetate (100 mL). The organic layer was washed with water (100 mL), dried over anhydrous sodium sulfate, filtered, and the filtrate was concentrated under reduced pressure to give a residue. The residue was purified by silica gel column chromatography (petroleum ether/ethyl acetate=1/1 to 0/1) to afford (3-hydroxy-2-methyl-5-nitrophenyl)-morpholino-methanone.

Step 4: A solution of (3-hydroxy-2-methyl-5-nitro-phenyl)-morpholino-methanone (2.00 g, 7.51 mmol, 1.00 eq), potassium carbonate (2.08 g, 15.0 mmol, 2.00 eq) and sodium 2-chloro-2,2-difluoroacetate (4.58 g, 30.0 mmol, 4.00 eq) in dimethylformamide (24.0 mL) and water (3.00 mL) was stirred at 100° C. for 12 h. The mixture was diluted with water (150 mL) and extracted with ethyl acetate (3×100 mL). The combined organic layers were washed with brine (50.0 mL), dried over sodium sulfate, filtered, and concentrated under reduced pressure to give a residue. The residue was purified by silica gel column chromatography (petroleum ether/ethyl acetate=3/1) to afford (3-(difluoromethoxy)-2-methyl-5-nitrophenyl)(morpholino)methanone.

Step 5: To a solution of (3-(difluoromethoxy)-2-methyl-5-nitrophenyl)(morpholino)methanone (1.70 g, 5.38 mmol, 1.00 eq) in tetrahydrofuran (3.00 mL) was added borane dimethyl sulfide complex (10 M, 1.08 mL, 2.00 eq) dropwise at 0° C. under nitrogen atmosphere. The reaction was stirred at 60° C. for 4 h. The reaction was quenched by addition with methanol (5.00 mL) and the solvents were removed under reduced pressure to afford 4-(3-(difluoromethoxy)-2-methyl-5-nitrobenzyl)morpholine.

Step 6: A solution of 4-(3-(difluoromethoxy)-2-methyl-5-nitrobenzyl)morpholine (1.50 g, 4.96 mmol, 1.00 eq), iron powder (1.94 g, 34.7 mmol, 7.00 eq) and ammonium chloride (1.86 g, 34.7 mmol, 7.00 eq) in methanol (5.00 mL) and water (5.00 mL) was stirred at 80° C. for 2 h. The mixture was filtered, and the filtrate was concentrated under reduced pressure to afford 3-(difluoromethoxy)-4-methyl-5-(morpholinomethyl)aniline.

Step 7: To a solution of 3-(difluoromethoxy)-4-methyl-5-(morpholinomethyl)aniline (500 mg, 1.84 mmol, 1.00 eq) in acetonitrile (5.00 mL) were added pyridine (0.45 mL, 5.51 mmol, 3.00 eq) and phenyl chloroformate (0.28 mL, 2.20 mmol, 1.20 eq). The reaction was stirred at 25° C. for 2 h. The mixture was diluted with ethyl acetate (80.0 mL) and water (80.0 mL). The organic layer was separated, and the aqueous phase was extracted with ethyl acetate (3×50.0 mL). The combined organic layers were dried over sodium sulfate, filtered, and concentrated and the obtained residue was purified by standard methods to afford phenyl (3-(difluoromethoxy)-4-methyl-5-(morpholinomethyl)phenyl) carbamate.

Compound 26: General procedure A with variant ii) was used for the preparation from compound VIII employing pyrrolidine. $^1$H NMR (400 MHz, DMSO-$d_6$) δ=10.99 (s, 1H), 7.70 (s, 1H), 7.65-7.58 (m, 2H), 5.17 (s, 2H), 5.12 (dd, J=5.1, 13.3 Hz, 1H), 4.51-4.41 (m, 1H), 4.37-4.27 (m, 1H), 3.31-3.25 (m, 4H), 2.98-2.86 (m, 1H), 2.60 (br d, J=17.5 Hz, 1H), 2.43-2.32 (m, 1H), 2.05-1.97 (m, 1H), 1.86-1.76 (m, 4H). MS (ESI) m/z 372.2 [M+H]$^+$ Compound 27: General procedure A with variant ii) was used for the preparation from compound VIII employing 3-methylbutan-1-amine. $^1$H NMR (400 MHz, DMSO-$d_6$) δ=10.99 (s, 1H), 7.70 (s, 1H), 7.66-7.55 (m, 2H), 7.28 (br t, J=5.4 Hz, 1H), 5.22-5.06 (m, 3H), 4.52-4.42 (m, 1H), 4.38-4.28 (m, 1H), 3.06-2.98 (m, 2H), 2.97-2.86 (m, 1H), 2.64-2.57 (m, 1H), 2.44-2.36 (m, 1H), 2.06-1.97 (m, 1H), 1.63-1.50 (m, 1H), 1.30 (q, J=6.9 Hz, 2H), 0.86 (d, J=6.6 Hz, 6H). MS (ESI) m/z 388.2 [M+H]$^+$ Compound 28: General procedure A with variant ii) was used for the preparation from compound VIII employing cyclohexanamine. $^1$H NMR (400 MHz, DMSO-$d_6$) δ=11.00 (s, 1H), 7.72 (s, 1H), 7.61 (s, 2H), 7.25 (br d, J=7.9 Hz, 1H), 5.18-5.08 (m, 3H), 4.50-4.42 (m, 1H), 4.37-4.29 (m, 1H), 3.30-3.22 (m, 1H), 2.98-2.86 (m, 1H), 2.61 (br dd, J=2.1, 15.6 Hz, 1H), 2.44-2.34 (m, 1H), 2.06-1.95 (m, 1H), 1.76 (br d, J=11.7 Hz, 2H), 1.71-1.61 (m, 2H), 1.54 (br d, J=12.8 Hz, 1H), 1.31-1.07 (m, 5H). MS (ESI) m/z 400.2 [M+H]$^+$ Compound 29: General procedure A with variant ii) was used for the preparation from compound VIII employing cyclopentanamine. $^1$H NMR (400 MHz, DMSO-$d_6$) δ=10.98 (br s, 1H), 7.71 (s, 1H), 7.60 (s, 2H), 7.31 (br d, J=7.1 Hz, 1H), 5.19-5.07 (m, 3H), 4.50-4.41 (m, 1H), 4.37-4.28 (m, 1H), 3.85-3.74 (m, 1H), 2.98-2.85 (m, 1H), 2.65-2.57 (m, 1H), 2.43-2.34 (m, 1H), 2.05-1.95 (m, 1H), 1.83-1.71 (m, 2H), 1.65-1.54 (m, 2H), 1.52-1.35 (m, 4H). MS (ESI) m/z 386.1 [M+H]$^+$ Compound 30: General procedure A with variant ii) was used for the preparation from compound VIII employing 3-phenoxypyrrolidine. $^1$H NMR (400 MHz, DMSO-$d_6$) δ=11.00 (s, 1H), 7.77-7.68 (m, 1H), 7.68-7.56 (m, 2H), 7.37-7.20 (m, 2H), 7.05-6.84 (m, 3H), 5.30-5.08 (m, 3H), 5.07-4.98 (m, 1H), 4.54-4.40 (m, 1H), 4.38-4.27 (m, 1H), 3.72-3.57 (m, 1H), 3.55-3.41 (m, 3H), 2.97-2.87 (m, 1H), 2.65-2.58 (m, 1H), 2.41 (br dd, J=4.5, 12.8 Hz, 1H), 2.19-1.99 (m, 3H). MS (ESI) m/z 464.1 [M+H]$^+$ Step 1: To a solution of tert-butyl 3-hydroxypyrrolidine-1-carboxylate (3.00 g, 16.0 mmol, 1.00 eq) and triethylamine (5.58 mL, 40.0 mmol, 2.50 eq) in dichloromethane (30.0 mL) was added methanesulfonyl chloride (1.74 mL, 22.4 mmol, 1.40 eq) dropwise at 0° C. The reaction was stirred at 25° C. for 2 h. The mixture was diluted with water (150 mL) and extracted with ethyl acetate (3×80.0 mL). The combined organic layers were washed with brine (60.0 mL), dried over sodium sulfate, filtered, and concentrated under reduced pressure to afford tert-butyl 3-((methylsulfonyl)oxy)pyrrolidine-1-carboxylate.

Step 2: To a solution of tert-butyl 3-((methylsulfonyl)oxy)pyrrolidine-1-carboxylate (1.00 g, 3.77 mmol, 1.00 eq) and phenol (0.40 mL, 4.52 mmol, 1.20 eq) in dimethylformamide (10.0 mL) was added caesium carbonate (3.68 g, 11.3 mmol, 3.00 eq) in one portion. The reaction was stirred at 80° C. for 12 h. The mixture was diluted with water (50.0 mL) and extracted with ethyl acetate (3×60.0 mL). The combined organic layers were washed with brine (20.0 mL), dried over sodium sulfate, filtered, and concentrated under reduced pressure to give a residue. The residue was purified by silica gel column chromatography (petroleum ether/ethyl acetate=20/1 to 5/1) and then by reversed phase preparative HPLC to afford tert-butyl 3-phenoxypyrrolidine-1-carboxylate.

Step 3: A solution of tert-butyl 3-phenoxypyrrolidine-1-carboxylate (460 mg, 1.75 mmol, 1.00 eq) in 4 M hydrochloric acid/dioxane (4.00 mL) was stirred at 25° C. for 1 h and concentrated to afford 3-phenoxypyrrolidine.

Compound 31: General procedure A with variant i) was used for the preparation from compound VIII employing phenyl (3-(difluoromethoxy)-5-fluorophenyl) carbamate. $^1$H NMR (400 MHz, DMSO-$d_6$) δ=11.00 (br s, 1H), 10.25 (s, 1H), 7.80 (s, 1H), 7.72-7.62 (m, 2H), 7.24 (t, J=73.2 Hz, 1H), 7.23-7.19 (m, 1H), 7.16 (s, 1H), 6.76 (td, J=2.2, 9.7 Hz, 1H), 5.30 (s, 2H), 5.13 (dd, J=5.1, 13.3 Hz, 1H), 4.51-4.45 (m, 1H), 4.38-4.32 (m, 1H), 2.95-2.86 (m, 1H), 2.64-2.60 (m, 1H), 2.46-2.36 (m, 1H), 2.05-1.98 (m, 1H). MS (ESI) m/z 478.1 [M+H]$^+$ Step 1: To a solution of methanol (3.00 mL, 74.1 mmol, 3.93 eq) in N-methyl-pyrrolidone (10.0 mL) was added sodium hydride (60% dispersion in mineral oil) (830 mg, 20.7 mmol, 1.10 eq). The reaction was stirred at 0° C. for 1 h, then 1,3-difluoro-5-nitro-benzene (3.00 g, 18.9 mmol, 1.00 eq) was added. The reaction was stirred at 25° C. for another 11 h. The reaction was quenched with 1M hydrochloric acid (40.0 mL) and extracted with ethyl acetate (3×30.0 mL). The combined organic layers were washed with brine (15.0 mL), dried over anhydrous sodium sulfate, filtered, and concentrated under reduced pressure give a residue. The residue was purified by silica gel column chromatography (petroleum ether/ethyl acetate=10/1 to 1/1) to afford 1-fluoro-3-methoxy-5-nitro-benzene.

Step 2: To a solution of 1-fluoro-3-methoxy-5-nitro-benzene (2.50 g, 14.6 mmol, 1.00 eq) in dichloromethane (15.0 mL) was added boron tribromide (11.0 g, 43.8 mmol, 4.22 mL, 3.00 eq) at −78° C. The reaction was stirred at −78° C. for 1 h, and then at 25° C. for 11 h. The reaction was quenched with methanol (30.0 mL) and concentrated under reduced pressure to give a residue. The residue was purified by silica gel column chromatography (petroleum ether/ethyl acetate=10/1 to 5/1) to afford 3-fluoro-5-nitro-phenol.

Step 3: A solution of 3-fluoro-5-nitro-phenol (0.500 g, 3.18 mmol, 1.00 eq), sodium 2-chloro-2,2-difluoro-acetate (1.46 g, 9.55 mmol, 3.00 eq) and potassium carbonate (879 mg, 6.37 mmol, 2.00 eq) in dimethylformamide (10.0 mL) and water (2.00 mL) was stirred at 100° C. for 12 h. The mixture was poured into water (20.0 mL). The aqueous phase was extracted with ethyl acetate (3×30 mL). The combined organic layers were washed with brine (30.0 mL), dried over anhydrous sodium sulfate, filtered, and concentrated under reduced pressure to give a residue. The residue was purified by silica gel column chromatography (petroleum ether/ethyl acetate=10/1 to 5/1) to afford 1-(difluoromethoxy)-3-fluoro-5-nitrobenzene.

Step 4: A mixture of 1-(difluoromethoxy)-3-fluoro-5-nitrobenzene (700 mg, 3.38 mmol, 1.00 eq), ferrous powder (566 mg, 10.1 mmol, 3.00 eq) and ammonium chloride (904 mg, 16.9 mmol, 5.00 eq) in methanol (6.00 mL) and water (3.00 mL) was stirred at 80° C. for 1 h. The mixture was filtered, and the filtrate was concentrated under reduced pressure to afford 3-(difluoromethoxy)-5-fluoroaniline.

Step 5: To a solution of 3-(difluoromethoxy)-5-fluoroaniline (300 mg, 1.69 mmol, 1.00 eq) in acetonitrile (20.0 mL) were added pyridine (0.68 mL, 8.42 mmol, 4.97 eq) and phenyl chloroformate (0.25 mL, 2.00 mmol, 1.18 eq) at 0° C. The reaction was stirred at 25° C. for 1 h. The mixture was concentrated and the obtained residue was purified by standard methods to afford phenyl (3-(difluoromethoxy)-5-fluorophenyl)carbamate.

Compound 32: General procedure A with variant i) was used for the preparation from compound VIII employing phenyl (3-(difluoromethoxy)-4-fluorophenyl) carbamate. $^1$H NMR (400 MHz, DMSO-$d_6$) δ=11.00 (s, 1H), 10.04 (s, 1H), 7.80 (s, 1H), 7.71-7.67 (m, 1H), 7.67-7.63 (m, 1H), 7.58 (br d, J=6.6 Hz, 1H), 7.37-7.27 (m, 2H), 7.21 (t, J=73.2 Hz, 1H), 5.29 (s, 2H), 5.13 (br d, J=8.2 Hz, 1H), 4.46 (s, 1H), 4.40-4.30 (m, 1H), 2.92 (br d, J=1.6 Hz, 1H), 2.64-2.59 (m, 1H), 2.46-2.37 (m, 1H), 2.06-1.98 (m, 1H). MS (ESI) m/z 478.1 [M+H]$^+$ Step 1: To a solution of 2-fluoro-5-nitrophenol (500 mg, 3.18 mmol, 1.00 eq) and methyl 2-chloro-2,2-difluoroacetate (2.43 g, 15.9 mmol, 5.00 eq) in dimethylformamide (20.0 mL) and water (3.00 mL) was added potassium carbonate (880 mg, 6.37 mmol, 2.00 eq). The reaction was stirred at 100° C. for 12 h. Water (50.0 mL) was added, and the aqueous layer was extracted with ethyl acetate (3×20.0 mL). The organic layers were gathered, dried over anhydrous sodium sulfate, filtered, and concentrated under reduced pressure to give a residue. The residue was purified by silica gel column chromatography (petroleum ether/ethyl acetate=20/1 to 10/1) to afford 2-(difluoromethoxy)-1-fluoro-4-nitrobenzene.

Step 2: To a solution of 2-(difluoromethoxy)-1-fluoro-4-nitrobenzene (400 mg, 1.93 mmol, 1.00 eq) in methanol (9.00 mL) and water (3.00 mL) were added ammonium chloride (516 mg, 9.66 mmol, 5.00 eq) and ferrous powder (539 mg, 9.66 mmol, 5.00 eq). The reaction was stirred at 80° C. for 2 h. The mixture was filtered and concentrated under reduced pressure to afford 3-(difluoromethoxy)-4-fluoroaniline.

Step 3: To a solution of 3-(difluoromethoxy)-4-fluoroaniline (110 mg, 621 μmol, 1.00 eq) in acetonitrile (2.00 mL) were added pyridine (0.25 mL, 3.11 mmol, 5.00 eq) and phenyl chloroformate (0.08 mL, 0.68 mmol, 1.10 eq) at 0° C. The reaction was stirred at 0° C. for 0.5 h. The mixture was filtered, and the filtrate was concentrated and the obtained residue was purified by standard methods to afford phenyl (3-(difluoromethoxy)-4-fluorophenyl)carbamate.

Compound 33: General procedure A with variant i) was used for the preparation from compound VIII employing phenyl (3-ethoxy-4-methylphenyl) carbamate. $^1$H NMR (400 MHz, DMSO-$d_6$) δ=10.99 (br s, 1H), 9.68 (br s, 1H), 7.79 (s, 1H), 7.69-7.65 (m, 1H), 7.65-7.61 (m, 1H), 7.14 (br s, 1H), 7.00 (d, J=8.2 Hz, 1H), 6.90 (br d, J=7.9 Hz, 1H), 5.25 (s, 2H), 5.12 (dd, J=5.1, 13.3 Hz, 1H), 4.50-4.43 (m, 1H), 4.38-4.29 (m, 1H), 3.95 (q, J=6.8 Hz, 2H), 2.96-2.86 (m, 1H), 2.63-2.56 (m, 1H), 2.40 (br dd, J=4.5, 13.1 Hz, 1H), 2.07-2.05 (m, 3H), 2.01 (dt, J=2.1, 6.2 Hz, 1H), 1.33 (t, J=6.9 Hz, 3H). MS (ESI) m/z 452.2 [M+H]$^+$ Step 1: To a solution of 2-methyl-5-nitrophenol (1.00 g, 6.53 mmol, 1.00 eq) and iodoethane (0.57 mL, 7.18 mmol, 1.10 eq) in dimethylformamide (10.0 mL) was added potassium carbonate (2.71 g, 19.6 mmol, 3.00 eq) under nitrogen. The reaction was stirred at 40° C. for 2 h under nitrogen atmosphere. The mixture was poured into water (20.0 mL) and extracted with ethyl acetate (3×20.0 mL). The combined organic layers were gathered, washed with brine (10.0 mL), dried over anhydrous sodium sulfate, filtered, and concentrated under reduced pressure to give a residue. The residue was purified by silica gel column chromatography (petroleum ether/ethyl acetate=1/0 to 10/1) to afford 2-ethoxy-1-methyl-4-nitrobenzene.

Step 2: To a solution of 2-ethoxy-1-methyl-4-nitrobenzene (0.900 g, 4.97 mmol, 1.00 eq) in methanol (10.0 mL) and water (10.0 mL) were added iron powder (1.39 g, 24.8 mmol, 5.00 eq) and ammonium chloride (1.33 g, 24.8 mmol, 5.00 eq). The reaction was stirred at 80° C. for 2 h. The mixture was concentrated under reduced pressure to give a slurry. The slurry was poured into saturated sodium bicarbonate solution (20.0 mL) and extracted with ethyl acetate (3×20.0 mL). The combined organic layers were washed with brine (20.0 mL), dried over anhydrous sodium sulfate, filtered, and concentrated under reduced pressure to afford 3-ethoxy-4-methylaniline.

Step 3: To a solution of 3-ethoxy-4-methylaniline (500 mg, 3.31 mmol, 1.00 eq) in acetonitrile (5.00 mL) were added pyridine (1.33 mL, 16.5 mmol, 5.00 eq) and phenyl chloroformate (0.50 mL, 3.97 mmol, 1.20 eq) at 0° C. The reaction was stirred at 25° C. for 1 h. The mixture was concentrated and the obtained residue was purified by standard methods to afford phenyl (3-ethoxy-4-methylphenyl) carbamate.

Compound 34: General procedure A with variant i) was used for the preparation from compound VIII employing phenyl (4-methyl-3-(morpholinomethyl)-5-(trifluoromethoxy)phenyl) carbamate.

$^1$H NMR (400 MHz, DMSO-$d_6$) δ=11.00 (s, 1H), 10.26 (br s, 1H), 10.20 (br s, 1H), 7.80 (s, 1H), 7.74-7.62 (m, 3H), 7.58 (br s, 1H), 5.31 (s, 2H), 5.12 (dd, J=5.1, 13.3 Hz, 1H), 4.52-4.30 (m, 4H), 3.94 (br d, J=12.1 Hz, 2H), 3.75 (br t, J=11.6 Hz, 2H), 3.30-3.15 (m, 3H), 2.99-2.84 (m, 1H), 2.61

(br d, J=17.0 Hz, 1H), 2.43 (br dd, J=8.7, 13.3 Hz, 2H), 2.35-2.30 (m, 3H), 2.07-1.98 (m, 1H). MS (ESI) m/z 591.1 [M+H]$^+$

Step 1: To a solution of 2-methyl-5-nitro-benzoic acid (10.0 g, 55.2 mmol, 1.00 eq) in sulfuric acid (20.0 mL) was added N-Iodosuccinimide (14.9 g, 66.3 mmol, 1.20 eq). The reaction was stirred at 60° C. for 2 h. The mixture was diluted with ice water (200 mL) and filtered. The filter cake was washed with water (100 mL) and dried under vacuum to afford 3-iodo-2-methyl-5-nitro-benzoic acid.

Step 2: To a solution of 3-iodo-2-methyl-5-nitro-benzoic acid (5.00 g, 16.3 mmol, 1.00 eq), copper iodide (310 mg, 1.63 mmol, 0.10 eq) and quinolin-8-ol (563 µL, 3.26 mmol, 0.20 eq) in water (3.00 mL) and dimethylsulfoxide (3.00 mL) was added a solution of potassium hydroxide (3.65 g, 65.1 mmol, 4.00 eq). The reaction was stirred at 100° C. for 12 h. The mixture was diluted with water (50.0 mL) and extracted with ethyl acetate (2×50.0 mL). The combined organic layers were washed with water (50.0 mL), dried over anhydrous sodium sulfate, filtered, and concentrated under reduced pressure to afford 3-hydroxy-2-methyl-5-nitro-benzoic acid.

Step 3: To a solution of 3-hydroxy-2-methyl-5-nitro-benzoic acid (3.20 g, 16.2 mmol, 1.00 eq) and morpholine (1.71 mL, 19.5 mmol, 1.20 eq) in dichloromethane (100 mL) were added triethylamine (2.26 mL, 16.2 mmol, 1.00 eq) and O-(7-azabenzotriazol-1-yl)-N,N,N,N-tetramethyluroniumhexafluorophosphate (7.41 g, 19.5 mmol, 1.20 eq) at 20° C. The reaction was stirred at 20° C. for 12 h. The mixture was concentrated under reduced pressure to give a residue. The residue was diluted with water (100 mL) and extracted with ethyl acetate (100 mL). The organic layer was washed with water (100 mL), dried over anhydrous sodium sulfate, filtered, and the filtrate was concentrated under reduced pressure to give a residue. The residue was purified by silica gel column chromatography (petroleum ether/ethyl acetate=1/1 to 0/1) to afford (3-hydroxy-2-methyl-5-nitro-phenyl)-morpholino-methanone.

Step 4: To a solution of (3-hydroxy-2-methyl-5-nitro-phenyl)-morpholino-methanone (1.30 g, 4.88 mmol, 1.00 eq), silver trifluoromethanesulfonate (6.27 g, 24.4 mmol, 5.00 eq), 1-(chloromethyl)-4-fluoro-1,4-diazoniabicyclo[2.2.2]octane bis(tetrafluoroborate) (3.46 g, 9.77 mmol, 2.00 eq), N-fluorobenzenesulfonimide (3.08 g, 9.77 mmol, 2.00 eq) and caesium fluoride (4.45 g, 29.3 mmol, 1.08 mL, 6.00 eq) in toluene (130 mL) were added trimethyl(trifluoromethyl)silane (3.47 g, 24.4 mmol, 5.00 eq) and 2-fluoropyridine (2.10 mL, 24.4 mmol, 5.00 eq) under nitrogen. The reaction was stirred at 20° C. for 12 h under nitrogen. The mixture was filtered, and the filtrate was concentrated under reduced pressure to give a residue. The residue was diluted with water (100 mL) and extracted with ethyl acetate (100 mL). The organic layer was washed with water (20.0 mL), dried over anhydrous sodium sulfate, filtered, and the filtrate was concentrated under reduced pressure to give a residue. The residue was purified by silica gel column chromatography (petroleum ether/ethyl acetate=1/0 to 2/1) to afford (2-methyl-5-nitro-3-(trifluoromethoxy)phenyl)(morpholino)methanone.

Step 5: To a solution of (2-methyl-5-nitro-3-(trifluoromethoxy)phenyl)-morpholino-methanone (900 mg, 2.69 mmol, 1.00 eq) in tetrahydrofuran (15.0 mL) was added borane dimethyl sulfide complex (10.0 M, 539 µL, 2.00 eq) at 0° C. The reaction was stirred at 60° C. for 30 min. The mixture was quenched with methanol (2.00 mL) and concentrated under reduced pressure to give a residue. The residue was purified by reversed phase preparative HPLC to afford 4-(2-methyl-5-nitro-3-(trifluoromethoxy)benzyl)morpholine.

Step 6: To a solution of 4-(2-methyl-5-nitro-3-(trifluoromethoxy)benzyl)morpholine (400 mg, 1.25 mmol, 1.00 eq) in methanol (5.00 mL) and water (5.00 mL) was added iron powder (488 mg, 8.74 mmol, 7.00 eq) and ammonium chloride (468 mg, 8.74 mmol, 7.00 eq). The reaction was stirred at 80° C. for 2 h. The mixture was diluted with saturated sodium carbonate (1.00 mL) and extracted with ethyl acetate (2×10.0 mL). The combined organic layers were washed with water (5.00 mL), dried over anhydrous sodium sulfate, filtered, and the filtrate was concentrated under reduced pressure to give a residue. The residue was purified by silica gel column chromatography (petroleum ether/ethyl acetate=3/1 to 1/1) to afford 4-methyl-3-(morpholinomethyl)-5-(trifluoromethoxy)aniline.

Step 7: To a solution of 4-methyl-3-(morpholinomethyl)-5-(trifluoromethoxy)aniline (100 mg, 344 µmol, 1.00 eq) and potassium carbonate (57.1 mg, 413 µmol, 1.20 eq) in acetone (1.00 mL) was added phenyl chloroformate (47 µL, 379µ, 1.10 eq) at 25° C. The reaction was stirred at 25° C. for 1 h. The mixture was diluted with water (6.00 mL) and extracted with ethyl acetate (10.0 mL). The organic layer was dried over anhydrous sodium sulfate, filtered, and the filtrate was concentrated to afford phenyl (4-methyl-3-(morpholinomethyl)-5-(trifluoromethoxy)phenyl)carbamate.

Compound 35: General procedure A with variant ii) was used for the preparation from compound VIII employing 1-(pyridin-2-yl)piperidin-4-amine. $^1$H NMR (400 MHz, DMSO-d$_6$) δ=11.00 (s, 1H), 8.35-8.27 (m, 1H), 8.09 (dd, J=1.4, 4.9 Hz, 1H), 7.72 (s, 1H), 7.61 (s, 2H), 7.53-7.47 (m, 1H), 7.36 (br d, J=7.5 Hz, 1H), 6.83 (d, J=8.4 Hz, 1H), 6.59 (dd, J=5.0, 6.8 Hz, 1H), 5.17-5.08 (m, 3H), 4.50-4.43 (m, 1H), 4.37-4.30 (m, 1H), 4.20 (br d, J=13.1 Hz, 2H), 3.58 (br s, 1H), 2.92 (br s, 3H), 2.63-2.58 (m, 1H), 2.43-2.38 (m, 1H), 2.04-1.98 (m, 1H), 1.80 (br d, J=10.3 Hz, 2H), 1.41-1.30 (m, 2H). MS (ESI) m/z 478.2 [M+H]$^+$ Step 1: A solution of 2-fluoropyridine (1.79 mL, 20.8 mmol, 1.00 eq), tert-butyl piperidin-4-ylcarbamate (5.00 g, 25.0 mmol, 1.20 eq) and potassium carbonate (5.75 g, 41.6 mmol, 2.00 eq) in dimethylacetamide (20.0 mL) was stirred at 120° C. for 12 h. The mixture was poured into water (20.0 mL) and extracted with ethyl acetate (3×20.0 mL). The combined organic layers were washed with brine (10.0 mL), dried over anhydrous sodium sulfate, filtered, and concentrated under reduced pressure to give a residue. The residue was purified by silica gel column chromatography (petroleum ether/ethyl acetate=5/1 to 3/1) to afford tert-butyl (1-(pyridin-2-yl)piperidin-4-yl)carbamate.

Step 2: A solution of tert-butyl (1-(pyridin-2-yl)piperidin-4-yl)carbamate (1.27 g, 4.58 mmol, 1.00 eq) and hydrochloric acid/ethyl acetate (8.00 mL) in ethyl acetate (24.0 mL) was stirred at 25° C. for 2 h. The mixture was concentrated and the obtained residue was purified by standard methods and filtered to afford 1-(pyridin-2-yl)piperidin-4-amine.

Compound 36: General procedure A with variant ii) was used for the preparation from compound VIII employing 1-phenylpiperazine. $^1$H NMR (400 MHz, DMSO-d$_6$) δ=11.00 (s, 1H), 7.74 (s, 1H), 7.69-7.59 (m, 2H), 7.27-7.18 (m, 2H), 6.95 (d, J=7.9 Hz, 2H), 6.81 (t, J=7.3 Hz, 1H), 5.22 (s, 2H), 5.12 (dd, J=5.1, 13.3 Hz, 1H), 4.52-4.42 (m, 1H), 4.39-4.29 (m, 1H), 3.55 (br s, 4H), 3.17-3.09 (m, 4H), 2.92 (ddd, J=5.4, 13.7, 17.4 Hz, 1H), 2.63-2.58 (m, 1H), 2.44-2.35 (m, 1H), 2.06-1.98 (m, 1H). MS (ESI) m/z 463.2 [M+H]$^+$ Compound 37: General procedure A with variant i) was used for the preparation from compound VIII employing phenyl (3-methoxy-4-methylphenyl)carbamate. $^1$H NMR (400 MHz, DMSO-d$_6$) δ=11.00 (br s, 1H), 9.71 (br s, 1H), 7.80 (s, 1H), 7.71-7.67 (m, 1H), 7.66-7.61 (m, 1H), 7.17 (s, 1H), 7.01 (d, J=8.2 Hz, 1H), 6.93 (s, 1H), 5.27 (s, 2H), 5.16-5.10 (m, 1H), 4.46 (s, 1H), 4.37 (s, 1H), 3.73 (s, 3H), 2.97-2.86 (m, 1H), 2.58 (br s, 1H), 2.43-2.35 (m, 1H), 2.07 (s, 3H), 2.03 (br s, 1H). MS (ESI) m/z 438.1 [M+H]$^+$ To a solution of 3-methoxy-4-methylaniline (500 mg, 3.64 mmol, 1.00 eq) in acetonitrile (5.00 mL) were added pyridine (1.47 mL, 18.2 mmol, 5.00 eq) and phenyl chloroformate (0.91 mL, 7.29 mmol, 2.00 eq) at 0° C. The reaction was stirred at 0° C. for 1 h. The mixture was concentrated under reduced pressure to give a residue. The residue was purified by reversed phase preparative HPLC.

The desired fraction was collected and concentrated under reduced pressure to give concentrated solution. The solution was diluted with water/ethyl acetate (40.0 ml/80.0 ml). The organic layer was separated, dried over anhydrous sodium sulfate, filtered, and concentrated by standard methods to afford phenyl (3-methoxy-4-methylphenyl)carbamate.

Compound 38: General procedure A with variant i) was used for the preparation from compound VIII employing phenyl (4-chloro-2-methoxyphenyl)carbamate. $^1$H NMR (400 MHz, DMSO-d$_6$) δ=11.08-10.95 (m, 1H), 8.86 (s, 1H), 7.81 (s, 1H), 7.71-7.61 (m, 3H), 7.10 (d, J=2.3 Hz, 1H), 6.98 (dd, J=2.3, 8.6 Hz, 1H), 5.26 (s, 2H), 5.18-5.10 (m, 1H), 4.51-4.44 (m, 1H), 4.39-4.30 (m, 1H), 3.83 (s, 3H), 2.97-2.88 (m, 1H), 2.62-2.59 (m, 1H), 2.41 (br dd, J=4.4, 12.9 Hz, 1H), 2.06-1.98 (m, 1H). MS (ESI) m/z 458.1 [M+H]$^+$ To a solution of 4-chloro-2-methoxyaniline (1.00 g, 6.35 mmol, 1.00 eq) in acetonitrile (5.00 mL) were added pyridine (2.57 mL, 31.8 mmol, 5.01 eq) and phenyl chloroformate (0.88 mL 7.03 mmol, 1.11 eq) at 0° C. The reaction was stirred at 0° C. for 1 h. The mixture was concentrated and the obtained residue was purified by standard methods to afford phenyl (4-chloro-2-methoxyphenyl)carbamate.

Compound 39: General procedure A with variant i) was used for the preparation with from compound VIII employing phenyl (4-cyclopropylphenyl)carbamate. $^1$H NMR (400 MHz, DMSO-d$_6$) δ=10.99 (s, 1H), 9.68 (br s, 1H), 7.78 (s, 1H), 7.71-7.59 (m, 2H), 7.34 (br d, J=8.4 Hz, 2H), 6.98 (d, J=8.6 Hz, 2H), 5.25 (s, 2H), 5.18-5.08 (m, 1H), 4.53-4.43 (m, 1H), 4.37-4.29 (m, 1H), 2.99-2.85 (m, 1H), 2.65-2.56 (m, 1H), 2.47-2.34 (m, 1H), 2.05-1.97 (m, 1H), 1.89-1.79 (m, 1H), 0.92-0.84 (m, 2H), 0.62-0.55 (m, 2H). MS (ESI) m/z 434.3 [M+H]$^+$ To a solution of 4-cyclopropylaniline (500 mg, 3.75 mmol, 1.00 eq) in acetonitrile (5.00 mL) was added pyridine (0.91 mL, 11.3 mmol, 3.00 eq) and phenyl chloroformate (0.56 mL, 4.50 mmol, 1.20 eq). The reaction was stirred at 25° C. for 2 h. The mixture was diluted with ethyl acetate (50.0 mL) and water (50.0 mL). The organic layer was separated, and the aqueous phase was extracted with ethyl acetate (3×100 mL). The combined organic layers were dried over sodium sulfate, filtered, and concentrated and the obtained residue was purified by standard methods to afford phenyl (4-cyclopropylphenyl)carbamate.

Compound 40: General procedure A with variant i) was used for the preparation from compound VIII employing phenyl (3-chloro-5-((1-methylpyrrolidin-3-yl)methoxy)phenyl)carbamate. $^1$H NMR (400 MHz, DMSO-d$_6$) δ=10.99 (s, 1H), 9.99 (s, 1H), 8.15 (s, 1H), 7.79 (s, 1H), 7.70-7.61 (m, 2H), 7.13 (s, 1H), 7.06 (s, 1H), 6.67 (t, J=1.9 Hz, 1H), 5.28 (s, 2H), 5.12 (dd, J=5.2, 13.1 Hz, 1H), 4.52-4.43 (m, 1H), 4.38-4.30 (m, 1H), 3.85 (br dd, J=4.7, 7.0 Hz, 2H), 2.96-2.88 (m, 1H), 2.74-2.68 (m, 1H), 2.62 (br s, 1H), 2.58 (br s, 2H), 2.55-2.52 (m, 2H), 2.43-2.38 (m, 1H), 2.35 (s, 3H), 2.04-1.91 (m, 2H), 1.53 (br dd, J=6.3, 12.5 Hz, 1H). MS (ESI) m/z 541.2 [M+H]$^+$ Step 1: To a solution of tert-butyl 3-(hydroxymethyl) pyrrolidine-1-carboxylate (3.00 g, 14.9 mmol, 1.00 eq) and triethylamine (3.77 g, 37.3 mmol, 5.19 mL, 2.50 eq) in dichloromethane (30.0 mL) at 0° C. was added methylsulfamoyl chloride (1.50 mL, 19.4 mmol, 1.30 eq) dropwise under nitrogen atmosphere. The reaction was stirred at 25° C. for 2 h. The mixture was diluted with ethyl acetate (100 mL) and water (150 mL). The organic layer was separated, and the aqueous layer was extracted with ethyl acetate (3×100 mL). The organic layers were gathered, dried over sodium sulfate, filtered, and concentrated under reduced pressure to afford tert-butyl 3-(((methylsulfonyl)oxy) methyl)pyrrolidine-1-carboxylate.

Step 2: To a solution of tert-butyl 3-(((methylsulfonyl) oxy)methyl) pyrrolidine-1-carboxylate (3.00 g, 10.8 mmol, 1.00 eq) in dimethylformamide (30.0 mL) was added 3-chloro-5-nitrophenol (2.05 g, 11.8 mmol, 1.10 eq) and cesium carbonate (10.5 g, 32.2 mmol, 3.00 eq). The reaction was stirred at 80° C. for 12 h. The mixture was diluted with ethyl acetate (100 mL) and water (100 mL). The organic layer was separated, and the aqueous layer was extracted with ethyl acetate (3×80.0 mL). The organic layers were gathered, dried over sodium sulfate, filtered, and concentrated under reduced pressure to give a residue. The residue was purified by silica gel column chromatography (petroleum ether/ethyl acetate=3/1) to afford tert-butyl 3-((3-chloro-5-nitrophenoxy)methyl) pyrrolidine-1-carboxylate.

Step 3: To a solution of tert-butyl 3-((3-chloro-5-nitrophenoxy)methyl)pyrrolidine-1-carboxylate (1.10 g, 3.08 mmol, 1.00 eq) in ethyl acetate (5.00 mL) was added hydrochloric acid in ethyl acetate (4 M, 10 mL). The reaction was stirred at 25° C. for 2 h. The mixture was concentrated under reduced pressure to afford 3-((3-chloro-5-nitrophenoxy) methyl)pyrrolidine.

Step 4: To a solution of 3-((3-chloro-5-nitrophenoxy) methyl)pyrrolidine (1.50 g, 5.84 mmol, 1.00 eq) in 2,2,2-trifluoroethanol (10.0 mL) was added paraformaldehyde (0.80 mL, 29.2 mmol, 5.00 eq). The reaction was stirred at 60° C. for 0.5 h. Sodium borohydride (442 mg, 11.7 mmol, 2.00 eq) was added in portions, and the reaction was stirred at 60° C. for 1 h. The reaction was quenched with saturated ammonium chloride solution (10.0 mL) and concentrated under reduced pressure to give a residue. The residue was purified by reversed phase preparative HPLC to afford 3-((3-chloro-5-nitrophenoxy)methyl)-1-methylpyrrolidine.

Step 5: To a solution of 3-((3-chloro-5-nitrophenoxy) methyl)-1-methylpyrrolidine (1.20 g, 4.43 mmol, 1.00 eq) in methanol (6.00 mL) and water (6.00 mL) was added ammonium chloride (1.66 g, 31.0 mmol, 7.00 eq) and iron powder (1.73 g, 31.0 mmol, 7.00 eq). The reaction was stirred at 80° C. for 2 h. The mixture was filtered over Celite, and the filtrate was concentrated under reduced pressure to afford 3-chloro-5-((1-methylpyrrolidin-3-yl)methoxy)aniline.

Step 6: To a solution of phenyl chloroformate (0.28 mL, 2.24 mmol, 1.20 eq) in acetonitrile (5.00 mL) was added pyridine (0.45 mL, 5.61 mmol, 3.00 eq) and 3-chloro-5-((1-methylpyrrolidin-3-yl) methoxy)aniline (450 mg, 1.87 mmol, 1.00 eq). The reaction was stirred at 25° C. for 2 h. The mixture was concentrated and the obtained residue was purified by standard methods to afford phenyl (3-chloro-5-((1-methylpyrrolidin-3-yl) methoxy)phenyl)carbamate.

Compound 41: General procedure A with variant i) was used for the preparation from compound VIII employing phenyl (3-fluoro-4-methyl-5-(morpholinomethyl)phenyl)carbamate. $^1$H NMR (400 MHz, DMSO-d$_6$) δ=10.99 (s, 1H), 10.90 (br s, 1H), 10.12 (s, 1H), 7.79 (s, 1H), 7.71-7.61 (m, 2H), 7.50 (s, 1H), 7.36 (br d, J=11.7 Hz, 1H), 5.29 (s, 2H), 5.11 (dd, J=5.1, 13.3 Hz, 1H), 4.51-4.43 (m, 1H), 4.38-4.29 (m, 3H), 3.90-3.81 (m, 4H), 3.34-3.14 (m, 4H), 2.97-2.86 (m, 1H), 2.60 (br d, J=17.7 Hz, 1H), 2.46-2.36 (m, 1H), 2.29 (d, J=1.7 Hz, 3H), 2.09-1.94 (m, 1H). MS (ESI) m/z 525.3 [M+H]$^+$ Step 1: To a solution of 3-fluoro-2-methylbenzoic acid (10.0 g, 64.9 mmol, 1.00 eq) in sulfuric acid (100 mL) was added potassium nitrate (7.22 g, 71.4 mmol, 1.10 eq) in portions at 0° C. The reaction was stirred at 0° C. for 1 h. The mixture was poured into water (100 mL) and the resulting precipitate was collected by filtration. The filter cake was dried under vacuum, then added to water (100 mL) and extracted with ethyl acetate (3×80.0 mL). The combined organic layers were washed with brine (60.0 mL), dried over sodium sulfate, filtered, and concentrated under reduced pressure to afford 3-fluoro-2-methyl-5-nitrobenzoic acid.

Step 2: To a solution of 3-fluoro-2-methyl-5-nitrobenzoic acid (11.0 g, 55.2 mmol, 1.00 eq) in tetrahydrofuran (100 mL) was added borane dimethyl sulfide complex (10 M, 11.0 mL, 2.00 eq) at 0° C. The reaction was stirred at 25° C. for 12 h. The mixture was poured into methanol (200 mL) and concentrated under reduced pressure to give a residue. Water (150 mL) was added, and the pH was adjusted to pH=10 by addition of 15% sodium hydroxide solution. The aqueous layer was extracted with ethyl acetate (3×80.0 mL). The combined organic layers were washed with brine (50.0 mL), dried over sodium sulfate, filtered, and concentrated under reduced pressure to give a residue. The residue was purified by silica gel column chromatography (petroleum ether/ethyl acetate=4/1) to afford (3-fluoro-2-methyl-5-nitrophenyl)methanol.

Step 3: To a solution of (3-fluoro-2-methyl-5-nitrophenyl)methanol (870 mg, 4.70 mmol, 1.00 eq) in dichloromethane (10.0 mL) was added thionyl chloride (1.70 mL, 23.5 mmol, 5.00 eq) dropwise at 0° C. The reaction was stirred at 25° C. for 12 h. The mixture was concentrated under reduced pressure to afford 1-(chloromethyl)-3-fluoro-2-methyl-5-nitrobenzene.

Step 4: To a solution of 1-(chloromethyl)-3-fluoro-2-methyl-5-nitrobenzene (950 mg, 4.67 mmol, 1.00 eq) and triethylamine (1.62 mL, 11.7 mmol, 2.50 eq) in acetonitrile (10.0 mL) was added morpholine (0.51 mL, 5.83 mmol, 1.25 eq) dropwise. The reaction was stirred at 25° C. for 12 h. The mixture was concentrated under reduced pressure to give a residue. The residue was diluted with water (80.0 mL) and extracted with ethyl acetate (3×60.0 mL). The combined organic layers were washed with brine (40.0 mL), dried over sodium sulfate, filtered, and concentrated under reduced pressure to give a residue. The residue was purified by silica gel column chromatography (petroleum ether/ethyl acetate=4/1) to afford 4-(3-fluoro-2-methyl-5-nitrobenzyl)morpholine.

Step 5: To a solution of 4-(3-fluoro-2-methyl-5-nitrobenzyl)morpholine (1.00 g, 3.93 mmol, 1.00 eq) and ammonium chloride (1.05 g, 19.7 mmol, 5.00 eq) in methanol (8.00 mL) and water (2.00 mL) was added iron powder (1.10 g, 19.7 mmol, 5.00 eq) in portions. The reaction was stirred at 80° C. for 2 h. The mixture was filtered, and the filtrate was diluted with water (80.0 mL) and extracted with ethyl acetate (3×60.0 mL). The combined organic layers were washed with brine (40.0 mL), dried over sodium sulfate, filtered, and concentrated under reduced pressure to afford 3-fluoro-4-methyl-5-(morpholinomethyl)aniline.

Step 6: To a solution of 3-fluoro-4-methyl-5-(morpholinomethyl)aniline (300 mg, 1.34 mmol, 1.00 eq) and pyridine (0.54 mL, 6.69 mmol, 5.00 eq) in acetonitrile (5.00 mL) was added phenyl chloroformate (0.20 mL, 1.61 mmol, 1.20 eq) dropwise at 0° C. The reaction was stirred at 25° C. for 12 h. The mixture was diluted with water (50.0 mL) and extracted with ethyl acetate (3×40.0 mL). The combined organic layers were washed with brine (30.0 mL), dried over sodium sulfate, filtered, and concentrated and the obtained residue was purified by standard methods to afford phenyl (3-fluoro-4-methyl-5-(morpholinomethyl)phenyl)carbamate.

Compound 42: General procedure A with variant i) was used for the preparation from compound VIII employing phenyl (6-phenylpyridin-3-yl)carbamate. $^1$H NMR (400 MHz, DMSO-d$_6$) δ=10.99 (s, 1H), 10.23 (br s, 1H), 8.75 (s, 1H), 8.06-7.95 (m, 4H), 7.82 (s, 1H), 7.73-7.68 (m, 1H), 7.67-7.62 (m, 1H), 7.51-7.45 (m, 2H), 7.44-7.39 (m, 1H), 5.33 (s, 2H), 5.13 (dd, J=5.1, 13.2 Hz, 1H), 4.51-4.45 (m, 1H), 4.38-4.32 (m, 1H), 2.97-2.86 (m, 1H), 2.60 (br d, J=17.2 Hz, 1H), 2.41 (br dd, J=4.4, 12.9 Hz, 1H), 2.05-1.97 (m, 1H). MS (ESI) m/z 471.2 [M+H]$^+$ To a solution of 6-phenylpyridin-3-amine (300 mg, 1.76 mmol, 1.00 eq) and pyridine (0.71 mL, 8.81 mmol, 5.00 eq) in acetonitrile (5.00 mL) was added phenyl chloroformate (0.26 mL, 2.12 mmol, 1.20 eq) in portions at 0° C. The reaction was stirred at 25° C. for 1 h. The mixture was concentrated and the obtained residue was purified by standard methods to afford phenyl (6-phenylpyridin-3-yl)carbamate.

Compound 43: General procedure A with variant i) was used for the preparation from compound VIII employing phenyl (6-(tert-butyl)pyridin-3-yl)carbamate. $^1$H NMR (400 MHz, DMSO-d$_6$) δ=11.01 (s, 1H), 10.80-10.56 (m, 1H), 8.91-8.80 (m, 1H), 8.29 (br d, J=8.5 Hz, 1H), 7.87 (br d, J=8.6 Hz, 1H), 7.82 (s, 1H), 7.73-7.69 (m, 1H), 7.68-7.63 (m, 1H), 5.35 (s, 2H), 5.13 (dd, J=5.1, 13.3 Hz, 1H), 4.53-4.43 (m, 1H), 4.38-4.32 (m, 1H), 2.97-2.87 (m, 1H), 2.66-2.57 (m, 1H), 2.47-2.35 (m, 1H), 2.06-1.97 (m, 1H), 1.45-1.37 (m, 9H). MS (ESI) m/z 451.2 [M+H]$^+$ To a solution of 6-(tert-butyl)pyridin-3-amine (150 mg, 1.00 mmol, 1.00 eq) and pyridine (0.40 mL, 5.00 mmol, 5.00 eq) in acetonitrile (5.00 mL) was added phenyl chloroformate (0.15 mL, 1.20 mmol, 1.20 eq). The reaction was stirred at 25° C. for 1 h. The mixture was concentrated and the obtained residue was purified by standard methods to afford phenyl (6-(tert-butyl)pyridin-3-yl)carbamate.

Compound 44:

Step 1: A solution of 3-chloro-2-methyl-5-nitrophenol (260 mg, 1.39 mmol, 1.00 eq), tert-butyl 3-((methylsulfonyl)oxy)pyrrolidine-1-carboxylate (441 mg, 1.66 mmol, 1.20 eq) and potassium carbonate (575 mg, 4.16 mmol, 3.00 eq) in dimethylformamide (10.0 mL) was stirred at 80° C. for 4 h. The mixture was poured into water (20.0 mL) and extracted with ethyl acetate (3×20.0 mL). The combined organic layers were washed with brine (10.0 mL), dried over anhydrous sodium sulfate, filtered, and concentrated under reduced pressure to give a residue. The residue was purified by silica gel column chromatography (petroleum ether/ethyl acetate=1/0 to 5/1) to afford tert-butyl 3-(3-chloro-2-methyl-5-nitrophenoxy)pyrrolidine-1-carboxylate.

Step 2: To a mixture of tert-butyl 3-(3-chloro-2-methyl-5-nitrophenoxy)pyrrolidine-1-carboxylate (430 mg, 1.21 mmol, 1.00 eq), iron powder (337 mg, 6.03 mmol, 5.00 eq) and ammonium chloride (322 g, 6.03 mmol, 5.00 eq) in methanol (10.0 mL) was added water (10.0 mL) at 25° C. The reaction was stirred at 80° C. for 2 h. The mixture was concentrated under reduced pressure to give a residue. The residue was added to saturated sodium bicarbonate (20.0 mL) and extracted with ethyl acetate (3×20.0 mL). The combined organic layers were washed with brine (20.0 mL), dried over anhydrous sodium sulfate, filtered, and concentrated under reduced pressure to afford tert-butyl 3-(5-amino-3-chloro-2-methylphenoxy)pyrrolidine-1-carboxylate.

Step 3: To a solution of tert-butyl 3-(5-amino-3-chloro-2-methylphenoxy)pyrrolidine-1-carboxylate (170 mg, 520 µmol, 1.00 eq) and pyridine (0.21 mL, 2.60 mmol, 5.00 eq) in acetonitrile (5.00 mL) was added phenyl chloroformate (78.0 µL, 623 µmol, 1.20 eq) in portions at 0° C. The reaction was stirred at 25° C. for 1 h. The mixture was concentrated under reduced pressure to give a residue, which was purified by reversed phase preparative HPLC to afford tert-butyl 3-(3-chloro-2-methyl-5-((phenoxycarbonyl)amino)phenoxy)pyrrolidine-1-carboxylate.

Step 4: To a solution of 3-(6-(hydroxymethyl)-1-oxoisoindolin-2-yl)piperidine-2,6-dione VIII (100 mg, 365 µmol, 1.00 eq) and tert-butyl 3-(3-chloro-2-methyl-5-((phenoxycarbonyl)amino)phenoxy)pyrrolidine-1-carboxylate (179 mg, 401 µmol, 1.10 eq) in dimethylformamide (3.00 mL) was added sodium hydride (60% dispersion in mineral oil) (30.0 mg, 750 µmol, 2.06 eq) in portions at 0° C. The reaction was stirred at 25° C. for 1 h. The reaction was quenched with hydrochloric acid (1 M, 0.50 mL), and the solvents were removed under reduced pressure to give a residue. The residue was purified by reversed phase preparative HPLC to afford tert-butyl 3-(3-chloro-5-((((2-(2,6-dioxopiperidin-3-yl)-3-oxoisoindolin-5-yl)methoxy)carbonyl)amino)-2-methylphenoxy)pyrrolidine-1-carboxylate.

Step 5: To a solution of tert-butyl 3-(3-chloro-5-((((2-(2,6-dioxopiperidin-3-yl)-3-oxoisoindolin-5-yl)methoxy)carbonyl)amino)-2-methylphenoxy)pyrrolidine-1-carboxylate (120 mg, 191 µmol, 1.00 eq) in ethyl acetate (10.0 mL) was added hydrochloric acid/ethyl acetate (4 M, 4.62 mL, 96.5 eq). The reaction was stirred at 25° C. for 1 h. The mixture was concentrated to give a residue, and purified by a standard method to afford Compound 44 (hydrochloride). $^1$H NMR (400 MHz, DMSO-$d_6$) δ=10.99 (s, 1H), 9.95 (br s, 1H), 9.54 (br s, 1H), 9.49-9.38 (m, 1H), 7.79 (s, 1H), 7.70-7.62 (m, 2H), 7.25-7.11 (m, 2H), 5.28 (s, 2H), 5.12 (dd, J=5.1, 13.2 Hz, 1H), 5.02 (br s, 1H), 4.52-4.44 (m, 1H), 4.38-4.31 (m, 1H), 3.51-3.43 (m, 2H), 3.37-3.31 (m, 2H), 3.27 (br dd, J=6.9, 9.9 Hz, 1H), 2.97-2.85 (m, 1H), 2.60 (br d, J=16.9 Hz, 1H), 2.40 (br dd, J=4.5, 13.1 Hz, 1H), 2.23-2.16 (m, 1H), 2.14 (s, 3H), 2.06-1.95 (m, 1H). MS (ESI) m/z 527.2 [M+H]$^+$ Compound 45: General procedure A with variant i) was used for the preparation with from compound VIII employing phenyl (3-chloro-5-ethyl-4-methylphenyl)carbamate. $^1$H NMR (400 MHz, DMSO-$d_6$) δ=10.99 (s, 1H), 9.85 (s, 1H), 7.79 (s, 1H), 7.70-7.61 (m, 2H), 7.46 (s, 1H), 7.22 (d, J=1.9 Hz, 1H), 5.27 (s, 2H), 5.12 (dd, J=5.1, 13.3 Hz, 1H), 4.50-4.44 (m, 1H), 4.37-4.31 (m, 1H), 2.99-2.86 (m, 1H), 2.65-2.61 (m, 1H), 2.60-2.56 (m, 2H), 2.46-2.36 (m, 1H), 2.22 (s, 3H), 2.06-1.98 (m, 1H), 1.11 (t, J=7.5 Hz, 3H). MS (ESI) m/z 470.2 [M+H]$^+$ Step 1: To a solution of 2-chloro-1-methyl-4-nitrobenzene (0.60 mL, 2.91 mmol, 1.00 eq) in sulfuric acid (5.00 mL, 98% purity) was added N-iodosuccinimide (787 mg, 3.50 mmol, 1.20 eq) in portions. The reaction was stirred at 60° C. for 1 h. The mixture was quenched with sodium carbonate (10%, 100 mL) and extracted with ethyl acetate (3×30.0 mL). The combined organic layers were washed with brine (50.0 mL), dried over anhydrous sodium sulfate, filtered, and concentrated under reduced pressure to give a residue. The residue was purified by silica gel column chromatography (petroleum ether/ethyl acetate=1/0 to 10/1) to afford 1-chloro-3-iodo-2-methyl-5-nitrobenzene.

Step 2: To a solution of 1-chloro-3-iodo-2-methyl-5-nitrobenzene (760 mg, 2.55 mmol, 1.00 eq) in toluene (15.0 mL) were added diisopropylethylamine (1.34 mL, 7.66 mmol, 3.00 eq), [1,1'-bis(diphenylphosphino)ferrocene]dichloropalladium(II) (187 mg, 256 µmol, 0.10 eq) and potassium vinyltrifluoroborate (685 mg, 5.11 mmol, 2.00 eq) in portions under nitrogen. The reaction was stirred at 110° C. for 12 h. The mixture was concentrated under reduced pressure to give a residue, which was purified by silica gel column chromatography (petroleum ether/ethyl acetate=1/0 to 10/1) to afford 1-chloro-2-methyl-5-nitro-3-vinylbenzene.

Step 3: To a solution of 1-chloro-2-methyl-5-nitro-3-vinylbenzene (370 mg, 1.87 mmol, 1.00 eq) in tetrahydrofuran (6.00 mL) and ethyl acetate (6.00 mL) were added zinc chloride (12.7 µL, 271 µmol, 0.140 eq) and palladium on activated carbon (10%) (wetted with ca. 55% water) (50.0 mg) in portions under H$_2$ (15 Psi). The reaction was stirred at 25° C. for 1 h. The mixture was filtered, and the filtrate was concentrated under reduced pressure to give a residue. The residue was purified by silica gel column chromatography (petroleum ether/ethyl acetate=20/1 to 5/1) to afford 3-chloro-5-ethyl-4-methylaniline.

Step 4: To a solution of 3-chloro-5-ethyl-4-methylaniline (125 mg, 737 µmol, 1.00 eq) in acetonitrile (8.00 mL) were added pyridine (0.30 mL, 3.72 mmol, 5.04 eq) and phenyl chloroformate (0.11 mL, 886 µmol, 1.20 eq) in portions at 0° C. The reaction was stirred at 25° C. for 1 h. The mixture was concentrated and the obtained residue was purified by standard methods to afford phenyl (3-chloro-5-ethyl-4-methylphenyl)carbamate.

Compound 46: General procedure A with variant i) was used for the preparation from compound VIII employing phenyl (3-chloro-5-((1-methylpyrrolidin-3-yl)oxy)phenyl)carbamate. $^1$H NMR (400 MHz, DMSO-$d_6$) δ=10.99 (s, 1H), 9.99 (s, 1H), 8.15 (s, 1H), 7.79 (s, 1H), 7.70-7.62 (m, 2H), 7.15 (s, 1H), 6.99 (s, 1H), 6.60 (s, 1H), 5.28 (s, 2H), 5.12 (dd, J=5.0, 13.2 Hz, 1H), 4.82 (br d, J=5.4 Hz, 1H), 4.50-4.44 (m, 1H), 4.37-4.31 (m, 1H), 2.97-2.88 (m, 2H), 2.77 (br d, J=5.5 Hz, 1H), 2.72 (br d, J=6.1 Hz, 2H), 2.62 (br d, J=1.5 Hz, 1H), 2.58 (br s, 2H), 2.29 (s, 3H), 2.04-1.98 (m, 1H), 1.80-1.71 (m, 1H). MS (ESI) m/z 527.2 [M+H]$^+$ Step 1: To a solution of tert-butyl 3-(3-chloro-5-nitrophenoxy)pyrrolidine-1-carboxylate (2.00 g, 5.83 mmol, 1.00 eq) in ethyl acetate (10.0 mL) was added hydrochloric acid in ethyl acetate (4 M, 20.0 mL, 13.7 eq). The reaction was stirred at 25° C. for 1 h. The mixture was concentrated under reduced pressure to afford 3-(3-chloro-5-nitrophenoxy)pyrrolidine.

Step 2: To a solution of 3-(3-chloro-5-nitrophenoxy)pyrrolidine (1.00 g, 4.12 mmol, 1.00 eq) in methanol (6.00 mL) was added paraformaldehyde 37% purity (6.00 mL, 80.6 mmol, 19.60 eq), acetic acid (0.23 mL, 4.11 mmol, 1.00 eq) and sodium cyanoborohydride (1.29 g, 20.6 mmol, 5.00 eq) in portions. The reaction was stirred at 25° C. for 1 h. The mixture was concentrated under reduced pressure to give a residue. The residue was purified first by silica gel column chromatography (petroleum ether/ethyl acetate to ethyl acetate/methanol=3/1 to 0/1), then by reversed phase preparative HPLC, to afford 3-(3-chloro-5-nitrophenoxy)-1-methylpyrrolidine.

Step 3: To a solution of 3-(3-chloro-5-nitrophenoxy)-1-methylpyrrolidine (460 mg, 1.79 mmol, 1.00 eq) in methanol (15.0 mL) and water (8.00 mL) was added iron powder (300 mg, 5.37 mmol, 3.00 eq) and ammonium chloride (479 mg, 8.95 mmol, 5.00 eq) in portions. The reaction was stirred at 80° C. for 1 h. The mixture was concentrated under reduced pressure to give a residue, which was diluted with water (50.0 mL) and extracted with ethyl acetate (3×20.0 mL). The combined organic layers were washed with water, dried over anhydrous sodium sulfate, filtered, and concentrated under reduced pressure to afford 3-chloro-5-((1-methylpyrrolidin-3-yl)oxy)aniline.

Step 4: To a solution of 3-chloro-5-((1-methylpyrrolidin-3-yl)oxy)aniline (290 mg, 1.28 mmol, 1.00 eq) in acetonitrile (5.00 mL) was added pyridine (0.52 mL, 6.39 mmol, 5.00 eq) and phenyl chloroformate (0.19 mL, 1.54 mmol, 1.20 eq) in portions. The reaction was stirred at 25° C. for 1 h. The mixture was concentrated and the obtained residue was purified by standard methods to afford phenyl (3-chloro-5-((1-methylpyrrolidin-3-yl)oxy) phenyl) carbamate.

Compound 47: General procedure A with variant i) was used for the preparation from compound VIII employing (4-(tert-butyl)phenyl)carbamate. $^1$H NMR (400 MHz, DMSO-$d_6$) δ=10.99 (s, 1H), 9.70 (br s, 1H), 7.79 (s, 1H), 7.72-7.60 (m, 2H), 7.38 (br d, J=8.7 Hz, 2H), 7.32-7.25 (m, 2H), 5.26 (s, 2H), 5.16-5.08 (m, 1H), 4.52-4.43 (m, 1H), 4.39-4.28 (m, 1H), 2.98-2.85 (m, 1H), 2.64-2.63 (m, 1H), 2.65-2.56 (m, 1H), 2.47-2.33 (m, 1H), 2.07-1.97 (m, 1H), 1.24 (s, 9H). MS (ESI) m/z 450.2 [M+H]$^+$ To a solution of phenyl carbamate (0.63 mL, 5.03 mmol, 1.50 eq) and pyridine (0.81 mL, 10.1 mmol, 3.00 eq) in acetonitrile (5.00 mL) was added 4-(tert-butyl)aniline (0.53 mL, 3.35 mmol, 1.00 eq). The reaction was stirred at 25° C. for 12 h. The mixture was diluted with ethyl acetate (50.0 mL) and water (50.0 mL). The organic layer was separated, and the aqueous phase was extracted with ethyl acetate (3×50.0 mL). The combined organic layers were dried over sodium sulfate, filtered, and concentrated and the obtained residue was purified by standard methods to afford phenyl (4-(tert-butyl)phenyl)carbamate.

Compound 48: General procedure A with variant i) was used for the preparation from compound VIII employing phenyl (3-chloro-4-methyl-5-(2-morpholinoethoxy)phenyl) carbamate. $^1$H NMR (400 MHz, DMSO-$d_6$) δ=11.00 (s, 1H), 9.89 (s, 1H), 8.20 (s, 1H), 7.79 (s, 1H), 7.71-7.60 (m, 2H), 7.14 (br d, J=19.5 Hz, 2H), 5.27 (s, 2H), 5.13 (dd, J=5.1, 13.3 Hz, 1H), 4.51-4.43 (m, 1H), 4.38-4.30 (m, 1H), 4.03 (t, J=5.7 Hz, 2H), 3.58-3.55 (m, 4H), 2.96-2.87 (m, 1H), 2.72 (t, J=5.6 Hz, 2H), 2.60 (br d, J=17.5 Hz, 1H), 2.47 (br d, J=4.6 Hz, 4H), 2.35 (br d, J=4.5 Hz, 1H), 2.12 (s, 3H), 2.05-1.97 (m, 1H). MS (ESI) m/z 571.2 [M+H]$^+$ Step 1: A solution of 2-chloro-1-methyl-4-nitrobenzene (12.1 mL, 58.3 mmol, 1.00 eq) and N-iodosuccinimide (14.4 g, 64.1 mmol, 1.10 eq) in sulfuric acid (100 mL) was stirred at 60° C. for 2 h. The reaction was quenched by addition of ice water (200 mL) at 0° C. The aqueous layer was extracted with ethyl acetate (3×50.0 mL). The combined organic layers were washed with brine (100 mL), dried over sodium sulfate, filtered, and concentrated under reduced pressure to give a residue. The residue was purified by silica gel column chromatography (petroleum ether/ethyl acetate=1/0) to afford 1-chloro-3-iodo-2-methyl-5-nitrobenzene.

Step 2: A solution of 1-chloro-3-iodo-2-methyl-5-nitrobenzene (7.80 g, 26.2 mmol, 1.00 eq), potassium hydroxide (4.41 g, 78.7 mmol, 3.00 eq), tris(dibenzylideneethylacetatecetone)dipalladium(0) (1.20 g, 1.31 mmol, 0.05 eq) and 2-di-tert-butylphosphino-2',4',6'-triisopropylbiphenyl (557 mg, 1.31 mmol, 0.050 eq) in dioxane (80.0 mL) and water (16.0 mL) was stirred at 80° C. for 12 h under nitrogen atmosphere. The mixture was acidified to pH~4 and concentrated under reduced pressure to give a residue. Brine (200 mL) was added, and the aqueous layer was extracted with ethyl acetate (3×50.0 mL). The combined organic layers were dried over sodium sulfate, filtered, and concentrated under reduced pressure to give a residue. The residue was purified by silica gel column chromatography (petroleum ether/ethyl acetate=1/0 to 17/3) to afford 3-chloro-2-methyl-5-nitrophenol.

Step 3: A suspension of 3-chloro-2-methyl-5-nitrophenol (500 mg, 2.67 mmol, 1.00 eq), 4-(2-chloroethyl) morpholine (479 mg, 3.20 mmol, 1.20 eq), potassium carbonate (553 mg, 4.00 mmol, 1.50 eq) and potassium iodide (133 mg, 0.80 mmol, 0.30 eq) in dimethylformamide (5.00 mL) was stirred at 80° C. for 1 h. The mixture was poured into brine (50.0 mL) and extracted with ethyl acetate (3×15.0 mL). The combined organic layers were dried over sodium sulfate, filtered, and concentrated under reduced pressure to afford 4-(2-(3-chloro-2-methyl-5-nitrophenoxy)ethyl)morpholine.

Step 4: To a solution of 4-(2-(3-chloro-2-methyl-5-nitrophenoxy)ethyl)morpholine (570 mg, 1.90 mmol, 1.00 eq) in methanol (5.00 mL) and water (1.00 mL) were added iron powder (529 mg, 9.48 mmol, 5.00 eq) and ammonium chloride (507 mg, 9.48 mmol, 5.00 eq). The reaction was stirred at 80° C. for 12 h under nitrogen. The mixture was filtered, and the filtrate was concentrated under reduced pressure to give a residue. The residue was treated with brine (5.00 mL) and saturated aqueous sodium bicarbonate (5.00 mL). The aqueous layer was extracted with ethyl acetate (3×10.0 mL), dried over sodium sulfate, filtered, and concentrated under reduced pressure to afford 3-chloro-4-methyl-5-(2-morpholinoethoxy)aniline.

Step 5: To a solution of 3-chloro-4-methyl-5-(2-morpholinoethoxy)aniline (300 mg, 1.11 mmol, 1.00 eq) in acetonitrile (10.0 mL) were added pyridine (0.45 mL, 5.54 mmol, 5.00 eq) and phenyl chloroformate (0.17 mL, 1.33 mmol, 1.20 eq) at 0° C. The reaction was stirred at 25° C. for 1 h. The mixture was concentrated and the obtained residue was purified by standard methods to afford phenyl (3-chloro-4-methyl-5-(2-morpholinoethoxy)phenyl)carbamate.

Compound 49: General procedure A with variant i) was used for the preparation from compound VIII employing phenyl (6-ethyl-5-methylpyridin-3-yl)carbamate. $^1$H NMR (400 MHz, DMSO-$d_6$) δ=11.11-10.94 (m, 1H), 10.81-10.66 (m, 1H), 8.67 (d, J=1.6 Hz, 1H), 8.20 (br s, 1H), 7.82 (s, 1H), 7.74-7.59 (m, 2H), 5.35 (s, 2H), 5.19-5.02 (m, 1H), 4.53-4.44 (m, 1H), 4.40-4.27 (m, 1H), 3.04-2.90 (m, 3H), 2.61 (br d, J=16.5 Hz, 1H), 2.43 (s, 3H), 2.42-2.35 (m, 1H), 2.07-1.97 (m, 1H), 1.24 (t, J=7.6 Hz, 3H). MS (ESI) m/z 437.1 [M+H]$^+$ Step 1: To a solution of 2-chloro-3-methyl-5-nitropyridine (2.00 g, 11.6 mmol, 1.00 eq), ethylboronic acid (2.14 g, 29.0 mmol, 2.50 eq) and potassium carbonate (4.81 g, 34.8 mmol, 3.00 eq) in dioxane (20.0 mL) was added tetrakis[triphenylphosphine]palladium(0) (1.34 g, 1.16 mmol, 0.100 eq) at 20° C. The reaction was stirred at 110° C. under nitrogen for 12 h. The mixture was concentrated under reduced pressure to give a residue. The residue was purified by silica gel column chromatography (petroleum ether/ethyl acetate=1/0 to 20/1) to afford 2-ethyl-3-methyl-5-nitropyridine.

Step 2: A mixture of 2-ethyl-3-methyl-5-nitropyridine (800 mg, 4.81 mmol, 1.00 eq), iron powder (806 mg, 14.4 mmol, 3.00 eq) and ammonium chloride (1.29 g, 24.0 mmol, 5.00 eq) in methanol (8.00 mL) and water (4.00 mL) was stirred at 80° C. for 1 h. The mixture was filtered, and the filtrate was concentrated under reduced pressure to give a residue. The residue was added to water (100 mL) and the solution was stirred for 10 min, then extracted with ethyl acetate (3×50.0 mL). The combined organic layers were washed with brine (100 mL), dried over anhydrous sodium sulfate, filtered, and concentrated under reduced pressure to afford 6-ethyl-5-methylpyridin-3-amine.

Step 3: To a solution of 6-ethyl-5-methyl-pyridin-3-amine (300 mg, 2.20 mmol, 1 eq) and pyridine (0.89 mL, 11.0 mmol, 5.00 eq) in acetonitrile (5.00 mL) was added phenyl chloroformate (0.41 mL, 3.30 mmol, 1.50 eq). The reaction was stirred at 25° C. for 1 h. The mixture was concentrated under reduced pressure to give a residue. The residue was added to water (80.0 mL) and stirred for 10 min, then extracted with ethyl acetate (3×40.0 mL). The combined organic layers were washed with brine (80.0 mL), dried over anhydrous sodium sulfate, filtered, and concentrated and the obtained residue was purified by standard methods to afford phenyl (6-ethyl-5-methylpyridin-3-yl)carbamate.

Compound 50: General procedure A with variant i) was used for the preparation from compound VIII employing phenyl (4-(pyridin-2-yl)phenyl)carbamate. $^1$H NMR (400 MHz, DMSO-d$_6$) δ=11.00 (s, 1H), 10.01 (s, 1H), 8.62 (d, J=4.1 Hz, 1H), 8.29 (s, 1H), 8.03 (d, J=8.8 Hz, 2H), 7.93-7.88 (m, 1H), 7.87-7.79 (m, 2H), 7.73-7.69 (m, 1H), 7.67-7.63 (m, 1H), 7.60 (d, J=8.6 Hz, 2H), 7.29 (dd, J=5.3, 6.7 Hz, 1H), 5.30 (s, 2H), 5.13 (dd, J=5.0, 13.3 Hz, 1H), 4.53-4.44 (m, 1H), 4.41-4.30 (m, 1H), 2.96-2.86 (m, 1H), 2.65-2.58 (m, 1H), 2.41 (dq, J=4.4, 13.2 Hz, 1H), 2.06-1.99 (m, 1H). MS (ESI) m/z 471.2 [M+H]$^+$ Step 1: To a solution of (4-nitrophenyl)boronic acid (1.41 g, 8.44 mmol, 1.00 eq) and 2-bromopyridine (1.20 mL, 12.7 mmol, 1.50 eq) in ethanol (35.0 mL) were added potassium carbonate (2.33 g, 16.9 mmol, 2.00 eq) and tetrakis[triphenylphosphine]palladium(0) (1.95 g, 1.69 mmol, 0.20 eq) in one portion. The reaction was stirred at 90° C. under nitrogen for 12 h. The mixture was diluted with water (30.0 mL) and exacted with ethyl acetate (3×30 mL). The combined organic layers were washed with brine (2×10.0 mL), dried over sodium sulfate, filtered, and concentrated under reduced pressure to give a residue. The residue was purified by silica gel column chromatography (petroleum ether/ethyl acetate=10/1 to 2/1) to afford 2-(4-nitrophenyl)pyridine.

Step 2: To a solution of 2-(4-nitrophenyl)pyridine (600 mg, 3.00 mmol, 1.00 eq) in methanol (6.00 mL) and water (3.00 mL) were added ferrous powder (502 mg, 8.99 mmol, 3.00 eq) and ammonium chloride (802 mg, 15.0 mmol, 5.00 eq). The reaction was stirred at 80° C. for 2 h. The mixture was filtered, and the filtrate was concentrated under reduced pressure to give a residue. The residue was diluted with water (30.0 mL) and exacted with ethyl acetate (3×30.0 mL). The combined organic layers were washed with brine (2×10.0 mL), dried over sodium sulfate, filtered, and concentrated under reduced pressure to afford 4-(2-pyridyl) aniline.

Step 3: To a solution of 4-(pyridin-2-yl)aniline (200 mg, 1.18 mmol, 1.00 eq) and pyridine (0.28 mL, 3.53 mmol, 3.00 eq) in acetonitrile (3.00 mL) was added phenyl chloroformate (0.22 mL, 1.76 mmol, 1.50 eq) dropwise at 0° C. The reaction was stirred at 25° C. for 12 h. The mixture was concentrated and the obtained residue was purified by standard methods to afford phenyl (4-(pyridin-2-yl)phenyl)carbamate.

Compound 51: General procedure A with variant i) was used for the preparation from compound VIII employing phenyl(5-methoxy-6-methylpyridin-3-yl)carbamate. $^1$H NMR (400 MHz, DMSO-d$_6$) δ=10.99 (s, 1H), 10.70 (br s, 1H), 8.34 (s, 1H), 7.98 (s, 1H), 7.81 (s, 1H), 7.73-7.62 (m, 2H), 5.35 (s, 2H), 5.12 (dd, J=5.1, 13.3 Hz, 1H), 4.51-4.45 (m, 1H), 4.37-4.30 (m, 1H), 3.93 (s, 3H), 2.97-2.86 (m, 1H), 2.60 (br d, J=17.6 Hz, 1H), 2.50-2.49 (m, 3H), 2.40 (dq, J=4.4, 13.2 Hz, 1H), 2.07-1.95 (m, 1H). MS (ESI) m/z 439.1[M+H]$^+$ Step 1: To a solution of 2-chloro-3-methoxy-5-nitropyridine (3.00 g, 15.9 mmol, 1.00 eq), methylboronic acid (1.90 g, 31.8 mmol, 2.00 eq) and potassium carbonate (6.60 g, 47.7 mmol, 3.00 eq) in dioxane (30.0 mL) was added tetrakis[triphenylphosphine]palladium(0) (1.84 g, 1.59 mmol, 0.10 eq) at 25° C. The reaction was stirred at 110° C. for 12 h under nitrogen. The mixture was concentrated under reduced pressure to give a residue. The residue was purified by silica gel column chromatography (petroleum ether/ethyl acetate=1/0 to 30/1) to afford 3-methoxy-2-methyl-5-nitropyridine.

Step 2: A mixture of 3-methoxy-2-methyl-5-nitropyridine (500 mg, 2.97 mmol, 1.00 eq), iron powder (498 mg, 8.92 mmol, 3.00 eq), and ammonium chloride (795 mg, 14.9 mmol, 5.00 eq) in methanol (4.00 mL) and water (2.00 mL) was stirred at 80° C. for 1 h. The mixture was filtered, and the filtrate was concentrated under reduced pressure to give a residue. The residue was added to water (80.0 mL) and stirred for 10 min. The solution was extracted with ethyl acetate (3×50.0 mL). The combined organic layers were washed with brine (80.0 mL), dried over anhydrous sodium sulfate, filtered, and concentrated under reduced pressure to afford 5-methoxy-6-methylpyridin-3-amine.

Step 3: To a solution of 5-methoxy-6-methylpyridin-3-amine (200 mg, 1.45 mmol, 1.00 eq), and pyridine (0.58 mL, 7.24 mmol, 5.00 eq) in acetonitrile (4.00 mL) was added phenyl chloroformate (0.22 mL, 1.74 mmol, 1.20 eq) dropwise at 0° C. The reaction was stirred at 25° C. for 12 h. The mixture was concentrated under reduced pressure to give a residue. The residue was diluted with water (50.0 mL) and extracted with ethyl acetate (3×40.0 mL). The combined organic layers were washed with brine (20.0 mL), dried over sodium sulfate, filtered, and concentrated and the obtained residue was purified by standard methods to afford phenyl (5-methoxy-6-methylpyridin-3-yl)carbamate.

Compound 52:

Step 1: To a solution of 2-chloro-1-methyl-4-nitrobenzene (10.0 g, 58.3 mmol, 12.1 mL, 1.00 eq) in sulfuric acid (100 mL) was added N-iodosuccinimide (14.4 g, 64.1 mmol, 1.10 eq) in portions. The reaction was stirred at 60° C. for 2 h. The mixture was poured into water (300 mL) and extracted with ethyl acetate (3×80.0 mL). The combined organic layers were washed with brine (50 mL) and dried over anhydrous sodium sulfate, filtered, and concentrated under reduced pressure to afford 1-chloro-3-iodo-2-methyl-5-nitrobenzene.

Step 2: To a solution of 1-chloro-3-iodo-2-methyl-5-nitrobenzene (7.00 g, 23.5 mmol, 1.00 eq) and potassium hydroxide (3.96 g, 70.6 mmol, 3.00 eq) in dioxane (70.0 mL) and water (10.0 mL) were added tris(dibenzylideneacetone) dipalladium(0) (2.15 g, 2.35 mmol, 0.10 eq) and 2-di-tert-butylphosphino-2,4,6-triisopropylbiphenyl (999 mg, 2.35 mmol, 0.10 eq) under nitrogen. The reaction was stirred at 80° C. for 12 h. The mixture was diluted with water (300 mL) and extracted with ethyl acetate (3×80.0 mL). The combined organic layers were washed with brine (50.0 mL), dried over anhydrous sodium sulfate, filtered, and concentrated under reduced pressure to give a residue. The residue was purified by silica gel column chromatography (petroleum ether/ethyl acetate=1/0 to 10/1) to afford 3-chloro-2-methyl-5-nitrophenol.

Step 3: To a solution of 3-chloro-2-methyl-5-nitrophenol (1.00 g, 5.33 mmol, 1.00 eq) and tert-butyl 3-(((methylsulfonyl)oxy)methyl)pyrrolidine-1-carboxylate (1.64 g, 5.86 mmol, 1.10 eq) in dimethylformamide (10.0 mL) was added potassium carbonate (2.21 g, 15.9 mmol, 3.00 eq) in portions. The reaction was stirred at 80° C. for 12 h. The mixture was filtered, and the filtrate was concentrated under reduced pressure to give a residue. The residue was purified by reversed phase preparative HPLC to afford tert-butyl 3-((3-chloro-2-methyl-5-nitrophenoxy)methyl) pyrrolidine-1-carboxylate.

Step 4: To a solution of tert-butyl 3-((3-chloro-2-methyl-5-nitrophenoxy)methyl)pyrrolidine-1-carboxylate (400 mg, 1.08 mmol, 1.00 eq) and ammonium chloride (289 mg, 5.39 mmol, 5.00 eq) in methanol (4.00 mL) and water (4.00 mL) was added iron powder (181 mg, 3.24 mmol, 3.00 eq) in portions. The reaction was stirred at 80° C. for 2 h. The mixture was filtered, and the filtrate was concentrated under reduced pressure to give a residue. The residue was diluted with water (100 mL) and extracted with ethyl acetate (3×30.0 mL). The combined organic layers were washed with brine (20.0 mL), dried over anhydrous sodium sulfate, filtered, and concentrated under reduced pressure to afford tert-butyl 3-((5-amino-3-chloro-2-methylphenoxy)methyl) pyrrolidine-1-carboxylate.

Step 5: To a solution of tert-butyl 3-((5-amino-3-chloro-2-methylphenoxy)methyl)pyrrolidine-1-carboxylate (200 mg, 587 µmol, 1.00 eq) and pyridine (0.14 mL, 1.76 mmol, 3.00 eq) in acetonitrile (5.00 mL) was added phenyl chloroformate (0.11 mL, 880 µmol, 1.50 eq) dropwise at 0° C. The reaction was stirred at 25° C. for 12 h. The mixture was concentrated under reduced pressure to give a residue. The residue was purified by reversed phase preparative HPLC to afford tert-butyl 3-((3-chloro-2-methyl-5-((phenoxycarbonyl)amino)phenoxy)methyl) pyrrolidine-1-carboxylate.

Step 6: To a solution of 3-(6-(hydroxymethyl)-1-oxoisoindolin-2-yl)piperidine-2,6-dione VIII (100 mg, 365 µmol, 1.00 eq) and tert-butyl 3-((3-chloro-2-methyl-5-((phenoxycarbonyl)amino)phenoxy)methyl)pyrrolidine-1-carboxylate (168 mg, 365 µmol, 1.00 eq) in dimethylformamide (1.00 mL) was added sodium hydride (60% dispersion in mineral oil) (29.2 mg, 729 µmol, 2.00 eq) in portions at 0° C. The reaction was stirred at 25° C. for 1 h. The mixture was quenched slowly with 1M hydrochloric acid (2.00 mL) and concentrated under reduced pressure to afford tert-butyl 3-((3-chloro-5-((((2-(2,6-dioxopiperidin-3-yl)-3-oxoisoindolin-5-yl)methoxy)carbonyl)amino)-2-methylphenoxy) methyl)pyrrolidine-1-carboxylate.

Step 7: A solution of tert-butyl 3-((3-chloro-5-((((2-(2,6-dioxopiperidin-3-yl)-3-oxoisoindolin-5-yl)methoxy)carbonyl)amino)-2-methylphenoxy)methyl)pyrrolidine-1-carboxylate (200 mg, 312 µmol, 1.00 eq) in hydrochloric acid/ethyl acetate (3 M, 5.00 mL) was stirred at 25° C. for 1 h. The mixture was concentrated to give a residue. The residue was purified by a standard method to afford Compound 52. $^1$H NMR (400 MHz, DMSO-d$_6$) δ=11.00 (s, 1H), 9.95 (s, 1H), 9.24 (br d, J=3.5 Hz, 2H), 7.79 (s, 1H), 7.71-7.62 (m, 2H), 7.17 (br d, J=13.4 Hz, 2H), 5.28 (s, 2H), 5.13 (dd, J=5.1, 13.3 Hz, 1H), 4.54-4.30 (m, 2H), 4.03-3.90 (m, 2H), 3.48-3.40 (m, 1H), 3.28-3.15 (m, 2H), 3.08-2.99 (m, 1H), 2.97-2.86 (m, 1H), 2.75 (td, J=7.2, 14.4 Hz, 1H), 2.61 (br d, J=17.6 Hz, 1H), 2.41 (dq, J=4.5, 13.2 Hz, 1H), 2.14 (s, 3H), 2.13-2.06 (m, 1H), 2.06-1.97 (m, 1H), 1.85-1.73 (m, 1H). MS (ESI) m/z 541.2 [M+H]$^+$ Compound 53: General procedure A with variant i) was used for the preparation from compound VIII employing phenyl N-(6,7-dihydro-5H-cyclopenta[b]pyridin-3-yl)carbamate. $^1$H NMR (400 MHz, DMSO-d$_6$) δ=11.01 (s, 1H), 10.59-10.34 (m, 1H), 8.67-8.54 (m, 1H), 8.18-8.01 (m, 1H), 7.86-7.77 (m, 1H), 7.73-7.69 (m, 1H), 7.67-7.63 (m, 1H), 5.33 (s, 2H), 5.13 (dd, J=5.2, 13.4 Hz, 1H), 4.53-4.44 (m, 1H), 4.39-4.32 (m, 1H), 3.02 (br dd, J=7.5, 18.5 Hz, 4H), 2.96-2.89 (m, 1H), 2.66-2.57 (m, 1H), 2.41 (dd, J=4.4, 13.2 Hz, 1H), 2.23-2.11 (m, 2H), 2.06-1.98 (m, 1H). MS (ESI) m/z 435.1 [M+H]$^+$ Step 1: To a solution of 3-nitro-6,7-dihydro-5H-cyclopenta[b]pyridine (600 mg, 3.65 mmol, 1.00 eq) in methanol (6.00 mL) and water (3.00 mL) were added ferrous powder (612 mg, 11.0 mmol, 3.00 eq) and ammonium chloride (977 mg, 18.3 mmol, 5.00 eq). The reaction was stirred at 80° C. for 2 h. The mixture was filtered, and the filtrate was concentrated under reduced pressure to give a residue. Water (30.0 mL) was added to the residue, and the mixture was exacted with ethyl acetate (3×30.0 mL). The combined organic phases were washed with brine (2×10.0 mL), dried over sodium sulfate, filtered, and concentrated under reduced pressure to afford 6,7-dihydro-5H-cyclopenta[b] pyridin-3-amine.

Step 2: To a solution of 6,7-dihydro-5H-cyclopenta[b] pyridin-3-amine (350 mg, 2.61 mmol, 1.00 eq) and phenyl chloroformate (0.49 mL, 3.91 mmol, 1.50 eq) in methanol (3.00 mL) was added pyridine (0.63 mL, 7.83 mmol, 3.00 eq) in one portion. The reaction was stirred at 25° C. for 2 h. The mixture was diluted with water (30.0 mL) and exacted with ethyl acetate (3×30.0 mL). The combined organic phases were washed with brine (2×10.0 mL), dried over sodium sulfate, filtered, and concentrated and the obtained residue was purified by standard methods to afford phenyl (6,7-dihydro-5H-cyclopenta[b]pyridin-3-yl)carbamate.

Compound 54: General procedure A with variant i) was used for the preparation from compound VIII employing phenyl (7,8-dihydro-5H-pyrano[4,3-b]pyridin-3-yl)carbamate. $^1$H NMR (400 MHz, DMSO-d$_6$) δ=10.99 (s, 1H), 10.72 (s, 1H), 8.69 (s, 1H), 8.11 (s, 1H), 7.81 (s, 1H), 7.74-7.63 (m, 2H), 5.34 (s, 2H), 5.12 (dd, J=5.2, 13.2 Hz, 1H), 4.81 (s, 2H), 4.51-4.44 (m, 1H), 4.37-4.31 (m, 1H), 3.98 (t, J=5.6 Hz, 2H), 3.05 (s, 2H), 2.97-2.85 (m, 1H), 2.60 (d, J=17.6 Hz, 1H), 2.40 (dq, J=4.4, 13.2 Hz, 1H), 2.07-1.97 (m, 1H). MS (ESI) m/z 451.1 [M+H]$^+$ To a solution of 7,8-dihydro-5H-pyrano[4,3-b]pyridin-3-amine (140 mg, 0.93 mmol, 1.00 eq) in acetonitrile (3.00 mL) were added phenyl chloroformate (0.13 mL, 1.03 mmol, 1.10 eq) and pyridine (0.23 mL, 2.80 mmol, 3.00 eq). The reaction was stirred at 25° C. for 2 h. The mixture was diluted with water 10.0 mL and ethyl acetate (10.0 mL). The aqueous layer was extracted with ethyl acetate (3×10.0 mL). The combined organic layers were dried over anhydrous sodium sulfate, filtered, and concentrated and the obtained residue was purified by standard methods to afford phenyl (7,8-dihydro-5H-pyrano[4,3-b]pyridin-3-yl)carbamate.

Compound 55: General procedure A with variant i) was used for the preparation from compound VIII employing phenyl (5-ethyl-6-methylpyridin-3-yl)carbamate. $^1$H NMR (400 MHz, DMSO-d$_6$) δ=11.00 (s, 1H), 9.85 (br s, 1H), 8.34 (s, 1H), 8.15 (s, 1H), 7.80 (s, 1H), 7.74-7.61 (m, 3H), 5.28 (s, 2H), 5.13 (dd, J=5.2, 13.2 Hz, 1H), 4.53-4.43 (m, 1H), 4.40-4.30 (m, 1H), 2.96-2.88 (m, 1H), 2.63-2.59 (m, 1H), 2.57 (d, J=7.8 Hz, 2H), 2.46-2.41 (m, 1H), 2.38 (s, 3H), 2.06-1.98 (m, 1H), 1.14 (t, J=7.4 Hz, 3H). MS (ESI) m/z 437.3 [M+H]$^+$ Step 1: To a solution of 3-bromo-2-methyl-5-nitropyridine (900 mg, 4.15 mmol, 1.00 eq), ethylboronic acid (919 mg, 12.4 mmol, 3.00 eq) and potassium carbonate (1.72 g, 12.4 mmol, 3.00 eq) in dioxane (10.0 mL) was added tetrakis[triphenylphosphine]palladium(0) (479 mg, 415

µmol, 0.100 eq) under nitrogen. The reaction was stirred at 110° C. for 12 h under nitrogen atmosphere. The mixture was concentrated under reduced pressure to give a residue. The residue was purified by silica gel column chromatography (petroleum ether/ethyl acetate=20/1 to 5/1) to afford 3-ethyl-2-methyl-5-nitropyridine.

Step 2: A mixture of 3-ethyl-2-methyl-5-nitropyridine (600 mg, 3.61 mmol, 1.00 eq), iron powder (605 mg, 10.8 mmol, 3.00 eq) and ammonium chloride (579 mg, 10.8 mmol, 3.00 eq) in methanol (10.0 mL) and water (10.0 mL) was stirred at 80° C. for 2 h. The mixture was concentrated under reduced pressure to give a residue. The residue was added to a saturated sodium bicarbonate solution (20.0 mL) and extracted with ethyl acetate (3×20.0 mL). The combined organic layers were washed with brine (20.0 mL), dried over anhydrous sodium sulfate, filtered, and concentrated under reduced pressure to afford 5-ethyl-6-methylpyridin-3-amine.

Step 3: To a solution of 5-ethyl-6-methylpyridin-3-amine (350 mg, 2.57 mmol, 1.00 eq) and pyridine (0.62 mL, 7.71 mmol, 3.00 eq) in acetonitrile (5.00 mL) was added phenyl chloroformate (0.48 mL, 3.85 mmol, 1.50 eq) at 25° C. The reaction was stirred at 25° C. for 2 h. The mixture was concentrated and the obtained residue was purified by standard methods to afford phenyl (5-ethyl-6-methylpyridin-3-yl)carbamate.

Compound 56: General procedure A with variant i) was used for the preparation from compound VIII employing phenyl (2,3-dihydro-1H-inden-5-yl)carbamate. $^1$H NMR (400 MHz, DMSO-$d_6$) δ=10.99 (s, 1H), 9.66 (br s, 1H), 7.79 (s, 1H), 7.73-7.61 (m, 2H), 7.47-7.30 (m, 1H), 7.20 (br d, J=8.0 Hz, 1H), 7.14-7.06 (m, 1H), 5.26 (s, 2H), 5.13 (dd, J=5.1, 13.3 Hz, 1H), 4.55-4.43 (m, 1H), 4.39-4.31 (m, 1H), 2.92 (ddd, J=5.4, 13.6, 17.5 Hz, 1H), 2.80 (td, J=7.2, 12.7 Hz, 4H), 2.61 (br d, J=17.6 Hz, 1H), 2.41 (dd, J=4.3, 13.1 Hz, 1H), 2.06-1.89 (m, 3H). MS (ESI) m/z 434.1 [M+H]$^+$ To a solution of 2,3-dihydro-1H-inden-5-amine (300 mg, 2.25 mmol, 1.00 eq) and pyridine (0.91 mL, 11.3 mmol, 5.00 eq) in acetonitrile (6.00 mL) was added phenyl chloroformate (0.42 mL, 3.38 mmol, 1.50 eq). The reaction was stirred at 25° C. for 1 h. The mixture concentrated under reduced pressure to give a residue. The residue was added to water (100 mL) and stirred for 10 min. The aqueous solution was extracted with ethyl acetate (3×40.0 mL). The combined organic layers were washed with brine (100 mL), dried over anhydrous sodium sulfate, filtered, and concentrated and the obtained residue was purified by standard methods to afford phenyl (2,3-dihydro-1H-inden-5-yl)carbamate.

Compound 57: General procedure A with variant i) was used for the preparation from compound VIII employing phenyl (3-fluoro-5-(trifluoromethoxy)phenyl)carbamate. $^1$H NMR (400 MHz, DMSO-$d_6$) δ=10.99 (br s, 1H), 10.35 (s, 1H), 7.80 (s, 1H), 7.71-7.67 (m, 1H), 7.67-7.61 (m, 1H), 7.39-7.31 (m, 2H), 6.99 (br d, J=8.8 Hz, 1H), 5.30 (s, 2H), 5.13 (dd, J=5.1, 13.3 Hz, 1H), 4.52-4.42 (m, 1H), 4.38-4.30 (m, 1H), 2.98-2.85 (m, 1H), 2.63-2.57 (m, 1H), 2.43-2.35 (m, 1H), 2.06-1.97 (m, 1H). MS (ESI) m/z 496.3 [M+H]$^+$ To a solution of 3-fluoro-5-(trifluoromethoxy)aniline (200 mg, 1.03 mmol, 1.00 eq) and pyridine (0.25 mL, 3.10 mmol, 3.02 eq) in acetonitrile (10.0 mL) was added phenyl chloroformate (0.15 mL, 1.23 mmol, 1.20 eq) in portions at 0° C. The reaction was stirred at 25° C. for 1 h. The mixture was concentrated and the obtained residue was purified by standard methods to afford phenyl (3-fluoro-5-(trifluoromethoxy)phenyl)carbamate.

Compound 58: General procedure A with variant i) was used for the preparation from compound VIII employing phenyl (4-(1-methylcyclopropyl)phenyl)carbamate. $^1$H NMR (400 MHz, DMSO-$d_6$) δ=11.00 (s, 1H), 9.71 (br s, 1H), 7.79 (s, 1H), 7.70-7.66 (m, 1H), 7.66-7.60 (m, 1H), 7.37 (br d, J=8.4 Hz, 2H), 7.17-7.09 (m, 2H), 5.26 (s, 2H), 5.13 (dd, J=5.1, 13.3 Hz, 1H), 4.52-4.43 (m, 1H), 4.39-4.29 (m, 1H), 2.96-2.87 (m, 1H), 2.62 (br d, J=2.0 Hz, 1H), 2.43-2.35 (m, 1H), 2.05-1.98 (m, 1H), 1.34 (s, 3H), 0.80-0.73 (m, 2H), 0.73-0.66 (m, 2H). MS (ESI) m/z 448.2 [M+H]$^+$ Step 1: To freshly distilled dichloromethane (50.0 mL) was added diethylzinc (1 M in toluene, 40.6 mL, 4.00 eq). The solution was cooled to −40° C., and diiodomethane (40.6 mL, 4.00 eq) in dichloromethane (10.0 mL) was added slowly. The mixture was stirred at −40° C. for 30 min, then trifluoroacetic acid (0.15 mL, 2.03 mmol, 0.20 eq) and N,N-dimethylacetamide (1.05 mL, 10.1 mmol, 1.00 eq) in dichloromethane (10.0 mL) were added. The reaction was stirred at −15° C. for 0.5 h, then 1-bromo-4-(prop-1-en-2-yl)benzene (2.00 g, 10.1 mmol, 1.00 eq) in dichloromethane (10.0 mL) was added at 0° C. The mixture was stirred at 25° C. for 12 h. The reaction was quenched with ice-water (50.0 mL) at 0° C. The organic layer was separated and concentrated under reduced pressure to give a residue. The residue was purified by silica gel column chromatography (petroleum ether 100%) to afford 1-bromo-4-(1-methylcyclopropyl)benzene.

Step 2: To a solution of 1-bromo-4-(1-methylcyclopropyl)benzene (2.00 g, 9.47 mmol, 1.00 eq) (crude) in tert-amyl alcohol (100 mL) were added tert-butyl carbamate (2.00 g, 17.1 mmol, 1.80 eq), methanesulfonato(2-di-tbutylphosphino-2,4,6-tri-ipropyl-1,1-biphenyl)(2-amino-1,1-biphenyl-2-yl)palladium(II) (600 mg, 755 µmol, 0.0800 eq) and sodium tert-butoxide (2 M in tetrahydrofuran, 14.0 mL, 2.96 eq). The reaction was stirred at 90° C. for 3 h under nitrogen. The mixture was diluted with ethyl acetate (200 mL) and water (200 mL). The organic layer was separated and concentrated under reduced pressure to give a residue. The residue was purified by reversed phase preparative HPLC to afford tert-butyl (4-(1-methylcyclopropyl)phenyl) carbamate.

Step 3: To a solution of tert-butyl (4-(1-methylcyclopropyl)phenyl) carbamate (520 mg, 2.10 mmol, 1.00 eq) in ethyl acetate (10.0 mL) was added hydrogen chloride/ethyl acetate (4 M, 10 mL, 19.0 eq). The reaction was stirred at 25° C. for 1 h. The mixture was concentrated under reduced pressure to afford 4-(1-methylcyclopropyl)aniline.

Step 4: To a solution of 4-(1-methylcyclopropyl)aniline (200 mg, 1.09 mmol, 1.00 eq, hydrochloric acid) in acetonitrile (50.0 mL) were added pyridine (0.50 mL, 6.19 mmol, 5.69 eq) and phenyl chloroformate (187 mg, 1.20 mmol, 1.10 eq) at 0° C. The reaction was stirred at 25° C. for 1 h. The mixture was concentrated and the obtained residue was purified by standard methods to afford phenyl (4-(1-methylcyclopropyl)phenyl)carbamate.

Compound 59: General procedure A with variant i) was used for the preparation from compound VIII employing phenyl (4-(trifluoromethoxy)pyridin-2-yl)carbamate. $^1$H NMR (400 MHz, DMSO-$d_6$) δ=10.99 (br s, 1H), 10.80 (s, 1H), 8.38 (d, J=5.6 Hz, 1H), 7.82 (s, 2H), 7.74-7.59 (m, 2H), 7.08 (br d, J=5.5 Hz, 1H), 5.32 (s, 2H), 5.13 (br dd, J=5.0, 13.4 Hz, 1H), 4.50-4.43 (m, 1H), 4.38-4.31 (m, 1H), 2.95-2.88 (m, 1H), 2.62 (br d, J=2.1 Hz, 1H), 2.44-2.35 (m, 1H), 2.06-1.97 (m, 1H). MS (ESI) m/z 479.1 [M+H]$^+$ To a solution of 4-(trifluoromethoxy)pyridin-2-amine (300 mg, 1.68 mmol, 1.00 eq) and pyridine (0.68 mL, 8.42 mmol, 5.00 eq) in acetonitrile (3.00 mL) was added phenyl chloroformate (0.25 mL, 2.02 mmol, 1.20 eq) dropwise at 0° C. The reaction was stirred at 25° C. for 3 h. The mixture was concentrated and the obtained residue was purified by standard methods to afford phenyl (4-(trifluoromethoxy)pyridin-2-yl)carbamate.

Compound 60: General procedure A with variant i) was used for the preparation from compound VIII employing phenyl (6-(pyrrolidin-1-yl)pyridin-3-yl)carbamate. $^1$H NMR (400 MHz, DMSO-d$_6$) δ=11.00 (s, 1H), 9.43 (br s, 1H), 8.16 (s, 1H), 8.09 (br s, 1H), 7.77 (s, 1H), 7.64 (q, J=7.7 Hz, 2H), 7.57 (br d, J=9.4 Hz, 1H), 6.40 (d, J=8.9 Hz, 1H), 5.23 (s, 2H), 5.12 (dd, J=5.1, 13.3 Hz, 1H), 4.50-4.42 (m, 1H), 4.37-4.30 (m, 1H), 3.33 (br d, J=6.7 Hz, 4H), 2.93-2.86 (m, 1H), 2.63-2.58 (m, 1H), 2.43-2.36 (m, 1H), 2.04-1.98 (m, 1H), 1.94-1.89 (m, 4H). MS (ESI) m/z 464.2 [M+H]$^+$ Step 1: To a solution of 2-chloro-5-nitropyridine (2.00 g, 12.6 mmol, 1.00 eq) in dimethylformamide (10.0 mL) were added pyrrolidine (1.58 mL, 18.9 mmol, 1.50 eq) and potassium carbonate (5.23 g, 37.8 mmol, 3.00 eq). The reaction was stirred at 60° C. for 1 h. After cooling to room temperature, the mixture was poured into ice-water (200 mL). The resulting yellow precipitate was collected by filtration and dried under reduced pressure to afford 5-nitro-2-(pyrrolidin-1-yl)pyridine.

Step 2: To a solution of 5-nitro-2-(pyrrolidin-1-yl)pyridine (2.40 g, 12.4 mmol, 1.00 eq) in methanol (240 mL) was added palladium on carbon (100 mg, 10% weight on C). The reaction was stirred at 25° C. for 1 h under hydrogen (15 Psi). The mixture was filtered, and the filtrate was concentrated under reduced pressure to afford 6-(pyrrolidin-1-yl)pyridin-3-amine.

Step 3: To a solution of 6-(pyrrolidin-1-yl)pyridin-3-amine (1.50 g, 9.19 mmol, 1.00 eq) in acetonitrile (15.0 mL) were added pyridine (3.71 mL, 45.9 mmol, 5.00 eq) and phenyl chloroformate (1.50 mL, 11.9 mmol, 1.30 eq). The reaction was stirred at 25° C. for 1 h. The mixture was concentrated and the obtained residue was purified by standard methods to afford phenyl (6-(pyrrolidin-1-yl)pyridin-3-yl)carbamate.

Compound 61: General procedure A with variant i) was used for the preparation from compound VIII employing phenyl (4-fluoro-3-(trifluoromethoxy)phenyl)carbamate. $^1$H NMR (400 MHz, DMSO-d$_6$) δ=11.00 (br s, 1H), 10.16 (br s, 1H), 7.84-7.62 (m, 4H), 7.50-7.38 (m, 2H), 5.30 (br s, 2H), 5.14 (br dd, J=4.6, 13.2 Hz, 1H), 4.54-4.30 (m, 2H), 3.06-2.84 (m, 1H), 2.612 (br d, J=16.8 Hz, 1H), 2.46-2.38 (m, 1H), 2.08-1.96 (m, 1H). MS (ESI) m/z 496.1 [M+H]$^+$ To a solution of 4-fluoro-3-(trifluoromethoxy)aniline (400 mg, 2.05 mmol, 1.00 eq) and phenyl chloroformate (0.28 mL, 2.26 mmol, 1.10 eq) in acetonitrile (3.00 mL) was added pyridine (0.50 mL, 6.15 mmol, 3.00 eq) in one portion. The reaction was stirred at 25° C. for 2 h. The mixture was diluted with water (30.0 mL) and exacted with ethyl acetate (3×30.0 mL). The combined organic phases were washed with brine (2×10.0 mL), dried over sodium sulfate, filtered, and concentrated and the obtained residue was purified by standard methods to afford phenyl (4-fluoro-3-(trifluoromethoxy)phenyl)carbamate.

Compound 62: General procedure A with variant i) was used for the preparation from compound VIII employing phenyl (4-(3-methyloxetan-3-yl)phenyl)carbamate. $^1$H NMR (400 MHz, DMSO-d$_6$) δ=11.03 (s, 1H), 9.82 (br s, 1H), 7.83 (s, 1H), 7.74-7.65 (m, 2H), 7.48 (br d, J=8.5 Hz, 2H), 7.21 (d, J=8.6 Hz, 2H), 5.30 (s, 2H), 5.16 (dd, J=5.2, 13.3 Hz, 1H), 4.80 (d, J=5.5 Hz, 2H), 4.55-4.48 (m, 3H), 4.40 (s, 1H), 2.95 (s, 1H), 2.66 (br s, 1H), 2.44 (br dd, J=4.5, 12.9 Hz, 1H), 2.08-2.01 (m, 1H), 1.63 (s, 3H). MS (ESI) m/z 464.2 [M+H]$^+$ Step 1: To a solution of diethyl 2-methylmalonate (13.6 g, 78.0 mmol, 13.3 mL, 1.10 eq) in dimethylformamide (80.0 mL) was added sodium hydride (60% dispersion in mineral oil) (3.40 g, 85.0 mmol, 1.20 eq) slowly at 0° C. The reaction was stirred at 0° C. for 0.5 h, then 1-fluoro-4-nitrobenzene (10.0 g, 70.8 mmol, 7.52 mL, 1.00 eq) was added. The mixture was stirred at 25° C. for 3 h. Water (200 mL) was added, and the mixture was extracted with ethyl acetate (3×50.0 mL). The combined organic layers were dried over sodium sulfate, filtered, and concentrated under reduced pressure to give a residue. The residue was purified by silica gel column chromatography (petroleum ether/ethyl acetate=10/1 to 8/1) to afford diethyl 2-methyl-2-(4-nitrophenyl)malonate.

Step 2: To a solution of diethyl 2-methyl-2-(4-nitrophenyl)malonate (7.00 g, 23.7 mmol, 1.00 eq) in tetrahydrofuran (15.0 mL) was added lithium aluminium hydride (953 mg, 25.1 mmol, 1.06 eq) slowly at 0° C. under nitrogen. The reaction was stirred at 0° C. for 3 h. The mixture was then partitioned between dichloromethane and 1 M hydrochloric acid. The organic layer was separated, and the aqueous layer was extracted with dichloromethane (3×50.0 mL). The combined organic layers were concentrated under reduced pressure to give a residue. The residue was purified by silica gel column chromatography (petroleum ether/ethyl acetate=10/1 to 0/1) to afford 2-methyl-2-(4-nitrophenyl)propane-1,3-diol.

Step 3: To a solution of 2-methyl-2-(4-nitrophenyl)propane-1,3-diol (200 mg, 947 μmol, 1.00 eq) in tetrahydrofuran (10.0 mL) was added n-butyllithium (2.5 M in hexane, 0.46 mL, 1.21 eq) and tosyl chloride (271 mg, 1.42 mmol, 1.50 eq) at 0° C. The reaction was stirred at 25° C. for 1 h. After cooling to 0° C., n-butyllithium (2.5 M in hexane, 0.46 mL, 1.21 eq) was added. The reaction was stirred at 65° C. for another 2 h. The reaction was quenched with saturated ammonium chloride (10 mL) and extracted with ethyl acetate (50.0 mL). The organic layer was separated and concentrated under reduced pressure to give a residue. The residue was purified by silica gel column chromatography (petroleum ether/ethyl acetate=3/1) to afford 3-methyl-3-(4-nitrophenyl)oxetane.

Step 4: To a solution of 3-methyl-3-(4-nitrophenyl)oxetane (56.0 mg, 290 μmol, 1.00 eq) in ethyl acetate (5.00 mL) was added wet palladium on carbon (10% weight on C) (20.0 mg). The reaction was stirred at 25° C. for 2 h under hydrogen (15.0 Psi). The mixture was filtered, and the filtrate was concentrated under reduced pressure to afford 4-(3-methyloxetan-3-yl)aniline.

Step 5: To a solution of 4-(3-methyloxetan-3-yl)aniline (60.0 mg, 368 μmol, 1.00 eq) in acetonitrile (3.00 mL) was added pyridine (0.15 mL, 1.84 mmol, 5.00 eq) and phenyl chloroformate (0.07 mL, 551 μmol, 1.50 eq) at 0° C. The reaction was stirred at 0° C. for 0.5 h. The mixture was filtered, and the filtrate was concentrated and the obtained residue was purified by standard methods to afford phenyl (4-(3-methyloxetan-3-yl)phenyl)carbamate.

Compound 63: General procedure A with variant i) was used for the preparation from compound VIII employing phenyl (2-ethylpyridin-4-yl)carbamate. $^1$H NMR (400 MHz, DMSO-d$_6$) δ=11.37 (br d, J=10.6 Hz, 1H), 11.00 (s, 1H), 8.54 (d, J=6.7 Hz, 1H), 7.85-7.80 (m, 2H), 7.77-7.70 (m, 2H), 7.69-7.64 (m, 1H), 5.40 (s, 2H), 5.13 (dd, J=5.1, 13.3 Hz, 1H), 4.54-4.45 (m, 1H), 4.40-4.32 (m, 1H), 2.97-2.87 (m, 3H), 2.61 (br d, J=17.1 Hz, 1H), 2.41 (br dd, J=4.5, 13.0 Hz, 1H), 2.06-1.98 (m, 1H), 1.27 (t, J=7.5 Hz, 3H). MS (ESI) m/z 423.2 [M+H]$^+$ To a solution of 2-ethylpyridin-4-amine (0.500 g, 4.09 mmol, 1.00 eq) and pyridine (1.65 mL, 20.4 mmol, 5.00 eq) in dimethylformamide (50.0 mL) was added phenyl chloroformate (0.77 mL, 6.19 mmol, 1.51 eq) at 0° C. The reaction was stirred at 0° C. for 12 h. The mixture was filtered and concentrated and the obtained residue was purified by standard methods to afford phenyl (2-ethylpyridin-4-yl)carbamate.

Compound 64: General procedure A with variant i) was used for the preparation from compound VIII employing phenyl (2-(piperidin-1-yl)pyrimidin-5-yl)carbamate. $^1$H NMR (400 MHz, DMSO-$d_6$) δ=11.00 (s, 1H), 9.55 (br s, 1H), 8.39 (br s, 2H), 7.78 (s, 1H), 7.70-7.61 (m, 2H), 5.26 (s, 2H), 5.17-5.07 (m, 1H), 4.53-4.28 (m, 2H), 3.71-3.64 (m, 4H), 3.00-2.85 (m, 1H), 2.66-2.57 (m, 1H), 2.44-2.34 (m, 1H), 2.08-1.97 (m, 1H), 1.67-1.57 (m, 2H), 1.55-1.42 (m, 4H). MS (ESI) m/z 479.1 [M+H]$^+$ Step 1: A solution of 2-chloro-5-nitro-pyrimidine (1.00 g, 6.27 mmol, 1.00 eq), piperidine (1.24 mL, 12.5 mmol, 2.00 eq) and potassium carbonate (2.60 g, 18.8 mmol, 3.00 eq) in dimethylformamide (5.00 mL) was stirred at 25° C. for 12 h. The mixture was diluted with ethyl acetate (100 mL) and water (100 mL). The organic layer was separated, and the aqueous layer was extracted with ethyl acetate (3×200 mL). The combined organic layers were dried over sodium sulfate, filtered, and concentrated under reduced pressure to afford 5-nitro-2-(piperidin-1-yl)pyrimidine.

Step 2: A mixture of 5-nitro-2-(1-piperidyl) pyrimidine (1.31 g, 6.27 mmol, 1.00 eq) and palladium on carbon (10% weight on C) (2.00 g, 6.27 mmol, 1.00 eq) in methanol (10.0 mL) was stirred at 25° C. for 12 h under hydrogen (15 Psi). The mixture was filtered over Celite, and the filtrate was concentrated under reduced pressure to afford 2-(piperidin-1-yl)pyrimidin-5-amine.

Step 3: To a solution of 2-(piperidin-1-yl)pyrimidin-5-amine (300 mg, 1.68 mmol, 1.00 eq), and pyridine (0.41 mL, 5.05 mmol, 3.00 eq) in acetonitrile (10.0 mL) was added phenyl chloroformate (0.32 mL, 2.52 mmol, 1.50 eq). The reaction was stirred at 25° C. for 12 h. The mixture was diluted with ethyl acetate (50.0 mL) and water (50.0 mL). The organic layer was separated, and the aqueous layer was extracted with ethyl acetate (3×100 mL). The combined organic layers were dried over sodium sulfate, filtered, and concentrated and the obtained residue was purified by standard methods to afford phenyl (2-(piperidin-1-yl)pyrimidin-5-yl)carbamate.

Compound 65: General procedure A with variant i) was used for the preparation from compound VIII employing phenyl (6-(8-oxa-3-azabicyclo[3.2.1]octan-3-yl)pyridin-3-yl)carbamate. $^1$H NMR (400 MHz, DMSO-$d_6$) δ=11.00 (s, 1H), 9.57 (br s, 1H), 8.28 (s, 1H), 8.17 (br s, 1H), 7.78 (s, 1H), 7.72-7.58 (m, 3H), 6.69 (d, J=9.1 Hz, 1H), 5.25 (s, 2H), 5.13 (dd, J=5.1, 13.3 Hz, 1H), 4.50-4.32 (m, 4H), 3.71 (d, J=11.6 Hz, 2H), 2.97-2.89 (m, 1H), 2.88 (d, J=2.4 Hz, 1H), 2.85 (d, J=2.4 Hz, 1H), 2.65-2.58 (m, 1H), 2.46-2.35 (m, 1H), 2.06-1.98 (m, 1H), 1.88-1.78 (m, 2H), 1.77-1.70 (m, 2H). MS (ESI) m/z 506.3 [M+H]$^+$ Step 1: To a solution of 2-chloro-5-nitropyridine (1.00 g, 6.31 mmol, 1.00 eq) and 8-oxa-3-azabicyclo[3.2.1]octane hydrochloride (1.00 g, 6.68 mmol, 1.06 eq, hydrochloride) in dimethylformamide (10.0 mL) was added potassium carbonate (2.62 g, 18.9 mmol, 3.00 eq) in portions. The reaction was stirred at 25° C. for 3 h. The mixture was diluted with water (100 mL) and extracted with ethyl acetate (3×30.0 mL). The combined organic layers were washed with brine (20.0 mL), dried over anhydrous sodium sulfate, filtered, and concentrated under reduced pressure to afford 3-(5-nitro-2-pyridyl)-8-oxa-3-azabicyclo[3.2.1]octane.

Step 2: To a solution of 3-(5-nitropyridin-2-yl)-8-oxa-3-azabicyclo[3.2.1]octane (800 mg, 3.40 mmol, 1.00 eq) in methanol (10.0 mL) was added palladium on carbon (10% weight on C) (80.0 mg) in one portion under nitrogen. The reaction was stirred at 25° C. for 1 h under hydrogen (15 Psi). The mixture was filtered, and the filtrate was concentrated under reduced pressure to afford 6-(8-oxa-3-azabicyclo[3.2.1]octan-3-yl)pyridin-3-amine.

Step 3: To a solution of 6-(8-oxa-3-azabicyclo[3.2.1]octan-3-yl)pyridin-3-amine (400 mg, 1.95 mmol, 1.00 eq) and pyridine (0.79 mL, 9.74 mmol, 5.00 eq) in acetonitrile (5.00 mL) was added phenyl chloroformate (0.32 mL, 2.53 mmol, 1.30 eq) at 0° C. The reaction was stirred at 25° C. for 12 h. The mixture was concentrated and the obtained residue was purified by standard methods to afford phenyl (6-(8-oxa-3-azabicyclo[3.2.1]octan-3-yl)pyridin-3-yl)carbamate.

Compound 66: General procedure A with variant i) was used for the preparation from compound VIII employing phenyl (2,3-dihydrobenzofuran-5-yl)carbamate. $^1$H NMR (400 MHz, DMSO-$d_6$) δ=11.00 (s, 1H), 9.56 (br s, 1H), 7.80 (s, 1H), 7.74-7.58 (m, 2H), 7.36 (br s, 1H), 7.14 (br d, J=8.0 Hz, 1H), 6.68 (d, J=8.6 Hz, 1H), 5.26 (s, 2H), 5.14 (dd, J=5.0, 13.4 Hz, 1H), 4.54-4.44 (m, 3H), 4.42-4.30 (m, 1H), 3.18-3.10 (m, 2H), 2.98-2.86 (m, 1H), 2.62 (br d, J=16.8 Hz, 1H), 2.48-2.32 (m, 1H), 2.10-1.98 (m, 1H). MS (ESI) m/z 436.2 [M+H]$^+$ To a mixture of 2,3-dihydrobenzofuran-5-amine (400 mg, 2.96 mmol, 1.00 eq) and phenyl chloroformate (0.41 mL, 3.26 mmol, 1.10 eq) in acetonitrile (3.00 mL) was added pyridine (0.72 mL, 8.88 mmol, 3.00 eq) in one portion. The reaction was stirred at 25° C. for 2 h. The mixture was diluted with water (30.0 mL) and exacted with ethyl acetate (3×30.0 mL). The combined organic phases were separated, washed with brine (2×10.0 mL), dried over sodium sulfate, filtered, and concentrated and the obtained residue was purified by standard methods to afford phenyl (2,3-dihydrobenzofuran-5-yl)carbamate.

Compound 67: General procedure A with variant i) was used for the preparation from compound VIII employing phenyl chroman-6-ylcarbamate. $^1$H NMR (400 MHz, DMSO-$d_6$) δ=11.00 (s, 1H), 9.52 (br s, 1H), 7.78 (s, 1H), 7.70-7.58 (m, 2H), 7.17 (br s, 1H), 7.10 (br d, J=8.8 Hz, 1H), 6.64 (d, J=8.8 Hz, 1H), 5.24 (s, 2H), 5.13 (dd, J=5.2, 13.2 Hz, 1H), 4.51-4.42 (m, 1H), 4.39-4.30 (m, 1H), 4.11-4.03 (m, 2H), 2.97-2.86 (m, 1H), 2.69 (t, J=6.4 Hz, 2H), 2.61 (br d, J=17.6 Hz, 1H), 2.41 (dt, J=8.8, 13.2 Hz, 1H), 2.06-1.98 (m, 1H), 1.93-1.84 (m, 2H). MS (ESI) m/z 450.3 [M+H]$^+$ Step 1: A solution of chromane (1.00 g, 7.45 mmol, 1.00 eq) in nitric acid (10.0 mL) was stirred at −10° C. for 1 h. The reaction mixture was diluted with ice water (50.0 mL) and then quenched by addition of sodium hydroxide aqueous solution (1 N, 50.0 mL) at 0° C. The mixture was extracted with dichloromethane (3×20.0 mL). The combined organic layers were washed with brine (20.0 mL), dried over anhydrous sodium sulfate, filtered, and concentrated under reduced pressure to give a residue. The residue was purified by silica gel column chromatography (petroleum ether/ethyl acetate=10/1 to 5/1) to afford 6-nitrochroman.

Step 2: To a solution of 6-nitrochromane (650 mg, 3.63 mmol, 1.00 eq) in ethyl acetate (6.00 mL) was added palladium on carbon (10% weight on C) (100 mg) under nitrogen atmosphere. The reaction mixture was stirred at 25°

C. for 2 h under hydrogen. The mixture was filtered and concentrated under reduced pressure to afford chroman-6-amine.

Step 3: To a solution of chroman-6-amine (120 mg, 804 µmol, 1.00 eq) and pyridine (0.20 mL, 2.41 mmol, 3.00 eq) in acetonitrile (2.00 mL) was added phenyl chloroformate (0.12 mL, 965 µmol, 1.20 eq) at 25° C. The reaction was stirred at 25° C. for 12 h. The mixture was concentrated and the obtained residue was purified by standard methods to afford phenyl chroman-6-ylcarbamate.

Compound 68: General procedure A with variant i) was used for the preparation from compound VIII employing phenyl (3-chloro-4-methyl-5-((1-methylpyrrolidin-3-yl)oxy)phenyl)carbamate. $^1$H NMR (400 MHz, DMSO-d$_6$) δ=11.70-11.08 (m, 1H), 10.70 (br s, 1H), 9.70 (s, 1H), 7.80 (s, 1H), 7.70-7.66 (m, 1H), 7.66-7.62 (m, 1H), 7.26 (br s, 1H), 7.12 (s, 1H), 5.30 (s, 2H), 5.08 (br dd, J=5.4, 13.0 Hz, 2H), 4.54-4.46 (m, 1H), 4.46-4.36 (m, 1H), 4.06-3.56 (m, 3H), 3.44-3.36 (m, 2H), 2.92-2.84 (m, 4H), 2.68-2.62 (m, 1H), 2.44 (dd, J=4.6, 13.2 Hz, 1H), 2.20 (s, 4H), 2.12-2.04 (m, 1H). MS (ESI) m/z 541.3 [M+H]$^+$ Step 1: A solution of tert-butyl 3-(3-chloro-2-methyl-5-nitrophenoxy)pyrrolidine-1-carboxylate (described in example 44) (730 mg, 2.05 µmol, 1.00 eq) and hydrochloric acid/ethyl acetate (10.0 mL) in ethyl acetate (20.0 mL) was stirred at 25° C. for 4 h. The mixture was concentrated under reduced pressure to give a residue. The residue was diluted with saturated sodium bicarbonate (50.0 mL) and extracted with ethyl acetate (3×20.0 mL). The combined organic layers were washed with brine (20.0 mL), dried over anhydrous sodium sulfate, filtered, and concentrated under reduced pressure to afford 3-(3-chloro-2-methyl-5-nitrophenoxy)pyrrolidine.

Step 2: To a solution of 3-(3-chloro-2-methyl-5-nitrophenoxy)pyrrolidine (400 mg, 1.56 mmol, 1.00 eq) and formaldehyde 37% (12.0 mL, 161 mmol, 103 eq) in methanol (3.00 mL) was added acetic acid (0.09 mL, 1.56 mmol, 1.00 eq) at 25° C. The reaction was stirred at 25° C. for 0.5 h. Then sodium cyanoborohydride (979 mg, 15.6 mmol, 10.0 eq) was added, and the reaction was stirred at 25° C. for another 1.5 h. The mixture was concentrated under reduced pressure to give a residue. The residue was diluted with water (50.0 mL) and extracted with ethyl acetate (3×20.0 mL). The combined organic layers were washed with brine (20.0 mL), dried over sodium sulfate, filtered, and concentrated under reduced pressure to give a residue. The residue was purified by reversed phase preparative HPLC to afford 3-(3-chloro-2-methyl-5-nitrophenoxy)-1-methylpyrrolidine.

Step 3: To a mixture of 3-(3-chloro-2-methyl-5-nitrophenoxy)-1-methylpyrrolidine (250 mg, 923 µmol, 1.00 eq), iron powder (258 mg, 4.62 mmol, 5.00 eq) and ammonium chloride (247 g, 4.62 mmol, 5.00 eq) in methanol (5.00 mL) was added water (5.00 mL) at 25° C. The reaction was stirred at 80° C. for 2 h. The mixture was concentrated under reduced pressure to give a residue. The residue was poured into saturated sodium bicarbonate (20.0 mL) and extracted with ethyl acetate (3×20.0 mL). The combined organic layers were washed with brine (20.0 mL), dried over anhydrous sodium sulfate, filtered, and concentrated under reduced pressure to afford 3-chloro-4-methyl-5-((1-methylpyrrolidin-3-yl)oxy)aniline.

Step 4: To a solution of 3-chloro-4-methyl-5-(1-methylpyrrolidin-3-yl)oxy-aniline (116 mg, 482 µmol, 1.00 eq) and phenyl chloroformate (0.66 mL, 530 µmol, 1.10 eq) in acetonitrile (5.00 mL) was added pyridine (0.12 mL, 1.45 mmol, 3.00 eq) in one portion at 25° C. The reaction was stirred at 25° C. for 2 h. The mixture was diluted with water (30.0 mL) and exacted with ethyl acetate (3×30.0 mL). The combined organic layers were washed with brine (2×10.0 mL), dried over sodium sulfate, filtered, and concentrated and the obtained residue was purified by standard methods to afford (3-chloro-4-methyl-5-((1-methylpyrrolidin-3-yl)oxy)phenyl)carbamate.

Compound 69: General procedure A with variant i) was used for the preparation from compound VIII employing phenyl (6-(3-methylpyrrolidin-1-yl)pyridin-3-yl)carbamate. $^1$H NMR (400 MHz, DMSO-d$_6$) δ=11.00 (s, 1H), 9.42 (br s, 1H), 8.15 (s, 1H), 8.10 (br s, 1H), 7.78 (s, 1H), 7.70-7.62 (m, 2H), 7.58 (br d, J=7.7 Hz, 1H), 6.38 (d, J=8.9 Hz, 1H), 5.24 (s, 2H), 5.13 (dd, J=5.1, 13.3 Hz, 1H), 4.52-4.43 (m, 1H), 4.39-4.31 (m, 1H), 3.54 (dd, J=7.3, 9.9 Hz, 1H), 3.47-3.43 (m, 1H), 3.29-3.27 (m, 1H), 2.98-2.85 (m, 2H), 2.65-2.56 (m, 1H), 2.47-2.38 (m, 1H), 2.36-2.29 (m, 1H), 2.12-1.95 (m, 2H), 1.55 (qd, J=8.3, 12.1 Hz, 1H), 1.07 (d, J=6.6 Hz, 3H). MS (ESI) m/z 478.2 [M+H]$^+$ Step 1: To a solution of 2-chloro-5-nitropyridine (2.00 g, 12.6 mmol, 1.00 eq) in dimethylformamide (20.0 mL) was added 3-methylpyrrolidine hydrochloride (2.30 g, 18.9 mmol, 1.50 eq) and potassium carbonate (5.23 g, 37.8 mmol, 3.00 eq). The reaction was stirred at 60° C. for 1 h. The mixture was poured into water (500 ml) at 0° C. The resulting precipitate was collected by filtration and dried under vacuum to afford 2-(3-methylpyrrolidin-1-yl)-5-nitropyridine.

Step 2: To a solution of 2-(3-methylpyrrolidin-1-yl)-5-nitropyridine (2.60 g, 12.5 mmol, 1.00 eq) in methanol (30.0 mL) was added palladium on carbon (10% weight on C) (50.0 mg). The reaction was stirred at 25° C. for 1 h under hydrogen (15 Psi). The mixture was filtered, and the filtrate was concentrated under reduced pressure to afford 6-(3-methylpyrrolidin-1-yl)pyridin-3-amine.

Step 3: To a solution of 6-(3-methylpyrrolidin-1-yl)pyridin-3-amine (1.60 g, 9.03 mmol, 1.00 eq) and pyridine (3.64 mL, 45.1 mmol, 5.00 eq) in acetonitrile (16.0 mL) was added phenyl chloroformate (1.47 mL, 11.7 mmol, 1.30 eq). The reaction was stirred at 25° C. for 1 h. The mixture was concentrated and the residue was purified by a standard method to afford phenyl(6-(3-methylpyrrolidin-1-yl)pyridin-3-yl)carbamate.

Compound 70: General procedure A with variant i) was used for the preparation from compound VIII employing phenyl (3-chloro-4-methyl-5-((1-methylpyrrolidin-3-yl)methoxy)phenyl)carbamate. $^1$H NMR (400 MHz, DMSO-d$_6$) δ=11.00 (s, 1H), 10.85 (br d, J=3.7 Hz, 1H), 9.95 (s, 1H), 7.79 (s, 1H), 7.73-7.60 (m, 2H), 7.26-7.10 (m, 2H), 5.28 (s, 2H), 5.13 (dd, J=5.1, 13.3 Hz, 1H), 4.54-4.44 (m, 1H), 4.41-4.29 (m, 1H), 4.08-3.93 (m, 2H), 3.75-3.69 (m, 1H), 3.49-3.41 (m, 1H), 3.26-3.16 (m, 1H), 3.13-3.01 (m, 1H), 2.97-2.86 (m, 2H), 2.81 (t, J=4.8 Hz, 3H), 2.61 (br d, J=17.9 Hz, 1H), 2.56-2.52 (m, 1H), 2.41 (dq, J=4.4, 13.2 Hz, 1H), 2.32-2.15 (m, 1H), 2.14 (s, 3H), 2.06-1.97 (m, 1H), 1.96-1.71 (m, 1H). MS (ESI) m/z 555.2 [M+H]$^+$ Step 1: A mixture of tert-butyl 3-((3-chloro-2-methyl-5-nitrophenoxy)methyl)pyrrolidine-1-carboxylate (described in example 52) (1.26 g, 3.40 mmol, 1.00 eq) in hydrochloric acid/ethyl acetate (4.0 M, 1.13 mL) was stirred at 25° C. for 1 h. The mixture was concentrated under reduced pressure to afford 3-((3-chloro-2-methyl-5-nitrophenoxy)methyl)pyrrolidine.

Step 2: To a solution of 3-((3-chloro-2-methyl-5-nitrophenoxy)methyl)pyrrolidine (900 mg, 3.32 mmol, 1.00 eq) in 2,2,2-trifluoroethanol (10.0 mL) was added paraformaldehyde (0.46 mL, 16.6 mmol, 5.00 eq). The reaction was stirred at 60° C. for 0.5 h. Then sodium borohydride (252 mg, 6.65 mmol, 2.00 eq) was added in portions, and the reaction was stirred at 60° C. for 1 h. The mixture was diluted with water (100 mL) and extracted with ethyl acetate (3×30.0 mL). The combined organic layers were washed with brine (20.0 mL), dried over anhydrous sodium sulfate, filtered, and concentrated under reduced pressure to afford 3-((3-chloro-2-methyl-5-nitrophenoxy)methyl)-1-methylpyrrolidine.

Step 3: To a solution of 3-((3-chloro-2-methyl-5-nitrophenoxy)methyl)-1-methylpyrrolidine (850 mg, 2.99 mmol, 1.00 eq) and ammonium chloride (798 mg, 14.9 mmol, 5.00 eq) in methanol (5.00 mL) and water (5.00 mL) was added iron powder (500 mg, 8.96 mmol, 3.00 eq) in portions. The reaction was stirred at 80° C. for 2 h. The mixture was concentrated under reduced pressure to give a residue. The residue was purified by reversed phase preparative HPLC to afford 3-chloro-4-methyl-5-((1-methylpyrrolidin-3-yl)methoxy)aniline.

Step 4: To a solution of 3-chloro-4-methyl-5-((1-methylpyrrolidin-3-yl)methoxy)aniline (300 mg, 1.18 mmol, 1.00 eq) and pyridine (0.29 mL, 3.53 mmol, 3.00 eq) in acetonitrile (5.00 mL) was added phenyl chloroformate (0.22 mL, 1.77 mmol, 1.50 eq) dropwise at 0° C. The reaction was stirred at 25° C. for 12 h. The mixture was concentrated and the obtained residue was purified by standard methods to afford phenyl (3-chloro-4-methyl-5-((1-methylpyrrolidin-3-yl) methoxy)phenyl)carbamate.

Compound 71: General procedure A with variant i) was used for the preparation from compound VIII employing phenyl (2-ethyl-6-methylpyridin-4-yl)carbamate. $^1$H NMR (400 MHz, DMSO-$d_6$) δ=11.00 (br s, 1H), 10.11 (s, 1H), 8.27 (br s, 1H), 7.80 (s, 1H), 7.72-7.59 (m, 2H), 7.14 (d, J=3.5 Hz, 2H), 5.30 (s, 2H), 5.13 (dd, J=5.1, 13.3 Hz, 1H), 4.51-4.31 (m, 2H), 2.98-2.87 (m, 1H), 2.61 (q, J=7.5 Hz, 3H), 2.41 (br dd, J=4.4, 13.1 Hz, 1H), 2.35 (s, 3H), 2.07-1.96 (m, 1H), 1.17 (t, J=7.6 Hz, 3H). MS (ESI) m/z 437.1[M+H]$^+$ Step 1: To a mixture of 2-chloro-6-methyl-4-nitropyridine (2.00 g, 11.6 mmol, 1.00 eq), ethylboronic acid (2.57 g, 34.8 mmol, 3.00 eq) and potassium carbonate (4.81 g, 34.8 mmol, 3.00 eq) in dioxane (20.0 mL) was added tetrakis(triphenylphosphine)palladium(0) (1.34 g, 1.16 mmol, 0.100 eq) under nitrogen atmosphere. The reaction was stirred at 110° C. for 12 h. The mixture was concentrated under reduced pressure to give a residue. The residue was purified by silica gel column chromatography (petroleum ether/ethyl acetate=10/1) to afford 2-ethyl-6-methyl-4-nitropyridine.

Step 2: To a solution of 2-ethyl-6-methyl-4-nitropyridine (650 mg, 3.91 mmol, 1.00 eq) in methanol (50.0 mL) was added palladium on carbon (10% weight on C) (10.0 mg) in one portion. The reaction was stirred at 25° C. for 2 h under hydrogen (15 Psi). The mixture was filtered, and the filtrate was concentrated under reduced pressure to afford 2-ethyl-6-methylpyridin-4-amine.

Step 3: To a solution of 2-ethyl-6-methylpyridin-4-amine (450 mg, 3.30 mmol, 1.00 eq) in dimethylformamide (5.00 mL) was added sodium hydride (60% dispersion in mineral oil) (396 mg, 9.91 mmol, 3.00 eq) in portions at 0° C. The reaction was stirred at 0° C. for 0.5 h. Then phenyl chloroformate (0.50 mL, 3.96 mmol, 1.20 eq) was added dropwise at 0° C. The reaction was stirred at 25° C. for 12 h, then it was quenched with 1M hydrochloric acid and filtered. The filtrate was concentrated and the obtained residue was purified by standard methods to afford phenyl (2-ethyl-6-methylpyridin-4-yl)carbamate.

Compound 72: General procedure A with variant i) was used for the preparation from compound VIII employing phenyl (5-fluoro-6-(piperidin-1-yl)pyridin-3-yl)carbamate. $^1$H NMR (400 MHz, DMSO-$d_6$) δ=11.00 (s, 1H), 9.92 (br s, 1H), 8.07 (s, 1H), 7.79 (s, 1H), 7.72-7.59 (m, 3H), 5.28 (s, 2H), 5.13 (dd, J=5.1, 13.3 Hz, 1H), 4.52-4.43 (m, 1H), 4.38-4.31 (m, 1H), 3.23 (br d, J=5.5 Hz, 4H), 2.97-2.87 (m, 1H), 2.65-2.57 (m, 1H), 2.46-2.35 (m, 1H), 2.07-1.97 (m, 1H), 1.66-1.54 (m, 6H). MS (ESI) m/z 496.2 [M+H]$^+$ Step 1: To a solution of 2-chloro-3-fluoro-5-nitropyridine (0.500 g, 2.83 mmol, 1.00 eq) in dimethylformamide (5.00 mL) were added piperidine (250 mg, 2.94 mmol, 1.04 eq) and potassium carbonate (800 mg, 5.79 mmol, 2.04 eq). The reaction was stirred at 25° C. for 2 h. The mixture was poured into water (100 mL). The resulting precipitate was collected by filtration and dried under vacuum to afford 3-fluoro-5-nitro-2-(piperidin-1-yl)pyridine.

Step 2: To a solution of 3-fluoro-5-nitro-2-(piperidin-1-yl)pyridine (515 mg, 2.29 mmol, 1.00 eq) in methanol (10.0 mL) was added wet palladium on carbon (10% weight on C) (50.0 mg) under hydrogen. The mixture was stirred at 25° C. for 2 h under hydrogen (15.0 Psi). The mixture was filtered, and the filtrate was concentrated under reduced pressure to afford 5-fluoro-6-(piperidin-1-yl)pyridin-3-amine.

Step 3: To a solution of 5-fluoro-6-(piperidin-1-yl)pyridin-3-amine (440 mg, 2.25 mmol, 1.00 eq) in acetonitrile (10.0 mL) were added pyridine (0.11 mL, 11.3 mmol, 5.00 eq) and phenyl chloroformate (0.34 mL, 2.70 mmol, 1.20 eq) at 0° C. The reaction was stirred at 0° C. for 1 h. The pH was adjusted to pH=5 with formic acid (1.00 mL) and the solution was filtered. The filtrate was concentrated and the obtained residue was purified by standard methods to afford phenyl (5-fluoro-6-(piperidin-1-yl)pyridin-3-yl)carbamate.

Compound 73: General procedure A with variant i) was used for the preparation from compound VIII employing phenyl (6-(3,3-difluoropiperidin-1-yl)pyridin-3-yl)carbamate. $^1$H NMR (400 MHz, DMSO-$d_6$) δ=11.00 (br s, 1H), 9.61 (br s, 1H), 8.32 (br s, 1H), 8.18 (br s, 1H), 7.79 (s, 1H), 7.72-7.60 (m, 3H), 6.91 (d, J=9.1 Hz, 1H), 5.26 (s, 2H), 5.13 (dd, J=5.1, 13.3 Hz, 1H), 4.52-4.44 (m, 1H), 4.39-4.30 (m, 1H), 3.80 (t, J=12.1 Hz, 2H), 3.51-3.47 (m, 2H), 2.98-2.86 (m, 1H), 2.64-2.58 (m, 1H), 2.47-2.36 (m, 1H), 2.11-1.99 (m, 3H), 1.77-1.69 (m, 2H). MS (ESI) m/z 514.2 [M+H]$^+$ Step 1: To a solution of 2-chloro-5-nitropyridine (300 mg, 1.89 mmol, 1.00 eq) in dimethylformamide (6.00 mL) were added potassium carbonate (784 mg, 5.68 mmol, 3.00 eq) and 3,3-difluoropiperidine hydrochloride (447 mg, 2.84 mmol, 1.50 eq). The reaction was stirred at 50° C. for 2 h. The mixture was poured slowly into ice-water (40.0 mL). The resulting precipitate was collected by filtration and dried under vacuum to afford 2-(3,3-difluoropiperidin-1-yl)-5-nitropyridine.

Step 2: To a solution of 2-(3,3-difluoropiperidin-1-yl)-5-nitropyridine (452 mg, 1.86 mmol, 1.00 eq) in methanol (10.0 mL) was added wet palladium on carbon (10% weight on C) (50.0 mg) under hydrogen. The mixture was stirred at 25° C. for 3 h under hydrogen (15 Psi). The mixture was filtered, and the filtrate was concentrated under reduced pressure to afford 6-(3,3-difluoropiperidin-1-yl)pyridin-3-amine.

Step 3: To a solution of 6-(3,3-difluoropiperidin-1-yl)pyridin-3-amine (380 mg, 1.78 mmol, 1.00 eq) and pyridine (0.72 mL, 8.91 mmol, 5.00 eq) in acetonitrile (10.0 mL) was added phenyl chloroformate (0.34 mL, 2.67 mmol, 1.50 eq) at 0° C. The reaction was stirred at 0° C. for 1 h. The mixture was concentrated and the obtained residue was purified by standard methods to afford phenyl (6-(3,3-difluoropiperidin-1-yl)pyridin-3-yl)carbamate.

Compound 74: General procedure A with variant i) was used for the preparation from compound VIII employing phenyl (6-(2-methylpyrrolidin-1-yl)pyridin-3-yl)carbamate. $^1$H NMR (400 MHz, DMSO-d$_6$) δ=11.00 (s, 1H), 9.42 (br s, 1H), 8.14 (s, 1H), 8.10 (br s, 1H), 7.78 (s, 1H), 7.65 (q, J=7.9 Hz, 2H), 7.57 (br d, J=7.8 Hz, 1H), 6.41 (d, J=9.1 Hz, 1H), 5.24 (s, 2H), 5.13 (dd, J=5.1, 13.3 Hz, 1H), 4.53-4.43 (m, 1H), 4.39-4.29 (m, 1H), 4.11-4.00 (m, 1H), 3.43 (ddd, J=2.4, 7.4, 9.8 Hz, 1H), 3.26-3.15 (m, 1H), 2.99-2.86 (m, 1H), 2.61 (br d, J=18.5 Hz, 1H), 2.41 (br dd, J=4.5, 13.1 Hz, 1H), 2.07-1.96 (m, 3H), 1.95-1.87 (m, 1H), 1.65 (br dd, J=2.9, 4.6 Hz, 1H), 1.13 (d, J=6.1 Hz, 3H). MS (ESI) m/z 478.3 [M+H]$^+$ Step 1: To a solution of 2-chloro-5-nitropyridine (400 mg, 2.52 mmol, 1.00 eq) in dimethylformamide (6.00 mL) were added potassium carbonate (1.05 g, 7.57 mmol, 3.00 eq) and 2-methylpyrrolidine hydrochloride (460 mg, 3.78 mmol, 1.50 eq). The reaction was stirred at 50° C. for 1 h. The mixture was slowly poured into ice-water (40.0 ml). The resulting precipitate was collected by filtration and dried under vacuum to afford 2-(2-methylpyrrolidin-1-yl)-5-nitropyridine.

Step 2: To a solution of 2-(2-methylpyrrolidin-1-yl)-5-nitropyridine (512 mg, 2.47 mmol, 1.00 eq) in methanol (10.0 mL) was added wet palladium on carbon (10% weight on C) (50.0 mg) under hydrogen. The reaction was stirred at 25° C. for 3 h under hydrogen (15.0 psi). The mixture was filtered, and the filtrate was concentrated under reduced pressure to afford 6-(2-methylpyrrolidin-1-yl)pyridin-3-amine.

Step 3: To a solution of 6-(2-methylpyrrolidin-1-yl)pyridin-3-amine (371 mg, 2.09 mmol, 1.00 eq) and pyridine (0.85 mL, 10.5 mmol, 5.00 eq) in acetonitrile (10.0 mL) was added phenyl chloroformate (0.39 mL, 3.14 mmol, 1.50 eq) at 0° C. The reaction was stirred at 0° C. for 1 h. The mixture was concentrated and the obtained residue was purified by standard methods to afford phenyl (6-(2-methylpyrrolidin-1-yl)pyridine-3-yl)carbamate.

Compound 75: General procedure A with variant i) was used for the preparation from compound VIII employing phenyl (6-(piperidin-1-yl)pyridazin-3-yl)carbamate. $^1$H NMR (400 MHz, DMSO-d$_6$) δ=11.08 (s, 1H), 11.00 (s, 1H), 8.24-8.15 (m, 1H), 8.13-8.04 (m, 1H), 7.82 (s, 1H), 7.76-7.60 (m, 2H), 5.34 (s, 2H), 5.13 (dd, J=5.1, 13.3 Hz, 1H), 4.52-4.45 (m, 1H), 4.39-4.33 (m, 1H), 3.70 (br s, 4H), 3.01-2.84 (m, 1H), 2.61 (br d, J=17.9 Hz, 1H), 2.45-2.36 (m, 1H), 2.07-1.97 (m, 1H), 1.65 (br s, 6H). MS (ESI) m/z 479.2 [M+H]$^+$ Step 1: To a solution of 6-chloropyridazin-3-amine (500 mg, 3.86 mmol, 1.00 eq) and piperidine (0.76 mL, 7.72 mmol, 2.00 eq) in dimethylformamide (3.00 mL) was added N,N-diisopropylethylamine (1.34 mL, 7.72 mmol, 2.00 eq) dropwise. The reaction was stirred at 180° C. for 2 h under microwave irradiation. The mixture was filtered, and the filtrate was concentrated under reduced pressure to give a residue. The residue was purified by reversed phase preparative HPLC to afford 6-(piperidin-1-yl)pyridazin-3-amine.

Step 2: To a solution of 6-(piperidin-1-yl)pyridazin-3-amine (180 mg, 1.01 mmol, 1.00 eq) and pyridine (0.25 mL, 3.03 mmol, 3.00 eq) in dimethylformamide (0.50 mL) and acetonitrile (3.00 mL) was added phenyl chloroformate (0.16 mL, 1.31 mmol, 1.30 eq) dropwise at 0° C. The reaction was stirred at 25° C. for 12 h. The mixture was concentrated and the obtained residue was purified by standard methods to afford phenyl (6-(piperidin-1-yl)pyridazin-3-yl)carbamate.

Compound 76: General procedure A with variant i) was used for the preparation from compound VIII employing phenyl (6-morpholinopyridin-3-yl)carbamate. $^1$H NMR (400 MHz, DMSO-d$_6$) δ=10.99 (br s, 1H), 9.61 (br s, 1H), 8.20 (br s, 1H), 7.78 (s, 1H), 7.70-7.61 (m, 3H), 6.81 (d, J=9.0 Hz, 1H), 5.25 (s, 2H), 5.12 (dd, J=5.1, 13.4 Hz, 1H), 4.51-4.43 (m, 1H), 4.37-4.30 (m, 1H), 3.70-3.66 (m, 4H), 3.35 (br s, 4H), 2.97-2.86 (m, 1H), 2.63-2.57 (m, 1H), 2.40 (br dd, J=4.6, 13.2 Hz, 1H), 2.05-1.97 (m, 1H). MS (ESI) m/z 480.2 [M+H]$^+$ To a solution of 6-morpholinopyridin-3-amine (300 mg, 1.67 mmol, 1.00 eq) and pyridine (0.41 mL, 5.02 mmol, 3.00 eq) in acetonitrile (8.00 mL) was added phenyl chloroformate (0.25 mL, 2.01 mmol, 1.20 eq) in portions at 0° C. The reaction was stirred at 25° C. for 1 h. The mixture was concentrated under reduced pressure to give a residue which was diluted with ethyl acetate (6.00 mL) and water (4.00 mL). The resulting precipitate was collected by filtration and dried by standard methods to afford phenyl (6-morpholinopyridin-3-yl)carbamate.

Compound 77: General procedure A with variant i) was used for the preparation from compound VIII employing phenyl (6-(2-methylpiperidin-1-yl)pyridin-3-yl)carbamate. $^1$H NMR (400 MHz, DMSO-d$_6$) δ=11.07-10.89 (m, 1H), 9.50 (br s, 1H), 8.14 (br s, 1H), 7.78 (s, 1H), 7.72-7.51 (m, 3H), 6.72 (d, J=9.3 Hz, 1H), 5.25 (s, 2H), 5.13 (dd, J=5.0, 13.3 Hz, 1H), 4.59-4.51 (m, 1H), 4.51-4.43 (m, 1H), 4.40-4.29 (m, 1H), 3.97 (br d, J=13.0 Hz, 1H), 2.99-2.86 (m, 1H), 2.79 (dt, J=2.8, 12.8 Hz, 1H), 2.65-2.57 (m, 1H), 2.48-2.38 (m, 1H), 2.07-1.96 (m, 1H), 1.73-1.54 (m, 5H), 1.47-1.31 (m, 1H), 1.02 (d, J=6.7 Hz, 3H). MS (ESI) m/z 492.2 [M+H]$^+$ Step 1: To a solution of 2-chloro-5-nitropyridine (2.00 g, 12.6 mmol, 1.00 eq) in dimethylformamide (10.0 mL) were added 2-methylpiperidine (2.24 mL, 18.9 mmol, 1.50 eq) and potassium carbonate (5.23 g, 37.8 mmol, 3.00 eq). The reaction was stirred at 60° C. for 1 h. The mixture was poured into water (200 mL) and extracted with ethyl acetate (2×100 mL). The combined organic layers were dried over sodium sulfate, filtered, and concentrated under reduced pressure to afford 2-(2-methylpiperidin-1-yl)-5-nitropyridine.

Step 2: To a solution of 2-(2-methylpiperidin-1-yl)-5-nitropyridine (2.70 g, 12.2 mmol, 1.00 eq) in methanol (30.0 mL) was added palladium on carbon (50.0 mg, 10% weight on C). The reaction was stirred at 25° C. for 1 h under hydrogen (15 Psi). The mixture was filtered, and the filtrate was concentrated under reduced pressure to afford 6-(2-methylpiperidin-1-yl)pyridin-3-amine.

Step 3: To a solution of 6-(2-methylpiperidin-1-yl)pyridin-3-amine (2.20 g, 11.5 mmol, 1.00 eq) and pyridine (4.64 mL, 57.5 mmol, 5.00 eq) in acetonitrile (30.0 mL) was added phenyl chloroformate (1.73 mL, 13.8 mmol, 1.20 eq). The reaction was stirred at 25° C. for 1 h. The mixture was concentrated and the obtained residue was purified by standard methods to afford phenyl (6-(2-methylpiperidin-1-yl) pyridin-3-yl)carbamate.

Compound 78: General procedure A with variant i) was used for the preparation from compound VIII employing phenyl (6-(4,4-difluoropiperidin-1-yl)pyridin-3-yl) carbamate. $^1$H NMR (400 MHz, DMSO-d$_6$) δ=11.00 (s, 1H), 9.63 (br s, 1H), 8.30-8.11 (m, 1H), 7.79 (s, 1H), 7.75-7.60 (m, 3H), 6.95 (d, J=9.2 Hz, 1H), 5.26 (s, 2H), 5.13 (dd, J=5.1, 13.3 Hz, 1H), 4.52-4.43 (m, 1H), 4.40-4.30 (m, 1H), 3.67-3.58 (m, 4H), 2.99-2.85 (m, 1H), 2.65-2.57 (m, 1H), 2.46-2.36 (m, 1H), 2.05-1.91 (m, 5H). MS (ESI) m/z 514.2 [M+H]$^+$ Step 1: To a solution of 2-chloro-5-nitropyridine (2.00 g, 12.6 mmol, 1.00 eq) in dimethylformamide (10.0 mL) was added 4,4-difluoropiperidine hydrochloride (2.00 g, 12.6 mmol, 1.01 eq, HCl) and potassium carbonate (4.00 g, 28.9 mmol, 2.29 eq). The reaction was stirred at 60° C. for 2 h. The mixture was poured into water (100 mL). The resulting yellow precipitate was collected by filtration and dried under vacuum to afford 2-(4,4-difluoropiperidin-1-yl)-5-nitropyridine.

Step 2: To a solution of 2-(4,4-difluoropiperidin-1-yl)-5-nitropyridine (2.70 g, 11.1 mmol, 1.00 eq) in methanol (30.0 mL) was added palladium on carbon (50.0 mg, 10% weight on C). The reaction was stirred at 25° C. for 1 h under hydrogen (15 Psi). The mixture was filtered, and the filtrate was concentrated under reduced pressure to afford 6-(4,4-difluoropiperidin-1-yl)pyridin-3-amine.

Step 3: To a solution of 6-(4,4-difluoropiperidin-1-yl)pyridin-3-amine (2.30 g, 10.7 mmol, 1.00 eq) and pyridine (4.35 mL, 53.9 mmol, 5.00 eq) in acetonitrile (30.0 mL) was added phenyl chloroformate (1.62 mL, 12.9 mmol, 1.20 eq). The reaction was stirred at 25° C. for 1 h. The mixture was concentrated under reduced pressure to give a residue. Water (30.0 mL) was added, and the mixture was exacted with ethyl acetate (3×30.0 mL). The combined organic layers were dried, filtered, and concentrated by standard methods to afford phenyl(6-(4,4-difluoropiperidin-1-yl) pyridin-3-yl)carbamate.

Compound 79: General procedure A with variant i) was used for the preparation from compound VIII employing (2,2-difluorobenzo[d][1,3]dioxol-5-yl)carbamate. $^1$H NMR (400 MHz, DMSO-$d_6$) δ=10.99 (br s, 1H), 10.06 (br s, 1H), 7.80 (s, 1H), 7.71-7.67 (m, 1H), 7.67-7.62 (m, 1H), 7.58 (d, J=1.6 Hz, 1H), 7.33 (d, J=8.8 Hz, 1H), 7.18 (dd, J=2.0, 8.8 Hz, 1H), 5.29 (s, 2H), 5.13 (dd, J=5.2, 13.2 Hz, 1H), 4.54-4.43 (m, 1H), 4.41-4.29 (m, 1H), 2.98-2.86 (m, 1H), 2.64-2.57 (m, 1H), 2.46-2.35 (m, 1H), 2.06-1.97 (m, 1H). MS (ESI) m/z 474.2 [M+H]$^+$ To a solution of 2,2-difluorobenzo[d][1,3]dioxol-5-amine (500 mg, 2.57 mmol, 1.00 eq) and pyridine (0.70 mL, 8.66 mmol, 3.00 eq) in acetonitrile (5.00 mL) was added phenyl chloroformate (0.43 mL, 3.47 mmol, 1.20 eq) at 25° C. The reaction was stirred at 25° C. for 2 h. The mixture was concentrated and the obtained residue was purified by standard methods to afford phenyl (2,2-difluorobenzo[d][1,3]dioxol-5-yl)carbamate.

Compound 80: General procedure A with variant i) was used for the preparation from compound VIII employing phenyl (6-cyclopropylpyridin-3-yl)carbamate. $^1$H NMR (400 MHz, DMSO-$d_6$) δ=10.99 (br s, 1H), 9.87 (br s, 1H), 8.44 (d, J=2.2 Hz, 1H), 8.30 (s, 1H), 7.79 (s, 1H), 7.74 (br d, J=7.6 Hz, 1H), 7.70-7.66 (m, 1H), 7.65-7.61 (m, 1H), 7.20 (d, J=8.6 Hz, 1H), 5.27 (s, 2H), 5.18-5.05 (m, 1H), 4.51-4.43 (m, 1H), 4.38-4.30 (m, 1H), 2.98-2.84 (m, 1H), 2.65-2.56 (m, 1H), 2.47-2.34 (m, 1H), 2.08-1.95 (m, 2H), 0.92-0.85 (m, 2H), 0.85-0.80 (m, 2H). MS (ESI) m/z 435.1 [M+H]$^+$ To a solution of 6-cyclopropylpyridin-3-amine (0.500 g, 3.73 mmol, 1.00 eq) and pyridine (0.90 mL, 11.2 mmol, 3.00 eq) in acetonitrile (5.00 mL) was added phenyl chloroformate (0.56 mL, 4.47 mmol, 1.20 eq). The reaction was stirred at 25° C. for 12 h. The mixture was diluted with ethyl acetate (50.0 mL) and water (50.0 mL). The organic layer was separated, and the aqueous phase was extracted with ethyl acetate (3×100 mL). The combined organic layers were dried over sodium sulfate, filtered, and concentrated and the obtained residue was purified by standard methods to afford phenyl (6-cyclopropylpyridin-3-yl)carbamate.

Compound 81: General procedure A with variant i) was used for the preparation from compound VIII employing phenyl(4-(oxetan-3-yl)phenyl)carbamate. $^1$H NMR (400 MHz, DMSO-$d_6$) δ=11.00 (br s, 1H), 9.82 (br s, 1H), 7.80 (s, 1H), 7.72-7.66 (m, 1H), 7.66-7.62 (m, 1H), 7.47 (br d, J=8.4 Hz, 2H), 7.32 (d, J=8.6 Hz, 2H), 5.28 (s, 2H), 5.20-5.07 (m, 1H), 4.97-4.85 (m, 2H), 4.58 (t, J=6.4 Hz, 2H), 4.51-4.44 (m, 1H), 4.39-4.30 (m, 1H), 4.24-4.14 (m, 1H), 2.97-2.87 (m, 1H), 2.65-2.57 (m, 1H), 2.48-2.34 (m, 1H), 2.06-1.96 (m, 1H). MS (ESI) m/z 450.2 [M+H]$^+$ To a solution of 4-(oxetan-3-yl)aniline (200 mg, 1.34 mmol, 1.00 eq) and pyridine (0.32 mL, 4.02 mmol, 3.00 eq) in acetonitrile (10.0 mL) was added phenyl chloroformate (0.20 mL, 1.61 mmol, 1.20 eq). The reaction was stirred at 25° C. for 12 h. The mixture was diluted with ethyl acetate (50.0 mL) and water (50.0 mL). The organic layer was separated, and the aqueous phase was extracted with ethyl acetate (3×100 mL). The combined organic layers were dried over sodium sulfate, filtered, and concentrated and the obtained residue was purified by standard methods to afford phenyl(4-(oxetan-3-yl)phenyl)carbamate.

Compound 82: General procedure A with variant i) was used for the preparation from compound VIII employing phenyl (6-(4-methylpiperazin-1-yl)pyridin-3-yl)carbamate. $^1$H NMR (400 MHz, DMSO-$d_6$) δ=10.99 (s, 1H), 9.57 (br s, 1H), 8.18 (s, 2H), 7.78 (s, 1H), 7.65 (q, J=7.8 Hz, 3H), 6.81 (d, J=9.2 Hz, 1H), 5.24 (s, 2H), 5.12 (dd, J=5.1, 13.3 Hz, 1H), 4.51-4.44 (m, 1H), 4.37-4.30 (m, 1H), 3.42-3.37 (m, 4H), 2.91 (ddd, J=5.3, 13.5, 17.5 Hz, 1H), 2.60 (br dd, J=2.0, 15.6 Hz, 1H), 2.46-2.42 (m, 4H), 2.38 (br d, J=4.4 Hz, 1H), 2.24 (s, 3H), 2.05-1.98 (m, 1H). MS (ESI) m/z 493.3 [M+H]$^+$ To a solution of 6-(4-methylpiperazin-1-yl)pyridin-3-amine (500 mg, 2.60 mmol, 1.00 eq) and pyridine (1.05 mL, 13.0 mmol, 5.00 eq) in acetonitrile (5.00 mL) was added phenyl chloroformate (0.39 mL, 3.12 mmol, 1.20 eq) at 0° C. The reaction was stirred at 25° C. for 12 h. The mixture was concentrated and the obtained residue was purified by standard methods to afford phenyl (6-(4-methylpiperazin-1-yl)pyridin-3-yl)carbamate.

Compound 83: General procedure A with variant i) was used for the preparation from compound VIII employing phenyl (3,3-dimethyl-2,3-dihydrobenzofuran-6-yl)carbamate. $^1$H NMR (400 MHz, DMSO-$d_6$) δ=11.00 (s, 1H), 9.74 (br s, 1H), 7.80 (s, 1H), 7.74-7.60 (m, 2H), 7.08 (d, J=8.0 Hz, 1H), 6.98 (s, 1H), 6.96-6.84 (m, 1H), 5.26 (s, 2H), 5.14 (dd, J=5.0, 13.4 Hz, 1H), 4.48 (d, J=17.4 Hz, 1H), 4.36 (d, J=17.4 Hz, 1H), 4.20 (s, 2H), 3.00-2.85 (m, 1H), 2.70-2.56 (m, 1H), 2.47-2.33 (m, 1H), 2.12-1.98 (m, 1H), 1.25 (s, 6H). MS (ESI) m/z 464.2 [M+H]$^+$ Step 1: To a solution of 2-bromo-5-nitrophenol (1.00 g, 4.59 mmol, 1.00 eq) and 3-bromo-2-methylprop-1-ene (0.60 mL, 5.96 mmol, 1.30 eq) in acetone (5.00 mL) was added potassium carbonate (1.27 g, 9.17 mmol, 2.00 eq) in one portion at 25° C. The reaction was stirred for 12 h at 25° C. The mixture was diluted with water (30.0 mL) and exacted with ethyl acetate (3×30.0 mL). The combined organic layers were washed with brine (2×10.0 mL), dried over sodium sulfate, filtered, and concentrated under reduced pressure to give a residue. The residue was purified by silica gel column chromatography (petroleum ether/ethyl acetate=10/1 to 2/1) to afford 1-bromo-2-((2-methylallyl)oxy)-4-nitrobenzene.

Step 2: To a solution of 1-bromo-2-((2-methylallyl)oxy)-4-nitrobenzene (900 mg, 3.31 mmol, 1.00 eq) in dimethylformamide (5.00 mL) were added sodium acetate (678 mg, 8.27 mmol, 2.50 eq), palladium acetate (149 mg, 662 μmol, 0.20 eq), tetraethylammonium iodide (936 mg, 3.64 mmol, 1.10 eq) and sodium formate (0.18 mL, 3.31 mmol, 1.00 eq) in one portion under nitrogen. The reaction was stirred for 12 h at 100° C. The mixture was diluted with water (30.0 mL) and extracted with ethyl acetate (3×30.0 mL). The combined organic layers were washed with brine (2×10.0 mL), dried over sodium sulfate, filtered, and concentrated under reduced pressure to give a residue. The residue was purified by silica gel column chromatography (petroleum ether/ethyl acetate=10/1 to 2/1) to afford 3,3-dimethyl-6-nitro-2H-benzofuran.

Step 3: To a solution of 3,3-dimethyl-6-nitro-2,3-dihydrobenzofuran (300 mg, 1.55 mmol, 1.00 eq) in water (3.00 mL) and methanol (6.00 mL) were added ammonium chloride (415 mg, 7.76 mmol, 5.00 eq) and iron powder (434 mg, 7.76 mmol, 5.00 eq). The reaction was stirred at 80° C. for 2 h. The mixture was filtered, and the filtrate was concentrated under reduced pressure to give a residue. The residue was diluted with water (30.0 mL) and exacted with ethyl acetate (3×30.0 mL). The combined organic layers were washed with brine (2×10.0 mL), dried over sodium sulfate, filtered, and concentrated under reduced pressure to afford 3,3-dimethyl-2,3-dihydrobenzofuran-6-amine.

Step 4: To a solution of 3,3-dimethyl-2,3-dihydrobenzofuran-6-amine (162 mg, 993 µmol, 1.00 eq) and pyridine (0.24 mL, 2.98 mmol, 3.00 eq) in acetonitrile (5.00 mL) was added phenyl chloroformate (0.14 mL, 1.09 mmol, 1.10 eq) in one portion at 25° C. The reaction was stirred at 25° C. for 12 h. The mixture was diluted with water (30.0 mL) and extracted with ethyl acetate (3×30.0 mL). The combined organic layers were washed with brine (2×10.0 mL), dried over sodium sulfate, filtered, and concentrated and the obtained residue was purified by standard methods to afford phenyl (3,3-dimethyl-2,3-dihydrobenzofuran-6-yl)carbamate.

Compound 84: General procedure A with variant i) was used for the preparation from compound VIII employing phenyl (6-(2-fluorophenyl)pyridin-3-yl)carbamate. $^1$H NMR (400 MHz, DMSO-d$_6$) δ=11.02 (s, 1H), 10.23 (br s, 1H), 8.78 (d, J=2.3 Hz, 1H), 8.07-8.00 (m, 1H), 7.92 (dt, J=1.8, 7.9 Hz, 1H), 7.83 (s, 1H), 7.80-7.74 (m, 1H), 7.74-7.69 (m, 1H), 7.68-7.63 (m, 1H), 7.45 (ddt, J=1.8, 5.3, 7.6 Hz, 1H), 7.36-7.23 (m, 2H), 5.33 (s, 2H), 5.14 (dd, J=5.1, 13.4 Hz, 1H), 4.53-4.44 (m, 1H), 4.39-4.32 (m, 1H), 2.99-2.86 (m, 1H), 2.65-2.56 (m, 1H), 2.46-2.37 (m, 1H), 2.06-1.97 (m, 1H). MS (ESI) m/z 489.2 [M+H]$^+$ Step 1: To a solution of 2-chloro-5-nitropyridine (2.00 g, 12.6 mmol, 1.00 eq) in dimethylformamide (20.0 mL) were added potassium carbonate (5.23 g, 37.8 mmol, 3.00 eq), (2-fluorophenyl)boronic acid (1.77 g, 12.6 mmol, 1.00 eq) and tetrakis(triphenylphosphine)palladium (728 mg, 630 µmol, 0.05 eq) under nitrogen. The reaction was stirred at 110° C. for 12 h. The mixture was diluted with water (200 mL) and extracted with ethyl acetate (2×100 mL). The combined organic layers were washed with brine (2×30.0 mL), dried over sodium sulfate, filtered, and concentrated under reduced pressure to give a residue. The residue was purified by column chromatography (petroleum ether/ethyl acetate=10/1 to 5/1) to afford 2-(2-fluorophenyl)-5-nitropyridine.

Step 2: To a solution of 2-(2-fluorophenyl)-5-nitropyridine (2.00 g, 9.17 mmol, 1.00 eq) in methanol (15.0 mL) and water (5.00 mL) were added iron powder (2.56 g, 45.8 mmol, 5.00 eq) and ammonium chloride (3.92 g, 73.3 mmol, 8.00 eq). The reaction was stirred at 80° C. for 1 h. The mixture was filtered, and the filtrate was concentrated under reduced pressure to give a residue. The residue was diluted with water (30.0 mL) and extracted with ethyl acetate (3×30.0 mL). The combined organic layers were washed with brine (2×10.0 mL), dried over sodium sulfate, filtered, and concentrated under reduced pressure to afford 6-(2-fluorophenyl)pyridin-3-amine.

Step 3: To a solution of 6-(2-fluorophenyl)pyridin-3-amine (1.70 g, 9.03 mmol, 1.00 eq) and pyridine (3.65 mL, 45.1 mmol, 5.00 eq) in acetonitrile (20.0 mL) was added phenyl chloroformate (1.60 mL, 12.8 mmol, 1.41 eq). The reaction was stirred at 25° C. for 1 h. The mixture was concentrated under reduced pressure to give a residue. The residue was triturated with water (100 mL) and the resulting solid was collected by filtration. The filter cake was washed with water (5 ml) and dried by standard methods to afford phenyl (6-(2-fluorophenyl)pyridin-3-yl)carbamate.

Compound 85: General procedure A with variant i) was used for the preparation from compound VIII employing phenyl (5-fluoro-6-phenylpyridin-3-yl)carbamate. $^1$H NMR (400 MHz, DMSO-d$_6$) δ=11.08-10.94 (m, 1H), 10.57-10.27 (m, 1H), 8.59 (d, J=1.6 Hz, 1H), 8.00-7.92 (m, 1H), 7.91-7.85 (m, 2H), 7.83 (s, 1H), 7.75-7.70 (m, 1H), 7.68-7.64 (m, 1H), 7.53-7.47 (m, 2H), 7.46-7.40 (m, 1H), 5.35 (s, 2H), 5.14 (dd, J=5.2, 13.2 Hz, 1H), 4.57-4.44 (m, 1H), 4.43-4.30 (m, 1H), 2.98-2.83 (m, 1H), 2.61 (br d, J=17.2 Hz, 1H), 2.46-2.36 (m, 1H), 2.05-1.97 (m, 1H). MS (ESI) m/z 489.3 [M+H]$^+$ Step 1: To a solution of 2-chloro-3-fluoro-5-nitropyridine (2.00 g, 11.3 mmol, 1.00 eq), phenylboronic acid (2.76 g, 22.6 mmol, 2.00 eq) and potassium carbonate (4.70 g, 34.0 mmol, 3.00 eq) in dioxane (20.0 mL) was added tetrakis[triphenylphosphine]palladium(0) (1.31 g, 1.13 mmol, 0.10 eq) at 25° C. The reaction was stirred at 110° C. for 12 h under nitrogen. The mixture was poured into water (120 mL) and stirred for 10 min. The aqueous phase was extracted with ethyl acetate (3×60.0 mL). The combined organic layers were washed with brine (50.0 mL), dried over anhydrous sodium sulfate, filtered, and concentrated under reduced pressure to give a residue. The residue was purified by silica gel column chromatography (petroleum ether/ethyl acetate=50/1) to afford 3-fluoro-5-nitro-2-phenylpyridine.

Step 2: To a solution of 3-fluoro-5-nitro-2-phenylpyridine (300 mg, 1.37 mmol, 1.00 eq), in methanol (4.00 mL) and water (2.00 mL) were added ammonium chloride (367 mg, 6.87 mmol, 5.00 eq) and iron powder (230 mg, 4.12 mmol, 3.00 eq). The reaction was stirred at 80° C. for 1 h. The mixture was filtered, and the filtrate was concentrated under reduced pressure to give a residue. Water (80.0 mL) was added, and the solution was stirred for 10 min. The aqueous layer was extracted with ethyl acetate (3×30.0 mL). The combined organic layers were washed with brine (50.0 mL), dried over anhydrous sodium sulfate, filtered, and concentrated under reduced pressure to afford 5-fluoro-6-phenylpyridin-3-amine.

Step 3: To a solution of 5-fluoro-6-phenylpyridin-3-amine (250 mg, 1.33 mmol, 1.00 eq) and pyridine (0.54 mL, 6.64 mmol, 5.00 eq) in acetonitrile (5.00 mL) was added phenyl chloroformate (0.25 mL, 1.99 mmol, 1.50 eq). The reaction was stirred at 25° C. for 1 h. The mixture was concentrated and the obtained residue was purified by standard methods to afford phenyl (5-fluoro-6-phenylpyridin-3-yl)carbamate.

Compound 86: General procedure A with variant i) was used for the preparation from compound VIII employing phenyl (6-(o-tolyl)pyridin-3-yl)carbamate. $^1$H NMR (400 MHz, DMSO-d$_6$) δ=11.02 (s, 1H), 10.69-10.33 (m, 1H), 8.95-8.73 (m, 1H), 8.35-8.00 (m, 1H), 7.86-7.63 (m, 4H), 7.47-7.29 (m, 4H), 5.36 (br s, 2H), 5.14 (dd, J=5.0, 13.4 Hz, 1H), 4.52-4.45 (m, 1H), 4.39-4.32 (m, 1H), 2.96-2.88 (m, 1H), 2.64-2.58 (m, 1H), 2.45-2.37 (m, 1H), 2.32 (s, 3H), 2.06-1.98 (m, 1H). MS (ESI) m/z 485.2 [M+H]$^+$ Step 1: To a solution of 2-chloro-5-nitropyridine (3.00 g, 18.9 mmol, 1.00 eq) in dimethylformamide (30.0 mL) were added O-tolylboronic acid (2.57 g, 18.9 mmol, 1.00 eq), potassium carbonate (7.85 g, 56.7 mmol, 3.00 eq) and tetrakis(triphenylphosphine)palladium (1.09 g, 946 μmol, 0.05 eq) under nitrogen. The reaction was stirred at 110° C. for 12 h. The mixture was diluted with water (300 mL) and exacted with ethyl acetate (3×300 mL). The combined organic layers were washed with brine (2×100 mL), dried over sodium sulfate, filtered, and concentrated under reduced pressure to give a residue. The residue was purified by silica gel column chromatography (petroleum ether/ethyl acetate=10/1) to afford 5-nitro-2-(o-tolyl)pyridine.

Step 2: To a solution of 5-nitro-2-(o-tolyl)pyridine (3.00 g, 14.0 mmol, 1.00 eq) in methanol (30.0 mL) and water (10.0 mL) were added iron powder (3.91 g, 70.0 mmol, 5.00 eq) and ammonium chloride (5.99 g, 112 mmol, 8.00 eq). The reaction was stirred at 80° C. for 1 h. The mixture was filtered, and the filtrate was concentrated under reduced pressure to give a residue. The residue was diluted with water (50.0 mL) and exacted with ethyl acetate (3×30.0 mL). The combined organic layers were washed with brine (2×10.0 mL), dried over sodium sulfate, filtered, and concentrated under reduced pressure to afford 6-(o-tolyl)pyridin-3-amine.

Step 3: To a solution of 6-(o-tolyl)pyridin-3-amine (2.50 g, 13.5 mmol, 1.00 eq) in acetonitrile (25.0 mL) were added pyridine (5.48 mL, 67.8 mmol, 5.00 eq) and phenyl chloroformate (2.21 mL, 17.6 mmol, 1.30 eq). The reaction was stirred at 25° C. for 1 h. The mixture was concentrated under reduced pressure to give a residue. The residue was triturated with water (100 mL) and the resulting solid was collected by filtration. The filter cake was washed with water (5.00 ml) and dried under standard methods to afford phenyl (6-(o-tolyl)pyridin-3-yl)carbamate.

Compound 87: General procedure A with variant i) was used for the preparation from compound VIII employing phenyl (6-(2-methoxyphenyl)pyridin-3-yl)carbamate. $^1$H NMR (400 MHz, DMSO-d$_6$) δ=11.02 (s, 1H), 10.75 (br s, 1H), 8.91 (br d, J=1.6 Hz, 1H), 8.32 (br d, J=8.7 Hz, 1H), 8.11 (d, J=8.9 Hz, 1H), 7.84 (s, 1H), 7.76-7.62 (m, 3H), 7.58-7.50 (m, 1H), 7.25 (d, J=8.3 Hz, 1H), 7.15 (t, J=7.5 Hz, 1H), 5.37 (s, 2H), 5.13 (dd, J=5.0, 13.3 Hz, 1H), 4.53-4.46 (m, 1H), 4.38-4.31 (m, 1H), 3.87 (s, 3H), 2.97-2.88 (m, 1H), 2.61 (br d, J=17.1 Hz, 1H), 2.45-2.35 (m, 1H), 2.07-1.97 (m, 1H). MS (ESI) m/z 501.2 [M+H]$^+$ Step 1: To a solution of 2-chloro-5-nitropyridine (2.00 g, 12.6 mmol, 1.00 eq) in dimethylformamide (5 mL) were added potassium carbonate (5.23 g, 37.8 mmol, 3.00 eq), (2-fluorophenyl)boronic acid (1.92 g, 12.6 mmol, 1.00 eq) and tetrakis(triphenylphosphine)palladium (1.46 g, 1.26 mmol, 0.10 eq) under nitrogen. The reaction was stirred at 100° C. for 12 h. The mixture was diluted with water (300 mL) and exacted with ethyl acetate (3×300 mL). The combined organic layers were washed with brine (2×100 mL), dried over sodium sulfate, filtered, and concentrated under reduced pressure to give a residue. The residue was purified by silica gel column chromatography (petroleum ether/ethyl acetate=10/1) to afford 2-(2-methoxyphenyl)-5-nitropyridine.

Step 2: To a solution of 2-(2-methoxyphenyl)-5-nitropyridine (2.90 g, 12.6 mmol, 1.00 eq) in methanol (30.0 mL) and water (10.0 mL) were added iron powder (3.52 g, 62.9 mmol, 5.00 eq) and ammonium chloride (5.39 g, 100 mmol, 8.00 eq). The reaction was stirred at 80° C. for 1 h. The mixture was filtered, and the filtrate was concentrated under reduced pressure to give a residue. The residue was diluted with water (50.0 mL) and extracted with ethyl acetate (3×50.0 mL). The combined organic layers were washed with brine (2×10.0 mL), dried over sodium sulfate, filtered, and concentrated under reduced pressure to afford 6-(2-methoxyphenyl)pyridin-3-amine.

Step 3: To a solution of 6-(2-methoxyphenyl)pyridin-3-amine (2.50 g, 12.4 mmol, 1.00 eq) in acetonitrile (25.0 mL) were added pyridine (3.02 mL, 37.4 mmol, 3.00 eq) and phenyl chloroformate (2.03 mL, 16.2 mmol, 1.30 eq). The reaction was stirred at 25° C. for 1 h. The mixture was concentrated under reduced pressure to give a residue. The residue was triturated with water (100 mL) and the resulting solid was collected by filtration. The filter cake was washed with water (5.00 mL) and dried by standard methods to afford phenyl (6-(2-methoxyphenyl)pyridin-3-yl)carbamate.

Compound 88: General procedure A with variant i) was used for the preparation from compound VIII employing phenyl (5-methyl-6-phenylpyridin-3-yl)carbamate. $^1$H NMR (400 MHz, DMSO-d$_6$) δ=11.02 (s, 1H), 10.76 (br s, 1H), 8.80-8.76 (m, 1H), 8.26 (s, 1H), 7.84 (s, 1H), 7.76-7.72 (m, 1H), 7.68-7.66 (m, 1H), 7.64-7.62 (m, 2H), 7.60 (br s, 3H), 5.38 (s, 2H), 5.22-5.04 (m, 1H), 4.50 (d, J=17.6 Hz, 1H), 4.36 (d, J=17.6 Hz, 1H), 2.98-2.86 (m, 1H), 2.68-2.58 (m, 1H), 2.46-2.34 (m, 4H), 2.10-1.98 (m, 1H). MS (ESI) m/z 485.4 [M+H]$^+$ Step 1: To a solution of 2-chloro-3-methyl-5-nitropyridine (5.00 g, 29.0 mmol, 1.00 eq) and phenylboronic acid (4.24 g, 34.8 mmol, 1.20 eq) in dioxane (50.0 mL) were added tetrakis[triphenylphosphine]palladium(0) (6.70 g, 5.79 mmol, 0.20 eq) and potassium carbonate (6.01 g, 43.5 mmol, 1.50 eq) in one portion at 25° C. under nitrogen. The reaction was stirred at 100° C. for 12 h. The mixture was diluted with water (30.0 mL) and exacted with ethyl acetate (3×30.0 mL). The combined organic layers were washed with brine (2×10.0 mL), dried over sodium sulfate, filtered, and concentrated under reduced pressure to give a residue. The residue was purified by silica gel column chromatography (petroleum ether/ethyl acetate=10/1 to 2/1) to afford 3-methyl-5-nitro-2-phenyl-pyridine.

Step 2: To a solution of 3-methyl-5-nitro-2-phenylpyridine (1.00 g, 4.67 mmol, 1.00 eq) in methanol (6.00 mL) and water (3.00 mL) were added iron powder (1.30 g, 23.3 mmol, 5.00 eq) and ammonium chloride (1.25 g, 23.3 mmol, 5.00 eq) in one portion at 25° C. The reaction was stirred at 80° C. for 2 h. The mixture was filtered, and the filtrate was concentrated under reduced pressure to give a residue. The residue was diluted with water (30.0 mL) and exacted with ethyl acetate (3×30.0 mL). The combined organic layers were washed with brine (2×10.0 mL), dried over sodium sulfate, filtered, and concentrated under reduced pressure to afford 5-methyl-6-phenylpyridin-3-amine.

Step 3: To a solution of 5-methyl-6-phenylpyridin-3-amine (843 mg, 4.58 mmol, 1.00 eq) and pyridine (1.11 mL, 13.7 mmol, 3.00 eq) in acetonitrile (2.00 mL) was added phenyl chloroformate (0.63 mL, 5.03 mmol, 1.10 eq) at 25° C. The reaction was stirred at 25° C. for 12 h. The mixture was concentrated and the obtained residue was purified by standard methods to afford phenyl (5-methyl-6-phenylpyridin-3-yl)carbamate.

Compound 89: General procedure A with variant i) was used for the preparation from compound VIII employing phenyl (6-(3-(dimethylamino)azetidin-1-yl)pyridin-3-yl) carbamate. $^1$H NMR (400 MHz, DMSO-d$_6$) δ=10.99 (s, 1H), 9.52 (br s, 1H), 8.17 (s, 1H), 8.12 (br s, 1H), 7.77 (s, 1H), 7.69-7.56 (m, 3H), 6.37 (d, J=8.9 Hz, 1H), 5.24 (s, 2H), 5.12 (dd, J=5.1, 13.3 Hz, 1H), 4.51-4.43 (m, 1H), 4.38-4.30 (m, 1H), 3.92 (t, J=7.4 Hz, 2H), 3.63 (dd, J=5.6, 8.1 Hz, 2H), 3.15 (quin, J=6.1 Hz, 1H), 2.97-2.86 (m, 1H), 2.64-2.56 (m, 1H), 2.45-2.38 (m, 1H), 2.10 (s, 6H), 2.04-1.98 (m, 1H). MS (ESI) m/z 493.2 [M+H]$^+$ Step 1: To a solution of 2-fluoro-5-nitropyridine (2.00 g, 14.1 mmol, 1.00 eq) and N,N-dimethylazetidin-3-amine dihydrochloride (3.65 g, 21.1 mmol, 1.50 eq, 2 HCl) in dimethylformamide (20.0 mL) was added potassium carbonate (9.73 g, 70.4 mmol, 5.00 eq) in one portion. The reaction was stirred at 60° C. for 12 h. The mixture was diluted with water (150 mL) and extracted with ethyl acetate (3×80.0 mL). The combined organic layers were washed with brine (60.0 mL), dried over sodium sulfate, filtered, and concentrated under reduced pressure to afford N,N-dimethyl-1-(5-nitropyridin-2-yl)azetidin-3-amine.

Step 2: To a solution of N,N-dimethyl-1-(5-nitropyridin-2-yl)azetidin-3-amine (2.00 g, 9.00 mmol, 1.00 eq) in methanol (40.0 mL) was added palladium on carbon (200 mg, 10% weight on C) in one portion under hydrogen (15 Psi). The reaction was stirred at 25° C. for 2 h. The mixture was filtered, and the filtrate was concentrated under reduced pressure to afford 6-(3-(dimethylamino)azetidin-1-yl)pyridin-3-amine.

Step 3: To a solution of 6-(3-(dimethylamino)azetidin-1-yl)pyridin-3-amine (500 mg, 2.60 mmol, 1.00 eq) and pyridine (1.05 mL, 13.0 mmol, 5.00 eq) in acetonitrile (5.00 mL) was added phenyl chloroformate (0.39 mL, 3.12 mmol, 1.20 eq) dropwise at 0° C. The reaction was stirred at 20° C. for 12 h. The mixture was concentrated and the obtained residue was purified by standard methods to afford phenyl (6-(3-(dimethylamino)azetidin-1-yl)pyridin-3-yl)carbamate.

Compound 90: General procedure A with variant i) was used for the preparation from compound VIII employing phenyl (5-methoxy-6-phenylpyridin-3-yl)carbamate. $^1$H NMR (400 MHz, DMSO-d$_6$) δ=11.02 (s, 1H), 10.80-10.36 (m, 1H), 8.60-8.38 (m, 1H), 8.12-7.92 (m, 1H), 7.88-7.78 (m, 3H), 7.76-7.64 (m, 2H), 7.50 (br d, J=7.2 Hz, 3H), 5.36 (s, 2H), 5.14 (dd, J=5.2, 13.2 Hz, 1H), 4.50 (d, J=17.6 Hz, 1H), 4.36 (d, J=17.6 Hz, 1H), 3.90 (s, 3H), 2.99-2.86 (m, 1H), 2.62 (br d, J=17. z Hz, 1H), 2.50-2.34 (m, 1H), 2.10-1.94 (m, 1H). MS (ESI) m/z 501.2 [M+H]$^+$ Step 1: To a solution of 2-chloro-3-methoxy-5-nitropyridine (1.00 g, 5.30 mmol, 1.00 eq) and phenylboronic acid (776 mg, 6.36 mmol, 1.20 eq) in dioxane (50.0 mL) were added tetrakis[triphenylphosphine]palladium(0) (1.23 g, 1.06 mmol, 0.20 eq) and potassium carbonate (1.10 g, 7.95 mmol, 1.50 eq) in one portion at 25° C. under nitrogen. The reaction was stirred at 100° C. for 12 h. The mixture was diluted with water (30.0 mL) and exacted with ethyl acetate (3×30.0 mL). The combined organic layers were washed with brine (2×10.0 mL), dried over anhydrous sodium sulfate, filtered, and concentrated under reduced pressure to give a residue. The residue was purified by silica gel column chromatography (petroleum ether/ethyl acetate=10/1 to 2/1) to afford 3-methoxy-5-nitro-2-phenylpyridine.

Step 2: To a solution of 3-methoxy-5-nitro-2-phenylpyridine (1.00 g, 4.34 mmol, 1.00 eq) in methanol (6.00 mL) and water (3.00 mL) were added iron powder (1.21 g, 21.7 mmol, 5.00 eq) and ammonium chloride (1.16 g, 21.7 mmol, 5.00 eq) in one portion at 25° C. The reaction was stirred at 80° C. for 2 h. The mixture was filtered, and the filtrate was concentrated under reduced pressure to give a residue. The residue was diluted with water (30.0 mL) and exacted with ethyl acetate (3×30.0 mL). The combined organic layers were washed with brine (2×10.0 mL), dried over anhydrous sodium sulfate, filtered, and concentrated under reduced pressure to afford 5-methoxy-6-phenylpyridin-3-amine.

Step 3: To a solution of 5-methoxy-6-phenylpyridin-3-amine (700 mg, 3.50 mmol, 1.00 eq) and pyridine (0.85 mL, 10.5 mmol, 3.00 eq) in acetonitrile (2.00 mL) was added phenyl chloroformate (0.48 mL, 3.85 mmol, 1.10 eq) at 25° C. The reaction was stirred at 25° C. for 12 h. The mixture was concentrated and the obtained residue was purified by standard methods to afford phenyl (5-methoxy-6-phenylpyridin-3-yl)carbamate.

Compound 91: General procedure A with variant i) was used for the preparation from compound VIII employing phenyl (6-methyl-5-(trifluoromethoxy)pyridin-3-yl)carbamate. $^1$H NMR (400 MHz, DMSO-d$_6$) δ=11.01 (br s, 1H), 10.30 (br s, 1H), 8.50 (d, J=2.0 Hz, 1H), 7.99 (br s, 1H), 7.80 (s, 1H), 7.72-7.67 (m, 1H), 7.66-7.62 (m, 1H), 5.30 (s, 2H), 5.16-5.09 (m, 1H), 4.52-4.43 (m, 1H), 4.38-4.30 (m, 1H), 2.97-2.85 (m, 1H), 2.65-2.63 (m, 1H), 2.65-2.58 (m, 1H), 2.40 (s, 3H), 2.40-2.33 (m, 1H), 2.05-1.97 (m, 1H). MS (ESI) m/z 493.2 [M+H]$^+$ Step 1: To a solution of 2-methyl-5-nitropyridin-3-amine (10.0 g, 65.3 mmol, 1.00 eq) in sulfuric acid (2.50 M, 107 mL, 4.10 eq) was added sodium nitrite (5.41 g, 78.4 mmol, 1.20 eq) dissolved in water (20.0 mL) dropwise at 0° C. The reaction was stirred at 0° C. for 0.5 h. Then sulfuric acid (1 M, 53.6 mL, 0.820 eq) was added dropwise, and the reaction was stirred at 70° C. for 1 h. The mixture was diluted with water (200 mL) and extracted with ethyl acetate (3×50.0 mL). The combined organic layers were washed brine (40.0 mL), dried over sodium sulfate, filtered, and concentrated under reduced pressure to give a residue. The residue was purified by silica gel column chromatography (petroleum ether/ethyl acetate=10/1 to 2/1) to afford 2-methyl-5-nitropyridin-3-ol.

Step 2: To a solution of 2-methyl-5-nitropyridin-3-ol (800 mg, 5.19 mmol, 1.00 eq) in dimethylformamide (8.00 mL) was added sodium hydride (60% dispersion in mineral oil) (415 mg, 10.4 mmol, 2.00 eq) in portions at 0° C. The reaction was stirred at 0° C. for 0.5 h. Then dibromodifluoromethane (0.96 mL, 10.4 mmol, 2.00 eq) was added dropwise at 0° C., and the reaction was stirred at 25° C. for 2 h. The mixture was quenched with an ammonium chloride solution (100 mL) and extracted with ethyl acetate (3×50.0 mL). The combined organic layers were washed with brine (40.0 mL), dried over sodium sulfate, filtered, and concentrated under reduced pressure to give a residue. The residue was purified by silica gel column chromatography (petroleum ether/ethyl acetate=10/1 to 5/1) to afford 3-(bromodifluoromethoxy)-2-methyl-5-nitropyridine.

Step 3: To a solution of 3-(bromodifluoromethoxy)-2-methyl-5-nitropyridine (180 mg, 636 μmol, 1.00 eq) in dichloromethane (3.00 mL) was added silver tetrafluoroborate (186 mg, 954 μmol, 1.50 eq) in portions. The reaction was stirred at 25° C. for 1 h. The mixture was filtered, and the filtrate was concentrated under reduced pressure to afford 2-methyl-5-nitro-3-(trifluoromethoxy)pyridine.

Step 4: A mixture of 2-methyl-5-nitro-3-(trifluoromethoxy)pyridine (100 mg, 450 μmol, 1.00 eq) and palladium on carbon (10% weight on C) (10.0 mg) in methanol (300 mL) was stirred at 25° C. for 2 h under hydrogen atmosphere (15 psi). The mixture was filtered over Celite, and the filtrate was concentrated under reduced pressure to afford 6-methyl-5-(trifluoromethoxy)pyridin-3-amine.

Step 5: A solution of phenyl chloroformate (16.0 μL, 124 μmol, 1.20 eq), 6-methyl-5-(trifluoromethoxy)pyridin-3-amine (20.0 mg, 104 μmol, 1.00 eq) and pyridine (25.0 μL, 312 μmol, 3.00 eq) in acetonitrile (10.0 mL) was stirred at 25° C. for 12 h. The mixture was concentrated and the obtained residue was purified by standard methods to afford phenyl (6-methyl-5-(trifluoromethoxy) pyridin-3-yl)carbamate.

Compound 92: General procedure A with variant i) was used for the preparation from compound VIII employing phenyl chroman-7-ylcarbamate. $^1$H NMR (400 MHz, DMSO-d$_6$) δ=11.00 (s, 1H), 9.66 (br s, 1H), 7.79 (s, 1H), 7.72-7.61 (m, 2H), 7.00-6.84 (m, 3H), 5.25 (s, 2H), 5.13 (dd, J=5.2, 13.2 Hz, 1H), 4.53-4.42 (m, 1H), 4.40-4.29 (m, 1H), 4.16-4.02 (m, 2H), 2.99-2.85 (m, 1H), 2.68-2.58 (m, 3H), 2.41 (dq, J=4.4, 13.2 Hz, 1H), 2.07-1.97 (m, 1H), 1.95-1.83 (m, 2H). MS (ESI) m/z 450.2 [M+H]$^+$ Step 1: To a mixture of chroman-6-amine (described in example 67) (1.20 g, 8.04 mmol, 1.00 eq) in dioxane (2.00 mL) was added acetic anhydride (1.51 mL, 16.1 mmol, 2.00 eq) and pyridine (0.65 mL, 8.04 mmol, 1.00 eq) at 0° C. The reaction was stirred at 25° C. for 16 h. The mixture was poured into water (20.0 mL) and extracted with ethyl acetate (3×20.0 mL). The combined organic layers were separated, washed with brine (10.0 mL), dried over anhydrous sodium sulfate, filtered, and concentrated under reduced pressure to afford N-(chroman-6-yl)acetamide.

Step 2: A solution of nitric acid (0.46 mL, 10.3 mmol, 1.40 eq) in acetic acid (2.00 mL) was added dropwise to a stirred solution of N-(chroman-6-yl)acetamide (1.40 g, 7.32 mmol, 1.00 eq) in acetic acid (10.0 mL) at 25° C. The reaction was stirred at 25° C. for 1 h. Then ice water (50.0 mL) was added, and the reaction was stirred at 25° C. for 0.5 h. The mixture was poured into water (20.0 mL) and extracted with ethyl acetate (3×20.0 mL). The combined organic layers were washed with brine (10.0 mL), dried over anhydrous sodium sulfate, filtered, and concentrated under reduced pressure to give a residue. The residue was purified by reversed phase preparative HPLC to afford N-(7-nitrochroman-6-yl)acetamide carbamate.

Step 3: A solution of N-(7-nitrochroman-6-yl)acetamide (410 mg, 1.74 mmol, 1.00 eq) and concentrated hydrochloric acid (2.60 mL) in ethanol (10.0 mL) was stirred at 80° C. for 2 h. The reaction mixture was neutralized with ammonium hydroxide solution and diluted with water (20.0 mL), then extracted with ethyl acetate (3×20.0 mL). The combined organic layers were washed with brine (10.0 mL), dried over anhydrous sodium sulfate, filtered, and concentrated under reduced pressure to afford 7-nitrochroman-6-amine.

Step 4: To a mixture of 7-nitrochroman-6-amine (330 mg, 1.70 mmol, 1.00 eq) in tetrahydrofuran (10.0 mL) was added isoamyl nitrite (0.69 mL, 5.10 mmol, 3.00 eq) dropwise at 0° C. The reaction was stirred at 0° C. for 30 min, then at 70° C. for 3 h. The mixture was poured into water (20.0 mL) and extracted with ethyl acetate (3×20.0 mL). The combined organic layers were separated, washed with brine (10.0 mL), dried over anhydrous sodium sulfate, filtered, and concentrated under reduced pressure to give a residue. The residue was purified by silica gel column chromatography (petroleum ether/ethyl acetate=1/0 to 15/1) to afford 7-nitrochromane.

Step 5: To a solution of 7-nitrochromane (130 mg, 726 µmol, 1.00 eq) in ethyl acetate (6.00 mL) was added palladium on carbon (10% weight on C) (13.0 mg) under nitrogen atmosphere. The reaction was stirred at 25° C. for 2 h under hydrogen. The mixture was filtered, and the filtrate was concentrated under reduced pressure to afford chroman-7-amine.

Step 6: To a solution of chroman-7-amine (110 mg, 737 µmol, 1.00 eq) and pyridine (0.18 mL, 2.21 mmol, 3.00 eq) in acetonitrile (5.00 mL) was added phenyl chloroformate (0.11 mL, 885 µmol, 1.20 eq) at 25° C. The reaction was stirred at 25° C. for 12 h. The mixture was concentrated and the obtained residue was purified by standard methods to afford phenyl chroman-7-ylcarbamate.

Compound 93: General procedure A with variant i) was used for the preparation from compound VIII employing phenyl (3-cyclopropoxyphenyl)carbamate. $^1$H NMR (400 MHz, DMSO-d$_6$) δ=11.00 (s, 1H), 9.81 (s, 1H), 7.80 (s, 1H), 7.72-7.62 (m, 2H), 7.28 (s, 1H), 7.21-7.14 (m, 1H), 7.05 (br d, J=8.3 Hz, 1H), 6.76-6.63 (m, 1H), 5.27 (s, 2H), 5.13 (dd, J=5.1, 13.3 Hz, 1H), 4.54-4.40 (m, 1H), 4.40-4.30 (m, 1H), 3.77 (td, J=3.0, 5.9 Hz, 1H), 3.01-2.83 (m, 1H), 2.61 (br dd, J=2.1, 15.7 Hz, 1H), 2.44-2.35 (m, 1H), 2.06-1.97 (m, 1H), 0.80-0.70 (m, 2H), 0.70-0.61 (m, 2H). MS (ESI) m/z 450.1 [M+H]$^+$ Step 1: To a mixture of 3-nitrophenol (0.71 mL, 3.59 mmol, 1.00 eq) and bromocyclopropane (0.86 mL, 10.8 mmol, 3.00 eq) in 1-methyl-2-pyrrolidinone (5.00 mL) was added cesium carbonate (2.34 g, 7.19 mmol, 2.00 eq) in portions. The reaction was stirred at 180° C. for 2 h under microwave irradiation. The mixture was concentrated under reduced pressure to give a residue. The residue was purified by silica gel column chromatography (petroleum ether/ethyl acetate=20/1 to 5/1) to afford 1-cyclopropoxy-3-nitrobenzene.

Step 2: To a solution of 1-cyclopropoxy-3-nitrobenzene (240 mg, 1.34 mmol, 1.00 eq) in tetrahydrofuran (5.00 mL) was added Pd/C (10% weight on C) (50.0 mg) under nitrogen. The reaction was stirred at 20° C. for 1 h under hydrogen (15 psi). The mixture was filtered, and the filtrate was concentrated under reduced pressure to afford 3-cyclopropoxyaniline.

Step 3: To a solution of 3-cyclopropoxyaniline (280 mg, 1.88 mmol, 1.00 eq) and pyridine (0.76 mL, 9.38 mmol, 5.00 eq) in acetonitrile (3.00 mL) was added phenyl chloroformate (0.35 mL, 2.82 mmol, 1.50 eq). The reaction was stirred at 20° C. for 12 h. The mixture was concentrated and the obtained residue was purified by standard methods to afford phenyl (3-cyclopropoxyphenyl)carbamate.

Compound 94: General procedure A with variant i) was used for the preparation from compound VIII employing phenyl (5-(piperidin-1-yl)pyrazin-2-yl)carbamate. $^1$H NMR (400 MHz, DMSO-d$_6$) δ=11.00 (s, 1H), 10.03 (s, 1H), 8.47 (s, 1H), 8.03 (d, J=1.2 Hz, 1H), 7.80 (s, 1H), 7.69-7.61 (m, 2H), 5.28 (s, 2H), 5.13 (dd, J=5.1, 13.2 Hz, 1H), 4.54-4.44 (m, 1H), 4.39-4.30 (m, 1H), 3.49 (br s, 4H), 2.97-2.89 (m, 1H), 2.63-2.58 (m, 1H), 2.43-2.35 (m, 1H), 2.05-1.97 (m, 1H), 1.61-1.51 (m, 6H). MS (ESI) m/z 479.2 [M+H]$^+$ Step 1: To a solution of 5-chloropyrazin-2-amine (1.00 g, 7.72 mmol, 1.00 eq) and di-tert-butyldicarbonate (1.95 mL, 8.49 mmol, 1.10 eq) in tetrahydrofuran (10.0 mL) was added 4-dimethylaminopyridine (94.3 mg, 772 µmol, 0.10 eq). The reaction was stirred at 20° C. for 2 h. The mixture was concentrated under reduced pressure to give a residue. The residue was purified by silica gel column chromatography (petroleum ether/ethyl acetate=10/1 to 5/1) to afford tert-butyl (5-chloropyrazin-2-yl)carbamate.

Step 2: To a solution of tert-butyl (5-chloropyrazin-2-yl)carbamate (800 mg, 3.48 mmol, 1.00 eq) and piperidine (1.72 mL, 17.4 mmol, 5.00 eq) in dimethylformamide (3.00 mL) was added cesium carbonate (2.27 g, 6.97 mmol, 2.00 eq). The reaction was stirred at 180° C. for 2 h under microwave irradiation. The mixture was diluted with water (50.0 mL) and extracted with ethyl acetate (3×30.0 mL). The combined organic layers were washed with brine (20.0 mL), dried over anhydrous sodium sulfate, filtered, and concentrated under reduced pressure to give a residue. The residue was purified by reversed phase preparative HPLC to afford 5-(piperidin-1-yl) pyrazin-2-amine.

Step 3: To a solution of 5-(piperidin-1-yl)pyrazin-2-amine (50.0 mg, 281 µmol, 1.00 eq) and pyridine (0.07 mL, 842 µmol, 3.00 eq) in acetonitrile (1.00 mL) was added phenyl chloroformate (0.05 mL, 421 µmol, 1.50 eq). The reaction was stirred at 20° C. for 3 h. The mixture was concentrated and the obtained residue was purified by standard methods to afford phenyl (5-(piperidin-1-yl)pyrazin-2-yl) carbamate.

Compound 95: General procedure A with variant i) was used for the preparation from compound VIII employing phenyl (3-(difluoromethoxy)-5-(morpholinomethyl)phenyl) carbamate. $^1$H NMR (400 MHz, DMSO-$d_6$) δ=11.00 (s, 1H), 10.01 (s, 1H), 8.19 (s, 1H), 7.80 (s, 1H), 7.71-7.62 (m, 2H), 7.29 (s, 2H), 7.17 (d, J=74 Hz, 1H), 6.76 (s, 1H), 5.29 (s, 2H), 5.13 (dd, J=5.1, 13.3 Hz, 1H), 4.52-4.44 (m, 1H), 4.39-4.31 (m, 1H), 3.60-3.55 (m, 4H), 3.42 (s, 2H), 2.97-2.87 (m, 1H), 2.64-2.58 (m, 1H), 2.45-2.40 (m, 1H), 2.35 (br s, 4H), 2.06-1.98 (m, 1H). MS (ESI) m/z 559.2 [M+H]$^+$ Step 1: To a solution of 3-hydroxy-5-nitrobenzoic acid (1.80 g, 9.83 mmol, 1.00 eq) in dimethylformamide (10.0 mL) were added morpholine (0.86 mL, 9.83 mmol, 1.00 eq), 0-(7-azabenzotriazol-1-yl)-N,N,N',N'-tetramethyluronium hexafluorophosphate (7.45 g, 19.6 mmol, 2.00 eq) and diisopropylethylamine (5.16 mL, 29.6 mmol, 3.00 eq). The reaction was stirred at 25° C. for 2 h. The mixture was extracted with ethyl acetate/water (200 ml/100 ml). The organic layer was collected, and the solvents were partly removed under reduced pressure to give a concentrated solution. The solution was purified by reversed phase preparative HPLC to afford (3-hydroxy-5-nitrophenyl)(morpholino)methanone.

Step 2: To a solution of (3-hydroxy-5-nitrophenyl)(morpholino)methanone (1.77 g, 7.02 mmol, 1.00 eq) in dimethylformamide (15.0 mL) were added (2-chloro-2,2-difluoroacetyl)oxysodium (2.67 g, 17.5 mmol, 2.50 eq) and cesium carbonate (4.57 g, 14.0 mmol, 2.00 eq). The reaction was stirred at 100° C. for 2 h. The mixture was extracted with water/ethyl acetate (100 ml/100 ml). The organic layer was collected, and the solvents were partly removed under reduced pressure to give a concentrated solution. The solution was purified by reversed phase preparative HPLC to afford (3-(difluoromethoxy)-5-nitrophenyl)(morpholino) methanone.

Step 3: To a solution of (3-(difluoromethoxy)-5-nitrophenyl)(morpholino)methanone (1.39 g, 4.60 mmol, 1.00 eq) in tetrahydrofuran (5.00 mL) was added borane dimethyl sulfide complex (2 M in THF) (0.92 mL, 2.00 eq) at 25° C. The mixture was stirred at 25° C. for 0.5 h, then at 60° C. for 1.5 h. Methanol (5.00 mL) was added, and the mixture was extracted with water/ethyl acetate (50.0 ml/50.0 ml). The organic layer was collected, and the solvents were partly removed under reduced pressure to give a concentrated solution. The solution was purified by reversed phase preparative HPLC to afford 4-(3-(difluoromethoxy)-5-nitrobenzyl)morpholine.

Step 4: To a solution of 4-(3-(difluoromethoxy)-5-nitrobenzyl)morpholine (795 mg, 2.76 mmol, 1.00 eq) in methanol (15.0 mL) and water (5.00 mL) were added iron power (770 mg, 13.8 mmol, 5.00 eq) and ammonium chloride (1.18 g, 22.0 mmol, 8.00 eq). The reaction was stirred at 80° C. for 2 h. The mixture was filtered, and the filtrate was concentrated under reduced pressure to give a concentrated solution. The solution was extracted with ethyl acetate/saturated sodium bicarbonate (40.0 ml/10.0 ml). The organic layer was collected, dried over sodium sulfate, filtered, and concentrated under reduced pressure to afford 3-(difluoromethoxy)-5-(morpholinomethyl)aniline.

Step 5: To a solution of 3-(difluoromethoxy)-5-(morpholinomethyl)aniline (100 mg, 387 µmol, 1.00 eq) in acetonitrile (2.00 mL) were added pyridine (0.10 mL, 1.18 mmol, 3.04 eq) and phenyl chloroformate (0.07 mL, 599 µmol, 1.55 eq). The reaction was stirred at 25° C. for 2 h. The mixture was filtered, and the filtrate was purified by standard methods to afford phenyl (3-(difluoromethoxy)-5-(morpholinomethyl) phenyl)carbamate.

Compound 96: General procedure A with variant i) was used for the preparation from compound VIII employing phenyl(3-(difluoromethoxy)-5-(2-morpholinoethoxy)phenyl)carbamate. $^1$H NMR (400 MHz, DMSO-$d_6$) δ=10.99 (s, 1H), 9.97 (s, 1H), 7.79 (s, 1H), 7.70-7.66 (m, 1H), 7.65-7.61 (m, 1H), 7.39-6.99 (m, 1H), 6.97-6.89 (m, 2H), 6.43 (t, J=2.1 Hz, 1H), 5.28 (s, 2H), 5.19-5.05 (m, 1H), 4.51-4.42 (m, 1H), 4.39-4.30 (m, 1H), 4.04 (t, J=5.7 Hz, 2H), 3.62-3.52 (m, 4H), 2.98-2.85 (m, 1H), 2.67 (t, J=5.6 Hz, 2H), 2.60 (br d, J=17.7 Hz, 1H), 2.48-2.40 (m, 4H), 2.40-2.31 (m, 1H), 2.06-1.96 (m, 1H). MS (ESI) m/z 589.4 [M+H]$^+$ Step 1: A mixture of 3-bromo-5-nitrophenol (5.00 g, 22.9 mmol, 1.00 eq), 4-(2-chloroethyl)morpholine (4.12 g, 27.5 mmol, 1.20 eq) and caesium carbonate (22.4 g, 68.8 mmol, 3.00 eq) in dimethylformamide (50.0 mL) was stirred at 60° C. for 12 h. The mixture was diluted with ethyl acetate (250 mL) and water (150 mL). The organic layer was separated, and the aqueous layer was extracted with ethyl acetate (3×150 mL). The combined organic layers were dried over sodium sulfate, filtered, and concentrated under reduced pressure to give a residue. The residue was purified by column chromatography on silica gel (petroleum ether/ethyl acetate=3/1) to afford 4-(2-(3-bromo-5-nitrophenoxy)ethyl) morpholine.

Step 2: To a solution of 4-(2-(3-bromo-5-nitro-phenoxy) ethyl)morpholine (5.00 g, 15.1 mmol, 1.00 eq) and potassium hydroxide (2.54 g, 45.3 mmol, 3.00 eq) in dioxane (10.0 mL) and water (10.0 mL) were added tris(dibenzylideneacetone)dipalladium(0) (1.38 g, 1.51 mmol, 0.10 eq) and di-tert-butyl-(2-(2,4,6-tri(propan-2-yl)phenyl)phenyl)phosphane (641 mg, 1.51 mmol, 0.10 eq) under nitrogen. The reaction was stirred at 80° C. for 12 h. The mixture was diluted with ethyl acetate (150 mL) and water (150 mL). The organic layer was separated, and the aqueous layer was extracted with ethyl acetate (3×150 mL). The combined organic layers were dried over sodium sulfate, filtered, and concentrated under reduced pressure to give a residue. The residue was purified by reversed phase preparative HPLC to afford 3-(2-morpholinoethoxy)-5-nitrophenol.

Step 3: A mixture of 3-(2-morpholinoethoxy)-5-nitrophenol (300 mg, 1.12 mmol, 1.00 eq), potassium carbonate (309 mg, 2.24 mmol, 2.00 eq) and sodium 2-chloro-2,2-difluoroacetate (682 mg, 4.47 mmol, 4.00 eq) in dimethylformamide (2.00 mL) and water (0.50 mL) was stirred at 100° C. for 12 h. The mixture was diluted with ethyl acetate (100 mL) and water (100 mL). The organic layer was separated, and the aqueous layer was extracted with ethyl acetate (3×80.0 mL). The combined organic layers were dried over sodium sulfate, filtered, and concentrated under reduced pressure to afford 4-(2-(3-(difluoromethoxy)-5-nitrophenoxy)ethyl)morpholine.

Step 4: A mixture of 4-(2-(3-(difluoromethoxy)-5-nitrophenoxy)ethyl)morpholine (0.50 g, 1.57 mmol, 1.00 eq) and palladium on carbon (10% weight on C) (50.0 mg) in methanol (5.00 mL) was stirred at 25° C. under hydrogen for 3 h. The mixture was filtered over Celite, and the filtrate was concentrated under reduced pressure to afford 3-(difluoromethoxy)-5-(2-morpholinoethoxy)aniline.

Step 5: A mixture of 3-(difluoromethoxy)-5-(2-morpholinoethoxy)aniline (130 mg, 451 μmol, 1.00 eq), phenyl chloroformate (68.0 μL, 541 μmol, 1.20 eq) and pyridine (0.11 mL, 1.35 mmol, 3.00 eq) in acetonitrile (2.00 mL) was stirred at 25° C. for 12 h. The mixture was diluted with ethyl acetate (50.0 mL) and water (50.0 mL). The organic layer was separated, and the aqueous layer was extracted with ethyl acetate (3×100 mL). The combined organic layers were dried over sodium sulfate, filtered, and concentrated and the obtained residue was purified by standard methods to afford phenyl (3-(difluoromethoxy)-5-(2-morpholinoethoxy)phenyl)carbamate.

Compound 97: General procedure A with variant ii) was used for the preparation from compound VIII employing (2-methoxyphenyl)methanamine. $^1$H NMR (400 MHz, DMSO-$d_6$) δ=10.98 (br s, 1H), 7.73 (s, 1H), 7.70 (br t, J=6.0 Hz, 1H), 7.61 (s, 2H), 7.25-7.13 (m, 2H), 6.98-6.86 (m, 2H), 5.16 (s, 2H), 5.14-5.08 (m, 1H), 4.49-4.42 (m, 1H), 4.36-4.29 (m, 1H), 4.18 (d, J=6.0 Hz, 2H), 3.78 (s, 3H), 2.97-2.85 (m, 1H), 2.60 (td, J=2.0, 15.4 Hz, 1H), 2.40 (br dd, J=4.4, 13.1 Hz, 1H), 2.05-1.96 (m, 1H). MS (ESI) m/z 438.1 [M+H]$^+$ Compound 98: General procedure A with variant ii) was used for the from compound VIII employing phenylmethanamine. $^1$H NMR (400 MHz, DMSO-$d_6$) δ=10.98 (br d, J=2.6 Hz, 1H), 7.90 (br t, J=6.2 Hz, 1H), 7.73 (s, 1H), 7.61 (s, 1H), 7.46-7.15 (m, 6H), 5.17 (s, 2H), 5.13 (dd, J=5.1, 13.4 Hz, 1H), 4.50-4.43 (m, 1H), 4.36-4.30 (m, 1H), 4.22 (d, J=6.1 Hz, 2H), 2.92 (ddd, J=5.4, 13.5, 17.4 Hz, 1H), 2.63-2.58 (m, 1H), 2.40 (br dd, J=4.4, 13.2 Hz, 1H), 2.05-1.98 (m, 1H). MS (ESI) m/z 408.1 [M+H]$^+$ Compound 99: General procedure A with variant i) was used for the preparation from compound VIII employing phenyl (4-(1,1-difluoroethyl)phenyl)carbamate. $^1$H NMR (400 MHz, DMSO-$d_6$) δ=11.00 (br s, 1H), 10.04 (s, 1H), 7.81 (s, 1H), 7.72-7.67 (m, 1H), 7.67-7.62 (m, 1H), 7.61-7.53 (m, 2H), 7.53-7.45 (m, 2H), 5.29 (s, 2H), 5.13 (dd, J=5.1, 13.3 Hz, 1H), 4.54-4.43 (m, 1H), 4.39-4.29 (m, 1H), 2.98-2.86 (m, 1H), 2.61 (td, J=2.1, 15.3 Hz, 1H), 2.44-2.35 (m, 1H), 2.06-1.99 (m, 1H), 1.99-1.88 (m, 3H). MS (ESI) m/z 438.1 [M+H]$^+$ To a solution of 4-(1,1-difluoroethyl)aniline·HCl (50.0 mg, 258 μmol, 1.00 eq, HCl salt) in acetonitrile (5.00 mL) were added pyridine (0.10 mL, 1.29 mmol, 5.00 eq) and phenyl chloroformate (42.0 μL, 335 μmol, 1.30 eq). The reaction was stirred at 25° C. for 0.5 h. The mixture was concentrated under reduced pressure to give a residue. The residue was purified by preparative silica gel TLC to afford phenyl (4-(1,1-difluoroethyl)phenyl)carbamate.

Compound 100: General procedure A with variant i) was used for the preparation from compound VIII employing phenyl (3-(2-oxa-5-azabicyclo[2.2.1]heptan-5-ylmethyl)-5-(difluoromethoxy)phenyl) carbamate. $^1$H NMR (400 MHz, DMSO-$d_6$) δ=11.00 (s, 1H), 9.99 (s, 1H), 8.17 (s, 1H), 7.80 (s, 1H), 7.71-7.62 (m, 2H), 7.32 (s, 1H), 7.26 (s, 1H), 7.13 (d, J=74 Hz, 1H), 6.78 (s, 1H), 5.29 (s, 2H), 5.13 (dd, J=5.1, 13.2 Hz, 1H), 4.46 (s, 1H), 4.38-4.32 (m, 2H), 3.90 (d, J=7.5 Hz, 1H), 3.68 (d, J=4.5 Hz, 2H), 3.53 (dd, J=1.6, 7.4 Hz, 1H), 3.45 (s, 1H), 2.97-2.88 (m, 1H), 2.71 (s, 1H), 2.63 (br s, 1H), 2.41 (br d, J=9.4 Hz, 2H), 2.05-1.99 (m, 1H), 1.80 (br d, J=8.2 Hz, 1H), 1.60 (br d, J=9.5 Hz, 1H). MS (ESI) m/z 571.2 [M+H]$^+$ Step 1: To a solution of 3-hydroxy-5-nitrobenzoic acid (2.80 g, 15.3 mmol, 1.00 eq) in dimethylformamide (5.00 mL) were added 2-oxa-5-azabicyclo[2.2.1]heptane·HCl (3.11 g, 22.9 mmol, 1.50 eq, HCl), O-(7-azabenzotriazol-1-yl)-N,N,N',N'-tetramethyluronium hexafluorophosphate (11.6 g, 30.6 mmol, 2.00 eq) and diisopropylethylamine (8.00 mL, 45.8 mmol, 3.00 eq). The reaction was stirred at 25° C. for 2 h. The mixture was extracted with water/ethyl acetate (100 ml/200 ml). The organic layer was separated, and most of the solvent was removed under reduced pressure to give a concentrated solution. The solution was purified by reversed phase preparative HPLC to afford 2-oxa-5-azabicyclo[2.2.1]heptan-5-yl(3-hydroxyl-5-nitrophenyl)methanone.

Step 2: To a solution of 2-oxa-5-azabicyclo[2.2.1]heptan-5-yl(3-hydroxy-5-nitrophenyl)methanone (3.79 g, 14.3 mmol, 1.00 eq) in dimethylformamide (150 mL) were added (2-chloro-2,2-difluoro-acetyl)oxysodium (5.47 g, 35.8 mmol, 2.50 eq) and cesium carbonate (9.35 g, 28.7 mmol, 2.00 eq). The reaction was stirred at 100° C. for 2 h. The mixture was extracted with water/ethyl acetate (100 ml/100 ml). The organic layer was separated, and most of the solvent was removed under reduced pressure to give a concentrated solution. The solution was purified by reversed phase preparative HPLC to afford 2-oxa-5-azabicyclo[2.2.1]heptan-5-yl(3-(difluoromethoxy)-5-nitrophenyl)methanone.

Step 3: To a solution of 2-oxa-5-azabicyclo[2.2.1]heptan-5-yl(3-(difluoromethoxy)-5-nitrophenyl)methanone (1.82 g, 5.79 mmol, 1.00 eq) in tetrahydrofuran (5.00 mL) was added borane dimethyl sulfide complex (10 M) (1.16 mL, 2.00 eq) at 25° C. under nitrogen. The reaction was stirred at 25° C. for 0.5 h, then at 60° C. for 1.5 h. Methanol (5.00 ml) was added, and the mixture was extracted with water/ethyl acetate (50.0 ml/50.0 ml). The organic layer was separated, and most of the solvent was removed under reduced pressure to give a concentrated solution. The solution was purified by reversed phase preparative HPLC to afford 5-(3-(difluoromethoxy)-5-nitrobenzyl)-2-oxa-5-azabicyclo[2.2.1]heptane.

Step 4: To a solution of 5-(3-(difluoromethoxy)-5-nitrobenzyl)-2-oxa-5-azabicyclo[2.2.1]heptane (902 mg, 3.00 mmol, 1.00 eq) in methanol (15.0 mL) and water (5.00 mL) were added iron power (839 mg, 15.0 mmol, 5.00 eq) and ammonium chloride (1.29 g, 24.0 mmol, 8.00 eq). The reaction was stirred at 80° C. for 2 h. The mixture was filtered, and the filtrate was concentrated under reduced pressure to give a concentrated solution. The solution was extracted with ethyl acetate/saturated sodium bicarbonate (40.0 mL/10.0 mL). The organic layer was collected, dried over sodium sulfate, filtered, and concentrated under reduced pressure to afford 3-(2-oxa-5-azabicyclo[2.2.1]heptan-5-ylmethyl)-5-(difluoromethoxy)aniline.

Step 5: To a solution of 3-(2-oxa-5-azabicyclo[2.2.1]heptan-5-ylmethyl)-5-(difluoromethoxy)aniline (200 mg, 740 μmol, 1.00 eq) in acetonitrile (2.00 mL) were added pyridine (0.18 mL, 2.23 mmol, 3.00 eq) and phenyl chloroformate (0.14 mL, 1.12 mmol, 1.50 eq). The reaction was stirred at 25° C. for 2 h. The mixture was filtered, and the filtrate was purified by standard methods to afford phenyl (3-(2-oxa-5-azabicyclo[2.2.1]heptan-5-ylmethyl)-5-(difluoromethoxy)phenyl)carbamate.

Compound 101: General procedure A with variant i) was used for the preparation from compound VIII employing phenyl (4-(2,2-difluorocyclopropyl)phenyl)carbamate. $^1$H NMR (400 MHz, DMSO-$d_6$) δ=10.99 (s, 1H), 9.82 (br s, 1H), 7.79 (s, 1H), 7.71-7.58 (m, 2H), 7.44 (br d, J=8.6 Hz, 2H), 7.18 (d, J=8.6 Hz, 2H), 5.27 (s, 2H), 5.13 (dd, J=5.0, 13.2 Hz, 1H), 4.52-4.42 (m, 1H), 4.39-4.30 (m, 1H), 2.96-2.86 (m, 2H), 2.62 (br s, 1H), 2.46-2.36 (m, 1H), 2.05-1.97 (m, 1H), 1.96-1.81 (m, 2H). MS (ESI) m/z 470.1 [M+H]$^+$ Step 1: To a solution of 1-nitro-4-vinylbenzene (500 mg, 3.35 mmol, 1.00 eq) and sodium iodide (251 mg, 1.68 mmol, 0.50 eq) in 1,2-dimethoxyethane (5.00 mL) was added (trifluoromethyl)trimethylsilane (1.19 g, 8.38 mmol, 2.50 eq) dropwise under nitrogen. The reaction was stirred at 150° C. for 2 h under microwave irradiation. The mixture was concentrated under reduced pressure to give a residue. The residue was purified by silica gel column chromatography (petroleum ether/ethyl acetate=10/1) to afford 1-(2,2-difluorocyclopropyl)-4-nitrobenzene.

Step 2: To a solution of 1-(2,2-difluorocyclopropyl)-4-nitrobenzene (380 mg, 1.91 mmol, 1.00 eq) in ethanol (8.00 mL) and water (2.00 mL) were added iron power (533 mg, 9.54 mmol, 5.00 eq) and ammonium chloride (510 mg, 9.54 mmol, 5.00 eq) in one portion. The reaction was stirred at 80° C. for 1 h. The mixture was diluted with water (80.0 mL) and extracted with ethyl acetate (3×60.0 mL). The combined organic layers were washed with brine (30.0 mL), dried over sodium sulfate, filtered, and concentrated under reduced pressure to afford 4-(2,2-difluorocyclopropyl)aniline.

Step 3: To a solution of 4-(2,2-difluorocyclopropyl)aniline (300 mg, 1.77 mmol, 1.00 eq) and pyridine (0.72 mL, 8.87 mmol, 5.00 eq) in acetonitrile (5.00 mL) was added phenyl chloroformate (0.27 mL, 2.13 mmol, 1.20 eq) dropwise at 0° C. The reaction was stirred at 25° C. for 12 h. The mixture was concentrated and the obtained residue was purified by standard methods to afford phenyl (4-(2,2-difluorocyclopropyl) phenyl)carbamate.

Compound 102: General procedure A with variant ii) was used for the preparation from compound VIII employing phenylmethanamine. $^1$H NMR (400 MHz, DMSO-$d_6$) δ=10.98 (br s, 1H), 7.89 (br d, J=8.2 Hz, 1H), 7.72 (s, 1H), 7.59 (s, 2H), 7.30 (d, J=4.4 Hz, 4H), 7.23-7.18 (m, 1H), 5.15-5.07 (m, 3H), 4.67 (quin, J=7.4 Hz, 1H), 4.48-4.41 (m, 1H), 4.35-4.28 (m, 1H), 2.96-2.86 (m, 1H), 2.63-2.57 (m, 1H), 2.39 (br dd, J=4.4, 13.2 Hz, 1H), 2.04-1.97 (m, 1H), 1.34 (d, J=7.0 Hz, 3H). MS (ESI) m/z 422.2 [M+H]$^+$ Compound 103: General procedure A with variant i) was used for the preparation from compound VIII employing phenyl (3-methyl-2,3-dihydrobenzofuran-6-yl)carbamate. $^1$H NMR (400 MHz, DMSO-$d_6$) δ=11.10-10.94 (m, 1H), 9.81-9.65 (m, 1H), 8.45 (s, 1H), 7.79 (s, 1H), 7.70-7.61 (m, 2H), 7.15-7.03 (m, 1H), 6.99-6.83 (m, 1H), 5.25 (s, 2H), 5.13 (dd, J=5.1, 13.2 Hz, 1H), 4.64 (t, J=8.8 Hz, 1H), 4.53-4.44 (m, 1H), 4.40-4.29 (m, 1H), 4.00 (dd, J=7.5, 8.5 Hz, 1H), 3.50-3.46 (m, 1H), 2.95-2.87 (m, 1H), 2.62 (br d, J=2.5 Hz, 1H), 2.41-2.31 (m, 1H), 2.04-1.98 (m, 1H), 1.22 (d, J=6.9 Hz, 3H). MS (ESI) m/z 450.1 [M+H]$^+$ Step 1: To a solution of 2-bromo-5-nitro-phenol (1.00 g, 4.59 mmol, 1.00 eq) and potassium carbonate (1.27 g, 9.17 mmol, 2.00 eq) in acetone (10.0 mL) was added 3-bromoprop-1-ene (665 mg, 5.50 mmol, 1.20 eq) at 25° C. The reaction was stirred at 25° C. for 12 h. The mixture was concentrated under reduced pressure to give a residue. Water (80.0 mL) was added, and the mixture was stirred for 10 min. The aqueous layer was extracted with ethyl acetate (3×40.0 mL). The combined organic layers were washed with brine (100 mL), dried over anhydrous sodium sulfate, filtered, and concentrated under reduced pressure to give a residue. The residue was purified by silica gel column chromatography (petroleum ether/ethyl acetate=50/1) to afford 2-(allyloxy)-1-bromo-4-nitrobenzene.

Step 2: To a solution of 2-(allyloxy)-1-bromo-4-nitrobenzene (800 mg, 3.10 mmol, 1.00 eq), sodium acetate (635 mg, 7.75 mmol, 2.50 eq), tetraethylammonium iodide (877 mg, 3.41 mmol, 1.10 eq) and sodium formate (210 mg, 3.10 mmol, 1.00 eq) in dimethylformamide (2.00 mL) was added palladium acetate (139 mg, 620 μmol, 0.20 eq) at 25° C. The reaction was stirred at 100° C. for 12 h. The mixture was poured into water (80.0 mL) and stirred for 10 min. The aqueous layer was extracted with ethyl acetate (3×30.0 mL). The combined organic layers were washed with brine (50.0 mL), dried over anhydrous sodium sulfate, filtered, and concentrated under reduced pressure to give a residue. The residue was purified by silica gel column chromatography (petroleum ether/ethyl acetate=20/1) to afford 3-methyl-6-nitrobenzofuran.

Step 3: To a solution of 3-methyl-6-nitro-benzofuran (150 mg, 846 μmol, 1.00 eq) in methanol (2.00 mL) was added palladium on carbon (10% weight on C) (30.0 mg). The reaction was stirred at 25° C. for 12 h under hydrogen. The mixture was filtered, and the filtrate was concentrated under reduced pressure to afford 3-methyl-2,3-dihydrobenzofuran-6-amine.

Step 4: To a solution of 3-methyl-2,3-dihydrobenzofuran-6-amine (120 mg, 804 μmol, 1.00 eq) and pyridine (0.32 mL, 4.02 mmol, 5.00 eq) in acetonitrile (3.00 mL) was added phenyl chloroformate (0.15 mL, 1.21 mmol, 1.50 eq). The reaction was stirred at 25° C. for 12 h. The mixture was concentrated and the obtained residue was purified by standard methods to afford phenyl (3-methyl-2,3-dihydrobenzofuran-6-yl)carbamate.

Compound 104: General procedure A with variant i) was used for the preparation from compound VIII employing phenyl N-(4-cyclobutylphenyl)carbamate. $^1$H NMR (400 MHz, DMSO-$d_6$) δ=11.00 (s, 1H), 9.72 (br s, 1H), 7.79 (s, 1H), 7.72-7.59 (m, 2H), 7.39 (br d, J=8.4 Hz, 2H), 7.15 (d, J=8.4 Hz, 2H), 5.26 (s, 2H), 5.13 (dd, J=5.2, 13.2 Hz, 1H), 4.55-4.43 (m, 1H), 4.40-4.26 (m, 1H), 3.47-3.44 (m, 1H), 2.97-2.83 (m, 1H), 2.63 (br s, 1H), 2.45-2.35 (m, 1H), 2.30-2.21 (m, 2H), 2.09-1.98 (m, 3H), 1.97-1.87 (m, 1H), 1.84-1.73 (m, 1H). MS (ESI) m/z 448.1 [M+H]$^+$ Step 1: To a solution of 4-bromoaniline (10.0 g, 58.1 mmol, 1.00 eq) and triethylamine (24.0 mL, 172 mmol, 2.97 eq) in dichloromethane (70.0 mL) was added trifluoroacetic anhydride (12.1 mL, 87.2 mmol, 1.50 eq) dropwise at 0° C. The reaction was stirred at 25° C. for 12 h. The mixture was purified by silica gel column chromatography (petroleum ether/ethyl acetate=10/1) to afford N-(4-bromophenyl)-2,2,2-trifluoro-acetamide.

Step 2: To a solution of N-(4-bromophenyl)-2,2,2-trifluoro-acetamide (2.00 g, 7.46 mmol, 1.00 eq) in tetrahydrofuran (15.0 mL) was added n-Butyllithium (2.50 M, 6.27 mL, 2.10 eq) dropwise at −78° C. The reaction was stirred at −78° C. for 0.5 h. Then cyclobutanone (0.67 mL, 8.95 mmol, 1.20 eq) was added, and the reaction was stirred at −78° C. for 2.5 h. The reaction was quenched by addition of saturated aqueous ammonium chloride, and the mixture was extracted with ethyl acetate (2×20.0 mL). The combined organic layers were washed with brine (20.0 mL), dried over anhydrous sodium sulfate, filtered, and concentrated under reduced pressure to give a residue. The residue was purified by silica gel column chromatography (petroleum ether/ethyl acetate=10/1 to 2/1) to afford 2,2,2-trifluoro-N-(4-(1-hydroxycyclobutyl)phenyl)acetamide.

Step 3: To a solution of 2,2,2-trifluoro-N-(4-(1-hydroxycyclobutyl)phenyl)acetamide (1.60 g, 6.17 mmol, 1.00 eq) in methanol (10.0 mL) was added sodium hydroxide solution (1.00 M, 6.17 mL, 1.00 eq). The reaction was stirred at 25° C. for 12 h. The mixture was concentrated under reduced pressure to give a residue. Water (10.0 mL) was added, and the mixture was extracted with ethyl acetate (2×20.0 mL). The combined organic layers were washed with brine (20.0 mL), dried over anhydrous sodium sulfate, filtered, and concentrated under reduced pressure to give a residue. The residue was purified by silica gel column chromatography (petroleum ether/ethyl acetate=5/1 to 2/1) to afford 1-(4-aminophenyl)cyclobutanol.

Step 4: To a solution of 1-(4-aminophenyl)cyclobutanol (0.70 g, 4.29 mmol, 1.00 eq) in tetrahydrofuran (10.0 mL) were added sodium borohydride (923 mg, 24.4 mmol, 5.69 eq) and aluminium trichloride (1.72 g, 12.9 mmol, 3.00 eq) in portions. The reaction was stirred at 70° C. for 3 h. The mixture was poured into water (100 mL) in portions. The aqueous layer was extracted with ethyl acetate (2×20.0 mL). The combined organic layers were washed with brine (30.0 mL), dried over anhydrous sodium sulfate, filtered, and concentrated under reduced pressure to give a residue. The residue was purified by silica gel column chromatography (petroleum ether/ethyl acetate=10/1 to 2/1) to afford 4-cyclobutylaniline.

Step 5: To a solution of 4-cyclobutylaniline (200 mg, 1.36 mmol, 1.00 eq) and pyridine (0.55 mL, 6.79 mmol, 5.00 eq) in acetonitrile (3.00 mL) was added phenyl chloroformate (0.20 mL, 1.63 mmol, 1.20 eq). The reaction was stirred at 25° C. for 1 h. The mixture was concentrated and the obtained residue was purified by standard methods to afford phenyl N-(4-cyclobutylphenyl)carbamate.

Compound 105: General procedure A with variant i) was used for the preparation from compound VIII employing phenyl (6-cyclobutylpyridin-3-yl)carbamate. $^1$H NMR (400 MHz, DMSO-$d_6$) δ=10.99 (s, 1H), 10.81 (s, 1H), 8.80 (d, J=2.1 Hz, 1H), 8.37 (dd, J=2.3, 8.8 Hz, 1H), 7.95 (d, J=8.8 Hz, 1H), 7.81 (s, 1H), 7.73-7.68 (m, 1H), 7.67-7.61 (m, 1H), 5.35 (s, 2H), 5.11 (dd, J=5.1, 13.3 Hz, 1H), 4.52-4.45 (m, 1H), 4.38-4.31 (m, 1H), 3.92 (br d, J=8.8 Hz, 1H), 2.96-2.87 (m, 1H), 2.60 (br d, J=17.5 Hz, 1H), 2.43-2.32 (m, 5H), 2.10-1.98 (m, 2H), 1.88 (dtd, J=3.2, 7.9, 11.1 Hz, 1H). MS (ESI) m/z 449.2 [M+H]$^+$ Step 1: To a solution of zinc bromide (2.49 g, 11.0 mmol, 3.50 eq) in tetrahydrofuran (15.0 mL) was added cyclobutylmagnesium bromide (0.5 M, 17.6 mL, 2.80 eq) dropwise at −78° C. under nitrogen. The reaction was stirred at −78° C. for 0.5 h, then at 0° C. for 0.5 h. 2-chloro-5-nitropyridine (500 mg, 3.15 mmol, 1.00 eq) and tetrakis(triphenylphosphine)palladium(0) (364 mg, 315 μmol, 0.10 eq) were added successively. The reaction was stirred at 0° C. for 10 min. Then the reaction was warmed to 60° C. and stirred at 60° C. for 2 h. The mixture was diluted with saturated ammonium chloride (100 mL) and extracted with ethyl acetate (3×80.0 mL). The combined organic layers were washed with brine (60.0 mL), dried over sodium sulfate, filtered, and concentrated under reduced pressure to give a residue. The residue was purified by silica gel column chromatography (petroleum ether/ethyl acetate=5/1) to afford 2-cyclobutyl-5-nitro-pyridine.

Step 2: To a solution of 2-cyclobutyl-5-nitropyridine (320 mg, 1.80 mmol, 1.00 eq) in methanol (10.0 mL) was added palladium on carbon (10% weight on C) (50.0 mg) in one portion. The reaction was stirred at 25° C. for 2 h under hydrogen (15 Psi). The mixture was filtered, and the filtrate was concentrated under reduced pressure to afford 6-cyclobutylpyridin-3-amine.

Step 3: To a solution of 6-cyclobutylpyridin-3-amine (230 mg, 1.55 mmol, 1.00 eq) and pyridine (0.63 mL, 7.76 mmol, 5.00 eq) in acetonitrile (5.00 mL) was added phenyl chloroformate (0.23 mL, 1.86 mmol, 1.20 eq) dropwise at 0° C. The reaction was stirred at 25° C. for 12 h. The mixture was concentrated under reduced pressure to give a residue. Dimethylformamide (2.00 mL) was added, and the solution was filtered. The filtrate was concentrated by standard methods to afford phenyl (6-cyclobutylpyridin-3-yl)carbamate.

Compound 106: General procedure A with variant i) was used for the preparation from compound VIII employing phenyl (3-(2-morpholinoethoxy)-5-(trifluoromethoxy)phenyl)carbamate. $^1$H NMR (400 MHz, DMSO-$d_6$) δ=11.09-10.90 (m, 1H), 10.08 (s, 1H), 8.23 (br s, 1H), 7.79 (s, 1H), 7.67 (br d, J=1.1 Hz, 1H), 7.66-7.62 (m, 1H), 7.14 (s, 1H), 7.07 (s, 1H), 6.59 (s, 1H), 5.28 (s, 2H), 5.17-5.04 (m, 1H), 4.51-4.43 (m, 1H), 4.38-4.30 (m, 1H), 4.06 (t, J=5.7 Hz, 2H), 3.60-3.53 (m, 4H), 2.97-2.86 (m, 1H), 2.67 (t, J=5.6 Hz, 2H), 2.64-2.57 (m, 1H), 2.48-2.42 (m, 4H), 2.40-2.31 (m, 1H), 2.05-1.97 (m, 1H). MS (ESI) m/z 607.4 [M+H]$^+$ Step 1: To a solution of 3-(2-morpholinoethoxy)-5-nitrophenol (110 mg, 410 μmol, 1.00 eq) in dimethylformamide (3.00 mL) was added sodium hydride (60% dispersion in mineral oil) (32.8 mg, 820 μmol, 2.00 eq) in portions at 0° C. The reaction was stirred at 0° C. for 0.5 h, then dibromodifluoromethane (75.8 μL, 820 μmol, 2.00 eq) was added dropwise. The reaction was stirred at 25° C. for 1 h. Saturated aqueous ammonium chloride solution (20.0 mL) was added, and the mixture was extracted with ethyl acetate (2×20.0 mL). The combined organic layers were washed with brine (10.0 mL), dried over sodium sulfate, filtered, and concentrated under reduced pressure to give a residue. The residue was purified by preparative silica gel TLC (petroleum ether/ethyl acetate=1/1) to afford 4-(2-(3-(bromodifluoromethoxy)-5-nitrophenoxy)ethyl)morpholine.

Step 2: To a solution of 4-(2-(3-(bromodifluoromethoxy)-5-nitrophenoxy)ethyl)morpholine (90.0 mg, 227 μmol, 1.00 eq) in dichloromethane (3.00 mL) was added silver tetrafluoroborate (88.2 mg, 453 μmol, 2.00 eq) in portions. The reaction was stirred at 25° C. for 1 h. The mixture was filtered, and the filtrate was concentrated under reduced pressure to afford 4-(2-(3-nitro-5-(trifluoromethoxy)phenoxy)ethyl)morpholine.

Step 3: A mixture of 4-(2-(3-nitro-5-(trifluoromethoxy)phenoxy)ethyl)morpholine (300 mg, 892 μmol, 1.00 eq) and palladium on carbon (10% weight on C) (100 mg) in methanol (10.0 mL) was stirred at 25° C. under hydrogen for 3 h. The mixture was filtered over Celite, and the filtrate was concentrated under reduced pressure to afford 3-(2-morpholinoethoxy)-5-(trifluoromethoxy)aniline.

Step 4: A solution of 3-(2-morpholinoethoxy)-5-(trifluoromethoxy)aniline (110 mg, 359 μmol, 1.00 eq), phenyl chloroformate (67.5 μL, 539 μmol, 1.50 eq) and pyridine (87.0 μL, 1.08 mmol, 3.00 eq) in acetonitrile (10.0 mL) was stirred at 25° C. for 12 h. The mixture was diluted with ethyl acetate (30.0 mL) and water (30.0 mL). The organic layer was separated, and the aqueous phase was extracted with ethyl acetate (3×30.0 mL). The combined organic layers were dried over sodium sulfate, filtered, and concentrated and the obtained residue was purified by standard methods to afford phenyl (3-(2-morpholinoethoxy)-5-(trifluoromethoxy) phenyl)carbamate.

Compound 107: General procedure A with variant i) was used for the preparation from compound VIII employing phenyl (6-(azetidin-1-yl)pyridin-3-yl)carbamate. $^1$H NMR (400 MHz, DMSO-$d_6$) δ=10.99 (s, 1H), 10.12-9.91 (m, 1H), 8.09 (br s, 1H), 7.84 (br d, J=7.8 Hz, 1H), 7.78 (s, 1H), 7.71-7.60 (m, 2H), 6.80 (br d, J=7.9 Hz, 1H), 5.28 (s, 2H), 5.12 (dd, J=5.1, 13.4 Hz, 1H), 4.51-4.41 (m, 1H), 4.38-4.29 (m, 1H), 4.27-4.06 (m, 4H), 2.96-2.87 (m, 1H), 2.63 (br s, 1H), 2.47-2.33 (m, 3H), 2.05-1.98 (m, 1H). MS (ESI) m/z 450.1 [M+H]$^+$ Step 1: To a solution of azetidine·HCl (5.14 mL, 46.5 mmol, 1.50 eq, HCl) and 2-fluoro-5-nitropyridine (4.40 g, 30.9 mmol, 1.00 eq) in dimethylformamide (40.0 mL) was added potassium carbonate (12.8 g, 92.9 mmol, 3.00 eq) in one portion. The reaction was stirred at 60° C. for 12 h. The mixture was poured into water (60.0 mL) and filtered. The filtrate was concentrated under reduced pressure to afford 2-(azetidin-1-yl)-5-nitropyridine.

Step 2: To a solution of 2-(azetidin-1-yl)-5-nitropyridine (2.00 g, 11.2 mmol, 1.00 eq) in methanol (40.0 mL) was added palladium on carbon (10% weight on C) (300 mg). The reaction was stirred at 25° C. for 2 h under hydrogen (15 Psi). The mixture was filtered, and the filtrate was concentrated under reduced pressure to afford 6-(azetidin-1-yl)pyridin-3-amine.

Step 3: To a solution of 6-(azetidin-1-yl)pyridin-3-amine (700 mg, 4.69 mmol, 1.00 eq) and pyridine (1.89 mL, 23.5 mmol, 5.00 eq) in acetonitrile (10.0 mL) was added phenyl chloroformate (0.71 mL, 5.63 mmol, 1.20 eq) dropwise at 0° C. The reaction was stirred at 25° C. for 12 h. The mixture was concentrated and the obtained residue was purified by standard methods to afford phenyl (6-(azetidin-1-yl)pyridin-3-yl)carbamate.

Compound 108:

Step 1: To a solution of 4-bromo-3,5-dimethylaniline (1.00 g, 5.00 mmol, 1.00 eq) in dimethyl formamide (10.0 mL) was added zinc cyanide (704 mg, 6.00 mmol, 381 uL, 1.20 eq) and 1,1-bis(diphenylphosphino)ferrocene (416 mg, 750 umol, 0.150 eq), tris(dibenzylideneacetone)dipalladium (0) (458 mg, 500 umol, 0.100 eq) under nitrogen. The mixture was stirred at 150° C. for 2 h under nitrogen in microwave. The mixture was filtered. The filtrate was diluted with water and ethyl acetate (50.0 ml/50.0 ml). The organic layer was collected, concentrated and purified by column chromatography on silica gel. The desired fraction was collected and concentrated to give 4-amino-2,6-dimethylbenzonitrile. $^1$H NMR (400 MHz, DMSO-d$_6$) δ=6.31 (s, 2H), 5.93 (s, 2H), 2.26 (s, 6H).

Step 2: To a solution of 4-amino-2,6-dimethylbenzonitrile (357 mg, 2.44 mmol, 1.00 eq) in Acetonitrile (5.00 mL) was added pyridine (578 mg, 7.31 mmol, 590 uL, 2.99 eq) and phenyl carbonochloridate (459 mg, 2.93 mmol, 367 uL, 1.20 eq). The mixture was stirred at 10° C. for 1 h. The mixture was filtered to give filtrate. The filtrate was purified by reversed-phase HPLC. The desired fraction was collected and concentrated to give phenyl (4-cyano-3,5-dimethylphenyl)carbamate. $^1$H NMR (400 MHz, DMSO-d$_6$) δ=10.59 (s, 1H), 7.50-7.41 (m, 3H), 7.39 (s, 2H), 7.27-7.22 (m, 2H), 2.42 (s, 6H). MS (ESI) m/z 267.1 [M+H]$^+$ Step 3: To a solution of 3-(6-(hydroxymethyl)-1-oxoisoindolin-2-yl)piperidine-2,6-dione VIII (90.0 mg, 328 umol, 1.00 eq) in dimethyl formamide (2.00 mL) was added phenyl (4-cyano-3,5-dimethylphenyl)carbamate (105 mg, 394 umol, 1.20 eq) and sodium hydride (26.2 mg, 656 umol, 60% purity, 2.00 eq) at 10° C. The mixture was stirred at 10° C. for 1 h. The mixture was adjusted pH=6 with formic acid (0.100 mL). The mixture was filtered to give filtrate. The filtrate was purified by prep-HPLC and the desired fraction was collected and lyophilized to give (2-(2,6-dioxopiperidin-3-yl)-3-oxoisoindolin-5-yl)methyl(4-cyano-3,5-dimethylphenyl)carbamate 108. $^1$H NMR (400 MHz, DMSO-d$_6$) δ=10.98 (s, 1H), 10.18 (s, 1H), 7.80 (s, 1H), 7.72-7.66 (m, 1H), 7.66-7.60 (m, 1H), 7.36 (s, 2H), 5.29 (s, 2H), 5.12 (dd, J=5.1, 13.3 Hz, 1H), 4.53-4.43 (m, 1H), 4.39-4.31 (m, 1H), 2.97-2.85 (m, 1H), 2.60 (br dd, J=1.8, 15.7 Hz, 1H), 2.44-2.37 (m, 7H), 2.05-1.96 (m, 1H). MS (ESI) m/z 447.2 [M+H]$^+$ Compound 109:

Step 1: To a solution of 1-(5-bromopyridin-2-yl)ethanone (8.00 g, 40.0 mmol, 1.00 eq) in dichloromethane (100 mL) was added triethylamine (12.4 g, 122 mmol, 17.0 mL, 3.05 eq) and chlorotrimethylsilane (8.56 g, 78.8 mmol, 10.0 mL, 1.97 eq). The mixture was stirred at 5° C. for 12 h. The mixture was concentrated under reduced pressure. The residue was purified by column chromatography on silica gel to give 5-bromo-2-(1-((trimethylsilyl)oxy)vinyl)pyridine.

Step 2: To a solution of 5-bromo-2-(1-((trimethylsilyl)oxy)vinyl)pyridine (4.50 g, 16.5 mmol, 1.00 eq) (crude) in dichloromethane (100 mL) was added diiodomethane (6.64 g, 24.8 mmol, 2.00 mL, 1.50 eq) and diethylzinc (1 M in toluene, 25.0 mL, 1.51 eq) at 0° C. The mixture was stirred at 5° C. for 6 h under nitrogen. The mixture was quenched with water (10.0 mL) and filtered. The organic layer was separated and concentrated under reduced pressure. The residue was purified by column chromatography on silica gel to give 5-bromo-2-(1-((trimethylsilyl)oxy)cyclopropyl)pyridine. $^1$H NMR (400 MHz, CDCl$_3$) δ=8.59 (d, J=2.3 Hz, 1H), 7.80 (dd, J=2.3, 8.4 Hz, 1H), 7.50 (d, J=8.5 Hz, 1H), 1.36-1.17 (m, 2H), 0.92-0.83 (m, 2H), 0.31-0.29 (m, 9H).

Step 3: To a solution of 5-bromo-2-(1-((trimethylsilyl)oxy)cyclopropyl)pyridine (360 mg, 1.26 mmol, 1.00 eq) in dioxane (10.0 mL) was added tert-butyl carbamate (350 mg, 2.99 mmol, 2.38 eq), cesium carbonate (1.23 g, 3.77 mmol, 2.99 eq) and methanesulfonato(2-dicyclohexylphosphino-2,6-di-i-propoxy-1,1-biphenyl)(2-amino-1,1-biphenyl-2-yl)palladium(II) (120 mg, 143 umol, 0.114 eq). The mixture was stirred at 90° C. for 2 h under nitrogen. The mixture was diluted with ethyl acetate (50.0 mL) and water (50.0 mL). The organic layer was separated and concentrated under reduced pressure. The residue was purified by column chromatography on silica gel to give tert-butyl (6-(1-((trimethylsilyl)oxy)cyclopropyl)pyridin-3-yl)carbamate. $^1$H NMR (400 MHz, CDCl$_3$) δ=8.25 (d, J=2.4 Hz, 1H), 7.55 (d, J=8.5 Hz, 1H), 7.49-7.39 (m, 1H), 6.52 (br s, 1H), 1.46 (s, 9H), 1.37-1.32 (m, 2H), 1.22-1.18 (m, 2H), 0.19-0.09 (m, 9H).

Step 4: To a solution of tert-butyl (6-(1-((trimethylsilyl)oxy)cyclopropyl)pyridin-3-yl)carbamate (320 mg, 992 umol, 1.00 eq) in dichloromethane (50.0 mL) was added diethylaminosulfur trifluoride (244 mg, 1.51 mmol, 200 uL, 1.53 eq) at −30° C. The mixture was stirred at −30° C. for 0.5 h. The mixture was quenched with saturated sodium bicarbonate (10%, 10.0 mL). The organic layer was separated and concentrated under reduced pressure. The residue was purified by prep-TLC to give tert-butyl (6-(1-fluorocyclopropyl)pyridin-3-yl)carbamate. $^1$H NMR (400 MHz, CDCl$_3$) δ=8.30 (d, J=2.4 Hz, 1H), 7.97 (br s, 1H), 7.55 (d, J=8.4 Hz, 1H), 6.50 (br s, 1H), 1.53 (s, 9H), 1.49-1.41 (m, 2H), 1.39-1.35 (m, 2H). MS (ESI) m/z 253.1 [M+H]$^+$ Step 5: To a solution tert-butyl (6-(1-fluorocyclopropyl)pyridin-3-yl)carbamate (25.0 mg, 99.1 umol, 1.00 eq) in ethyl acetate (5.00 mL) was added hydrochloric acid/ethyl acetate (4 M, 2.00 mL) in portions. The mixture was stirred at 10° C. for 3 h. The reaction mixture was concentrated under reduced pressure to give 6-(1-fluorocyclopropyl)pyridin-3-amine. MS (ESI) m/z 153.1 [M+H]$^+$ Step 6: To a solution of 6-(1-fluorocyclopropyl)pyridin-3-amine (20.0 mg, 131 umol, 1.00 eq) in Acetonitrile (2.00 mL) was added pyridine (31.2 mg, 394 umol, 31.8 uL, 3.00 eq) and phenyl carbonochloridate (24.6 mg, 157 umol, 19.7 uL, 1.20 eq). The mixture was stirred at 10° C. for 1 h and concentrated to give a residue, which was purified by prep-TLC to give pyridin-3-yl (6-(1-fluorocyclopropyl)pyridin-3-yl)carbamate. MS (ESI) m/z 273.0 [M+H]$^+$ Step 7: To a solution of 3-(6-(hydroxymethyl)-1-oxoisoindolin-2-yl)piperidine-2,6-dione VIII (13.0 mg, 47.4 umol, 1.30 eq) in dimethyl formamide (1.00 mL) was added pyridin-3-yl (6-(1-fluorocyclopropyl)pyridin-3-yl) carbamate (9.96 mg, 36.5 umol, 1.00 eq) and sodium hydride (2.92 mg, 72.9 umol, 60% purity, 2.00 eq). The mixture was stirred at 0° C. for 1 h. The mixture was adjusted pH=6 with Formic acid (0.100 mL). The mixture was diluted with water/ethyl acetate (2.00 ml/2.00 ml). The organic layer was collected and concentrated to give a residue. The residue was purified by prep-HPLC and the desired fraction was collected and lyophilized to give (2-(2,6-dioxopiperidin-3-yl)-3-oxoisoindolin-5-yl)methyl (6-(1-fluorocyclopropyl)pyridin-3-yl)carbamate 109. $^1$H NMR (400 MHz, DMSO-d$_6$) δ=11.14-10.79 (m, 1H), 10.07 (br s, 1H), 8.56 (s, 1H), 8.00-7.90 (m, 1H), 7.80 (s, 1H), 7.74-7.66 (m, 1H), 7.66-7.60 (m, 1H), 7.53 (d, J=7.7 Hz, 1H), 5.29 (s, 2H), 5.12 (dd, J=5.1, 13.3 Hz, 1H), 4.51-4.42 (m, 1H), 4.39-4.29 (m, 1H), 2.96-2.86 (m, 1H), 2.62-2.58 (m, 1H), 2.45-2.34 (m, 1H), 2.06-1.96 (m, 1H), 1.49-1.39 (m, 2H), 1.30-1.22 (m, 2H). MS (ESI) m/z 453.2 [M+H]$^+$ Compound 110:

Step 1: A mixture of 5-amino-2-methylbenzonitrile (1.00 g, 7.57 mmol, 1.00 eq), pyridine (1.80 g, 22.7 mmol, 1.83 mL, 3.00 eq) in Acetonitrile (20.0 mL) was added phenyl carbonochloridate (1.30 g, 8.32 mmol, 1.04 mL, 1.10 eq) at 0° C. The mixture was stirred at 25° C. for 1 h. The reaction mixture was concentrated under reduced pressure to give a residue. The residue was purified by reversed-phase HPLC and lyophilized to give phenyl (3-cyano-4-methylphenyl)carbamate. MS (ESI) m/z. 253.1 [M+H]$^+$ Step 2: To a solution of phenyl (3-cyano-4-methylphenyl)carbamate (80.9 mg, 321 umol, 1.10 eq) and 3-(6-(hydroxymethyl)-1-oxoisoindolin-2-yl)piperidine-2,6-dione VIII (80.0 mg, 292 umol, 1.00 eq) in dimethyl formamide (1.50 mL) was added sodium hydride (23.3 mg, 583 umol, 60% purity, 2.00 eq) at 0° C. The mixture was stirred at 25° C. for 1 h. The pH of the mixture was adjusted to around 6 by adding hydrochloric acid. The mixture was extracted with ethyl acetate (3×10.0 mL). The combined organic layers were dried over anhydrous sodium sulfate, sodium sulfate, filtered and concentrated under reduced pressure to give a residue. The residue was purified by prep-HPLC and lyophilized to afford (2-(2,6-dioxopiperidin-3-yl)-3-oxoisoindolin-5-yl)methyl(3-cyano-4-methylphenyl)carbamate 110. $^1$H NMR (400 MHz, DMSO-d$_6$) δ=10.99 (s, 1H), 10.09 (s, 1H), 7.81 (d, J=2.0 Hz, 1H), 7.80 (s, 1H), 7.70-7.67 (m, 1H), 7.65-7.60 (m, 2H), 7.38 (d, J=8.6 Hz, 1H), 5.29 (s, 2H), 5.12 (dd, J=5.0, 13.3 Hz, 1H), 4.52-4.44 (m, 1H), 4.37-4.30 (m, 1H), 2.96-2.86 (m, 1H), 2.60 (br d, J=17.9 Hz, 1H), 2.40 (s, 3H), 2.35 (br d, J=3.8 Hz, 1H), 2.05-1.97 (m, 1H). MS (ESI) m/z. 433.0[M+H]$^+$ Compound 111:

Step 1: To a solution of 3-amino-5-chlorobenzonitrile (0.500 g, 3.28 mmol, 1.00 eq) in Acetonitrile (10.0 mL) was added pyridine (1.30 g, 16.3 mmol, 1.32 mL, 5.00 eq) and phenyl carbonochloridate (564 mg, 3.60 mmol, 451 uL, 1.10 eq). The mixture was stirred at 10° C. for 0.5 h. The reaction mixture was concentrated under reduced pressure to give a residue. The crude product was purified by reversed-phase HPLC to give phenyl (3-chloro-5-cyanophenyl)carbamate. $^1$H NMR (400 MHz, DMSO-d$_6$) δ=10.81 (br s, 1H), 7.94-7.81 (m, 3H), 7.48-7.44 (m, 2H), 7.32-7.25 (m, 3H).

Step 2: To a solution of 3-(6-(hydroxymethyl)-1-oxoisoindolin-2-yl)piperidine-2,6-dione VIII (80.0 mg, 291 umol, 1.00 eq) in dimethyl formamide (2.00 mL) was added phenyl (3-chloro-5-cyanophenyl)carbamate (87.4 mg, 320 umol, 1.10 eq) and sodium hydride (23.3 mg, 583 umol, 60% purity, 2.00 eq) at 0° C. The mixture was stirred at 0° C. for 20 min. The reaction mixture was quenched with Formic acid (1.00 ml) to give a solution. The solution was purified by prep-HPLC and lyophilized to give (2-(2,6-dioxopiperidin-3-yl)-3-oxoisoindolin-5-yl)methyl (3-chloro-5-cyanophenyl)carbamate 111. $^1$H NMR (400 MHz, DMSO-d$_6$) δ=11.00 (br s, 1H), 10.41 (br s, 1H), 7.86 (t, J=1.9 Hz, 1H), 7.81 (dd, J=2.3, 4.0 Hz, 2H), 7.72-7.69 (m, 1H), 7.69-7.63 (m, 2H), 5.32 (s, 2H), 5.13 (dd, J=5.1, 13.3 Hz, 1H), 4.53-4.45 (m, 1H), 4.39-4.30 (m, 1H), 2.97-2.87 (m, 1H), 2.65-2.61 (m, 1H), 2.46-2.38 (m, 1H), 2.06-1.98 (m, 1H). MS (ESI) m/z 453.1 [M+H]$^+$ Compound 112:

Step 1: To a solution of 3-methyl-5-nitrobenzonitrile (1.00 g, 6.17 mmol, 1.00 eq) in the mixture of methanol (10.0 mL) and water (5.00 mL) was added iron powder (1.72 g, 30.8 mmol, 5.00 eq) and ammonium chloride (2.64 g, 49.3 mmol, 8.00 eq). The mixture was stirred at 80° C. for 2 h.

The mixture was filtered to give filter liquor and concentrated under reduced pressure to give a residue. The crude product was diluted with water (30.0 mL) and exacted with ethyl acetate (2×50.0 mL). The organic phase was separated, washed with brine, dried over sodium sulfate, filtered and concentrated under reduced pressure to give 3-amino-5-methylbenzonitrile. $^1$H NMR (400 MHz, DMSO-d$_6$) δ=6.68 (br d, J=8.8 Hz, 3H), 5.51 (br s, 2H), 2.19 (br s, 3H).

Step 2: To a solution of 3-amino-5-methylbenzonitrile (750 mg, 5.67 mmol, 1.00 eq) in Acetonitrile (10.0 mL) was added pyridine (2.24 g, 28.3 mmol, 2.29 mL, 5.00 eq) and phenyl carbonochloridate (977 mg, 6.24 mmol, 781 uL, 1.10 eq). The mixture was stirred at 10° C. for 0.5 h. The reaction mixture was concentrated under reduced pressure to give a residue. The crude product was purified by reversed-phase HPLC to give phenyl (3-cyano-5-methylphenyl)carbamate. MS (ESI) m/z 253.0 [M+H]$^+$ Step 3: To a solution of 3-(6-(hydroxymethyl)-1-oxoisoindolin-2-yl)piperidine-2,6-dione VIII (80.0 mg, 291 umol, 1.00 eq) in dimethyl formamide (2.00 mL) was added phenyl (3-cyano-5-methylphenyl)carbamate (80.9 mg, 320 umol, 1.10 eq) and sodium hydride (23.3 mg, 583 umol, 60% purity, 2.00 eq) at 0° C. The mixture was stirred at 0° C. for 20 min. The reaction mixture was quenched with Formic acid (1.00 ml) to give a solution. The solution was purified by prep-HPLC and lyophilized to give (2-(2,6-dioxopiperidin-3-yl)-3-oxoisoindolin-5-yl)methyl (3-cyano-5-methylphenyl)carbamate 112. $^1$H NMR (400 MHz, DMSO-d$_6$) δ=11.00 (s, 1H), 10.15 (s, 1H), 7.81 (s, 1H), 7.73-7.67 (m, 2H), 7.67-7.63 (m, 1H), 7.58 (s, 1H), 7.31 (s, 1H), 5.30 (s, 2H), 5.13 (dd, J=5.1, 13.3 Hz, 1H), 4.51-4.43 (m, 1H), 4.39-4.31 (m, 1H), 2.98-2.86 (m, 1H), 2.61 (br dd, J=2.4, 15.3 Hz, 1H), 2.41 (dd, J=4.5, 13.1 Hz, 1H), 2.32 (s, 3H), 2.05-1.96 (m, 1H). MS (ESI) m/z 433.2 [M+H]$^+$ Compound 113:

Step 1: A mixture of sodium hydroxide (12.0 g, 299 mmol, 10.0 eq) and dimethyl formamide (10.0 mL) was stirred at 95° C. for 0.5 h, then 2-hydroxy-5-nitrobenzaldehyde (5.00 g, 29.9 mmol, 1.00 eq) and sodium; 2-chloro-2,2-difluoroacetate (23.0 g, 151 mmol, 5.04 eq) in dimethyl formamide (30.0 mL) was slowly added to the mixture was stirred at 95° C. for another 1.5 h. After being cooled to room temperature, the reaction mixture was diluted with water (250 mL) and extracted with ethyl acetate (300 mL). The organic layer was collected and dried over anhydrous sodium sulfate. After filtration, the filtrate was concentrated under reduced pressure to give a residue, which was purified by column chromatography on silica gel and further purified by reversed-phase HPLC. The desired fraction was collected and lyophilized to give 2,2-difluoro-5-nitro-2,3-dihydrobenzofuran-3-ol. $^{1}$H NMR (400 MHz, CDCl$_3$) δ=8.39 (d, J=2.1 Hz, 1H), 8.35 (dd, J=2.3, 8.8 Hz, 1H), 7.13 (d, J=8.9 Hz, 1H), 5.40 (dt, J=4.2, 8.9 Hz, 1H), 2.59 (dd, J=1.8, 8.2 Hz, 1H).

Step 2: To a solution of 2,2-difluoro-5-nitro-2,3-dihydrobenzofuran-3-ol (1.00 g, 4.61 mmol, 1.00 eq) in tetrahydrofuran (15.0 mL) was added sodium hydride (60%, dispersion in paraffin liquid) (221 mg, 5.53 mmol, 60% purity, 1.20 eq) and 4-methylbenzene-1-sulfonyl chloride (1.76 g, 9.21 mmol, 2.00 eq) in portions. The mixture was stirred at 10° C. for 3 h, sodium hydride (60%, dispersion in paraffin liquid) (270 mg, 6.75 mmol, 60% purity, 1.47 eq) was added into the mixture. The mixture was stirred at 0° C. for 0.5 h, then 4-methylbenzene-1-sulfonyl chloride (1.05 g, 5.53 mmol, 1.20 eq) was added into the reaction mixture was stirred at 0° C. for another 1.5 h. The reaction mixture was adjusted pH=8 with formic acid and diluted with ethyl acetate. The organic layer was separated and concentrated under reduced pressure to give a crude product. The crude product was purified by column chromatography on silica gel to give 2,2-difluoro-5-nitro-2,3-dihydrobenzofuran-3-yl 4-methylbenzenesulfonate. $^{1}$H NMR (400 MHz, CDCl$_3$) δ=8.36 (dd, J=2.3, 8.9 Hz, 1H), 8.00 (d, J=2.2 Hz, 1H), 7.91 (d, J=8.2 Hz, 2H), 7.46 (d, J=8.3 Hz, 2H), 7.12 (d, J=9.0 Hz, 1H), 5.96 (dd, J=2.1, 9.2 Hz, 1H), 2.53 (s, 3H).

Step 3: To a solution of 2,2-difluoro-5-nitro-2,3-dihydrobenzofuran-3-yl 4-methylbenzenesulfonate (740 mg, 1.99 mmol, 1.00 eq) in ethyl acetate (20.0 mL) and tetrahydrofuran (20.0 mL) was added palladium on activated carbon (10%) (150 mg, wet) in portions under hydrogen (15.0 Psi). The mixture was stirred at 10° C. for 30 min. The reaction mixture was filtered to give the filtrates and concentrated under reduced pressure to give a crude product. The crude product purified by column chromatography on silica gel to give 2,2-difluoro-2,3-dihydrobenzofuran-5-amine. $^{1}$H NMR (400 MHz, DMSO-d$_6$) δ=7.47 (d, J=8.0 Hz, 1H), 7.11 (d, J=7.9 Hz, 1H), 6.79 (d, J=8.5 Hz, 1H), 6.65 (s, 1H), 6.58-6.54 (m, 1H), 3.68 (t, J=14.7 Hz, 2H). MS (ESI) m/z 172.2 [M+H]$^{+}$ Step 4: To a solution of 2,2-difluoro-2,3-dihydrobenzofuran-5-amine (76.0 mg, 444 umol, 1.00 eq) in Acetonitrile (5.00 mL) was added pyridine (106 mg, 1.34 mmol, 108 uL, 3.01 eq) and phenyl carbonochloridate (82.5 mg, 527 umol, 66.0 uL, 1.19 eq) in portions at 0° C. The mixture was stirred at 10° C. for 0.5 h. The reaction mixture was concentrated under reduced pressure to give a residue. The crude product was purified by column chromatography on silica gel to give phenyl (2,2-difluoro-2,3-dihydrobenzofuran-5-yl)carbamate. $^{1}$H NMR (400 MHz, CDCl$_3$) δ=7.59-7.50 (m, 1H), 7.43-7.39 (m, 2H), 7.26-7.15 (m, 4H), 6.93 (d, J=8.7 Hz, 1H), 6.90-6.79 (m, 1H), 3.61 (t, J=13.9 Hz, 2H). MS (ESI) m/z 291.9 [M+H]$^{+}$ Step 5: To a solution of 3-(6-(hydroxymethyl)-1-oxoisoindolin-2-yl)piperidine-2,6-dione VIII (20.0 mg, 72.9 umol, 1.00 eq) and phenyl (2,2-difluoro-2,3-dihydrobenzofuran-5-yl)carbamate (25.5 mg, 87.5 umol, 1.20 eq) in dimethyl formamide (2.00 mL) was added triethylamine (29.1 mg, 287 umol, 40.0 uL, 3.94 eq) in portions. The mixture was stirred at 25° C. for 12 h. The mixture was diluted with water (10.0 mL) and extracted with ethyl acetate (20.0 mL). The combined organic layer was dried over anhydrous sodium sulfate. After filtration, the filtrate was concentrated under reduced pressure to give a residue. The crude product was purified by column chromatography on silica gel to give a residue. The residue was dissolved in acetonitrile/dimethyl formamide (1/1, 2.00 mL) and purified by prep-HPLC. The desired fraction was collected and concentrated under pressure to give a solution, which was lyophilized to give (2-(2,6-dioxopiperidin-3-yl)-3-oxoisoindolin-5-yl)methyl (2,2-difluoro-2,3-dihydrobenzofuran-5-yl)carbamate 113. $^{1}$H NMR (400 MHz, DMSO-d$_6$) δ=10.99 (br s, 1H), 9.83 (br s, 1H), 7.79 (s, 1H), 7.70-7.66 (m, 1H), 7.65-7.60 (m, 1H), 7.52 (br s, 1H), 7.32 (br d, J=8.3 Hz, 1H), 7.01 (d, J=8.8 Hz, 1H), 5.26 (s, 2H), 5.12 (dd, J=5.0, 13.3 Hz, 1H), 4.50-4.44 (m, 1H), 4.37-4.30 (m, 1H), 3.80 (t, J=14.7 Hz, 2H), 2.97-2.86 (m, 1H), 2.62-2.57 (m, 1H), 2.43-2.34 (m, 1H), 2.04-1.98 (m, 1H). MS (ESI) m/z 472.0 [M+H]$^{+}$ Compound 114:

Step 1: To a solution of 2-(tert-butyl)isonicotinic acid (150 mg, 837 umol, 1.00 eq) in dioxane (1.00 mL) was added diphenylphosphoryl azide (461 mg, 1.67 mmol, 363 uL, 2.00 eq) and triethylamine (254 mg, 2.51 mmol, 349 uL, 3.00 eq) at 25° C. The mixture was stirred at 25° C. for 0.5 h under nitrogen, then added 3-(6-(hydroxymethyl)-1-oxoisoindolin-2-yl)piperidine-2,6-dione VIII (230 mg, 837 umol, 1.00 eq). The mixture was stirred at 90° C. for 12 h under nitrogen. The reaction mixture was added hydrochloric acid (1 M, 2.00 mL) and filtered to give a filter cake. The filter cake was purified twice by Prep-HPLC to give (2-(2, 6-dioxopiperidin-3-yl)-3-oxoisoindolin-5-yl)methyl(2-(tert-butyl)pyridin-4-yl)carbamate 144. $^{1}$H NMR (400 MHz, DMSO-d$_6$) δ=11.00 (br s, 1H), 10.18 (s, 1H), 8.34 (d, J=5.6 Hz, 1H), 7.82 (s, 1H), 7.72-7.68 (m, 1H), 7.68-7.64 (m, 1H), 7.52 (d, J=1.6 Hz, 1H), 7.28 (dd, J=2.0, 5.6 Hz, 1H), 5.32 (s, 2H), 5.14 (dd, J=5.2, 13.2 Hz, 1H), 4.54-4.44 (m, 1H), 4.38-4.32 (m, 1H), 2.98-2.88 (m, 1H), 2.64-2.58 (m, 1H), 2.44-2.38 (m, 1H), 2.06-1.98 (m, 1H), 1.28 (s, 9H). MS (ESI) m/z 451.2[M+H]$^{+}$ Compound 115:

Step 1: Triethylamine (9.61 g, 94.9 mmol, 13.2 mL, 2.10 eq) and chloro(trimethyl)silane (10.3 g, 94.9 mmol, 12.1 mL, 2.10 eq) were added into a stirred solution of 1-(4-bromophenyl)ethanone (9.00 g, 45.2 mmol, 1.00 eq) in Acetonitrile (100 mL) at 0° C. The mixture was stirred at 25° C. for 16 h under nitrogen atmosphere. The reaction mixture was quenched by addition saturated ammonium chloride (500 mL) at 0° C., and extracted with ethyl acetate (3×500 mL). The combined organic layers were dried over anhydrous sodium sulfate, filtered and concentrated under reduced pressure to give a residue. The residue was purified by column chromatography to give ((1-(4-bromophenyl)vinyl)oxy) trimethylsilane. $^{1}$H NMR (400 MHz, CDCl$_3$) δ=7.46 (s, 4H), 4.91 (d, J=1.9 Hz, 1H), 4.45 (d, J=1.9 Hz, 1H), 0.31-0.24 (m, 9H).

Step 2: A mixture of ((1-(4-bromophenyl)vinyl)oxy)trimethylsilane (6.50 g, 23.9 mmol, 1.00 eq), diiodomethane (9.63 g, 35.9 mmol, 2.90 mL, 1.50 eq) in dichloromethane (50.0 mL) was degassed and purged with nitrogen for 3 times, and then diethylzinc (1 M in toluene, 36.0 mL, 1.50 eq) was added into the mixture at 0° C. The mixture was stirred at 20° C. for 12 h under nitrogen atmosphere. The reaction mixture was quenched by addition water (100 mL), and extracted with ethyl acetate (2×100 mL). The combined organic layers were dried over anhydrous sodium sulfate, filtered and concentrated under reduced pressure to give a residue. The residue was purified by column chromatography to give (1-(4-bromophenyl)cyclopropoxy)trimethylsilane. $^{1}$H NMR (400 MHz, CDCl$_3$) δ=7.43 (d, J=8.4 Hz, 2H), 7.15 (d, J=8.5 Hz, 2H), 1.26-1.22 (m, 2H), 1.01-0.97 (m, 2H), 0.09 (s, 9H).

Step 3: A mixture of (1-(4-bromophenyl)cyclopropoxy) trimethylsilane (200 mg, 701 umol, 1.00 eq), tert-butyl carbamate (164 mg, 1.40 mmol, 2.00 eq), and cesium carbonate (685 mg, 2.10 mmol, 3.00 eq) in dioxane (10.0 mL) was degassed and purged with nitrogen for 3 times, and then palladium(1+)$_2$-amino-1,1-biphenyl-2-yl[2,6-bis(propan-2-yloxy)-[1,1-biphenyl]-2-yl]dicyclohexylphosphane methanesulfonate (58.6 mg, 70.1 umol, 0.100 eq) was added into the mixture. The mixture was stirred at 90° C. for 6 h under nitrogen atmosphere. The reaction mixture was diluted with water (100 mL), and then extracted with ethyl acetate (3×150 mL). The combined organic layers were dried over anhydrous sodium sulfate, filtered and concentrated under reduced pressure to give a residue. The residue was purified by flash silica gel chromatography to give tert-butyl (4-(1-((trimethylsilyl)oxy)cyclopropyl)phenyl) carbamate. $^1$H NMR (400 MHz, CDCl$_3$) δ=7.34-7.27 (m, 2H), 7.24-7.20 (m, 2H), 6.44 (br s, 1H), 1.52 (s, 9H), 1.19-1.15 (m, 2H), 0.99-0.93 (m, 2H), 0.06 (s, 9H).

Step 4: A mixture of tert-butyl (4-(1-((trimethylsilyl)oxy) cyclopropyl)phenyl)carbamate (490 mg, 1.52 mmol, 1.00 eq), diethylaminosulfur trifluoride (491 mg, 3.05 mmol, 403 uL, 2.00 eq) in dichloromethane (10.0 mL) was stirred at −30° C. for 1 h under nitrogen. The reaction mixture was concentrated under reduced pressure to give a residue. The residue was purified by column chromatography to give tert-butyl (4-(1-fluorocyclopropyl)phenyl)carbamate. $^1$H NMR (400 MHz, CDCl$_3$) δ=7.36 (br d, J=8.4 Hz, 2H), 7.24 (d, J=8.3 Hz, 2H), 6.50 (s, 1H), 1.53 (s, 9H), 1.48-1.44 (m, 1H), 1.43-1.39 (m, 1H), 1.04-0.98 (m, 2H). MS (ESI) m/z 196.0 [M+H−56]$^+$ Step 5: To a solution of tert-butyl (4-(1-fluorocyclopropyl)phenyl)carbamate (150 mg, 597 umol, 1.00 eq) in ethyl acetate (5.00 mL) was added hydrochloric acid/ethyl acetate (4 M, 5.00 mL). The mixture was stirred at 10° C. for 2 h. The reaction mixture was concentrated under reduced pressure to give a residue to give 4-(1-fluorocyclopropyl)aniline. $^1$H NMR (400 MHz, DMSO-d$_6$) δ=10.50-9.62 (m, 2H), 7.40-7.28 (m, 4H), 1.53-1.43 (m, 2H), 1.19-1.11 (m, 2H).

Step 6: A mixture of 4-(1-fluorocyclopropyl)aniline (120 mg, 639 umol, 1.00 eq, hydrochloric acid), phenyl carbonochloridate (110 mg, 703 umol, 88.1 uL, 1.10 eq), pyridine (152 mg, 1.92 mmol, 154 uL, 3.00 eq) in Acetonitrile (10.0 mL) was stirred at 0° C. The mixture was stirred at 25° C. for 1 h. The mixture was concentrated under reduced pressure to give a residue. The residue was purified by column chromatography to give phenyl (4-(1-fluorocyclopropyl) phenyl)carbamate. $^1$H NMR (400 MHz, DMSO-d$_6$) δ=10.29 (br s, 1H), 7.53 (d, J=8.4 Hz, 2H), 7.46-7.40 (m, 2H), 7.29-7.20 (m, 5H), 1.46-1.37 (m, 2H), 1.13-1.05 (m, 2H). MS (ESI) m/z. 272.1 [M+H]$^+$ Step 7: To a solution of phenyl (4-(1-fluorocyclopropyl) phenyl)carbamate (90.0 mg, 332 umol, 1.00 eq), 3-(6-(hydroxymethyl)-1-oxoisoindolin-2-yl)piperidine-2,6-dione VIII (100 mg, 365 umol, 1.10 eq) in dimethyl formamide (1.50 mL) was added sodium hydride (26.5 mg, 664 umol, 60% purity, 2.00 eq). The mixture was stirred at 0° C. for 1 h. The pH of the mixture was adjusted to around 6 with Formic acid. The mixture was diluted with water (50.0 mL) and extracted with ethyl acetate (3×50.0 mL). The combined organic layers were dried over anhydrous sodium sulfate, filtered and concentrated under reduced pressure to give a residue. The residue was purified by column chromatography to afford (2-(2,6-dioxopiperidin-3-yl)-3-oxoisoindolin-5-yl)methyl(4-(1-fluorocyclopropyl)phenyl) carbamate 115. $^1$H NMR (400 MHz, DMSO-d$_6$) δ=10.98 (s, 1H), 9.88 (s, 1H), 7.80 (s, 1H), 7.70-7.62 (m, 2H), 7.49 (br d, J=8.3 Hz, 2H), 7.24 (d, J=8.7 Hz, 2H), 5.27 (s, 2H), 5.12 (dd, J=5.1, 13.3 Hz, 1H), 4.50-4.43 (m, 1H), 4.37-4.30 (m, 1H), 2.96- 2.86 (m, 1H), 2.63-2.58 (m, 1H), 2.40 (dd, J=4.4, 13.3 Hz, 1H), 2.05-1.99 (m, 1H), 1.45-1.34 (m, 2H), 1.11-1.02 (m, 2H). MS (ESI) m/z. 903.2 [2M+H]$^+$ Compound 116:

Step 1: To a solution of diethyl malonate (1.86 g, 11.6 mmol, 1.76 mL, 1.50 eq) in tetrahydrofuran (20.0 mL) was added sodium hydride (619 mg, 15.5 mmol, 60% purity, 2.00 eq) at 0° C. The mixture was stirred at 0° C. for 30 min, then 1-chloro-2,3-difluoro-5-nitrobenzene (1.50 g, 7.75 mmol, 1.00 eq) was added to the mixture and stirred at 25° C. for another 11.5 h. The mixture was quenched with saturated ammonium chloride solution and extracted with ethyl acetate (3×30.0 mL). The combined organic phase was washed with brine (50.0 mL), dried with anhydrous sodium sulfate, filtered and concentrated in vacuum to give a residue. The residue was purified by silica gel chromatography to give diethyl 2-(2-chloro-6-fluoro-4-nitrophenyl)malonate 1. $^1$H NMR (400 MHz, CDCl$_3$) δ=8.17 (t, J=1.6 Hz, 1H), 7.94 (dd, J=2.4, 9.2 Hz, 1H), 5.23 (s, 1H), 4.30 (q, J=7.2 Hz, 4H), 1.33-1.31 (m, 6H). MS (ESI) m/z 334.0 [M+H]$^+$ Step 2: A mixture of diethyl 2-(2-chloro-6-fluoro-4-nitrophenyl)malonate (1.00 g, 3.00 mmol, 1.00 eq) and magnesium chloride (855 mg, 8.99 mmol, 369 uL, 3.00 eq) in dimethylacetamide (10.0 mL) and water (647 mg, 35.9 mmol, 647 uL, 12.0 eq) was stirred at 140° C. for 5 h. The reaction mixture was poured into water (50.0 mL) and extracted with ethyl acetate (3×30.0 mL). The combined organic layers were washed with brine (50.0 mL), dried over anhydrous sodium sulfate, filtered and concentrated in vacuum to give a residue. The residue was purified by silica gel chromatography to give 1-chloro-3-fluoro-2-methyl-5-nitrobenzene. $^1$H NMR (400 MHz, CDCl$_3$) δ=8.11 (s, 1H), 7.86 (dd, J=2.0, 8.8 Hz, 1H), 2.43 (d, J=2.4 Hz, 3H).

Step 3: To a mixture of 1-chloro-3-fluoro-2-methyl-5-nitrobenzene (80.0 mg, 422 umol, 1.00 eq), iron powder (118 mg, 2.11 mmol, 5.00 eq) and ammonium chloride (112 mg, 2.11 mmol, 5.00 eq) in methanol (2.00 mL) and water (500 uL) was stirred at 80° C. for 2 h. The reaction mixture was concentrated to give a residue. The residue was purified by reversed-phase HPLC and lyophilized to give 3-chloro-5-fluoro-4-methylaniline. MS (ESI) m/z 160.1 [M+H]$^+$ Step 4: To a solution of 3-chloro-5-fluoro-4-methylaniline (60.0 mg, 375 umol, 1.00 eq) and pyridine (89.2 mg, 1.13 mmol, 91.0 uL, 3.00 eq) in Acetonitrile (1.00 mL) was added phenyl carbonochloridate (70.6 mg, 451 umol, 56.5 uL, 1.20 eq) at 25° C. The reaction mixture was stirred at 25° C. for 2 h. The reaction mixture was concentrated to give a residue, which was purified by reversed-phase HPLC and lyophilized to give phenyl (3-chloro-5-fluoro-4-methylphenyl)carbamate. MS (ESI) m/z 280.0 [M+H]$^+$ Step 5: To a mixture of 3-(6-(hydroxymethyl)-1-oxoisoindolin-2-yl)piperidine-2,6-dione VIII (78.4 mg, 286 umol, 1.00 eq) and phenyl (3-chloro-5-fluoro-4-methylphenyl)carbamate (80.0 mg, 286 umol, 1.00 eq) in dimethyl formamide (2.00 mL) was added sodium hydride (11.4 mg, 286 umol, 60% purity, 1.00 eq) at 0° C. The reaction mixture was stirred at 25° C. for 1 h. The reaction mixture was added Formic acid (1.00 mL) and filtered to give a filtrate. The filtrate was purified by Prep-HPLC and lyophilized to give (2-(2,7-dioxoazepan-3-yl)-3-oxoisoindolin-5-yl)methyl (3-chloro-4-methylphenyl) carbamate 116. $^1$H NMR (400 MHz, DMSO-d$_6$) δ=11.07-10.93 (m, 1H), 10.14 (s, 1H), 7.80 (s, 1H), 7.72-7.67 (m, 1H), 7.67-7.63 (m, 1H), 7.40 (s, 1H), 7.34-7.29 (m, 1H), 5.29 (s, 2H), 5.13 (dd, J=5.2, 13.2 Hz, 1H), 4.52-4.44 (m, 1H), 4.39-4.31 (m, 1H), 2.92 (ddd, J=5.6, 13.6, 17.6 Hz, 1H), 2.64-2.58 (m, 1H), 2.43 (dt, J=4.4, 13.2 Hz, 1H), 2.18 (d, J=1.6 Hz, 3H), 2.07-1.97 (m, 1H). MS (ESI) m/z 460.3 [M+H]$^+$.

Compound 117:

Step 1: To a solution of 3-fluoro-5-methylaniline (2.00 g, 15.9 mmol, 1.00 eq) in dimethyl formamide (10.0 mL) was added N-bromosuccinimide (2.87 g, 16.1 mmol, 1.01 eq) in portions at 0° C. The mixture was stirred at 20° C. for 1 h. The mixture was diluted with water (180 mL) and extracted with ethyl acetate (3×50.0 mL). The combined organic layer was washed with brine and dried over anhydrous sodium sulfate, filtered and concentrated to give 4-bromo-3-fluoro-5-methylaniline. $^1$H NMR (400 MHz, DMSO-d$_6$) δ=6.37 (s, 1H), 6.32 (dd, J=2.5, 11.3 Hz, 1H), 5.47 (br s, 2H), 2.22 (s, 3H).

Step 2: To a solution of 4-bromo-3-fluoro-5-methylaniline (1.00 g, 4.90 mmol, 1.00 eq), potassium methyltrifluoroborate (2.00 g, 16.4 mmol, 3.35 eq) and potassium carbonate (2.03 g, 14.7 mmol, 3.00 eq) in dioxane (10.0 mL) and water (2.00 mL) was added [1,1'-bis(diphenylphosphino)ferrocene] dichloropalladium(II) (400 mg, 490 umol, 0.100 eq) under nitrogen atmosphere. The mixture was stirred at 110° C. for 6 h. The mixture was diluted with water (50.0 mL) and extracted with ethyl acetate (3×30.0 mL). The combined organic layer was washed with brine and dried over anhydrous sodium sulfate, filtered and concentrated to give crude product. The crude product was purified by silica gel chromatography to give 3-fluoro-4,5-dimethylaniline. $^1$H NMR (400 MHz, DMSO-d$_6$) δ=6.22 (s, 1H), 6.14 (dd, J=1.9, 12.2 Hz, 1H), 5.01 (s, 2H), 2.10 (s, 3H), 1.94 (d, J=1.4 Hz, 3H). MS (ESI) m/z 140.2 [M+H]$^+$ Step 3: To a solution of 3-fluoro-4,5-dimethylaniline (300 mg, 2.16 mmol, 1.00 eq) and pyridine (511 mg, 6.47 mmol, 521 uL, 3.00 eq) in Acetonitrile (5.00 mL) was added phenyl carbonochloridate (371 mg, 2.37 mmol, 297 uL, 1.10 eq) at 0° C. The mixture was stirred at 25° C. for 12 h. The mixture was concentrated to give crude product and purified by reversed-phase HPL to give phenyl (3-fluoro-4,5-dimethylphenyl)carbamate. MS (ESI) m/z 260.0 [M+H]$^+$ Step 4: To a solution of 3-(6-(hydroxymethyl)-1-oxoisoindolin-2-yl)piperidine-2,6-dione VIII (80.0 mg, 292 umol, 1.00 eq) and phenyl (3-fluoro-4,5-dimethylphenyl)carbamate (83.1 mg, 320 umol, 1.10 eq) in dimethyl formamide (1.00 mL) was added sodium hydride (23.3 mg, 583 umol, 60% purity, 2.00 eq) in portions at 0° C. The mixture was stirred at 20° C. for 1 h. The mixture was quenched with 1M hydrochloric acid (1.00 mL) and purified by prep-HPLC. The desired fraction was collected and lyophilized to give (2-(2,6-dioxopiperidin-3-yl)-3-oxoisoindolin-5-yl)methyl (3-fluoro-4,5-dimethylphenyl)carbamate 117. $^1$H NMR (400 MHz, DMSO-d$_6$) δ=10.99 (s, 1H), 9.85 (s, 1H), 7.79 (s, 1H), 7.71-7.66 (m, 1H), 7.66-7.61 (m, 1H), 7.19 (br d, J=11.7 Hz, 1H), 7.05 (s, 1H), 5.27 (s, 2H), 5.13 (dd, J=5.1, 13.3 Hz, 1H), 4.52-4.43 (m, 1H), 4.39-4.31 (m, 1H), 2.98-2.86 (m, 1H), 2.61 (br d, J=17.7 Hz, 1H), 2.41 (dt, J=8.8, 13.2 Hz, 1H), 2.21 (s, 3H), 2.06 (s, 3H), 2.04-1.98 (m, 1H). MS (ESI) m/z 440.1 [M+H]$^+$ Compound 118:

Step 1: To a solution of 2-methylpyridine-4-carbonitrile (1.00 g, 8.46 mmol, 1.00 eq), 2,2-dimethylpropanoic acid (951 mg, 9.31 mmol, 1.07 mL, 1.10 eq) and sulfuric acid (18.4 g, 18.8 mmol, 10.0 mL, 10% purity, 2.22 eq) in Acetonitrile (10.0 mL) was added silver nitrate (863 mg, 5.08 mmol, 0.600 eq). The mixture was stirred at 70° C. for 0.5 h, then ammonium persulfate (5.80 g, 25.4 mmol, 5.52 mL, 3.00 eq) in water (10.0 mL) was added to the mixture at 70° C. The mixture was stirred at 70° C. for 0.5 h. The reaction was cooled to 0° C. and 30% ammonium hydroxide was added slowly until pH=9-10. The mixture was filtered and extracted with ethyl acetate (3×100 mL). The combined organic phase was washed with brine, dried with anhydrous sodium sulfate, filtered and concentrated in vacuum. The residue was purified by column chromatography to afford 2-(tert-butyl)-6-methylisonicotinonitrile. $^1$H NMR (400 MHz, CDCl$_3$) δ=7.34 (s, 1H), 7.17 (d, J=0.6 Hz, 1H), 2.59 (s, 3H), 1.36 (s, 9H).

Step 2: To a solution of 2-(tert-butyl)-6-methylisonicotinonitrile (950 mg, 5.45 mmol, 1.00 eq) and potassium carbonate (3.01 g, 21.8 mmol, 4.00 eq) in dimethyl sulfoxide (4.50 mL) and water (4.50 mL) was added hydrogen peroxide (5.31 g, 46.8 mmol, 4.50 mL, 30% purity, 8.59 eq) at 0° C. The mixture was stirred at 25° C. for 2 h. The reaction was quenched with sodium persulfate aqueous solution and extracted with ethyl acetate. The combined organic phase was washed with brine, dried over anhydrous sodium sulfate and then filtered. The filtration was concentrated in vacuum to afford 2-(tert-butyl)-6-methylisonicotinamide. $^1$H NMR (400 MHz, CDCl$_3$) δ=7.47 (s, 1H), 7.25 (d, J=1.1 Hz, 1H), 6.34-5.99 (m, 2H), 2.59 (s, 3H), 1.37 (s, 9H).

Step 3: To a solution of 2-(tert-butyl)-6-methylisonicotinamide (1.00 g, 5.20 mmol, 1.00 eq) and N,N-diisopropylethylamine (739 mg, 5.72 mmol, 997 uL, 1.10 eq) in Acetonitrile (20.0 mL) and water (20.0 mL) was added (diacetoxyiodo)benzene (1.84 g, 5.72 mmol, 1.10 eq). The mixture was stirred at 30° C. for 3 h. The reaction mixture was concentrated under reduced pressure to remove Acetonitrile. The aqueous phase was added saturated sodium carbonate solution to pH=8 and extracted with ethyl acetate (3×20.0 mL). The combined organic layers were washed with brine (2×10.0 mL), dried over sodium sulfate, filtered and concentrated under reduced pressure. The residue was purified by Prep-HPLC and lyophilized to afford 2-(tert-butyl)-6-methylpyridin-4-amine. $^1$H NMR (400 MHz, DMSO-d$_6$) δ=6.33 (d, J=1.6 Hz, 1H), 6.14 (d, J=1.5 Hz, 1H), 5.72 (br s, 2H), 2.21 (s, 3H), 1.21 (s, 9H).

Step 4: To a solution of 2-(tert-butyl)-6-methylpyridin-4-amine (0.100 g, 609 umol, 1.00 eq) and pyridine (241 mg, 3.04 mmol, 246 uL, 5.00 eq) in Acetonitrile (3.00 mL) was added phenyl carbonochloridate (143 mg, 913 umol, 114 uL, 1.50 eq) at 0° C. The mixture was stirred at 25° C. for 12 h. The mixture was concentrated in vacuum. The residue was purified by prep-HPLC and lyophilized to afford phenyl (2-(tert-butyl)-6-methylpyridin-4-yl)carbamate. $^1$H NMR (400 MHz, DMSO-d$_6$) δ=10.49 (br s, 1H), 7.48-7.41 (m, 2H), 7.39 (s, 1H), 7.31-7.26 (m, 1H), 7.25-7.21 (m, 2H), 7.16 (s, 1H), 2.40 (s, 3H), 1.26 (s, 9H).

Step 5: To a solution of 3-(6-(hydroxymethyl)-1-oxoisoindolin-2-yl)piperidine-2,6-dione VIII (48.0 mg, 175 umol, 1.00 eq) and phenyl (2-(tert-butyl)-6-methylpyridin-4-yl) carbamate (59.7 mg, 210 umol, 1.20 eq) in dimethyl formamide (2.00 mL) was added sodium hydride (10.5 mg, 263 umol, 60% purity, 1.50 eq) at 0° C. The mixture was stirred at 0° C. for 1 h. The reaction was quenched by acetic acid (0.500 mL) slowly and then filtered and concentrated in vacuum. The residue was purified by prep-HPLC and lyophilized to afford (2-(2,6-dioxopiperidin-3-yl)-3-oxoisoindolin-5-yl)methyl(2-(tert-butyl)-6-methylpyridin-4-yl)carbamate 118. $^1$H NMR (400 MHz, DMSO-d$_6$) δ=10.99 (s, 1H), 10.07 (s, 1H), 8.15 (s, 1H), 7.80 (s, 1H), 7.71-7.66 (m, 1H), 7.66-7.61 (m, 1H), 7.31 (d, J=1.3 Hz, 1H), 7.15 (d, J=1.5 Hz, 1H), 5.29 (s, 2H), 5.13 (dd, J=5.1, 13.3 Hz, 1H), 4.51-4.42 (m, 1H), 4.39-4.30 (m, 1H), 2.91 (ddd, J=5.4, 13.5, 17.5 Hz, 1H), 2.60 (br d, J=17.6 Hz, 1H), 2.46-2.39 (m, 1H), 2.37 (s, 3H), 2.07-1.97 (m, 1H), 1.25 (s, 9H). MS (ESI) m/z 465.2 [M+H]+

Compound 119:

Step 1: To a solution of 1,4-dichloro-2-methylbenzene (5.00 g, 31.0 mmol, 1.00 eq) in sulfuric acid (7.00 mL) and acetic acid (3.00 mL) was added a mixture of nitric acid (3.08 g, 34.2 mmol, 2.20 mL, 70% purity, 1.10 eq) and sulfuric acid (4.05 g, 40.4 mmol, 2.20 mL, 98% purity, 1.30 eq) dropwise over 10 min. The mixture was warmed slowly to 10° C. and stirred for 2 h. The reaction was poured into ice water slowly and extracted with ethyl acetate. The combined organic layer was washed with brine and dried over anhydrous sodium sulfate, filtered and concentrated to give 1,4-dichloro-2-methyl-5-nitrobenzene. $^1$H NMR (400 MHz, DMSO-d$_6$) δ=8.23 (s, 1H), 7.84 (s, 1H), 2.41 (s, 3H).

Step 2: A mixture of 1,4-dichloro-2-methyl-5-nitrobenzene (3.00 g, 14.6 mmol, 1.00 eq), iron powder (2.44 g, 43.7 mmol, 3.00 eq) and ammonium chloride (3.89 g, 72.8 mmol, 5.00 eq) in water (10.0 mL) and methanol (30.0 mL) was stirred at 80° C. for 2 h. The mixture was filtered and the filtrate was concentrated under reduced pressure. The residue was diluted with sodium hydrogencarbonate and extracted with ethyl acetate. The organic layer was dried over anhydrous sodium sulfate, filtered and concentrated in vacuum to give 2,5-dichloro-4-methylaniline. $^1$H NMR (400 MHz, DMSO-d$_6$) δ=7.18 (s, 1H), 6.84 (s, 1H), 5.39 (br s, 2H), 2.15 (s, 3H). MS (ESI) m/z 176.1 [M+H]+

Step 3: To a solution of 2,5-dichloro-4-methylaniline (1.00 g, 5.68 mmol, 1.00 eq) and pyridine (1.35 g, 17.0 mmol, 1.38 mL, 3.00 eq) in Acetonitrile (10.0 mL) was added phenyl carbonochloridate (978 mg, 6.25 mmol, 783 uL, 1.10 eq) dropwise at 0° C. The mixture was stirred at 20° C. for 2 h. The mixture was concentrated in vacuum to give crude product. The crude product was purified by reversed-phase HPLC and lyophilized to give phenyl (2,5-dichloro-4-methylphenyl)carbamate. MS (ESI) m/z 296.0 [M+H]+

Step 4: To a solution of 3-(6-(hydroxymethyl)-1-oxoisoindolin-2-yl)piperidine-2,6-dione VIII (80.0 mg, 292 umol, 1.00 eq) and phenyl (2,5-dichloro-4-methylphenyl)carbamate (95.0 mg, 321 umol, 1.10 eq) in dimethyl formamide (1.00 mL) was added sodium hydride (23.3 mg, 583 umol, 60% purity, 2.00 eq) in portions at 0° C. The mixture was stirred at 20° C. for 1 h. The mixture was quenched with 1M hydrochloric acid (1.00 mL), purified by prep-HPLC and the desired fraction was lyophilized to give (2-(2,6-dioxopiperidin-3-yl)-3-oxoisoindolin-5-yl)methyl(2,5-dichloro-4-methylphenyl)carbamate 119. $^1$H NMR (400 MHz, DMSO-d$_6$) δ=11.00 (s, 1H), 9.38 (s, 1H), 7.82 (s, 1H), 7.73-7.59 (m, 3H), 7.53 (s, 1H), 5.28 (s, 2H), 5.14 (dd, J=5.1, 13.3 Hz, 1H), 4.53-4.44 (m, 1H), 4.39-4.31 (m, 1H), 2.99-2.86 (m, 1H), 2.61 (br d, J=17.4 Hz, 1H), 2.41 (dt, J=8.9, 13.2 Hz, 1H), 2.30 (s, 3H), 2.06-1.98 (m, 1H). MS (ESI) m/z 476.1 [M+H]+

Compound 120:

To a solution of 3-(tert-butyl)bicyclo[1.1.1]pentane-1-carboxylic acid (25.0 mg, 148 umol, 1.00 eq) in dioxane (2.00 mL) was added triethylamine (45.4 mg, 449 umol, 62.5 uL, 3.02 eq) and (79.3 mg, 288 umol, 62.5 uL, 1.94 eq) at 20° C. The mixture was stirred at 20° C. for 1 h. Then 3-(6-(hydroxymethyl)-1-oxoisoindolin-2-yl)piperidine-2,6-dione VIII (45.0 mg, 164 umol, 1.10 eq) was added. The mixture was stirred at 100° C. for 2 h under nitrogen atmosphere. The mixture was concentrated under reduced pressure. The residue was purified by Prep-HPLC and the desired fraction was collected and lyophilized to give (2-(2,6-dioxopiperidin-3-yl)-3-oxoisoindolin-5-yl)methyl (3-(tert-butyl) bicyclo[1.1.1]pentan-1-yl)carbamate 120. $^1$H NMR (400 MHz, DMSO-d$_6$) δ=10.98 (br s, 1H), 7.93 (br s, 1H), 7.71 (s, 1H), 7.61 (s, 2H), 5.23-5.02 (m, 3H), 4.51-4.41 (m, 1H), 4.38-4.29 (m, 1H), 2.98-2.86 (m, 1H), 2.65-2.58 (m, 1H), 2.41 (br dd, J=4.4, 13.2 Hz, 1H), 2.06-1.97 (m, 1H), 1.71 (s, 6H), 0.84 (s, 9H). MS (ESI) m/z 440.2 [M+H]+

Compound 121:

Step 1: To a solution of 2-(2,6-dioxo-1-((2-(trimethylsilyl)ethoxy)methyl)piperidin-3-yl)-3-oxoisoindoline-5-carbaldehyde (1.00 g, 2.48 mmol, 1.00 eq) in dichloromethane (10.0 mL) at −78° C. was added methyl magnesium bromide (3.00 M in diethyl ether, 1.24 mL, 1.50 eq) drop-wise over 5 min under nitrogen atmosphere. Then the mixture was stirred at 0° C. for 3 h. The reaction was quenched with saturated ammonium chloride aqueous solution (10.0 mL). The reaction mixture was diluted with water (100 mL) and extracted with ethyl acetate (100 mL). The organic layer was washed with brine (50 mL), dried over anhydrous sodium sulfate, filtered and concentrated under reduced pressure to give a residue. The residue was purified by column chromatography to afford 3-(6-(1-hydroxyethyl)-1-oxoisoindolin-2-yl)-1-((2-(trimethylsilyl)ethoxy)methyl)piperidine-2,6-dione. $^1$H NMR (400 MHz, DMSO-d$_6$) δ=7.71 (s, 1H), 7.64-7.58 (m, 1H), 7.57-7.50 (m, 1H), 5.31 (d, J=4.5 Hz, 1H), 5.26-5.20 (m, 1H), 5.10-5.00 (m, 2H), 4.88-4.81 (m, 1H), 4.45 (br d, J=17.1 Hz, 1H), 4.31-4.22 (m, 1H), 3.59-3.47 (m, 2H), 3.13-2.99 (m, 1H), 2.85-2.73 (m, 1H), 2.46-2.31 (m, 1H), 1.35 (d, J=6.5 Hz, 3H), 0.87-0.81 (m, 2H), −0.01-−0.07 (m, 9H).

Step 2: A mixture of 3-(6-(1-hydroxyethyl)-1-oxoisoindolin-2-yl)-1-((2-(trimethylsilyl)ethoxy)methyl)piperidine-2,6-dione (700 mg, 1.67 mmol, 1.00 eq) in hydrochloric acid/dioxane (4.00 M, 20.0 mL, 47.8 eq) was stirred at 25° C. for 3 h. The mixture was concentrated under reduced pressure to afford 3-(6-(1-hydroxyethyl)-1-oxoisoindolin-2-yl)-1-(hydroxymethyl)piperidine-2,6-dione.

Step 3: A mixture of 3-(6-(1-hydroxyethyl)-1-oxoisoindolin-2-yl)piperidine-2,6-dione (500 mg, 1.57 mmol, 1.00 eq) and ammonium hydroxide (91.0 mg, 649 umol, 0.100 mL, 25% purity) in Acetonitrile (5.00 mL) was stirred at 25° C. for 5 h. The pH of the mixture was adjusted to 3-4 with hydrochloric acid (1 M). The mixture was concentrated under reduced pressure to give a residue, which was purified by reversed phase column chromatography and lyophilized to afford 3-(6-(1-hydroxyethyl)-1-oxoisoindolin-2-yl) piperidine-2,6-dione. $^1$H NMR (400 MHz, DMSO-d$_6$) δ=10.98 (s, 1H), 7.75 (br s, 1H), 7.64-7.58 (m, 1H), 7.57-7.50 (m, 1H), 5.30 (br d, J=3.5 Hz, 1H), 5.15-4.99 (m, 1H), 4.84 (br d, J=5.1 Hz, 1H), 4.50-4.38 (m, 1H), 4.34-4.23 (m, 1H), 3.12-2.85 (m, 1H), 2.60 (br d, J=17.4 Hz, 1H), 2.47-2.30 (m, 1H), 2.01 (br d, J=6.1 Hz, 1H), 1.35 (br d, J=6.4 Hz, 3H).

Step 4: A mixture of 3-(trifluoromethoxy) aniline (500 mg, 2.82 mmol, 376 uL, 1.00 eq), pyridine (670 mg, 8.47 mmol, 684 uL, 3.00 eq) and phenyl carbonochloridate (663 mg, 4.23 mmol, 530 uL, 1.50 eq) in Acetonitrile (5.00 mL) was stirred at 25° C. for 12 h. The mixture was concentrated under reduced pressure to give a residue. The residue was purified by reversed phase column chromatography (C18; condition: water/Acetonitrile=1/0 to 0/1, 0.1% Formic acid) and lyophilized to afford phenyl (3-(trifluoromethoxy)phenyl)carbamate (680 mg, 2.29 mmol, 81% yield) as colorless oil. MS (ESI) m/z 298.1 [M+H]+

Step 5: To a mixture of 3-(6-(1-hydroxyethyl)-1-oxoisoindolin-2-yl)piperidine-2,6-dione (85.0 mg, 295 umol, 1.00 eq) and phenyl (3-(trifluoromethoxy)phenyl)carbamate (105 mg, 354 umol, 1.20 eq) in dimethyl formamide (2.00 mL) was added sodium hydride (23.6 mg, 590 umol, 60% purity, 2.00 eq) under nitrogen atmosphere and the mixture was stirred at 0° C. for 3 h. The mixture was quenched with hydrochloric acid (1 M) and filtered. The filtrate was purified by Prep-HPLC and lyophilized to afford 1-(2-(2,6-dioxopiperidin-3-yl)-3-oxoisoindolin-5-yl)ethyl(3-(trifluoromethoxy)phenyl)carbamate 121. $^1$H NMR (400 MHz, DMSO-d$_6$) δ=10.99 (s, 1H), 10.14 (s, 1H), 8.47 (s, 1H), 7.78 (s, 1H), 7.70-7.65 (m, 1H), 7.65-7.60 (m, 1H), 7.56 (s, 1H), 7.42-7.37 (m, 2H), 6.96 (br d, J=3.8 Hz, 1H), 5.97-5.89 (m, 1H), 5.16-5.09 (m, 1H), 4.50-4.42 (m, 1H), 4.37-4.29 (m, 1H), 2.97-2.85 (m, 1H), 2.65-2.56 (m, 1H), 2.46-2.34 (m, 1H), 2.01-1.99 (m, 1H), 1.58 (d, J=6.8 Hz, 3H). MS (ESI) m/z 492.1 [M+H]$^+$ Compound 122:

Step 1: To a solution of 2,4-dimethyl-6-nitroaniline (5.00 g, 30.1 mmol, 1.00 eq) in tetrahydrofuran (50.0 mL) was added nitrosonium tetrafluoroborate (5.27 g, 45.1 mmol, 1.50 eq) in portions at −5° C. After the mixture was stirred at −5° C. for 0.5 h, the mixture was filtered. The filter cake was washed with tetrahydrofuran (20.0 mL) then dissolved in 1,2-dichlorobenzene (50.0 mL) and heated at 170° C. for 1 h. The mixture was filtered and the filtrate was concentrated to give crude product. The crude product was purified by silica gel chromatography to give 2-fluoro-1,5-dimethyl-3-nitrobenzene. $^1$H NMR (400 MHz, DMSO-d$_6$) δ=7.79-7.74 (m, 1H), 7.55-7.50 (m, 1H), 2.33 (s, 3H), 2.29 (d, J=2.3 Hz, 3H).

Step 2: To a mixture of 2-fluoro-1,5-dimethyl-3-nitrobenzene (1.00 g, 5.91 mmol, 1.00 eq) in tetrahydrofuran (10.0 mL) was added Pd/C (200 mg, 10% purity) under nitrogen. The suspension was degassed under vacuum and purged with hydrogen several times. The mixture was stirred at 20° C. for 2 h under hydrogen (15 psi). The mixture was filtered and the filtrate was concentrated to give crude product then purified by reversed-phase HPLC to give 2-fluoro-3,5-dimethylaniline. $^1$H NMR (400 MHz, DMSO-d$_6$) δ=6.38 (dd, J=1.8, 8.3 Hz, 1H), 6.25-6.10 (m, 1H), 4.88 (s, 2H), 2.10 (s, 6H). MS (ESI) m/z 140.1 [M+H]

Step 3: To a solution of 2-fluoro-3,5-dimethylaniline (150 mg, 1.08 mmol, 1.00 eq) and pyridine (426 mg, 5.39 mmol, 435 uL, 5.00 eq) in Acetonitrile (2.00 mL) was added phenyl carbonochloridate (202 mg, 1.29 mmol, 162 uL, 1.20 eq) dropwise at 0° C. The mixture was stirred at 25° C. for 2 h. The mixture was concentrated to give crude product then purified reversed-phase HPLC to give phenyl (2-fluoro-3,5-dimethylphenyl). MS (ESI) m/z 260.1 [M+H]

Step 4: To a solution of 3-(6-(hydroxymethyl)-1-oxoisoindolin-2-yl)piperidine-2,6-dione VIII (80.0 mg, 292 umol, 1.00 eq) and phenyl (2-fluoro-3,5-dimethylphenyl)carbamate (83.2 mg, 321 umol, 1.10 eq) in dimethyl formamide (1.00 mL) was added sodium hydride (23.3 mg, 583 umol, 60% purity, 2.00 eq) in portions at 0° C. The mixture was stirred at 20° C. for 1 h. The mixture was quenched by 1M hydrochloric acid (1 mL) then filtered, the filtrate was purified by prep-HPLC and lyophilized to give (2-(2,6-dioxopiperidin-3-yl)-3-oxoisoindolin-5-yl)methyl (2-fluoro-3,5-dimethylphenyl)carbamate 122. $^1$H NMR (400 MHz, DMSO-d$_6$) δ=11.00 (s, 1H), 9.38 (br s, 1H), 7.80 (s, 1H), 7.72-7.59 (m, 2H), 7.28 (br d, J=6.1 Hz, 1H), 6.82 (br d, J=5.6 Hz, 1H), 5.26 (s, 2H), 5.14 (dd, J=5.0, 13.3 Hz, 1H), 4.55-4.42 (m, 1H), 4.39-4.27 (m, 1H), 2.99-2.85 (m, 1H), 2.61 (br d, J=18.1 Hz, 1H), 2.41 (dt, J=8.8, 13.1 Hz, 1H), 2.22 (s, 3H), 2.19 (d, J=1.8 Hz, 3H), 2.06-1.98 (m, 1H). MS (ESI) m/z 440.1 [M+H]$^+$ Compound 123:

Step 1: A mixture of 1-chloro-2,4-dimethyl-5-nitrobenzene (1.00 g, 5.39 mmol, 1.00 eq), iron powder (903 mg, 16.2 mmol, 3.00 eq) and ammonium chloride (1.44 g, 26.9 mmol, 5.00 eq) in water (3.00 mL) and methanol (10.0 mL) was stirred at 80° C. for 2 h. The mixture was filtered and the filtrate was concentrated under reduced pressure. The mixture was diluted with sodium hydrogen carbonate and extracted with ethyl acetate. The organic layer was dried over sodium sulfate, filtered and concentrated in vacuum to give 5-chloro-2,4-dimethylaniline. $^1$H NMR (400 MHz, DMSO-d$_6$) δ=6.85 (s, 1H), 6.64 (s, 1H), 4.89 (br s, 2H), 2.12 (s, 3H), 1.99 (s, 3H). MS (ESI) m/z 156.2 [M+H]

Step 2: To a solution of 5-chloro-2,4-dimethylaniline (400 mg, 2.57 mmol, 1.00 eq) and pyridine (610 mg, 7.71 mmol, 622 uL, 3.00 eq) in Acetonitrile (5.00 mL) was added phenyl carbonochloridate (604 mg, 3.86 mmol, 483 uL, 1.50 eq) dropwise at 0° C. The mixture was then stirred at 25° C. for 12 h. The mixture was concentrated in vacuum to give crude product. The crude product was purified by reversed-phase HPLC and lyophilized to give phenyl (5-chloro-2,4-dimethylphenyl)carbamate. MS (ESI) m/z 276.1 [M+H]

Step 3: To a solution of 3-(6-(hydroxymethyl)-1-oxoisoindolin-2-yl)piperidine-2,6-dione VIII (80.0 mg, 292 umol, 1.00 eq) and phenyl (5-chloro-2,4-dimethylphenyl)carbamate (88.5 mg, 321 umol, 1.10 eq) in dimethyl formamide (1.00 mL) was added sodium hydride (23.3 mg, 583 umol, 60% purity, 2.00 eq) at 0° C. The mixture was stirred at 20° C. for 1 h. The mixture was quenched by 1M hydrochloric acid (1.00 mL) then purified by prep-HPLC and lyophilized to give (2-(2,6-dioxopiperidin-3-yl)-3-oxoisoindolin-5-yl)methyl (5-chloro-2,4-dimethylphenyl)carbamate 123. $^1$H NMR (400 MHz, DMSO-d$_6$) δ=11.00 (s, 1H), 9.11 (s, 1H), 7.80 (s, 1H), 7.72-7.60 (m, 2H), 7.46 (s, 1H), 7.17 (s, 1H), 5.27 (s, 2H), 5.13 (dd, J=5.1, 13.4 Hz, 1H), 4.53-4.43 (m, 1H), 4.41-4.29 (m, 1H), 3.00-2.84 (m, 1H), 2.61 (br d, J=16.8 Hz, 1H), 2.46-2.36 (m, 1H), 2.26 (s, 3H), 2.16 (s, 3H), 2.06-1.97 (m, 1H). MS (ESI) m/z 456.1 [M+H]$^+$ Compound 124:

Step 1: To a mixture of 4-fluoro-3,5-dimethylaniline (500 mg, 3.59 mmol, 1.00 eq) and pyridine (853 mg, 10.8 mmol, 870 uL, 3.00 eq) in Acetonitrile (5.00 mL) was added phenyl carbonochloridate (731 mg, 4.67 mmol, 585 uL, 1.30 eq) dropwise. The mixture was stirred at 15° C. for 12 h. The mixture was concentrated to give crude product. The crude product was purified by reversed-phase column and the desired fraction was collected and lyophilized to give phenyl (4-fluoro-3,5-dimethylphenyl)carbamate. $^1$H NMR (400 MHz, DMSO-d$_6$) δ=10.09 (br s, 1H), 7.48-7.43 (m, 2H), 7.41-7.36 (m, 3H), 7.20 (br d, J=7.6 Hz, 2H), 2.18 (d, J=2.0 Hz, 6H).

Step 2: To a mixture of phenyl (4-fluoro-3,5-dimethylphenyl)carbamate (113 mg, 438 umol, 1.20 eq) and 3-(6-(hydroxymethyl)-1-oxoisoindolin-2-yl)piperidine-2,6-dione VIII (100 mg, 365 umol, 1.00 eq) in dimethyl formamide (2.00 mL) was added sodium hydride (21.9 mg, 547 umol, 60% purity, 1.50 eq) in portions at 0° C. The mixture was stirred at 15° C. for 1 h. The mixture was quenched with 1 M hydrochloric and filtered. The filtrate was purified by prep-HPLC and lyophilized to give (2-(2,6-dioxopiperidin-3-yl)-3-oxoisoindolin-5-yl)methyl (4-fluoro-3,5-dimethylphenyl)carbamate 124. $^1$H NMR (400 MHz, DMSO-d$_6$) δ=10.99 (br s, 1H), 9.68 (br s, 1H), 7.79 (s, 1H), 7.70-7.62 (m, 2H), 7.17 (br d, J=6.4 Hz, 2H), 5.26 (s, 2H), 5.13 (dd, J=5.2, 13.2 Hz, 1H), 4.53-4.43 (m, 1H), 4.40-4.30 (m, 1H), 3.00-2.85 (m, 1H), 2.65-2.58 (m, 1H), 2.46-2.36 (m, 1H), 2.17 (d, J=1.6 Hz, 6H), 2.06-1.98 (m, 1H). MS (ESI) m/z 440.1 [M+H]$^+$ Compound 125:
Step 1: To a mixture of 2-chloro-5-(trifluoromethoxy) aniline (500 mg, 2.36 mmol, 1.00 eq) and pyridine (561 mg, 7.09 mmol, 572 uL, 3.00 eq) in Acetonitrile (5.00 mL) was added phenyl carbonochloridate (481 mg, 3.07 mmol, 385 uL, 1.30 eq) dropwise. The mixture was stirred at 15° C. for 2 h. The mixture was concentrated to give crude product. The crude product was purified by reversed-phase column and the desired fraction was collected and lyophilized to give phenyl (2-chloro-5-(trifluoromethoxy)phenyl)carbamate. $^1$H NMR (400 MHz, DMSO-$d_6$) δ=9.95 (s, 1H), 7.78 (d, J=2.3 Hz, 1H), 7.66 (d, J=8.9 Hz, 1H), 7.50-7.39 (m, 2H), 7.33-7.19 (m, 4H).

Step 2: To a mixture of phenyl (2-chloro-5-(trifluoromethoxy)phenyl)carbamate (116 mg, 350 umol, 1.20 eq) and 3-(6-(hydroxymethyl)-1-oxoisoindolin-2-yl)piperidine-2,6-dione VIII (80.0 mg, 292 umol, 1.00 eq) in dimethyl formamide (2.00 mL) was added sodium hydride (17.5 mg, 438 umol, 60% purity, 1.50 eq) in one portion at 0° C. The mixture was stirred at 15° C. for 1 h. The mixture was quenched with 1 M hydrochloric and filtered. The filtrate was purified by prep-HPLC and lyophilized to give (2-(2,6-dioxopiperidin-3-yl)-3-oxoisoindolin-5-yl)methyl(2-chloro-5-(trifluoromethoxy)phenyl)carbamate 125. $^1$H NMR (400 MHz, DMSO-$d_6$) δ=10.99 (s, 1H), 9.53 (s, 1H), 7.83 (s, 1H), 7.75 (d, J=2.2 Hz, 1H), 7.72-7.66 (m, 1H), 7.66-7.59 (m, 2H), 7.20 (dd, J=2.4, 8.6 Hz, 1H), 5.31 (s, 2H), 5.13 (dd, J=5.1, 13.3 Hz, 1H), 4.53-4.42 (m, 1H), 4.40-4.30 (m, 1H), 2.97-2.86 (m, 1H), 2.60 (br d, J=17.9 Hz, 1H), 2.46-2.35 (m, 1H), 2.06-1.98 (m, 1H). MS (ESI) m/z 512.1 [M+H]$^+$ Compound 126:
To a solution of 3-phenylbicyclo[1.1.1]pentane-1-carboxylic acid (10.0 mg, 53.1 umol, 1.00 eq) in dioxane (2.00 mL) was added triethylamine (18.1 mg, 179 umol, 25.0 uL, 3.38 eq) and diphenylphosphoryl azide (25.4 mg, 92.3 umol, 20.0 uL, 1.74 eq) at 20° C. The mixture was stirred at 20° C. for 1 h. Then 3-(6-(hydroxymethyl)-1-oxoisoindolin-2-yl)piperidine-2,6-dione VIII (15.0 mg, 54.6 umol, 1.03 eq) was added. The mixture was stirred at 100° C. for 2 h. The mixture was concentrated under reduced pressure. The residue was purified by Prep-HPLC and the desired fraction was collected and lyophilized to give (2-(2,6-dioxopiperidin-3-yl)-3-oxoisoindolin-5-yl)methyl (3-phenylbicyclo[1.1.1]pentan-1-yl carbamate 126. $^1$H NMR (400 MHz, DMSO-$d_6$) δ=10.89 (brs, 1H), 8.11 (brs, 1H), 7.73 (s, 1H), 7.63 (s, 2H), 7.34-7.27 (m, 2H), 7.23 (br d, J=6.5 Hz, 3H), 5.22-5.07 (m, 3H), 4.50-4.42 (m, 1H), 4.39-4.30 (m, 1H), 2.98-2.86 (m, 1H), 2.64-2.59 (m, 1H), 2.41 (br dd, J=4.3, 13.1 Hz, 1H), 2.20 (s, 6H), 2.06-1.98 (m, 1H). MS (ESI) m/z 460.2 [M+H]$^+$ Compound 127:
Step 2: To a solution of 1,3-difluoro-2-methyl-5-nitrobenzene (500 mg, 2.89 mmol, 1.00 eq) in tetrahydrofuran (5.00 mL) was added palladium on carbon (80.0 mg, 10% purity). The mixture was stirred under hydrogen at 25° C. for 3 h. The mixture was filtered, and the filtrate was concentrated under reduced pressure to afford 3,5-difluoro-4-methylaniline. $^1$H NMR (400 MHz, DMSO-$d_6$) δ=6.16 (d, J=10.0 Hz, 2H), 5.45 (s, 2H), 2.55-2.46 (m, 3H).

Step 2: To a solution of 3,5-difluoro-4-methylaniline (180 mg, 1.26 mmol, 1.00 eq) in Acetonitrile (3.00 mL) was added pyridine (298 mg, 3.77 mmol, 304 uL, 3.00 eq) and phenyl carbonochloridate (236 mg, 1.51 mmol, 189 uL, 1.20 eq). The mixture was stirred at 25° C. for 3 h. The reaction mixture was concentrated under reduced pressure to afford a residue. The residue was diluted with water (40.0 mL) and extracted with ethyl acetate (3×20.0 mL). The organic layer was washed with brine, dried over anhydrous sodium sulfate, filtered and concentrated under reduced pressure to afford a residue. The residue was purified by Reversed-Phase Flash and the desired eluent was lyophilized to afford phenyl (3,5-difluoro-4-methylphenyl)carbamate. $^1$H NMR (400 MHz, DMSO-$d_6$) δ=10.54 (br s, 1H), 7.51-7.38 (m, 2H), 7.33-7.10 (m, 5H), 2.09 (s, 3H). MS (ESI) m/z 264.1 [M+H]$^+$ Step 3: To a solution of phenyl (3,5-difluoro-4-methylphenyl) carbamate (107 mg, 408 umol, 1.40 eq) and 3-(6-(hydroxymethyl)-1-oxoisoindolin-2-yl)piperidine-2,6-dione VIII (80.0 mg, 291 umol, 1.00 eq) in dimethyl formamide (1.00 mL) was added sodium hydride (23.3 mg, 583 umol, 60% purity, 2.00 eq). The mixture was stirred at 25° C. for 1 h. The pH of the mixture was adjusted to 7 with 1M hydrochloric acid, then the mixture was diluted with dimethyl formamide (1.00 mL). The mixture was purified by Prep-HPLC and lyophilized in vacuo to afford (2-(2,6-dioxopiperidin-3-yl)-3-oxoisoindolin-5-yl)methyl (3,5-difluoro-4-methylphenyl)carbamate 127. $^1$H NMR (400 MHz, DMSO-$d_6$) δ=11.00 (s, 1H), 10.14 (s, 1H), 7.79 (s, 1H), 7.73-7.58 (m, 2H), 7.26-7.06 (m, 2H), 5.28 (s, 2H), 5.13 (dd, J=5.2, 13.2 Hz, 1H), 4.51-4.42 (m, 1H), 4.39-4.30 (m, 1H), 2.97-2.85 (m, 1H), 2.63-2.56 (m, 1H), 2.40 (br dd, J=4.4, 13.2 Hz, 1H), 2.09-2.04 (m, 3H), 2.04-1.97 (m, 1H). MS (ESI) m/z 444.2 [M+H]$^+$ Compound 128:
Step 1: To a mixture of 2-methyl-5-(trifluoromethoxy) aniline (500 mg, 2.62 mmol, 1.00 eq) and pyridine (621 mg, 7.85 mmol, 633 uL, 3.00 eq) in Acetonitrile (5.00 mL) was added phenyl carbonochloridate (614 mg, 3.92 mmol, 491 uL, 1.50 eq) dropwise at 0° C. The mixture was stirred at 25° C. for 12 h. The mixture was concentrated in vacuum to give crude product. The crude product was purified by reversed-phase HPLC and lyophilized to give phenyl (2-methyl-5-(trifluoromethoxy)phenyl)carbamate. MS (ESI) m/z 312.0 [M+H]$^+$ Step 2: To a solution of 3-(6-(hydroxymethyl)-1-oxoisoindolin-2-yl)piperidine-2,6-dione VIII (100 mg, 365 umol, 1.00 eq) and phenyl (2-methyl-5-(trifluoromethoxy)phenyl) carbamate (136 mg, 438 umol, 1.20 eq) in dimethyl formamide (1.00 mL) was added sodium hydride (29.2 mg, 729 umol, 60% purity, 2.00 eq) at 0° C. The mixture was stirred at 20° C. for 1 h. The mixture was quenched by 1M hydrochloric acid (2.00 mL) and filtered. The filtrate was purified by prep-HPLC and lyophilized to give (2-(2,6-dioxopiperidin-3-yl)-3-oxoisoindolin-5-yl)methyl(2-methyl-5-(trifluoromethoxy)phenyl)carbamate 128. $^1$H NMR (400 MHz, DMSO-$d_6$) δ=11.00 (s, 1H), 9.24 (s, 1H), 7.82 (s, 1H), 7.72-7.68 (m, 1H), 7.67-7.62 (m, 1H), 7.52 (br s, 1H), 7.31 (d, J=8.4 Hz, 1H), 7.04 (dd, J=1.3, 8.3 Hz, 1H), 5.29 (s, 2H), 5.14 (dd, J=5.1, 13.4 Hz, 1H), 4.53-4.44 (m, 1H), 4.39-4.31 (m, 1H), 2.98-2.86 (m, 1H), 2.61 (br d, J=17.6 Hz, 1H), 2.47-2.36 (m, 1H), 2.24 (s, 3H), 2.07-1.97 (m, 1H). MS (ESI) m/z 492.1 [M+H]$^+$ Compound 129:
Step 1: To a mixture of 3,4-dimethylaniline (500 mg, 4.13 mmol, 1.00 eq) and pyridine (979 mg, 12.4 mmol, 999 uL, 3.00 eq) in Acetonitrile (5.00 mL) was added phenyl carbonochloridate (969 mg, 6.19 mmol, 775 uL, 1.50 eq) dropwise. The mixture was stirred at 15° C. for 2 h. The mixture was concentrated to give crude product. The crude product was purified by reversed-phase HPLC. The desired fraction was collected and lyophilized to give phenyl (3,4-dimethylphenyl)carbamate. $^1$H NMR (400 MHz, DMSO-$d_6$)

δ=10.05 (br s, 1H), 7.44-7.40 (m, 2H), 7.31-7.19 (m, 5H), 7.07 (d, J=8.1 Hz, 1H), 2.18 (d, J=8.7 Hz, 6H).

Step 2: To a mixture of phenyl (3,4-dimethylphenyl) carbamate (84.5 mg, 350 umol, 1.20 eq) and 3-(6-(hydroxymethyl)-1-oxoisoindolin-2-yl)piperidine-2,6-dione VIII (80.0 mg, 292 umol, 1.00 eq) in dimethyl formamide (2.00 mL) was added sodium hydride (17.5 mg, 438 umol, 60% purity, 1.50 eq) in portions at 0° C. The mixture was stirred at 15° C. for 2 h. The mixture was quenched with 1 M hydrochloric and filtered. The filtrate was purified by prep-HPLC and lyophilized to give (2-(2,6-dioxopiperidin-3-yl)-3-oxoisoindolin-5-yl)methyl(3,4-dimethylphenyl)carbamate 129. $^1$H NMR (400 MHz, DMSO-d$_6$) δ=10.99 (s, 1H), 9.61 (br s, 1H), 7.78 (s, 1H), 7.70-7.60 (m, 2H), 7.24 (s, 1H), 7.18 (br d, J=8.3 Hz, 1H), 7.02 (d, J=8.2 Hz, 1H), 5.25 (s, 2H), 5.12 (dd, J=5.0, 13.2 Hz, 1H), 4.51-4.43 (m, 1H), 4.38-4.30 (m, 1H), 2.97-2.86 (m, 1H), 2.60 (br d, J=17.6 Hz, 1H), 2.44-2.34 (m, 1H), 2.15 (d, J=9.0 Hz, 6H), 2.06-1.96 (m, 1H). MS (ESI) m/z 422.1 [M+H]$^+$ Compound 130:

Step 1: To a solution of 2-aminopropane-1,3-diol (10.0 g, 110 mmol, 1.00 eq) in ethyl alcohol (90.0 mL) was added triethylamine (16.7 g, 165 mmol, 23.0 mL, 1.51 eq) and benzyl carbonochloridate (56.2 g, 329 mmol, 46.8 mL, 3.00 eq) at 0° C. The mixture was stirred at 25° C. for 1 h. The mixture was filtered to give filtrate solution that was concentrated to give a residue. The residue was purified by column chromatography on silica gel. The desired fraction was collected and concentrated to give benzyl (1,3-dihydroxypropan-2-yl)carbamate. $^1$H NMR (400 MHz, DMSO-d$_6$) δ=7.41-7.28 (m, 5H), 6.87 (br d, J=7.8 Hz, 1H), 5.01 (s, 2H), 4.58 (t, J=5.4 Hz, 2H), 3.50-3.36 (m, 5H).

Step 2: To a solution of benzyl (1,3-dihydroxypropan-2-yl)carbamate (3.00 g, 13.3 mmol, 1.00 eq) in toluene (40.0 mL) was added benzaldehyde (2.83 g, 26.6 mmol, 2.69 mL, 2.00 eq) and p-toluenesulfonic acid (230 mg, 1.34 mmol, 0.100 eq). The mixture was refluxed under a Dean-Stark water separator for 2 h at 130° C. The mixture was concentrated to give a residue, which was purified by column chromatography on silica gel. The desired fraction was collected and concentrated to give benzyl (2-phenyl-1,3-dioxan-5-yl)carbamate. $^1$H NMR (400 MHz, CDCl$_3$) δ=7.51-7.34 (m, 10H), 5.86 (br d, J=8.4 Hz, 1H), 5.56 (s, 1H), 5.14 (s, 2H), 4.20-4.14 (m, 4H), 3.77 (br d, J=9.0 Hz, 1H).

Step 3: To a solution of benzyl (2-phenyl-1,3-dioxan-5-yl)carbamate (1.28 g, 4.08 mmol, 1.00 eq) in ethyl alcohol (10.0 mL) was added wet palladium on carbon (30.0 mg, 10% purity) under nitrogen. The mixture was stirred at 25° C. for 12 h under hydrogen (15 psi). The mixture was filtered to give filtrate that was concentrated to give 2-phenyl-1,3-dioxan-5-amine. $^1$H NMR (400 MHz, CDCl$_3$) δ=7.53-7.36 (m, 5H), 5.54 (s, 1H), 4.21-4.15 (m, 2H), 4.14-3.99 (m, 2H), 2.89-2.78 (m, 1H), 1.79 (br s, 2H). MS (ESI) m/z 180.3 [M+H]$^+$.

Step 4: To a solution of 2-phenyl-1,3-dioxan-5-amine (350 mg, 1.95 mmol, 1.00 eq) in Acetonitrile (10.0 mL) was added pyridine (463 mg, 5.86 mmol, 473 uL, 3.00 eq) and phenyl carbonochloridate (459 mg, 2.93 mmol, 367 uL, 1.50 eq) at 0° C. The mixture was stirred at 0° C. for 1 h. The mixture was filtered to give filtrate. The filtrate was purified by reversed-phase HPLC (0.1% Formic acid). The desired fraction was collected and concentrated to give phenyl (2-phenyl-1,3-dioxan-5-yl)carbamate. $^1$H NMR (400 MHz, DMSO-d$_6$) δ=8.24 (br d, J=6.5 Hz, 1H), 7.58-7.50 (m, 2H), 7.41-7.35 (m, 5H), 7.23-7.18 (m, 1H), 7.13 (br d, J=7.6 Hz, 2H), 5.60 (s, 1H), 4.12 (q, J=11.5 Hz, 4H), 3.37 (s, 1H). MS (ESI) m/z 300.1 [M+H]$^+$.

Step 5: To a solution of 3-(6-(hydroxymethyl)-1-oxoisoindolin-2-yl)piperidine-2,6-dione VIII (80.0 mg, 292 umol, 1.00 eq) in dimethyl formamide (2.00 mL) was added phenyl (2-phenyl-1,3-dioxan-5-yl)carbamate (131 mg, 438 umol, 1.50 eq) and sodium hydride (23.3 mg, 583 umol, 60% purity, 2.00 eq) at 0° C. The mixture was stirred at 0° C. for 1 h. The mixture was added hydrochloric acid (0.500 ml, 1M). The mixture was extracted with water/ethyl acetate (10.0 ml/10.0 ml). The organic layer was collected and concentrated to give a residue. The residue was purified by prep-HPLC and the desired fraction was collected and lyophilized to give (2-(2,6-dioxopiperidin-3-yl)-3-oxoisoindolin-5-yl)methyl(2-phenyl-1,3-dioxan-5-yl)carbamate 128. $^1$H NMR (400 MHz, DMSO-d$_6$) δ=10.99 (s, 1H), 7.86-7.73 (m, 2H), 7.67-7.59 (m, 2H), 7.54-7.46 (m, 2H), 7.43-7.31 (m, 3H), 5.57 (s, 1H), 5.18 (s, 2H), 5.12 (br dd, J=5.1, 13.3 Hz, 1H), 4.51-4.42 (m, 1H), 4.37-4.27 (m, 1H), 4.16-4.07 (m, 2H), 4.06-3.98 (m, 2H), 3.50 (br d, J=6.1 Hz, 1H), 3.04-2.76 (m, 1H), 2.60 (br d, J=16.8 Hz, 1H), 2.40 (br d, J=8.4 Hz, 1H), 2.04-1.97 (m, 1H). MS (ESI) m/z 480.2 [M+H]$^+$.

Compound 131:

Step 1: To a solution of 5-tert-butyl-2-chloro-pyridine (770 mg, 4.54 mmol, 1.00 eq), diphenylmethanimine (987 mg, 5.45 mmol, 914 uL, 1.20 eq), cesium carbonate (2.22 g, 6.81 mmol, 1.50 eq) and 4,5-bis(diphenylphosphino)-9,9-dimethylxanthene (525 mg, 908 umol, 0.200 eq) in dioxane (25.0 mL) was added tris(dibenzylideneacetone)dipalladium (416 mg, 454 umol, 0.100 eq). The mixture was stirred at 90° C. for 2 h. The mixture was filtered and concentrated in vacuum. The crude product was purified by reversed-phase HPLC to afford 5-(tert-butyl)-N-(diphenylmethylene)pyridin-2-amine. $^1$H NMR (400 MHz, DMSO-d$_6$) δ=8.26 (d, J=2.0 Hz, 1H), 7.83-7.81 (m, 2H), 7.70-7.63 (m, 2H), 7.60-7.54 (m, 2H), 7.33-7.28 (m, 3H), 7.16-7.10 (m, 2H), 6.58 (d, J=8.4 Hz, 1H), 1.22 (s, 9H).

Step 2: To a solution of 5-(tert-butyl)-N-(diphenylmethylene)pyridin-2-amine (720 mg, 2.29 mmol, 1.00 eq) in tetrahydrofuran (7.50 mL) and methanol (7.50 mL) was added hydrochloric acid (2.00 M, 7.20 mL, 6.29 eq). The mixture was stirred at 25° C. for 2 h. The reaction mixture was concentrated under reduced pressure to remove methanol and extracted with ethyl acetate (3×10 mL). The combined aqueous phase layers were added saturated sodium carbonate solution to pH=8 and extracted with ethyl acetate (3×20 mL). The combined organic layers were washed with brine, dried over sodium sulfate, filtered and concentrated in vacuum to afford 5-(tert-butyl)pyridin-2-amine. $^1$H NMR (400 MHz, DMSO-d$_6$) δ=7.89 (d, J=2.4 Hz, 1H), 7.40 (dd, J=2.6, 8.7 Hz, 1H), 6.38 (d, J=8.7 Hz, 1H), 5.62 (s, 2H), 1.21 (s, 9H).

Step 3: To a solution of 5-(tert-butyl)pyridin-2-amine (0.200 g, 1.33 mmol, 1.00 eq) and pyridine (316 mg, 3.99 mmol, 322 uL, 3.00 eq) in Acetonitrile (5.00 mL) was added phenyl carbonochloridate (313 mg, 2.00 mmol, 250 uL, 1.50 eq) at 0° C. The mixture was stirred at 25° C. for 12 h. The mixture was concentrated in vacuum. The crude product was purified by reversed-phase HPLC to afford phenyl (5-(tert-butyl)pyridin-2-yl)carbamate. $^1$H NMR (400 MHz, DMSO-d$_6$) δ=10.6 (s, 1H), 8.35 (d, J=2.1 Hz, 1H), 7.83 (dd, J=2.6, 8.7 Hz, 1H), 7.78-7.70 (m, 1H), 7.45-7.40 (m, 2H), 7.29-7.24 (m, 1H), 7.21 (d, J=7.7 Hz, 2H), 1.29 (s, 9H).

Step 4: To a solution of 3-(6-(hydroxymethyl)-1-oxoisoindolin-2-yl)piperidine-2,6-dione VIII (53 mg, 193 umol, 1.00 eq) and phenyl (5-(tert-butyl)pyridin-2-yl)carbamate (62.7 mg, 232 umol, 1.20 eq) in dimethyl formamide (2.00 mL) was added sodium hydride (11.6 mg, 290 umol, 60% purity, 1.50 eq) at 0° C. The mixture was stirred at 0° C. for 1 h. The reaction was quenched by acetic acid (0.500 mL) slowly and then filtered and concentrated in vacuum. The residue was purified by prep-HPLC (column: Phenomenex Synergi C18 150*25 mm*10 um; mobile phase: water (0.225% Formic acid)-Acetonitrile; B %: 19%-49%, 10 min) and lyophilized. The crude product was purified by prep-HPLC and lyophilized to afford (2-(2,6-dioxopiperidin-3-yl)-3-oxoisoindolin-5-yl)methyl (5-(tert-butyl)pyridin-2-yl)carbamate 131. $^1$H NMR (400 MHz, DMSO-$d_6$) δ=10.98 (br s, 1H), 10.25 (s, 1H), 8.29 (d, J=2.3 Hz, 1H), 7.82-7.77 (m, 2H), 7.76-7.72 (m, 1H), 7.69-7.65 (m, 1H), 7.65-7.61 (m, 1H), 5.28 (s, 2H), 5.13 (dd, J=5.1, 13.3 Hz, 1H), 4.50-4.42 (m, 1H), 4.38-4.29 (m, 1H), 2.97-2.86 (m, 1H), 2.60 (br dd, J=2.1, 15.1 Hz, 1H), 2.40 (dd, J=4.5, 13.2 Hz, 1H), 2.06-1.96 (m, 1H), 1.28 (s, 9H). MS (ESI) m/z 451.2 [M+H]$^+$ Compound 132:

Step 1: To a mixture of 1-chloro-2,3-difluoro-5-nitrobenzene (1.00 g, 5.17 mmol, 1.00 eq) and iron powder (1.44 g, 25.8 mmol, 5.00 eq) and ammonium chloride (1.38 g, 25.8 mmol, 5.00 eq) in methanol (16.0 mL) was added water (16.0 mL). The reaction mixture was stirred at 80° C. for 2 h. Then the reaction mixture was washed with methanol (80.0 mL) and then filtered. The filtrate was concentrated under reduced pressure to afford a residue. The residue was diluted with water (80.0 mL), and extracted with ethyl acetate (3×25.0 mL). Then the organic phase was washed with brine, dried over anhydrous sodium sulfate and concentrated under reduced pressure to afford 3-chloro-4,5-difluoroaniline. $^1$H NMR (400 MHz, DMSO-$d_6$) δ=6.56-6.40 (m, 2H), 5.53 (s, 2H). MS (ESI) m/z 164.0 [M+H]$^+$ Step 2: To a mixture of 3-chloro-4,5-difluoroaniline (1.00 g, 6.11 mmol, 1.00 eq) and pyridine (1.45 g, 18.3 mmol, 1.48 mL, 3.00 eq) in Acetonitrile (12.0 mL) was added phenyl carbonochloridate (1.34 g, 8.56 mmol, 1.07 mL, 1.40 eq) at 25° C. The reaction mixture was stirred at 25° C. for 12 h. The reaction mixture was concentrated under reduced pressure to afford a residue. The residue was diluted with water (80.0 mL) and extracted with ethyl acetate (3×20.0 mL). Then the organic phase was combined and concentrated under reduced pressure to afford a residue. The residue was purified by reverse phase HPLC and the desired eluent was lyophilized to afford phenyl (3-chloro-4,5-difluorophenyl)carbamate. $^1$H NMR (400 MHz, DMSO-$d_6$) δ=9.32 (br s, 1H), 7.68-7.20 (m, 5H), 6.79-6.72 (m, 2H). MS (ESI) m/z 284.1 [M+H]$^+$ Step 3: To a solution of phenyl (3-chloro-4,5-difluorophenyl)carbamate (50.7 mg, 179 umol, 1.40 eq) and 3-(6-(hydroxymethyl)-1-oxoisoindolin-2-yl)piperidine-2,6-dione VIII (35.0 mg, 128 umol, 1.00 eq) in dimethyl formamide (1.00 mL) was added sodium hydride (10.2 mg, 255 umol, 60% purity, 2.00 eq). The mixture was stirred at 25° C. for 1 h. The pH of the mixture was adjusted to 7 with hydrochloric acid (1 M) to give a solution. The solution was purified by Prep-HPLC and lyophilized to afford (2-(2,6-dioxopiperidin-3-yl)-3-oxoisoindolin-5-yl)methyl(3-chloro-4,5-difluorophenyl)carbamate 132. $^1$H NMR (400 MHz, DMSO-$d_6$) δ=10.99 (br s, 1H), 10.23 (s, 1H), 7.79 (s, 1H), 7.70-7.66 (m, 1H), 7.66-7.62 (m, 1H), 7.51 (ddd, J=2.8, 6.4, 12.4 Hz, 1H), 7.47-7.43 (m, 1H), 5.29 (s, 2H), 5.12 (dd, J=5.2, 13.2 Hz, 1H), 4.51-4.44 (m, 1H), 4.38-4.31 (m, 1H), 2.97-2.85 (m, 1H), 2.63-2.58 (m, 1H), 2.47-2.34 (m, 1H), 2.06-1.97 (m, 1H). MS (ESI) m/z 464.1 [M+H]$^+$ Compound 133:

Step 1: To a mixture of 3-Fluoro-4-tolylamine (250 mg, 2.00 mmol, 229 uL, 1.00 eq) and pyridine (474 mg, 5.99 mmol, 484 uL, 3.00 eq) in Acetonitrile (3.00 mL) was added phenyl carbonochloridate (437 mg, 2.80 mmol, 350 uL, 1.40 eq) at 25° C. The reaction mixture was stirred at 25° C. for 12 h. The reaction mixture was concentrated under reduced pressure to afford a residue. The residue was purified by Reversed-Phase Flash and lyophilized to afford phenyl (3-fluoro-4-methylphenyl)carbamate. $^1$H NMR (400 MHz, DMSO-$d_6$) δ=9.31 (s, 1H), 7.47-7.36 (m, 5H), 7.22-7.16 (m, 3H), 2.17 (d, J=1.6 Hz, 3H). MS (ESI) m/z 246.0 [M+H]$^+$ Step 2: To a solution of phenyl (3-fluoro-4-methylphenyl)carbamate (100 mg, 407 umol, 1.40 eq) and 3-(6-(hydroxymethyl)-1-oxoisoindolin-2-yl)piperidine-2,6-dione VIII (80.0 mg, 292 umol, 1.00 eq) in dimethyl formamide (1.20 mL) was added sodium hydride (23.3 mg, 583 umol, 60% purity, 2.00 eq). The mixture was stirred at 25° C. for 1 h. The pH of the mixture was adjusted to 7 with hydrochloric acid (1 M) to give a solution. The solution was purified by Prep-HPLC and lyophilized to afford (2-(2,6-dioxopiperidin-3-yl)-3-oxoisoindolin-5-yl)methyl (3-fluoro-4-methylphenyl)carbamate 133. $^1$H NMR (400 MHz, DMSO-$d_6$) δ=10.99 (s, 1H), 9.93 (s, 1H), 7.79 (s, 1H), 7.72-7.60 (m, 2H), 7.33 (br d, J=12.0 Hz, 1H), 7.22-7.09 (m, 2H), 5.27 (s, 2H), 5.13 (dd, J=5.2, 13.2 Hz, 1H), 4.51-4.43 (m, 1H), 4.38-4.30 (m, 1H), 2.97-2.86 (m, 1H), 2.60 (td, J=2.0, 15.2 Hz, 1H), 2.40 (dq, J=4.4, 13.2 Hz, 1H), 2.15 (d, J=1.2 Hz, 3H), 2.05-1.96 (m, 1H). MS (ESI) m/z 426.2 [M+H]$^+$ Compound 134:

Step 1: To a mixture of 4-bromo-3,5-difluoroaniline (1.00 g, 4.81 mmol, 1.00 eq) and phenylboronic acid (703 mg, 5.77 mmol, 1.20 eq) in dioxane (15.0 mL) was added tetrakis(triphenylphosphine)palladium(0) (1.11 g, 962 umol, 0.200 eq) and potassium carbonate (997 mg, 7.21 mmol, 1.50 eq) at 25° C. under nitrogen. The mixture was stirred at 100° C. for 12 h. The reaction mixture was diluted with water (20.0 mL) and extracted with ethyl acetate (3×20.0 mL). The combined organic phase was separated, washed with brine (2×10.0 mL), dried over sodium sulfate, filtered and concentrated under reduced pressure to give a residue. The residue was purified by silica gel chromatography to afford 2,6-difluoro-[1,1'-biphenyl]-4-amine. MS (ESI) m/z 206.2 [M+H]$^+$.

Step 2: To a mixture of 2,6-difluoro-[1,1'-biphenyl]-4-amine (400 mg, 1.95 mmol, 294 uL, 1.00 eq) and phenyl carbonochloridate (336 mg, 2.14 mmol, 269 uL, 1.10 eq) in Acetonitrile (2.00 mL) was added pyridine (463 mg, 5.85 mmol, 472 uL, 3.00 eq) at 0° C. The mixture was stirred at 25° C. for 2 h. The reaction mixture was diluted with water (20.0 mL) and extracted with ethyl acetate (3×20.0 mL). The organic phase was combined, washed with brine (20.0 mL), dried over sodium sulfate, filtered and concentrated under reduced pressure to give a residue. The residue was purified by reversed phase-HPLC to afford phenyl (2,6-difluoro-[1,1'-biphenyl]-4-yl)carbamate. MS (ESI) m/z 326.1 [M+H]$^+$ Step 3: To a mixture of phenyl (2,6-difluoro-[1,1'-biphenyl]-4-yl)carbamate (65.2 mg, 201 umol, 1.10 eq) and 3-(6-(hydroxymethyl)-1-oxoisoindolin-2-yl)piperidine-2,6-dione VIII (50.0 mg, 182 umol, 1.00 eq) in dimethyformamide (2.00 mL) was added sodium hydride (14.6 mg, 365 umol, 60% purity, 2.00 eq) at 0° C. under nitrogen. The mixture was stirred at 25° C. for 1 h. The mixture was quenched with 1 M hydrochloric acid and filtered. The filter cake was triturated with water and filtered. The filter cake was washed with acetonitrile and dried to afford (2-(2,6-dioxopiperidin-3-yl)-3-oxoisoindolin-5-yl)methyl(2,6-difluoro-[1,1'-biphenyl]-4-yl)carbamate 134. ¹H NMR (400 MHz, DMSO-d₆) δ=11.00 (br s, 1H), 10.34 (br s, 1H), 7.82 (s, 1H), 7.74-7.62 (m, 2H), 7.54-7.46 (m, 2H), 7.44 (br s, 3H), 7.30 (br d, J=9.6 Hz, 2H), 5.34 (s, 2H), 5.18-5.08 (m, 1H), 4.54-4.46 (m, 1H), 4.42-4.32 (m, 1H), 2.96-2.88 (m, 1H), 2.68-2.62 (m, 1H), 2.38-2.32 (m, 1H), 2.08-1.98 (m, 1H). MS (ESI) m/z 506.2 [M+H]⁺

Compound 135:

Step 1: To a solution of 4-bromo-2-fluoroaniline (3.00 g, 15.8 mmol, 1.00 eq) and 4,4,4',4',5,5,5',5'-octamethyl-2,2'-bi(1,3,2-dioxaborolane) (6.01 g, 23.7 mmol, 1.50 eq) in dioxane (30.0 mL) was added potassium acetate (4.65 g, 47.4 mmol, 3.00 eq) and [1,1'-bis(diphenylphosphino)ferrocene]dichloropalladium(II) (1.29 g, 1.58 mmol, 0.100 eq) under nitrogen atmosphere. The mixture was stirred at 80° C. for 12 h under nitrogen atmosphere. The mixture was diluted with water (80.0 mL) and extracted with ethyl acetate (3×60.0 mL). The combined organic layer were washed with saturated brine (20.0 mL), dried with anhydrous sodium sulfate, filtered and concentrated in vacuum. The residue was purified by column chromatography on silica gel to give 2-fluoro-4-(4,4,5,5-tetramethyl-1,3,2-dioxaborolan-2-yl)aniline. ¹H NMR (400 MHz, DMSO-d₆) δ=7.23-7.09 (m, 2H), 6.73 (dd, J=8.0, 8.8 Hz, 1H), 5.55 (s, 2H), 1.24 (s, 12H).

Step 2: To a solution of 2-fluoro-4-(4,4,5-trimethyl-1,3,2-dioxaborolan-2-yl)aniline (2.80 g, 11.8 mmol, 1.00 eq) and 2-bromopyridine (2.80 g, 17.7 mmol, 1.69 mL, 1.50 eq) in dioxane (20.0 mL) and water (5.00 mL) was added [1,1'-bis(diphenylphosphino)ferrocene]dichloropalladium (II) (964 mg, 1.18 mmol, 0.100 eq) and tripotassium phosphate (7.52 g, 35.4 mmol, 3.00 eq) in portions. The mixture was stirred at 80° C. for 12 h under nitrogen atmosphere. The mixture was diluted with water (80.0 mL) and extracted with ethyl acetate (3×60.0 mL). The combined organic layers were washed with saturated brine (20.0 mL), dried with anhydrous sodium sulfate, filtered and concentrated in vacuum. The residue was purified by column chromatography on silica gel to give 2-fluoro-4-(2-pyridyl)aniline. ¹H NMR (400 MHz, DMSO-d₆) δ=8.55 (br d, J=4.5 Hz, 1H), 7.82-7.72 (m, 3H), 7.67 (br d, J=8.3 Hz, 1H), 7.23-7.15 (m, 1H), 6.84 (t, J=8.4 Hz, 1H), 5.49 (s, 2H).

Step 3: To a solution of 2-fluoro-4-(pyridin-2-yl)aniline (500 mg, 2.66 mmol, 1.00 eq) and phenyl carbonochloridate (624 mg, 3.99 mmol, 499 uL, 1.50 eq) in Acetonitrile (5.00 mL) was added pyridine (630 mg, 7.97 mmol, 643 uL, 3.00 eq) dropwise. The mixture was stirred at 25° C. for 12 h. The mixture was concentrated to give crude product. The crude product was purified by reversed-phase HPLC and the desired fraction was collected and lyophilized to give phenyl (2-fluoro-4-(pyridin-2-yl)phenyl)carbamate. ¹H NMR (400 MHz, DMSO-d₆) δ=10.14 (br s, 1H), 8.70-8.63 (m, 1H), 8.02-7.94 (m, 3H), 7.88 (br t, J=7.7 Hz, 2H), 7.49-7.43 (m, 5H), 7.25 (br s, 1H).

Step 4: To a mixture of phenyl (2-fluoro-4-(pyridin-2-yl)phenyl)carbamate (108 mg, 350 umol, 1.20 eq) and 3-(6-(hydroxymethyl)-1-oxoisoindolin-2-yl)piperidine-2,6-dione VIII (80.0 mg, 292 umol, 1.00 eq) in dimethyl formamide (2.00 mL) was added sodium hydride (17.5 mg, 438 umol, 60% purity, 1.50 eq) in portions at 0° C. The mixture was stirred at 15° C. for 2 h. The mixture was quenched with 1 M hydrochloric acid and filtered. The filtrate was purified by prep-HPLC and lyophilized to afford (2-(2,6-dioxopiperidin-3-yl)-3-oxoisoindolin-5-yl)methyl (2-fluoro-4-(pyridin-2-yl)phenyl)carbamate 135. ¹H NMR (400 MHz, DMSO-d₆) δ=11.00 (s, 1H), 9.74 (s, 1H), 8.65 (dd, J=0.9, 4.8 Hz, 1H), 8.14 (s, 1H), 8.00-7.86 (m, 5H), 7.84 (s, 1H), 7.73-7.68 (m, 1H), 7.66-7.62 (m, 1H), 7.36 (ddd, J=0.9, 4.8, 7.4 Hz, 1H), 5.31 (s, 2H), 5.13 (dd, J=5.1, 13.3 Hz, 1H), 4.53-4.44 (m, 1H), 4.42-4.29 (m, 1H), 2.99-2.85 (m, 1H), 2.61 (br d, J=16.6 Hz, 1H), 2.46-2.35 (m, 1H), 2.09-1.95 (m, 1H). MS (ESI) m/z 489.1 [M+H]⁺

Compound 136:

Step 1: To a mixture of 4-bromo-3-fluoroaniline (2.00 g, 10.5 mmol, 1.00 eq), phenylboronic acid (1.93 g, 15.8 mmol, 1.50 eq), potassium carbonate (4.36 g, 31.6 mmol, 3.00 eq) in dioxane (20.0 mL) and water (2.00 mL) was added [1,1'-bis(diphenylphosphino)ferrocene]dichloropalladium(II) (1.16 g, 1.58 mmol, 0.150 eq). The mixture was stirred at 100° C. for 12 h. The mixture was concentrated to give a residue, which was purified by flash silica gel chromatography to give 2-fluoro-[1,1'-biphenyl]-4-amine. MS (ESI) m/z 188.1 [M+H]⁺

Step 2: To a mixture of 2-fluoro-[1,1'-biphenyl]-4-amine (2.00 g, 10.7 mmol, 1.00 eq) in Acetonitrile (20.0 mL) was added pyridine (2.54 g, 32.1 mmol, 2.59 mL, 3.00 eq) and phenyl carbonochloridate (1.84 g, 11.7 mmol, 1.47 mL, 1.10 eq) at 0° C. The mixture was stirred at 0° C. for 1 h. The reaction mixture was concentrated under reduced pressure to give a residue, which was purified by column chromatography to give phenyl(2-fluoro-[1,1'-biphenyl]-4-yl)carbamate. MS (ESI) m/z 308 [M+H]⁺

Step 3: To a mixture of phenyl (2-fluoro-[1,1'-biphenyl]-4-yl)carbamate (107 mg, 350 umol, 1.20 eq) and 3-(6-(hydroxymethyl)-1-oxoisoindolin-2-yl)piperidine-2,6-dione VIII (80.0 mg, 291 umol, 1.00 eq) in dimethyl formamide (1.50 mL) was added sodium hydride (23.3 mg, 583 umol, 60% purity, 2.00 eq) at 0° C. The mixture was stirred at 0° C. for 1 h under nitrogen atmosphere. The mixture was adjusted to pH=4 with hydrochloric acid (1M) to give a solution. The solution was purified by Prep-HPLC and lyophilized to afford (2-(2,6-dioxopiperidin-3-yl)-3-oxoisoindolin-5-yl)methyl (2-fluoro-[1,1'-biphenyl]-4-yl) carbamate 136. ¹H NMR (400 MHz, DMSO-d₆) δ=10.98 (br s, 1H), 10.17 (br s, 1H), 8.50 (s, 1H), 7.82 (s, 1H), 7.72-7.68 (m, 1H), 7.67-7.62 (m, 1H), 7.53-7.43 (m, 6H), 7.35 (br t, J=9.3 Hz, 2H), 5.31 (s, 2H), 5.13 (br dd, J=4.6, 13.1 Hz, 1H), 4.51-4.44 (m, 1H), 4.38-4.31 (m, 1H), 2.97-2.86 (m, 1H), 2.61 (br d, J=16.3 Hz, 1H), 2.41 (br dd, J=3.5, 13.0 Hz, 1H), 2.05-1.98 (m, 1H). MS (ESI) m/z 488.3 [M+H]⁺

Compound 137:

Step 1: To a solution of 4-bromo-3-methylaniline (2.00 g, 10.8 mmol, 1.00 eq), phenylboronic acid (1.97 g, 16.1 mmol, 1.50 eq) and potassium phosphate (6.85 g, 32.3 mmol, 3.00 eq) in dioxane (20.0 mL) and water (5.00 mL) was added [1,1'-bis(diphenylphosphino)ferrocene]dichloropalladium(II) (787 mg, 1.07 mmol, 0.100 eq) under nitrogen atmosphere. The mixture was stirred at 80° C. for 12 h. The reaction mixture was cooled to room temperature, ethyl acetate (40.0 mL) and water (60.0 mL) were added and organic layers were separated. The aqueous phase was extracted with ethyl acetate (3×30.0 mL). Combined extracts were washed with brine (60.0 mL), dried over sodium sulfate, filtered and concentrated under vacuum. The residue was purified by column chromatography on silica gel to give 2-methyl-[1,1'-biphenyl]-4-amine. ¹H NMR (400 MHz, DMSO-d₆) δ=7.42-7.31 (m, 2H), 7.29-7.21 (m, 3H), 6.87 (d, J=8.0 Hz, 1H), 6.54-6.41 (m, 2H), 5.04 (s, 2H), 2.12 (s, 3H). MS (ESI) m/z 184.0 [M+H]

Step 2: To a mixture of 2-methyl-[1,1'-biphenyl]-4-amine (500 mg, 2.73 mmol, 1.00 eq) and pyridine (1.08 g, 13.6 mmol, 1.10 mL, 5.00 eq) in Acetonitrile (10.0 mL) was added phenyl carbonochloridate (555 mg, 3.55 mmol, 444 uL, 1.30 eq) dropwise at 0° C. The mixture was then stirred at 20° C. for 2 h. The mixture was concentrated in vacuum to give crude product which was purified by reversed-phase HPLC. The desired fraction was collected and lyophilized to give phenyl (2-methyl-[1,1'-biphenyl]-4-yl)carbamate. MS (ESI) m/z 304.2 [M+H]$^+$ Step 3: To a solution of 3-(6-(hydroxymethyl)-1-oxoisoindolin-2-yl)piperidine-2,6-dione VIII (140 mg, 510 umol, 1.00 eq) and phenyl (2-methyl-[1,1'-biphenyl]-4-yl)carbamate (185 mg, 613 umol, 1.20 eq) in dimethyl formamide (1.00 mL) was added sodium hydride (40.8 mg, 1.02 mmol, 60% purity, 2.00 eq) at 0° C. The mixture was stirred at 20° C. for 1 h. The mixture was quenched by 1 M hydrochloric acid (1.00 mL) and filtered. The filtrate was purified by prep-HPLC and lyophilized to give (2-(2,6-dioxopiperidin-3-yl)-3-oxoisoindolin-5-yl)methyl(2-methyl-[1,1'-biphenyl]-4-yl)carbamate 137. $^1$H NMR (400 MHz, DMSO-d$_6$) δ=11.00 (s, 1H), 9.83 (s, 1H), 7.82 (s, 1H), 7.73-7.68 (m, 1H), 7.67-7.63 (m, 1H), 7.45-7.40 (m, 3H), 7.39 (br s, 1H), 7.36-7.33 (m, 1H), 7.33-7.29 (m, 2H), 7.13 (d, J=8.2 Hz, 1H), 5.29 (s, 2H), 5.14 (dd, J=5.1, 13.3 Hz, 1H), 4.53-4.43 (m, 1H), 4.40-4.29 (m, 1H), 2.98-2.87 (m, 1H), 2.64-2.58 (m, 1H), 2.41 (br dd, J=4.4, 13.1 Hz, 1H), 2.20 (s, 3H), 2.06-1.98 (m, 1H). MS (ESI) m/z 484.2 [M+H]$^+$ Compound 138:

Step 1: A mixture of aniline (300 mg, 3.22 mmol, 294 uL, 1.00 eq), phenyl carbonochloridate (555 mg, 3.54 mmol, 444 uL, 1.10 eq) and pyridine (1.27 g, 16.1 mmol, 1.30 mL, 5.00 eq) in Acetonitrile (3.00 mL) was stirred at 25° C. for 2 h. The mixture was concentrated to give crude product. The crude product was purified by reversed phase column chromatography. The desired fraction was collected and lyophilized to afford phenyl phenylcarbamate. MS (ESI) m/z 214.1 [M+H]$^+$ Step 2: To a mixture of phenyl phenylcarbamate (42.8 mg, 201 umol, 1.10 eq) and 3-(6-(hydroxymethyl)-1-oxoisoindolin-2-yl)piperidine-2,6-dione (50.0 mg, 183 umol, 1.00 eq) in dimethyformamide (2.00 mL) was added sodium hydride (14.6 mg, 365 umol, 60% purity, 2.00 eq) at 0° C. The mixture was stirred at 25° C. for 1 h. The mixture was quenched with 1 M hydrochloric acid and filtered. The filtrate was purified by Prep-HPLC and the desired fraction was collected and lyophilized to afford (2-(2,6-dioxopiperidin-3-yl)-3-oxoisoindolin-5-yl)methyl phenylcarbamate 138. $^1$H NMR (400 MHz, DMSO-d$_6$) δ=11.00 (s, 1H), 9.81 (s, 1H), 7.81 (s, 1H), 7.72-7.62 (m, 2H), 7.48 (br d, J=7.6 Hz, 2H), 7.28 (t, J=8.0 Hz, 2H), 7.00 (t, J=7.6 Hz, 1H), 5.28 (s, 2H), 5.14 (dd, J=5.2, 13.6 Hz, 1H), 4.54-4.44 (m, 1H), 4.38-4.30 (m, 1H), 2.98-2.86 (m, 1H), 2.68-2.56 (m, 1H), 2.44-2.32 (m, 1H), 2.12-1.94 (m, 1H). MS (ESI) m/z 394.2 [M+H]$^+$ Compound 139:

Step 1: To a solution of 3-(trifluoromethyl)isothiazol-5-amine (100 mg, 594 umol, 1.00 eq) in ethyl acetate (2.00 mL), tetrahydrofuran (0.500 mL) and water (0.500 mL) was added sodium carbonate (37.8 mg, 356 umol, 0.600 eq) and phenyl carbonochloridate (102 mg, 654 umol, 81.9 uL, 1.10 eq) at 0° C. The mixture was stirred at 25° C. for 1 h. The mixture was diluted with water (10.0 mL), and then extracted with ethyl acetate (2×10.0 mL). The combined organic phase was washed with brine (20.0 mL), dried over anhydrous sodium sulfate, filtered and concentrated in vacuum. The residue was purified by flash silica gel chromatography to give phenyl (3-(trifluoromethyl)isothiazol-5-yl)carbamate. $^1$H NMR (400 MHz, CDCl$_3$) δ=8.20 (br s, 1H), 7.41-7.30 (m, 3H), 7.28-7.20 (m, 1H), 7.17-7.10 (m, 2H), 6.93 (s, 1H).

Step 2: To a solution of phenyl (3-(trifluoromethyl)isothiazol-5-yl)carbamate (150 mg, 520 umol, 1.20 eq) in dimethylformamide (2.00 mL) was added N,N-diisopropylethylamine (168 mg, 1.30 mmol, 226 uL, 3.00 eq) and 1-hydroxybenzotriazole (70.3 mg, 520 umol, 1.20 eq) and 3-(6-(hydroxymethyl)-1-oxoisoindolin-2-yl) piperidine-2,6-dione (119 mg, 433 umol, 1.00 eq) at 25° C. The mixture was stirred at 40° C. for 2 h. The mixture was diluted with water (10.0 mL), then extracted with ethyl acetate (2×20.0 mL). The combined organic phase was washed with water (20.0 mL) and brine (20.0 mL), dried over anhydrous sodium sulfate, filtered and concentrated in vacuum. The crude product was purified by prep-HPLC to give (2-(2,6-Dioxo-piperidin-3-yl)-3-oxoisoindolin-5-yl)methyl(3-(trifluoro-methyl)isothiazol-5-yl)carbamate 139. $^1$H NMR (400 MHz, DMSO-d$_6$) δ=12.13 (s, 1H), 11.00 (s, 1H), 7.83 (s, 1H), 7.75-7.70 (m, 1H), 7.69-7.64 (m, 1H), 7.06 (s, 1H), 5.42 (s, 2H), 5.13 (dd, J=5.2, 13.3 Hz, 1H), 4.53-4.44 (m, 1H), 4.40-4.32 (m, 1H), 2.92 (ddd, J=5.6, 13.6, 17.4 Hz, 1H), 2.61 (br d, J=17.2 Hz, 1H), 2.41 (dd, J=4.4, 13.2 Hz, 1H), 2.08-1.97 (m, 1H). $^{19}$F NMR (400 MHz, DMSO-d$_6$) δ=−63.62 (s, 1F). MS (ESI) m/z 469.0 [M+H]$^+$ Compound 140:

Step 1: To a solution of 3-nitrophenol (1.00 g, 7.19 mmol, 1.43 mL, 1.00 eq) in acetone (20.0 mL) was added 1,2-dibromoethane (2.00 g, 10.6 mmol, 1.48 eq) and potassium carbonate (3.00 g, 21.7 mmol, 3.02 eq). The mixture was stirred at 80° C. for 12 h. The mixture was concentrated under reduced pressure. The residue was purified by column chromatography on silica gel to give 1-(2-bromoethoxy)-3-nitrobenzene. $^1$H NMR (400 MHz, CDCl$_3$) δ=7.88 (ddd, J=0.8, 2.1, 8.1 Hz, 1H), 7.75 (t, J=2.3 Hz, 1H), 7.47 (t, J=8.2 Hz, 1H), 7.29-7.26 (m, 1H), 4.39 (t, J=6.1 Hz, 2H), 3.69 (t, J=6.1 Hz, 2H).

Step 2: To a solution of 1-(2-bromoethoxy)-3-nitrobenzene (1.20 g, 4.88 mmol, 1.00 eq) in tetrahydrofuran (20.0 mL) was added potassium tert-butoxide (650 mg, 5.79 mmol, 1.19 eq). The mixture was stirred at 20° C. for 0.5 h. The mixture was diluted with ethyl acetate and water. The organic layer was separated and concentrated under reduced pressure to give 1-nitro-3-(vinyloxy)benzene. $^1$H NMR (400 MHz, CDCl$_3$) δ=8.01-7.94 (m, 1H), 7.88 (t, J=2.3 Hz, 1H), 7.52 (t, J=8.2 Hz, 1H), 7.36 (td, J=1.2, 8.2 Hz, 1H), 6.69 (dd, J=6.0, 13.6 Hz, 1H), 4.94 (dd, J=1.9, 13.6 Hz, 1H), 4.66 (dd, J=2.0, 6.0 Hz, 1H).

Step 3: To a solution of 1-nitro-3-(vinyloxy)benzene (500 mg, 3.03 mmol, 1.00 eq) in xylene (10.0 mL) was added sodium fluoride (75.0 mg, 1.79 mmol, 0.59 eq) and trimethylsilyl 2,2-difluoro-2-(fluorosulfonyl)acetate (1.50 g, 5.99 mmol, 1.18 mL, 1.98 eq). The mixture was stirred at 120° C. for 12 h under nitrogen atmosphere. After being cooled to room temperature, the mixture was diluted with ethyl acetate and water. The organic layer was separated and concentrated to give a residue. The residue was purified by column chromatography on silica gel to give 1-(2,2-difluorocyclopropoxy)-3-nitrobenzene. $^1$H NMR (400 MHz, CDCl$_3$) δ=7.97-7.91 (m, 1H), 7.87 (t, J=2.3 Hz, 1H), 7.51 (t, J=8.3 Hz, 1H), 7.34 (ddd, J=0.8, 2.5, 8.3 Hz, 1H), 4.21-4.14 (m, 1H), 2.00-1.86 (m, 1H), 1.76-1.67 (m, 1H).

Step 4: To a solution of 1-(2,2-difluorocyclopropoxy)-3-nitrobenzene (520 mg, 2.42 mmol, 1.00 eq) in methanol (20.0 mL) and water (4.00 mL) was added iron powder (680 mg, 12.2 mmol, 5.04 eq) and ammonium chloride (1.04 g, 19.4 mmol, 8.04 eq). The mixture was stirred at 50° C. for 1 h. After being cooled to room temperature, the mixture was concentrated under reduced pressure. The residue was diluted with ethyl acetate and water. The organic layer was separated and concentrated under reduced pressure to give 3-(2,2-difluorocyclopropoxy)aniline. $^1$H NMR (400 MHz, CDCl$_3$) δ=7.11 (t, J=8.1 Hz, 1H), 6.45-6.42 (m, 1H), 6.39 (ddd, J=0.7, 2.1, 7.9 Hz, 1H), 6.36-6.33 (m, 1H), 4.08-3.98 (m, 1H), 3.74 (br s, 2H), 1.86-1.74 (m, 1H), 1.67-1.59 (m, 1H).

Step 5: To a solution of 3-(2,2-difluorocyclopropoxy) aniline (200 mg, 1.08 mmol, 1.00 eq) in Acetonitrile (20.0 mL) was added pyridine (254 mg, 3.22 mmol, 3.00 eq) and phenyl carbonochloridate (187 mg, 1.20 mmol, 1.11 eq) at 0° C. The mixture was stirred at 0° C. for 1 h. The mixture was concentrated under reduced pressure. The residue was purified by column chromatography on silica gel to give phenyl (3-(2,2-difluorocyclopropoxy)phenyl)carbamate. MS (ESI) m/z 306.1 [M+H]$^+$ Step 6: To a solution of 3-(6-(hydroxymethyl)-1-oxoisoindolin-2-yl)piperidine-2,6-dione VIII (90.0 mg, 328 umol, 1.00 eq) in dimethyl formamide (2.00 mL) was added (3-(2,2-difluorocyclopropoxy)phenyl)carbamate (110 mg, 360 umol, 1.10 eq) and sodium hydride (26.0 mg, 650 umol, 60% purity, 1.98 eq). The mixture was stirred at 0° C. for 1 h. The mixture was quenched with hydrochloric acid (1M, 1.00 mL) to give solution. The solution was purified by Prep-HPLC and the desired fraction was collected and lyophilized to afford (3-(2,2-difluorocyclopropoxy)phenyl carbamate 140. $^1$H NMR (400 MHz, DMSO-d$_6$) δ=11.00 (br s, 1H), 9.92 (s, 1H), 7.80 (s, 1H), 7.72-7.60 (m, 2H), 7.31-7.21 (m, 2H), 7.12 (br d, J=8.2 Hz, 1H), 6.69 (dd, J=1.9, 8.2 Hz, 1H), 5.28 (s, 2H), 5.13 (dd, J=5.1, 13.3 Hz, 1H), 4.51-4.40 (m, 2H), 4.38-4.31 (m, 1H), 2.99-2.84 (m, 1H), 2.65-2.58 (m, 1H), 2.41 (br dd, J=4.6, 13.1 Hz, 1H), 2.08-1.98 (m, 2H), 1.83-1.71 (m, 1H). MS (ESI) m/z 486.1 [M+H]$^+$ Compound 141:

Step 1: A mixture of 1-chloro-4-fluoro-2-methyl-5-nitrobenzene (500 mg, 2.64 mmol, 1.00 eq), ammonium chloride (988 mg, 18.5 mmol, 7.00 eq) and iron powder (1.03 g, 18.5 mmol, 7.00 eq) in methanol (10.0 mL) and water (2.00 mL) was stirred at 80° C. for 2 h. The resulting mixture was filtered over celite, and the filtrate was concentrated under reduced pressure to give 5-chloro-2-fluoro-4-methylaniline.

Step 2: A mixture of phenyl carbonochloridate (236 mg, 1.50 mmol, 188 uL, 1.20 eq), 5-chloro-2-fluoro-4-methylaniline (200 mg, 1.25 mmol, 1.00 eq) and pyridine (298 mg, 3.76 mmol, 304 uL, 3.00 eq) in Acetonitrile (10.0 mL) was stirred at 25° C. for 12 h. The mixture was concentrated in vacuum. The crude product was purified by reversed-phase HPLC and the desired fraction was collected and lyophilized to give phenyl (5-chloro-2-fluoro-4-methylphenyl)carbamate. MS (ESI) m/z 280.1 [M+H]$^+$ Step 3: To a mixture of phenyl(5-chloro-2-fluoro-4-methylphenyl)carbamate (122 mg, 438 umol, 1.20 eq) and 3-(6-(hydroxymethyl)-1-oxoisoindolin-2-yl)piperidine-2,6-dione VIII (100 mg, 365 umol, 1.00 eq) in dimethyl formamide (2.00 mL) was added sodium hydride (29.2 mg, 729 umol, 60% purity, 2.00 eq) under nitrogen atmosphere. Then the mixture was stirred at 0° C. for 2 h. The residue was diluted with ethyl acetate (30.0 mL) and water (30.0 mL). The organic layer was separated and the aqueous phase was extracted with ethyl acetate (3×30.0 mL). The organic layer was dried over sodium sulfate, filtered and concentrated in vacuum. The residue was purified by prep-HPLC and the desired fraction was collected and lyophilized. The lyophilized residue was purified again by Prep-HPLC and the desired fraction was collected and lyophilized to give (2-(2, 6-dioxopiperidin-3-yl)-3-oxoisoindolin-5-yl)methyl (5-chloro-2-fluoro-4-methylphenyl)carbamate 141. $^1$H NMR (400 MHz, DMSO-d$_6$) δ=10.99 (br s, 1H), 9.67 (br s, 1H), 7.80 (s, 1H), 7.75 (br d, J=7.1 Hz, 1H), 7.69-7.61 (m, 2H), 7.29 (d, J=11.4 Hz, 1H), 5.27 (s, 2H), 5.17-5.09 (m, 1H), 4.51-4.43 (m, 1H), 4.38-4.28 (m, 1H), 2.98-2.85 (m, 1H), 2.64-2.57 (m, 1H), 2.44-2.37 (m, 1H), 2.27 (s, 3H), 2.06-1.96 (m, 1H). MS (ESI) m/z 460.1 [M+H]$^+$ Compound 142:

Step 1: To a mixture of 4-(tert-butyl)aniline (2.00 g, 13.4 mmol, 2.12 mL, 1.00 eq) in dichloromethane (20.0 mL) was added acetic anhydride (1.64 g, 16.1 mmol, 1.51 mL, 1.20 eq) dropwise at 0° C. The mixture was stirred at 0° C. for 15 min. The reaction was quenched with water (100 mL) and extracted with ethyl acetate (3×30.0 mL). The combined organic layer was washed with brine (20.0 mL), dried over anhydrous sodium sulfate and concentrated in vacuum to afford N-(4-(tert-butyl)phenyl)acetamide. $^1$H NMR (400 MHz, CDCl$_3$) δ=7.43-7.37 (m, 2H), 7.35-7.31 (m, 2H), 2.16 (s, 3H), 1.30 (s, 9H). MS (ESI) m/z 192.2 [M+H]$^+$ Step 2: To a mixture of N-(4-(tert-butyl)phenyl)acetamide (1.00 g, 5.23 mmol, 1.00 eq) in Acetonitrile (10.0 mL) was added Selectfluor (1.85 g, 5.23 mmol, 1.00 eq) in one portion. The mixture was stirred at 80° C. for 16 h under nitrogen atmosphere. The reaction mixture was cooled to room temperature and diluted with water (50 mL), extracted with ethyl acetate (3×30 mL). Combined organic layer was washed with brine (60.0 mL), dried over anhydrous sodium sulfate filtered, and concentrated under vacuum. The residue was purified by column chromatography on silica gel to afford N-(4-(tert-butyl)-2-fluorophenyl) acetamide. $^1$H NMR (400 MHz, CDCl$_3$) δ=8.15 (t, J=8.6 Hz, 1H), 7.17-7.04 (m, 2H), 2.21 (s, 3H), 1.29 (s, 9H). MS (ESI) m/z 210.2[M+H]$^+$ Step 3: To a solution of N-(4-(tert-butyl)-2-fluorophenyl) acetamide (300 mg, 1.43 mmol, 1.00 eq) in ethanol (4.00 mL) was added hydrochloric acid (12 M, 2.00 mL, 16.7 eq) dropwise. The mixture was stirred at 80° C. for 2 h. The reaction was quenched with saturated sodium hydrogencarbonate solution and extracted with ethyl acetate. The combined organic layer was washed with brine, dried over anhydrous sodium sulfate, filtered and concentrated in vacuum to afford 4-(tert-butyl)-2-fluoroaniline. MS (ESI) m/z 168.0[M+H]$^+$ Step 4: To a mixture of 4-(tert-butyl)-2-fluoroaniline (110 mg, 658 umol, 1.00 eq) and pyridine (260 mg, 3.29 mmol, 265 uL, 5.00 eq) in Acetonitrile (5.00 mL) was added phenyl carbonochloridate (154 mg, 987 umol, 124 uL, 1.50 eq) dropwise at 0° C. The mixture was stirred at 20° C. for 2 h. The reaction was concentrated to give crude product which was purified by reversed-phase HPLC to afford phenyl (4-(tert-butyl)-2-fluorophenyl)carbamate. MS (ESI) m/z 288.2 [M+H]$^+$ Step 5: To a solution of 3-(6-(hydroxymethyl)-1-oxoisoindolin-2-yl)piperidine-2,6-dione VIII (80.0 mg, 292 umol, 1.00 eq) and phenyl (4-(tert-butyl)-2-fluorophenyl)carbamate (109 mg, 379 umol, 1.30 eq) in dimethyl formamide (1.00 mL) was added sodium hydride (23.3 mg, 583 umol, 60% purity, 2.00 eq) at 0° C. The mixture was stirred at 20° C. for 0.5 h. The mixture was quenched by 1M hydrochloric acid (1.00 mL) slowly and purified by Prep-HPLC. The desired fraction was collected and lyophilized to afford (2-(2,6-dioxopiperidin-3-yl)-3-oxoisoindolin-5-yl)methyl (4-(tert-butyl)-2-fluorophenyl)carbamate 142. $^1$H NMR (400 MHz, DMSO-d$_6$) δ=11.00 (s, 1H), 9.42 (br s, 1H), 7.80 (s, 1H), 7.72-7.59 (m, 2H), 7.52 (br t, J=8.3 Hz, 1H), 7.26-7.11 (m, 2H), 5.26 (s, 2H), 5.13 (dd, J=5.0, 13.3 Hz, 1H), 4.53-4.42 (m, 1H), 4.39-4.29 (m, 1H), 2.97-2.87 (m, 1H), 2.61 (br d, J=17.8 Hz, 1H), 2.44-2.35 (m, 1H), 2.06-1.98 (m, 1H), 1.26 (s, 9H). MS (ESI) m/z 468.1 [M+H]$^+$ Compound 143:

Step 1: To a solution of 5-phenylpyridin-2-amine (500 mg, 2.94 mmol, 1.00 eq) in Acetonitrile (5.00 mL) and dimethyl formamide (2.00 mL) was added pyridine (1.16 g, 14.7 mmol, 1.19 mL, 5.00 eq) and phenyl carbonochloridate (690 mg, 4.41 mmol, 552 uL, 1.50 eq). The mixture was stirred at 25° C. for 1 h. The mixture was filtered to give filtrate. The filtrate was concentrated and purified by reversed phase column chromatography. The desired fraction was collected and concentrated to give phenyl (5-phenylpyridin-2-yl)carbamate. MS (ESI) m/z 291.1 [M+H]$^+$ Step 2: To a solution of 3-(6-(hydroxymethyl)-1-oxoisoindolin-2-yl)piperidine-2,6-dione VIII (90.0 mg, 328 umol, 1.00 eq) in dimethyl formamide (1.00 mL) was added phenyl (5-phenylpyridin-2-yl)carbamate (190 mg, 656 umol, 2.00 eq) and sodium hydride (26.2 mg, 656 umol, 60% purity, 2.00 eq) at 0° C. The mixture was stirred at 0° C. for 1 h. The mixture was adjusted to pH=5 with hydrochloric acid (1 M). Solid was precipitated from the mixture. The solid was collected by filtration and triturated with dimethyl formamide (2.00 mL). The mixture was filtered to give a filter cake which was lyophilized to afford (2-(2,6-dioxopiperidin-3-yl)-3-oxoisoindolin-5-yl)methyl (5-phenylpyridin-2-yl)carbamate 143. $^1$H NMR (400 MHz, DMSO-d$_6$) δ=11.90 (br d, J=2.9 Hz, 1H), 10.97 (s, 1H), 8.65 (d, J=2.1 Hz, 1H), 8.57 (br d, J=9.0 Hz, 1H), 7.87 (d, J=9.0 Hz, 1H), 7.82 (s, 1H), 7.72 (d, J=7.5 Hz, 3H), 7.66 (s, 1H), 7.53-7.49 (m, 2H), 7.45 (d, J=7.4 Hz, 1H), 5.40 (s, 2H), 5.08 (br dd, J=4.9, 13.1 Hz, 1H), 4.51-4.43 (m, 1H), 4.38-4.28 (m, 1H), 2.93-2.84 (m, 1H), 2.60 (br s, 1H), 2.45-2.35 (m, 1H), 2.04-1.96 (m, 1H). MS (ESI) m/z 471.2 [M+H]$^+$.

Compound 144:

Step 1: To a solution of 3-chloro-5-methylaniline (1.00 g, 7.06 mmol, 1.00 eq) in Acetonitrile (5.00 mL) was added pyridine (2.79 g, 35.3 mmol, 2.85 mL, 5.00 eq) and phenyl carbonochloridate (1.66 g, 10.6 mmol, 1.33 mL, 1.50 eq) at 0° C. The mixture was stirred at 0° C. for 2 h. The mixture was filtered to give a filtrate which was concentrated and purified by reversed phase column chromatography. The desired fraction was collected and concentrated to give phenyl (3-chloro-5-methylphenyl)carbamate. $^1$H NMR (400 MHz, DMSO-d$_6$) δ=10.38 (br s, 1H), 7.47-7.41 (m, 3H), 7.31-7.20 (m, 4H), 6.96 (s, 1H), 2.28 (s, 3H). MS (ESI) m/z 262.0 [M+H]$^+$ Step 2: To a solution of 3-(6-(hydroxymethyl)-1-oxoisoindolin-2-yl)piperidine-2,6-dione VIII (80.0 mg, 292 umol, 1.00 eq) in dimethyl formamide (1.00 mL) was added phenyl (3-chloro-5-methylphenyl)carbamate (114 mg, 438 umol, 1.50 eq) and sodium hydride (23.3 mg, 583 umol, 60% purity, 2.00 eq) at 0° C. The mixture was stirred at 0° C. for 1 h. The mixture was adjusted to pH=5 with hydrochloric acid (1 M). The mixture was diluted with water/ethyl acetate (10.0 ml/10.0 ml). The organic layer was separated and concentrated to give a residue. The residue was purified by Prep-HPLC and the desired fraction was collected and lyophilized to afford (2-(2,6-dioxopiperidin-3-yl)-3-oxoisoindolin-5-yl)methyl (3-chloro-5-methylphenyl)carbamate 144. $^1$H NMR (400 MHz, DMSO-d$_6$) δ=11.00 (br s, 1H), 9.97 (s, 1H), 7.80 (s, 1H), 7.73-7.62 (m, 2H), 7.41 (s, 1H), 7.22 (s, 1H), 6.90 (s, 1H), 5.28 (s, 2H), 5.13 (br dd, J=5.0, 13.3 Hz, 1H), 4.52-4.44 (m, 1H), 4.39-4.30 (m, 1H), 2.97-2.87 (m, 1H), 2.63 (br d, J=1.6 Hz, 1H), 2.41 (br dd, J=4.3, 12.9 Hz, 1H), 2.26 (s, 3H), 2.06-1.97 (m, 1H). MS (ESI) m/z 442.1 [M+H]$^+$.

Compound 145:

Step 1: A mixture of 2-fluoro-5-(trifluoromethoxy)aniline (500 mg, 2.56 mmol, 305 uL, 1.00 eq), phenyl carbonochloridate (441 mg, 2.82 mmol, 353 uL, 1.10 eq) and pyridine (608 mg, 7.69 mmol, 621 uL, 3.00 eq) in Acetonitrile (3.00 mL) was stirred at 25° C. for 2 h. The mixture was concentrated to give crude product. The crude product was purified by reversed phase column chromatography and the desired fraction was collected and lyophilized to give phenyl (2-fluoro-5-(trifluoromethoxy)phenyl)carbamate. MS (ESI) m/z 316.1 [M+H]$^+$ Step 2: To a mixture of phenyl (2-fluoro-5-(trifluoromethoxy)phenyl)carbamate (126 mg, 401 umol, 1.10 eq) and 3-(6-(hydroxymethyl)-1-oxoisoindolin-2-yl)piperidine-2,6-dione VIII (100 mg, 365 umol, 1.00 eq) in dimethyformamide (2.00 mL) was added sodium hydride (29.2 mg, 729 umol, 60% purity, 2.00 eq) at 0° C. The mixture was stirred at 25° C. for 1 h. The mixture was quenched with 1 M hydrochloric acid and filtered. The filtrate was purified by prep-HPLC and the desired fraction was collected and lyophilized to afford (2-(2,6-dioxopiperidin-3-yl)-3-oxoisoindolin-5-yl)methyl(2-fluoro-5-(trifluoromethoxy) phenyl)carbamate 145. $^1$H NMR (400 MHz, DMSO-d$_6$) δ=11.02 (s, 1H), 9.94 (s, 1H), 7.88-7.80 (m, 2H), 7.72-7.62 (m, 2H), 7.38 (dd, J=9.2, 10.4 Hz, 1H), 7.18-7.10 (m, 1H), 5.32 (s, 2H), 5.14 (dd, J=5.2, 13.4 Hz, 1H), 4.52-4.44 (m, 1H), 4.38-4.30 (m, 1H), 2.98-2.86 (m, 1H), 2.68-2.58 (m, 1H), 2.44-2.32 (m, 1H), 2.06-1.98 (m, 1H). MS (ESI) m/z 496.1 [M+H]$^+$ Compound 146:

Step 1: To a solution of 3-fluoro-5-methylaniline (1.00 g, 7.99 mmol, 1.00 eq) in Acetonitrile (5.00 mL) was added pyridine (3.16 g, 39.9 mmol, 3.22 mL, 5.00 eq) and phenyl carbonochloridate (1.88 g, 12.0 mmol, 1.50 mL, 1.50 eq). The mixture was stirred at 25° C. for 1 h. The mixture was filtered to give a filtrate which was purified by reversed phase column chromatography. The desired fraction was collected and concentrated to give phenyl (3-fluoro-5-methylphenyl)carbamate. $^1$H NMR (400 MHz, DMSO-d$_6$) δ=10.39 (br s, 1H), 7.50-7.38 (m, 3H), 7.29-7.21 (m, 3H), 7.12 (s, 1H), 6.72 (br d, J=9.3 Hz, 1H), 2.29 (s, 3H). MS (ESI) m/z 246.0 [M+H]$^+$ Step 2: To a solution of 3-(6-(hydroxymethyl)-1-oxoisoindolin-2-yl)piperidine-2,6-dione VIII (90.0 mg, 328 umol, 1.00 eq) in dimethyl formamide (2.00 mL) was added phenyl (3-fluoro-5-methylphenyl)carbamate (121 mg, 492 umol, 1.50 eq) and sodium hydride (26.2 mg, 656 umol, 60% purity, 2.00 eq) at 0° C. The mixture was stirred at 0° C. for 1 h. The mixture was adjusted to pH=5 with hydrochloric acid (1 M). The mixture was diluted with water/ethyl acetate (20.0 ml/20.0 ml). The organic layer was collected and concentrated to give a residue. The residue was purified by Prep-HPLC and the desired fraction was collected and lyophilized to afford (2-(2,6-dioxopiperidin-3-yl)-3-oxoisoindolin-5-yl)methyl (3-fluoro-5-methylphenyl) carbamate 146. $^1$H NMR (400 MHz, DMSO-d$_6$) δ=11.00 (br s, 1H), 9.97 (s, 1H), 7.80 (s, 1H), 7.71-7.66 (m, 1H), 7.66-7.61 (m, 1H), 7.19 (br d, J=11.4 Hz, 1H), 7.07 (s, 1H), 6.65 (br d, J=9.7 Hz, 1H), 5.28 (s, 2H), 5.14 (dd, J=5.1, 13.2 Hz, 1H), 4.53-4.43 (m, 1H), 4.39-4.30 (m, 1H), 2.96-2.87 (m, 1H), 2.64-2.58 (m, 1H), 2.42 (br d, J=4.5 Hz, 1H), 2.27 (s, 3H), 2.02 (br d, J=5.3 Hz, 1H). MS (ESI) m/z 426.2 [M+H]$^+$.

Compound 147:

Step 1: To a solution of propanamide (9.00 g, 123 mmol, 1.00 eq) in toluene (400 mL) was added S-chloro chloromethanethioate (17.7 g, 135 mmol, 1.10 eq). The reaction mixture was allowed to stir at 100° C. for 5 h. The reaction mixture was concentrated under reduced pressure to give the crude product 5-ethyl-1,3,4-oxathiazol-2-one, which was used directly in next step without further purification. $^1$H NMR (400 MHz, DMSO-$d_6$) δ=2.59 (q, J=7.6 Hz, 2H), 1.09 (t, J=7.6 Hz, 3H).

Step 2: To a solution of 5-ethyl-1,3,4-oxathiazol-2-one (8.50 g, 64.8 mmol, 1.00 eq) in 1,2-dichlorobenzene (100 mL) was added ethyl prop-2-ynoate (25.4 g, 259 mmol, 25.4 mL, 4.00 eq), the reaction mixture was allowed to stir at 140° C. for 48 h. The reaction mixture was diluted with tert-butyl methyl ether (500 mL) and washed with saturated aqueous sodium bicarbonate (3×200 mL), the organic phase was washed with brine (200 mL), dried over sodium sulfate, filtered and concentrated under reduced pressure. The residue was purified by column chromatography to afford a mixture of ethyl 3-ethylisothiazole-5-carboxylate/ethyl 3-ethylisothiazole-4-carboxylate (1/1), which was further to afford ethyl 3-ethylisothiazole-4-carboxylate. $^1$H NMR (400 MHz, DMSO-$d_6$) δ=9.61 (s, 1H), 4.28 (q, J=7.2 Hz, 2H), 3.04 (q, J=7.6 Hz, 2H), 1.31 (t, J=7.2 Hz, 3H), 1.23 (t, J=7.6 Hz, 3H).

Step 3: To a solution of ethyl 3-ethylisothiazole-4-carboxylate (100 mg, 540 umol, 1.00 eq) in methanol (1.00 mL) was added a solution of lithium hydroxide monohydrate (113 mg, 2.70 mmol, 5.00 eq) in water (0.500 mL). The reaction mixture was stirred at 25° C. for 1 h. The reaction was concentrated under reduced pressure. The residue was diluted with water (5.00 mL) and adjusted pH=2-3 with 1 mol/L hydrochloric acid solution. The precipitate was formed and filtered to afford 3-ethylisothiazole-4-carboxylic acid, which was used for next step directly without further purification. $^1$H NMR (400 MHz, DMSO-$d_6$) δ=13.21-12.77 (m, 1H), 9.56 (s, 1H), 3.05 (q, J=7.6 Hz, 2H), 1.23 (t, J=7.6 Hz, 3H).

Step 4: To a solution of 3-ethylisothiazole-4-carboxylic acid (40.0 mg, 254 umol, 1.00 eq) in dioxane (2.00 mL) was added triethylamine (77.2 mg, 763 umol, 106 uL, 3.00 eq) and diphenylphosphoryl azide (105 mg, 382 umol, 82.7 uL, 1.50 eq), the mixture was stirred at 25° C. for 1 h, then 3-[6-(hydroxymethyl)-1-oxo-isoindolin-2-yl]piperidine-2,6-dione (69.8 mg, 254 umol, 1.00 eq) was added. The reaction mixture was allowed to stir at 100° C. for 2 h under nitrogen. The reaction mixture was concentrated under reduced pressure and diluted with water (50.0 mL), extracted with ethyl acetate (3×30.0 mL), the organic phase was washed with brine (30.0 mL), dried over sodium sulfate, filtered and concentrated. The residue was purified by column chromatography to give crude product, which was purified by prep-HPLC to afford 2-(2,6-Dioxopiperidin-3-yl)-3-oxoisoindolin-5-yl)methyl (3-ethylisothiazol-4-yl)carbamate 147. $^1$H NMR (400 MHz, DMSO-$d_6$) δ=11.00 (s, 1H), 9.73-9.45 (m, 1H), 8.76 (s, 1H), 7.81 (s, 1H), 7.73-7.59 (m, 2H), 5.30 (s, 2H), 5.13 (dd, J=5.2, 13.2 Hz, 1H), 4.53-4.30 (m, 2H), 2.98-2.85 (m, 1H), 2.74 (q, J=7.6 Hz, 2H), 2.61 (br dd, J=2.0, 15.6 Hz, 1H), 2.41 (br dd, J=4.8, 13.2 Hz, 1H), 2.07-1.96 (m, 1H), 1.19 (t, J=7.6 Hz, 3H). MS (ESI) m/z 429.0 [M+H]$^+$ Compound 148:

Step 1: To a mixture of 2-fluoro-4-(trifluoromethoxy) aniline (220 mg, 1.13 mmol, 1.00 eq) and phenyl carbonochloridate (265 mg, 1.69 mmol, 212 uL, 1.50 eq) in Acetonitrile (5.00 mL) was added pyridine (268 mg, 3.38 mmol, 273 uL, 3.00 eq) dropwise. The mixture was stirred at 25° C. for 1 h. The mixture was concentrated to give crude product. The crude product was purified by reversed-phase HPLC. The desired fraction was collected and lyophilized to give phenyl (2-fluoro-4-(trifluoromethoxy) phenyl)carbamate Step 2: To a mixture of phenyl(2-fluoro-4-(trifluoromethoxy)phenyl)carbamate (110 mg, 350 umol, 1.20 eq) and 3-(6-(hydroxymethyl)-1-oxoisoindolin-2-yl)piperidine-2,6-dione VIII (80.0 mg, 292 umol, 1.00 eq) in dimethyformamide (2.00 mL) was added sodium hydride (17.5 mg, 438 umol, 60% purity, 1.50 eq) in portions. The mixture was stirred at 25° C. for 1 h. The mixture was quenched with 1M hydrochloric acid and filtered. The filtrate was purified by Prep-HPLC and lyophilized to afford (2-(2,6-dioxopiperidin-3-yl)-3-oxoisoindolin-5-yl)methyl(2-fluoro-4-(trifluoromethoxy)phenyl)carbamate 148. $^1$H NMR (400 MHz, DMSO-$d_6$) δ=11.00 (s, 1H), 9.74 (br s, 1H), 7.84-7.74 (m, 2H), 7.70-7.61 (m, 2H), 7.45 (dd, J=2.3, 10.9 Hz, 1H), 7.23 (br d, J=8.9 Hz, 1H), 5.29 (s, 2H), 5.13 (dd, J=5.1, 13.2 Hz, 1H), 4.51-4.43 (m, 1H), 4.38-4.30 (m, 1H), 2.97-2.86 (m, 1H), 2.60 (br d, J=18.2 Hz, 1H), 2.40 (dt, J=9.0, 13.2 Hz, 1H), 2.06-1.96 (m, 1H). MS (ESI) m/z 496.1 [M+H]$^+$ Compound 149:

Step 1: To a solution of 2-phenylpyridin-4-amine (500 mg, 2.94 mmol, 1.00 eq) and pyridine (1.16 g, 14.7 mmol, 1.19 mL, 5.00 eq) in Acetonitrile (5.00 mL) was added phenyl carbonochloridate (689 mg, 4.41 mmol, 552 uL, 1.50 eq) dropwise at 0° C. The mixture was stirred at 20° C. for 12 h. The mixture was concentrated to give crude product, which was purified by reversed-phase HPLC to give phenyl (2-phenylpyridin-4-yl)carbamate. MS (ESI) m/z 291.0 [M+H]$^+$ Step 2: To a solution of 3-(6-(hydroxymethyl)-1-oxoisoindolin-2-yl)piperidine-2,6-dione VIII (80.0 mg, 292 umol, 1.00 eq) and phenyl (2-phenylpyridin-4-yl)carbamate (110 mg, 379 umol, 1.30 eq) in dimethyl formamide (1.00 mL) was added sodium hydride (23.3 mg, 583 umol, 60% purity, 2.00 eq) in portions at 0° C. The mixture was stirred at 20° C. for 1 h. The mixture was quenched with 1M hydrochloric acid (1.00 mL) and the mixture was purified by Prep-HPLC to afford (2-(2,6-dioxopiperidin-3-yl)-3-oxoisoindolin-5-yl) methyl(2-phenylpyridin-4-yl)carbamate 149. $^1$H NMR (400 MHz, DMSO-$d_6$) δ=11.00 (s, 1H), 10.38 (s, 1H), 8.49 (d, J=5.5 Hz, 1H), 8.01-7.92 (m, 3H), 7.84 (s, 1H), 7.75-7.70 (m, 1H), 7.68-7.64 (m, 1H), 7.53-7.48 (m, 2H), 7.47-7.38 (m, 2H), 5.34 (s, 2H), 5.14 (dd, J=5.1, 13.4 Hz, 1H), 4.53-4.44 (m, 1H), 4.41-4.30 (m, 1H), 2.96-2.89 (m, 1H), 2.63 (br d, J=2.3 Hz, 1H), 2.44-2.35 (m, 1H), 2.07-1.97 (m, 1H). MS (ESI) m/z 471.2 [M+H]$^+$ Compound 150:

Step 1: A mixture of 2-methyl-5-nitrobenzoic acid (20.0 g, 110 mmol, 1.00 eq) and 1,3-dichloro-5,5-dimethylimidazolidine-2,4-dione (21.8 g, 110 mmol, 1.00 eq) in sulfuric acid (20.0 mL) was stirred at 80° C. for 10 h. The reaction mixture was poured into ice water (about 300 mL), after stirring, the precipitated solid was collected by filtration and washed with water to give 3-chloro-2-methyl-5-nitrobenzoic acid, which was used for next step without further purification. $^1$H NMR (400 MHz, CDCl$_3$) δ=8.67 (d, J=2.4 Hz, 1H), 8.36 (d, J=2.4 Hz, 1H), 2.72 (s, 3H).

Step 2: To a solution of 3-chloro-2-methyl-5-nitrobenzoic acid (24.0 g, 111 mmol, 1.00 eq) in tetrahydrofuran (200 mL) was added borane dimethyl sulfide complex (10.0 M, 22.3 mL, 2.00 eq) at 0° C. Then the mixture was stirred at 25° C. for 10 h. The reaction mixture was quenched by addition water (50.0 mL), and then extracted with ethyl acetate (3×200 mL). The combined organic layers were washed with brine, dried over sodium sulfate, filtered and concentrated under reduced pressure to give 3-chloro-2-methyl-5-nitrophenyl)methanol. $^1$H NMR (400 MHz, CDCl$_3$) δ=8.16 (d, J=2.2 Hz, 1H), 8.09 (d, J=2.2 Hz, 1H), 4.72 (s, 2H), 2.35 (s, 3H).

Step 3: To a solution of (3-chloro-2-methyl-5-nitrophenyl)methanol (23.0 g, 114 mmol, 1.00 eq) in dichloromethane (200 mL) was added thionyl chloride (67.9 g, 570 mmol, 41.4 mL, 5.00 eq). Then the mixture was stirred at 25° C. for 10 h. The reaction mixture was poured into ice water and then extracted with dichloromethane. The combined organic layers were washed with saturated sodium bicarbonate and brin), dried over magnesium sulfate, filtered and concentrated under reduced pressure to give 1-chloro-3-(chloromethyl)-2-methyl-5-nitrobenzene. $^1$H NMR (400 MHz, CDCl$_3$) δ=8.24 (d, J=2.4 Hz, 1H), 8.14 (d, J=2.4 Hz, 1H), 4.67 (s, 2H), 2.56 (s, 3H).

Step 4: To a solution of sodium hydride (1.00 g, 25.0 mmol, 60% purity, 1.10 eq) in N,N-dimethylformamide (50.0 mL) was added diethyl 2-acetamidomalonate (5.92 g, 27.3 mmol, 1.20 eq) at 0° C. After 5 mins, 1-chloro-3-(chloromethyl)-2-methyl-5-nitrobenzene (5.00 g, 22.7 mmol, 1.00 eq) was added. Then the mixture was stirred at 25° C. for 10 h. The reaction mixture was quenched by addition water, then extracted with ethyl acetate. The combined organic layers were washed with brine, dried over sodium sulfate, filtered and concentrated under reduced pressure to give diethyl 2-acetamido-2-(3-chloro-2-methyl-5-nitrobenzyl)malonate. $^1$H NMR (400 MHz, CDCl$_3$) δ=8.13 (d, J=2.4 Hz, 1H), 7.77 (d, J=2.4 Hz, 1H), 6.60 (s, 1H), 4.33-4.26 (m, 4H), 3.85 (s, 2H), 2.35 (s, 3H), 2.04 (s, 3H), 1.33-1.30 (m, 6H).

Step 5: A mixture of diethyl 2-acetamido-2-(3-chloro-2-methyl-5-nitrobenzyl)malonate (9.20 g, 23.0 mmol, 1.00 eq) in hydrochloric acid (24.3 g, 240 mmol, 40.0 mL, 36% purity, 10.5 eq) was stirred at 110° C. for 10 h. The reaction mixture was filtered and the filtrate was lyophilized to afford 2-amino-3-(3-chloro-2-methyl-5-nitrophenyl)propanoic acid. $^1$H NMR (400 MHz, DMSO-d$_6$) δ=8.85 (br s, 2H), 8.62-8.54 (m, 1H), 8.22 (d, J=2.4 Hz, 1H), 8.16 (d, J=2.4 Hz, 1H), 4.13 (br t, J=7.2 Hz, 1H), 3.38-3.35 (m, 2H), 2.47 (s, 3H).

Step 6: To a solution of 2-amino-3-(3-chloro-2-methyl-5-nitrophenyl)propanoic acid (3.00 g, 11.6 mmol, 1.00 eq) in tetrahydrofuran (30.0 mL) was added borane dimethyl sulfide complex (10.0 M, 3.48 mL, 3.00 eq). Then the mixture was stirred at 70° C. for 10 h. The reaction mixture was quenched by addition methanol at 0° C., then concentrated under reduced pressure to give 2-amino-3-(3-chloro-2-methyl-5-nitrophenyl)propan-1-ol. MS (ESI) m/z 245.1 [M+H]$^+$.

Step 7: To a solution of 2-amino-3-(3-chloro-2-methyl-5-nitrophenyl)propan-1-ol (3.00 g, 12.3 mmol, 1.00 eq) and triethylamine (1.49 g, 14.7 mmol, 2.05 mL, 1.20 eq) in tetrahydrofuran (30.0 mL) was added 2-chloroacetyl chloride (1.66 g, 14.7 mmol, 1.17 mL, 1.20 eq) at 0° C. Then the mixture was stirred at 25° C. for 1 h, quenched by addition water, and then extracted with ethyl acetate. The combined organic layers were washed with brine, dried over sodium sulfate, filtered and concentrated under reduced pressure to give a residue. The residue was purified by column chromatography to afford 2-chloro-N-(1-(3-chloro-2-methyl-5-nitrophenyl)-3-hydroxypropan-2-yl)acetamide. $^1$H NMR (400 MHz, CDCl$_3$) δ=8.15 (d, J=2.4 Hz, 1H), 7.99 (d, J=2.4 Hz, 1H), 7.05 (br d, J=8.0 Hz, 1H), 4.26-4.15 (m, 1H), 4.04 (d, J=5.6 Hz, 2H), 3.78-3.70 (m, 1H), 3.69-3.62 (m, 1H), 3.10 (dd, J=7.6, 9.6 Hz, 2H), 2.56 (s, 3H).

Step 8: To a solution of 2-chloro-N-(1-(3-chloro-2-methyl-5-nitrophenyl)-3-hydroxypropan-2-yl)acetamide (1.20 g, 3.74 mmol, 1.00 eq) in t-butyl alcohol (3.00 mL) was added potassium tert-butoxide (839 mg, 7.47 mmol, 2.00 eq). Then the mixture was stirred at 100° C. for 0.5 h. The reaction mixture was concentrated under reduced pressure to remove t-nutyl alcohol. The residue was diluted with water and extracted with ethyl acetate. The combined organic layers were washed with brine, dried over sodium sulfate, filtered and concentrated under reduced pressure to give a residue. The residue was purified by column chromatography to afford 5-(3-chloro-2-methyl-5-nitrobenzyl)morpholin-3-one. $^1$H NMR (400 MHz, DMSO-d$_6$) δ=8.17 (d, J=2.4 Hz, 1H), 8.13 (s, 1H), 8.02 (d, J=2.4 Hz, 1H), 4.00 (d, J=5.0 Hz, 2H), 3.63-3.54 (m, 2H), 3.50-3.42 (m, 1H), 3.08-2.97 (m, 2H), 2.44 (s, 3H).

Step 9: To a solution of 5-(3-chloro-2-methyl-5-nitrobenzyl)morpholin-3-one (240 mg, 843 umol, 1.00 eq) in tetrahydrofuran (3.00 mL) was added borane dimethyl sulfide complex (10.0 M, 253 uL, 3.00 eq). Then the mixture was stirred at 70° C. for 10 h. The reaction mixture was quenched by addition methanol, then concentrated under reduced pressure to give 3-(3-chloro-2-methyl-5-nitrobenzyl)morpholine. MS (ESI) m/z 271.2 [M+H]$^+$.

Step 10: To a solution of 3-(3-chloro-2-methyl-5-nitrobenzyl)morpholine (0.150 g, 554 umol, 1.00 eq) and formaldehyde (981 mg, 12.1 mmol, 900 uL, 37% purity, 21.8 eq) in methanol (2.00 mL) was added acetic acid (66.6 mg, 1.11 mmol, 63.4 uL, 2.00 eq). After 0.5 h, sodium cyanoborohydride (174 mg, 2.77 mmol, 5.00 eq) was added and the mixture was stirred at 25° C. for 10 h. The reaction mixture was quenched by addition water, and then extracted with dichloromethane. The combined organic layers were washed with brine, dried over sodium sulfate, filtered and concentrated under reduced pressure to give a residue. The crude product was purified by reversed-phase HPLC to afford 3-(3-chloro-2-methyl-5-nitrobenzyl)-4-methylmorpholine. $^1$H NMR (400 MHz, CDCl$_3$) δ=8.08 (d, J=2.4 Hz, 1H), 7.87 (d, J=2.4 Hz, 1H), 3.78 (br dd, J=3.4, 5.2 Hz, 2H), 3.50-3.37 (m, 2H), 3.21 (br dd, J=4.2, 13.8 Hz, 1H), 2.97-2.79 (m, 3H), 2.71-2.64 (m, 1H), 2.56 (s, 3H), 2.43 (s, 3H).

Step 11: A mixture of 3-(3-chloro-2-methyl-5-nitrobenzyl)-4-methylmorpholine (0.140 g, 492 umol, 1.00 eq), ferrous powder (137 mg, 2.46 mmol, 5.00 eq) and ammonium chloride (26.3 mg, 492 umol, 1.00 eq) in ethyl alcohol (2.00 mL) and water (1.00 mL) was stirred at 60° C. for 10 h. The reaction mixture was concentrated under reduced pressure to remove ethyl alcohol. The residue was diluted with water and extracted with ethyl acetate. The combined organic layers were washed with brine, dried over sodium sulfate, filtered and concentrated under reduced pressure to give 3-chloro-4-methyl-5-((4-methylmorpholin-3-yl)methyl)aniline. $^1$H NMR (400 MHz, CDCl$_3$) δ=6.55 (d, J=2.4 Hz, 1H), 6.29 (d, J=2.4 Hz, 1H), 3.74-3.58 (m, 3H), 3.46 (br dd, J=2.0, 11.4 Hz, 1H), 3.27-3.20 (m, 1H), 3.06-3.01 (m, 1H), 2.69 (td, J=3.2, 11.8 Hz, 1H), 2.39 (s, 3H), 2.34 (br t, J=3.8 Hz, 2H), 2.18 (s, 3H).

Step 12: To a solution of 3-chloro-4-methyl-5-((4-methylmorpholin-3-yl)methyl)aniline (0.100 g, 393 umol, 1.00 eq) and potassium carbonate (109 mg, 785 umol, 2.00 eq) in acetone (2.00 mL) was added phenyl carbonochloridate (73.8 mg, 471 umol, 59.0 uL, 1.20 eq) at 0° C. Then the mixture was stirred at 25° C. for 10 h. The reaction mixture was diluted with water and extracted with ethyl acetate. The combined organic layers were washed with brine, dried over sodium sulfate, filtered and concentrated under reduced pressure to give phenyl (3-chloro-4-methyl-5-((4-methylmorpholin-3-yl) methyl)phenyl)carbamate. MS (ESI) m/z 375.2 [M+H]$^+$.

Step 13: To a solution of 3-(6-(hydroxymethyl)-1-oxoisoindolin-2-yl)piperidine-2,6-dione VIII (40.0 mg, 146 umol, 1.00 eq) and phenyl (3-chloro-4-methyl-5-((4-methylmorpholin-3-yl)methyl)phenyl)carbamate (60.0 mg, 160 umol, 1.10 eq) in dimethyl formamide (2.00 mL) was added sodium hydride (60.0%, dispersion in paraffin liquid) (11.5 mg, 288 umol, 60.0% purity, 1.97 eq) in portions at 0° C. The mixture was stirred at 25° C. for 1 h. The mixture was adjusted to pH=7 with hydrochloric acid (1 M) and filtered to give a solution. The solution was purified by Prep-HPLC. The desired fraction was collected and lyophilized to give a solid, which was further purified by Prep-HPLC. The desired fraction was collected and lyophilized to afford (2-(2,6-dioxopiperidin-3-yl)-3-oxoisoindolin-5-yl) methyl (3-chloro-4-methyl-5-((4-methylmorpholin-3-yl)methyl) phenyl)carbamate 150. $^1$H NMR (400 MHz, DMSO-$d_6$) δ=11.71 (br s, 1H), 11.00 (s, 1H), 9.95 (br s, 1H), 7.78 (s, 1H), 7.72-7.66 (m, 1H), 7.65-7.60 (m, 1H), 7.50 (s, 1H), 7.33-7.24 (m, 1H), 5.27 (s, 2H), 5.12 (dd, J=5.1, 13.2 Hz, 1H), 4.51-4.43 (m, 1H), 4.37-4.29 (m, 1H), 3.93 (br d, J=12.3 Hz, 1H), 3.88-3.78 (m, 1H), 3.68-3.58 (m, 1H), 3.56-3.48 (m, 1H), 3.47-3.38 (m, 2H), 3.29-3.13 (m, 1H), 3.12-2.92 (m, 1H), 2.92-2.89 (m, 3H), 2.89-2.84 (m, 1H), 2.60 (br d, J=17.3 Hz, 1H), 2.48-2.32 (m, 2H), 2.32-2.23 (m, 3H), 2.05-1.96 (m, 1H). MS (ESI) m/z 555.2 [M+H]$^+$ Compound 151:

Step 1: To a solution of propanamide (9.00 g, 123 mmol, 1.00 eq) in toluene (400 mL) was added chlorocarbonylsulfenylchloride (17.7 g, 135 mmol, 1.10 eq). The reaction mixture was allowed to stir at 100° C. for 5 h. The reaction mixture was concentrated under reduced pressure to give the crude product 5-ethyl-1,3,4-oxathiazol-2-one, which was used directly in next step without further purification. $^1$H NMR (400 MHz, DMSO-$d_6$) δ=2.59 (q, J=7.6 Hz, 2H), 1.09 (t, J=7.6 Hz, 3H).

Step 2: To a solution of 5-ethyl-1,3,4-oxathiazol-2-one (8.50 g, 64.8 mmol, 1.00 eq) in 1,2-dichlorobenzene (100 mL) was added ethyl prop-2-ynoate (25.4 g, 259 mmol, 25.4 mL, 4.00 eq), the reaction mixture was allowed to stir at 140° C. for 48 h. The reaction mixture was diluted with tert-butyl methyl ether (500 mL) and washed with saturated aqueous sodium bicarbonate (3×200 mL), the organic phase was washed with brine, dried over sodium sulfate, filtered and concentrated under reduced pressure. The residue was purified by column chromatography to afford a mixture of ethyl 3-ethylisothiazole-5-carboxylate/ethyl 3-ethylisothiazole-4-carboxylate (1/1). $^1$H NMR (400 MHz, DMSO-$d_6$) δ=9.55 (s, 1H), 7.72 (s, 1H), 4.35-4.16 (m, 2H), 2.98 (q, J=7.6 Hz, 1H), 2.77 (q, J=7.6 Hz, 1H), 1.28-1.13 (m, 6H). MS (ESI) m/z 186.0 [M+H]$^+$ Step 3: To a mixture of ethyl 3-ethylisothiazole-5-carboxylate and ethyl 3-ethylisothiazole-4-carboxylate (1.00 g, 5.40 mmol, 1.00 eq) in tetrahydrofuran (9 mL) was added a solution of lithium hydroxide monohydrate (453 mg, 10.8 mmol, 2.00 eq) in water (3 mL), the reaction mixture was stirred at 25° C. for 1 h. Tetrahydrofuran was removed under reduced pressure. The residue was diluted with water and adjusted pH=2-3 with 1 mol/L hydrochloric acid solution. The precipitate was formed and filtered to collect the solid, which was dried in vacuum to afford a mixture of 3-ethylisothiazole-5-carboxylic acid/3-ethylisothiazole-4-carboxylic acid (1/1), which was used for next step directly without further purification. $^1$H NMR (400 MHz, DMSO-$d_6$) δ=9.55 (s, 1H), 7.69 (s, 1H), 3.04 (q, J=7.6 Hz, 3H), 2.81 (q, J=7.6 Hz, 3H), 1.23 (td, J=7.6, 9.2 Hz, 6H).

Step 4: To a mixture of 3-ethylisothiazole-5-carboxylic acid/3-ethylisothiazole-4-carboxylic acid (100 mg, 636 umol, 1.00 eq) in dioxane (6 mL) was added triethylamine (193 mg, 1.91 mmol, 3.00 eq) and diphenylphosphoryl azide (262 mg, 954 umol, 206 uL, 1.50 eq), the mixture was stirred at 25° C. for 1 h, then 3-(6-(hydroxymethyl)-1-oxoisoindolin-2-yl)piperidine-2,6-dione VIII (174 mg, 636 umol, 1.00 eq) was added. The reaction mixture was allowed to stir at 110° C. for 2 h under nitrogen. The reaction mixture was concentrated under reduced pressure and diluted with water, extracted with ethyl acetate, the organic phase was washed with brine, dried over sodium sulfate, filtered and concentrated. The residue was purified by column chromatography to give crude product, which was purified by prep-HPLC to afford (2-(2,6-dioxopiperidin-3-yl)-3-oxoisoindolin-5-yl) methyl (3-methylisothiazol-5-yl)carbamate 151. $^1$H NMR (400 MHz, DMSO-$d_6$) δ=11.54 (br d, J=1.2 Hz, 1H), 11.00 (br s, 1H), 7.80 (s, 1H), 7.73-7.60 (m, 2H), 6.60 (s, 1H), 5.36 (s, 2H), 5.13 (dd, J=5.2, 13.2 Hz, 1H), 4.55-4.28 (m, 2H), 3.00-2.85 (m, 1H), 2.68-2.58 (m, 3H), 2.44-2.33 (m, 1H), 2.07-1.95 (m, 1H), 1.17 (t, J=7.6 Hz, 3H). MS (ESI) m/z 429.0 [M+H]$^+$ Compound 152:

Step 1: To a solution of 2-chloro-5-nitropyridine (5.00 g, 31.5 mmol, 1.00 eq), potassium trifluoro(prop-1-en-2-yl) borate (7.00 g, 47.3 mmol, 1.50 eq) and potassium carbonate (13.1 g, 94.6 mmol, 3.00 eq) in dioxane (50.0 mL) and water (10.0 mL) was added [1,1'-bis(diphenylphosphino)ferrocene]dichloropalladium(II) (2.58 g, 3.15 mmol, 0.100 eq) then evacuated with vacuum and back filled with nitrogen 3 times. The mixture was stirred at 80° C. for 2 h. The mixture was diluted with water and extracted with ethyl acetate. The combined organic layer was washed with brine and dried over sodium sulfate, filtered and concentrated to give crude product, which was purified by reversed-phase HPLC to give 5-nitro-2-(prop-1-en-2-yl)pyridine. MS (ESI) m/z 165.1 [M+H]$^+$ Step 2: To dichloromethane (20.0 mL) was added diethylzinc (1.00 M solution in toluene, 73.1 mL, 4.00 eq). The solution was cooled to –40° C. then diiodomethane (19.6 g, 73.1 mmol, 5.90 mL, 4.00 eq) in dichloromethane (10.0 mL) was added very slowly into the reaction mixture. The mixture was stirred at –40° C. for 30 min. Then trifluoroacetic acid (417 mg, 3.65 mmol, 271 uL, 0.200 eq) and N,N-dimethylacetamide (1.59 g, 18.3 mmol, 1.70 mL, 1.00 eq) in dichloromethane (5.00 mL) was added to and the mixture was stirred at –15° C. for another 0.5 h. Then 5-nitro-2-(prop-1-en-2-yl)pyridine (3.00 g, 18.3 mmol, 1.00 eq) in dichloromethane (10.0 mL) was added to at 0° C. The mixture was stirred at 20° C. for another 12 h, diluted with water and extracted with ethyl acetate. The combined organic layer was washed with brine and dried over sodium sulfate, filtered and concentrated to give crude product, which was purified by silica gel chromatography to give 2-(1-methylcyclopropyl)-5-nitropyridine. MS (ESI) m/z 179.0 [M+H]$^+$ Step 3: To a solution of 2-(1-methylcyclopropyl)-5-nitropyridine (500 mg, 2.81 mmol, 1.00 eq) in tetrahydrofuran (10.0 mL) was added Pd/C (100 mg, 10% purity) and stirred at 20° C. for 1 h under hydrogen (15 Psi). The mixture was filtered and the filtrate was concentrated in vacuum. The residue was purified by reversed-phase HPLC to give 6-(1-methylcyclopropyl)pyridin-3-amine. MS (ESI) m/z 149.3 [M+H]$^+$ Step 4: To a solution of 6-(1-methylcyclopropyl)pyridin-3-amine (40.0 mg, 269 umol, 1.00 eq) and pyridine (106 mg, 1.35 mmol, 108 uL, 5.00 eq) in Acetonitrile (1.00 mL) was added phenyl carbonochloridate (54.9 mg, 351 umol, 43.9 uL, 1.30 eq) at 0° C. The mixture was stirred at 20° C. for 2 h. The mixture was concentrated to give crude product and purified by reversed-phase HPLC to give phenyl (6-(1-methylcyclopropyl)pyridin-3-yl)carbamate. MS (ESI) m/z 269.1 [M+H]+

Step 5: To a solution of 3-(6-(hydroxymethyl)-1-oxoisoindolin-2-yl)piperidine-2,6-dione VIII (46.5 mg, 169 umol, 1.00 eq) and phenyl (6-(1-methylcyclopropyl)pyridin-3-yl) carbamate (50.0 mg, 186 umol, 1.10 eq) in dimethyl formamide (1.00 mL) was added sodium hydride (13.5 mg, 339 umol, 60% purity, 2.00 eq) at 0° C. The mixture was stirred at 20° C. for 1 h. The mixture was quenched by 1M hydrochloric acid, purified by prep-HPLC (and lyophilized to give (2-(2,6-dioxopiperidin-3-yl)-3-oxoisoindolin-5-yl) methyl (6-(1-methylcyclopropyl)pyridin-3-yl)carbamate 152. $^1$H NMR (400 MHz, DMSO-$d_6$) δ=11.00 (s, 1H), 10.51-10.25 (m, 1H), 8.64 (br d, J=2.9 Hz, 1H), 8.17-7.96 (m, 1H), 7.81 (s, 1H), 7.73-7.68 (m, 1H), 7.67-7.64 (m, 1H), 7.60 (br s, 1H), 5.32 (s, 2H), 5.13 (dd, J=5.0, 13.3 Hz, 1H), 4.52-4.45 (m, 1H), 4.38-4.31 (m, 1H), 2.96-2.87 (m, 1H), 2.61 (br d, J=17.8 Hz, 1H), 2.45-2.36 (m, 1H), 2.07-1.97 (m, 1H), 1.48 (s, 3H), 1.17 (br s, 2H), 0.91 (br d, J=2.8 Hz, 2H). MS (ESI) m/z 449.2 [M+H]+

Compound 153:

Step 1: A mixture of 3-(tert-butyl)aniline (500 mg, 3.35 mmol, 1.00 eq), phenyl carbonochloridate (787 mg, 5.03 mmol, 629 uL, 1.50 eq) and pyridine (795 mg, 10.1 mmol, 811 uL, 3.00 eq) in Acetonitrile (5.00 mL) was stirred at 25° C. for 12 h. The mixture was concentrated to give crude product. The crude product was purified by reversed-phase HPLC. The desired fraction was collected and lyophilized to give phenyl (3-(tert-butyl)phenyl)carbamate. $^1$H NMR (400 MHz, DMSO-$d_6$) δ=10.13 (br s, 1H), 7.59 (br s, 1H), 7.47-7.40 (m, 2H), 7.33 (br d, J=8.1 Hz, 1H), 7.29-7.19 (m, 4H), 7.09 (br d, J=7.6 Hz, 1H), 1.27 (s, 9H).

Step 2: To a mixture of phenyl (3-(tert-butyl)phenyl) carbamate (94.3 mg, 350 umol, 1.20 eq) and 3-(6-(hydroxymethyl)-1-oxoisoindolin-2-yl)piperidine-2,6-dione VIII (80.0 mg, 292 umol, 1.00 eq) in dimethyformamide (2.00 mL) was added sodium hydride (17.5 mg, 438 umol, 60% purity, 1.50 eq) in one portion at 0° C. The mixture was stirred at 20° C. for 1 h. The mixture was quenched with 1 M hydrochloric acid and filtered. The filtrate was purified by prep-HPLC and lyophilized to give (2-(2,6-dioxopiperidin-3-yl)-3-oxoisoindolin-5-yl)methyl (3-(tert-butyl)phenyl)carbamate 153. $^1$H NMR (400 MHz, DMSO-$d_6$) δ=10.99 (s, 1H), 9.71 (br s, 1H), 7.79 (s, 1H), 7.71-7.60 (m, 2H), 7.51 (br s, 1H), 7.30 (br d, J=7.7 Hz, 1H), 7.19 (t, J=7.9 Hz, 1H), 7.03 (br d, J=7.6 Hz, 1H), 5.27 (s, 2H), 5.13 (br dd, J=5.0, 13.2 Hz, 1H), 4.51-4.42 (m, 1H), 4.39-4.29 (m, 1H), 2.98-2.84 (m, 1H), 2.60 (br d, J=17.1 Hz, 1H), 2.40 (dq, J=4.4, 13.2 Hz, 1H), 2.06-1.96 (m, 1H), 1.24 (s, 9H). MS (ESI) m/z 450.2 [M+H]+

Compound 154:

Step 1: A mixture of 4-(trifluoromethoxy)aniline (400 mg, 2.26 mmol, 305 uL, 1.00 eq), phenyl carbonochloridate (389 mg, 2.48 mmol, 311 uL, 1.10 eq) and pyridine (536 mg, 6.77 mmol, 547 uL, 3.00 eq) in Acetonitrile (3.00 mL) was stirred at 25° C. for 2 h. The mixture was concentrated to give crude product, which was purified by reversed-phase HPLC. The desired fraction was collected and lyophilized to give phenyl (4-(trifluoromethoxy)phenyl)carbamate. MS (ESI) m/z 298.0 [M+H]+

Step 2: To a mixture of phenyl (4-(trifluoromethoxy) phenyl)carbamate (141 mg, 474 umol, 1.30 eq) and 3-(6-(hydroxymethyl)-1-oxoisoindolin-2-yl)piperidine-2,6-dione VIII (100 mg, 365 umol, 1.00 eq) in dimethyformamide (2.00 mL) was added sodium hydride (29.2 mg, 729 umol, 60% purity, 2.00 eq) in one portion at 0° C. The mixture was stirred at 25° C. for 1 h. The mixture was quenched with 1 M hydrochloric acid and filtered. The filtrate was purified by prep-HPLC and lyophilized to give (2-(2,6-dioxopiperidin-3-yl)-3-oxoisoindolin-5-yl)methyl (4-(trifluoromethoxy) phenyl)carbamate 154. $^1$H NMR (400 MHz, DMSO-$d_6$) δ=11.02 (s, 1H), 10.04 (s, 1H), 7.82 (s, 1H), 7.72-7.68 (m, 1H), 7.66-7.64 (m, 1H), 7.58 (d, J=9.2 Hz, 2H), 7.32 (d, J=8.4 Hz, 2H), 5.28 (s, 2H), 5.14 (dd, J=5.2, 13.4 Hz, 1H), 4.48 (d, J=17.6 Hz, 1H), 4.36 (d, J=17.4 Hz, 1H), 2.98-2.86 (m, 1H), 2.66-2.56 (m, 1H), 2.48-2.36 (m, 1H), 2.08-1.98 (m, 1H). MS (ESI) m/z 478.1 [M+H]+

Compound 155:

Step 1: To a solution of 4-phenylpyridin-2-amine (500 mg, 2.94 mmol, 1.00 eq) in Acetonitrile (10.0 mL) was added pyridine (1.16 g, 14.6 mmol, 1.19 mL, 5.00 eq) and phenyl carbonochloridate (597 mg, 3.82 mmol, 478 uL, 1.30 eq). The mixture was stirred at 25° C. for 0.5 h. The reaction mixture was concentrated under reduced pressure to give a residue. The crude product was triturated with water (10.0 ml) and filtered. The filter cake was washed with water and dried to give phenyl (4-phenylpyridin-2-yl)carbamate. $^1$H NMR (400 MHz, DMSO-$d_6$) δ=10.86 (s, 1H), 8.40 (d, J=5.3 Hz, 1H), 8.13 (d, J=0.9 Hz, 1H), 7.77-7.70 (m, 2H), 7.53-7.49 (m, 3H), 7.47-7.43 (m, 3H), 7.30-7.22 (m, 3H).

Step 2: To a solution of 3-(6-(hydroxymethyl)-1-oxoisoindolin-2-yl)piperidine-2,6-dione VIII (80.0 mg, 291 umol, 1.00 eq) in dimethyl formamide (2.00 mL) was added phenyl (4-phenylpyridin-2-yl)carbamate (127 mg, 437 umol, 1.50 eq) and sodium hydride (23.3 mg, 583 umol, 60% purity, 2.00 eq) at 0° C. The mixture was stirred at 0° C. for 0.5 h. The reaction mixture was quenched with hydrochloric acid (1.00M, 1.00 ml) to give a solution. The solution was purified by prep-HPLC and lyophilized to give (2-(2,6-dioxopiperidin-3-yl)-3-oxoisoindolin-5-yl)methyl (4-phenylpyridin-2-yl)carbamate 155 d. $^1$H NMR (400 MHz, DMSO-$d_6$) δ=11.07-10.92 (m, 2H), 8.37 (d, J=5.5 Hz, 1H), 8.07 (d, J=1.1 Hz, 1H), 7.85 (s, 1H), 7.78-7.63 (m, 4H), 7.61-7.47 (m, 4H), 5.37 (s, 2H), 5.13 (dd, J=5.1, 13.3 Hz, 1H), 4.52-4.43 (m, 1H), 4.40-4.30 (m, 1H), 2.98-2.85 (m, 1H), 2.65-2.57 (m, 1H), 2.41 (br dd, J=4.4, 13.1 Hz, 1H), 2.06-1.97 (m, 1H). MS (ESI) m/z 471.2 [M+H]+.

Compound 156:

Step 1: To a mixture of 2-chloro-5-nitropyridine (652 mg, 4.11 mmol, 1.00 eq) and (S)-2-methylpyrrolidine hydrochloride (500 mg, 4.11 mmol, 1.00 eq, HCl) in dimethylformamide (2.00 mL) was added potassium carbonate in one portion at 25° C. The mixture was stirred at 60° C. for 2 h. The reaction mixture was diluted with water and extracted with ethyl acetate. The organic phase was separated, washed with brine, dried over anhydrous sodium sulfate, filtered and concentrated under reduced pressure to give (S)-2-(2-methylpyrrolidin-1-yl)-5-nitropyridine. MS (ESI) m/z 208.2 [M+H]+.

Step 2: To a solution of (S)-2-(2-methylpyrrolidin-1-yl)-5-nitropyridine (620 mg, 2.99 mmol, 1.00 eq) in methanol (6.00 mL) and water (3.00 mL) was added iron powder (835 mg, 15.0 mmol, 5.00 eq) and ammonium chloride (800 mg, 15.0 mmol, 5.00 eq) in one portion at 25° C. and stirred at 80° C. for 2 h. The mixture was filtered to give a filtrate, which was concentrated under reduced pressure to give a residue. The residue was diluted with water and extracted with ethyl acetate. The organic phase was separated, washed with brine, dried over anhydrous sodium sulfate, filtered and concentrated under reduced pressure to give (S)-6-(2-methylpyrrolidin-1-yl)pyridin-3-amine.

Step 3: To a solution of (S)-6-(2-methylpyrrolidin-1-yl) pyridin-3-amine (500 mg, 2.82 mmol, 1.00 eq) and pyridine (669 mg, 8.46 mmol, 683 uL, 3.00 eq) in Acetonitrile (2.00 mL) was added phenyl carbonochloridate (486 mg, 3.10 mmol, 389 uL, 1.10 eq) at 25° C. The reaction mixture was stirred at 25° C. for 2 h. The reaction mixture was concentrated to give a residue, which was purified by reversed phase and lyophilized to give (S)-phenyl (6-(2-methylpyrrolidin-1-yl)pyridin-3-yl)carbamate. MS (ESI) m/z 298.2 [M+H]$^+$.

Step 4: To a mixture of 3-(6-(hydroxymethyl)-1-oxoisoindolin-2-yl)piperidine-2,6-dione VIII (80.0 mg, 292 umol, 1.00 eq) and (S)-phenyl (6-(2-methylpyrrolidin-1-yl)pyridin-3-yl)carbamate (113 mg, 379 umol, 1.30 eq) in dimethyl formamide (2.00 mL) was added sodium hydride (23.3 mg, 583 umol, 60% purity, 2.00 eq) at 0° C. The reaction mixture was stirred at 25° C. for 2 h. The reaction mixture was added hydrochloric acid (1 M, 2.00 mL) and filtered to give a filter cake. The filter cake was purified by prep-HPLC and lyophilized to give (2-(2,6-dioxopiperidin-3-yl)-3-oxoisoindolin-5-yl)methyl (6-((S)-2-methylpyrrolidin-1-yl)pyridin-3-yl)carbamate 156.1H NMR (400 MHz, DMSO-d$_6$) δ=13.74 (br s, 1H), 11.00 (s, 1H), 10.16 (br s, 1H), 8.20 (br s, 1H), 7.98 (br d, J=9.6 Hz, 1H), 7.80 (s, 1H), 7.72-7.62 (m, 2H), 7.18 (br d, J=9.8 Hz, 1H), 5.30 (s, 2H), 5.14 (dd, J=5.0, 13.4 Hz, 1H), 4.48 (s, 1H), 4.36 (br d, J=17.6 Hz, 1H), 4.32 (br s, 1H), 3.68 (br t, J=8.8 Hz, 1H), 3.50-3.36 (m, 1H), 3.04-2.80 (m, 1H), 2.62 (br d, J=17.4 Hz, 1H), 2.48-2.34 (m, 1H), 2.20-1.98 (m, 4H), 1.84-1.72 (m, 1H), 1.18 (d, J=6.4 Hz, 3H). MS (ESI) m/z 478.2 [M+H]$^+$.

Compound 157

Step 1: To a solution of 2-chloro-5-nitropyridine (652 mg, 4.11 mmol, 1.00 eq) and (R)-2-methylpyrrolidine hydrochloride (500 mg, 4.11 mmol, 1.00 eq, HCl) in dimethyl formamide (3.00 mL) was added potassium carbonate (1.70 g, 12.3 mmol, 3.00 eq) and stirred at 60° C. for 2 h. The mixture was diluted with water (50.0 mL) and extracted with ethyl acetate (3×30.0 mL). The combined organic layer was washed with brine (20.0 mL) and dried over anhydrous sodium sulfate, filtered and concentrated to give (R)-2-(2-methylpyrrolidin-1-yl)-5-nitropyridine. $^1$H NMR (400 MHz, DMSO-d$_6$) δ=8.96 (d, J=2.7 Hz, 1H), 8.18 (dd, J=2.8, 9.5 Hz, 1H), 6.57 (br s, 1H), 4.51-4.13 (m, 1H), 3.61 (br s, 1H), 3.50-3.39 (m, 1H), 2.16-1.94 (m, 3H), 1.73 (br s, 1H), 1.19 (br d, J=6.2 Hz, 3H). MS (ESI) m/z 208.0 [M+H]$^+$ Step 2: To a solution of (R)-2-(2-methylpyrrolidin-1-yl)-5-nitropyridine (900 mg, 4.34 mmol, 1.00 eq) in tetrahydrofuran (10.0 mL) was added Pd/C (100 mg, 10% purity) in portions under nitrogen. The mixture was stirred at 20° C. for 1 h under hydrogen (15 Psi). The mixture was filtered and the filtrate was concentrated to give (R)-6-(2-methylpyrrolidin-1-yl)pyridin-3-amine. MS (ESI) m/z 178.2 [M+H]$^+$ Step 3: To a solution of (R)-6-(2-methylpyrrolidin-1-yl)pyridin-3-amine (770 mg, 4.34 mmol, 1.00 eq) and pyridine (1.72 g, 21.7 mmol, 1.75 mL, 5.00 eq) in Acetonitrile (10.0 mL) was added phenyl carbonochloridate (884 mg, 5.65 mmol, 707 uL, 1.30 eq) dropwise at 0° C. The mixture was stirred at 20° C. for 2 h. The mixture was concentrated and purified by reversed-phase HPLC to give (R)-phenyl (6-(2-methylpyrrolidin-1-yl)pyridin-3-yl)carbamate. MS (ESI) m/z 298.1 [M+H]$^+$ Step 4: To a solution of 3-(6-(hydroxymethyl)-1-oxoisoindolin-2-yl)piperidine-2,6-dione VIII (80.0 mg, 292 umol, 1.00 eq) and (R)-phenyl (6-(2-methylpyrrolidin-1-yl)pyridin-3-yl)carbamate (113 mg, 379 umol, 1.30 eq) in dimethyl formamide (1.00 mL) was added sodium hydride (23.3 mg, 583 umol, 60% purity, 2.00 eq) in portions at 0° C. The mixture was stirred at 20° C. for 1 h. The mixture was quenched by 1 M hydrochloric acid, purified by prep-HPLC and lyophilized to give (2-(2,6-dioxopiperidin-3-yl)-3-oxoisoindolin-5-yl)methyl (6-((R)-2-methylpyrrolidin-1-yl)pyridin-3-yl)carbamate 157. $^1$H NMR (400 MHz, DMSO-d$_6$) δ=11.00 (s, 1H), 9.41 (br s, 1H), 8.16 (s, 1H), 8.09 (br s, 1H), 7.78 (s, 1H), 7.65 (q, J=7.8 Hz, 2H), 7.57 (br d, J=7.2 Hz, 1H), 6.41 (d, J=9.0 Hz, 1H), 5.24 (s, 2H), 5.13 (dd, J=5.0, 13.3 Hz, 1H), 4.53-4.42 (m, 1H), 4.40-4.30 (m, 1H), 4.10-4.01 (m, 1H), 3.43 (br d, J=2.3 Hz, 1H), 3.20 (br s, 1H), 2.96-2.87 (m, 1H), 2.63 (br d, J=2.6 Hz, 1H), 2.41 (br dd, J=4.3, 13.3 Hz, 1H), 2.07-1.96 (m, 3H), 1.95-1.87 (m, 1H), 1.69-1.59 (m, 1H), 1.13 (d, J=6.2 Hz, 3H). MS (ESI) m/z 478.2 [M+H]$^+$ Compound 158: To a mixture of (1s,3s)-3-phenylcyclobutanamine (100 mg, 679 umol, 294 uL, 1.00 eq) and pyridine (161 mg, 2.04 mmol, 164 uL, 3.00 eq) in acetonitrile (2.00 mL) was added phenyl carbonochloridate (117 mg, 747 umol, 93.6 uL, 1.10 eq) dropwise. The mixture was stirred at 25° C. for 2 h. The mixture was concentrated to give crude product. The crude product was purified by reverse phase HPLC (column: spherical C18, 20-45 um, 100 Å, SW 120, mobile phase: [water (0.1% Formic Acid)-ACN]). The desired fraction was collected and lyophilized to give phenyl ((1s,3s)-3-phenylcyclobutyl)carbamate (120 mg, 449 umol, 66% yield) as a yellow solid. MS (ESI) m/z 268.0 [M+H]$^+$ To a mixture of phenyl ((1s,3s)-3-phenylcyclobutyl)carbamate (120 mg, 449 umol, 1.00 eq) and 3-(6-(hydroxymethyl)-1-oxoisoindolin-2-yl)piperidine-2,6-dione I (148 mg, 539 umol, 1.20 eq) in dimethyl formamide (1.00 mL) was added sodium hydride (35.9 mg, 898 umol, 60% purity, 2.00 eq) at 0° C. The mixture was stirred at 20° C. for 1 h. The mixture was quenched with 1 M hydrochloric and filtered. The filtrate was purified by prep-HPLC (column: Phenomenex Synergi C18 150*25 mm*10 um; mobile phase: [water (0.225% FA)-ACN]; B %: 31%-61%, 10 min) and lyophilized to give (2-(2,6-dioxopiperidin-3-yl)-3-oxoisoindolin-5-yl)methyl ((1s,3s)-3-phenylcyclobutyl)carbamate #158 (79.18 mg, 177 umol, 39% yield) as a white solid. $^1$H NMR (400 MHz, DMSO-d$_6$) δ=10.98 (br s, 1H), 7.72 (s, 1H), 7.68 (br d, J=8.3 Hz, 1H), 7.62 (s, 2H), 7.32-7.24 (m, 4H), 7.22-7.16 (m, 1H), 5.18-5.12 (m, 3H), 4.50-4.44 (m, 1H), 4.38-4.30 (m, 1H), 4.06-3.96 (m, 1H), 3.14-3.04 (m, 1H), 2.98-2.88 (m, 1H), 2.66-2.58 (m, 3H), 2.46-2.38 (m, 1H), 2.08-1.98 (m, 3H). MS (ESI) m/z 448.1 [M+H]$^+$ Compound #159: To a solution of 3-phenylcyclobutanamine (100 mg, 544 umol, 1.00 eq, hydrochloric acid) and pyridine (215 mg, 2.72 mmol, 219 uL, 5.00 eq) in acetonitrile (2.00 mL) was added phenyl carbonochloridate (102 mg, 653 umol, 81.8 uL, 1.20 eq), the mixture was stirred at 25° C. for 1 h. The reaction mixture was concentrated to give a residue. The residue was purified by reverse phase HPLC (column: spherical C18, 20-45 um, 100 Å, SW 120, mobile phase: [water (0.1% Formic Acid)-ACN) to afford phenyl ((1r,3r)-3-phenylcyclobutyl)carbamate (100 mg, 374 umol, 68% yield) as a yellow solid. MS (ESI) m/z 268.1 [M+H]$^+$ To a solution of phenyl ((1r,3r)-3-phenylcyclobutyl)carbamate (93.6 mg, 350 umol, 1.20 eq) and 3-(6-(hydroxymethyl)-1-oxoisoindolin-2-yl)piperidine-2,6-dione I (80.0 mg, 291 umol, 1.00 eq) in dimethylformamide (1.00 mL) was added sodium hydride (23.3 mg, 583 umol, 60% purity, 2.00 eq). The mixture was stirred at 25° C. for 1 h. The reaction mixture was quenched with water (0.200 mL) and filtered to give a filtrate. The filtrate was purified by Prep-HPLC (column: Unisil 3-100 C18 Ultra 150*50 mm*3 um; mobile phase: [water (0.225% FA)-ACN]; B %: 35%-65%, 10 min) to afford (2-(2,6-dioxopiperidin-3-yl)-3-oxoisoindolin-5-yl)methyl((1r,3r)-3-phenylcyclobutyl)carbamate #159 (70.16 mg, 156 umol, 53% yield) as a white solid. $^1$H NMR (400 MHz, DMSO-d$_6$) δ=10.99 (br s, 1H), 7.84 (br d, J=7.2 Hz, 1H), 7.73 (s, 1H), 7.62 (s, 2H), 7.36-7.25 (m, 4H), 7.22-7.14 (m, 1H), 5.11 (br d, J=5.0 Hz, 3H), 4.52-4.41 (m, 1H), 4.39-4.28 (m, 1H), 4.20-4.06 (m, 1H), 3.58-3.46 (m, 1H), 2.99-2.86 (m, 1H), 2.62-2.57 (m, 1H), 2.41-2.30 (m, 5H), 2.06-1.96 (m, 1H). MS (ESI) m/z 448.0[M+H]$^+$ Compound #160: To a solution of m-toluidine (200 mg, 1.87 mmol, 202 uL, 1.00 eq) in acetonitrile (5.00 mL) was added pyridine (443 mg, 5.60 mmol, 452 uL, 3.00 eq) and phenyl carbonochloridate (351 mg, 2.24 mmol, 280 uL, 1.20 eq). The mixture was stirred at 25° C. for 1 h. The mixture was filtered to give filtrate. The filtrate was purified by reverse phase HPLC (column: spherical C18, 20-45 um, 100 Å, SW 120, mobile phase: [water (0.1% Formic Acid)-ACN). The desired fraction was collected and concentrated to give phenyl m-tolylcarbamate (395 mg, 1.56 mmol, 84% yield, 90% purity) as a white solid. MS (ESI) m/z 228.0 [M+H]$^+$ To a solution of 3-(6-(hydroxymethyl)-1-oxoisoindolin-2-yl)piperidine-2,6-dione I (80.0 mg, 292 umol, 1.00 eq) in dimethyl formamide (2.00 mL) was added phenyl m-tolylcarbamate (79.5 mg, 350 umol, 1.20 eq) and sodium hydride (23.3 mg, 583 umol, 60% purity, 2.00 eq) at 0° C. The mixture was stirred at 0° C. for 1 h. The mixture was adjusted pH=6 with formic acid (0.500 ml). The mixture was filtered to give filtrate. The filtrate was purified by prep-HPLC (column: Unisil 3-100 C18 Ultra 150*50 mm*3 um; mobile phase: [water (0.225% FA)-ACN]; B %: 30%-60%, 10 min). The desired fraction was collected and lyophilized to give (2-(2,6-dioxopiperidin-3-yl)-3-oxoisoindolin-5-yl) methyl m-tolylcarbamate #160 (62.88 mg, 152 umol, 52% yield, 99% purity) as a white solid. $^1$H NMR (400 MHz, DMSO-d$_6$) δ=11.14-10.74 (m, 1H), 9.73 (s, 1H), 7.79 (s, 1H), 7.71-7.66 (m, 1H), 7.65-7.59 (m, 1H), 7.30 (s, 1H), 7.26 (br d, J=8.3 Hz, 1H), 7.15 (t, J=7.8 Hz, 1H), 6.81 (d, J=7.5 Hz, 1H), 5.26 (s, 2H), 5.13 (dd, J=5.1, 13.3 Hz, 1H), 4.51-4.42 (m, 1H), 4.38-4.29 (m, 1H), 2.97-2.86 (m, 1H), 2.60 (td, J=2.0, 15.3 Hz, 1H), 2.40 (dt, J=8.8, 13.2 Hz, 1H), 2.25 (s, 3H), 2.06-1.95 (m, 1H). MS (ESI) m/z 408.1 [M+H]$^+$ Compound #161: To a solution of 4,6-dimethylpyridin-2-amine (1.00 g, 8.19 mmol, 1.00 eq) and pyridine (1.94 g, 24.5 mmol, 1.98 mL, 3.00 eq) in acetonitrile (10.0 mL) was added phenyl carbonochloridate (1.41 g, 9.00 mmol, 1.13 mL, 1.10 eq) dropwise at 0° C. The mixture was stirred at 20° C. for 1 h. The mixture was concentrated to give crude product and purified by silica gel chromatography (petroleum ether/ethyl acetate=1/0 to 20/1) to give phenyl (4,6-dimethylpyridin-2-yl)carbamate (600 mg, 2.48 mmol, 30% yield) as a white solid. MS (ESI) m/z 243.1 [M+H]$^+$ To a solution of 3-(6-(hydroxymethyl)-1-oxoisoindolin-2-yl)piperidine-2,6-dione I (80.0 mg, 292 umol, 1.00 eq) and phenyl (4,6-dimethylpyridin-2-yl)carbamate (77.7 mg, 321 umol, 1.10 eq) in dimethyl formamide (1.00 mL) was added sodium hydride (23.3 mg, 583 umol, 60% purity, 2.00 eq) in portions at 0° C. The mixture was stirred at 0° C. for 1 h. The mixture was quenched by 1M hydrochloric acid (1.00 mL) and filtered. The filtrate was purified by prep-HPLC (column: 3_Phenomenex Luna C18 75*30 mm*3 um; mobile phase: [water (0.05% HCl)-ACN]; B %: 18%-38%, 6.5 min) and lyophilized to give (2-(2,6-dioxopiperidin-3-yl)-3-oxoisoindolin-5-yl)methyl (4,6-dimethylpyridin-2-yl)carbamate #161 (34.72 mg, 79.7 umol, 27% yield, 97% purity) as a white solid. $^1$H NMR (400 MHz, DMSO-d$_6$) δ=10.98 (s, 1H), 10.60 (br s, 1H), 7.80 (s, 1H), 7.71-7.62 (m, 2H), 7.50 (s, 1H), 6.94 (s, 1H), 5.32 (s, 2H), 5.12 (dd, J=5.1, 13.2 Hz, 1H), 4.50-4.45 (m, 1H), 4.36-4.32 (m, 1H), 2.96-2.85 (m, 1H), 2.63-2.57 (m, 1H), 2.42 (s, 3H), 2.39 (br d, J=4.5 Hz, 1H), 2.32 (s, 3H), 2.05-1.97 (m, 1H). MS (ESI) m/z 423.1 [M+H]$^+$ Compound #162: To a solution of p-toluidine (200 mg, 1.87 mmol, 205 uL, 1.00 eq) in acetonitrile (5.00 mL) was added pyridine (443 mg, 5.60 mmol, 452 uL, 3.00 eq) and phenyl carbonochloridate (351 mg, 2.24 mmol, 281 uL, 1.20 eq). The mixture was stirred at 25° C. for 1 h. The mixture was filtered to give filtrate. The filtrate was purified by reversed-phase HPLC (column: spherical C18, 20-45 um, 100 Å, SW 120, mobile phase: [water (0.1% Formic acid)-ACN]). The desired fraction was collected and concentrated to give phenyl p-tolylcarbamate (375 mg, 1.49 mmol, 79% yield, 90% purity) as a white solid. MS (ESI) m/z 228.2 [M+H]$^+$ To a solution of 3-(6-(hydroxymethyl)-1-oxoisoindolin-2-yl)piperidine-2,6-dione I (80.0 mg, 292 umol, 1.00 eq) in dimethyl formamide (2.00 mL) was added phenyl p-tolylcarbamate (79.5 mg, 350 umol, 1.20 eq) and sodium hydride (23.3 mg, 583 umol, 60% purity, 2.00 eq) at 0° C. The mixture was stirred at 0° C. for 1 h. The mixture was adjusted pH=6 with formic acid (0.500 mL). The mixture was filtered to give filtrate. The filtrate was purified by prep-HPLC (column: Phenomenex luna C18 150*25 mm*10 um; mobile phase: [water (0.225% FA)-ACN]; B %: 29%-59%, 10 min) and further purified by prep-HPLC (column: Phenomenex Synergi C18 150*25 mm*10 um; mobile phase: [water (0.225% FA)-ACN]; B %: 34%-54%, 10 min). The desired fraction was collected and lyophilized to give (2-(2,6-dioxopiperidin-3-yl)-3-oxoisoindolin-5-yl) methyl p-tolylcarbamate #162 (50.45 mg, 122 umol, 42% yield, 99% purity) as a white solid. $^1$H NMR (400 MHz, DMSO-d$_6$) δ=10.95 (br s, 1H), 9.69 (br s, 1H), 7.79 (s, 1H), 7.71-7.60 (m, 2H), 7.35 (br d, J=8.1 Hz, 2H), 7.08 (br d, J=8.2 Hz, 2H), 5.25 (s, 2H), 5.13 (br dd, J=4.9, 13.3 Hz, 1H), 4.51-4.43 (m, 1H), 4.38-4.27 (m, 1H), 2.96-2.86 (m, 1H), 2.62 (br s, 1H), 2.40 (br dd, J=4.1, 13.1 Hz, 1H), 2.23 (s, 3H), 2.05-1.97 (m, 1H). MS (ESI) m/z 408.2 [M+H]$^+$ Compound #163: To a solution of 5-chloro-2-fluoroaniline (0.500 g, 3.43 mmol, 1.00 eq), pyridine (0.80 g, 10.1 mmol, 816 uL, 2.94 eq) in acetonitrile (3.00 mL) was added phenyl carbonochloridate (600 mg, 3.83 mmol, 480 uL, 1.12 eq). The mixture was stirred at 25° C. for 16 h. The reaction mixture was concentrated under reduced pressure to give a residue. The residue was purified by reversed-phase HPLC (column: spherical C18, 20-45 um, 100 Å, SW 120, mobile phase: [water (0.1% Formic acid)-ACN). Compound phenyl (5-chloro-2-fluorophenyl)carbamate (171 mg, 643 umol, 19% yield) was obtained as a white solid. $^1$H NMR (400 MHz, CDCl$_3$) δ=8.30-8.18 (m, 1H), 7.45-7.41 (m, 3H), 7.30 (br s, 1H), 7.21 (br d, J=7.7 Hz, 2H), 7.09-7.02 (m, 2H).

To a solution of phenyl (5-chloro-2-fluorophenyl)carbamate (85.3 mg, 321 umol, 1.10 eq) and 3-(6-(hydroxymethyl)-1-oxoisoindolin-2-yl)piperidine-2,6-dione I (80.0 mg, 292 umol, 1.00 eq) in dimethyl formamide (1.50 mL) was added sodium hydride (23.3 mg, 583 umol, 60% purity, 2.00 eq) at 0° C. The mixture was stirred at 0° C. for 1 h. The pH of the mixture was adjusted to around 6 by adding hydrochloric acid. The mixture was extracted with ethyl acetate (3×10.0 mL). The combined organic layers were dried over anhydrous sodium sulfate, filtered and concentrated under reduced pressure to give a residue. The residue was purified by prep-IPLC (column: Phenomenex Synergi C18 150*25 mm*10 um; mobile phase: [water (0.225% FA)-ACN]; B %: 29%-62%, 11 min) and lyophilized to afford (2-(2,6-dioxopiperidin-3-yl)-3-oxoisoindolin-5-yl)methyl (5-chloro-2-fluorophenyl)carbamate #163 (44.1 mg, 98.0 umol, 34% yield, 99% purity) as a white solid. $^1$H NMR (400 MHz, DMSO-d$_6$) δ=11.00 (br s, 1H), 9.83 (br s, 1H), 7.89-7.78 (m, 2H), 7.70-7.62 (m, 2H), 7.29 (dd, J=8.9, 10.5 Hz, 1H), 7.20-7.15 (m, 1H), 5.29 (s, 2H), 5.13 (dd, J=5.0, 13.3 Hz, 1H), 4.50-4.44 (m, 1H), 4.37-4.31 (m, 1H), 2.92 (ddd, J=5.4, 13.5, 17.5 Hz, 1H), 2.60 (td, J=2.0, 15.4 Hz, 1H), 2.43-2.35 (m, 1H), 2.05-1.97 (m, 1H). MS (ESI) m/z 446.2 [M+H]$^+$.

Compound #164: To a solution of 3-fluoro-4-nitrophenol (500 mg, 3.18 mmol, 1.00 eq) in dichloromethane (10.0 mL) was added trifluoromethanesulfonic anhydride (1.35 g, 4.77 mmol, 788 uL, 1.50 eq) and triethylamine (966 mg, 9.55 mmol, 1.33 mL, 3.00 eq) at 0° C., the mixture was stirred at 0° C. for 1 h. The mixture was diluted with water (20.0 mL), extracted with ethyl acetate (3×30.0 mL). The combined organic layers were concentrated to give a residue. The residue was purified by silica gel chromatography (Petroleum ether/Ethyl acetate=0/1, 20/1) to afford 3-fluoro-4-nitrophenyl trifluoromethanesulfonate (900 mg, 3.11 mmol, 98% yield) as yellow oil. $^1$H NMR (400 MHz, DMSO-d$_6$) δ=8.40 (t, J=8.9 Hz, 1H), 8.12 (dd, J=2.6, 11.1 Hz, 1H), 7.70-7.66 (m, 1H).

To a solution of 3-fluoro-4-nitrophenyl trifluoromethanesulfonate (800 mg, 2.77 mmol, 1.00 eq), cyclobutylboronic acid (415 mg, 4.15 mmol, 1.50 eq), cesium carbonate (2.00 M, 2.07 mL, 1.50 eq) in toluene (10.0 mL) were added [1,1-bis(diphenylphosphino)ferrocene]dichloropalladium (II) (162 mg, 221 umol, 0.080 eq). The mixture was stirred at 90° C. for 12 h under nitrogen atmosphere. The mixture was diluted with water (20.0 mL) and extracted with ethyl acetate (3×20.0 mL). The combined organic layers were dried over anhydrous sodium sulfate, filtered and concentrated under reduced pressure to give a residue. The residue was purified by silica gel chromatography (petroleum ether/ethyl acetate=1/0 to 1/1) to afford 4-cyclobutyl-2-fluoro-1-nitrobenzene (250 mg, 1.28 mmol, 46% yield) as yellow oil. $^1$H NMR (400 MHz, DMSO-d$_6$) δ=8.10 (t, J=8.3 Hz, 1H), 7.46 (dd, J=1.5, 12.8 Hz, 1H), 7.32-7.28 (m, 1H), 3.66 (quin, J=8.8 Hz, 1H), 2.36-2.28 (m, 2H), 2.18-2.12 (m, 2H), 2.04-1.98 (m, 1H), 1.88-1.80 (m, 1H).

To a mixture of 4-cyclobutyl-2-fluoro-1-nitrobenzene (250 mg, 1.28 mmol, 1.00 eq) in methanol (20.0 mL) was added palladium on carbon (25.0 mg, 10% purity) in one portion under hydrogen atmosphere. The mixture was stirred at 20° C. for 1 h. The mixture was filtered to give filter liquor, the filter liquor was concentrated under reduced pressure to afford 4-cyclobutyl-2-fluoroaniline (170 mg, 1.03 mmol, 80% yield) as brown oil. MS (ESI) m/z. 166.2 [M+H]$^+$ To a mixture of 4-cyclobutyl-2-fluoroaniline (170 mg, 1.03 mmol, 294 uL, 1.00 eq) and phenyl carbonochloridate (177 mg, 1.13 mmol, 142 uL, 1.10 eq) in acetonitrile (1.00 mL) was added pyridine (244 mg, 3.09 mmol, 249 uL, 3.00 eq). The mixture was stirred at 25° C. for 1 h. The reaction mixture was concentrated under reduced pressure to give a residue. The residue was purified by reversed phase-HPLC (column: spherical C18, 20-45 um, 100 Å, SW 120, mobile phase: [water (0.1% Formic Acid)-acetonitrile]) to afford phenyl (4-cyclobutyl-2-fluorophenyl)carbamate (210 mg, 736 umol, 72% yield) as a white solid. MS (ESI) m/z. 286.1 [M+H]$^+$ To a mixture of phenyl (4-cyclobutyl-2-fluorophenyl)carbamate (125 mg, 438 umol, 1.20 eq) and 3-(6-(hydroxymethyl)-1-oxoisoindolin-2-yl)piperidine-2,6-dione I (100 mg, 365 umol, 1.00 eq) in dimethylformamide (1.00 mL) was added sodium hydride (29.2 mg, 729 umol, 60% purity, 2.00 eq) at 0° C. The mixture was stirred at 25° C. for 1 h. The reaction mixture was added hydrochloric acid (1 M, 2.00 mL) and filtered to give a filtrate. The filtrate was purified by Prep-HPLC (column: Phenomenex Luna C18 150*25 mm*10 um; mobile phase: [water (0.225% FA)-ACN]; B %: 38%-68%, 10 min) to afford (2-(2,6-dioxopiperidin-3-yl)-3-oxoisoindolin-5-yl)methyl (4-cyclobutyl-2-fluorophenyl)carbamate #164 (61.21 mg, 132 umol, 36% yield) as a white solid. $^1$H NMR (400 MHz, DMSO-d$_6$) δ=10.98 (br s, 1H), 9.42 (br s, 1H), 7.80 (s, 1H), 7.68-7.62 (m, 2H), 7.52 (br t, J=8.0 Hz, 1H), 7.08 (dd, J=1.8, 12.0 Hz, 1H), 7.02 (dd, J=1.5, 8.3 Hz, 1H), 5.26 (s, 2H), 5.14 (dd, J=5.1, 13.4 Hz, 1H), 4.52-4.44 (m, 1H), 4.38-4.32 (m, 1H), 3.56-3.44 (m, 1H), 2.98-2.86 (m, 1H), 2.66-2.58 (m, 1H), 2.42 (dd, J=4.5, 13.1 Hz, 1H), 2.32-2.24 (m, 2H), 2.08-2.04 (m, 2H), 2.04-1.98 (m, 1H), 1.96-1.90 (m, 1H), 1.84-1.78 (m, 1H). MS (ESI) m/z. 466.1 [M+H]$^+$ Compound #165: To a solution of 4-chloro-3-methylaniline (500 mg, 3.53 mmol, 1.00 eq), pyridine (279 mg, 3.53 mmol, 285 uL, 1.00 eq) in acetonitrile (10.0 mL) was added phenyl carbonochloridate (608 mg, 3.88 mmol, 486 uL, 1.10 eq) at 0° C. The mixture was stirred at 20° C. for 1 h. The reaction mixture was concentrated under reduced pressure to give a residue. The residue was purified by reversed-phase HPLC (column: spherical C18, 20-45 um, 100 Å, SW 80, mobile phase: [water (0.1% Formic acid)-ACN]). Compound phenyl (4-chloro-3-methylphenyl)carbamate (1.34 g, 5.07 mmol, 72% yield, 99% purity) was obtained as a white solid. MS (ESI) m/z 262.0 [M+H]$^+$ To a solution of phenyl (4-chloro-3-methylphenyl)carbamate (84.0 mg, 321 umol, 1.10 eq) and 3-(6-(hydroxymethyl)-1-oxoisoindolin-2-yl)piperidine-2,6-dione I (80.0 mg, 292 umol, 1.00 eq) in dimethyl formamide (1.50 mL) was added sodium hydride (23.3 mg, 583 umol, 60% purity, 2.00 eq) at 0° C. The mixture was stirred at 0° C. for 1 h. The pH of the mixture was adjusted to around 6 by adding hydrochloric acid. The mixture was extracted with ethyl acetate (3×10.0 mL). The combined organic layers were dried over anhydrous sodium sulfate, filtered and concentrated under reduced pressure to give a residue. The residue was purified by prep-HPLC (column: Phenomenex Synergi C18 150*25 mm*10 um; mobile phase: [water (0.225% FA)-ACN]; B %: 32%-62%, 10 min) and lyophilized to afford (2-(2,6-dioxopiperidin-3-yl)-3-oxoisoindolin-5-yl)methyl (4-chloro-3-methylphenyl)carbamate #165 (83.9 mg, 189 umol, 64% yield, 99% purity) as a white solid. $^1$H NMR (400 MHz, DMSO-d$_6$) δ=10.98 (br s, 1H), 9.88 (s, 1H), 7.79 (s, 1H), 7.70-7.61 (m, 2H), 7.45 (s, 1H), 7.37-7.26 (m, 2H), 5.27 (s, 2H), 5.12 (dd, J=5.1, 13.3 Hz, 1H), 4.51-4.42 (m, 1H), 4.37-4.30 (m, 1H), 2.97-2.85 (m, 1H), 2.60 (td, J=2.0, 15.3 Hz, 1H), 2.46-2.37 (m, 1H), 2.28 (s, 3H), 2.05-1.97 (m, 1H). MS (ESI) m/z 442.1 [M+H]$^+$ Compound #166: To a solution of 1,3-difluoro-5-methyl-2-nitrobenzene (500 mg, 2.89 mmol, 1.00 eq) in tetrahydrofuran (5.00 mL) was added palladium/carbon (50.0 mg, 10% purity) under nitrogen. The mixture was stirred at 20° C. for 1 h under hydrogen (15 Psi). The mixture was filtered and the filtrate was concentrated under reduced pressure to give 2,6-difluoro-4-methylaniline (386 mg, 2.70 mmol, 93% yield) as yellow oil. $^1$H NMR (400 MHz, DMSO-d$_6$) δ=6.71-6.57 (m, 2H), 4.80 (br s, 2H), 2.09 (s, 3H). MS (ESI) m/z 144.2 [M+H]$^+$.

To a solution of 2,6-difluoro-4-methylaniline (350 mg, 2.45 mmol, 1.00 eq) and pyridine (580 mg, 7.34 mmol, 592 uL, 3.00 eq) in acetonitrile (5.00 mL) was added phenyl carbonochloridate (421 mg, 2.69 mmol, 337 uL, 1.10 eq) dropwise at 0° C. The mixture was then stirred at 25° C. for 1 h. The reaction mixture was concentrated under reduced pressure to give crude product. The crude product was purified by reversed-phase HPLC (column: spherical C18, 20-45 um, 100A, SW 40, mobile phase: [water (0.1% Formic Acid)-ACN]) and lyophilized to give phenyl (2,6-difluoro-4-methylphenyl) carbamate (435 mg, 1.65 mmol, 68% yield) as a white solid. $^1$H NMR (400 MHz, DMSO-d$_6$) δ=9.32 (s, 1H), 7.32-7.09 (m, 5H), 6.77-6.74 (m, 2H), 2.33 (s, 3H). MS (ESI) m/z 264.0 [M+H]$^+$.

To a solution of phenyl (2,6-difluoro-4-methylphenyl) carbamate (92.1 mg, 350 umol, 1.20 eq) and 3-(6-(hydroxymethyl)-1-oxoisoindolin-2-yl)piperidine-2,6-dione (80.0 mg, 292 umol, 1.00 eq) in dimethyl formamide (1.00 mL) was added sodium hydride (23.3 mg, 583 umol, 60% purity, 2.00 eq) in portions at 0° C. The mixture was stirred at 20° C. for 1 h. The mixture was quenched by 1 M hydrochloric acid (1.00 mL) and filtered. The filtrate was purified by prep-HPLC (column: 3_Phenomenex Luna C18 75*30 mm*3 um; mobile phase: [water (0.05% HCl)-ACN]; B %: 35%-45%, 6 min) to give (2-(2,6-dioxopiperidin-3-yl)-3-oxoisoindolin-5-yl)methyl (2,6-difluoro-4-methylphenyl)carbamate #166 (71.1 mg, 157 umol, 54% yield, 99% purity) as a white solid. $^1$H NMR (400 MHz, DMSO-d$_6$) δ=11.01 (s, 1H), 9.22 (br d, J=1.5 Hz, 1H), 7.76 (br s, 1H), 7.64 (s, 2H), 7.00 (d, J=8.7 Hz, 2H), 5.25 (s, 2H), 5.13 (dd, J=5.0, 13.3 Hz, 1H), 4.52-4.43 (m, 1H), 4.39-4.31 (m, 1H), 2.98-2.86 (m, 1H), 2.61 (br d, J=17.6 Hz, 1H), 2.41 (br dd, J=4.5, 13.1 Hz, 1H), 2.32 (s, 3H), 2.06-1.97 (m, 1H). MS (ESI) m/z 444.1 [M+H]$^+$.

Compound #167: To a solution of bromobenzene (1.00 g, 6.37 mmol, 671 uL, 1.00 eq), tert-butyl azetidin-3-ylcarbamate (2.66 g, 12.7 mmol, 2.00 eq, hydrochloric acid) and cesium carbonate (6.23 g, 19.1 mmol, 3.00 eq) in dioxane (20.0 mL) was added 4,5-bis(diphenylphosphino)-9,9-dimethylxanthene (553 mg, 955 umol, 0.15 eq) and tris(dibenzylideneacetone)dipalladium(0) (292 mg, 318 umol, 0.05 eq). The mixture was stirred at 90° C. for 12 h under nitrogen atmosphere. The reaction mixture was quenched by addition water (50.0 mL), and extracted with ethyl acetate (2×100 mL). The combined organic layers were dried over anhydrous sodium sulfate, filtered and concentrated under reduced pressure to give a residue. The residue was purified by column chromatography (SiO$_2$, petroleum ether/ethyl acetate=1/0 to 10/1) to give tert-butyl (1-phenylazetidin-3-yl)carbamate (1.20 g, 4.83 mmol, 76% yield) as a yellow solid. $^1$H NMR (400 MHz, DMSO-d$_6$) δ=7.50 (br d, J=7.2 Hz, 1H), 7.15 (t, J=7.8 Hz, 2H), 6.67 (t, J=7.3 Hz, 1H), 6.41 (d, J=7.9 Hz, 2H), 4.47-4.33 (m, 1H), 4.04 (t, J=7.3 Hz, 2H), 3.53 (t, J=6.8 Hz, 2H), 1.39 (s, 9H).

To a solution of tert-butyl (1-phenylazetidin-3-yl)carbamate (1.20 g, 4.83 mmol, 1.00 eq) in dichloromethane (20.0 mL) was added trifluoroacetic acid (6.16 g, 54.0 mmol, 4.00 mL, 11.2 eq). The mixture was stirred at 20° C. for 1 h. The reaction mixture was concentrated under reduced pressure to give 1-phenylazetidin-3-amine (700 mg, crude) as yellow oil. $^1$H NMR (400 MHz, DMSO-d$_6$) δ=8.33 (br s, 2H), 7.19 (dd, J=7.5, 8.4 Hz, 2H), 6.73 (t, J=7.3 Hz, 1H), 6.50 (d, J=7.6 Hz, 2H), 4.14-4.04 (m, 3H), 3.81-3.73 (m, 2H).

To a solution of 1-phenylazetidin-3-amine (700 mg, 4.72 mmol, 1.00 eq) in acetonitrile (20.0 mL) was added pyridine (2.94 g, 37.2 mmol, 3.00 mL, 7.87 eq). Then phenyl carbonochloridate (813 mg, 5.20 mmol, 650 uL, 1.10 eq) was added into the mixture at 0° C. The mixture was stirred at 20° C. for 1 h. The reaction mixture was concentrated under reduced pressure to give a residue. The residue was purified by reversed-phase HPLC (column: spherical C18, 20-45 um, 100 Å, SW 120, mobile phase: [water (0.1% Formic Acid)-ACN]) to give phenyl (1-phenylazetidin-3-yl)carbamate (1.01 g, 2.94 mmol, 62% yield, 78% purity) as a white solid. MS (ESI) m/z 269.0 [M+H]$^+$ To a solution of phenyl (1-phenylazetidin-3-yl)carbamate (86.1 mg, 321 umol, 1.10 eq) and 3-(6-(hydroxymethyl)-1-oxoisoindolin-2-yl)piperidine-2,6-dione I (80.0 mg, 292 umol, 1.00 eq) in dimethyl formamide (1.50 mL) was added sodium hydride (23.3 mg, 583 umol, 60% purity, 2.00 eq) at 0° C. The mixture was stirred at 0° C. for 1 h. The pH of the mixture was adjusted to around 6 by adding hydrochloric acid. The mixture was extracted with ethyl acetate (3×10.0 mL). The combined organic layers were dried over anhydrous sodium sulfate, filtered and concentrated under reduced pressure to give a residue. The residue was purified by prep-HPLC (column: Phenomenex Synergi C18 150*25 mm*10 um; mobile phase: [water (0.225% FA)-ACN]; B %: 24%-54%, 10 min), and lyophilized to afford (2-(2,6-dioxopiperidin-3-yl)-3-oxoisoindolin-5-yl)methyl(1-phenylazetidin-3-yl)carbamate #167 (62.7 mg, 138 umol, 47% yield, 99% purity, formate) as a white solid. $^1$H NMR (400 MHz, DMSO-d6) δ=10.99 (br s, 1H), 8.01 (br d, J=7.6 Hz, 1H), 7.72 (s, 1H), 7.61 (s, 2H), 7.15 (t, J=7.9 Hz, 2H), 6.68 (t, J=7.3 Hz, 1H), 6.43 (br d, J=7.8 Hz, 2H), 5.18-5.09 (m, 3H), 4.50-4.42 (m, 2H), 4.35-4.28 (m, 1H), 4.08 (t, J=7.3 Hz, 2H), 3.57 (br t, J=6.7 Hz, 2H), 2.96-2.86 (m, 1H), 2.63-2.57 (m, 1H), 2.40 (br d, J=8.6 Hz, 1H), 2.04-1.97 (m, 1H). MS (ESI) m/z 449.3 [M+H]$^+$ Compound #168: To a solution of tert-butyl (1-benzylazetidin-3-yl)carbamate (0.500 g, 1.91 mmol, 1.00 eq) in dichloromethane (5.00 mL) was added trifluoroacetic acid (1.54 g, 13.5 mmol, 1.00 mL, 7.09 eq). The mixture was stirred at 25° C. for 12 h. The mixture was concentrated to give 1-benzylazetidin-3-amine (250 mg, 1.54 mmol, 80% yield) as yellow oil. $^1$H NMR (400 MHz, DMSO-d$_6$) δ=8.55 (br s, 2H), 7.46 (s, 5H), 4.43 (s, 2H), 4.33-4.11 (m, 5H).

To a solution of 1-benzylazetidin-3-amine (250 mg, 1.54 mmol, 1.00 eq) in acetonitrile (10.0 mL) was added pyridine (609 mg, 7.71 mmol, 622 uL, 5.00 eq) and phenyl carbonochloridate (289 mg, 1.85 mmol, 232 uL, 1.20 eq). The mixture was stirred at 25° C. for 1 h. The mixture was filtered to give filtrate. The filtrate was purified by reversed-phase HPLC (column: spherical C18, 20-45 um, 100 Å, SW 120, mobile phase: [water (0.1% Formic Acid)-ACN]). The desired fraction was collected and concentrated to give phenyl (1-benzylazetidin-3-yl)carbamate (390 mg, 1.24 mmol, 80% yield, 90% purity) as yellow oil. $^1$H NMR (400 MHz, DMSO-d$_6$) δ=8.15 (s, 1H), 7.40-7.17 (m, 10H), 4.18 (br d, J=7.1 Hz, 1H), 3.66 (s, 2H), 3.61 (br d, J=8.4 Hz, 2H), 3.10 (br d, J=6.4 Hz, 2H).

To a solution of 3-(6-(hydroxymethyl)-1-oxoisoindolin-2-yl)piperidine-2,6-dione I (100 mg, 365 umol, 1.00 eq) in dimethyl formamide (1.00 mL) was added phenyl (1-benzylazetidin-3-yl)carbamate (144 mg, 510 umol, 1.40 eq) and sodium hydride (29.2 mg, 729 umol, 60% purity, 2.00 eq) at 0° C. The mixture was stirred at 0° C. for 1 h. The mixture was adjusted pH=6 with formic acid (0.500 mL). The mixture was filtered to give filtrate. The filtrate was purified by prep-HPLC (column: Phenomenex Synergi C18 150*25 mm*10 um; mobile phase: [water (0.225% FA)-ACN]; B %: 2%-32%, 10 min) and further purified by prep-NPLC (column: Welch Ultimate XB-SiOH 250*50*10 um; mobile phase: [Hexane-EtOH]; B %: 15%-55%, 15 min). The desired fraction was collected and concentrated to give a residue. The residue was purified by prep-HPLC (column: Unisil 3-100 C18 Ultra 150*50 mm*3 um; mobile phase: [water (0.225% FA)-ACN]; B %: 2%-32%, 10 min). The desired fraction was collected and lyophilized to give (2-(2, 6-dioxopiperidin-3-yl)-3-oxoisoindolin-5-yl)methyl(1-benzylazetidin-3-yl)carbamate #168 (53.91 mg, 115 umol, 32% yield, 99% purity) as an off-white solid. $^1$H NMR (400 MHz, DMSO-d$_6$) δ=10.99 (s, 1H), 8.17 (s, 1H), 7.84 (br d, J=7.3 Hz, 1H), 7.70 (s, 1H), 7.60 (s, 2H), 7.33-7.26 (m, 2H), 7.26-7.20 (m, 2H), 5.24-4.88 (m, 3H), 4.49-4.40 (m, 1H), 4.37-4.27 (m, 1H), 4.19-4.05 (m, 1H), 3.62-3.41 (m, 4H), 2.99-2.78 (m, 3H), 2.60 (br dd, J=1.8, 15.7 Hz, 1H), 2.40 (br dd, J=4.5, 13.1 Hz, 1H), 2.07-1.94 (m, 1H). MS (ESI) m/z 463.1 [M+H]$^+$ Compound #169: To a mixture of 2-fluoro-3-(trifluoromethoxy)aniline (500 mg, 2.56 mmol, 1.00 eq) and pyridine (608 mg, 7.69 mmol, 620 uL, 3.00 eq) in acetonitrile (5.00 mL) was added phenyl carbonochloridate (521 mg, 3.33 mmol, 417 uL, 1.30 eq) dropwise. The mixture was stirred at 15° C. for 12 h. The mixture was concentrated to give crude product. The crude product was purified by reversed-phase HPLC (column: spherical C18, 20-45 um, 100 Å, SW 80, mobile phase: [water (0.1% Formic Acid)-ACN]). The desired fraction was collected and lyophilized to give phenyl (2-fluoro-3-(trifluoromethoxy)phenyl)carbamate (600 mg, 1.90 mmol, 74% yield) as a white solid. $^1$H NMR (400 MHz, DMSO-d$_6$) δ=10.29 (br s, 1H), 7.81-7.75 (m, 1H), 7.48 (s, 1H), 7.35-7.31 (m, 2H), 7.30 (br d, J=1.1 Hz, 1H), 7.25 (br t, J=7.6 Hz, 3H).

To a mixture of 3-(6-(hydroxymethyl)-1-oxoisoindolin-2-yl)piperidine-2,6-dione I (80.0 mg, 291 umol, 1.00 eq) and phenyl (2-fluoro-3-(trifluoromethoxy)phenyl)carbamate (110 mg, 350 umol, 1.20 eq) in dimethyl formamide (1.00 mL) was added sodium hydride (17.5 mg, 437 umol, 60% purity, 1.50 eq) in one portion at 0° C. The mixture was stirred at 15° C. for 1 h. The mixture was quenched with 1 M hydrochloric acid (0.500 mL) and filtered. The filtrate was purified by Prep-HPLC (column: 3_Phenomenex Luna C18 75*30 mm*3 um; mobile phase: [water (0.05% HCl)-ACN]; B %: 44%-54%, 6 min) and lyophilization to give (2-(2,6-dioxopiperidin-3-yl)-3-oxoisoindolin-5-yl)methyl(2-fluoro-3-(trifluoromethoxy)phenyl)carbamate #169 (13.99 mg, 27.9 umol, 9% yield, 99% purity) as a white solid. $^1$H NMR (400 MHz, DMSO-d$_6$) δ=10.99 (br s, 1H), 9.87 (br s, 1H), 7.81 (s, 1H), 7.74 (br t, J=7.5 Hz, 1H), 7.70-7.66 (m, 1H), 7.66-7.61 (m, 1H), 7.31-7.24 (m, 2H), 5.30 (s, 2H), 5.13 (dd, J=5.0, 13.3 Hz, 1H), 4.50-4.44 (m, 1H), 4.37-4.31 (m, 1H), 2.94-2.86 (m, 1H), 2.62-2.59 (m, 1H), 2.40 (br dd, J=4.2, 13.1 Hz, 1H), 2.05-1.97 (m, 1H). MS (ESI) m/z 496.0 [M+H]$^+$ Compound #170: To a mixture of 6-(tert-butyl)pyridin-2-amine (100 mg, 665 umol, 1.00 eq) and pyridine (157 mg, 2.00 mmol, 161 uL, 3.00 eq) in acetonitrile (2.00 mL) was added phenyl carbonochloridate (135 mg, 865 umol, 108 uL, 1.30 eq) dropwise. The mixture was stirred at 15° C. for 2 h. The mixture was concentrated to give crude product. The crude product was purified by reversed-phase HPLC (column: spherical C18, 20-45 um, 100 Å, SW 20, mobile phase: [water (0.1% Formic Acid)-ACN]). The desired fraction was collected and lyophilized to give phenyl (6-(tert-butyl)pyridin-2-yl)carbamate (85.0 mg, 314 umol, 47% yield) as a white solid. $^1$H NMR (400 MHz, DMSO-d$_6$) δ=10.43 (s, 1H), 7.70 (d, J=7.9 Hz, 2H), 7.61-7.57 (m, 1H), 7.46-7.40 (m, 2H), 7.23-7.19 (m, 2H), 7.18-7.16 (m, 1H), 1.30 (s, 9H).

To a mixture of 3-(6-(hydroxymethyl)-1-oxoisoindolin-2-yl)piperidine-2,6-dione I (70.0 mg, 255 umol, 1.00 eq) and phenyl (6-(tert-butyl)pyridin-2-yl)carbamate (82.7 mg, 306 umol, 1.20 eq) in dimethyl formamide (0.500 mL) was added sodium hydride (15.3 mg, 382 umol, 60% purity, 1.50 eq) in one portion at 0° C. The mixture was stirred at 15° C. for 1 h. The mixture was quenched with 1 M hydrochloric acid (0.500 mL) and filtered. The filtrate was purified by prep-HPLC (column: 3_Phenomenex Luna C18 75*30 mm*3 um; mobile phase: [water (0.05% HCl)-ACN]; B %: 24%-34%, 6 min) followed by prep-HPLC (column: Phenomenex Synergi C18 150*25 mm*10 um; mobile phase: [water (0.225% FA)-ACN]; B %: 32%-52%, 10 min) and lyophilized to give (2-(2,6-dioxopiperidin-3-yl)-3-oxoisoindolin-5-yl)methyl (6-(tert-butyl)pyridin-2-yl)carbamate #170 (29.83 mg, 64.2 umol, 25% yield, 97% purity) as a white solid. $^1$H NMR (400 MHz, DMSO-d$_6$) δ=10.99 (br s, 1H), 10.08 (s, 1H), 7.84 (s, 1H), 7.68 (t, J=7.7 Hz, 2H), 7.65-7.59 (m, 2H), 7.07 (d, J=7.5 Hz, 1H), 5.29 (s, 2H), 5.13 (dd, J=5.1, 13.3 Hz, 1H), 4.49-4.44 (m, 1H), 4.38-4.31 (m, 1H), 2.91 (ddd, J=5.3, 13.4, 17.5 Hz, 1H), 2.61 (br s, 1H), 2.45-2.36 (m, 1H), 2.05-1.98 (m, 1H), 1.28 (s, 9H). MS (ESI) m/z 451.2 [M+H]$^+$ Compound #171: To a solution of 1-phenylcyclopropanamine (200 mg, 1.18 mmol, 1.00 eq, hydrochloric acid) and pyridine (280 mg, 3.54 mmol, 285 uL, 3.00 eq) in acetonitrile (5.00 mL) was added phenyl carbonochloridate (203 mg, 1.30 mmol, 162 uL, 1.10 eq) at 0° C. The mixture was stirred at 20° C. for 1 h. The reaction mixture was concentrated under reduced pressure to give a residue. The residue was purified by reversed-phase HPLC (C18, 80 g; condition: water/acetonitrile=1/0 to 1/4, 0.1% formic acid) to give phenyl (1-phenylcyclopropyl)carbamate (220 mg, 799 umol, 68% yield, 92% purity) as a white solid. $^1$H NMR (400 MHz, DMSO-d$_6$) δ=8.62 (s, 1H), 7.42-7.26 (m, 5H), 7.25-7.16 (m, 4H), 7.11 (d, J=7.6 Hz, 1H), 1.28-1.23 (m, 2H), 1.23-1.16 (m, 2H). MS (ESI) m/z 254.0 [M+H]$^+$ A mixture of phenyl (1-phenylcyclopropyl)carbamate (81.3 mg, 321 umol, 1.10 eq), 3-(6-(hydroxymethyl)-1-oxoisoindolin-2-yl)piperidine-2,6-dione I (80.0 mg, 292 umol, 1.00 eq) in dimethyl formamide (1.50 mL) was added sodium hydride (23.3 mg, 583 umol, 60% purity, 2.00 eq) at 0° C. And then the mixture was stirred at 20° C. for 1 h. The pH of the mixture was adjusted to around 6 by adding hydrochloric acid. The mixture was extracted with ethyl acetate (3×10 mL). The combined organic layers were dried over anhydrous sodium sulfate, filtered and concentrated under reduced pressure to give a residue. The residue was purified by prep-IPLC (column: Phenomenex Synergi C18 150*25 mm*10 um; mobile phase: [water (0.225% FA)-ACN]; B %: 28%-50%, 11 min) and lyophilized to give a white solid. The white solid was re-purified by column chromatography (SiO$_2$, Petroleum ether/Ethyl acetate=1/0 to 5/1) to afford (2-(2,6-dioxopiperidin-3-yl)-3-oxoisoindolin-5-yl)methyl (1-phenylcyclopropyl)carbamate #171 (13.2 mg, 28.8 umol, 10% yield, 95% purity) as a white solid. $^1$H NMR (400 MHz, DMSO-d$_6$) δ=11.16-10.78 (m, 1H), 8.21 (s, 1H), 7.74 (s, 1H), 7.61 (s, 2H), 7.30-7.23 (m, 2H), 7.22-7.07 (m, 3H), 5.18-5.07 (m, 3H), 4.50-4.42 (m, 1H), 4.38-4.27 (m, 1H), 2.96-2.87 (m, 1H), 2.62 (br d, J=2.4 Hz, 1H), 2.44-2.36 (m, 1H), 2.06-1.97 (m, 1H), 1.16 (br d, J=5.0 Hz, 4H). MS (ESI) m/z 434.3 [M+H]$^+$ Compound #172: To a solution of 1-(tert-butyl)azetidin-3-amine (500 mg, 3.90 mmol, 1.00 eq) and pyridine (925 mg, 11.7 mmol, 944 uL, 3.00 eq) in acetonitrile (10.0 mL) was added phenyl carbonochloridate (672 mg, 4.29 mmol, 537 uL, 1.10 eq) at 0° C. The mixture was stirred at 20° C. for 1 h. The reaction mixture was concentrated under reduced pressure to give a residue. The residue was purified by reversed-phase HPLC (C18, 80 g; condition: water/acetonitrile=1/0 to 8/1, 0.1% formic acid) to give phenyl (1-(tert-butyl)azetidin-3-yl) carbamate (595 mg, 2.01 mmol, 52% yield, 84% purity) as a white solid. $^1$H NMR (400 MHz, DMSO-d$_6$) δ=8.11-7.89 (m, 1H), 7.42-7.37 (m, 2H), 7.25-7.20 (m, 1H), 7.12 (br d, J=7.7 Hz, 2H), 4.40-4.35 (m, 1H), 4.10-3.95 (m, 4H), 1.27-1.22 (m, 9H). MS (ESI) m/z 249.2 [M+H]$^+$ To a solution of phenyl (1-(tert-butyl)azetidin-3-yl)carbamate (145 mg, 583 umol, 1.00 eq) and 3-(6-(hydroxymethyl)-1-oxoisoindolin-2-yl)piperidine-2,6-dione I (160 mg, 583 umol, 1.00 eq) in dimethyl formamide (3.00 mL) was added sodium hydride (46.7 mg, 1.17 mmol, 60% purity, 2.00 eq) at 0° C. The mixture was stirred at 0° C. for 16 h. The pH of the mixture was adjusted to around 6 by adding hydrochloric acid. The mixture was filtered and concentrated under reduced pressure to give a residue. The residue was purified by prep-HPLC (column: Phenomenex Synergi C18 150*25 mm*10 um; mobile phase: [water (0.225% FA)-ACN]; B %: 0%-25%, 10 min) and lyophilized to afford (2-(2,6-dioxopiperidin-3-yl)-3-oxoisoindolin-5-yl)methyl (1-(tert-butyl)azetidin-3-yl)carbamate #172 (97.2 mg, 193 umol, 33% yield, 94% purity, formate) as a white solid. $^1$H NMR (400 MHz, DMSO-d$_6$) δ=10.99 (s, 1H), 7.82 (br d, J=6.0 Hz, 1H), 7.71 (s, 1H), 7.60 (s, 2H), 5.15-5.08 (m, 3H), 4.48-4.43 (m, 1H), 4.35-4.30 (m, 1H), 4.05-4.01 (m, 1H), 3.38 (br d, J=4.5 Hz, 2H), 3.10 (br d, J=3.5 Hz, 2H), 2.95-2.87 (m, 1H), 2.60 (br d, J=17.5 Hz, 1H), 2.40 (br d, J=8.8 Hz, 1H), 2.04-1.97 (m, 1H), 0.92 (br s, 9H). MS (ESI) m/z 429.0 [M+H]$^+$ Compound #173: To a solution of 2,3-dihydrobenzofuran-7-amine (500 mg, 3.70 mmol, 1.00 eq) and pyridine (877 mg, 11.1 mmol, 895 uL, 3.00 eq) in acetonitrile (5.00 mL) was added phenyl carbonochloridate (695 mg, 4.44 mmol, 556 uL, 1.20 eq). The reaction mixture was stirred at 20° C. for 1 h. The reaction mixture was concentrated to give a residue, which was poured into water (100 mL) and extracted with ethyl acetate (3×50.0 mL). The combined organic phase was separated, washed with brine (20.0 mL), dried over anhydrous sodium sulfate, filtered and concentrated to give phenyl (2,3-dihydrobenzofuran-7-yl)carbamate (950 mg, crude) as colorless oil.

A mixture of 3-(6-(hydroxymethyl)-1-oxoisoindolin-2-yl) piperidine-2,6-dione I (80.0 mg, 291 umol, 1.00 eq) in dimethyl formamide (1.00 mL) was added sodium hydride (23.3 mg, 583 umol, 60% purity, 2.00 eq) and phenyl (2,3-dihydrobenzofuran-7-yl)carbamate (89.3 mg, 350 umol, 1.20 eq) at 0° C. The reaction mixture was stirred at 20° C. for 1 h. The reaction mixture was added formic acid (2.00 mL) and filtered to give a filtrate, which was purified by Prep-HPLC (column: Phenomenex luna C18 150*25 mm*10 um; mobile phase: [water (0.225% formic acid)-acetonitrile]; B %: 27%-57%, 10 min) and lyophilized to afford (2-(2,6-dioxopiperidin-3-yl)-3-oxoisoindolin-5-yl) methyl(2,3-dihydrobenzofuran-7-yl)carbamate #173 (90.38 mg, 203 umol, 69% yield, 98% purity) as a white solid. $^1$H NMR (400 MHz, DMSO-d$_6$) δ=11.01 (s, 1H), 9.08 (br s, 1H), 7.80 (s, 1H), 7.64 (q, J=8.0 Hz, 2H), 7.28 (br s, 1H), 7.00 (d, J=7.2 Hz, 1H), 6.83-6.74 (m, 1H), 5.24 (s, 2H), 5.14 (dd, J=5.2, 13.2 Hz, 1H), 4.55 (t, J=8.8 Hz, 2H), 4.50-4.43 (m, 1H), 4.39-4.29 (m, 1H), 3.21 (t, J=8.8 Hz, 2H), 2.98-2.87 (m, 1H), 2.64-2.58 (m, 1H), 2.44-2.36 (m, 1H), 2.07-1.96 (m, 1H). MS (ESI) m/z 436.1 [M+H]$^+$.

Compound #174: To a solution of 1-bromo-2-fluorobenzene (32.2 g, 184 mmol, 20.1 mL, 2.10 eq) in tetrahydrofuran (200 mL) was added n-butyllithium (2.50 M, 73.6 mL, 2.10 eq) at −78° C. under nitrogen atmosphere, the reaction was stirred at −78° C. for 1.5 h. A solution of 3-oxocyclobutanecarboxylic acid (10.0 g, 87.6 mmol, 1.00 eq) in tetrahydrofuran (20.0 mL) was added to the reaction slowly. The mixture was stirred at same temperature for another 1 h. The reaction was quenched by saturated ammonium chloride (200 mL) and the mixture was acidified with 11.8 M concentrated hydrochloric acid to pH=3. The mixture was extracted with ethyl acetate (3×200 mL) and the combined organic layers were concentrated to afford 3-(2-fluorophenyl)-3-hydroxycyclobutanecarboxylic acid (16.5 g, 78.5 mmol, 89% yield) as a white solid. $^1$H NMR (400 MHz, DMSO-d$_6$) δ=12.16 (br s, 1H), 7.59-7.44 (m, 1H), 7.40-7.29 (m, 1H), 7.22-7.11 (m, 2H), 5.67 (br s, 1H), 2.85-2.76 (m, 2H), 2.63-2.54 (m, 1H), 2.49-2.44 (m, 2H).

To a solution of 3-(2-fluorophenyl)-3-hydroxycyclobutanecarboxylic acid (16.5 g, 78.5 mmol, 1.00 eq) in toluene (120 mL) was added concentrated hydrochloric acid (12.0 M, 82.5 mL, 12.4 eq), the reaction was stirred at 20° C. for 4 h. The organic phase was separated, washed with water (20.0 mL), saturated sodium chloride solution (20.0 mL) and concentrated to give a residue. The residue was washed with petroleum ether (300 mL) to afford 3-chloro-3-(2-fluorophenyl)cyclobutanecarboxylic acid (16.3 g, 71.2 mmol, 90% yield) as a brown solid. $^1$H NMR (400 MHz, DMSO-d$_6$) δ=12.43 (br s, 1H), 7.47-7.35 (m, 2H), 7.27-7.20 (m, 2H), 3.56 (quin, J=8.8 Hz, 1H), 2.98 (br d, J=8.0 Hz, 4H).

To a solution of 3-chloro-3-(2-fluorophenyl)cyclobutanecarboxylic acid (16.3 g, 71.2 mmol, 1.00 eq) and potassium carbonate (21.6 g, 156 mmol, 2.20 eq) in dimethylformamide (120 mL) was added iodomethane (20.2 g, 142 mmol, 8.88 mL, 2.00 eq). The mixture was stirred at 25° C. for 12 h. The mixture was filtered and diluted with water (100 ml), extracted with ethyl acetate (3×50.0 mL). The combined organic layers were concentrated to give a residue. The residue was purified by column chromatography (ISCO®; 120 g SepaFlash® Silica Flash Column, Eluent of 0~100% ethyl acetate/petroleum ether @ 80 mL/min) to afford methyl 3-chloro-3-(2-fluorophenyl)cyclobutanecarboxylate (10.7 g, 44.0 mmol, 61% yield) as yellow oil. $^1$H NMR (400 MHz, DMSO-d$_6$) δ=7.45-7.37 (m, 2H), 7.29-7.20 (m, 2H), 3.70-3.63 (m, 1H), 3.59 (s, 3H), 3.08-2.95 (m, 4H).

To a solution of sodium bis(trimethylsilyl)amide (2.00 M, 15.4 mL, 1.50 eq) in tetrahydrofuran (25.0 mL) was added a solution of methyl 3-chloro-3-(2-fluorophenyl)cyclobutanecarboxylate (5.00 g, 20.6 mmol, 1.00 eq) in tetrahydrofuran (25.0 mL) dropwise. The mixture was stirred at 70° C. for 5 h. The reaction was quenched by ammonium chloride solution (100 mL) and the mixture was extracted with ethyl acetate (3×50 mL), the combined organic layers were dried over sodium sulfate and concentrated to give a residue. The residue was purified by column chromatography (ISCO®; 120 g SepaFlash® Silica Flash Column, Eluent of 0~100% ethyl acetate/petroleum ether @40 mL/min) to afford methyl 3-(2-fluorophenyl)bicyclo[1.1.0] butane-1-carboxylate (2.70 g, 13.0 mmol, 63% yield) as yellow oil. $^1$H NMR (400 MHz, DMSO-d$_6$) δ=7.40-7.35 (m, 1H), 7.34-7.28 (m, 1H), 7.23-7.16 (m, 2H), 3.50 (s, 3H), 2.87 (s, 2H), 1.67 (s, 2H).

A mixture of methyl 3-(2-fluorophenyl)bicyclo[1.1.0]butane-1-carboxylate (1.00 g, 4.85 mmol, 1.00 eq) and 1-methoxy-2-(2-methoxyethoxy)ethane (3.75 g, 27.9 mmol, 4.00 mL, 5.76 eq) in tetrachloroethylene (40.0 mL) was heated to 120° C., then sodium trichloroacetate (3.37 g, 18.1 mmol, 3.75 eq) was added in one portion. The mixture was stirred at 140° C. for 6 h. The reaction was filtered to give a filtrate, the filtrate was concentrated to give a residue. The residue was purified by Prep-HPLC (column: Phenomenex luna C18 150*25 mm*10 um; mobile phase: [water (0.225% FA)-ACN]; B %: 62%-92%, 10 min) to give a crude product. The crude product was purified by Prep-HPLC (column: Phenomenex luna C18 150*25 mm*10 um; mobile phase: [water (0.225% FA)-ACN]; B %: 49%-79%, 10 min) followed purified by Prep-HPLC (column: Phenomenex luna C18 150*25 mm*10 um; mobile phase: [water (0.225% FA)-ACN]; B %: 49%-79%, 10 min) to afford methyl 2,2-dichloro-3-(2-fluorophenyl)bicyclo[1.1.1]pentane-1-carboxylate (400 mg, 1.33 mmol, 27% yield) as yellow oil. $^1$H NMR (400 MHz, DMSO-$d_6$) δ=7.53-7.39 (m, 2H), 7.33-7.21 (m, 2H), 3.76 (s, 3H), 3.05 (s, 2H), 2.68 (s, 2H).

To a solution of methyl 2,2-dichloro-3-(2-fluorophenyl)bicyclo[1.1.1]pentane-1-carboxylate (0.300 g, 1.04 mmol, 1.00 eq) in toluene (3.00 mL) were added (E)-1,1'-(diazene-1,2-diyl)dicyclohexanecarbonitrile (12.6 mg, 51.8 umol, 0.0500 eq) and tris(trimethylsilyl)silane (1.48 g, 5.95 mmol, 1.83 mL, 5.73 eq), the mixture was stirred at 80° C. for 2 h, (E)-1,1'-(diazene-1,2-diyl)dicyclohexanecarbonitrile (304 mg, 1.25 mmol, 1.20 eq) was added portionwise over 3 h. The reaction was stirred at 110° C. for another 216 h. The mixture was concentrated to give a residue.

The residue was purified by flash silica gel chromatography (ISCO®; 40 g SepaFlash® Silica Flash Column, Eluent of 0~100% ethyl acetate/petroleum ether @ 40 mL/min) to afford methyl 3-(2-fluorophenyl)bicyclo[1.1.1]pentane-1-carboxylate (0.4 g, crude) as yellow oil which was used to next step without further purification. $^1$H NMR (400 MHz, DMSO-$d_6$) δ=7.35-7.28 (m, 1H), 7.26-7.19 (m, 1H), 7.18-7.10 (m, 2H), 3.64 (s, 3H), 2.34 (s, 6H).

To a mixture of 3-(2-fluorophenyl)bicyclo[1.1.1]pentane-1-carboxylate (0.300 g, 1.36 mmol, 1.00 eq) in methanol (3.00 mL) was added lithium hydroxide (114 mg, 2.72 mmol, 2.00 eq), the reaction was stirred at 25° C. for 3 h. The reaction was concentrated to give a residue. The residue was purified by reversed-phase HPLC (column: Shim-pack C18 150*25*10 um; mobile phase: [water (0.1% formic acid)-acetonitrile]) to afford 3-(2-fluorophenyl)bicyclo[1.1.1]pentane-1-carboxylic acid (0.150 g, 727 umol, 53% yield) as a yellow solid. $^1$H NMR (400 MHz, DMSO-$d_6$) δ=12.78-12.12 (m, 1H), 7.30 (ddt, J=2.0, 5.4, 7.8 Hz, 1H), 7.22 (dt, J=2.0, 7.8 Hz, 1H), 7.18-7.08 (m, 2H), 2.29 (s, 6H).

To a mixture of 3-(2-fluorophenyl)bicyclo[1.1.1]pentane-1-carboxylic acid (0.0400 g, 193 umol, 1.00 eq) in dioxane (2.00 mL) was added diphenylphosphoryl azide (106 mg, 387 umol, 84.0 uL, 2.00 eq) and triethylamine (58.8 mg, 581 umol, 81.0 uL, 3.00 eq) under nitrogen atmosphere, the mixture was stirred at 25° C. for 1 h. Then 3-(6-(hydroxymethyl)-1-oxoisoindolin-2-yl)piperidine-2,6-dione I (58.5 mg, 213 umol, 1.10 eq) was added, the reaction mixture was stirred at 100° C. for another 2 h. The reaction was concentrated to give a residue. The residue was purified by Prep-HPLC (column: Phenomenex luna C18 150*25 mm*10 um; mobile phase: [water (0.225% FA)-ACN]; B %: 40%-70%, 10 min) to afford (2-(2,6-dioxopiperidin-3-yl)-3-oxoisoindolin-5-yl)methyl (3-(2-fluorophenyl)bicyclo[1.1.1]pentan-1-yl) carbamate #174 (41.5 mg, 85.1 umol, 43% yield, 98% purity) as a white solid. $^1$H NMR (400 MHz, DMSO-$d_6$) δ=11.00 (br d, J=2.4 Hz, 1H), 8.17 (br s, 1H), 7.72 (s, 1H), 7.62 (s, 2H), 7.32-7.24 (m, 1H), 7.24-7.17 (m, 1H), 7.16-7.07 (m, 2H), 5.19-5.07 (m, 3H), 4.49-4.42 (m, 1H), 4.38-4.28 (m, 1H), 2.98-2.85 (m, 1H), 2.60 (br dd, J=2.2, 15.2 Hz, 1H), 2.40 (br dd, J=4.2, 13.2 Hz, 1H), 2.27 (s, 6H), 2.04-1.97 (m, 1H). MS (ESI) m/z 478.2 [M+H]$^+$ Compounds #175 and #176: The (2-(2,6-dioxopiperidin-3-yl)-3-oxoisoindolin-5-yl)methyl (3-chloro-4-methylphenyl)carbamate (990 mg, 2.24 mmol) was purified by SFC (column: DAICEL CHIRALPAK IC (250 mm*30 mm, 10 um); mobile phase: [isopropanol-acetonitrile]; B %: 60%-60%, 5.2; 250 min) and lyophilized to afford (R)-(2-(2,6-dioxopiperidin-3-yl)-3-oxoisoindolin-5-yl)methyl(3-chloro-4-methylphenyl)carbamate #175 (353 mg, 791 umol, 35% yield, 99% purity) as a white solid and (S)-(2-(2,6-dioxopiperidin-3-yl)-3-oxoisoindolin-5-yl)methyl(3-chloro-4-methylphenyl)carbamate #176 (344 mg, 771 umol, 34% yield, 99% purity) as a white solid. (The absolute configuration was assigned arbitrarily)

175: $^1$H NMR (400 MHz, DMSO-$d_6$) δ=11.00 (br s, 1H), 9.93 (br s, 1H), 7.80 (s, 1H), 7.72-7.67 (m, 1H), 7.66-7.62 (m, 1H), 7.60 (s, 1H), 7.33-7.28 (m, 1H), 7.27-7.23 (m, 1H), 5.28 (s, 2H), 5.13 (dd, J=5.2, 13.2 Hz, 1H), 4.55-4.43 (m, 1H), 4.39-4.30 (m, 1H), 2.92 (ddd, J=5.2, 13.6, 17.6 Hz, 1H), 2.61 (td, J=2.0, 15.2 Hz, 1H), 2.47-2.35 (m, 1H), 2.26 (s, 3H), 2.07-1.98 (m, 1H). MS (ESI) m/z 442.0 [M+H]$^+$.

176: $^1$H NMR (400 MHz, DMSO-$d_6$) δ=11.01 (s, 1H), 9.94 (s, 1H), 7.80 (s, 1H), 7.71-7.67 (m, 1H), 7.66-7.62 (m, 1H), 7.60 (s, 1H), 7.32-7.28 (m, 1H), 7.27-7.23 (m, 1H), 5.28 (s, 2H), 5.13 (dd, J=5.2, 13.2 Hz, 1H), 4.51-4.44 (m, 1H), 4.39-4.31 (m, 1H), 2.98-2.86 (m, 1H), 2.60 (td, J=2.0, 17.2 Hz, 1H), 2.46-2.36 (m, 1H), 2.25 (s, 3H), 2.06-1.97 (m, 1H). MS (ESI) m/z 442.0 [M+H]$^+$.

Compound #177: A mixture of 2-chloro-6-methyl-4-nitroaniline (3.00 g, 16.1 mmol, 1.00 eq), cuprous bromide (2.77 g, 19.3 mmol, 587 uL, 1.20 eq) in acetonitrile (15.0 mL) was stirred for 5 min at 0° C., then tert-butylnitrite (2.49 g, 24.1 mmol, 2.87 mL, 1.50 eq) was dissolved in acetonitrile (15.0 mL) was added dropwise to the mixture. The mixture was stirred at 20° C. for 36 h. The reaction mixture was concentrated under reduced pressure to give a residue, and purified by column chromatography on silica gel (petroleum ether/ethyl acetate=1/0) to give 2-bromo-1-chloro-3-methyl-5-nitrobenzene (2.88 g, 11.5 mmol, 71% yield) as a white solid. $^1$H NMR (400 MHz, DMSO-$d_6$) δ=8.28 (d, J=2.6 Hz, 1H), 8.23 (d, J=2.6 Hz, 1H), 2.55 (s, 3H).

A mixture of 2-bromo-1-chloro-3-methyl-5-nitrobenzene (2.70 g, 10.8 mmol, 1.00 eq), iron powder (1.81 g, 32.3 mmol, 3.00 eq) and ammonium chloride (2.88 g, 53.9 mmol, 5.00 eq) in methanol (30.0 mL) and water (10.0 mL) was stirred at 80° C. for 2 h. The mixture was filtered and the filtrate was concentrated under reduced pressure. The mixture was diluted with sodium hydrogencarbonate (150 mL) and extracted with ethyl acetate (3×50.0 mL). The organic layer was dried over anhydrous sodium sulfate, filtered and concentrated in vacuum to give 4-bromo-3-chloro-5-methylaniline (2.40 g, crude) as a yellow solid. $^1$H NMR (400 MHz, DMSO-$d_6$) δ=6.61 (s, 1H), 6.48 (d, J=2.5 Hz, 1H), 5.45 (s, 2H), 2.24 (s, 3H).

To a solution of 4-bromo-3-chloro-5-methylaniline (1.00 g, 4.54 mmol, 1.00 eq) and zinc cyanide (799 mg, 6.80 mmol, 432 uL, 1.50 eq) in dimethyl formamide (20.0 mL) was added tetrakis[triphenylphosphine] palladium(0) (524 mg, 454 umol, 0.100 eq) under nitrogen. The mixture was stirred at 150° C. for 1 h under microwave. The mixture was filtered, the filtrate was diluted with water (50.0 mL) and extracted with ethyl acetate (3×30.0 mL). The combined organic layer was washed with brine (20.0 mL) and dried over anhydrous sodium sulfate, filtered and concentrated to give crude product, the filter cake and the aqueous phase was quenched by sodium hydroxide to pH>11 then dip in sodium hypochlorite overnight. The crude product was purified by reversed-phase HPLC (column: spherical C18, 20-45 um, 100 Å, SW 80, mobile phase: [water (0.1% FormicAcid)-ACN]) and lyophilized to give 4-amino-2-chloro-6-methylbenzonitrile (380 mg, 2.28 mmol, 50% yield) as a white solid. $^1$H NMR (400 MHz, DMSO-$d_6$) δ=6.56 (d, J=1.6 Hz, 1H), 6.45-6.42 (m, 1H), 6.38 (s, 2H), 2.30 (s, 3H). MS (ESI) m/z 167.1 [M+H]$^+$ To a solution of 4-amino-2-chloro-6-methylbenzonitrile (380 mg, 2.28 mmol, 1.00 eq) and pyridine (541 mg, 6.84 mmol, 552 uL, 3.00 eq) in acetonitrile (5.00 mL) was added phenyl carbonochloridate (393 mg, 2.51 mmol, 314 uL, 1.10 eq) dropwise at 0° C. The mixture was stirred at 25° C. for 2 h. The reaction mixture was concentrated under reduced pressure to give crude product. The crude product was purified by reversed-phase HPLC (column: spherical C18, 20-45 um, 100 Å, SW 40, mobile phase: [water (0.1% Formic Acid)-ACN]) and lyophilized to give phenyl (3-chloro-4-cyano-5-methylphenyl)carbamate (340 mg, 1.17 mmol, 51% yield, 99% purity) as a black solid. MS (ESI) m/z 287.0 [M+H]$^+$ To a solution of phenyl (3-chloro-4-cyano-5-methylphenyl)carbamate (100 mg, 350. umol, 1.20 eq) and 3-(6-(hydroxymethyl)-1-oxoisoindolin-2-yl)piperidine-2,6-dione I (80.0 mg, 297 umol, 1.00 eq) in dimethyl formamide (2.00 mL) was added sodium hydride (23.3 mg, 583 umol, 60% purity, 2.00 eq) in portions at 0° C. The mixture was stirred at 20° C. for 0.5 h. The mixture was quenched by 1 M hydrochloric acid (1.00 mL) and filtered. The filtrate was purified by prep-HPLC (column: 3_Phenomenex Luna C18 75*30 mm*3 um; mobile phase: [water (0.05% HCl)-ACN]; B %: 41%-51%, 6 min) to give (2-(2,6-dioxopiperidin-3-yl)-3-oxoisoindolin-5-yl)methyl(3-chloro-4-cyano-5-methylphenyl)carbamate #177 (19.7 mg, 42.0 umol, 14% yield, 99% purity) as a white solid. $^1$H NMR (400 MHz, DMSO-d$_6$) δ=10.65-10.31 (m, 1H), 8.41 (br s, 1H), 7.80 (s, 1H), 7.72-7.67 (m, 1H), 7.67-7.60 (m, 2H), 7.46 (s, 1H), 5.31 (s, 2H), 5.12 (br dd, J=4.7, 13.5 Hz, 1H), 4.51-4.43 (m, 1H), 4.38-4.30 (m, 1H), 2.95-2.87 (m, 1H), 2.62 (br s, 1H), 2.45 (s, 3H), 2.39 (br s, 1H), 2.04-1.97 (m, 1H). MS (ESI) m/z 467.1 [M+H]$^+$ Compound #178: To a solution of 3-chloro-2,6-difluoroaniline (500 mg, 3.06 mmol, 1.00 eq) and pyridine (726 mg, 9.17 mmol, 740 uL, 3.00 eq) in acetonitrile (5.00 mL) was added phenyl carbonochloridate (526 mg, 3.36 mmol, 421 uL, 1.10 eq) at 0° C. The mixture was stirred at 20° C. for 1 h. The reaction mixture was concentrated under reduced pressure to give a residue. The residue was purified by reversed-phase HPLC (C18, 80 g; condition: 0.1% formic acid/acetonitrile) to give phenyl (3-chloro-2,6-difluorophenyl)carbamate (297 mg, 1.04 mmol, 34% yield, 99% purity) as a white solid. $^1$H NMR (400 MHz, CDCl$_3$) δ=7.45-7.39 (m, 2H), 7.38-7.27 (m, 2H), 7.26-7.21 (m, 2H), 6.99 (dt, J=2.0, 9.0 Hz, 1H), 6.55 (br s, 1H). MS (ESI) m/z 283.9 [M+H]$^+$ To a solution of phenyl (3-chloro-2,6-difluorophenyl) carbamate (91.0 mg, 321 umol, 1.10 eq) and 3-(6-(hydroxymethyl)-1-oxoisoindolin-2-yl)piperidine-2,6-dione I (80.0 mg, 292 umol, 1.00 eq) in dimethyl formamide (1.50 mL) was added sodium hydride (23.3 mg, 583 umol, 60% purity, 2.00 eq) at 0° C. The mixture was stirred at 0° C. for 1 h. The pH of the mixture was adjusted to around 6 by adding hydrochloric acid. The mixture was extracted with ethyl acetate (3×10.0 mL). The combined organic layers were dried over anhydrous sodium sulfate, filtered and concentrated under reduced pressure to give a residue. The residue was purified by prep-HPLC (column: Phenomenex luna C18 150*25 mm*10 um; mobile phase: [water (0.2% FA)-ACN]; B %: 30%-50%, 10 min) and lyophilized to afford (2-(2,6-dioxopiperidin-3-yl)-3-oxoisoindolin-5-yl) methyl (3-chloro-2,6-difluorophenyl)carbamate #178 (72.5 mg, 155 umol, 53% yield, 99% purity) as a white solid. $^1$H NMR (400 MHz, DMSO-d$_6$) δ=10.99 (br s, 1H), 9.78-9.43 (m, 1H), 7.76 (s, 1H), 7.64 (s, 1H), 7.57 (dt, J=5.5, 8.7 Hz, 1H), 7.26 (dt, J=1.8, 9.3 Hz, 1H), 5.27 (s, 2H), 5.12 (dd, J=5.0, 13.3 Hz, 1H), 4.52-4.43 (m, 1H), 4.42-4.24 (m, 1H), 2.95-2.87 (m, 1H), 2.61 (td, J=2.0, 15.4 Hz, 1H), 2.40 (br dd, J=4.3, 13.1 Hz, 1H), 2.05-1.97 (m, 1H). MS (ESI) m/z 464.2 [M+H]$^+$ Compound #179: To a solution of 3-chloro-2-fluoroaniline (2.00 g, 13.7 mmol, 1.00 eq) in acetonitrile (30.0 mL) was added N-bromosuccinimide (2.20 g, 12.3 mmol, 0.900 eq). The mixture was stirred at 25° C. for 12 h. The reaction mixture was concentrated under reduced pressure to give oil. The residue was purified by column chromatography (petroleum ether/ethyl acetate=8/1 to 3/1) to give 4-bromo-3-chloro-2-fluoroaniline (3.00 g, 13.3 mmol, 97% yield) as a black oil. $^1$H NMR (400 MHz, DMSO-d$_6$) δ=7.22 (dd, J=1.7, 8.8 Hz, 1H), 6.72-6.66 (m, 1H), 5.65 (s, 2H).

To a solution of 4-bromo-3-chloro-2-fluoroaniline (1.00 g, 4.46 mmol, 1.00 eq) in water (2.00 mL) and dioxane (10.0 mL) was added potassium trifluoro(methyl)borate (2.17 g, 17.8 mmol, 4.00 eq), potassium carbonate (1.85 g, 13.3 mmol, 3.00 eq) and [1,1'-bis(diphenylphosphino)ferrocene] dichloropalladium(II) (325 mg, 445 umol, 0.100 eq) under nitrogen. The mixture was stirred at 110° C. for 12 h. The reaction mixture was diluted with water (30.0 mL) and exacted with ethyl acetate (3×30.0 mL). The organic phase was separated, washed with brine (2×10.0 mL), dried over sodium sulfate, filtered and concentrated under reduced pressure to give a residue. The residue was purified by column chromatography (petroleum ether/ethyl acetate=8/1 to 5/1) to give 3-chloro-2-fluoro-4-methylaniline (0.700 g, 4.39 mmol, 98% yield) as a yellow solid. $^1$H NMR (400 MHz, DMSO-d$_6$) δ=6.83 (d, J=7.8 Hz, 1H), 6.63 (t, J=8.5 Hz, 1H), 5.19 (s, 2H), 2.18 (s, 3H).

To a solution of 3-chloro-2-fluoro-4-methylaniline (0.700 g, 4.39 mmol, 1.00 eq) in acetonitrile (10.0 mL) was added phenyl carbonochloridate (824 mg, 5.26 mmol, 659 uL, 1.20 eq) and pyridine (1.73 g, 21.9 mmol, 1.77 mL, 5.00 eq). The mixture was stirred at 25° C. for 0.5 h. The reaction mixture was concentrated under reduced pressure to give a residue. The crude product was purified by reversed-phase HPLC (0.1% FA condition) to give phenyl (3-chloro-2-fluoro-4-methylphenyl)carbamate (0.900 g, 3.22 mmol, 73% yield) as a yellow solid. $^1$H NMR (400 MHz, DMSO-d$_6$) δ=10.05 (br s, 1H), 7.53 (br t, J=7.9 Hz, 1H), 7.46-7.40 (m, 2H), 7.29-7.14 (m, 4H), 2.34 (s, 3H). MS (ESI) m/z 280.0 [M+H]$^+$ To a solution of phenyl phenyl (3-chloro-2-fluoro-4-methylphenyl)carbamate (97.9 mg, 350 umol, 1.20 eq) in dimethyl formamide (2.00 mL) was added 3-(6-(hydroxymethyl)-1-oxoisoindolin-2-yl)piperidine-2,6-dione (80.0 mg, 291 umol, 1.00 eq) and sodium hydride (23.3 mg, 583 umol, 60% purity, 2.00 eq) at 0° C. The mixture was stirred at 0° C. for 0.5 h. The reaction mixture was quenched with formic acid (1.00 ml) to give a solution. The crude product was dissolved in dimethyl formamide (2.00 mL) and purified by prep-HPLC (column: Waters Xbridge 150*25 mm*5um; mobile phase: [water (0.05% ammonia hydroxide v/v)-ACN]; B %: 15%-45%, 9 min) and lyophilized to give (2-(2,6-dioxopiperidin-3-yl)-3-oxoisoindolin-5-yl) methyl (3-chloro-2-fluoro-4-methylphenyl)carbamate #179 (79.1 mg, 172 umol, 59% yield) as a white solid. $^1$H NMR (400 MHz, DMSO-d$_6$) δ=11.00 (br s, 1H), 9.64 (br s, 1H), 7.81 (s, 1H), 7.71-7.61 (m, 2H), 7.51 (br t, J=7.9 Hz, 1H), 7.16 (br d, J=8.3 Hz, 1H), 5.28 (s, 2H), 5.14 (dd, J=5.1, 13.2 Hz, 1H), 4.51-4.44 (m, 1H), 4.39-4.32 (m, 1H), 2.98-2.87 (m, 1H), 2.64-2.58 (m, 1H), 2.41 (br dd, J=4.6, 13.1 Hz, 1H), 2.33 (s, 3H), 2.07-1.99 (m, 1H). MS (ESI) m/z 460.0 [M+H]$^+$ Compound #180: To a solution of 2-fluoro-3-methylaniline (500 mg, 4.00 mmol, 1.00 eq) in dimethyl formamide (10.0 mL) was added 1-chloropyrrolidine-2,5-dione (533 mg, 4.00 mmol, 1.00 eq). The mixture was stirred at 25° C. for 12 h. The reaction mixture was quenched by addition water (50.0 mL) and extracted with ethyl acetate (3×50.0 mL). The combined organic layers were washed with water (2×100 mL), dried over anhydrous sodium sulfate, filtered and concentrated under reduced pressure to give a residue. The residue was purified by flash silica gel chromatography (ISCO®; 80 g SepaFlash® Silica Flash Column, Eluent of 0~50% Ethyl acetate/Petroleum ether gradient @ 80 mL/min) to give 4-chloro-2-fluoro-3-methylaniline (300 mg, 1.75 mmol, 22% yield, 93% purity) as purple oil. $^1$H NMR (400 MHz, CDCl$_3$) δ=6.94 (dd, J=1.6, 8.5 Hz, 1H), 6.56 (t, J=8.9 Hz, 1H), 3.96-3.42 (m, 2H), 2.05 (s, 3H). MS (ESI) m/z 160.1 [M+H]$^+$ To a mixture of 4-chloro-2-fluoro-3-methylaniline (300 mg, 1.88 mmol, 1.00 eq), pyridine (446 mg, 5.64 mmol, 455 uL, 3.00 eq) in acetonitrile (5.00 mL) was added phenyl carbonochloridate (324 mg, 2.07 mmol, 259 uL, 1.10 eq) at 0° C. Then the mixture was stirred at 20° C. for 1 h. The reaction mixture was concentrated under reduced pressure to give a residue. The residue was purified by reversed-phase HPLC (C18, 80 g; condition: water/acetonitrile=1/0 to 0/1, 0.1% formic acid) to give phenyl (4-chloro-2-fluoro-3-methylphenyl)carbamate (294 mg, 1.04 mmol, 55% yield, 99% purity) as a pink solid. $^1$H NMR (400 MHz, DMSO-d$_6$) δ=10.04 (br s, 1H), 7.59 (br t, J=8.4 Hz, 1H), 7.45-7.40 (m, 2H), 7.30-7.21 (m, 4H), 2.28 (d, J=2.3 Hz, 3H). MS (ESI) m/z 280.1 [M+H]$^+$ To a solution of phenyl (4-chloro-2-fluoro-3-methylphenyl)carbamate (112 mg, 401 umol, 1.10 eq) and 3-(6-(hydroxymethyl)-1-oxoisoindolin-2-yl)piperidine-2,6-dione I (100 mg, 365 umol, 1.00 eq) in dimethyl formamide (1.50 mL) was added sodium hydride (29.2 mg, 729 umol, 60% purity, 2.00 eq) at 0° C. The mixture was stirred at 0° C. for 1 h. The pH of the mixture was adjusted to around 6 by adding hydrochloric acid (1M). The mixture was extracted with ethyl acetate (3×10 mL). The combined organic layers were dried over anhydrous sodium sulfate, filtered and concentrated under reduced pressure to give a residue. The residue was purified by prep-HPLC (column: Phenomenex luna C18 150*25 mm*10 um; mobile phase: [water (0.2% FA)-ACN]; B %: 42%-62%, 10 min) and lyophilized to afford (2-(2,6-dioxopiperidin-3-yl)-3-oxoisoindolin-5-yl) methyl(4-chloro-2-fluoro-3-methylphenyl)carbamate #180 (97.2 mg, 207 umol, 57% yield, 98% purity) as a white solid. $^1$H NMR (400 MHz, DMSO-d$_6$) δ=10.98 (br s, 1H), 9.61 (br s, 1H), 7.80 (s, 1H), 7.69-7.61 (m, 2H), 7.56 (br t, J=8.7 Hz, 1H), 7.25 (dd, J=1.3, 8.8 Hz, 1H), 5.28 (s, 2H), 5.13 (dd, J=5.1, 13.3 Hz, 1H), 4.51-4.43 (m, 1H), 4.38-4.30 (m, 1H), 2.97-2.87 (m, 1H), 2.64-2.57 (m, 1H), 2.40 (br dd, J=4.4, 13.2 Hz, 1H), 2.25 (d, J=2.4 Hz, 3H), 2.05-1.97 (m, 1H). MS (ESI) m/z 459.9 [M+H]$^+$ Compound #181: To a solution of 5-bromo-2-nitropyridine (2.00 g, 9.85 mmol, 1.00 eq) in toluene (25.0 mL) was added cyclobutylboronic acid (1.48 g, 14.8 mmol, 1.50 eq), cesium carbonate (4.82 g, 14.8 mmol, 1.50 eq) and [1,1'-bis(diphenylphosphino)ferrocene]dichloropalladium(II) (577 mg, 788 umol, 0.0800 eq) under nitrogen atmosphere. The mixture was stirred at 100° C. for 12 h. The residue was diluted with water (200 mL) and extracted with ethyl acetate (3×40.0 mL). The combined organic layers were washed with brine (30.0 mL), dried over sodium sulfate, filtered and concentrated under reduced pressure to give a residue. The residue was purified by column chromatography on silica gel (Petroleum ether/Ethyl acetate=1/0 to Petroleum ether/Ethyl acetate=5/1) to afford 5-cyclobutyl-2-nitropyridine (650 mg, 3.61 mmol, 36% yield) as a white solid. $^1$H NMR (400 MHz, DMSO-d$_6$) δ=8.54 (d, J=2.4 Hz, 1H), 8.26 (d, J=8.4 Hz, 1H), 8.11 (dd, J=2.3, 8.4 Hz, 1H), 3.73 (quin, J=8.8 Hz, 1H), 2.37 (tq, J=2.6, 8.4 Hz, 2H), 2.27-2.12 (m, 2H), 2.12-2.00 (m, 1H), 1.93-1.82 (m, 1H). MS (ESI) m/z 179.1 [M+H]$^+$.

To a solution of 5-cyclobutyl-2-nitropyridine (600 mg, 3.37 mmol, 1.00 eq) in ethyl acetate (20.0 mL) was added palladium on carbon (3.37 mmol, 10% purity, 1.00 eq) under hydrogen atmosphere. The mixture was stirred at 25° C. for 2 h. The reaction mixture was filtered and the filtrate was concentrated under reduced pressure to afford 5-cyclobutylpyridin-2-amine (480 mg, 3.24 mmol, 96% yield) as a white solid. $^1$H NMR (400 MHz, DMSO-d$_6$) δ=7.74 (d, J=2.4 Hz, 1H), 7.30 (dd, J=2.4, 8.4 Hz, 1H), 6.40 (d, J=8.4 Hz, 1H), 5.66 (s, 2H), 3.34-3.28 (m, 1H), 2.19 (tq, J=2.3, 8.0 Hz, 2H), 2.03-1.93 (m, 2H), 1.91-1.72 (m, 2H).

To a solution of 5-cyclobutylpyridin-2-amine (300 mg, 2.02 mmol, 1.00 eq) in acetonitrile (3.00 mL) were added pyridine (480 mg, 6.07 mmol, 490 uL, 3.00 eq) and phenyl carbonochloridate (349 mg, 2.23 mmol, 279 uL, 1.10 eq). The mixture was stirred at 25° C. for 2 h. The reaction mixture was concentrated under reduced pressure to afford a residue. The residue was triturated with dimethyl formamide (5.00 mL) at 25° C. for 5 min to afford phenyl (5-cyclobutylpyridin-2-yl)carbamate (100 mg, 365 umol, 18% yield) as a white solid. MS (ESI) m/z 269.2 [M+H]$^+$ To a solution of phenyl (5-cyclobutylpyridin-2-yl)carbamate (40.0 mg, 149 umol, 1.00 eq) in dimethyl formamide (500 uL) was added sodium hydride (11.9 mg, 298 umol, 60% purity, 2.00 eq) and 3-(6-(hydroxymethyl)-1-oxoisoindolin-2-yl)piperidine-2,6-dione I (45.0 mg, 164 umol, 1.10 eq). The mixture was stirred at 25° C. for 1 h. The pH of the mixture was adjusted to 7 with formic acid. Then the mixture was filtered and the filter cake was obtained as a crude product. The crude product was triturated with dimethyl formamide (5.00 mL) at 25° C. for 5 min to afford (2-(2,6-dioxopiperidin-3-yl)-3-oxoisoindolin-5-yl)methyl (5-cyclobutylpyridin-2-yl)carbamate #181 (49.77 mg, 99.6 umol, 67% yield, 99% purity, formic acid) as a white solid. $^1$H NMR (400 MHz, DMSO-d$_6$) δ=11.13-10.84 (m, 1H), 10.25 (s, 1H), 8.12 (s, 1H), 7.82-7.73 (m, 2H), 7.71-7.58 (m, 3H), 5.28 (s, 2H), 5.12 (br dd, J=5.1, 13.2 Hz, 1H), 4.52-4.41 (m, 1H), 4.39-4.29 (m, 1H), 3.51-3.46 (m, 1H), 2.98-2.83 (m, 1H), 2.63-2.57 (m, 1H), 2.40 (br dd, J=4.3, 13.2 Hz, 1H), 2.27 (q, J=8.4 Hz, 2H), 2.14-2.05 (m, 2H), 2.04-1.90 (m, 2H), 1.88-1.75 (m, 1H). MS (ESI) m/z 449.3 [M+H]$^+$ Compound #182: To a solution of 7-bromo-5-methylbenzofuran (200 mg, 947 umol, 1.00 eq), diphenylmethanimine (206 mg, 1.14 mmol, 190 uL, 1.20 eq), diphenyl phosphine (118 mg, 189 umol, 0.200 eq) and sodium tert-butoxide (136 mg, 1.42 mmol, 1.50 eq) in toluene (3.00 mL) was added tris(dibenzylideneacetone)dipalladium(0) (86.8 mg, 94.8 umol, 0.100 eq), the mixture was stirred at 110° C. for 12 h. The reaction mixture was poured into water (80.0 mL) and stirred for 10 min. The aqueous phase was extracted with ethyl acetate (3×40.0 mL). The combined organic phase was washed with brine (100 mL), dried over anhydrous sodium sulfate, filtered and concentrated in vacuum to give a residue. The residue was purified by silica gel chromatography (Petroleum ether/Ethyl acetate=1/0 to 5/1) to afford N-(diphenylmethylene)-5-methylbenzofuran-7-amine (350 mg, crude) as a yellow oil. $^1$H NMR (400 MHz, CDCl$_3$) δ=7.92-7.79 (m, 3H), 7.55-7.42 (m, 5H), 7.27-7.15 (m, 5H), 6.61 (d, J=2.1 Hz, 1H), 2.29 (s, 3H).

To a solution of N-(diphenylmethylene)-5-methylbenzofuran-7-amine (350 mg, 1.12 mmol, 1.00 eq) in tetrahydrofuran (6.00 mL) was added hydrochloric acid (5 M, 1.00 mL, 4.45 eq), the mixture was stirred at 25° C. for 1 h. The reaction mixture was adjust pH=8-9 with 4 M sodium hydroxide (2.00 mL) and then poured into water (60.0 mL). The aqueous phase was extracted with ethyl acetate (3×40.0 mL). The combined organic phase was washed with brine (80.0 mL), dried over anhydrous sodium sulfate, filtered and concentrated in vacuum to give a residue. The residue was purified by silica gel chromatography (Petroleum ether/Ethyl acetate=1/0 to 10/1) to afford 5-methylbenzofuran-7-amine (100 mg, 679 umol, 60% yield) as a yellow oil. $^1$H NMR (400 MHz, CDCl$_3$) δ=7.57 (d, J=2.2 Hz, 1H), 6.85 (s, 1H), 6.68 (d, J=2.1 Hz, 1H), 6.52 (d, J=0.6 Hz, 1H), 4.03-3.62 (m, 2H), 2.39 (s, 3H).

To a solution of 5-methylbenzofuran-7-amine (100 mg, 679 umol, 1.00 eq) in methanol (5.00 mL) was added palladium/carbon (20.0 mg, 10% purity), the mixture was stirred at 25° C. for 1 h under hydrogen atmospher. The reaction mixture was filtered to give a filtrate, the filtrate was concentrated to afford 5-methyl-2,3-dihydrobenzofuran-7-amine (70.0 mg, 469 umol, 69% yield) as a yellow oil. $^1$H NMR (400 MHz, CDCl$_3$) δ=6.40 (s, 1H), 6.31 (s, 1H), 4.47 (t, J=8.7 Hz, 2H), 3.10-3.03 (m, 2H), 2.14 (s, 3H).

To a solution of 5-methyl-2,3-dihydrobenzofuran-7-amine (70.0 mg, 469 umol, 1.00 eq) and pyridine (111 mg, 1.41 mmol, 113 uL, 3.00 eq) in acetonitrile (2.00 mL) was added phenyl carbonochloridate (88.2 mg, 563 umol, 70.5 uL, 1.20 eq), the mixture was stirred at 25° C. for 1 h. The reaction mixture was concentrated to give a residue. The residue was purified by reversed-phase HPLC (column: spherical C18, 20-45 um, 40A, SW 120, mobile phase: [water (0.1% Formic Acid)-acetonitrile) to afford phenyl (5-methyl-2,3-dihydrobenzofuran-7-yl)carbamate (100 mg, 371 umol, 79% yield) as a white solid.

To a solution of phenyl (5-methyl-2,3-dihydrobenzofuran-7-yl)carbamate (100 mg, 371 umol, 1.20 eq) and 3-(6-(hydroxymethyl)-1-oxoisoindolin-2-yl)piperidine-2,6-dione I (84.9 mg, 309 umol, 1.00 eq) in dimethylformamide (1.00 mL) was added sodium hydride (20.0 mg, 500 umol, 60% purity, 1.62 eq), the mixture was stirred at 25° C. for 1 h. The reaction mixture was quenched with 1M hydrochloric acid (0.500 mL) and filtered to give a filtrate. The filtrate was purified by Prep-HPLC (column: Phenomenex luna C18 150*25 mm*10 um; mobile phase: [water (0.225% FA)-ACN]; B %: 29%-59%, 10 min) to afford (2-(2,6-dioxopiperidin-3-yl)-3-oxoisoindolin-5-yl)methyl(5-methyl-2,3-dihydrobenzofuran-7-yl)carbamate #182 (70.11 mg, 155 umol, 50% yield) as a white solid. $^1$H NMR (400 MHz, DMSO-d$_6$) δ=10.99 (br s, 1H), 8.99 (br s, 1H), 7.79 (s, 1H), 7.70-7.59 (m, 2H), 7.08 (br s, 1H), 6.81 (s, 1H), 5.23 (s, 2H), 5.14 (br dd, J=5.1, 13.3 Hz, 1H), 4.59-4.43 (m, 3H), 4.40-4.29 (m, 1H), 3.15 (br t, J=8.6 Hz, 2H), 2.99-2.85 (m, 1H), 2.61 (br d, J=17.6 Hz, 1H), 2.45-2.34 (m, 1H), 2.20 (s, 3H), 2.08-1.98 (m, 1H). MS (ESI) m/z 450.1 [M+H]$^+$ Compound #183: To a solution of 6-chloro-5-methylpyridin-2-amine (1.00 g, 7.01 mmol, 1.00 eq) in acetonitrile (10.0 mL) were added phenyl carbonochloridate (1.21 g, 7.71 mmol, 967 uL, 1.10 eq) and pyridine (1.66 g, 21.0 mmol, 1.70 mL, 3.00 eq). The mixture was stirred at 25° C. for 12 h. The mixture was added water (10 mL) and extracted with ethyl acetate (3×25 mL). The combined organic phases were washed with brine (10 mL), dried over anhydrous sodium sulfate, filtered and concentrated in vacuum to give a residue. The residue was purified by silica gel chromatography (petroleum ether/ethyl acetate=10/1 to 5/1) to afford phenyl (6-chloro-5-methylpyridin-2-yl)carbamate (0.400 g, 1.46 mmol, 21% yield, 96% purity) as a white solid. $^1$H NMR (400 MHz, CDCl$_3$) δ=7.83 (d, J=8.4 Hz, 1H), 7.66 (br s, 1H), 7.58 (d, J=8.4 Hz, 1H), 7.44-7.39 (m, 2H), 7.27 (s, 1H), 7.22-7.16 (m, 2H), 2.35 (s, 3H).

To a solution of 3-(6-(hydroxymethyl)-1-oxoisoindolin-2-yl)piperidine-2,6-dione I (105 mg, 383 umol, 1.00 eq) in N',N'-dimethyl formamide (1.00 mL) were added phenyl (6-chloro-5-methylpyridin-2-yl)carbamate (121 mg, 460 umol, 1.20 eq) and sodium hydride (30.6 mg, 766 umol, 60% purity, 2.00 eq) at 0° C. The mixture was stirred at 0° C. for 1 h. The pH of the mixture was adjusted to 7 with hydrochloric acid (1 M). The mixture was purified by Prep-HPLC (column: Phenomenex Synergi C18 150×25 mm×10 um; mobile phase: [water (0.225% formic acid)-acetonitrile]; B %: 31%-61%, 10 min) and lyophilized to afford (2-(2,6-dioxopiperidin-3-yl)-3-oxoisoindolin-5-yl)methyl (6-chloro-5-methylpyridin-2-yl)carbamate #183 (81.33 mg, 182 umol, 47% yield, 99% purity) as a white solid. $^1$H NMR (400 MHz, DMSO-d$_6$) δ=10.99 (br s, 1H), 10.57 (s, 1H), 7.79 (s, 1H), 7.76 (br d, J=8.4 Hz, 1H), 7.74 (br d, J=8.0 Hz, 1H), 7.66 (dd, J=1.6 Hz, 8.0 Hz 1H), 7.63 (br d, J=8.0 Hz, 1H), 5.29 (s, 2H), 5.13 (dd, J=5.2, 13.2 Hz, 1H), 4.46 (br d, J=17.2 Hz, 1H), 4.34 (br d, J=17.6 Hz, 1H), 2.97-2.86 (m, 1H), 2.64-2.56 (m, 1H), 2.46-2.34 (m, 1H), 2.26 (s, 3H), 2.05-1.96 (m, 1H). MS (ESI) m/z 442.9 [M+H]$^+$ Compounds #184 and #185: To a stirred solution of 3-(tert-butyl)cyclobutanone (450 mg, 3.57 mmol, 1.00 eq) in ethyl alcohol (27.0 mL) were added hydroxylamine (495 mg, 7.13 mmol, 2.00 eq, hydride acid) and sodium acetate (1.17 g, 14.2 mmol, 4.00 eq), then the resulting mixture was heated to 80° C. and stirred for 16 h. The reaction mixture was quenched by addition water (10.0 mL), and then extracted with ethyl acetate (3×20.0 mL). The combined organic layers were washed with brine (3×20.0 mL), dried over sodium sulfate, filtered and concentrated under reduced pressure to give 3-tert-butylcyclobutanone oxime (440 mg, 3.12 mmol, 87% yield) as a white solid. $^1$H NMR (400 MHz, CDCl$_3$) δ=2.84-2.67 (m, 2H), 2.63-2.56 (m, 2H), 2.18 (tt, J=9.07, 7.44 Hz, 1H), 0.81 (s, 1H). MS (ESI) m/z 142.2 [M+H]$^+$ To a stirred solution of 3-tert-butylcyclobutanone oxime (200 mg, 1.42 mmol, 1.00 eq) in concentrated hydrochloric acid (1.00 mL) and methanol (10.0 mL), palladium on carbon (100 mg, 10% purity) was then added. Then the resulting solution was degassed with nitrogen for three times and degassed with hydrogen for three times. The reaction mixture was stirred at 15° C. for 12 h. The reaction mixture was filtrated through diatomite, and the filter cake was washed with ethyl alcohol, the filtrate was concentrated under reduced pressure to give 3-(tert-butyl)cyclobutanamine (220 mg, crude, hydride acid) as a yellow solid. $^1$H NMR (400 MHz, CDCl$_3$) δ=8.49-8.36 (m, 3H), 3.74 (br, 0.6H), 3.60 (br, 0.4H), 2.52 (br, 0.6H), 2.32-2.28 (m, 3H), 2.09-2.07 (m, 1H), 1.94-1.92 (m, 1H), 0.86 (d, J=4.38 Hz).

To a stirred solution of 3-(tert-butyl)cyclobutanamine (220 mg, 1.34 mmol, 1.00 eq, hydride acid) and phenyl carbonochloridate (231 mg, 1.48 mmol, 0.185 mL, 1.10 eq) in nitrile (10.0 mL) was added pyridine (318 mg, 4.03 mmol, 0.325 mL, 3.00 eq), then the mixture was stirred at 20° C. for 16 h. The reaction mixture was quenched by addition water (10.0 mL), and extracted with ethyl acetate (3×10.0 mL). The combined organic layers were washed with brine (3×10.0 mL), dried over sodium sulfate, filtered and concentrated under reduced pressure to give a residue. The residue was purified by flash silica gel chromatography (ISCO®; 10 g SepaFlash® Silica Flash Column, Eluent of 0~30% Ethylacetate/Petroleum ether gradient @ 12 mL/min) to give phenyl (3-(tert-butyl)cyclobutyl)carbamate (220 mg, 0.890 mmol, 66% yield) as a white solid. $^1$H NMR (400 MHz, CDCl$_3$) δ=7.41-7.13 (m, 5H), 5.25-5.06 (m, 1H), 4.18-4.08 (m, 0.5H), 4.0.6-3.96 (m, 0.4H), 2.34-2.25 (m, 2.5H), 2.01-1.97 (m, 1H), 1.89-1.80 (m, 0.5H), 1.68-1.60 (m, 1H), 0.87 (d, J=11.62 Hz). MS (ESI) m/z 248.2 [M+H]$^+$ To a stirred solution of phenyl (3-(tert-butyl)cyclobutyl)carbamate (87.3 mg, 0.353 mmol, 1.10 eq) and 3-(6-(hydroxymethyl)-1-oxoisoindolin-2-yl)piperidine-2,6-dione I (110 mg, 0.321 mmol, 80% purity, 1.00 eq) in dimethylformamide (2.00 mL) was added sodium hydride (25.6 mg, 0.642 mmol, 60% purity, 2.00 eq) at 0° C., then the mixture was stirred at 20° C. for 1.5 h. The reaction mixture was quenched by addition the mixture to aqueous formic acid at 0° C., and then extracted with ethyl acetate (3×10.0 mL). The combined organic layers were washed with brine (3×10.0 mL), dried over sodium sulfate, filtered and concentrated under reduced pressure to give a residue. The residue was purified by prep-HPLC (formic acid condition: column: Unisil 3-100 C18 Ultra 150*50 mm*3 um; mobile phase: [water (0.225% formic acid)-acetonitrile]; B %: 40%-60%, 10 min) to give desired compound #184 cis-(2-(2,6-dioxopiperidin-3-yl)-3-oxoisoindolin-5-yl)methyl ((1s,3s)-3-(tert-butyl)cyclobutyl)carbamate (42.2 mg, 98.6 umol, yield 30.74%) as a white solid, (formic acid condition: column: Phenomenex luna C18 150*25 mm*10 um; mobile phase: [water (0.225% formic acid)-acetonitrile]; B %: 37%-67%, 10 min) compound #185 trans-(2-(2,6-dioxopiperidin-3-yl)-3-oxoisoindolin-5-yl)methyl ((1s,3s)-3-(tert-butyl)cyclobutyl)carbamate (26.4 mg, 61.7 umol, yield 19.25%) as an off-white solid.

184: $^1$H NMR (400 MHz, DMSO-d$_6$) δ=10.99 (s, 1H), 7.71 (s, 1H), 7.66 (d, J=6.9 Hz, 1H), 7.60 (s, 2H), 5.15-5.12 (m, 3H), 4.49-4.44 (m, 1H), 4.35-4.31 (m, 1H), 3.87-3.82 (m, 1H), 2.97-2.88 (m, 1H), 2.63-2.58 (m, 1H), 2.43-2.35 (m, 1H), 2.10-1.98 (m, 4H), 1.94-1.87 (m, 2H), 0.81 (s, 9H). MS (ESI) m/z 428.2 [M+H]$^+$

185: $^1$H NMR (400 MHz, DMSO-d$_6$) δ=10.99 (s, 1H), 7.70 (s, 1H), 7.60 (s, 2H), 7.53 (d, J=7.88 Hz, 1H), 5.15-5.11 (m, 3H), 4.49-4.44 (m, 1H), 4.35-4.31 (m, 1H), 3.76-3.70 (m, 1H), 2.97-2.87 (m, 1H), 2.63-2.58 (m, 1H), 2.45-2.33 (m, 1H), 2.07-1.99 (m, 3H), 1.72-1.58 (m, 3H), 0.78 (s, 9H). MS (ESI) m/z 428.2 [M+H]$^+$

Compound #186: A mixture of 1-bromo-2,3-dimethyl-5-nitrobenzene (400 mg, 1.74 mmol, 1.00 eq) in dimethyl formamide (5.00 mL) was added Zinc cyanide (204 mg, 1.74 mmol, 110 uL, 1.00 eq), tris(dibenzylideneacetone)dipalladium(0) (159 mg, 174 umol, 0.10 eq) and diphenylphosphoryl azide (193 mg, 348 umol, 0.20 eq). The mixture was stirred at 130° C. for 3 h under nitrogen atmosphere. The reaction mixture was filtered. The filtrate was diluted with water (30.0 mL) and extracted with ethyl acetate (3×30.0 mL). The combined organic layers were washed with brine (2×30.0 mL), dried over anhydrous sodium sulfate, filtered and concentrated under reduced pressure to give a residue. The residue was purified by column chromatography (SiO$_2$, petroleum ether/ethyl acetate=1/0 to 10/1) to give 2,3-dimethyl-5-nitrobenzonitrile (315 mg, crude) as a yellow solid. $^1$H NMR (400 MHz, CDCl$_3$) δ=8.34 (d, J=2.3 Hz, 1H), 8.23 (d, J=2.3 Hz, 1H), 2.60 (s, 3H), 2.47 (s, 3H).

To a solution of 2,3-dimethyl-5-nitrobenzonitrile (300 mg, 1.70 mmol, 1.00 eq) in methanol (10.0 mL) and water (2.00 mL) was added ferrous powder (475 mg, 8.51 mmol, 5.00 eq) and saturated ammonium chloride (728 mg, 13.6 mmol, 8.00 eq). The mixture was stirred at 80° C. for 2 h. The reaction mixture was filtered and concentrated under reduced pressure to give a residue. The reaction mixture was diluted with aqueous saturated sodium bicarbonate (20.0 mL) and extracted with ethyl acetate (3×30.0 mL). The combined organic layers were washed with dried over anhydrous sodium sulfate, filtered and concentrated under reduced pressure to give 5-amino-2,3-dimethylbenzonitrile (150 mg, 821 umol, 48% yield, 80% purity) as a yellow solid. MS (ESI) m/z 147.2 [M+H]$^+$ To a solution of 5-amino-2,3-dimethylbenzonitrile (150 mg, 1.03 mmol, 1.00 eq) and pyridine (243 mg, 3.08 mmol, 248 uL, 3.00 eq) in acetonitrile (5.00 mL) was added phenyl carbonochloridate (177 mg, 1.13 mmol, 141 uL, 1.10 eq) at 0° C. The mixture was stirred at 20° C. for 1 h. The reaction mixture was concentrated under reduced pressure to give a residue. The residue was purified by flash silica gel chromatography (ISCO®; 20 g SepaFlash® Silica Flash Column, Eluent of 0-25% Ethylacetate/Petroleum ether gradient @ 60 mL/min) to give phenyl (3-cyano-4,5-dimethylphenyl)carbamate (150 mg, 552 umol, 54% yield, 98% purity) as an off-white solid. $^1$H NMR (400 MHz, DMSO-d$_6$) δ=10.43 (br s, 1H), 7.68 (d, J=2.0 Hz, 1H), 7.56 (d, J=1.8 Hz, 1H), 7.46-7.41 (m, 2H), 7.29-7.22 (m, 3H), 2.35 (s, 3H), 2.27 (s, 3H). MS (ESI) m/z 267.1 [M+H]$^+$ To a solution of phenyl phenyl (3-cyano-4,5-dimethylphenyl)carbamate (107 mg, 401 umol, 1.10 eq) and 3-(6-(hydroxymethyl)-1-oxoisoindolin-2-yl)piperidine-2,6-dione I (100 mg, 365 umol, 1.00 eq) in dimethyl formamide (1.50 mL) was added sodium hydride (29.2 mg, 729 umol, 60% purity, 2.00 eq) at 0° C. The mixture was stirred at 0° C. for 1 h. The pH of the mixture was adjusted to around 6 by adding hydrochloric acid. The mixture was extracted with ethyl acetate (3×10.0 mL). The combined organic layers were dried over anhydrous sodium sulfate, filtered and concentrated under reduced pressure to give a residue. The residue was purified by prep-HPLC (column: Phenomenex luna C18 150*25 mm*10 um; mobile phase: [water (0.2% FA)-ACN]; B %: 32%-62%, 10 min) and lyophilized to give (2-(2,6-dioxopiperidin-3-yl)-3-oxoisoindolin-5-yl)methyl (3-cyano-4,5-dimethylphenyl)carbamate #186 (71.81 mg, 144 umol, 85% yield, 99% purity, formate) as a white solid. $^1$H NMR (400 MHz, DMSO-d$_6$) δ=10.99 (br s, 1H), 10.03 (s, 1H), 7.79 (s, 1H), 7.73-7.60 (m, 3H), 7.52 (s, 1H), 5.28 (s, 2H), 5.13 (dd, J=5.1, 13.2 Hz, 1H), 4.51-4.43 (m, 1H), 4.38-4.29 (m, 1H), 2.98-2.85 (m, 1H), 2.60 (td, J=2.0, 15.4 Hz, 1H), 2.40 (br dd, J=4.4, 13.1 Hz, 1H), 2.33 (s, 3H), 2.25 (s, 3H), 2.05-1.97 (m, 1H). MS (ESI) m/z 447.0 [M+H]$^+$ Compound #187: A mixture of 5-fluoro-2,3-dihydrobenzofuran (0.500 g, 3.62 mmol, 1.00 eq) in nitric acid (5.00 mL) was stirred at −10° C. for 0.5 h. The mixture was quenched by addition water (5.00 mL) at −10° C. and extracted with ethyl acetate (3×10.0 mL). The combined organic layers were concentrated to afford 5-fluoro-7-nitro-2,3-dihydrobenzofuran (600 mg, 3.28 mmol, 90% yield) as a yellow solid. $^1$H NMR (400 MHz, CDCl$_3$) δ=7.63 (dd, J=2.8, 8.8 Hz, 1H), 7.23 (tdd, J=1.2, 2.8, 7.2 Hz, 1H), 4.86 (s, 2H), 3.34 (dt, J=1.2, 8.8 Hz, 2H).

A solution of 5-fluoro-7-nitro-2,3-dihydrobenzofuran (600 mg, 3.28 mmol, 1.00 eq) in ethyl acetate (15.0 mL) was added palladium on carbon (500 mg, 10% purity), the reaction mixture was stirred at 25° C. for 12 h under hydrogen atmosphere. The reaction mixture was filtered and the filtrate was concentrated to afford 5-fluoro-2,3-dihydrobenzofuran-7-amine (400 mg, 2.61 mmol, 79% yield) as a red solid. $^1$H NMR (400 MHz, DMSO-d$_6$) δ=6.23 (br d, J=8.8 Hz, 2H), 4.91 (s, 2H), 4.47 (t, J=8.8 Hz, 2H), 3.09 (t, J=8.8 Hz, 2H). MS (ESI) m/z 274.0 [M+H]$^+$ To a mixture of 5-fluoro-2,3-dihydrobenzofuran-7-amine (0.400 g, 2.61 mmol, 1.00 eq) in acetonitrile (15.0 mL) were added phenyl carbonochloridate (429 mg, 2.74 mmol, 343 uL, 1.05 eq) and pyridine (413 mg, 5.22 mmol, 421 uL, 2.00 eq), the reaction mixture was stirred at 25° C. for 12 h. The reaction was concentrated to give a residue. The residue was purified by reversed-phase HPLC (column: Shim-pack C18 150*25*10 um; mobile phase: [water (0.1% formic acid)-acetonitrile]) to afford phenyl (5-fluoro-2,3-dihydrobenzofuran-7-yl)carbamate (0.500 g, 1.83 mmol, 70% yield) as a red solid. $^1$H NMR (400 MHz, DMSO-$d_6$) δ=9.68 (br s, 1H), 7.45-7.39 (m, 2H), 7.29-7.16 (m, 4H), 6.90 (dd, J=2.6, 7.8 Hz, 1H), 4.60 (t, J=8.8 Hz, 2H), 3.23 (t, J=8.8 Hz, 2H).

To a mixture of 3-(6-(hydroxymethyl)-1-oxoisoindolin-2-yl)piperidine-2,6-dione I (80.0 mg, 291 umol, 1.00 eq) and phenyl (5-fluoro-2,3-dihydrobenzofuran-7-yl)carbamate (79.7 mg, 291 umol, 1.00 eq) in dimethylformamide (1.00 mL) was added sodium hydride (23.3 mg, 583 umol, 60% purity, 2.00 eq), the mixture was stirred at 25° C. for 1 h. The pH of the mixture was adjusted to 7 with formic acid, the mixture was diluted with dimethylformamide (1.00 mL). The mixture was purified by Prep-HPLC (column: Phenomenex Luna C18 150*25 mm*10 um; mobile phase: [water (0.225% formic acid)-acetonitrile]; B %: 26%-56%, 10 min) to afford (2-(2,6-dioxopiperidin-3-yl)-3-oxoisoindolin-5-yl)methyl(5-fluoro-2,3-dihydrobenzofuran-7-yl) carbamate #187 (68.1 mg, 148 umol, 50% yield, 99% purity) as a white solid. $^1$H NMR (400 MHz, DMSO-$d_6$) δ=10.99 (br s, 1H), 9.32 (br s, 1H), 7.81 (s, 1H), 7.70-7.58 (m, 2H), 7.24 (br d, J=10.4 Hz, 1H), 6.85 (dd, J=2.4, 8.0 Hz, 1H), 5.25 (s, 2H), 5.13 (dd, J=5.2, 13.2 Hz, 1H), 4.56 (t, J=8.8 Hz, 2H), 4.50-4.43 (m, 1H), 4.37-4.30 (m, 1H), 3.20 (t, J=8.8 Hz, 2H), 2.91 (ddd, J=5.4, 13.2, 17.6 Hz, 1H), 2.64-2.57 (m, 1H), 2.45-2.35 (m, 1H), 2.05-1.97 (m, 1H). MS (ESI) m/z 453.9 [M+H]$^+$ Compound #188: To a solution of 5-bromo-2-nitropyridine (5.00 g, 24.6 mmol, 1.00 eq), potassium trifluoro(prop-1-en-2-yl) borate (5.47 g, 36.9 mmol, 1.50 eq) and [1,1'-bis(diphenylphosphino)ferrocene] dichloropalladium(II) (901 mg, 1.23 mmol, 0.0500 eq) in dioxane (50.0 mL) and water (5.00 mL) was added potassium carbonate (10.2 g, 73.8 mmol, 3.00 eq), then evacuated with vacuum and back filled with nitrogen 3 times. The mixture was stirred at 80° C. for 2 h. The reaction mixture was poured into water (200 mL) and extracted with ethyl acetate (3×50.0 mL). The combined organic phase was separated, washed with brine (100 mL), dried over anhydrous sodium sulfate, filtered and concentrated to give a residue which was purified by silica gel chromatography (petroleum ether/ethyl acetate=20/1 to 10/1) to afford 2-nitro-5-(prop-1-en-2-yl)pyridine (2.80 g, 17.0 mmol, 69% yield) as a yellow solid. $^1$H NMR (400 MHz, DMSO-$d_6$) δ=8.82 (dd, J=0.8, 2.0 Hz, 1H), 8.33-8.26 (m, 2H), 5.79 (s, 1H), 5.44 (s, 1H), 2.19 (s, 3H). MS (ESI) m/z 165.1 [M+H]$^+$ To a mixture of trimethyl sulfoxonium iodide (5.43 g, 24.6 mmol, 1.50 eq) in dimethylsulfoxide (90.0 mL) was added potassium tert-butoxide (2.77 g, 24.6 mmol, 1.50 eq). The reaction mixture was stirred at 20° C. for 1 h. Then 2-nitro-5-(prop-1-en-2-yl)pyridine (2.70 g, 16.4 mmol, 1.00 eq) in tetrahydrofuran (30.0 mL) was added and the reaction mixture was stirred at 20° C. for another 3 h. The reaction mixture was poured into water (500 mL) and extracted with ethyl acetate (3×200 mL). The combined organic phase was separated, washed with brine (100 mL), dried over anhydrous sodium sulfate, filtered and concentrated to give a residue, which was purified by silica gel chromatography (petroleum ether/ethyl acetate=1/0 to 10/1) to afford 5-(1-methylcyclopropyl)-2-nitropyridine (450 mg, 2.53 mmol, 15% yield) as an off-white solid. $^1$H NMR (400 MHz, DMSO-$d_6$) δ=8.51 (d, J=2.4 Hz, 1H), 8.21 (d, J=8.8 Hz, 1H), 7.98 (dd, J=2.4, 8.8 Hz, 1H), 1.48 (s, 3H), 1.12-1.07 (m, 2H), 1.01-0.95 (m, 2H).

To a mixture of 5-(1-methylcyclopropyl)-2-nitropyridine (450 mg, 2.53 mmol, 1.00 eq) in ethyl acetate (10.0 mL) was added palladium on carbon (45.0 mg, 10% purity). The reaction mixture was stirred at 20° C. for 1 h under hydrogen atmosphere. The reaction mixture was filtered and concentrated to give 5-(1-methylcyclopropyl)pyridin-2-amine (380 mg, crude) as a white solid. MS (ESI) m/z 149.2 [M+H]$^+$ To a solution of 5-(1-methylcyclopropyl)pyridin-2-amine (360 mg, 2.43 mmol, 1.00 eq) and pyridine (384 mg, 4.86 mmol, 392 uL, 2.00 eq) in acetonitrile (5.00 mL) was added phenyl carbonochloridate (418 mg, 2.67 mmol, 334 uL, 1.10 eq). The reaction mixture was stirred at 20° C. for 1 h. The reaction mixture was concentrated to give a residue. The residue was purified by silica gel chromatography (petroleum ether/ethyl acetate=20/1 to 10/1) to give phenyl (5-(1-methylcyclopropyl)pyridin-2-yl)carbamate (280 mg, 1.04 mmol, 42% yield) as a white solid. $^1$H NMR (400 MHz, DMSO-$d_6$) δ=10.63 (s, 1H), 8.22 (d, J=2.0 Hz, 1H), 7.74-7.70 (m, 1H), 7.66-7.61 (m, 1H), 7.47-7.41 (m, 2H), 7.31-7.25 (m, 1H), 7.21 (d, J=7.6 Hz, 2H), 1.39 (s, 3H), 0.89-0.84 (m, 2H), 0.79-0.74 (m, 2H). MS (ESI) m/z 269.0 [M+H]$^+$ A mixture of 3-(6-(hydroxymethyl)-1-oxoisoindolin-2-yl) piperidine-2,6-dione I (80.0 mg, 291 umol, 1.00 eq) in dimethyl formamide (1.00 mL) was added sodium hydride (17.5 mg, 437 umol, 60% purity, 1.50 eq) and phenyl (5-(1-methylcyclopropyl)pyridin-2-yl)carbamate (86.0 mg, 41.0 umol, 1.10 eq) at 0° C. The reaction mixture was stirred at 20° C. for 1 h. The reaction mixture was added formic acid (2.00 mL) and filtered to give a filtrate, which was purified by Prep-HPLC (column: 3_Phenomenex Luna C18 75*30 mm*3 um; mobile phase: [water (0.05% hydrochloric acid)-acetonitrile]; B %: 17%-37%, 6 min) and filtered to give a filter cake. The filter cake was lyophilized to give (2-(2,6-dioxopiperidin-3-yl)-3-oxoisoindolin-5-yl)methyl(5-(1-methylcyclopropyl)pyridin-2-yl)carbamate #188 (42.16 mg, 93.0 umol, 31% yield, 99% purity) as a white solid. $^1$H NMR (400 MHz, DMSO-$d_6$) δ=11.00 (s, 1H), 10.26 (s, 1H), 8.16 (d, J=2.0 Hz, 1H), 7.81 (s, 1H), 7.74 (d, J=8.8 Hz, 1H), 7.70-7.66 (m, 1H), 7.65-7.62 (m, 1H), 7.60 (dd, J=2.4, 8.8 Hz, 1H), 5.29 (s, 2H), 5.13 (dd, J=5.2, 13.2 Hz, 1H), 4.51-4.43 (m, 1H), 4.38-4.31 (m, 1H), 3.03-2.84 (m, 1H), 2.60 (br dd, J=2.0, 16.8 Hz, 1H), 2.44-2.35 (m, 1H), 2.06-1.98 (m, 1H), 1.37 (s, 3H), 0.88-0.80 (m, 2H), 0.77-0.70 (m, 2H). MS (ESI) m/z 449.0 [M+H]$^+$ Compound #189: 5-chloro-2,3-dihydrobenzofuran (500 mg, 3.23 mmol, 1.00 eq) was added to nitric acid (5.00 mL). The mixture was stirred at −10° C. for 2 h. The reaction mixture was poured into ice water (30.0 mL) slowly. The reaction solution was extracted with ethyl acetate (3×15.0 mL). The organic phases were combined, dried with anhydrous sodium sulfate, and concentrated under reduced pressure to afford 5-chloro-7-nitro-2,3-dihydrobenzofuran (600 mg, 3.01 mmol, 93 yield) as a yellow solid. $^1$H NMR (400 MHz, DMSO-$d_6$) δ=7.92-7.82 (m, 1H), 7.74-7.67 (m, 1H), 4.81 (t, J=8.8 Hz, 2H), 3.31 (t, J=8.8 Hz, 2H).

To a solution of 5-chloro-7-nitro-2,3-dihydrobenzofuran (600 mg, 3.01 mmol, 1.00 eq) in methanol (8.00 mL) was added saturated ammonium chloride (804 mg, 15.0 mmol, 5.00 eq) and iron powder (839 mg, 15.0 mmol, 5.00 eq) and water (8.00 mL). The mixture was stirred at 80° C. for 2 h. The reaction mixture was filtered and the filtrate was concentrated under reduced pressure to afford a residue. The residue was diluted with saturated sodium bicarbonate (60.0 mL) and extracted with ethyl acetate (3×30.0 mL). The combined organic layers were dried over anhydrous sodium sulfate, filtered and concentrated under reduced pressure to afford 5-chloro-2,3-dihydrobenzofuran-7-amine (350 mg, 1.94 mmol, 65% yield) as a brown solid. $^1$H NMR (400 MHz, DMSO-$d_6$) δ=6.45 (s, 2H), 4.92 (s, 2H), 4.48 (t, J=8.8 Hz, 2H), 3.10 (t, J=8.8 Hz, 2H).

To a solution of 5-chloro-2,3-dihydrobenzofuran-7-amine (200 mg, 1.18 mmol, 1.00 eq) in acetonitrile (3.00 mL) was added pyridine (280 mg, 3.54 mmol, 286 uL, 3.00 eq) and phenyl carbonochloridate (185 mg, 1.18 mmol, 148 uL, 1.00 eq). The mixture was stirred at 25° C. for 12 h. The reaction mixture was concentrated under reduced pressure to afford a residue. The residue was purified by reverse-phase HPLC (column: spherical C18, 20-45 um, 100 Å, SW 120, mobile phase: [water (0.1% formic acid)-acetonitrile]) and the desired eluent was lyophilized to afford phenyl (5-chloro-2,3-dihydrobenzofuran-7-yl)carbamate (280 mg, 966 umol, 81% yield) as a white solid. $^1$H NMR (400 MHz, DMSO-$d_6$) δ=9.34 (br s, 1H), 7.19-7.12 (m, 2H), 6.79-6.72 (m, 3H), 6.45 (s, 2H), 4.48 (t, J=8.8 Hz, 2H), 3.10 (t, J=8.8 Hz, 2H).

To a solution of phenyl (5-chloro-2,3-dihydrobenzofuran-7-yl)carbamate (93.0 mg, 321 umol, 1.10 eq) in dimethyl formamide (500 uL) was added sodium hydride (23.3 mg, 583 umol, 60% purity, 2.00 eq) and 3-(6-(hydroxymethyl)-1-oxoisoindolin-2-yl)piperidine-2,6-dione I (80.0 mg, 292 umol, 1.00 eq). The mixture was stirred at 25° C. for 1 h. The pH of the mixture was adjusted to 7 with formic acid, then the mixture was diluted with dimethyl formamide (1.00 mL). The residue was purified by Prep-HPLC (column: Phenomenex luna C18 150*25 mm*10 um; mobile phase: [water (0.225% formic acid)-acetonitrile]; B %: 30%-60%, 10 min) and the desired eluent was lyophilized to afford (2-(2,6-dioxopiperidin-3-yl)-3-oxoisoindolin-5-yl)methyl (5-chloro-2,3-dihydrobenzofuran-7-yl)carbamate #189 (68.81 mg, 144 umol, 49% yield, 99% purity) as a white solid. $^1$H NMR (400 MHz, DMSO-$d_6$) δ=10.99 (br s, 1H), 9.33 (br s, 1H), 7.81 (s, 1H), 7.70-7.59 (m, 2H), 7.43 (br s, 1H), 7.04 (d, J=2.0 Hz, 1H), 5.25 (s, 2H), 5.13 (dd, J=5.6, 13.2 Hz, 1H), 4.58 (t, J=8.8 Hz, 2H), 4.51-4.41 (m, 1H), 4.39-4.28 (m, 1H), 3.21 (br t, J=8.8 Hz, 2H), 2.97-2.85 (m, 1H), 2.63-2.57 (m, 1H), 2.40 (br dd, J=4.8, 13.0 Hz, 1H), 2.06-1.95 (m, 1H). MS (ESI) m/z 470.2 [M+H]$^+$ Compound #190: A mixture of 3-(6-(hydroxymethyl)-1-oxoisoindolin-2-yl)piperidine-2,6-dione I (80.0 mg, 291 umol, 1.00 eq) in dimethyl formamide (1.00 mL) was added sodium hydride (17.5 mg, 437 umol, 60% purity, 1.50 eq) and phenyl (3-fluorobicyclo[1.1.1]pentan-1-yl)carbamate (67.7 mg, 306 umol, 1.05 eq) at 0° C. The reaction mixture was stirred at 20° C. for 1 h. The reaction mixture was added formic acid (2.00 mL) and filtered to give a filtrate, which was purified by Prep-HPLC (column: Phenomenex luna C18 150*25 mm*10 um; mobile phase: [water (0.225% formic acid)-acetonitrile]; B %: 21%-51%, 10 min) and lyophilized to give (2-(2,6-dioxopiperidin-3-yl)-3-oxoisoindolin-5-yl)methyl(3-fluorobicyclo[1.1.1]pentan-1-yl)carbamate #190 (48.8 mg, 120 umol, 41% yield, 99% purity) as a white solid. $^1$H NMR (400 MHz, DMSO-$d_6$) δ=11.00 (br s, 1H), 8.20 (br s, 1H), 7.71 (s, 1H), 7.61 (s, 2H), 5.14 (br s, 2H), 5.11 (br d, J=5.2 Hz, 1H), 4.51-4.42 (m, 1H), 4.39-4.29 (m, 1H), 2.97-2.86 (m, 1H), 2.61 (br dd, J=2.0, 15.6 Hz, 1H), 2.41 (dq, J=4.8, 13.2 Hz, 1H), 2.27 (s, 6H), 2.07-1.97 (m, 1H). MS (ESI) m/z 401.9 [M+H]$^+$ Compound #191: To a solution of 2,6-difluorophenol (0.500 g, 3.84 mmol, 1.00 eq) in dimethyl formamide (5.00 mL) was added sodium 2-chloro-2,2-difluoroacetate (1.17 g, 7.69 mmol, 2.00 eq) and potassium carbonate (640 mg, 4.63 mmol, 1.20 eq). The mixture was stirred at 100° C. for 3 h. The reaction mixture was diluted with water (100 mL) and exacted with ethyl acetate (3×100 mL). The organic phase was separated, washed with brine (2×50.0 mL), dried over sodium sulfate, filtered and concentrated under reduced pressure to give 2-(difluoromethoxy)-1,3-difluorobenzene (500 mg, 2.78 mmol, 72% yield) as a yellow solid. $^1$H NMR (400 MHz, CDCl$_3$) δ=7.24-7.14 (m, 1H), 7.03-6.95 (m, 2H), 6.59 (t, J=73.6 Hz, 1H).

To a solution of sulfuric acid (2.00 mL) was added nitric acid (2.80 g, 28.8 mmol, 2.00 mL, 65% purity, 10.4 eq) at −10° C. Then 2-(difluoromethoxy)-1,3-difluorobenzene (500 mg, 2.78 mmol, 1.00 eq) was added slowly at −10° C. The mixture was stirred at −10° C. for 0.5 h. The reaction mixture was diluted with cold water (100 mL) and extracted with ethyl acetate (3×50.0 mL). The combined organic layer was washed with saturated sodium bicarbonate (50.0 mL), dried over anhydrous sodium sulfate and concentrated under vacuum. The residue was purified by column chromatography (SiO$_2$, Petroleum ether/Ethyl acetate=20/1 to 0/1) to give 2-(difluoromethoxy)-1,3-difluoro-4-nitrobenzene (170 mg, 755 umol, 27% yield) as yellow oil. $^1$H NMR (400 MHz, CDCl$_3$) δ=8.09 (ddd, J=5.2, 8.0, 9.6 Hz, 1H), 7.17 (ddd, J=2.0, 8.4, 9.6 Hz, 1H), 6.67 (t, J=72.0 Hz, 1H).

To a solution of 2-(difluoromethoxy)-1,3-difluoro-4-nitrobenzene (170 mg, 755 umol, 1.00 eq) in methanol (10.0 mL) and water (2.00 mL) was added iron powder (210 mg, 3.78 mmol, 5.00 eq) and ammonium chloride (323 mg, 6.04 mmol, 8.00 eq). The mixture was stirred at 80° C. for 2 h. The mixture was filtered and the filtrate was concentrated under reduced pressure to give a residue. The crude product was diluted with saturated sodium bicarbonate (30.0 mL) and exacted with ethyl acetate (3×30.0 mL). The organic phase was separated, washed with brine (2×10.0 mL), dried over sodium sulfate, filtered and concentrated under reduced pressure to give 3-(difluoromethoxy)-2,4-difluoroaniline (60.0 mg, 307 umol, 40% yield) as yellow oil.

To a solution of 3-(difluoromethoxy)-2,4-difluoroaniline (60.0 mg, 307 umol, 1.00 eq) in acetonitrile (5.00 mL) was added pyridine (121 mg, 1.54 mmol, 124 uL, 5.00 eq) and phenyl carbonochloridate (52.9 mg, 338 umol, 42.3 uL, 1.10 eq). The mixture was stirred at 25° C. for 1 h. The reaction mixture was concentrated under reduced pressure to give oil. The oil was diluted with water (30.0 mL) and exacted with ethyl acetate (30.0 mL). The organic phase was separated and concentrated under reduced pressure to give a residue. The crude product was purified by prep-TLC (SiO$_2$, petroleum ether/ethyl acetate=5/1) to give phenyl (3-(difluoromethoxy)-2,4-difluorophenyl)carbamate (90.0 mg, 285 umol, 92% yield) as yellow oil. $^1$H NMR (400 MHz, CDCl$_3$) δ=8.01 (br s, 1H), 7.45-7.39 (m, 2H), 7.26-7.19 (m, 3H), 7.02 (dt, J=2.4, 9.6 Hz, 1H), 6.94 (t, J=7.6 Hz, 1H), 6.62 (t, J=73.2 Hz, 1H). MS (ESI) m/z 316.0 [M+H]$^+$ To a solution of phenyl phenyl (3-(difluoromethoxy)-2,4-difluorophenyl)carbamate (90.0 mg, 285 umol, 1.00 eq) in dimethyl formamide (2.00 mL) was added 3-(6-(hydroxymethyl)-1-oxoisoindolin-2-yl) piperidine-2,6-dione (86.1 mg, 314 umol, 1.10 eq) and sodium hydride (22.8 mg, 571 umol, 60% purity, 2.00 eq) at 0° C. The mixture was stirred at 0° C. for 0.5 h. The reaction mixture was quenched with formic acid (0.500 ml) to give a solution. The solution was purified by prep-HPLC (column: Phenomenex Synergi C18 150*25 mm*10 um; mobile phase: [water (0.225% FA)-ACN]; B %: 29%-59%, 10 min) and lyophilized to give (2-(2,6-dioxopiperidin-3-yl)-3-oxoisoindolin-5-yl)methyl (3-(difluoromethoxy)-2,4-difluorophenyl) carbamate #191 (84.14 mg, 169 umol, 59% yield) as a white solid. $^1$H NMR (400 MHz, DMSO-$d_6$) δ=10.99 (br s, 1H), 9.74 (br s, 1H), 7.80 (s, 1H), 7.71-7.55 (m, 3H), 7.30-7.25 (m, 1H), 7.24 (t, J=72.0 Hz, 1H), 5.28 (s, 2H), 5.13 (dd, J=5.2, 13.2 Hz, 1H), 4.51-4.44 (m, 1H), 4.39-4.31 (m, 1H), 2.97-2.86 (m, 1H), 2.65-2.57 (m, 1H), 2.40 (dq, J=4.4, 13.2 Hz, 1H), 2.06-1.97 (m, 1H). MS (ESI) m/z 496.1 [M+H]$^+$ Compound #192: To a solution of 5-fluoro-2-nitropyridine (300 mg, 2.11 mmol, 1.00 eq) in dimethyl formamide (2.00 mL) was added (R)-2-methylpyrrolidine (260 mg, 2.14 mmol, 1.01 eq, hydrochloric acid) and potassium carbonate (875 mg, 6.33 mmol, 3.00 eq). The mixture was stirred at 60° C. for 2 h. The reaction mixture was concentrated under reduced pressure to give a residue. The crude product was purified by column chromatography (SiO$_2$, Petroleum ether/Ethyl acetate=5/1 to 3/1) to give (R)-5-(2-methylpyrrolidin-1-yl)-2-nitropyridine (400 mg, 1.93 mmol, 91% yield) as a yellow solid. $^1$H NMR (400 MHz, CDCl$_3$) δ=8.17 (d, J=9.2 Hz, 1H), 7.86 (d, J=2.8 Hz, 1H), 6.87 (dd, J=2.8, 9.2 Hz, 1H), 4.14-4.01 (m, 1H), 3.61-3.53 (m, 1H), 3.39-3.29 (m, 1H), 2.21-2.10 (m, 3H), 1.91-1.80 (m, 1H), 1.25 (d, J=6.4 Hz, 3H).

To a solution of (R)-5-(2-methylpyrrolidin-1-yl)-2-nitropyridine (400 mg, 1.93 mmol, 1.00 eq) in methanol (20.0 mL) and water (2.00 mL) was added iron power (538 mg, 9.65 mmol, 5.00 eq) and ammonium chloride (826 mg, 15.4 mmol, 8.00 eq). The mixture was stirred at 80° C. for 2 h. The mixture was filtered and the filtrate was concentrated under reduced pressure to give a residue. The crude product was diluted with saturated sodium bicarbonate (30.0 mL) and exacted with ethyl acetate (3×30.0 mL). The organic phase was separated, washed with brine (2×10.0 mL), dried over sodium sulfate, filtered and concentrated under reduced pressure to give (R)-5-(2-methylpyrrolidin-1-yl)pyridin-2-amine (300 mg, 1.69 mmol, 87% yield) as a yellow solid. $^1$H NMR (400 MHz, CDCl$_3$) δ=7.52 (d, J=2.8 Hz, 1H), 6.88 (dd, J=2.8, 8.8 Hz, 1H), 6.50 (d, J=8.8 Hz, 1H), 3.74 (dd, J=2.4, 6.4 Hz, 1H), 3.42-3.36 (m, 1H), 3.08 (q, J=8.4 Hz, 1H), 2.09-1.97 (m, 3H), 1.73-1.65 (m, 1H), 1.14 (d, J=6.4 Hz, 3H). MS (ESI) m/z 178.2 [M+H]$^+$ To a solution of (R)-5-(2-methylpyrrolidin-1-yl)pyridin-2-amine (300 mg, 1.69 mmol, 1.00 eq) in acetonitrile (10.0 mL) was added pyridine (669 mg, 8.46 mmol, 683 uL, 5.00 eq) and phenyl carbonochloridate (318 mg, 2.03 mmol, 254 uL, 1.20 eq). The mixture was stirred at 25° C. for 0.5 h. The reaction mixture was concentrated under reduced pressure to give a residue. The crude product was triturated with water (5.00 ml) and dried to give (R)-phenyl (5-(2-methylpyrrolidin-1-yl)pyridin-2-yl)carbamate (300 mg, 1.01 mmol, 59% yield) as a white solid. $^1$H NMR (400 MHz, DMSO-d6) δ=10.18 (br s, 1H), 7.66 (d, J=2.8 Hz, 1H), 7.56 (d, J=8.8 Hz, 1H), 7.45-7.36 (m, 2H), 7.27-7.21 (m, 1H), 7.21-7.15 (m, 2H), 7.02 (dd, J=3.2, 9.2 Hz, 1H), 3.92-3.82 (m, 1H), 3.40-3.37 (m, 1H), 3.14-3.04 (m, 1H), 2.07-1.92 (m, 3H), 1.71-1.63 (m, 1H), 1.09 (d, J=6.0 Hz, 3H). MS (ESI) m/z 298.2 [M+H]$^+$ To a solution of 3-(6-(hydroxymethyl)-1-oxoisoindolin-2-yl)piperidine-2,6-dione I (70.0 mg, 255 umol, 1.00 eq) in dimethyl formamide (2.00 mL) was added (R)-phenyl (5-(2-methylpyrrolidin-1-yl)pyridin-2-yl) carbamate (76.0 mg, 255 umol, 1.00 eq) and sodium hydride (20.4 mg, 510 umol, 60% purity, 2.00 eq) at 0° C. The mixture was stirred at 0° C. for 0.5 h. The reaction mixture was quenched with formic acid (1.00 ml) to give a solution. The solution was purified by prep-HPLC (column: Phenomenex Synergi C18 150*25 mm*10 um; mobile phase: [water (0.225% FA)-ACN]; B %: 13%-46%, 11 min) and lyophilized to give (2-(2,6-dioxopiperidin-3-yl)-3-oxoisoindolin-5-yl)methyl(5-((R)-2-methylpyrrolidin-1-yl)pyridin-2-yl)carbamate #192 (23.8 mg, 45.5 umol, 17% yield, formate) as an off-white solid. $^1$H NMR (400 MHz, DMSO-d$_6$) δ=10.99 (br s, 1H), 9.81 (s, 1H), 7.80 (s, 1H), 7.69-7.57 (m, 4H), 7.00 (dd, J=2.8, 9.2 Hz, 1H), 5.26 (s, 2H), 5.13 (dd, J=5.2, 13.2 Hz, 1H), 4.51-4.43 (m, 1H), 4.38-4.30 (m, 1H), 3.90-3.82 (m, 1H), 3.39-3.37 (m, 1H), 3.08 (q, J=8.4 Hz, 1H), 2.97-2.88 (m, 1H), 2.61 (br dd, J=2.0, 15.2 Hz, 1H), 2.41 (br dd, J=4.4, 13.2 Hz, 1H), 2.06-1.98 (m, 3H), 1.97-1.91 (m, 1H), 1.69-1.60 (m, 1H), 1.09 (d, J=6.0 Hz, 3H). MS (ESI) m/z 478.1 [M+H]$^+$ Compound #193: A mixture of phenyl bicyclo[1.1.1]pentan-1-ylcarbamate I (20.0 mg, 98.4 umol, 1.00 eq) and 3-(6-(hydroxymethyl)-1-oxoisoindolin-2-yl)piperidine-2,6-dione I (32.4 mg, 118 umol, 1.20 eq) in dimethyl formamide (1.00 mL) was added sodium hydride (5.90 mg, 148 umol, 60% purity, 1.50 eq) at 0° C. The reaction mixture was stirred at 25° C. for 1 h. The reaction mixture was added formic acid (1.00 mL) and filtered to give a filtrate, which was purified by Prep-HPLC (column: Phenomenex Luna C18 150*25 mm*10 um; mobile phase: [water (0.225% formic acid)-acetonitrile]; B %: 19%-49%, 10 min) and lyophilized to give (2-(2,6-dioxopiperidin-3-yl)-3-oxoisoindolin-5-yl)methyl bicyclo[1.1.1]pentan-1-ylcarbamate #193 (19 mg, 49.6 umol, 50% yield, 99% purity) as a white solid. $^1$H NMR (400 MHz, DMSO-d$_6$) δ=10.99 (br s, 1H), 8.02 (br s, 1H), 7.70 (s, 1H), 7.62 (s, 2H), 5.21-5.07 (m, 3H), 4.51-4.42 (m, 1H), 4.40-4.29 (m, 1H), 2.99-2.85 (m, 1H), 2.61 (td, J=2.2, 15.4 Hz, 1H), 2.47-2.33 (m, 2H), 2.06-1.98 (m, 1H), 1.96-1.87 (m, 6H). MS (ESI) m/z 384.1 [M+H]$^+$ Compound #194: To a solution of 5-chloro-4-methylpyridin-2-amine (3.00 g, 21.0 mmol, 1.00 eq) in sulfuric acid (30.0 mL) was added hydrogen peroxide (23.8 g, 210 mmol, 20.2 mL, 30% purity, 10.0 eq) dropwise at 0° C. The mixture was stirred at 15° C. for 12 h. The mixture was poured into water (100 mL), then the mixture was quenched with saturated sodium sulfite to potassium iodide starch paper from blue to colorless. Then the mixture was diluted with saturated sodium carbonate (200 mL) and exacted with ethyl acetate (3×100 mL). The organic phase was separated, washed with brine (2×10.0 mL), dried over sodium sulfate, filtered and concentrated under reduced pressure to give a residue. The residue was purified by column chromatography (SiO$_2$, petroleum ether/ethyl acetate=20/1 to 1/1) to give 5-chloro-4-methyl-2-nitropyridine (2.70 g, 15.6 mmol, 74% yield) as a white solid. $^1$H NMR (400 MHz, CDCl$_3$) δ=8.51 (s, 1H), 8.16 (s, 1H), 2.56 (s, 3H).

To a solution of 5-chloro-4-methyl-2-nitropyridine (1.50 g, 8.69 mmol, 1.00 eq) and pyrrolidine (3.09 g, 43.4 mmol, 3.63 mL, 5.00 eq) in dimethylformamide (15.0 mL) was added potassium carbonate (3.60 g, 26.0 mmol, 3.00 eq). The mixture was stirred at 60° C. for 12 h. The mixture was filtered and the filtrate was concentrated to give crude product. The crude product was purified by silica gel chromatography (petroleum ether/ethyl acetate=10/1 to 1/1) to give 4-methyl-2-nitro-5-(pyrrolidin-1-yl)pyridine (700 mg, 3.38 mmol, 38% yield) as a yellow solid. $^1$H NMR (400 MHz, DMSO-d$_6$) δ=8.01 (s, 1H), 7.82 (s, 1H), 3.65-3.52 (m, 4H), 2.51 (s, 3H), 1.98-1.85 (m, 4H).

To a mixture of 4-methyl-2-nitro-5-(pyrrolidin-1-yl)pyridine (300 mg, 1.45 mmol, 1.00 eq) in methanol (10.0 mL) was added Pd/C (100 mg, 10% purity). The mixture was stirred at 15° C. for 1 h under hydrogen (15 Psi). The mixture was filtered to give a filtrate. The filtrate was concentrated to give 4-methyl-5-(pyrrolidin-1-yl)pyridin-2-amine (340 mg, crude) as yellow oil. $^1$H NMR (400 MHz, DMSO-d$_6$) δ=7.56 (s, 1H), 6.26 (s, 1H), 5.30 (s, 2H), 2.93 (br t, J=6.1 Hz, 4H), 2.11 (s, 3H), 1.82 (td, J=3.1, 6.4 Hz, 4H).

To a mixture of 4-methyl-5-(pyrrolidin-1-yl)pyridin-2-amine (340 mg, 1.92 mmol, 1.00 eq) and pyridine (759 mg, 9.59 mmol, 774 uL, 5.00 eq) in acetonitrile (5.00 mL) was added phenyl carbonochloridate (360 mg, 2.30 mmol, 288 uL, 1.20 eq) dropwise at 0° C. The mixture was stirred at 15° C. for 12 h. The mixture was concentrated in vacuum. The residue was triturated with ethyl acetate (4.00 mL) and filtered to give phenyl (4-methyl-5-(pyrrolidin-1-yl)pyridin-2-yl)carbamate (400 mg, 1.35 mmol, 70% yield) as a yellow solid.

To a mixture of phenyl (4-methyl-5-(pyrrolidin-1-yl)pyridin-2-yl)carbamate (130 mg, 438 umol, 1.20 eq) and 3-(6-(hydroxymethyl)-1-oxoisoindolin-2-yl)piperidine-2,6-dione I (100 mg, 365 umol, 1.00 eq) in dimethyformamide (2.00 mL) was added sodium hydride (21.9 mg, 547 umol, 60% purity, 1.50 eq) in portions. The mixture was stirred at 15° C. for 2 h. The mixture was quenched with 1 M hydrochloric acid (0.500 mL) and filtered. The residue was purified by prep-HPLC (column: 3_Phenomenex Luna C18 75*30 mm*3 um; mobile phase: [water (0.05% HCl)-ACN]; B %: 14%-34%, 9 min) and lyophilized to give (2-(2,6-dioxopiperidin-3-yl)-3-oxoisoindolin-5-yl)methyl (4-methyl-5-(pyrrolidin-1-yl)pyridin-2-yl) carbamate #194 (25.28 mg, 52.4 umol, 14% yield, 99% purity) as a yellow solid. $^1$H NMR (400 MHz, DMSO-$d_6$) δ=11.29 (br d, J=2.9 Hz, 1H), 10.99 (s, 1H), 8.02-7.87 (m, 1H), 7.82 (s, 1H), 7.72-7.69 (m, 1H), 7.67-7.62 (m, 1H), 7.53 (br s, 1H), 5.37 (s, 2H), 5.12 (br dd, J=5.1, 13.3 Hz, 1H), 4.52-4.43 (m, 1H), 4.39-4.31 (m, 1H), 3.39 (br s, 4H), 2.99-2.82 (m, 1H), 2.60 (br d, J=17.4 Hz, 1H), 2.52 (s, 3H), 2.46-2.36 (m, 1H), 2.05-1.95 (m, 5H). MS (ESI) m/z 478.2 [M+H]$^+$ Compound #195: To a solution of methyl 4-aminobenzoate (1.00 g, 6.62 mmol, 1.00 eq) in tetrahydrofuran (100 mL) was added methylmagnesium bromide (3.00 M, 11.0 mL, 5.00 eq) (3.00 M in diethyl ether) under nitrogen atmosphere at −40° C. The mixture was stirred at 25° C. for 12 h. Methylmagnesium bromide (3.00 M, 11.0 mL, 5.00 eq) was added into the reaction mixture at −40° C. The mixture was stirred at 25° C. for another 12 h. The reaction mixture was quenched with saturated ammonium chloride (400 mL) at 0° C. and extracted with ethyl acetate (300 mL). The combined organic layer was washed with water and dried over anhydrous sodium sulfate. After filtration, the filtrate was concentrated under reduced pressure to give a residue. The crude product was purified by column chromatography on silica gel eluted with petroleum ether/ethyl acetate=1/0 to 0/1 to give 2-(4-aminophenyl)propan-2-ol (250 mg, 1.65 mmol, 25% yield) as yellow oil. $^1$H NMR (400 MHz, DMSO-$d_6$) δ=7.12-7.07 (m, 2H), 6.49-6.46 (m, 2H), 4.81 (s, 2H), 4.64 (s, 1H), 1.34 (s, 6H). MS (ESI) m/z 152.2 [M+H]$^+$ To a solution of 2-(4-aminophenyl)propan-2-ol (130 mg, 860 umol, 1.00 eq) in acetonitrile (5.00 mL) was added pyridine (204 mg, 2.58 mmol, 208 uL, 3.00 eq) and phenyl carbonochloridate (163 mg, 1.04 mmol, 130 uL, 1.21 eq) in portions. The mixture was stirred at 15° C. for 1 h. The reaction mixture was concentrated under reduced pressure to give a residue. The crude product was purified by column chromatography on silica gel eluted with petroleum ether/ethyl acetate=20/1 to 0/1 to give phenyl (4-(2-hydroxypropan-2-yl)phenyl)carbamate (60.0 mg, 221 umol, 26% yield) as a white solid. $^1$H NMR (400 MHz, DMSO-$d_6$) δ=10.12 (br s, 1H), 7.45-7.38 (m, 6H), 7.28-7.19 (m, 3H), 4.93 (s, 1H), 1.40 (s, 6H). MS (ESI) m/z 254.0 [M+H−18]$^+$ To a solution of 3-(6-(hydroxymethyl)-1-oxoisoindolin-2-yl)piperidine-2,6-dione I (50.0 mg, 182 umol, 1.00 eq) and phenyl (4-(2-hydroxypropan-2-yl)phenyl)carbamate (59.0 mg, 217 umol, 1.19 eq) in N,N-dimethyl formamide (1.00 mL) was added sodium hydride (60%, dispersion in paraffin liquid) (15.0 mg, 375 umol, 60% purity, 2.06 eq) at 0° C. in portions. The mixture was stirred at 15° C. for 1 h. The reaction mixture was quenched with hydrochloric acid (1 M, 15.0 mL) and extracted with ethyl acetate (30.0 mL). The combined organic layer was washed with water (10.0 mL) and dried over anhydrous sodium sulfate. After filtration, the filtrate was concentrated under reduced pressure to give a residue which was dissolved in N,N-dimethyl formamide (2.00 mL) and purified by prep-HPLC (column: Unisil 3-100 C18 Ultra 150*50 mm*3 um; mobile phase: [water (0.225% FA)-ACN]; B %: 20%-50%, 10 min). The desired fraction was collected and concentrated under pressure to give a solution. The residual solution was lyophilized to give (2-(2,6-dioxopiperidin-3-yl)-3-oxoisoindolin-5-yl)methyl (4-(2-hydroxypropan-2-yl)phenyl)carbamate #195 (45.01 mg, 89.6 umol, 49% yield, 99% purity, formic acid) as a white solid. $^1$H NMR (400 MHz, DMSO-$d_6$) δ=10.99 (br s, 1H), 9.72 (br s, 1H), 7.79 (s, 1H), 7.70-7.59 (m, 2H), 7.44-7.30 (m, 4H), 5.26 (s, 2H), 5.13 (dd, J=5.1, 13.3 Hz, 1H), 4.91 (s, 1H), 4.52-4.42 (m, 1H), 4.39-4.28 (m, 1H), 2.98-2.86 (m, 1H), 2.63-2.56 (m, 1H), 2.40 (dd, J=4.5, 13.1 Hz, 1H), 2.05-1.96 (m, 1H), 1.38 (s, 6H). MS (ESI) m/z 434.2 [M+H−18]$^+$ Compound #196: To a solution of tert-butyl (3-aminobicyclo[1.1.1]pentan-1-yl)carbamate (100 mg, 504 umol, 1.00 eq) in acetonitrile (2.00 mL) was added cesium carbonate (493 mg, 1.51 mmol, 3.00 eq) and phenyl carbonochloridate (102 mg, 655 umol, 82.1 uL, 1.30 eq). The mixture was stirred at 25° C. for 1 h. The mixture was filtered to give a filter liquor which was concentrated under reduced pressure to give tert-butyl phenyl bicyclo[1.1.1]pentane-1,3-diyldicarbamate (60.0 mg, 188 umol, 37% yield) as a white solid. $^1$H NMR (400 MHz, DMSO-$d_6$) δ=9.36-9.27 (m, 1H), 7.18-7.14 (m, 2H), 6.79-6.73 (m, 3H), 2.06-1.97 (m, 4H), 1.81 (s, 2H), 1.37 (s, 9H).

To a solution of tert-butyl phenyl bicyclo[1.1.1]pentane-1,3-diyldicarbamate (50.0 mg, 157 umol, 1.00 eq) in dimethyl formamide (2.00 mL) was added 3-(6-(hydroxymethyl)-1-oxoisoindolin-2-yl)piperidine-2,6-dione (43.0 mg, 157 umol, 1.00 eq) and sodium hydride (12.5 mg, 314 umol, 60% purity, 2.00 eq) at 0° C. The mixture was stirred at 0° C. for 0.5 h. The reaction mixture was quenched with formic acid (0.500 ml) to give a solution. The solution was purified by prep-HPLC (column: Phenomenex Synergi C18 150*25 mm*10 um; mobile phase: [water (0.225% FA)-ACN]; B %: 25%-52%, 9 min) and lyophilized to give tert-butyl((2-(2,6-dioxopiperidin-3-yl)-3-oxoisoindolin-5-yl)methyl)bicyclo[1.1.1]pentane-1,3-diyldicarbamate #196 (10.3 mg, 18.9 umol, 12% yield, formate) as a white solid. $^1$H NMR (400 MHz, DMSO-$d_6$) δ=10.99 (br s, 1H), 8.01 (br s, 1H), 7.69 (s, 1H), 7.60 (s, 2H), 7.56-7.43 (m, 1H), 5.20-5.05 (m, 3H), 4.49-4.41 (m, 1H), 4.37-4.29 (m, 1H), 2.96-2.86 (m, 1H), 2.63-2.57 (m, 1H), 2.40 (br dd, J=4.4, 13.2 Hz, 1H), 2.12-1.97 (m, 7H), 1.36 (br s, 9H). MS (ESI) m/z 443.0 [M+H−56]$^+$ Compound #197: To a mixture of 5-bromo-2-fluoro-4-methylaniline (300 mg, 1.47 mmol, 1.00 eq) and pyridine (349 mg, 4.41 mmol, 356 uL, 3.00 eq) in acetonitrile (3.00 mL) was added phenyl carbonochloridate (253 mg, 1.62 mmol, 203 uL, 1.10 eq) at 0° C. After addition, the mixture was stirred at 25° C. for 2 h. The reaction mixture was poured into water (30.0 mL) and extracted with ethyl acetate (2×50.0 mL). The combined organic layers were washed with brine (2×25.0 mL), dried over anhydrous sodium sulfate, filtered and concentrated under reduced pressure to give a residue. The crude product was purified by silica gel chromatography (petroleum ether/ethyl acetate=20/1 to 10/1) to afford phenyl (5-bromo-2-fluoro-4-methylphenyl) carbamate (330 mg, 967 umol, 66% yield, 95% purity) as a white solid. $^1$H NMR (400 MHz, CDCl$_3$) δ=8.37 (s, 1H), 7.46-7.41 (m, 2H), 7.32-7.29 (m, 1H), 7.24-7.20 (m, 2H), 7.11 (s, 1H), 7.03 (d, J=11.6 Hz, 1H), 2.37 (s, 3H).

To a solution of 3-(6-(hydroxymethyl)-1-oxoisoindolin-2-yl)piperidine-2,6-dione I (100 mg, 365 umol, 1.00 eq) in tetrahydrofuran (2.00 mL) was added sodium hydride (20.0 mg, 500 umol, 60% purity, 1.37 eq) at 0° C. under nitrogen atmosphere. After stirring the mixture at 0° C. for 15 min, phenyl (5-bromo-2-fluoro-4-methylphenyl)carbamate (130 mg, 401 umol, 1.10 eq) was added at 0° C. After addition, the mixture was stirred at 25° C. for 1 h. The reaction mixture was poured into water (30.0 mL) and extracted with ethyl acetate (2×50.0 mL). The combined organic layers were washed with brine (2×25.0 mL), dried over anhydrous sodium sulfate, filtered and concentrated under reduced pressure to give a residue. The residue was purified by prep-HPLC (column: Phenomenex Synergi C18 150*25 mm*10 um; mobile phase: [water (0.225% FA)-ACN]; B %: 35%-68%, 11 min) to afford (2-(2,6-dioxopiperidin-3-yl)-3-oxoisoindolin-5-yl)methyl (5-bromo-2-fluoro-4-methylphenyl)carbamate #197 (66.07 mg, 131 umol, 36% yield, 99% purity) as a white solid. $^1$H NMR (400 MHz, DMSO-d$_6$) δ=11.00 (s, 1H), 9.67 (s, 1H), 7.91 (d, J=7.6 Hz, 1H), 7.80 (s, 1H), 7.69-7.62 (m, 2H), 7.30 (d, J=11.6 Hz, 2H), 5.27 (s, 2H), 5.10 (dd, J=5.2, 13.6 Hz, 1H), 4.49-4.31 (m, 2H), 2.99-2.85 (m, 1H), 2.65-2.57 (m, 1H), 2.47-2.35 (m, 1H), 2.30 (s, 3H), 2.05-1.97 (m, 1H). MS (ESI) m/z 505.5 [M+H]$^+$ Compound #198: A mixture of phenyl (3-(piperidin-1-yl)bicyclo[1.1.1]pentan-1-yl)carbamate (20.0 mg, 69.8 umol, 1.00 eq) and 3-(6-(hydroxymethyl)-1-oxoisoindolin-2-yl)piperidine-2,6-dione I (23.0 mg, 83.8 umol, 1.20 eq) in dimethyl formamide (1.00 mL) was added sodium hydride (5.59 mg, 140 umol, 60% purity, 2.00 eq) at 0° C. The reaction mixture was stirred at 25° C. for 1 h. The reaction mixture was added formic acid (1.00 mL) and filtered to give a filtrate, which was purified by Prep-HPLC (column: Phenomenex Luna C18 150*25 mm*10 um; mobile phase: [water (0.225% formic acid)-acetonitrile]; B %: 1%-30%, 10 min) and lyophilized to give (2-(2,6-dioxopiperidin-3-yl)-3-oxoisoindolin-5-yl)methyl(3-(piperidin-1-yl)bicyclo[1.1.1]pentan-1-yl)carbamate #198 (8.54 mg, 18.1 umol, 26% yield, 99% purity) as a white solid. $^1$H NMR (400 MHz, DMSO-d$_6$) δ=11.00 (s, 1H), 8.08-7.95 (m, 1H), 7.70 (s, 1H), 7.61 (s, 2H), 5.17-5.08 (m, 3H), 4.51-4.42 (m, 1H), 4.38-4.30 (m, 1H), 2.98-2.86 (m, 1H), 2.61 (br d, J=17.0 Hz, 1H), 2.48-2.41 (m, 1H), 2.41-2.28 (m, 4H), 2.05-1.98 (m, 1H), 1.88 (br s, 6H), 1.49 (br s, 4H), 1.40-1.32 (m, 2H). MS (ESI) m/z 467.2 [M+H]$^+$ Compound #199: To a mixture of methyl 5-aminopicolinate (1.00 g, 6.57 mmol, 1.00 eq) in tetrahydrofuran (10.0 mL) was added methylmagnesium bromide (3 mol/L in ethyl ether, 9.20 mL, 4.20 eq) drop-wise at −30° C. under nitrogen. After stirring the mixture at 10° C. for 1 h, the reaction was quenched with saturated ammonium chloride (50.0 mL) and extracted with ethyl acetate (3×50.0 mL). The combined organic layers were dried over sodium sulfate, filtered and concentrated to give the crude product. The residue was purified by flash silica gel chromatography (ISCO®; 20 g SepaFlash® Silica Flash Column, Eluent of 0-80% ethyl acetate/petroleum ether gradient @40 mL/min) to afford 2-(5-aminopyridin-2-yl)propan-2-ol (500 mg, 3.29 mmol, 50% yield) as yellow solid. $^1$H NMR (400 MHz, DMSO-d$_6$) δ=7.82 (d, J=2.8 Hz, 1H), 7.26 (d, J=8.8 Hz, 1H), 6.89 (dd, J=2.8, 8.8 Hz, 1H), 5.07 (s, 2H), 4.90 (s, 1H), 1.35 (s, 6H).

To a mixture of 2-(5-aminopyridin-2-yl)propan-2-ol (300 mg, 1.97 mmol, 1.00 eq), pyridine (311 mg, 3.94 mmol, 2.00 eq) in tetrahydrofuran (10.0 mL) was added phenyl carbonochloridate (326 mg, 2.08 mmol, 1.06 eq) at 0° C. After addition, the mixture was stirred at 0° C. for 1 h. The reaction mixture was diluted with ethyl acetate (30.0 mL) and washed with brine (2×30.0 mL). The separated organic layer was dried over anhydrous sodium sulfate, filtered and concentrated to give the crude product. The crude product was purified by flash silica gel chromatography (ISCO®; 20 g SepaFlash® Silica Flash Column, Eluent of 0-30% ethyl acetate/petroleum ether gradient @ 30 mL/min) to afford phenyl (6-(2-hydroxypropan-2-yl)pyridin-3-yl)carbamate (300 mg, 1.10 mmol, 55% yield) as a white solid. $^1$H NMR (400 MHz, CDCl$_3$) δ=8.45 (d, J=2.0 Hz, 1H), 7.98 (d, J=6.8 Hz, 1H), 7.38-7.29 (m, 3H), 7.21-7.17 (m, 1H), 7.15-7.09 (m, 2H), 1.48 (s, 6H).

To a mixture of 3-(6-(hydroxymethyl)-1-oxoisoindolin-2-yl)piperidine-2,6-dione I (100 mg, 364.60 μmol, 1.00 eq) in tetrahydrofuran (5.00 mL) was added sodium hydride (25 mg, 625.06 mol, 60% purity, 1.71 eq), and then the mixture was stirred at 0° C. for 0.5 h. Phenyl (6-(2-hydroxypropan-2-yl)pyridin-3-yl)carbamate (100 mg, 367.24 μmol, 1.01 eq) was added to the above mixture and then the resulting mixture was stirred at 0° C. for another 1 h. The mixture was poured into saturated ammonium chloride (30.0 mL) and extracted with ethyl acetate (3×30.0 mL). The organic layers were dried over anhydrous sodium sulfate, filtered and concentrated to give the crude product. The crude product was purified by prep-HPLC (column: Unisil 3-100 C18 μLtra 150*50 mm*3 um; mobile phase: [water (0.225% FA)-ACN]; B %: 1%-30%, 10 min). The eluent was concentrated to remove organic solvents, and then the aqueous solution was lyophilized to give (2-(2,6-dioxopiperidin-3-yl)-3-oxoisoindolin-5-yl)methyl (6-(2-hydroxypropan-2-yl)pyridin-3-yl)carbamate #199 (112 mg, 225 μmol, 61% yield, 99% purity) as a white solid. 108.46 mg of the final product has been delivered and the rest of it has been used to run analytic data. $^1$H NMR (400 MHz, DMSO-d$_6$) δ=10.99 (s, 1H), 9.95 (s, 1H), 8.52 (d, J=2.0 Hz, 1H), 7.89-7.82 (m, 1H), 7.80 (s, 1H), 7.71-7.66 (m, 1H), 7.65-7.61 (m, 1H), 7.56 (d, J=8.8 Hz, 1H), 5.29 (s, 2H), 5.12 (dd, J=5.2, 13.6 Hz, 1H), 4.50-4.44 (m, 1H), 4.38-4.31 (m, 1H), 2.96-2.87 (m, 1H), 2.64-2.57 (m, 1H), 2.45-2.35 (m, 1H), 2.05-1.97 (m, 1H), 1.40 (s, 6H). MS (ESI) m/z 453.1 [M+H]$^+$ Compound #200: To a mixture of 2,4-difluoro-5-(trifluoromethoxy)aniline (300 mg, 1.41 mmol, 1.00 eq) and pyridine (167 mg, 2.11 mmol, 1.50 eq) in tetrahydrofuran (10.0 mL) was added phenyl carbonochloridate (231 mg, 1.48 mmol, 1.05 eq) dropwise at 0° C. The mixture was stirred at 25° C. for 0.5 h. The reaction mixture was poured into hydrochloric acid (50.0 mL, 0.5 mol/L) and extracted with ethyl acetate (3×20.0 mL). The organic phase was concentrated under vacuum to give a residue. The residue was purified by silica gel chromatography (petroleum ether/ethyl acetate=50/1 to 20/1) to give phenyl (2,4-difluoro-5-(trifluoromethoxy)phenyl)carbamate (400 mg, 1.02 mmol, 72% yield) as a white solid. $^1$H NMR (400 MHz, CDCl$_3$) δ=8.25 (s, 1H), 7.44-7.41 (m, 2H), 7.30 (d, J=7.6 Hz, 1H), 7.21-7.19 (m, 2H), 7.15 (s, 1H), 7.09-7.04 (m, 1H).

A mixture of 3-(6-(hydroxymethyl)-1-oxoisoindolin-2-yl)piperidine-2,6-dione I (61.5 mg, 224 umol, 1.10 eq) in tetrahydrofuran (5.00 mL) was purged with nitrogen for 3 times, and then sodium hydride (12.2 mg, 306 umol, 60% purity, 1.50 eq) was added at 0° C. After stirring the mixture at 0° C. for 0.2 h, phenyl (2,4-difluoro-5-(trifluoromethoxy) phenyl)carbamate (80.0 mg, 204 umol, 1.00 eq) was added. After addition, the mixture was stirred at 0° C. for 0.3 h. The reaction mixture was poured into saturated ammonium chloride (50.0 ml) and extracted with ethyl acetate (3×20.0 mL). The organic phase was concentrated under vacuum to give a residue. The residue was purified by prep-HPLC (column: Phenomenex Synergi C18 150*25 mm*10 um; mobile phase: [water (0.225% FA)-ACN]; B %: 36%-69%, 11 min) and lyophilized to give (2-(2,6-dioxopiperidin-3-yl)-3-oxoisoindolin-5-yl)methyl (2,4-difluoro-5-(trifluoromethoxy)phenyl)carbamate #200 (74.3 mg, 143 umol, 70% yield, 99% purity) as a white solid. $^1$H NMR (400 MHz, DMSO-$d_6$) δ=11.00 (s, 1H), 9.89 (s, 1H), 7.97-7.93 (m, 1H), 7.82 (s, 1H), 7.73-7.67 (m, 2H), 7.66-7.60 (m, 1H), 5.30 (s, 2H), 5.15-5.10 (m, 1H), 4.52-4.44 (m, 1H), 4.38-4.30 (m, 1H), 2.99-2.85 (m, 1H), 2.63-2.58 (m, 1H), 2.45-2.35 (m, 1H), 2.06-1.96 (m, 1H). MS (ESI) m/z: 514.0 [M+H]$^+$ Compound #201: To a solution of 4-fluoro-2-methylphenol (10.0 g, 79.2 mmol, 1.00 eq) in tetrahydrofuran (100 mL) was added sodium hydride (3.17 g, 79.2 mmol, 60% purity, 1.00 eq) at 0° C., after gas evolution ceased, methyl carbonochloridate (7.49 g, 79.2 mmol, 6.14 mL, 1.00 eq) was added. The reaction was stirred at 25° C. for 3 h. The mixture was washed with cooled water (100 mL), extracted with ethyl acetate (3×100 mL). The combined organic layers were concentrated to afford 4-fluoro-2-methylphenyl methyl carbonate (14.5 g, 78.7 mmol, 99% yield) as brown oil. $^1$H NMR (400 MHz, DMSO-$d_6$) δ=7.27-7.17 (m, 2H), 7.12-7.04 (m, 1H), 3.84 (s, 3H), 2.15 (s, 3H).

To a solution of 4-fluoro-2-methylphenyl methyl carbonate (14.5 g, 78.7 mmol, 1.00 eq) in sulfuric acid (100 mL) was added potassium nitrate (7.96 g, 78.7 mmol, 1.00 eq) at 0° C. under nitrogen atmosphere, the mixture was stirred at 25° C. for 2 h. The mixture was poured onto water (300 mL) and extracted with ethyl acetate (3×100 mL), the combined organic layers were concentrated to afford 4-fluoro-2-methyl-5-nitrophenyl methyl carbonate (18.0 g, 78.5 mmol, 99% yield) as a red solid. $^1$H NMR (400 MHz, DMSO-$d_6$) δ=8.17 (d, J=6.8 Hz, 1H), 7.63 (d, J=12.0 Hz, 1H), 3.87 (s, 3H), 2.27 (s, 3H).

To a solution of 4-fluoro-2-methyl-5-nitrophenyl methyl carbonate (17.9 g, 78.1 mmol, 1.00 eq) in methanol (160 mL) was added lithium hydroxide (3.74 g, 156 mmol, 2.00 eq), the mixture was stirred at 25° C. for 3 h. The reaction was filtered to give a filtrate. The filtrate was concentrated to give a residue. The residue was purified by flash silica gel chromatography (ISCO®; 20 g SepaFlash® Silica Flash Column, Eluent of 0~5% petroleum ether/ethyl acetate @ 100 mL/min) to afford 4-fluoro-2-methyl-5-nitrophenol (12.0 g, 70.1 mmol, 89% yield) as a red solid. $^1$H NMR (400 MHz, DMSO-$d_6$) δ=10.32 (br s, 1H), 7.45 (d, J=6.6 Hz, 1H), 7.30 (d, J=12.1 Hz, 1H), 2.19 (s, 3H).

To a solution of 4-fluoro-2-methyl-5-nitro-phenol (1.00 g, 5.84 mmol, 1.00 eq) in dimethylformamide (10.5 mL) and water (1.50 mL) were added potassium carbonate (1.62 g, 11.6 mmol, 2.00 eq) and sodium 2-chloro-2,2-difluoroacetate (4.45 g, 29.2 mmol, 5.00 eq), the mixture was stirred at 100° C. for 12 h. The mixture was dissolved in water (50.0 mL) and extracted with ethyl acetate (3×20.0 mL), the combined organic layers were dried over anhydrous sodium sulfate and concentrated to give a residue. The residue was purified by column chromatography (silica gel, Petroleum ether/Ethyl acetate=20/1 to 10/1) to afford 1-(difluoromethoxy)-4-fluoro-2-methyl-5-nitrobenzene (120 mg, 542 umol, 9% yield) as yellow oil.

To a solution of 1-(difluoromethoxy)-4-fluoro-2-methyl-5-nitrobenzene (120 mg, 542 umol, 1.00 eq) in methanol (1.00 mL) and water (1.00 mL) were added ammonium chloride (145 mg, 2.71 mmol, 5.00 eq) and iron powder (151 mg, 2.71 mmol, 5.00 eq), the reaction was stirred at 80° C. for 2 h. The reaction was filtered to give a filtrate, the filtrate was concentrated to give a residue. The residue was poured into water (50.0 mL) and extracted with ethyl acetate (3×20.0 mL), the combined organic layers were concentrated to afford 5-(difluoromethoxy)-2-fluoro-4-methylaniline (90.0 mg, 470 umol, 86% yield) as yellow oil. MS (ESI) m/z 192.0 [M+H]$^+$ To a solution of 5-(difluoromethoxy)-2-fluoro-4-methylaniline (90.0 mg, 470 umol, 1.00 eq) in acetonitrile (1.00 mL) were added phenyl carbonochloridate (77.4 mg, 494 umol, 61.9 uL, 1.05 eq) and pyridine (74.5 mg, 941 umol, 76.0 uL, 2.00 eq), the mixture was stirred at 25° C. for 2 h. The reaction was concentrated to give a residue. The residue was purified by reversed-phase HPLC (column: Shim-pack C18 150*25*10 um; mobile phase: [water (0.1% formic acid)-acetonitrile]) to afford phenyl (5-(difluoromethoxy)-2-fluoro-4-methylphenyl)carbamate (100 mg, 321 umol, 68% yield) as yellow oil. MS (ESI) m/z 312.0 [M+H]$^+$ To a solution of 3-(6-(hydroxymethyl)-1-oxoisoindolin-2-yl)piperidine-2,6-dione I (80.0 mg, 291 umol, 1.00 eq) in dimethylformamide (1.00 mL) were added phenyl (5-(difluoromethoxy)-2-fluoro-4-methylphenyl) carbamate (99.8 mg, 320 umol, 1.10 eq) and sodium hydride (23.3 mg, 583 umol, 60% purity, 2.00 eq), the mixture was stirred at 25° C. for 1 h. The pH of the mixture was adjusted to 7 with formic acid (0.500 mL), then the mixture was diluted with dimethylformamide (1.00 mL). The reaction was purified by Prep-HPLC (column: Phenomenex luna C18 150*25 mm*10 um; mobile phase: [water (0.225% formic acid)-acetonitrile]; B %: 31%-61%, 10 min) to afford (2-(2,6-dioxopiperidin-3-yl)-3-oxoisoindolin-5-yl) methyl (5-(difluoromethoxy)-2-fluoro-4-methylphenyl)carbamate #201 (77.1 mg, 155 umol, 53% yield, 99% purity) as a white solid. $^1$H NMR (400 MHz, DMSO-$d_6$) δ=10.99 (br s, 1H), 9.65 (br s, 1H), 7.80 (s, 1H), 7.69-7.61 (m, 2H), 7.56 (br d, J=6.2 Hz, 1H), 7.22 (d, J=11.4 Hz, 1H), 7.09 (t, J=74 Hz, 1H), 5.28 (s, 2H), 5.12 (dd, J=5.2, 13.2 Hz, 1H), 4.51-4.44 (m, 1H), 4.38-4.30 (m, 1H), 2.97-2.86 (m, 1H), 2.60 (td, J=1.9, 15.4 Hz, 1H), 2.46-2.35 (m, 1H), 2.18 (s, 3H), 2.06-1.98 (m, 1H). MS (ESI) m/z 491.9 [M+H]$^+$ Compound #202: To a solution of 3-(fluoromethyl)bicyclo[1.1.1]pentan-1-amine (180 mg, 1.19 mmol, 1.00 eq, hydrochloric acid) and pyridine (470 mg, 5.94 mmol, 479 uL, 5.00 eq) in acetonitrile (5.00 mL) was added phenyl carbonochloridate (558 mg, 3.56 mmol, 446 uL, 3.00 eq) at 0° C. The mixture was stirred at 20° C. for 1 h. The mixture was concentrated under reduced pressure to give a residue. The residue was triturated with dimethylformamide (1 mL) and water (2 mL), filtered and the filter cake was concentrated to afford phenyl (3-(fluoromethyl)bicyclo[1.1.1]pentan-1-yl)carbamate (160 mg, 680 umol, 57% yield) as a brown solid. $^1$H NMR (400 MHz, DMSO-$d_6$) δ=8.50 (br s, 1H), 7.40-7.34 (m, 2H), 7.24-7.17 (m, 1H), 7.09 (br d, J=7.8 Hz, 2H), 4.55 (s, 1H), 4.43 (s, 1H), 1.96 (s, 6H).

To a solution of 3-(6-(hydroxymethyl)-1-oxoisoindolin-2-yl)piperidine-2,6-dione I (80.0 mg, 292 umol, 1.00 eq) and phenyl (3-(fluoromethyl)bicyclo[1.1.1]pentan-1-yl)carbamate (82.3 mg, 350 umol, 1.20 eq) in dimethylformamide (1.00 mL) was added sodium hydride (17.5 mg, 438 umol, 60% purity, 1.50 eq) at 0° C. The mixture was stirred at 20° C. for 1 h. The mixture was quenched by formic acid (1 mL) and filtered. The filtrate was purified by prep-HPLC (column: Phenomenex Synergi C18 150*25 mm*10 um; mobile phase: [water (0.225% formic acid)-acetonitrile]; B %: 21%-51%, 10 min) and lyophilized to afford (2-(2,6-dioxopiperidin-3-yl)-3-oxoisoindolin-5-yl)methyl (3-(fluoromethyl)bicyclo[1.1.1]pentan-1-yl) carbamate #202 (69.3 mg, 163 umol, 56% yield, 98% purity) as a white solid. $^1$H NMR (400 MHz, DMSO-d$_6$) δ=10.99 (s, 1H), 8.07 (br s, 1H), 7.70 (s, 1H), 7.60 (s, 2H), 5.20-5.07 (m, 3H), 4.53 (s, 1H), 4.49-4.43 (m, 1H), 4.41 (s, 1H), 4.37-4.28 (m, 1H), 2.97-2.86 (m, 1H), 2.63-2.57 (m, 1H), 2.45-2.31 (m, 1H), 2.03-1.98 (m, 1H), 1.91 (s, 6H). MS (ESI) m/z 416.1 [M+H]$^+$ Compound #203: To a solution of 3-(methoxycarbonyl)bicyclo[1.1.1]pentane-1-carboxylic acid (100 mg, 588 umol, 1.00 eq) in dioxane (5.00 mL) was added diphenylphosphoryl azide (243 mg, 881 umol, 191 uL, 1.50 eq) and triethylamine (119 mg, 1.18 mmol, 164 uL, 2.00 eq). The mixture was stirred at 25° C. for 1 h. Then 3-(6-(hydroxymethyl)-1-oxoisoindolin-2-yl)piperidine-2,6-dione I (161 mg, 588 umol, 1.00 eq) was added into the mixture. The reaction mixture was stirred at 80° C. for 2 h under nitrogen. The mixture was concentrated to give a residue. The residue was purified by prep-HPLC (column: Phenomenex Synergi C18 150*25 mm*10 um; mobile phase: [water (0.225% FA)-ACN]; B %: 16%-46%, 10 min). The desired fraction was collected and lyophilized to give a residue. The residue was further purified by column chromatography on silica gel (ethyl acetate) and prep-HPLC (column: Phenomenex Synergi C18 150*25 mm*10 um; mobile phase: [water (0.225% FA)-ACN]; B %: 17%-47%, 10 min). The desired fraction was collected and lyophilized to give methyl 3-((((2-(2,6-dioxopiperidin-3-yl)-3-oxoisoindolin-5-yl) methoxy)carbonyl)amino)bicyclo[1.1.1]pentane-1-carboxylate #203 (51.39 mg, 115 umol, 46% yield, 99% purity) as a white solid. $^1$H NMR (400 MHz, DMSO-d$_6$) δ=10.99 (s, 1H), 8.16 (br s, 1H), 7.56-7.73 (m, 3H), 5.07-5.17 (m, 3H), 4.42-4.50 (m, 1H), 4.29-4.37 (m, 1H), 3.60 (s, 3H), 2.86-2.97 (m, 1H), 2.60 (br dd, J=15.53, 2.08 Hz, 1H), 2.40 (br dd, J=13.20, 4.40 Hz, 1H), 2.14-2.22 (m, 6H), 1.97-2.05 (m, 1H). MS (ESI) m/z 442.2 [M+H]$^+$ Compound #204: To a solution of 4-fluoro-2-methyl-5-nitrophenol (1.00 g, 5.84 mmol, 1.00 eq) in dimethyl formamide (10.0 mL) was added sodium hydride (467 mg, 11.6 mmol, 60% purity, 2.00 eq) in portions at 0° C. The mixture was stirred at 0° C. for 0.5 h. Then the mixture was added dibromodifluoromethane (3.68 g, 17.5 mmol, 1.62 mL, 3.00 eq) dropwise at 0° C. and stirred at 25° C. for 2 h. The reaction was quenched by addition ammonium chloride (20.0 mL), extracted with ethyl acetate (3×30.0 mL), the combined organic layers were concentrated to give a residue. The residue was purified by flash silica gel chromatography (40 g SepaFlash® Silica Flash Column, Eluent of 0~50% Ethyl acetate/Petroleum ether gradient @ 100 mL/min) to afford 1-(bromodifluoromethoxy)-4-fluoro-2-methyl-5-nitrobenzene (710 mg, 2.37 mmol, 40% yield) as yellow oil. $^1$H NMR (400 MHz, DMSO-d$_6$) δ=8.07 (d, J=6.5 Hz, 1H), 7.77 (d, J=11.9 Hz, 1H), 2.38 (s, 3H).

To a solution of 1-(bromodifluoromethoxy)-4-fluoro-2-methyl-5-nitrobenzene (710 mg, 2.37 mmol, 1.00 eq) in dichloromethane (7.00 mL) was added silver tetrafluoroborate (691 mg, 3.55 mmol, 1.50 eq), the mixture was stirred at 25° C. for 2 h. The reaction was filtered to give a filtrate. The filtrate was concentrated to afford 1-fluoro-5-methyl-2-nitro-4-(trifluoromethoxy)benzene (500 mg, 2.09 mmol, 88% yield) as brown oil. $^1$H NMR (400 MHz, DMSO-d$_6$) δ=8.13 (d, J=6.5 Hz, 1H), 7.75 (d, J=11.9 Hz, 1H), 2.39 (s, 3H).

To a solution of 1-fluoro-5-methyl-2-nitro-4-(trifluoromethoxy)benzene (250 mg, 1.05 mmol, 1.00 eq) in ethyl acetate (10.0 mL) was added palladium/carbon (50.0 mg, 10% purity), the mixture was stirred at 25° C. for 12 h under hydrogen atmosphere. The reaction was filtered to give a filtrate, the filtrate was concentrated to afford 2-fluoro-4-methyl-5-(trifluoromethoxy)aniline (210 mg, 1.00 mmol, 96% yield) as a yellow solid. MS (ESI) m/z 209.9 [M+H]$^+$ To a solution of 2-fluoro-4-methyl-5-(trifluoromethoxy)aniline (210 mg, 1.00 mmol, 1.00 eq) in acetonitrile (3.00 mL) were added phenyl carbonochloridate (165 mg, 1.05 mmol, 132 uL, 1.05 eq) and pyridine (158 mg, 2.01 mmol, 162 uL, 2.00 eq), the mixture was stirred at 25° C. for 2 h. The reaction was concentrated to give a residue. The residue was purified by reversed-phase HPLC (column: Shim-pack C18 150*25*10 um; mobile phase: [water (0.1% formic acid)-acetonitrile]) to afford phenyl (2-fluoro-4-methyl-5-(trifluoromethoxy)phenyl)carbamate (200 mg, 607 umol, 60% yield) as yellow oil. MS (ESI) m/z 330.0 [M+H]$^+$ To a solution of 3-(6-(hydroxymethyl)-1-oxoisoindolin-2-yl)piperidine-2,6-dione I (80.0 mg, 291 umol, 1.00 eq) in dimethylformamide (1.00 mL) were added phenyl (2-fluoro-4-methyl-5-(trifluoromethoxy)phenyl) carbamate (105 mg, 320 umol, 1.10 eq) and sodium hydride (23.3 mg, 583 umol, 60% purity, 2.00 eq), the mixture was stirred at 25° C. for 1 h. The pH of the mixture was adjusted to 7 with formic acid (0.500 mL), then the mixture was diluted with dimethylformamide (1.00 mL). The reaction was purified by Prep-HPLC (column: Phenomenex luna C18 150*25 mm*10 um; mobile phase: [water (0.225% formic acid)-acetonitrile]; B %: 33%-63%, 10 min) to afford (2-(2,6-dioxopiperidin-3-yl)-3-oxoisoindolin-5-yl) methyl (2-fluoro-4-methyl-5-(trifluoromethoxy)phenyl)carbamate #204 (60.6 mg, 117 umol, 40% yield, 99% purity) as a white solid. $^1$H NMR (400 MHz, DMSO-d$_6$) δ=11.01 (s, 1H), 9.80 (br s, 1H), 7.81 (s, 1H), 7.76 (br d, J=5.4 Hz, 1H), 7.70-7.60 (m, 2H), 7.33 (d, J=11.4 Hz, 1H), 5.29 (s, 2H), 5.13 (dd, J=5.1, 13.3 Hz, 1H), 4.53-4.43 (m, 1H), 4.38-4.30 (m, 1H), 2.98-2.87 (m, 1H), 2.60 (br d, J=17.7 Hz, 1H), 2.46-2.35 (m, 1H), 2.22 (s, 3H), 2.05-1.97 (m, 1H). MS (ESI) m/z 509.9 [M+H]$^+$ Compound #205: To a solution of 5-bromo-2-fluoroaniline (500 mg, 2.63 mmol, 1.00 eq), potassium trifluoro(prop-1-en-2-yl) borate (1.17 g, 7.89 mmol, 3.00 eq) and tetrakis [triphenylphosphine]palladium(0) (304 mg, 263 umol, 0.100 eq) in dioxane (10.0 mL) was added cesium carbonate (2.57 g, 7.89 mmol, 3.00 eq), then evacuated with vacuum and back filled with nitrogen 3 times. The mixture was stirred at 100° C. for 12 h. The reaction mixture was filtered and concentrated to give a residue, which was purified by silica gel chromatography (petroleum ether/ethyl acetate=20/1 to 10/1) to afford 2-fluoro-5-(prop-1-en-2-yl)aniline (270 mg, 1.79 mmol, 67% yield) as colorless oil. $^1$H NMR (400 MHz, DMSO-d$_6$) δ=6.96-6.87 (m, 2H), 6.64 (ddd, J=2.4, 4.4, 8.4 Hz, 1H), 5.24 (s, 1H), 5.09 (s, 2H), 5.01-4.98 (m, 1H), 2.03 (s, 3H). MS (ESI) m/z 152.2 [M+H]$^+$ To a mixture of 2-fluoro-5-(prop-1-en-2-yl)aniline (270 mg, 1.79 mmol, 1.00 eq) in methanol (10.0 mL) was added palladium on carbon (30.0 mg, 10% purity). The reaction mixture was stirred at 20° C. for 2 h under hydrogen atmosphere. The reaction mixture was filtered and concentrated to give 2-fluoro-5-isopropylaniline (270 mg, 1.76 mmol, 98% yield) as colorless oil. $^1$H NMR (400 MHz, DMSO-d$_6$) δ=6.85 (dd, J=8.4, 11.6 Hz, 1H), 6.63 (dd, J=2.4, 8.8 Hz, 1H), 6.37 (ddd, J=2.4, 4.4, 8.2 Hz, 1H), 4.98 (s, 2H), 2.72 (quin, J=6.8 Hz, 1H), 1.15 (s, 3H), 1.13 (s, 3H). MS (ESI) m/z 154.0 [M+H]$^+$ To a solution of 2-fluoro-5-isopropylaniline (270 mg, 1.79 mmol, 1.00 eq) and pyridine (278 mg, 3.52 mmol, 284 uL, 2.00 eq) in acetonitrile (10.0 mL) was added phenyl carbonochloridate (289 mg, 1.85 mmol, 231 uL, 1.05 eq). The reaction mixture was stirred at 20° C. for 2 h. The reaction mixture was poured into water (50.0 mL) and extracted with ethyl acetate (3×20.0 mL). The combined organic phase was separated, washed with brine (3×10.0 mL), dried over anhydrous sodium sulfate, filtered and concentrated to give phenyl (2-fluoro-5-isopropylphenyl)carbamate (350 mg, 1.28 mmol, 72% yield) as colorless oil. MS (ESI) m/z 274.1 [M+H]$^+$ A mixture of 3-(6-(hydroxymethyl)-1-oxoisoindolin-2-yl)piperidine-2,6-dione I (80.0 mg, 291 umol, 1.00 eq) in dimethyl formamide (1.00 mL) was added sodium hydride (17.5 mg, 437 umol, 60% purity, 1.50 eq) and phenyl (2-fluoro-5-isopropylphenyl)carbamate (83.7 mg, 306 umol, 1.05 eq) at 0° C. The reaction mixture was stirred at 20° C. for 1 h. The reaction mixture was added formic acid (2.00 mL) and filtered to give a filtrate, which was purified by Prep-HPLC (column: Phenomenex luna C18 150*25 mm*10 um; mobile phase: [water (0.225% Formic acid)-acetonitrile]; B %: 37%-67%, 10 min) and lyophilized to give (2-(2,6-dioxopiperidin-3-yl)-3-oxoisoindolin-5-yl)methyl (2-fluoro-5-isopropylphenyl)carbamate #205 (70.29 mg, 153 umol, 52% yield, 99% purity) as a white solid. $^1$H NMR (400 MHz, DMSO-d$_6$) δ=10.99 (br s, 1H), 9.44 (br s, 1H), 7.81 (s, 1H), 7.71-7.61 (m, 2H), 7.51 (br d, J=7.2 Hz, 1H), 7.13 (dd, J=8.4, 10.6 Hz, 1H), 7.05-6.98 (m, 1H), 5.27 (s, 2H), 5.13 (dd, J=5.2, 13.2 Hz, 1H), 4.52-4.44 (m, 1H), 4.39-4.31 (m, 1H), 2.98-2.88 (m, 1H), 2.88-2.80 (m, 1H), 2.65-2.56 (m, 1H), 2.41 (dq, J=4.4, 13.2 Hz, 1H), 2.07-1.98 (m, 1H), 1.17 (d, J=6.8 Hz, 6H). MS (ESI) m/z 454.0 [M+H]$^+$ Compound #206: To a solution of sulfuric acid (6.00 mL) was added nitric acid (8.40 g, 86.6 mmol, 6.00 mL, 65% purity, 3.90 eq) at −10° C. Then 2-(difluoromethoxy)-1,3-difluorobenzene (4.00 g, 22.2 mmol, 1.00 eq) was added slowly at −10° C. The mixture was stirred at −10° C. for 0.5 h. The reaction mixture was diluted with cold water (100 mL) and extracted with ethyl acetate (100 mL). The combined organic layer was washed with saturated sodium bicarbonate (100 mL), dried over anhydrous sodium sulfate and concentrated under vacuum. The residue was purified by column chromatography (SiO$_2$, Petroleum ether/Ethyl acetate=50/1 to 10/1) to give 2-(difluoromethoxy)-1,3-difluoro-5-nitrobenzene (170 mg, 755 umol, 3% yield) as yellow oil. $^1$H NMR (400 MHz, CDCl$_3$) δ=8.02-7.90 (m, 2H), 6.71 (t, J=72.4 Hz, 1H).

To a solution of 2-(difluoromethoxy)-1,3-difluoro-5-nitrobenzene (170 mg, 755 umol, 1.00 eq) in the mixture of methanol (10.0 mL) and water (2.00 mL) was added iron powder (210 mg, 3.78 mmol, 5.00 eq) and ammonium chloride (323 mg, 6.04 mmol, 8.00 eq). The mixture was stirred at 80° C. for 1 h. The mixture was filtered to give a filter liquor, then was concentrated under reduced pressure to give a residue. The crude product was diluted with saturated sodium bicarbonate (30.0 mL) and exacted with ethyl acetate (30.0 mL). The organic phase was separated, washed with brine (10.0 mL), dried over sodium sulfate, filtered and concentrated under reduced pressure to give 4-(difluoromethoxy)-3,5-difluoroaniline (140 mg, 717 umol, 95% yield) as a yellow solid. MS (ESI) m/z 196.1 [M+H]$^+$ To a solution of 4-(difluoromethoxy)-3,5-difluoroaniline (140 mg, 717 umol, 1.00 eq) in acetonitrile (10.0 mL) was added pyridine (283 mg, 3.59 mmol, 289 uL, 5.00 eq) and phenyl carbonochloridate (134 mg, 861 umol, 107 uL, 1.20 eq). The mixture was stirred at 25° C. for 0.5 h. The reaction mixture was concentrated under reduced pressure to give a residue. The crude product was purified by prep-TLC (SiO$_2$, Petroleum ether/Ethyl acetate=5/1) to give phenyl (4-(difluoromethoxy)-3,5-difluorophenyl)carbamate (180 mg, 571 umol, 79% yield) as a yellow solid. $^1$H NMR (400 MHz, CDCl$_3$) δ=7.47-7.40 (m, 2H), 7.32-7.28 (m, 1H), 7.22-7.16 (m, 4H), 7.11 (br s, 1H), 6.57 (t, J=72.4 Hz, 1H). MS (ESI) m/z 316.0 [M+H]$^+$ To a solution of phenyl (4-(difluoromethoxy)-3,5-difluorophenyl)carbamate (101 mg, 320 umol, 1.10 eq) in dimethyl formamide (2.00 mL) was added 3-(6-(hydroxymethyl)-1-oxoisoindolin-2-yl)piperidine-2,6-dione I (80.0 mg, 291 umol, 1.00 eq) and sodium hydride (23.3 mg, 583 umol, 60% purity, 2.00 eq) at 0° C. The mixture was stirred at 0° C. for 0.5 h. The reaction mixture was quenched with formic acid (0.500 ml) to give a solution. The solution was purified by prep-HPLC (column: Phenomenex Synergi C18 150*25 mm*10 um; mobile phase: [water (0.225% FA)-ACN]; B %: 33%-63%, 10 min) and lyophilized to give a residue. The crude product was dissolved in dimethyl formamide (2.00 mL) and purified by prep-HPLC (column: Phenomenex Synergi C18 150*25 mm*10 um; mobile phase: [water (0.225% FA)-ACN]; B %: 32%-65%, 11 min) and lyophilized to give a residue. The crude product was purified by column chromatography (SiO$_2$, Petroleum ether/Ethyl acetate=5/1 to 0/1) to give (2-(2,6-dioxopiperidin-3-yl)-3-oxoisoindolin-5-yl) methyl (4-(difluoromethoxy)-3,5-difluorophenyl)carbamate #206 (64.7 mg, 130 umol, 44% yield) as a white solid. $^1$H NMR (400 MHz, DMSO-d$_6$) δ=11.01 (s, 1H), 10.34 (s, 1H), 7.80 (s, 1H), 7.71-7.67 (m, 1H), 7.66-7.62 (m, 1H), 7.32 (d, J=10.3 Hz, 2H), 7.17 (t, J=72.0 Hz, 1H), 5.30 (s, 2H), 5.13 (dd, J=5.1, 13.3 Hz, 1H), 4.52-4.43 (m, 1H), 4.40-4.29 (m, 1H), 2.97-2.86 (m, 1H), 2.63-2.56 (m, 1H), 2.40 (dq, J=4.3, 13.2 Hz, 1H), 2.05-1.97 (m, 1H). MS (ESI) m/z 496.1 [M+H]$^+$ Compound #207: To a solution of 5-bromo-2-fluoroaniline (500 mg, 2.63 mmol, 1.00 eq), cyclopropylboronic acid (271 mg, 3.16 mmol, 1.20 eq) and tetrakis[triphenylphosphine]palladium(0) (304 mg, 263 umol, 0.100 eq) in dioxane (10.0 mL) was added cesium carbonate (2.57 g, 7.89 mmol, 3.00 eq), then evacuated with vacuum and back filled with nitrogen 3 times. The mixture was stirred at 100° C. for 12 h. The reaction mixture was filtered and concentrated to give a residue, which was purified by silica gel chromatography (petroleum ether/ethyl acetate=20/1 to 10/1) to afford 5-cyclopropyl-2-fluoroaniline (220 mg, 1.46 mmol, 55% yield) as colorless oil. $^1$H NMR (400 MHz, DMSO-d$_6$) δ=6.81 (dd, J=8.4, 11.4 Hz, 1H), 6.45 (dd, J=2.4, 8.8 Hz, 1H), 6.22 (ddd, J=2.4, 4.4, 8.4 Hz, 1H), 4.98 (br s, 2H), 1.74 (tt, J=5.2, 8.4 Hz, 1H), 0.88-0.80 (m, 2H), 0.54-0.48 (m, 2H).

To a solution of 5-cyclopropyl-2-fluoroaniline (220 mg, 1.46 mmol, 1.00 eq) and pyridine (230 mg, 2.91 mmol, 234 uL, 2.00 eq) in acetonitrile (10.0 mL) was added phenyl carbonochloridate (239 mg, 1.53 mmol, 191 uL, 1.05 eq). The reaction mixture was stirred at 20° C. for 2 h. The reaction mixture was poured into water (50.0 mL) and extracted with ethyl acetate (3×20.0 mL). The combined organic phase was separated, washed with brine (3×10.0 mL), dried over anhydrous sodium sulfate, filtered and concentrated to give phenyl (5-cyclopropyl-2-fluorophenyl)carbamate (360 mg, 1.33 mmol, 91% yield) as a yellow solid. $^1$H NMR (400 MHz, DMSO-d$_6$) δ=9.85 (br s, 1H), 7.45-7.41 (m, 2H), 7.29-7.24 (m, 1H), 7.21 (br d, J=7.8 Hz, 2H), 7.16-7.13 (m, 1H), 6.95-6.86 (m, 1H), 6.75 (d, J=7.8 Hz, 1H), 1.96-1.87 (m, 1H), 0.97-0.90 (m, 2H), 0.64-0.58 (m, 2H). MS (ESI) m/z 272.0 [M+H]$^+$ A mixture of 3-(6-(hydroxymethyl)-1-oxoisoindolin-2-yl)piperidine-2,6-dione I (80.0 mg, 291 umol, 1.00 eq) in dimethyl formamide (1.00 mL) was added sodium hydride (17.5 mg, 437 umol, 60% purity, 1.50 eq) and phenyl (5-cyclopropyl-2-fluorophenyl) carbamate (83.0 mg, 306 umol, 1.05 eq) at 0° C. The reaction mixture was stirred at 20° C. for 1 h. The reaction mixture was added formic acid (2.00 mL) and filtered to give a filtrate, which was purified by Prep-HPLC (column: Phenomenex Luna C18 150*25 mm*10 um; mobile phase: [water (0.225% formic acid)-acetonitrile]; B %: 36%-66%, 10 min) and lyophilized to give (2-(2,6-dioxopiperidin-3-yl)-3-oxoisoindolin-5-yl)methyl (5-cyclopropyl-2-fluorophenyl) carbamate #207 (62.3 mg, 136 umol, 46% yield, 99% purity) as a white solid. $^1$H NMR (400 MHz, DMSO-$d_6$) δ=10.98 (br s, 1H), 9.43 (br s, 1H), 7.80 (s, 1H), 7.73-7.59 (m, 2H), 7.35 (br d, J=7.2 Hz, 1H), 7.08 (dd, J=8.8, 10.4 Hz, 1H), 6.89-6.77 (m, 1H), 5.26 (s, 2H), 5.13 (dd, J=5.2, 13.2 Hz, 1H), 4.52-4.43 (m, 1H), 4.39-4.30 (m, 1H), 2.97-2.85 (m, 1H), 2.64-2.57 (m, 1H), 2.40 (dq, J=4.4, 13.2 Hz, 1H), 2.06-1.97 (m, 1H), 1.94-1.84 (m, 1H), 0.95-0.88 (m, 2H), 0.63-0.55 (m, 2H). MS (ESI) m/z 452.3 [M+H]$^+$ Compound #208: A mixture of 5-bromo-2-fluoro-4-methyl-aniline (0.570 g, 2.79 mmol, 1.00 eq), 2,4,6-trimethyl-1,3,5,2,4,6-trioxatriborinane (1.40 g, 5.59 mmol, 1.56 mL, 50% purity, 2.00 eq), [1,1-Bis(diphenylphosphino)ferrocene]dichloropalladium (II) (102 mg, 140 umol, 0.05 eq), potassium phosphate (1.19 g, 5.59 mmol, 2.00 eq) in dioxane (10.0 mL) and water (0.500 mL) was degassed under vacuum and then purged with nitrogen for 3 times. The mixture was stirred at 90° C. for 12 h under nitrogen atmosphere. After filtration, the filtrate was concentrated under vacuum to give a residue. The residue was purified by silica gel column chromatography (petroleum ether, then petroleum ether/ethyl acetate=50/1) to afford 2-fluoro-4,5-dimethyl-aniline (0.350 g, 2.26 mmol, 81% yield, 90% purity) as light yellow solid. $^1$H NMR (400 MHz, CDCl$_3$) δ=6.78 (d, J=12.0 Hz, 1H), 6.61 (d, J=8.8 Hz, 1H), 2.15 (s, 6H).

To a solution of 2-fluoro-4,5-dimethyl-aniline (0.200 g, 1.29 mmol, 90% purity, 1.00 eq) and pyridine (307 mg, 3.88 mmol, 313 uL, 3.00 eq) in acetonitrile (5.0 mL) was added phenyl carbonochloridate (223 mg, 1.42 mmol, 178 uL, 1.10 eq) at 0° C. The mixture was stirred at 25° C. for 12 h. The mixture was poured into water (20.0 mL) and extracted with ethyl acetate (3×10.0 mL). The organic phase was washed with hydrochloric acid solution (50.0 mL, 0.5 M), brine (50.0 mL), dried over anhydrous sodium sulfate, filtered and concentrated under reduced pressure to give a residue. The residue was purified by silica gel column chromatography (petroleum ether, then petroleum ether/ethyl acetate=50/1) to afford phenyl N-(2-fluoro-4,5-dimethyl-phenyl)carbamate (330 mg, 1.15 mmol, 89% yield, 90% purity) as light yellow solid. $^1$H NMR (400 MHz, DMSO-$d_6$) δ=9.83-9.64 (m, 1H), 7.45-7.37 (m, 3H), 7.28-7.16 (m, 3H), 7.06 (d, J=11.6 Hz, 1H), 2.19 (s, 3H), 2.17 (s, 3H).

To a solution of 3-[6-(hydroxymethyl)-1-oxo-isoindolin-2-yl]piperidine-2,6-dione (105 mg, 364 umol, 95% purity, 1.00 eq) in tetrahydrofuran (4.00 mL) was added sodium hydride (29.2 mg, 729 umol, 60% purity, 2.00 eq) at 0° C., and then phenyl N-(2-fluoro-4,5-dimethyl-phenyl)carbamate (105 mg, 365 umol, 90% purity, 1.00 eq) was added. The mixture was stirred at 25° C. for 1 h. The mixture was poured into saturated ammonium chloride aqueous solution (20.0 mL) and extracted with ethyl acetate (3×10.0 mL). The organic phase was washed with saturated calcium chloride solution (20.0 ml), brine (20.0 mL), dried over anhydrous sodium sulfate, filtered and concentrated under reduced pressure to give a residue. The residue was purified by prep-HPLC (column: Phenomenex Synergi C18 150*25 mm*10 um; mobile phase: [water (0.225% FA)-ACN]; B %: 31%-61%, 10 min) and then lyophilized to afford (2-(2,6-dioxopiperidin-3-yl)-3-oxoisoindolin-5-yl)methyl (2-fluoro-4,5-dimethylphenyl)carbamate #208 (41.54 mg, 93.6 umol, 26% yield, 99% purity) was obtained as a white solid $^1$H NMR (400 MHz, DMSO-$d_6$) δ=10.99 (s, 1H), 9.31 (s, 1H), 7.78 (s, 1H), 7.71-7.59 (m, 2H), 7.33 (d, J=8.0 Hz, 1H), 7.01 (d, J=11.6 Hz, 1H), 5.24 (s, 2H), 5.13 (dd, J=5.2, 13.2 Hz, 1H), 4.53-4.28 (m, 2H), 2.99-2.85 (m, 1H), 2.71-2.55 (m, 1H), 2.31-2.44 (m, 1H), 2.17 (s, 3H), 2.15 (s, 3H), 2.06-1.96 (m, 1H). MS (ESI) m/z 440.1 [M+H]$^+$ Compound #209: To a solution of 1-(4-bromophenyl)-2,2,2-trifluoroethanone (5.00 g, 19.8 mmol, 3.01 mL, 1.00 eq) and tert-butyl carbamate (2.78 g, 23.7 mmol, 1.20 eq) and cesium carbonate (19.3 g, 59.3 mmol, 3.00 eq) in dioxane (100 mL) was added RuPhos Pd G3 (826.40 mg, 988.08 umol, 0.05 eq) under nitrogen. The mixture was stirred at 90° C. for 12 h. The mixture was diluted with water (150 mL) and extracted with ethyl acetate (3×80.0 mL). The combined organic layer was washed with brine (60.0 mL), dried over sodium sulfate, filtered and concentrated in vacuum. The residue was purified by silica gel chromatography (petroleum ether/ethyl acetate=5/1 to 2/1) to give tert-butyl (4-(2,2,2-trifluoroacetyl) phenyl)carbamate (2.60 g, 8.99 mmol, 45% yield) as a yellow solid. $^1$H NMR (400 MHz, DMSO-$d_6$) δ=10.12 (s, 1H), 7.98 (d, J=8.2 Hz, 2H), 7.77-7.68 (m, 2H), 1.50 (s, 9H).

To a solution of tert-butyl (4-(2,2,2-trifluoroacetyl)phenyl)carbamate (2.60 g, 8.99 mmol, 1.00 eq) in methanol (30.0 mL) was added sodium borohydride (680 mg, 17.9 mmol, 2.00 eq) at 0° C. The mixture was stirred at 15° C. for 2 h. The mixture was poured into methanol (100 mL) and concentrated in vacuum. The residue was purified by silica gel chromatography (petroleum ether/ethyl acetate=4/1) to give tert-butyl (4-(2,2,2-trifluoro-1-hydroxyethyl)phenyl) carbamate (1.70 g, 5.84 mmol, 65% yield) as yellow solid. $^1$H NMR (400 MHz, DMSO-$d_6$) δ=9.41 (s, 1H), 7.46 (d, J=8.7 Hz, 2H), 7.35 (d, J=8.6 Hz, 2H), 6.70 (d, J=5.6 Hz, 1H), 5.14-4.96 (m, 1H), 1.47 (s, 9H).

A solution of tert-butyl (4-(2,2,2-trifluoro-1-hydroxyethyl)phenyl)carbamate (1.50 g, 5.15 mmol, 1.00 eq) in dichloromethane (12.0 mL) and trifluoroacetic acid (4.00 mL) was stirred at 15° C. for 2 h. The mixture was concentrated in vacuum. The residue was purified by reverse phase chromatography (column: spherical C18, 20-45 um, 100 Å, SW 120, mobile phase: [water (0.1% Formic Acid)-ACN) and lyophilized to give 1-(4-aminophenyl)-2,2,2-trifluoroethanol (980 mg, 5.13 mmol, 99% yield) as yellow oil. $^1$H NMR (400 MHz, DMSO-$d_6$) δ=7.09 (d, J=8.3 Hz, 2H), 6.54 (d, J=8.6 Hz, 2H), 6.44 (d, J=5.4 Hz, 1H), 5.16 (s, 2H), 4.91-4.80 (m, 1H).

To a mixture of 1-(4-aminophenyl)-2,2,2-trifluoroethanol (100 mg, 523 umol, 1.00 eq) and pyridine (207 mg, 2.62 mmol, 211 uL, 5.00 eq) in acetonitrile (2.00 mL) was added phenyl carbonochloridate (98.3 mg, 628 umol, 78.6 uL, 1.20 eq) dropwise at 0° C. The mixture was stirred at 15° C. for 2 h. The mixture was concentrated in vacuum. The residue was purified by silica gel chromatography (petroleum ether/ethyl acetate=10/1 to 3/1) to give phenyl (4-(2,2,2-trifluoro-1-hydroxyethyl)phenyl)carbamate (80.0 mg, 257 umol, 49% yield) as a white solid. $^1$H NMR (400 MHz, DMSO-$d_6$) δ=10.31 (br s, 1H), 7.53 (br d, J=8.6 Hz, 2H), 7.46-7.40 (m, 4H), 7.28-7.20 (m, 3H), 6.77 (d, J=5.6 Hz, 1H), 5.09 (quin, J=6.8 Hz, 1H).

A solution of 3-(6-(hydroxymethyl)-1-oxoisoindolin-2-yl)piperidine-2,6-dione I (123 mg, 449 umol, 1.00 eq) in dimethylformamide (2.00 mL) was added triethylamine (137 mg, 1.35 mmol, 188 uL, 3.00 eq) in portions. The mixture was stirred at 0° C. for 20 min. Then the mixture was added phenyl phenyl (4-(2,2,2-trifluoro-1-hydroxyethyl)phenyl carbamate (140 mg, 449 umol, 1.00 eq) and the mixture was stirred at 15° C. for 18 h. The mixture was quenched with 1 M hydrochloric acid (0.500 mL) and filtered. The filtrate was purified by prep-HPLC (column: YMC Triart 30*150 mm*7 um; mobile phase: [water (0.05% HCl)-ACN]; B %: 35%-55%, 7 min) and lyophilized to give (2-(2,6-dioxopiperidin-3-yl)-3-oxoisoindolin-5-yl)methyl (4-(2,2,2-trifluoro-1-hydroxyethyl)phenyl) carbamate #209 (19.62 mg, 37.1 umol, 8% yield, 93% purity) as an off-white solid. $^1$H NMR (400 MHz, DMSO-$d_6$) δ=10.99 (s, 1H), 9.91 (s, 1H), 7.80 (s, 1H), 7.71-7.61 (m, 2H), 7.49 (br d, J=8.6 Hz, 2H), 7.42-7.36 (m, 2H), 6.87-6.63 (m, 1H), 5.28 (s, 2H), 5.13 (dd, J=5.1, 13.3 Hz, 1H), 5.06 (q, J=7.4 Hz, 1H), 4.52-4.42 (m, 1H), 4.40-4.30 (m, 1H), 2.98-2.85 (m, 1H), 2.60 (br d, J=17.9 Hz, 1H), 2.46-2.34 (m, 1H), 2.05-1.97 (m, 1H). MS (ESI) m/z 492.1 [M+H]$^+$ Compound #210: To a solution of 5-bromo-2-fluoroaniline (500 mg, 2.63 mmol, 1.00 eq), ethylboronic acid (583 mg, 7.89 mmol, 3.00 eq) and tetrakis[triphenylphosphine]palladium(0) (304 mg, 263 umol, 0.100 eq) in dioxane (10.0 mL) was added cesium carbonate (2.57 g, 7.89 mmol, 3.00 eq), then evacuated with vacuum and back filled with nitrogen 3 times. The mixture was stirred at 90° C. for 12 h. The reaction mixture was filtered and concentrated to give a residue, which was purified by silica gel chromatography (petroleum ether/ethyl acetate=20/1 to 10/1) to afford 5-ethyl-2-fluoroaniline (220 mg, 1.55 mmol, 58% yield, 98% purity) as colorless oil. $^1$H NMR (400 MHz, DMSO-$d_6$) δ=6.84 (dd, J=8.4, 11.6 Hz, 1H), 6.59 (dd, J=2.0, 8.8 Hz, 1H), 6.32 (ddd, J=2.2, 4.5, 8.0 Hz, 1H), 4.97 (s, 2H), 2.43 (q, J=7.6 Hz, 2H), 1.11 (t, J=7.6 Hz, 3H). MS (ESI) m/z 140.0 [M+H]$^+$ To a solution of 5-ethyl-2-fluoroaniline (220 mg, 1.58 mmol, 1.00 eq) and pyridine (250 mg, 3.16 mmol, 255 uL, 2.00 eq) in acetonitrile (10.0 mL) was added phenyl carbonochloridate (259 mg, 1.66 mmol, 207 uL, 1.05 eq). The reaction mixture was stirred at 20° C. for 2 h. The reaction mixture was poured into water (50.0 mL) and extracted with ethyl acetate (3×20.0 mL). The combined organic phase was separated, washed with brine (3×10.0 mL), dried over anhydrous sodium sulfate, filtered and concentrated to give phenyl (5-ethyl-2-fluorophenyl)carbamate (350 mg, 1.35 mmol, 85% yield) as colorless oil. MS (ESI) m/z 260.1 [M+H]$^+$ A mixture of 3-(6-(hydroxymethyl)-1-oxoisoindolin-2-yl)piperidine-2,6-dione I (80.0 mg, 291 umol, 1.00 eq) in dimethyl formamide (1.00 mL) was added sodium hydride (17.5 mg, 437 umol, 60% purity, 1.50 eq) and phenyl (5-ethyl-2-fluorophenyl)carbamate (79.4 mg, 306 umol, 1.05 eq) at 0° C. The reaction mixture was stirred at 20° C. for 1 h. The reaction mixture was added formic acid (2.00 mL) and filtered to give a filtrate, which was purified by Prep-HPLC (column: Phenomenex luna C18 150*25 mm*10 um; mobile phase: [water (0.225% formic acid)-acetonitrile]; B %: 34%-64%, 10 min) and lyophilized to give (2-(2,6-dioxopiperidin-3-yl)-3-oxoisoindolin-5-yl)methyl (5-ethyl-2-fluorophenyl)carbamate #210 (48.48 mg, 98.8 umol, 33% yield, 99% purity, formic acid) as a white solid. $^1$H NMR (400 MHz, DMSO-$d_6$) δ=11.00 (s, 1H), 9.45 (br s, 1H), 7.81 (s, 1H), 7.71-7.66 (m, 1H), 7.66-7.62 (m, 1H), 7.48 (br d, J=7.6 Hz, 1H), 7.12 (dd, J=8.4, 10.8 Hz, 1H), 7.00-6.95 (m, 1H), 5.27 (s, 2H), 5.14 (dd, J=5.0, 13.2 Hz, 1H), 4.52-4.44 (m, 1H), 4.39-4.31 (m, 1H), 2.92 (ddd, J=5.5, 13.4, 17.6 Hz, 1H), 2.63-2.59 (m, 1H), 2.57 (d, J=7.6 Hz, 2H), 2.47-2.35 (m, 1H), 2.06-1.98 (m, 1H), 1.15 (t, J=7.6 Hz, 3H). MS (ESI) m/z 440.3 [M+H]$^+$ Compound #211: To a solution of 1,3-difluoro-5-methyl-2-nitrobenzene (500 mg, 2.89 mmol, 1.00 eq) in ethanol (3.00 mL) and water (3.00 mL) was added iron (806 mg, 14.4 mmol, 5.00 eq) and ammonium chloride (772 mg, 14.4 mmol, 5.00 eq). After addition, the mixture was stirred at 80° C. for 1 h. The reaction mixture was filtered through celite, and then the filtrate was extracted with ethyl acetate (3×10.0 mL). The combined organic layers were washed with brine (10.0 mL), dried over sodium sulfate, filtered and the filtrate was concentrated in vacuum to give 2,6-difluoro-4-methyl-aniline (260 mg, 1.82 mmol, 62% yield) as brown oil. $^1$H NMR (400 MHz, CDCl$_3$) δ=6.67-6.59 (m, 2H), 3.26 (s, 2H), 2.23 (s, 3H).

To a solution of 2,6-difluoro-4-methyl-aniline (260 mg, 1.82 mmol, 1.00 eq) in sulfuric acid (3.00 mL) was added N-chlorosuccinimide (333 mg, 2.50 mmol, 1.37 eq) at 0° C. After stirring the mixture at 60° C. for 2 h, the reaction was quenched by ice. The resulting mixture was adjust pH to 7 with sodium bicarbonate and extracted with ethyl acetate (3×10.0 mL). The combined organic layers were washed with brine (10.0 mL), dried over sodium sulfate, filtered and concentrated under vacuum to give product 3-chloro-2,6-difluoro-4-methyl-aniline (270 mg, 1.52 mmol, 83% yield) as a black solid. $^1$H NMR (400 MHz, CDCl$_3$) δ=6.71 (d, J=10.8 Hz, 1H), 3.64 (s, 2H), 2.26 (s, 3H).

To a solution of 3-chloro-2,6-difluoro-4-methyl-aniline (50.0 mg, 281 umol, 1.00 eq) in tetrahydrofuran (1.00 mL) was added pyridine (44.5 mg, 563 umol, 2.00 eq) and phenyl carbonochloridate (52.9 mg, 337 umol, 1.20 eq). After addition, the mixture was stirred at 0° C. for 1 h. The reaction mixture was quenched by water (5.00 mL) and extracted with ethyl acetate (3×5.00 mL). The combined organic layers were washed with hydrochloric acid aqueous solution (5.00 mL, 0.5 M), saturated sodium bicarbonate aqueous solution (5.00 mL) and brine (5.00 mL). The separated organic layer was dried over sodium sulfate, filtered and concentrated under vacuum to give phenyl N-(3-chloro-2,6-difluoro-4-methyl-phenyl)carbamate (84 mg, crude) as brown oil.

To a solution of sodium hydride (16.9 mg, 423 umol, 60% purity, 1.50 eq) in N,N-dimethylformamide (1.00 mL) was added 3-[6-(hydroxymethyl)-1-oxo-isoindolin-2-yl]piperidine-2,6-dione (77.3 mg, 282 umol, 1.00 eq). The mixture was stirred at 0° C. under nitrogen atmosphere for 0.5 h, and hen phenyl N-(3-chloro-2,6-difluoro-4-methyl-phenyl)carbamate (84.0 mg, 282 umol, 1.00 eq) in N,N-dimethylformamide (0.500 mL) was added. After addition, the resulting mixture was stirred at 0° C. for 1 hour under nitrogen atmosphere. The reaction mixture was quenched with ammonium chloride solution (5.00 mL) at 0° C. and extracted with ethyl acetate (3×5.00 mL). The combined organic layers were washed with brine (5.00 mL), dried over sodium sulfate, filtered and concentrated under vacuum to give a residue. The residue was purified by prep-HPLC (FA condition, column: Phenomenex Synergi C18 150*25 mm*10 um; mobile phase: [water (0.225% FA)-ACN]; B %: 30%-60%, 10 min) and then lyophilized to give (2-(2,6-dioxopiperidin-3-yl)-3-oxoisoindolin-5-yl)methyl (3-chloro-2,6-difluoro-4-methylphenyl)carbamate #211 (38.5 mg, 80.0 umol, 28% yield, 99% purity) as an off-white solid. $^1$H NMR (400 MHz, DMSO-$d_6$) δ=11.01 (s, 1H), 9.50 (s, 1H), 7.76 (s, 1H), 7.64 (s, 2H), 7.28 (d, J=9.2 Hz, 1H), 5.26 (s, 2H), 5.13 (dd, J=5.2, 13.2 Hz, 1H), 4.55-4.29 (m, 2H), 2.99-2.84 (m, 1H), 2.65-2.56 (m, 1H), 2.47-2.38 (m, 1H), 2.36 (s, 3H), 2.06-1.95 (m, 1H). MS (ESI) m/z 478.0 [M+H]$^+$ Compound #212: To a solution of 2-bromo-6-fluorophenol (2.00 g, 10.5 mmol, 1.00 eq) in acetonitrile (20.0 mL) was added 1,2-dibromoethane (3.93 g, 20.9 mmol, 1.58 mL, 2.00 eq) and potassium carbonate (2.89 g, 20.9 mmol, 2.00 eq). The mixture was stirred at 50° C. for 4 h. The mixture was diluted with water (100 mL) and extracted with ethyl acetate (3×30.0 mL). The combined organic layers were washed with brine (50.0 mL), dried over sodium sulfate, filtered and concentrated under reduced pressure to give a residue. The residue was purified by column chromatography on silica gel (Petroleum ether/Ethyl acetate=1/0 to Petroleum ether/Ethylacetate=100/1) to afford 1-bromo-2-(2-bromoethoxy)-3-fluorobenzene (1.20 g, 4.03 mmol, 38% yield) as white oil. $^1$H NMR (400 MHz, DMSO-d$_6$) δ=7.47 (td, J=1.5, 8.0 Hz, 1H), 7.34 (ddd, J=1.3, 8.4, 10.8 Hz, 1H), 7.17-7.07 (m, 1H), 4.37 (dd, J=5.0, 6.0 Hz, 2H), 3.84-3.73 (m, 2H).

To a solution of 1-bromo-2-(2-bromoethoxy)-3-fluorobenzene (1.40 g, 4.70 mmol, 1.00 eq) in tetrahydrofuran (20.0 mL) cooled to −78° C. was added n-butyllithium (2.5 M, 2.80 mL, 1.49 eq) under nitrogen atmosphere. The mixture was stirred at −78° C. for 2 h and then the mixture was gradually raised to 25° C., the reaction mixture was stirred at 25° C. for 1 h. The reaction solution was quenched with water (50.0 mL), then the reaction solution was extracted with ethyl acetate (3×20.0 mL). The combined organic phases was washed with brine (20.0 mL), dried over anhydrous sodium sulfate, and concentrated under reduced pressure to afford a residue. The residue was purified by column chromatography on silica gel (Petroleum ether/Ethyl acetate=1/0 to Petroleum ether/Ethyl acetate=5/1) to afford 7-fluoro-2,3-dihydrobenzofuran (370 mg, 2.68 mmol, 57% yield) as a yellow solid. $^1$H NMR (400 MHz, DMSO-d$_6$) δ=7.08-6.95 (m, 2H), 6.80 (dt, J=4.5, 7.6 Hz, 1H), 4.61 (t, J=8.8 Hz, 2H), 3.24 (t, J=8.8 Hz, 2H).

To a solution of 7-fluoro-2,3-dihydrobenzofuran (310 mg, 2.24 mmol, 1.00 eq) was added to nitric acid (3.10 mL). The mixture was stirred at −10° C. for 2 h. The reaction mixture was poured into ice water (60.0 mL) slowly. The reaction solution was extracted with ethyl acetate (3×15.0 mL). The organic phases were combined, dried with anhydrous sodium sulfate, and concentrated under reduced pressure to give a residue. The residue was purified by column chromatography on silica gel (Petroleum ether/Ethyl acetate=1/0 to 5/1) to afford 7-fluoro-5-nitro-2,3-dihydrobenzofuran (210 mg, 1.15 mmol, 51% yield) as a brown solid. $^1$H NMR (400 MHz, DMSO-d$_6$) δ=8.10-8.00 (m, 2H), 4.84 (t, J=8.8 Hz, 2H), 3.39-3.35 (m, 2H)

To a solution of 7-fluoro-5-nitro-2,3-dihydrobenzofuran (200 mg, 1.09 mmol, 1.00 eq) in ethyl acetate (5.00 mL) was added palladium on carbon (200 mg, 10% purity) under hydrogen atmosphere. The mixture was stirred at 25° C. for 12 h. The reaction mixture was filtered and the filtrate was concentrated under reduced pressure to afford 7-fluoro-2,3-dihydrobenzofuran-5-amine (120 mg, 784 umol, 72% yield,) as a white solid To a solution of 7-fluoro-2,3-dihydrobenzofuran-5-amine (120 mg, 784 umol, 1.00 eq) in acetonitrile (2.00 mL) was added pyridine (186 mg, 2.35 mmol, 190 uL, 3.00 eq) and phenyl carbonochloridate (135 mg, 862 umol, 108 uL, 1.10 eq). The mixture was stirred at 25° C. for 4 h. The reaction mixture was concentrated under reduced pressure to afford a residue. The residue was purified by reverse-phase HPLC (column: spherical C18, 20-45 um, 100 Å, SW 120, mobile phase: [water (0.1% formic acid)-acetonitrile]) and the desired eluent was lyophilized to afford phenyl (7-fluoro-2,3-dihydrobenzofuran-5-yl)carbamate (120 mg, 422 umol, 54% yield, 96% purity) as a white solid. $^1$H NMR (400 MHz, DMSO-d$_6$) δ=10.21 (br s, 1H), 7.47-7.38 (m, 2H), 7.25-7.15 (m, 4H), 6.79-6.72 (m, 1H), 4.59 (t, J=8.8 Hz, 2H), 3.23 (t, J=8.8 Hz, 2H).

To a solution of phenyl (7-fluoro-2,3-dihydrobenzofuran-5-yl)carbamate (80.0 mg, 293 umol, 1.00 eq) in dimethyl formamide (300 uL) was added sodium hydride (23.4 mg, 586 umol, 60% purity, 2.00 eq) and 3-(6-(hydroxymethyl)-1-oxoisoindolin-2-yl)piperidine-2,6-dione I (88.3 mg, 322 umol, 1.10 eq). The mixture was stirred at 25° C. for 1 h. The pH of the mixture was adjusted to 7 with formic acid, then the mixture was diluted with dimethyl formamide (1.00 mL). The residue was purified by Prep-HPLC (column: Phenomenex luna C18 150*25 mm*10 um; mobile phase: [water (0.225% formic acid)-acetonitrile]; B %: 24%-54%, 10 min) and the desired eluent was lyophilized to afford (2-(2,6-dioxopiperidin-3-yl)-3-oxoisoindolin-5-yl)methyl (7-fluoro-2,3-dihydrobenzofuran-5-yl)carbamate #212 (40.42 mg, 80.1 umol, 27% yield, 99% purity, formic acid) as a white solid. $^1$H NMR (400 MHz, DMSO-d$_6$) δ=10.99 (br s, 1H), 9.77 (br s, 1H), 7.78 (s, 1H), 7.71-7.60 (m, 2H), 7.24-7.10 (m, 2H), 5.25 (s, 2H), 5.12 (dd, J=5.4, 13.2 Hz, 1H), 4.57 (t, J=8.8 Hz, 2H), 4.51-4.43 (m, 1H), 4.40-4.30 (m, 1H), 3.21 (t, J=8.8 Hz, 2H), 2.91 (ddd, J=5.4, 13.6, 17.6 Hz, 1H), 2.63-2.58 (m, 1H), 2.46-2.34 (m, 1H), 2.06-1.96 (m, 1H). MS (ESI) m/z 454.1 [M+H]$^+$ Compound #213: To a solution of 2,5-difluoro-4-methylaniline (300 mg, 2.10 mmol, 1.00 eq) and pyridine (498 mg, 6.29 mmol, 508 uL, 3.00 eq) in acetonitrile (5.00 mL) was added phenyl carbonochloridate (345 mg, 2.20 mmol, 276 uL, 1.05 eq) dropwise at 0° C. After addition, the resulting mixture was stirred at 25° C. for 2 h. The mixture was poured into water (30.0 mL) and extracted with ethyl acetate (3×10.0 mL). The organic phase was washed with brine (50.0 mL), dried over anhydrous sodium sulfate, filtered and concentrated under reduced pressure to give a residue. The residue was purified by silica gel column chromatography (petroleum ether, then petroleum ether/ethyl acetate=5/1) to afford phenyl (2,5-difluoro-4-methylphenyl)carbamate (370 mg, 1.12 mmol, 54% yield, 80% purity) as a light yellow solid. $^1$H NMR (400 MHz, DMSO-d$_6$) δ=10.07 (s, 1H), 7.46-7.39 (m, 2H), 7.29-7.20 (m, 4H), 6.78-6.73 (m, 1H), 2.20 (s, 3H)

To a solution of 3-(6-(hydroxymethyl)-1-oxoisoindolin-2-yl)piperidine-2,6-dione I (39.5 mg, 137 umol, 95% purity, 0.90 eq) in N,N-dimethylformamide (2.00 mL) was added sodium hydride (12.2 mg, 304 umol, 60% purity, 2.00 eq) at 0° C., then phenyl (2,5-difluoro-4-methylphenyl)carbamate (50.0 mg, 152 umol, 80% purity, 1.00 eq) was added. The mixture was stirred at 25° C. for 1 h. The mixture was poured into saturated ammonium chloride aqueous solution (30.0 mL) and extracted with ethyl acetate (3×20.0 mL). The organic phase was washed with saturated calcium chloride aqueous solution (20.0 ml), brine (20.0 mL), dried over anhydrous sodium sulfate, filtered and concentrated under reduced pressure to give a residue. The residue was purified by prep-HPLC (FA condition; column: Phenomenex Gemini-NX C18 75*30 mm*3 um; mobile phase: [water (0.225% FA)-ACN]; B %: 32%-62%, 7 min) and then lyophilized to afford (2-(2,6-dioxopiperidin-3-yl)-3-oxo isoindolin-5-yl)methyl (2,5-difluoro-4-methylphenyl)carbamate #213 (51.13 mg, 114 umol, 75% yield, 99% purity) as a white solid. $^1$H NMR (400 MHz, DMSO-d$_6$) δ=10.99 (s, 1H), 9.67 (s, 1H), 7.81 (s, 1H), 7.70-7.61 (m, 2H), 7.55-7.48 (m, 1H), 7.19 (dd, J=6.8, 10.8 Hz, 1H), 5.28 (s, 2H), 5.13 (dd, J=4.0, 13.2 Hz, 1H), 4.52-4.30 (m, 2H), 2.98-2.84 (m, 1H), 2.70-2.56 (m, 1H), 2.44-2.32 (m, 1H), 2.18 (s, 3H), 2.07-1.95 (m, 1H). MS (ESI) m/z 444.1 [M+H]$^+$ Compound #214: To a solution of 3-(difluoro(4-methoxyphenyl)methyl)bicyclo[1.1.1]pentan-1-amine (100 mg, 363 umol, 1.00 eq, hydrochloride) and pyridine (143 mg, 1.81 mmol, 146 uL, 5.00 eq) in acetonitrile (1.00 mL) was added phenyl carbonochloridate (170 mg, 1.09 mmol, 136 uL, 3.00 eq) at 0° C. The mixture was stirred at 20° C. for 1 h. The reaction mixture was quenched with water (15 mL), extracted with ethyl acetate (3×20 mL). The organic layers were washed with brine (20 mL), dried over anhydrous sodium sulfate, filtered and concentrated to afford a residue. The residue was purified by reversed phase (C18, 40 g; condition: water/acetonitrile=I/O to 0/1, 0.1% formic acid) and lyophilized to afford phenyl (3-(difluoro(4-methoxyphenyl)methyl)bicyclo[1.1.1]pentan-1-yl)carbamate (100 mg, 278 umol, 77% yield) as a white solid. $^1$H NMR (400 MHz, DMSO-$d_6$) δ=8.59 (s, 1H), 7.38-7.32 (m, 4H), 7.23-7.17 (m, 1H), 7.08 (d, J=7.7 Hz, 2H), 7.02 (d, J=8.5 Hz, 2H), 3.79 (s, 3H), 1.99 (s, 6H).

To a solution of 3-(6-(hydroxymethyl)-1-oxoisoindolin-2-yl)piperidine-2,6-dione I (70.0 mg, 255 umol, 1.00 eq) and phenyl (3-(difluoro(4-methoxyphenyl)methyl)bicyclo[1.1.1]pentan-1-yl)carbamate (91.7 mg, 255 umol, 1.00 eq) in dimethylformamide (1.00 mL) was added sodium hydride (12.3 mg, 306 umol, 60% purity, 1.20 eq) at 0° C. The mixture was stirred at 20° C. for 1 h. The mixture was quenched by formic acid (1 mL) and filtered. The filtrate was purified by prep-HPLC (column: Phenomenex Synergi C18 150*25 mm*10 um; mobile phase: [water (0.225% formic acid)-acetonitrile]; B %: 37%-67%, 10 min) and lyophilized to afford (2-(2,6-dioxopiperidin-3-yl)-3-oxoisoindolin-5-yl)methyl(3-(difluoro(4-methoxyphenyl)methyl) bicyclo[1.1.1]pentan-1-yl)carbamate #214 (41.76 mg, 76.6 umol, 30% yield, 99% purity) as a white solid. $^1$H NMR (400 MHz, DMSO-$d_6$) δ=10.98 (br s, 1H), 8.15 (br s, 1H), 7.68 (s, 1H), 7.62-7.56 (m, 2H), 7.32 (br d, J=8.5 Hz, 2H), 7.02 (d, J=8.7 Hz, 2H), 5.14-5.07 (m, 3H), 4.49-4.42 (m, 1H), 4.36-4.28 (m, 1H), 3.79 (s, 3H), 2.96-2.86 (m, 1H), 2.63-2.57 (m, 1H), 2.45-2.37 (m, 1H), 2.03-1.98 (m, 1H), 1.94 (s, 6H). MS (ESI) m/z 520.2 [M−19]$^+$ Compound #215: To a solution of 3-morpholinobicyclo[1.1.1]pentan-1-amine (100 mg, 489 umol, 1.00 eq, hydrochloride) and cesium carbonate (478 mg, 1.47 mmol, 3.00 eq) in acetonitrile (1.00 mL) was added phenyl carbonochloridate (229 mg, 1.47 mmol, 184 uL, 3.00 eq) at 0° C. The mixture was stirred at 20° C. for 1 h. The mixture was quenched by ice water (20 mL), extracted with ethyl acetate (3×40 mL). The organic layers were washed with brine (30 mL), dried over anhydrous sodium sulfate, filtered and concentrated to afford a residue. The residue was purified by reversed phase (C18, 40 g; condition: water/acetonitrile=1/0 to 0/1, 0.1% formic acid) and lyophilized to afford phenyl (3-morpholinobicyclo [1.1.1]pentan-1-yl) carbamate (100 mg, 347 umol, 71% yield) as a white solid. $^1$H NMR (400 MHz, DMSO-$d_6$) δ=8.47 (s, 1H), 7.41-7.32 (m, 2H), 7.24-7.16 (m, 1H), 7.09 (br d, J=7.8 Hz, 2H), 3.59-3.54 (m, 4H), 2.37-2.30 (m, 4H), 1.92 (s, 6H).

To a solution of 3-(6-(hydroxymethyl)-1-oxoisoindolin-2-yl)piperidine-2,6-dione I (80.0 mg, 292 umol, 1.00 eq) and phenyl (3-morpholinobicyclo[1.1.1]pentan-1-yl)carbamate (92.5 mg, 321 umol, 1.10 eq) in dimethylformamide (1.00 mL) was added sodium hydride (17.5 mg, 438 umol, 60% purity, 1.50 eq) at 0° C. The mixture was stirred at 20° C. for 1 h. The mixture was quenched by formic acid (1 mL) and filtered. The filtrate was purified by prep-HPLC (column: Phenomenex Synergi C18 150*25 mm*10 um; mobile phase: [water (0.225% formic acid)-acetonitrile]; B %: 1%-29%, 10 min) and lyophilized to afford (2-(2,6-dioxopiperidin-3-yl)-3-oxoisoindolin-5-yl)methyl (3-morpholinobicyclo[1.1.1]pentan-1-yl)carbamate #215 (82.42 mg, 174 umol, 60% yield, 99% purity) as a white solid. $^1$H NMR (400 MHz, DMSO-$d_6$) δ=10.99 (s, 1H), 8.03 (br s, 1H), 7.70 (s, 1H), 7.60 (s, 2H), 5.16-5.08 (m, 3H), 4.50-4.42 (m, 1H), 4.36-4.30 (m, 1H), 3.58-3.53 (m, 4H), 2.96-2.86 (m, 1H), 2.64-2.57 (m, 1H), 2.40 (br dd, J=4.4, 13.2 Hz, 1H), 2.31 (br s, 4H), 2.04-1.97 (m, 1H), 1.87 (s, 6H). MS (ESI) m/z 469.2 [M+H]$^+$ Compound #216: To a solution of 3-cyclopropylaniline (200 mg, 1.50 mmol, 1.00 eq) in acetonitrile (2.00 mL) was added phenyl carbonochloridate (247 mg, 1.58 mmol, 197 uL, 1.05 eq) and pyridine (356 mg, 4.50 mmol, 364 uL, 3.00 eq). The mixture was stirred at 25° C. for 2 h. The reaction mixture was concentrated under reduced pressure to afford a residue. The residue was diluted with water (30.0 mL) and extracted with ethyl acetate (3×10.0 mL). The combined organic layers were washed with brine (10.0 mL), dried over sodium sulfate, filtered and concentrated under reduced pressure to give a residue. The residue was purified by column chromatography (SiO$_2$, Petroleum ether/Ethyl acetate=1/0 to 5/1) to afford phenyl (3-cyclopropylphenyl) carbamate (353 mg, 1.39 mmol, 93% yield) as white oil. $^1$H NMR (400 MHz, DMSO-$d_6$) δ=10.13 (br s, 1H), 7.46-7.41 (m, 2H), 7.30-7.15 (m, 6H), 6.77 (d, J=7.6 Hz, 1H), 1.92-1.84 (m, 1H), 0.98-0.91 (m, 2H), 0.62 (q, J=5.2 Hz, 2H).

To a solution of phenyl (3-cyclopropylphenyl)carbamate (81.3 mg, 321 umol, 1.10 eq) in dimethyl formamide (500 uL) was added sodium hydride (23.3 mg, 583 umol, 60% purity, 2.00 eq) and 3-(6-(hydroxymethyl)-1-oxoisoindolin-2-yl)piperidine-2,6-dione I (80.0 mg, 292 umol, 1.00 eq). The mixture was stirred at 25° C. for 1 h. The pH of the mixture was adjusted to 7 with formic acid, then the mixture was diluted with dimethyl formamide (1.00 mL). The residue was purified by Prep-HPLC (column: Phenomenex luna C18 150*25 mm*10 um; mobile phase: [water (0.225% formic acid)-acetonitrile]; B %: 32%-62%, 10 min) and the desired eluent was lyophilized to afford (2-(2,6-dioxopiperidin-3-yl)-3-oxoisoindolin-5-yl)methyl (3-cyclopropylphenyl)carbamate #216 (58.73 mg, 139 umol, 48% yield, 99% purity) as a white solid. $^1$H NMR (400 MHz, DMSO-$d_6$) δ=10.99 (s, 1H), 9.70 (s, 1H), 7.79 (s, 1H), 7.70-7.61 (m, 2H), 7.26-7.18 (m, 2H), 7.17-7.10 (m, 1H), 6.71 (d, J=7.6 Hz, 1H), 5.26 (s, 2H), 5.13 (dd, J=5.1, 13.2 Hz, 1H), 4.50-4.42 (m, 1H), 4.40-4.28 (m, 1H), 2.97-2.85 (m, 1H), 2.60 (br dd, J=1.9, 15.6 Hz, 1H), 2.40 (dq, J=4.3, 13.2 Hz, 1H), 2.06-1.96 (m, 1H), 1.90-1.80 (m, 1H), 0.96-0.88 (m, 2H), 0.60 (dd, J=2.0, 5.2 Hz, 2H). MS (ESI) m/z 434.0 [M+H]$^+$ Compound #217: To a solution of 3-isopropylaniline (200 mg, 1.48 mmol, 208 uL, 1.00 eq) in acetonitrile (2.00 mL) was added phenyl carbonochloridate (243 mg, 1.55 mmol, 195 uL, 1.05 eq) and pyridine (351 mg, 4.44 mmol, 358 uL, 3.00 eq). The mixture was stirred at 25° C. for 2 h. The reaction mixture was concentrated under reduced pressure to afford a residue. The residue was diluted with water (30.0 mL) and extracted with ethyl acetate (3×10.0 mL). The combined organic layers were washed with brine (10.0 mL), dried over sodium sulfate, filtered and concentrated under reduced pressure to give a residue. The residue was purified by column chromatography (SiO$_2$, Petroleum ether/Ethyl acetate=1/0 to 5/1) to afford phenyl (3-isopropylphenyl)

carbamate (357 mg, 1.38 mmol, 94% yield, 99% purity) as pink oil. $^1$H NMR (400 MHz, DMSO-$d_6$) δ=10.15 (br s, 1H), 7.48-7.39 (m, 3H), 7.35-7.17 (m, 5H), 6.94 (d, J=7.6 Hz, 1H), 2.85 (spt, J=6.8 Hz, 1H), 1.19 (d, J=7.2 Hz, 6H).

To a solution of phenyl (3-isopropylphenyl)carbamate (81.9 mg, 321 umol, 1.10 eq) in dimethyl formamide (500 uL) was added sodium hydride (23.3 mg, 583 umol, 60% purity, 2.00 eq) and 3-(6-(hydroxymethyl)-1-oxoisoindolin-2-yl)piperidine-2,6-dione I (80.0 mg, 292 umol, 1.00 eq). The mixture was stirred at 25° C. for 1 h. The pH of the mixture was adjusted to 7 with formic acid, then the mixture was diluted with dimethyl formamide (1.00 mL). The residue was purified by Prep-HPLC (column: Phenomenex luna C18 150*25 mm*10 um; mobile phase: [water (0.225% formic acid)-acetonitrile]; B %: 35%-65%, 10 min) and the desired eluent was lyophilized to afford (2-(2,6-dioxopiperidin-3-yl)-3-oxoisoindolin-5-yl)methyl (3-isopropylphenyl)carbamate #217 (84.17 mg, 191 umol, 66% yield, 99% purity) as a white solid. $^1$H NMR (400 MHz, DMSO-$d_6$) δ=10.99 (br s, 1H), 9.72 (s, 1H), 7.79 (s, 1H), 7.71-7.60 (m, 2H), 7.37 (s, 1H), 7.28 (br d, J=8.0 Hz, 1H), 7.22-7.15 (m, 1H), 6.88 (d, J=7.6 Hz, 1H), 5.26 (s, 2H), 5.13 (dd, J=5.2, 13.2 Hz, 1H), 4.51-4.43 (m, 1H), 4.38-4.30 (m, 1H), 2.98-2.86 (m, 1H), 2.82 (td, J=6.9, 13.6 Hz, 1H), 2.60 (td, J=2.1, 15.2 Hz, 1H), 2.46-2.33 (m, 1H), 2.06-1.96 (m, 1H), 1.17 (d, J=6.8 Hz, 6H). MS (ESI) m/z 436.0 [M+H]$^+$ Compound #218: To a solution of 2,4-difluoro-5-nitrophenol (3.00 g, 17.1 mmol, 1.00 eq) in acetonitrile (60.0 mL) was added potassium hydroxide (2.88 g, 51.4 mmol, 3.00 eq) at 0° C. After addition, the mixture was stirred at 0° C. for 30 min. Then diethyl (2-bromo-2,2-difluoroethyl)phosphonate (14.5 g, 51.4 mmol, 3.00 eq) was added to the mixture dropwise at 0° C. After stirring at 20° C. for 3 h, the resulting mixture was poured into ammonium chloride aqueous solution (100 mL) and extracted with ethyl acetate (3×50.0 mL). The organic layer was washed with brine, dried over anhydrous sodium sulfate and filtered. The filtrate was concentrated under vacuum to give a residue. The residue was purified by silica gel column chromatography (petroleum ether) to give 1-(difluoromethoxy)-2,4-difluoro-5-nitrobenzene (1.90 g, 8.02 mmol, 47% yield, 95% purity) as colourless oil. $^1$H NMR (400 MHz, DMSO-$d_6$) δ=8.30 (t, J=8.0 Hz, 1H), 8.02 (t, J=10.8 Hz, 1H), 7.39 (t, J=72.4 Hz, 1H).

To a solution of 1-(difluoromethoxy)-2,4-difluoro-5-nitrobenzene (1.90 g, 8.02 mmol, 95% purity, 1.00 eq) in methanol (20.0 mL) was added palladium on carbon (190 mg, 10% purity) under nitrogen atmosphere. The suspension was degassed under vacuum and purged with hydrogen for 3 times. After stirring at 20° C. for 16 h under hydrogen atmosphere (15 Psi), the mixture was filtered. The filter cake was washed with ethyl acetate (20.0 mL). The filtrate was concentrated under vacuum to give 5-(difluoromethoxy)-2,4-difluoroaniline (1.30 g, 6.33 mmol, 79% yield, 95% purity) as brown oil. It was used for next step directly without purification. $^1$H NMR (400 MHz, DMSO-$d_6$) δ=7.26 (d, J=11.6 Hz, 1H), 7.09 (t, J=73.2 Hz, 1H), 6.73 (t, J=8.4 Hz, 1H), 5.27 (s, 2H).

To a solution of 5-(difluoromethoxy)-2,4-difluoroaniline (800 mg, 3.90 mmol, 95% purity, 1.00 eq) and pyridine (462 mg, 5.84 mmol, 1.50 eq) in acetonitrile (8.00 mL) was added phenyl carbonochloridate (640 mg, 4.09 mmol, 1.05 eq) at 0° C. After addition, the mixture was stirred at 20° C. for 5 h. The mixture was poured into water (50 mL) and extracted with ethyl acetate (3×50 mL). The separated organic layer was washed with brine, dried over anhydrous sodium sulfate and filtered. The filtrate was concentrated under vacuum to give a residue. The residue was purified by silica gel column chromatography (petroleum ether/ethyl acetate=100/1 to 20/1) to give phenyl (5-(difluoromethoxy)-2,4-difluorophenyl)carbamate (1.20 g, 3.72 mmol, 95% yield, 97% purity) as colourless oil. MS (ESI) m/z 316.1 [M+H]$^+$ To a mixture of 3-(6-(hydroxymethyl)-1-oxoisoindolin-2-yl)piperidine-2,6-dione I (47.9 mg, 174 umol, 1.10 eq) in tetrahydrofuran (1.00 mL) was added sodium hydride (7.61 mg, 190 umol, 60% purity, 1.20 eq) at 0° C. After stirring at 0° C. for 15 min, phenyl (5-(difluoromethoxy)-2,4-difluorophenyl)carbamate (50.0 mg, 159 umol, 1.00 eq) was added to the mixture. The resulting mixture was stirred at 20° C. for 1 h. The mixture was poured into saturated ammonium chloride aqueous solution (5 mL) and extracted with ethyl acetate (3×10 mL). The organic layer was washed with brine, dried over anhydrous sodium sulfate and filtered. The filtrate was concentrated under vacuum to give a residue. The residue was purified by Prep-HPLC (column: Phenomenex Gemini-NX C18 75*30 mm*3 um; mobile phase: [water (0.225% FA)-ACN]; B %: 30%-60%, 7 min) and lyophilized to give (2-(2,6-dioxopiperidin-3-yl)-3-oxoisoindolin-5-yl)methyl(5-(difluoromethoxy)-2,4-difluorophenyl) carbamate #218 (47.89 mg, 96.2 umol, 61% yield, 99% purity) as a white solid. $^1$H NMR (400 MHz, DMSO-$d_6$) δ=11.00 (s, 1H), 9.76 (s, 1H), 7.81 (s, 1H), 7.75 (t, J=8.4 Hz, 1H), 7.71-7.62 (m, 2H), 7.58 (t, J=6.8 Hz, 1H), 7.20 (t, J=73.2 Hz, 1H), 5.29 (s, 2H), 5.13 (dd, J=5.2, 13.2 Hz, 1H), 4.52-4.44 (m, 1H), 4.40-4.31 (m, 1H), 2.98-2.85 (m, 1H), 2.65-2.57 (m, 1H), 2.47-2.35 (m, 1H), 2.07-1.96 (m, 1H). MS (ESI) m/z 496.1 [M+H]$^+$ Compound #219: To a solution of 3-(difluoromethyl) bicyclo[1.1.1]pentan-1-amine (100 mg, 590 umol, 1.00 eq, hydrochloride) and pyridine (233 mg, 2.95 mmol, 238 uL, 5.00 eq) in acetonitrile (1.00 mL) was added phenyl carbonochloridate (277 mg, 1.77 mmol, 222 uL, 3.00 eq) at 0° C. The mixture was stirred at 20° C. for 1 h. The mixture was quenched by ice water (20 mL), extracted with ethyl acetate (3×40 mL). The organic layers were washed with brine (30 mL), dried over anhydrous sodium sulfate, filtered and concentrated to afford a crude product. The crude product was purified by prep-NPLC (column: Welch Ultimate XB-CN 250*70*10 um; mobile phase: [Heptane-ethyl alcohol (0.1% ammonium hydroxide)]; B %: 1%-40%, 15 min) and concentrated to afford phenyl (3-(difluoromethyl)bicyclo [1.1.1]pentan-1-yl)carbamate (100 mg, 395 umol, 67% yield) as a white solid. $^1$H NMR (400 MHz, DMSO-$d_6$) δ=8.60 (br s, 1H), 7.40-7.35 (m, 2H), 7.24-7.19 (m, 1H), 7.10 (br d, J=7.8 Hz, 2H), 6.17 (br t, J=56.4 Hz, 1H), 2.06 (s, 6H).

To a solution of 3-(6-(hydroxymethyl)-1-oxoisoindolin-2-yl)piperidine-2,6-dione I (80.0 mg, 292 umol, 1.00 eq) and phenyl (3-(difluoromethyl)bicyclo[1.1.1]pentan-1-yl)carbamate (81.3 mg, 321 umol, 1.10 eq) in dimethylformamide (1.00 mL) was added sodium hydride (17.5 mg, 438 umol, 60% purity, 1.50 eq) at 0° C. The mixture was stirred at 20° C. for 1 h. The mixture was quenched by formic acid (1 mL) and filtered. The filtrate was purified by prep-HPLC (column: Phenomenex Synergi C18 150*25 mm*10 um; mobile phase: [water (0.225% formic acid)-acetonitrile]; B %: 23%-53%, 10 min) and lyophilized to afford a residue. The residue was further purified by prep-HPLC (column: Phenomenex luna C18 150*25 mm*10 um; mobile phase: [water (0.225% formic acid)-acetonitrile]; B %: 22%-52%, 10 min) and lyophilized to afford (2-(2,6-dioxopiperidin-3-yl)-3-oxoisoindolin-5-yl)methyl (3-(difluoromethyl)bicyclo [1.1.1]pentan-1-yl) carbamate #219 (57.33 mg, 131 umol, 45% yield, 99% purity) as a white solid. $^1$H NMR (400

MHz, DMSO-d$_6$) δ=11.00 (br s, 1H), 8.18 (br s, 1H), 7.71 (s, 1H), 7.61 (s, 2H), 6.16 (br t, J=56.4 Hz, 1H), 5.12 (m, 3H), 4.46 (m, 1H), 4.34 (m, 1H), 2.91 (m, 1H), 2.60 (m, 1H), 2.53 (m, 1H), 2.41 (m, 1H), 2.01 (s, 6H). MS (ESI) m/z 434.1 [M+H]$^+$

Compound #220: To a solution of 3-ethylaniline (200 mg, 1.65 mmol, 206 uL, 1.00 eq) in acetonitrile (2.00 mL) was added pyridine (392 mg, 4.95 mmol, 400 uL, 3.00 eq) and phenyl carbonochloridate (271 mg, 1.73 mmol, 217 uL, 1.05 eq). The mixture was stirred at 25° C. for 2 h. The reaction mixture was concentrated under reduced pressure to afford a residue. The residue was diluted with water (30.0 mL) and extracted with ethyl acetate (3×10.0 mL). The combined organic layers were washed with brine (10.0 mL), dried over, filtered and concentrated under reduced pressure to give a residue. The residue was purified by column chromatography (SiO2, Petroleum ether/Ethyl acetate=1/0 to 9/1) to afford phenyl (3-ethylphenyl)carbamate (369 mg, 1.53 mmol, 93% yield) as yellow oil. $^1$H NMR (400 MHz, DMSO-d$_6$) δ=10.15 (br s, 1H), 7.46-7.37 (m, 3H), 7.33 (br d, J=8.4 Hz, 1H), 7.29-7.19 (m, 4H), 6.91 (d, J=7.6 Hz, 1H), 2.58 (q, J=7.6 Hz, 2H), 1.20-1.15 (m, 3H).

To a solution of phenyl (3-ethylphenyl)carbamate (77.4 mg, 321 umol, 1.10 eq) in dimethyl formamide (500 uL) was added sodium hydride (23.3 mg, 583 umol, 60% purity, 2.00 eq) and 3-(6-(hydroxymethyl)-1-oxoisoindolin-2-yl)piperidine-2,6-dione I (80 mg, 291.68 umol, 1 eq). The mixture was stirred at 25° C. for 1 h. The pH of the mixture was adjusted to 7 with formic acid, then the mixture was diluted with dimethyl formamide (1.00 mL). The residue was purified by Prep-HPLC (column: Phenomenex luna C18 150*25 mm*10 um; mobile phase: [water (0.225% formic acid)-acetonitrile]; B %: 32%-62%, 10 min) and the desired eluent was lyophilized to afford (2-(2,6-dioxopiperidin-3-yl)-3-oxoisoindolin-5-yl)methyl (3-ethylphenyl)carbamate #220 (48.65 mg, 114 umol, 39% yield, 99% purity) as a white solid. $^1$H NMR (400 MHz, DMSO-d$_6$) δ=11.00 (br s, 1H), 9.74 (s, 1H), 7.80 (s, 1H), 7.71-7.61 (m, 2H), 7.34 (s, 1H), 7.28 (br d, J=8.0 Hz, 1H), 7.21-7.14 (m, 1H), 6.85 (d, J=7.6 Hz, 1H), 5.27 (s, 2H), 5.13 (dd, J=5.1, 13.2 Hz, 1H), 4.53-4.44 (m, 1H), 4.39-4.29 (m, 1H), 2.97-2.87 (m, 1H), 2.70-2.59 (m, 1H), 2.59-2.53 (m, 2H), 2.41 (br dd, J=4.5, 13.2 Hz, 1H), 2.08-1.97 (m, 1H), 1.16 (t, J=7.6 Hz, 3H). MS (ESI) m/z 422.0 [M+H]$^+$ Compound #221: To a solution of 4-fluoro-3-nitrophenol (1.00 g, 6.37 mmol, 1.00 eq) in acetone (20.0 mL) were added 2-iodopropane (3.25 g, 19.1 mmol, 1.91 mL, 3.00 eq) and potassium carbonate (2.64 g, 19.1 mmol, 3.00 eq), the mixture was stirred at 70° C. for 12 h. The reaction was filtered to give a filtrate, the filtrate was concentrated to give a residue. The residue was purified by flash silica gel chromatography (ISCO®; 80 g SepaFlash® Silica Flash Column, Eluent of 5~10% Petroleum ether/Ethyl acetate @ 100 mL/min) to afford 1-fluoro-4-isopropoxy-2-nitrobenzene (1.00 g, 5.02 mmol, 78% yield) as yellow oil. $^1$H NMR (400 MHz, DMSO-d$_6$) δ=7.59 (dd, J=3.2, 6.0 Hz, 1H), 7.50 (dd, J=9.2, 10.8 Hz, 1H), 7.36 (td, J=3.6, 9.2 Hz, 1H), 4.70 (spt, J=6.0 Hz, 1H), 1.28 (s, 3H), 1.27 (s, 3H).

To a solution of 1-fluoro-4-isopropoxy-2-nitrobenzene (300 mg, 1.51 mmol, 1.00 eq) in ethyl acetate (6.00 mL) was added wet palladium on carbon (50.0 mg, 10% purity), the mixture was stirred at 25° C. for 12 h. The reaction was filtered to give a filtrate, the filtrate was concentrated to afford 2-fluoro-5-isopropoxyaniline (180 mg, 1.06 mmol, 70% yield) as yellow oil. MS (ESI) m/z 170.1 [M+H]$^+$ To a solution of 2-fluoro-5-isopropoxyaniline (180 mg, 1.06 mmol, 1.00 eq) in acetonitrile (2.00 mL) were added phenyl carbonochloridate (174 mg, 1.12 mmol, 139 uL, 1.05 eq) and pyridine (168 mg, 2.13 mmol, 171 uL, 2.00 eq), the mixture was stirred at 25° C. for 2 h. The reaction was concentrated to give a residue. The residue was purified by reversed-phase HPLC (column: Shim-pack C18 150*25*10 um; mobile phase: [water (0.1% formic acid)-acetonitrile]) to afford phenyl (2-fluoro-5-isopropoxyphenyl)carbamate (200 mg, 691 umol, 64% yield) as yellow oil. MS (ESI) m/z 290.1 [M+H]$^+$ To a solution of 3-(6-(hydroxymethyl)-1-oxoisoindolin-2-yl)piperidine-2,6-dione I (80.0 mg, 291 umol, 1.00 eq) in dimethylformamide (1.00 mL) were added phenyl (2-fluoro-5-isopropoxyphenyl)carbamate (92.8 mg, 320 umol, 1.10 eq) and sodium hydride (23.3 mg, 583 umol, 4.86 uL, 60% purity, 2.00 eq), the mixture was stirred at 25° C. for 1 h. The pH of the mixture was adjusted to 7 with formic acid (0.500 mL), then the mixture was diluted with dimethyl formamide (1.00 mL). The reaction was purified by Prep-HPLC (column: Phenomenex luna C18 150*25 mm*10 um; mobile phase: [water (0.225% formic acid)-acetonitrile]; B %: 33%-63%, 10 min) to afford (2-(2,6-dioxopiperidin-3-yl)-3-oxoisoindolin-5-yl)methyl (2-fluoro-5-isopropoxyphenyl)carbamate #221 (48.3 mg, 101 umol, 34% yield, 99% purity) as a white solid. $^1$H NMR (400 MHz, DMSO-d$_6$) δ=10.99 (br s, 1H), 9.52 (br s, 1H), 7.81 (s, 1H), 7.70-7.60 (m, 2H), 7.26 (br d, J=3.2 Hz, 1H), 7.10 (dd, J=9.2, 10.2 Hz, 1H), 6.64 (td, J=3.6, 8.8 Hz, 1H), 5.27 (s, 2H), 5.13 (dd, J=5.2, 13.2 Hz, 1H), 4.52-4.43 (m, 2H), 4.38-4.28 (m, 1H), 2.98-2.86 (m, 1H), 2.60 (br dd, J=2.4, 15.4 Hz, 1H), 2.40 (dq, J=4.6, 13.2 Hz, 1H), 2.05-1.97 (m, 1H), 1.23 (d, J=6.0 Hz, 6H). MS (ESI) m/z 470.0 [M+H]$^+$ Compound #222: To a mixture of 4-fluoro-3-nitrophenol (1.00 g, 6.37 mmol, 1.00 eq) and magnesium perchlorate (852 mg, 3.82 mmol, 0.600 eq) in dichloromethane (10.0 mL) was added the solution of di-tert-butyldicarbonate (6.25 g, 28.6 mmol, 6.58 mL, 4.50 eq) in dichloromethane (10.0 mL) dropwise, the mixture was stirred at 40° C. for 12 h. The reaction mixture was partitioned between dichloromethane (20 mL) and water (30 mL). The organic phase was separated, dried over sodium sulfate, filtered and to give a filtrate, the filtrate was concentrated under reduced pressure to give a residue. The residue was purified by flash silica gel chromatography (ISCO®; 80 g SepaFlash® Silica Flash Column, Eluent of 1~3% Petroleum ether/Ethyl acetate @ 100 mL/min) to afford 4-(tert-butoxy)-1-fluoro-2-nitrobenzene (1.00 g, 4.69 mmol, 73% yield) as yellow oil. $^1$H NMR (400 MHz, DMSO-d$_6$) δ=7.66 (dd, J=3.0, 6.4 Hz, 1H), 7.54-7.48 (m, 1H), 7.46-7.41 (m, 1H), 1.32 (s, 9H).

To a solution of 4-(tert-butoxy)-1-fluoro-2-nitrobenzene (321 mg, 1.51 mmol, 1.00 eq) in ethyl acetate (6.00 mL) was added wet palladium on carbon (50.0 mg, 10% purity), the mixture was stirred at 25° C. for 12 h. The reaction was filtered to give a filtrate, the filtrate was concentrated to afford 5-(tert-butoxy)-2-fluoroaniline (220 mg, 1.20 mmol, 79% yield) as yellow oil. MS (ESI) m/z 184.1 [M+H]$^+$ To a solution of 5-(tert-butoxy)-2-fluoroaniline (210 mg, 1.15 mmol, 1.00 eq) in acetonitrile (2.00 mL) were added phenyl carbonochloridate (188 mg, 1.20 mmol, 150 uL, 1.05 eq) and pyridine (181 mg, 2.29 mmol, 185 uL, 2.00 eq), the mixture was stirred at 25° C. for 2 h. The reaction was concentrated to give a residue. The residue was purified by reversed-phase HPLC (column: Shim-pack C18 150*25*10 um; mobile phase: [water (0.1% formic acid)-acetonitrile]) to afford phenyl (5-(tert-butoxy)-2-fluorophenyl)carbamate (220 mg, 725.29 umol, 63.28% yield) as a yellow solid. MS (ESI) m/z 248.1 [M−55]$^+$ To a solution of 3-(6-(hydroxymethyl)-1-oxoisoindolin-2-yl)piperidine-2,6-dione I (80.0 mg, 291 umol, 1.00 eq) in dimethylformamide (1.00 mL) were added phenyl (5-(tert-butoxy)-2-fluorophenyl)carbamate (97.3 mg, 320 umol, 1.10 eq) and sodium hydride (23.3 mg, 583 umol, 60% purity, 2.00 eq), the mixture was stirred at 25° C. for 1 h. The pH of the mixture was adjusted to 7 with formic acid (0.500 mL), then the mixture was diluted with dimethyl formamide (1.00 mL). The reaction was purified by Prep-HPLC (column: Phenomenex luna C18 150*25 mm*10 um; mobile phase: [water (0.225% FA)-ACN]; B %: 34%-64%, 10 min) to afford (2-(2,6-dioxopiperidin-3-yl)-3-oxoisoindolin-5-yl)methyl (5-(tert-butoxy)-2-fluorophenyl)carbamate #222 (48.2 mg, 98.8 umol, 33% yield, 99% purity) as a white solid. $^1$H NMR (400 MHz, DMSO-d$_6$) δ=10.99 (br s, 1H), 9.53 (br s, 1H), 7.81 (s, 1H), 7.70-7.61 (m, 2H), 7.34 (br d, J=4.2 Hz, 1H), 7.11 (dd, J=9.0, 10.6 Hz, 1H), 6.70 (td, J=3.6, 8.8 Hz, 1H), 5.27 (s, 2H), 5.13 (dd, J=5.2, 13.2 Hz, 1H), 4.51-4.44 (m, 1H), 4.38-4.31 (m, 1H), 2.98-2.86 (m, 1H), 2.64-2.56 (m, 1H), 2.40 (dq, J=4.6, 13.2 Hz, 1H), 2.07-1.96 (m, 1H), 1.26 (s, 9H). MS (ESI) m/z 427.9 [M−55]$^+$ Compound #223: To a solution of 4-fluoro-3-nitrophenol (500 mg, 3.18 mmol, 1.00 eq) and potassium carbonate (879 mg, 6.37 mmol, 2.00 eq) in dimethylformamide (5.00 mL) was added iodoethane (595 mg, 3.82 mmol, 305 uL, 1.20 eq), the mixture was stirred at 50° C. for 5 h. The reaction mixture was poured into water (100 mL) and stirred for 10 min. The aqueous phase was extracted with ethyl acetate (3×50.0 mL). The combined organic phase was washed with brine (100 mL), dried over anhydrous sodium sulfate, filtered and concentrated in vacuum to give a residue. The residue was purified by silica gel chromatography (Petroleum ether/Ethyl acetate=I/O to 50/1) to afford 4-ethoxy-1-fluoro-2-nitrobenzene (500 mg, 2.70 mmol, 84% yield) as colorless oil. $^1$H NMR (400 MHz, CDCl$_3$) δ=7.51-7.41 (m, 1H), 7.17-7.03 (m, 2H), 3.99 (q, J=7.0 Hz, 2H), 1.37 (dt, J=0.9, 7.0 Hz, 3H).

To a solution of 4-ethoxy-1-fluoro-2-nitrobenzene (500 mg, 2.70 mmol, 1.00 eq) in methanol (10.0 mL) was added palladium/carbon (50.0 mg, 2.70 mmol, 10% purity), the mixture was stirred at 25° C. for 1 h under hydrogen. The reaction mixture was filtered to give a filtrate, the filtrate was concentrated to give 5-ethoxy-2-fluoro-aniline (400 mg, 2.58 mmol, 95% yield) as yellow oil. MS (ESI) m/z 156.2 [M+H]$^+$ To a solution of 5-ethoxy-2-fluoro-aniline (200 mg, 1.29 mmol, 1.00 eq) and pyridine (509 mg, 6.44 mmol, 520 uL, 5.00 eq) in acetonitrile (4.00 mL) was added phenyl carbonochloridate (242 mg, 1.55 mmol, 193 uL, 1.20 eq) at 0° C., the mixture was stirred at 25° C. for 1 h. The reaction mixture was concentrated to give a residue. The residue was purified by reversed-phase HPLC (column: spherical C18, 20-45 um, 40 Å, SW 40, mobile phase: [water (0.1% Formic Acid)-acetonitrile]) to afford phenyl (5-ethoxy-2-fluorophenyl)carbamate (300 mg, 1.09 mmol, 84% yield) as yellow oil. MS (ESI) m/z 276.0[M+H]$^+$ To a solution of phenyl (5-ethoxy-2-fluorophenyl)carbamate (120 mg, 437 umol, 1.20 eq) and 3-(6-(hydroxymethyl)-1-oxoisoindolin-2-yl)piperidine-2,6-dione I (100 mg, 364 umol, 1.00 eq) in dimethylformamide (1.00 mL) was added sodium hydride (28.0 mg, 700 umol, 60% purity, 1.92 eq) at 0° C., the mixture was stirred at 25° C. for 1 h. The reaction mixture was quenched with formic acid (0.100 mL) and filtered to give a filtrate. The filtrate was purified by Prep-HPLC (column: Phenomenex Synergi C18 150*25 mm*10 um; mobile phase: [water (0.225% formic acid)-acetonitrile]; B %: 30%-60%, 10 min) to afford a crude product. The crude product was purified by Prep-HPLC (column: YMC Triart 30*150 mm*7 um; mobile phase: [water (0.05% hydrochloric acid)-acetonitrile]; B %: 43%-63%, 9 min) to afford (2-(2,6-dioxopiperidin-3-yl)-3-oxoisoindolin-5-yl)methyl (5-ethoxy-2-fluorophenyl)carbamate #223 (33.82 mg, 74.2 umol, 20% yield) as an off white solid. $^1$H NMR (400 MHz, DMSO-d$_6$) δ=11.00 (s, 1H), 9.53 (br s, 1H), 7.82 (s, 1H), 7.74-7.58 (m, 2H), 7.38-7.21 (m, 1H), 7.12 (dd, J=9.0, 10.4 Hz, 1H), 6.65 (td, J=3.4, 9.0 Hz, 1H), 5.28 (s, 2H), 5.14 (dd, J=5.1, 13.2 Hz, 1H), 4.56-4.43 (m, 1H), 4.40-4.30 (m, 1H), 3.96 (q, J=7.0 Hz, 2H), 2.98-2.86 (m, 1H), 2.66-2.57 (m, 1H), 2.47-2.35 (m, 1H), 2.07-1.96 (m, 1H), 1.30 (t, J=7.0 Hz, 3H). MS (ESI) m/z 456.0 [M+H]$^+$ Compound #224: To a solution of 3-(tert-butoxycarbonyl)bicyclo[1.1.1]pentane-1-carboxylic acid (100 mg, 471 umol, 1.00 eq) in dioxane (2.00 mL) was added diphenylphosphoryl azide (259 mg, 942 umol, 204 uL, 2.00 eq) and triethylamine (143 mg, 1.41 mmol, 197 uL, 3.00 eq). The mixture was stirred at 25° C. for 0.5 h under nitrogen. Then the 3-(6-(hydroxymethyl)-1-oxoisoindolin-2-yl)piperidine-2,6-dione I (129 mg, 471 umol, 1.00 eq) was added into the mixture and it was stirred at 90° C. for 11.5 h. The mixture was concentrated under reduced pressure to give a residue. The residue was quenched by water (30 mL) and then extracted with ethyl acetate (3×30 mL). The combined organic phases were washed with brine (2×20 mL), dried over anhydrous sodium sulfate, filtered and concentrated in vacuum to give a crude product. The crude product was purified by prep-HPLC (column: Phenomenex Synergi C18 150*25 mm*10 um; mobile phase: [water (0.225% formic acid)-acetonitrile]; B %: 30%-60%, 10 min) and lyophilized to afford tert-butyl 3-((((2-(2,6-dioxopiperidin-3-yl)-3-oxoisoindolin-5-yl)methoxy)carbonyl)amino)bicyclo[1.1.1]pentane-1-carboxylate #224 (34.33 mg, 63.5 umol, 13% yield, 98% purity, formate) as a white solid. $^1$H NMR (400 MHz, DMSO-d$_6$) δ=11.22-10.78 (m, 1H), 8.47 (s, 1H), 8.19-8.06 (m, 1H), 7.69 (s, 1H), 7.60 (s, 2H), 5.17-5.08 (m, 3H), 4.49-4.43 (m, 1H), 4.38-4.28 (m, 1H), 2.96-2.86 (m, 1H), 2.64-2.57 (m, 1H), 2.46-2.37 (m, 1H), 2.11 (s, 6H), 2.04-1.98 (m, 1H), 1.38 (s, 9H). MS (ESI) m/z 428.2 [M−55]$^+$ Compound #225: To a solution of dimethyl cubane-1,4-dicarboxylate (200 mg, 908 umol, 1.00 eq) in tetrahydrofuran (6.00 mL) was added sodium hydroxide (2 M in methanol, 499 uL, 1.10 eq). The mixture was stirred at 25° C. for 12 h. The mixture was concentrated dryness to give a residue. The residue was dissolved in water (10.0 mL) and extracted with dichloromethane (10.0 mL). The pH of aqueous phase was adjust to 3-4, and then extracted with ethyl acetate (10.0 mL). The organic phase was concentrated to dryness to give 4-methoxycarbonylcubane-1-carboxylic acid (168 mg, 815 umol, 90% yield) as a white solid. $^1$H NMR (400 MHz, CDCl3) δ=4.29 (s, 6H), 3.74 (s, 3H).

To a solution of 4-methoxycarbonylcubane-1-carboxylic acid (100 mg, 485 umol, 1.00 eq) in benzene (20.0 mL) was added lead acetate (280 mg, 630 umol, 1.30 eq) at 25° C. The mixture was stirred at 80° C. for 14 h under irradiation with a mercury lamp. The mixture was filtered and the filtrate was concentrated to dryness to give a residue. The residue was purified by Prep-TLC (Petroleum ether/Ethyl acetate=10/1) to give methyl 4-phenylcubane-1-carboxylate (40.0 mg, 168 umol, 35% yield) as a yellow solid. $^1$H NMR (400 MHz, CDCl$_3$) δ=7.32-7.26 (m, 2H), 7.16-7.11 (m, 3H), 4.20-4.13 (m, 3H), 4.12-4.04 (m, 3H), 3.67 (s, 3H).

To a solution of methyl 4-phenylcubane-1-carboxylate (36.0 mg, 151 umol, 1.00 eq) in tetrahydrofuran (1.00 mL) and methanol (1.00 mL) was added hydrated lithium hydroxide (12.7 mg, 302 umol, 2.00 eq). The mixture was stirred at 25° C. for 12 h. 1N hydrochloric acid was added to the mixture to pH=3-4, then water (5.00 mL) was added and extracted with ethyl acetate (15.0 mL). The organic phase was washed with brine (5.00 mL), dried over sodium sulfate, filtered and concentrated in vacuum to give 4-phenylcubane-1-carboxylic acid (27.0 mg, 120 umol, 80% yield) as a yellow solid which was used to next step without further purification.

To a mixture of 4-phenylcubane-1-carboxylic acid (27.0 mg, 120 umol, 1.00 eq) and diphenyl phosphoryl azide (53.0 mg, 193 umol, 1.60 eq) in dioxane (2.00 mL) was added triethylamine (24.4 mg, 241 umol, 2.00 eq). The mixture was stirred at 25° C. for 1 h and 3-(6-(hydroxymethyl)-1-oxoisoindolin-2-yl) piperidine-2,6-dione (36.3 mg, 132 umol, 1.10 eq) was added and then stirred at 100° C. for 2 h. The mixture was purified by Prep-HPLC (column: Phenomenex luna C18 150*25 mm*10 um; mobile phase: [water (0.225% FA)-ACN]; B %: 39%-69%, 10 min) to give (2-(2,6-dioxopiperidin-3-yl)-3-oxoisoindolin-5-yl)methyl (4-phenylcuban-1-yl)carbamate #225 (4.44 mg, 8.96 umol, 7.4% yield) as a white solid. $^1$H NMR (400 MHz, DMSO-d$_6$) δ=10.84 (br s, 1H), 8.26 (br s, 1H), 7.74 (s, 1H), 7.63 (s, 2H), 7.39-7.31 (m, 2H), 7.26-7.15 (m, 3H), 5.23-5.08 (m, 3H), 4.52-4.43 (m, 1H), 4.39-4.30 (m, 1H), 3.99 (br d, J=17.8 Hz, 6H), 2.98-2.84 (m, 1H), 2.61 (br d, J=17.4 Hz, 1H), 2.45-2.30 (m, 1H), 2.05-1.96 (m, 1H). MS (ESI) m/z 496.1 [M+1]$^+$ Compound #226: To a solution of 4-fluoro-3-nitrophenol (1.00 g, 6.37 mmol, 1.00 eq) in acetone (10.0 mL) was added potassium carbonate (1.76 g, 12.7 mmol, 2.00 eq) and 1-iodopropane (1.30 g, 7.64 mmol, 746 uL, 1.20 eq). The mixture was stirred at 60° C. for 4 h. The reaction mixture was concentrated under reduced pressure to afford a residue. The residue was diluted with water (80.0 mL) and extracted with ethyl acetate (3×30.0 mL). The combined organic layers were washed with brine (30.0 mL), dried over anhydrous sodium sulfate, filtered and concentrated under reduced pressure to give a residue. The residue was purified by column chromatography (SiO$_2$, petroleum ether/ethyl acetate=1/0 to 10/1) to afford 1-fluoro-2-nitro-4-propoxybenzene (567 mg, 2.85 mmol, 45% yield) as white oil. $^1$H NMR (400 MHz, CDCl$_3$) δ=7.53 (dd, J=2.8, 5.6 Hz, 1H), 7.25-7.12 (m, 2H), 3.97 (t, J=6.4 Hz, 2H), 1.85 (sxt, J=7.2 Hz, 2H), 1.07 (t, J=7.2 Hz, 3H).

To a solution of 1-fluoro-2-nitro-4-propoxybenzene (560 mg, 2.81 mmol, 1.00 eq) in methanol (7.00 mL) was added palladium on carbon (600 mg, 10% purity). The mixture was stirred at 25° C. for 2 h under hydrogen atmosphere (15 Psi). The mixture was filtered, and the filtrate was concentrated under reduced pressure to afford 2-fluoro-5-propoxyaniline (375 mg, 2.22 mmol, 79% yield) as orange oil. $^1$H NMR (400 MHz, DMSO-d$_6$) δ=6.84 (dd, J=8.8, 11.2 Hz, 1H), 6.32 (dd, J=2.9, 7.6 Hz, 1H), 6.03 (td, J=3.2, 8.8 Hz, 1H), 5.07 (s, 2H), 3.79 (t, J=6.4 Hz, 2H), 1.68 (sxt, J=7.2 Hz, 2H), 0.95 (t, J=7.6 Hz, 3H).

To a solution of 2-fluoro-5-propoxy-aniline (200 mg, 1.18 mmol, 1.00 eq) in acetonitrile (2.00 mL) was added phenyl carbonochloridate (194 mg, 1.24 mmol, 155 uL, 1.05 eq) and pyridine (281 mg, 3.55 mmol, 286 uL, 3.00 eq). The mixture was stirred at 25° C. for 2 h. The reaction mixture was concentrated under reduced pressure to afford a residue. The residue was diluted with water (40.0 mL) and extracted with ethyl acetate (3×10.0 mL). The combined organic layers were washed with brine (15.0 mL), dried over anhydrous sodium sulfate, filtered and concentrated under reduced pressure to give a residue. The residue was purified by column chromatography (SiO2, petroleum ether/ethyl acetate=1/0 to 5/1) to afford phenyl (2-fluoro-5-propoxyphenyl)carbamate (258 mg, 892 umol, 75% yield) as colorless oil. $^1$H NMR (400 MHz, DMSO-d$_6$) δ=9.95 (br s, 1H), 7.50-7.37 (m, 2H), 7.36-7.09 (m, 5H), 6.78-6.66 (m, 1H), 3.88 (t, J=6.4 Hz, 2H), 1.71 (t, J=7.2 Hz, 2H), 0.96 (t, J=7.2 Hz, 3H).

To a solution of phenyl (2-fluoro-5-propoxyphenyl)carbamate (92.8 mg, 321 umol, 1.10 eq) in dimethylformamide (500 uL) was added 3-(6-(hydroxymethyl)-1-oxoisoindolin-2-yl)piperidine-2,6-dione I (80.0 mg, 292 umol, 1.00 eq) and sodium hydride (23.3 mg, 583 umol, 60% purity, 2.00 eq). The mixture was stirred at 25° C. for 1 h. The pH was adjusted to around 7 by progressively adding formic acid, then the mixture was diluted with dimethyl formamide (1.00 mL). The residue was purified by prep-HPLC (column: Phenomenex luna C18 150*25 mm*10 um; mobile phase: [water (formic acid)-acetonitrile]; B %: 33%-63%, 10 min) and Prep-NPLC (column: Welch Ultimate XB-SiOH 250*50*10 um; mobile phase: [Hexane-ethyl alcohol (0.1% formic acid)]; B %: 1%-35%, 15 min) to afford (2-(2,6-dioxopiperidin-3-yl)-3-oxoisoindolin-5-yl)methyl (2-fluoro-5-propoxyphenyl)carbamate #226 (41.49 mg, 87.5 umol, 30% yield, 99% purity) as a white solid. $^1$H NMR (400 MHz, DMSO-d$_6$) δ=11.00 (br s, 1H), 9.55 (br s, 1H), 7.81 (s, 1H), 7.72-7.59 (m, 2H), 7.35-7.23 (m, 1H), 7.16-7.07 (m, 1H), 6.65 (td, J=3.2, 9.2 Hz, 1H), 5.27 (s, 2H), 5.13 (dd, J=5.1, 13.2 Hz, 1H), 4.53-4.42 (m, 1H), 4.39-4.29 (m, 1H), 3.85 (t, J=6.8 Hz, 2H), 2.99-2.85 (m, 1H), 2.60 (br dd, J=2.0, 15.6 Hz, 1H), 2.47-2.31 (m, 1H), 2.07-1.95 (m, 1H), 1.69 (sxt, J=7.2 Hz, 2H), 0.95 (t, J=7.2 Hz, 3H). MS (ESI) m/z 470.3 [M+H]$^+$ Compound #227: To a mixture of 2-chloro-5-fluoropyridin-4-ol (1.00 g, 6.78 mmol, 1.00 eq) and potassium carbonate (2.00 g, 14.5 mmol, 2.13 eq) in N,N-dimethyl formamide (10.0 mL) was added sodium 2-chloro-2,2-difluoroacetate (2.01 g, 13.12 mmol, 1.94 eq). After stirring at 100° C. for 2 h, the mixture was poured into water (50 mL) and extracted with ethyl acetate (2×50 mL). The organic layer was washed with brine (30 mL), dried over anhydrous sodium sulfate, filtered and concentrated to give the crude product. The crude product was purified by flash silica gel chromatography (ISCO®; 20 g SepaFlash® Silica Flash Column, 0~10% ethyl acetate/petroleum ether=0~10%, 30 mL/min) to afford 2-chloro-4-(difluoromethoxy)-5-fluoropyridine (1.20 g, 6.07 mmol, 90% yield) as colorless oil. $^1$H NMR (400 MHz, CDCl$_3$) δ=8.31 (d, J=1.6 Hz, 1H), 7.24 (d, J=5.6 Hz, 1H), 6.71 (t, J=71.2 Hz, 1H).

A mixture of sodium 2-chloro-2,2-difluoroacetate (1.00 g, 5.06 mmol, 1.00 eq), tert-butyl carbamate (889 mg, 7.59 mmol, 1.50 eq), cesium carbonate (4.95 g, 15.2 mmol, 3.00 eq), tris(dibenzylideneacetone)dipalladium (0) (463 mg, 506 umol, 0.100 eq) and 4,5-bis(diphenylphosphino)-9,9-dimethylxanthene (585 mg, 1.01 mmol, 0.200 eq) in dioxane (20.0 mL) was degassed under vacuum and purged with nitrogen for 3 times. After stirring at 110° C. for 16 h under nitrogen atmosphere, the reaction mixture was poured into saturated ammonium chloride aqueous solution (50 mL) and extracted with ethyl acetate (2×50 mL). The combined organic layer was washed with brine (30 mL), dried over anhydrous sodium sulfate, filtered and concentrated under vacuum to give a residue. The residue was purified by flash silica gel chromatography (ISCO®; 20 g SepaFlash® Silica Flash Column, ethyl acetate/petroleum ether=0~20%, 50.0 mL/min) to afford tert-butyl N-(4-(difluoromethoxy)-5-fluoro-2-pyridyl)carbamate (500 mg, 1.64 mmol, 32% yield, 91% purity) as a yellow solid. $^1$H NMR (400 MHz, CDCl$_3$)

δ=8.18 (s, 1H), 8.11 (s, 1H), 7.94 (d, J=4.4 Hz, 1H), 6.76 (t, J=72.4 Hz, 1H), 1.54 (s, 9H). MS (ESI) m/z 222.9 [M+H]$^+$

A solution of tert-butyl (4-(difluoromethoxy)-5-fluoro-pyridin-2-yl)carbamate (500 mg, 1.64 mmol, 91% purity, 1.00 eq) in hydrochloric acid/dioxane (4 moL/L, 10.0 mL) was stirred at 25° C. for 16 h. The mixture was concentrated under vacuum. The residue was triturated with ethyl acetate (10 mL) and filtered. The filter cake was basified with saturated sodium bicarbonate solution to pH=9. The resulting mixture was extracted with dichloromethane/methanol (10/1, 3×20 mL). The combined organic layers were washed with brine (2×15 mL), dried over anhydrous sodium sulfate, filtered and concentrated under reduced pressure to afford 4-(difluoromethoxy)-5-fluoro-pyridin-2-amine (300 mg, 1.60 mmol, 98% yield, 95% purity) as a white solid. MS (ESI) m/z 179.1[M+H]$^+$ To a solution of 4-(difluoromethoxy)-5-fluoro-pyridin-2-amine (270 mg, 1.44 mmol, 95% purity, 1.00 eq) and pyridine (342 mg, 4.32 mmol, 349 uL, 3.00 eq) in acetonitrile (3.00 mL) was added phenyl carbonochloridate (237 mg, 1.51 mmol, 189 uL, 1.05 eq) at 0° C. After stirring at 25° C. for 2 h, the mixture was poured into water (20 mL) and extracted with ethyl acetate (2×30 mL). The combined organic phase were washed with brine (2×20 mL), dried over anhydrous sodium sulfate, filtered and concentrated under vacuum to give a residue. The residue was purified by flash silica gel chromatography (20 g, ethyl acetate/petroleum ether=0/1-1/4) to afford phenyl (4-(difluoromethoxy)-5-fluoropyridin-2-yl)carbamate (350 mg, 1.16 mmol, 81% yield, 99% purity) as a yellow solid. $^1$H NMR (400 MHz, DMSO-d$_6$) δ=11.07 (s, 1H), 8.47 (d, J=2.0 Hz, 1H), 7.83 (d, J=6.0 Hz, 1H), 7.48-7.41 (m, 3H), 7.31-7.26 (m, 1H), 7.25-7.20 (m, 2H). MS (ESI) m/z 299.0 [M+H]$^+$ To a solution of 3-(6-(hydroxymethyl)-1-oxoisoindolin-2-yl)piperidine-2,6-dione I (80.0 mg, 292 umol, 1.00 eq) in N,N-dimethyl formamide (2.00 mL) was added sodium hydride (17.5 mg, 437 umol, 60% purity, 1.50 eq) at 0° C. under nitrogen atmosphere. The mixture was stirred at 0° C. for 15 min. Then phenyl (4-(difluoromethoxy)-5-fluoropyridin-2-yl)carbamate (91.5 mg, 292 umol, 95.0% purity, 1.00 eq) was added to the mixture at 0° C. After stirring at 25° C. for 1 h, the reaction mixture was poured into saturated ammonium chloride aqueous solution (10 mL) and extracted with ethyl acetate (2×20 mL). The combined organic layers were washed with brine (20 mL), dried over anhydrous sodium sulfate, filtered and concentrated under vacuum to give a residue. The residue was purified by Prep-HPLC (column: Phenomenex Synergi C18 150*25 mm*10 um; mobile phase: [water (FA)-ACN]; B %: 32%-52%, 10 min) and lyophilized to afford (2-(2,6-dioxopiperidin-3-yl)-3-oxoisoindolin-5-yl)methyl (4-(difluoromethoxy)-5-fluoropyridin-2-yl)carbamate #227 (25.77 mg, 53.3 umol, 18% yield, 99% purity, formate) as an off-white solid. $^1$H NMR (400 MHz, DMSO-d$_6$) δ=10.99 (s, 1H), 10.70 (s, 1H), 8.50 (s, 1H), 8.40 (d, J=2.0 Hz, 1H), 7.85 (d, J=6.4 Hz, 1H), 7.80 (s, 1H), 7.70-7.64 (m, 2H), 7.50 (t, J=72.0 Hz, 1H), 5.32 (s, 2H), 5.16-5.08 (m, 1H), 4.51-4.29 (m, 2H), 2.98-2.85 (m, 1H), 2.65-2.56 (m, 1H), 2.44-2.35 (m, 1H), 2.06-1.96 (m, 1H). MS (ESI) m/z 478.9 [M+H]$^+$ Compound #228: To a mixture of 2-bromo-4-fluoro-5-nitro-phenol (5.00 g, 21.1 mmol, 1.00 eq), methylboronic acid (3.80 g, 63.5 mmol, 3.00 eq), 1,1-bis(diphenylphosphino)ferrocene]dichloropalladium(II) (1.55 g, 2.12 mmol, 0.100 eq) and potassium phosphate (13.4 g, 63.5 mmol, 3.00 eq) in dioxane (100 mL) was purged with nitrogen for 3 times. After stirring at 80° C. for 12 h under nitrogen atmosphere, the reaction mixture was poured into saturated ammonium chloride aqueous solution (400 mL) and extracted with ethyl acetate (3×100 mL). The organic phase was concentrated under vacuum to give a residue. The residue was purified by column chromatography (SiO$_2$, petroleum ether/ethyl acetate=20/1 to 10/1) to afford 4-fluoro-2-methyl-5-nitrophenol (950 mg, 5.00 mmol, 23% yield, 90% purity) as a yellow solid. $^1$H NMR (400 MHz, CDCl$_3$) δ=7.48 (d, J=6.4 Hz, 1H), 7.06 (d, J=11.2 Hz, 1H), 5.59 (s, 1H), 2.33 (s, 3H).

A mixture of 4-fluoro-2-methyl-5-nitro-phenol (400 mg, 2.10 mmol, 90% purity, 1.00 eq), iodoethane (656 mg, 4.21 mmol, 2.00 eq) and sodium carbonate (668 mg, 6.31 mmol, 3.00 eq) in N,N-dimethylformamide (10.0 mL) was stirred at 25° C. for 12 h. The reaction mixture was poured into saturated ammonium chloride aqueous solution (50 mL) and extracted with ethyl acetate (3×20 mL). The organic phase was concentrated under vacuum to give a residue. The residue was purified by column chromatography (petroleum ether/ethyl acetate=30/1 to 10/1) to afford 1-ethoxy-4-fluoro-2-methyl-5-nitro-benzene (420 mg, 1.79 mmol, 85% yield, 85% purity) as colorless oil. $^1$H NMR (400 MHz, CDCl$_3$) δ=7.45 (d, J=6.2 Hz, 1H), 7.06 (d, J=11.2 Hz, 1H), 4.08 (q, J=2.8 Hz, 2H), 2.30 (s, 3H), 1.47 (t, J=2.8 Hz, 3H).

A mixture of 1-ethoxy-4-fluoro-2-methyl-5-nitro-benzene (420 mg, 1.79 mmol, 85% purity, 1.00 eq) and palladium on carbon (42.0 mg, 179 umol, 10% purity, 0.100 eq) in tetrahydrofuran (10.0 mL) was stirred at 25° C. for 4 h under hydrogen atmosphere (15 Psi). The reaction mixture was filtrated and the filtrate was concentrated under reduced pressure to give a residue. The residue was purified by column chromatography (SiO$_2$, petroleum ether/ethyl acetate=20/1 to 10/1) to afford 5-ethoxy-2-fluoro-4-methyl-aniline (200 mg, 1.12 mmol, 62% yield, 95% purity) as red oil. $^1$H NMR (400 MHz, CDCl$_3$) δ=6.77 (d, J=11.2 Hz, 1H), 6.29 (d, J=7.6 Hz, 1H), 3.94 (q, J=7.2 Hz, 2H), 2.11 (s, 3H), 1.41-1.37 (t, J=7.2 Hz, 3H).

To a mixture of 5-ethoxy-2-fluoro-4-methyl-aniline (200 mg, 1.12 mmol, 95% purity, 1.00 eq) and pyridine (133 mg, 1.68 mmol, 1.50 eq) in tetrahydrofuran (2.00 mL) was added phenyl carbonochloridate (184 mg, 1.18 mmol, 1.05 eq) at 0° C. After addition, the mixture was stirred at 25° C. for 0.5 h. The reaction mixture was poured into saturated ammonium chloride aqueous solution (15 mL) and extracted with ethyl acetate (3×8 mL). The organic phase was concentrated under vacuum to give a residue. The residue was purified by column chromatography (SiO$_2$, petroleum ether/ethyl acetate=50/1 to 20/1) and concentrated to afford phenyl (5-ethoxy-2-fluoro-4-methylphenyl)carbamate (350 mg, 967 umol, 86% yield, 80% purity) as a white solid. $^1$H NMR (400 MHz, DMSO-d$_6$) δ=9.83 (s, 1H), 7.44-7.38 (m, 2H), 7.26-7.16 (m, 4H), 7.07 (d, J=11.2 Hz, 1H), 3.96 (q, J=7.2 Hz, 2H), 2.11 (s, 3H), 1.31 (t, J=7.2 Hz, 3H).

To a mixture of 3-(6-(hydroxymethyl)-1-oxoisoindolin-2-yl)piperidine-2,6-dione I (79.6 mg, 290 umol, 1.05 eq) in N,N-dimethyl formamide (3.00 mL) was added sodium hydride (16.5 mg, 414 umol, 60% purity, 1.50 eq) at 0° C. The mixture was stirred at 0° C. for 0.2 h. Phenyl (5-ethoxy-2-fluoro-4-methylphenyl) carbamate (100 mg, 276 umol, 80% purity, 1.00 eq) was added to the mixture. After stirring at 0° C. for 0.3 h, the reaction mixture was poured into saturated ammonium chloride aqueous solution (20 ml) and extract with ethyl acetate (3×8 mL). The organic phase was concentrated under vacuum to give a residue. The residue was purified by Prep-HPLC (column: Phenomenex Synergi C18 150*25 mm*10 um; mobile phase: [water (FA)-ACN]; B %: 40%-60%, 10 min) and lyophilized to afford (2-(2,6-dioxopiperidin-3-yl)-3-oxoisoindolin-5-yl)methyl(5- ethoxy-2-fluoro-4-methylphenyl)carbamate #228 (91.2 mg, 192 umol, 69% yield, 99% purity) as a white solid. $^1$H NMR (400 MHz, DMSO-$d_6$) δ=10.97 (s, 1H), 9.39 (s, 1H), 7.79 (s, 1H), 7.67-7.61 (m, 2H), 7.25-7.18 (m, 1H), 7.02 (d, J=11.0 Hz, 1H), 5.25 (s, 2H), 5.14-5.09 (m, 1H), 4.46 (d, J=17.6 Hz, 1H), 4.33 (d, J=17.6 Hz, 1H), 3.94 (q, J=6.8 Hz, 2H), 2.98-2.85 (m, 1H), 2.64-2.57 (m, 1H), 2.44-2.35 (m, 1H), 2.09 (s, 3H), 2.04-1.96 (m, 1H), 1.31 (t, J=6.8 Hz, 3H). MS (ESI) m/z 470.2 [M+H]$^+$ Compound #229: To a solution of 4-fluoro-2-methyl-5-nitrophenol (400 mg, 2.10 mmol, 90% purity, 1.00 eq) and potassium carbonate (582 mg, 4.21 mmol, 2.00 eq) in N,N-dimethylformamide (5.00 mL) was added iodomethane (896 mg, 6.31 mmol, 393 uL, 3.00 eq). After stirring at 25° C. for 12 h, the mixture was poured into water (20 mL) and extracted with ethyl acetate (3×10 mL). The organic phase was washed with brine (20 mL), dried over anhydrous sodium sulfate, filtered and concentrated under vacuum to give 1-fluoro-4-methoxy-5-methyl-2-nitrobenzene (740 mg, crude) as light-yellow oil. The crude product was used for next step directly without purification. $^1$H NMR (400 MHz, DMSO-$d_6$) δ=7.57 (d, J=6.4 Hz, 1H), 7.45 (d, J=11.2 Hz, 1H), 3.88 (s, 3H), 2.24 (s, 3H).

To a solution of 1-fluoro-4-methoxy-5-methyl-2-nitrobenzene (700 mg, 3.59 mmol, 1.00 eq) in methanol (30 mL) was added palladium on carbon (10% purity, 0.10 g) under nitrogen atmosphere. The suspension was degassed under vacuum and purged with hydrogen for 3 times. The mixture was stirred at 25° C. for 12 h under hydrogen atmosphere (15 Psi). After filtration, the filtrate was concentrated under vacuum to give a residue. The residue was purified by column chromatography (SiO$_2$, petroleum ether then petroleum ether/ethyl acetate=5/1) to afford 2-fluoro-5-methoxy-4-methylaniline (240 mg, 1.47 mmol, 41% yield, 95% purity) as a red solid. $^1$H NMR (400 MHz, DMSO-$d_6$) δ=6.75 (d, J=12.0 Hz, 1H), 6.37 (d, J=8.0 Hz, 1H), 4.87 (s, 2H), 3.67 (s, 3H), 1.98 (s, 3H)

To a solution of 2-fluoro-5-methoxy-4-methylaniline (200 mg, 1.22 mmol, 95% purity, 1.00 eq) in acetonitrile (3.00 mL) was added pyridine (291 mg, 3.67 mmol, 297 uL, 3.00 eq) at 0° C. After stirring the mixture at 0° C. for 0.2 h, phenyl carbonochloridate (211 mg, 1.35 mmol, 169 uL, 1.10 eq) was added to the mixture. After addition, the mixture was stirred at 25° C. for 1.8 h. The mixture was poured into water (50 mL) and extracted with ethyl acetate (3×10 mL). The organic phase was washed with brine (20 mL), dried over anhydrous sodium sulfate, filtered and concentrated under vacuum to give a residue. The residue was purified by column chromatography (SiO$_2$, petroleum ether then petroleum ether/ethyl acetate=4/1) to afford phenyl (2-fluoro-5-methoxy-4-methylphenyl)carbamate (240 mg, 828 umol, 68% yield, 95% purity) as white solid. $^1$H NMR (400 MHz, DMSO-$d_6$)=9.84 (s, 1H), 7.45-7.37 (m, 2H), 7.23-7.17 (m, 3H), 6.76-6.71 (m, 2H), 3.73 (s, 3H), 2.11 (s, 3H).

To a solution of 3-(6-(hydroxymethyl)-1-oxoisoindolin-2-yl)piperidine-2,6-dione I (99.6 mg, 363 umol, 1.00 eq) in N,N-dimethylformamide (3.00 mL) was added sodium hydride (29.1 mg, 727 umol, 60% purity, 2.00 eq) at 0° C. The mixture was stirred at 0° C. for 0.1 h. Then phenyl (2-fluoro-5-methoxy-4-methylphenyl)carbamate (100 mg, 363 umol, 1.00 eq) in N,N-dimethylformamide (0.500 mL) was added dropwise to the mixture at 0° C. After stirring at 25° C. for 0.4 h, the mixture was poured into saturated ammonium chloride aqueous solution (20 mL) and extracted with ethyl acetate (3×10 mL). The organic phase was washed with saturated sodium chloride aqueous solution (20 mL), brine (20 ml), dried over anhydrous sodium sulfate, filtered and concentrated under vacuum to give a residue. The residue was purified by Prep-HPLC (column: Phenomenex Synergi C18 150*25 mm*10 um; mobile phase: [water (FA)-ACN]; B %: 30%-60%, 10 min). to afford (2-(2,6-dioxopiperidin-3-yl)-3-oxoisoindolin-5-yl)methyl (2-fluoro-5-methoxy-4-methylphenyl)carbamate #229 (61.48 mg, 134 umol, 37% yield, 99% purity) as white solid. $^1$H NMR (400 MHz, DMSO-$d_6$) δ=10.98 (s, 1H), 9.41 (s, 1H), 7.80 (s, 1H), 7.70-7.60 (m, 2H), 7.25-7.17 (m, 1H), 7.03 (d, J=11.2 Hz, 1H), 5.26 (s, 2H), 5.17-5.06 (m, 1H), 4.52-4.28 (m, 2H), 3.72 (s, 3H), 2.98-2.85 (m, 1H), 2.69-2.56 (m, 1H), 2.44-2.37 (m, 1H), 2.10 (s, 3H), 2.06-1.96 (m, 1H). MS (ESI) m/z 456.2 [M+H]$^+$ Compound #230: To a mixture of 4-fluoro-2-methyl-5-nitro-phenol (250 mg, 1.46 mmol, 1.00 eq) and potassium carbonate (605 mg, 4.38 mmol, 3.00 eq) in N,N-dimethylformamide (10.0 mL) was added 2-iodopropane (745 mg, 4.38 mmol, 3.00 eq). After stirring at 50° C. for 2 h, the reaction mixture was poured into saturated ammonium chloride aqueous solution (40 mL) and extracted with ethyl acetate (3×20 mL). The organic phase was concentrated under vacuum to give a residue. The residue was purified by column chromatography (SiO$_2$, petroleum ether/ethyl acetate=50/1 to 20/1) to afford 1-fluoro-4-isopropoxy-5-methyl-2-nitro-benzene (150 mg, 633 umol, 43% yield, 90% purity) as colorless oil. $^1$H NMR (400 MHz, CDCl$_3$) δ=7.47 (d, J=6.4 Hz, 1H), 7.06 (d, J=11.2 Hz, 1H), 4.59-4.53 (m, 1H), 2.27 (s, 3H), 1.38 (d, J=6.0 Hz, 6H).

A mixture of 1-fluoro-4-isopropoxy-5-methyl-2-nitro-benzene (120 mg, 506 umol, 90% purity, 1.00 eq) and palladium on carbon (12.0 mg, 50.6 umol, 10% purity, 0.100 eq) in tetrahydrofuran (5.00 mL) was stirred at 25° C. for 5 h under hydrogen atmosphere (15 Psi). The reaction mixture was filtered and the filtrate was concentrated under vacuum to give a residue. The residue was purified by column chromatography (SiO$_2$, petroleum ether/ethyl acetate=30/1 to 10/1) and concentrated to afford 2-fluoro-5-isopropoxy-4-methylaniline (110 mg, 90% yield, 90% purity) as red oil. $^1$H NMR (400 MHz, CDCl$_3$) δ=6.77 (d, J=11.4 Hz, 1H), 6.33 (d, J=8.0 Hz, 1H), 4.38-4.29 (m, 1H), 3.51 (br s, 2H), 2.09 (s, 3H), 1.30 (d, J=6.0 Hz, 6H).

To a mixture of phenyl (2-fluoro-5-isopropoxy-4-methylphenyl)carbamate (100 mg, 491 umol, 90% purity, 1.00 eq) and pyridine (58.2 mg, 736 umol, 1.50 eq) in tetrahydrofuran (5.00 mL) was added phenyl carbonochloridate (80.7 mg, 515 umol, 1.05 eq) at 0° C. After addition, the mixture was stirred at 25° C. for 0.5 h. The reaction mixture was poured into saturated ammonium chloride aqueous solution (30 mL) and extracted with ethyl acetate (3×15 mL). The organic phase was concentrated under vacuum to give a residue. The residue was purified by column chromatography (SiO$_2$, petroleum ether/ethyl acetate=50/1 to 20/1) to afford phenyl (2-fluoro-5-isopropoxy-4-methylphenyl)carbamate (140 mg, 85% yield, 90% purity) as a red solid. $^1$H NMR (400 MHz, CDCl$_3$) δ=7.72-7.71 (m, 1H), 7.46-7.38 (m, 2H), 7.27-7.24 (m, 1H), 7.23-7.19 (m, 2H), 7.12 (s, 1H), 6.90 (d, J=11.6 Hz, 1H), 4.50-4.44 (m, 1H), 2.16 (s, 3H), 1.31 (d, J=6.0 Hz, 6H).

To a mixture of 3-(6-(hydroxymethyl)-1-oxoisoindolin-2-yl)piperidine-2,6-dione I (87.9 mg, 321 umol, 0.90 eq) in N,N-dimethylformamide (2.00 mL) was added sodium hydride (28.5 mg, 712 umol, 60% purity, 2.00 eq) at 0° C. After stirring at 0° C. for 0.2 h, phenyl (2-fluoro-5-isopropoxy-4-methylphenyl)carbamate (120 mg, 356 umol, 90% purity, 1.00 eq) in N,N-dimethylformamide (0.50 mL) was added to the mixture. After stirring at 25° C. for 0.3 h, the reaction mixture was poured into saturated ammonium chloride aqueous solution (20 mL), extracted with ethyl acetate (3×20 mL), washed with brine (20 mL), dried over anhydrous sodium sulfate, filtered and concentrated. The organic phase was concentrated under vacuum to give a residue. The residue was purified by Prep-HPLC (column: Phenminomenex Synergi C18 150*25 mm*10 um; mobile phase: [water (FA)-ACN]; B %: 43%-63%, 10 min) and then lyophilized to afford (2-(2,6-dioxopiperidin-3-yl)-3-oxoisoindolin-5-yl)methyl (2-fluoro-5-isopropoxy-4-methylphenyl)carbamate #230 (92.22 mg, 189 umol, 53% yield, 99% purity) as a white solid. $^1$H NMR (400 MHz, DMSO-d$_6$) δ=11.99 (s, 1H), 9.38 (s, 1H), 7.80 (s, 1H), 7.71-7.59 (m, 2H), 7.28-7.17 (m, 1H), 7.01 (d, J=11.2 Hz, 1H), 5.26 (s, 2H), 5.17-5.08 (m, 1H), 4.53-4.29 (m, 3H), 2.98-2.86 (m, 1H), 2.64-2.56 (m, 1H), 2.44-2.37 (m, 1H), 2.11-2.05 (m, 3H), 2.05-1.96 (m, 1H), 1.24 (d, J=6.0 Hz, 6H). MS (ESI) m/z 484.1 [M+H]$^+$ Compound #231: To a solution of 4-fluoro-2-methyl-5-nitrophenol (400 mg, 1.99 mmol, 1.00 eq) in N,N-dimethylformamide (10.0 mL) were added 1-iodopropane (1.01 g, 5.96 mmol, 582 uL, 3.00 eq) and potassium carbonate (823 mg, 5.96 mmol, 3.00 eq). After addition, the mixture was stirred at 25° C. for 1 h. The mixture was poured into water (20 mL) and extracted with ethyl acetate (3×10 mL). The organic phase was washed with brine (20 ml), dried over anhydrous sodium sulfate, filtered and concentrated under vacuum to give 1-fluoro-5-methyl-2-nitro-4-propoxybenze (700 mg, crude) as red oil. The crude product was used for next step directly without purification. $^1$H NMR (400 MHz, DMSO-d$_6$) δ=7.56 (d, J=6.4 Hz, 1H), 7.46 (d, J=12.4 Hz, 1H), 4.03 (t, J=6.4 Hz, 2H), 2.25 (s, 3H), 1.82-1.71 (m, 2H), 1.00 (t, J=7.2 Hz, 3H).

To a solution of 1-fluoro-5-methyl-2-nitro-4-propoxybenzene (700 mg, 3.28 mmol, 1.00 eq) in methanol (10.0 mL) was added palladium on carbon (10% purity, 0.10 g) under nitrogen atmosphere. The suspension was degassed and purged with hydrogen for 3 times. The mixture was stirred at 25° C. for 2 h under hydrogen atmosphere (15 Psi). After filtration, the filtrate was concentrated under vacuum to give a residue. The residue was purified by column chromatography (SiO$_2$, petroleum ether/ethyl acetate=1/0 to 4/1) to afford 2-fluoro-4-methyl-5-propoxyaniline (240 mg, 1.27 mmol, 39% yield, 97% purity) as a yellow solid. $^1$H NMR (400 MHz, DMSO-d$_6$) δ=6.78 (d, J=11.2 Hz, 1H), 6.34 (d, J=7.6 Hz, 1H), 3.83 (t, J=6.4 Hz, 2H), 3.50-2.63 (m, 2H), 2.12 (s, 3H), 1.86-1.75 (m, 2H), 1.04 (t, J=7.2 Hz, 3H).

To a solution of 2-fluoro-4-methyl-5-propoxy-aniline (140 mg, 764 umol, 1.00 eq) in acetonitrile (3.00 mL) was added pyridine (181 mg, 2.29 mmol, 185 uL, 3.00 eq) at 0° C. After stirring the mixture for 10 min, phenyl carbonochloridate (132 mg, 841 umol, 105 uL, 1.10 eq) was added to the mixture. After addition, the mixture was stirred at 25° C. for 1 h. The mixture was poured into water (20 mL) and extracted with ethyl acetate (3×10 mL). The organic phase was washed with brine (30 mL), dried over anhydrous sodium sulfate, filtered and concentrated under vacuum to give a residue. The residue was purified by column chromatography (SiO$_2$, petroleum ether then petroleum ether/ethyl acetate=10/1) to afford phenyl (2-fluoro-4-methyl-5-propoxyphenyl)carbamate (100 mg, 320 umol, 42% yield, 97% purity) as a yellow solid. $^1$H NMR (400 MHz, DMSO-d$_6$) δ=9.84 (s, 1H), 7.42 (t, J=8.0 Hz, 2H), 7.28-7.22 (m, 1H), 7.22-7.18 (m, 2H), 7.07 (d, J=11.2 Hz, 1H), 6.78-6.72 (m, 1H), 3.86 (t, J=6.4 Hz, 2H), 2.12 (s, 3H), 1.77-1.67 (m, 2H), 0.98 (t, J=7.2 Hz, 3H).

To a solution of 3-(6-(hydroxymethyl)-1-oxoisoindolin-2-yl)piperidine-2,6-dione I (81.4 mg, 297 umol, 1.00 eq) in N,N-dimethylformamide (3.00 mL) was added sodium hydride (23.7 mg, 593 umol, 60% purity, 2.00 eq) at 0° C. After addition, the mixture was stirred at 0° C. for 10 min, then phenyl (2-fluoro-4-methyl-5-propoxyphenyl)carbamate (90 mg, 297 umol, 1.00 eq) in N,N-dimethylformamide (1.00 mL) was added dropwise to the mixture at 0° C. After stirring at 25° C. for 20 min, the mixture was poured into saturated ammonium chloride aqueous solution (20 mL) and extracted with ethyl acetate (3×10 mL). The organic phase was washed with brine (20.0 ml), dried over anhydrous sodium sulfate, filtered and concentrated under vacuum to give a residue. The residue was purified by Prep-HPLC (FA condition; column: Phenomenex Synergi C18 150*25 mm*10 um; mobile phase: [water (FA)-ACN]; B %: 45%-67%, 11 min) to afford (2-(2,6-dioxopiperidin-3-yl)-3-oxoisoindolin-5-yl)methyl (2-fluoro-4-methyl-5-propoxyphenyl)carbamate #231 (62.0 mg, 127 umol, 43% yield, 99% purity) as a white solid. $^1$H NMR (400 MHz, DMSO-d$_6$) δ=10.99 (s, 1H), 9.41 (s, 1H), 7.80 (s, 1H), 7.72-7.56 (m, 2H), 7.29-7.13 (m, 1H), 7.02 (d, J=11.2 Hz, 1H), 5.26 (s, 2H), 5.19-5.09 (m, 1H), 4.52-4.28 (m, 2H), 3.84 (t, J=6.4 Hz, 2H), 2.99-2.83 (m, 1H), 2.64-2.57 (m, 1H), 2.44-2.37 (m, 1H), 2.10 (s, 3H), 2.04-1.94 (m, 1H), 1.78-1.65 (m, 2H), 0.97 (t, J=7.2 Hz, 3H). MS (ESI) m/z 484.0 [M+H]$^+$ Compound #232: To a solution of 2,5-dibromo-3-fluoropyridine (5.00 g, 19.6 mmol, 1.00 eq) in dioxane (50.0 mL) was added diphenylmethanimine (3.91 g, 21.6 mmol, 3.62 mL, 1.10 eq), cesium carbonate (19.2 g, 58.9 mmol, 3.00 eq), 4,5-bis(diphenylphosphino)-9,9-dimethylxanthene (2.27 g, 3.92 mmol, 0.200 eq) and tris(dibenzylideneacetone)dipalladium(0) (1.80 g, 1.96 mmol, 0.100 eq) under nitrogen atmosphere. The mixture was stirred at 80° C. for 12 h. The mixture was diluted with water (300 mL) and extracted with ethyl acetate (3×80 mL). The combined organic layer was washed with brine (50 mL), dried over anhydrous sodium sulfate, filtered and concentrated to give a crude product. The crude product was purified by column chromatography on silica gel (petroleum ether/ethyl acetate=1/0 to 10/1) to afford 5-bromo-N-(diphenylmethylene)-3-fluoropyridin-2-amine (4.50 g, 9.25 mmol, 47% yield) as a yellow solid. $^1$H NMR (400 MHz, DMSO-d6) δ=8.24 (d, J=1.6 Hz, 1H), 7.99 (dd, J=2.0, 9.6 Hz, 1H), 7.72 (br d, J=7.6 Hz, 2H), 7.66-7.58 (m, 1H), 7.56-7.47 (m, 2H), 7.41-7.32 (m, 3H), 7.13 (br d, J=6.4 Hz, 2H).

To a solution of 5-bromo-N-(diphenylmethylene)-3-fluoropyridin-2-amine (300 mg, 845 umol, 1.00 eq) in dioxane (3.00 mL) was added (R)-2-methylpyrrolidine (154 mg, 1.27 mmol, 1.50 eq, hydrochloric acid), cesium carbonate (1.10 g, 3.38 mmol, 4.00 eq) and (2-dicyclohexylphosphino-2',6'-dimethoxybiphenyl)[2-(2'-amino-1,1'-biphenyl)]palladium(II)methanesulfonate (65.9 mg, 84.5 umol, 0.100 eq) under nitrogen atmosphere. The mixture was stirred at 110° C. for 12 h. The reaction mixture was diluted with water (30 mL) and extracted with ethyl acetate (3×10 mL). The combined organic layers were washed with brine (10 mL), dried over anhydrous sodium sulfate, filtered and concentrated under reduced pressure to give a residue. The residue was purified by column chromatography on silica gel (petroleum ether/ethyl acetate=1/0 to 3/1) to afford (R)—N-(diphenylmethylene)-3-fluoro-5-(2-methylpyrrolidin-1-yl)pyridin-2-amine (450 mg, 1.25 mmol, 49% yield) as a yellow solid. $^1$H NMR (400 MHz, DMSO-d6) δ=7.70-7.63 (m, 2H), 7.58-7.51 (m, 1H), 7.50-7.44 (m, 2H), 7.42 (d, J=1.2 Hz, 1H), 7.36-7.29 (m, 3H), 7.10 (dd, J=2.7, 6.0 Hz, 2H), 6.71 (dd, J=2.2, 13.2 Hz, 1H), 3.81 (br t, J=6.0 Hz, 1H), 3.29 (br t, J=7.6 Hz, 1H), 3.01 (q, J=8.4 Hz, 1H), 2.01-1.84 (m, 3H), 1.61 (br s, 1H), 1.01 (d, J=6.0 Hz, 3H).

To a solution of (R)—N-(diphenylmethylene)-3-fluoro-5-(2-methylpyrrolidin-1-yl)pyridin-2-amine (400 mg, 1.11 mmol, 1.00 eq) in tetrahydrofuran (24.0 mL) was added hydrochloric acid (5 M, 4.00 mL, 18.0 eq). The mixture was stirred at 25° C. for 2 h. The pH of the mixture was adjust to 8 with sodium hydroxide saturated solution. Then the mixture was diluted with water (50 mL) and extracted with ethyl acetate (4×20 mL). The residue was purified by column chromatography on silica gel (Petroleum ether/Ethyl acetate=1/0 to 3/1) to afford (R)-3-fluoro-5-(2-methylpyrrolidin-1-yl)pyridin-2-amine (200 mg, 1.02 mmol, 92% yield) as a white solid. $^1$H NMR (400 MHz, DMSO-d6) δ=7.21 (d, J=2.0 Hz, 1H), 6.80 (dd, J=2.4, 13.2 Hz, 1H), 5.14 (s, 2H), 3.77-3.64 (m, 1H), 3.30-3.24 (m, 1H), 2.98 (q, J=8.4 Hz, 1H), 2.00-1.84 (m, 3H), 1.66-1.55 (m, 1H), 1.04 (d, J=6.4 Hz, 3H).

To a solution of (R)-3-fluoro-5-(2-methylpyrrolidin-1-yl)pyridin-2-amine (100 mg, 512 umol, 1.00 eq) in acetonitrile (0.500 mL) was added pyridine (122 mg, 1.54 mmol, 124 uL, 3.00 eq) and phenyl carbonochloridate (84.2 mg, 538 umol, 67.4 uL, 1.05 eq). The mixture was stirred at 25° C. for 2 h. The reaction mixture was concentrated under reduced pressure to afford a residue. The residue was purified by reverse-phase HPLC (column: spherical C18, 20-45 um, 100 A, SW 120, mobile phase: [water (0.1% formic acid)-acetonitrile]) and the desired eluent was lyophilized to afford (R)-phenyl(3-fluoro-5-(2-methylpyrrolidin-1-yl)pyridin-2-yl)carbamate (100 mg, 311 umol, 61% yield, 98% purity) as a black solid. $^1$H NMR (400 MHz, DMSO-d6) δ=9.37 (br s, 1H), 7.54 (d, J=2.0 Hz, 1H), 7.20 (d, J=2.0 Hz, 1H), 7.15 (t, J=8.0 Hz, 3H), 6.93 (dd, J=2.3, 12.8 Hz, 1H), 6.80 (dd, J=2.4, 13.6 Hz, 1H), 3.89 (br t, J=6.0 Hz, 1H), 3.16-3.05 (m, 1H), 2.98 (q, J=8.4 Hz, 1H), 2.01-1.93 (m, 3H), 1.57-1.53 (m, 1H), 1.04 (d, J=6.0 Hz, 3H). MS (ESI) m/z 316.1 [M+H]$^+$ To a solution of 3-(6-(hydroxymethyl)-1-oxoisoindolin-2-yl)piperidine-2,6-dione I (45.4 mg, 166 umol, 0.950 eq) in dimethyl formamide (300 uL) was added sodium hydride (14.0 mg, 349 umol, 60% purity, 2.00 eq). The mixture was stirred at 0° C. for 0.5 h. Then a solution of (R)-phenyl (3-fluoro-5-(2-methylpyrrolidin-1-yl)pyridin-2-yl)carbamate (55.0 mg, 174 umol, 1.00 eq) in dimethyl formamide (200 uL) was added to the mixture dropwise. The mixture was stirred at 25° C. for 1 h. The pH of the mixture was adjusted to 7 with formic acid, then the mixture was diluted with dimethyl formamide (1.00 mL). The mixture was purified by prep-HPLC (column: Phenomenex luna C18 150*25 mm*10 um; mobile phase: [water (formic acid)-acetonitrile]; B %: 26%-56%, 10 min) and the desired eluent was lyophilized to afford (2-(2,6-dioxopiperidin-3-yl)-3-oxoisoindolin-5-yl)methyl (3-fluoro-5-((R)-2-methylpyrrolidin-1-yl)pyridin-2-yl)carbamate #232 (18.23 mg, 35.3 umol, 20% yield, 96% purity) as a white solid. $^1$H NMR (400 MHz, DMSO-d6) δ=11.00 (br s, 1H), 9.33 (s, 1H), 7.75 (s, 1H), 7.63 (s, 2H), 7.56 (d, J=2.0 Hz, 1H), 6.87 (dd, J=2.2, 12.4 Hz, 1H), 5.21 (s, 2H), 5.13 (dd, J=4.9, 13.2 Hz, 1H), 4.51-4.42 (m, 1H), 4.38-4.28 (m, 1H), 3.95-3.86 (m, 1H), 3.40-3.37 (m, 1H), 3.16-3.06 (m, 1H), 2.97-2.87 (m, 1H), 2.62-2.58 (m, 1H), 2.40 (br dd, J=4.6, 13.2 Hz, 1H), 2.05-1.93 (m, 4H), 1.67 (br s, 1H), 1.09 (d, J=6.0 Hz, 3H). MS (ESI) m/z 496.3 [M+H]$^+$ Compound #233: To a mixture of 1-bromo-4-fluoro-2-methyl-5-nitro-benzene (4.00 g, 17.1 mmol, 1.00 eq) in N-methyl pyrrolidone (40.0 mL) were added copper (I) iodide (4.88 g, 25.6 mmol, 1.50 eq) and methyl 2,2-difluoro-2-fluorosulfonyl-acetate (18.1 g, 94.3 mmol, 12.0 mL, 5.52 eq). After stirring at 150° C. for 16 h under nitrogen atmosphere, the reaction mixture was poured into saturated ammonium chloride aqueous solution (50 mL) and extracted with ethyl acetate (2×100 mL). The combined organic layers were washed with brine (30 mL), dried over anhydrous sodium sulfate, filtered and concentrated under vacuum to give a residue. The residue was purified by flash silica gel chromatography (ISCO®; 20 g SepaFlash® Silica Flash Column, ethyl acetate/petroleum ether=0~10%, 50.0 mL/min) to afford 1-fluoro-5-methyl-2-nitro-4-(trifluoromethyl)benzene (3.00 g, 13.4 mmol, 78% yield) as yellow oil. $^1$H NMR (400 MHz, CDCl$_3$) δ=8.39 (d, J=7.2 Hz, 1H), 7.27 (d, J=11.2 Hz, 1H), 2.60 (s, 3H).

To a solution of 1-fluoro-5-methyl-2-nitro-4-(trifluoromethyl)benzene (1.00 g, 4.48 mmol, 1.00 eq) in methanol (20.0 mL) was added palladium on carbon (500 mg, 10% purity) under nitrogen atmosphere. The suspension was degassed under vacuum and purged with hydrogen (15 Psi) for 3 times. After stirring at 25° C. for 16 h under hydrogen atmosphere (15 Psi). The reaction mixture was filtered. The filtrate was concentrated to give a residue. The residue was purified by flash silica gel chromatography (ISCO®; 20 g SepaFlash® Silica Flash Column, ethyl acetate/petroleum ether=0-20%, 40 mL/min) to afford 2-fluoro-4-methyl-5-(trifluoromethyl)aniline (140 mg, 725 umol, 160% yield) as yellow oil. $^1$H NMR (400 MHz, CDCl$_3$) δ=7.10 (d, J=8.4 Hz, 1H), 6.95-6.87 (m, 1H), 2.36 (s, 3H).

To a solution of 2-fluoro-4-methyl-5-(trifluoromethyl)aniline (120 mg, 621 umol, 1.00 eq) and pyridine (147 mg, 1.86 mmol, 150 uL, 3.00 eq) in acetonitrile (2.00 mL) was added phenyl carbonochloridate (97.3 mg, 621 umol, 77.8 uL, 1.00 eq) at 0° C. After stirring the mixture at 25° C. for 1 h, the mixture was poured into water (10 mL) and extracted with ethyl acetate (2×20 mL). The combined organic phase was washed with brine (2×10 mL), dried over anhydrous sodium sulfate, filtered and concentrated to give a residue. The residue was purified by flash silica gel chromatography (ethyl acetate/petroleum ether=0/1 to 1/10) to afford phenyl (2-fluoro-4-methyl-5-(trifluoromethyl)phenyl)carbamate (70.0 mg, 185 umol, 30% yield, 83% purity) as yellow oil. $^1$H NMR (400 MHz, DMSO-d$_6$) δ=8.53-8.40 (m, 1H), 7.47-7.39 (m, 2H), 7.28 (s, 1H), 7.24-7.19 (m, 2H), 7.09-7.03 (m, 1H), 2.50-2.43 (m, 3H). MS (ESI) m/z 314.0 [M+H]$^+$ To a solution of 3-(6-(hydroxymethyl)-1-oxoisoindolin-2-yl)piperidine-2,6-dione I (26.3 mg, 95.8 umol, 1.00 eq) in N,N-dimethyl formamide (1.00 mL) was added sodium hydride (6.00 mg, 150 umol, 60% purity, 1.57 eq) at 0° C. under nitrogen atmosphere. The mixture was stirred at 0° C. for 15 min, and then phenyl (2-fluoro-4-methyl-5-(trifluoromethyl)phenyl)carbamate (30.0 mg, 95.8 umol, 1.00 eq) was added to the mixture at 0° C. After stirring at 25° C. for 1 h, the reaction mixture was poured into saturated ammonium chloride aqueous solution (10 mL) and extracted with ethyl acetate (2×20 mL). The combined organic layers were washed with brine (20 mL), dried over anhydrous sodium sulfate, filtered and concentrated under vacuum to give a residue. The residue was purified by Prep-HPLC (column: Phenomenex Synergi C18 150*25 mm*10 um; mobile phase: [water (FA)-ACN]; B %: 41%-61%, 10 min) and lyophilized to afford (2-(2,6-dioxopiperidin-3-yl)-3-oxoisoindolin-5-yl)methyl(2-fluoro-4-methyl-5-(trifluoromethyl)phenyl)carbamate #233 (23.0 mg, 45.3 umol, 47% yield, 97% purity, formate) as a white solid. $^1$H NMR (400 MHz, DMSO-d$_6$) δ=11.00 (s, 1H), 9.82 (s, 1H), 8.45 (s, 1H), 8.06 (d, J=6.0 Hz, 1H), 7.82 (s, 1H), 7.74-7.67 (m, 1H), 7.66-7.61 (m, 1H), 7.40 (d, J=11.6 Hz, 1H), 5.30 (s, 2H), 5.18-5.09 (m, 1H), 4.52-4.31 (m, 2H), 2.98-2.86 (m, 1H), 2.65-2.57 (m, 1H), 2.44-2.36 (m, 4H), 2.06-1.97 (m, 1H). MS (ESI) m/z 494.2 [M+H]$^+$ Compound #234: To a solution of 1-(4-fluoro-3-nitrophenyl)ethanone (5.00 g, 27.3 mmol, 1.00 eq) in dichloromethane (60.0 mL) was added diethylaminosulfur trifluoride (22.0 g, 137 mmol, 18.0 mL, 5.00 eq) dropwise at −70° C. The mixture was stirred at 25° C. for 12 h. The reaction mixture was poured into sodium bicarbonate aqueous solution (300 mL). The mixture was extracted with ethyl acetate (3×100 mL), washed with brine, dried over anhydrous sodium sulfate, filtered and concentrated under reduced pressure to give a residue. The residue was purified by column chromatography (SiO$_2$, petroleum ether/ethyl acetate=20/1 to 8/1) to afford 4-(1,1-difluoroethyl)-1-fluoro-2-nitrobenzene (4.10 g, 20.0 mmol, 73% yield) as colorless oil. $^1$H NMR (400 MHz, DMSO-d$_6$) δ=8.32-8.28 (m, 1H), 8.06-8.02 (m, 1H), 7.77-7.71 (m, 1H), 2.04 (t, J=19.2 Hz, 3H).

To a solution of 4-(1,1-difluoroethyl)-1-fluoro-2-nitrobenzene (1.50 g, 7.31 mmol, 1.00 eq) in methanol (20.0 mL) and water (20.0 mL) were added iron powder (2.04 g, 36.6 mmol, 5.00 eq) and ammonium chloride (3.91 g, 73.1 mmol, 10.0 eq). The mixture was stirred at 80° C. for 12 h. After filtration, the filtrate was concentrated under vacuum to give a residue. The residue was purified by column chromatography (SiO$_2$, petroleum ether then petroleum ether/ethyl acetate=5/1) to afford 5-(1,1-difluoroethyl)-2-fluoro-aniline (490 mg, 2.52 mmol, 34% yield, 90% purity) as light-yellow oil. $^1$H NMR (400 MHz, DMSO-d$_6$) δ=7.05 (dd, J=8.4, 11.2 Hz, 1H), 6.94 (dd, J=2.4, 8.8 Hz, 1H), 6.70-6.62 (m, 1H), 5.36 (s, 2H), 1.88 (t, J=18.8 Hz, 3H).

To a solution of 5-(1,1-difluoroethyl)-2-fluoro-aniline (200 mg, 1.03 mmol, 90% purity, 1.00 eq) and pyridine (244 mg, 3.08 mmol, 249 uL, 3.00 eq) in acetonitrile (3.00 mL) was added phenyl carbonochloridate (177 mg, 1.13 mmol, 142 uL, 1.10 eq) dropwise at 0° C. over 30 min. The resulting mixture was stirred at 25° C. for 2.5 h. The mixture was poured into water (50.0 mL) and extracted with ethyl acetate (3×10.0 mL). The organic phase was washed by brine (20.0 mL), dried over anhydrous sodium sulfate, filtered and concentrated under reduced pressure to give a residue. The residue was purified by column chromatography (SiO$_2$, petroleum ether/ethyl acetate=1/0 to 20/1) to afford phenyl (5-(1,1-difluoroethyl)-2-fluorophenyl)carbamate (320 mg, 759 umol, 74% yield, 70% purity) as a light yellow solid. $^1$H NMR (400 MHz, DMSO-d$_6$) δ=10.16 (s, 1H), 7.94 (d, J=6.8 Hz, 1H), 7.44-7.38 (m, 3H), 7.30-7.22 (m, 3H), 7.18-7.13 (m, 1H), 1.95 (t, J=18.8 Hz, 3H).

To a solution of phenyl (5-(1,1-difluoroethyl)-2-fluorophenyl)carbamate (120 mg, 285 umol, 70% purity, 1.00 eq) and 3-(6-(hydroxymethyl)-1-oxoisoindolin-2-yl)piperidine-2,6-dione I (78.0 mg, 285 umol, 1.00 eq) in N,N-dimethylformamide (2.00 mL) was added 4-dimethylaminopyridine (69.5 mg, 569 umol, 2.00 eq). The mixture was stirred at 50° C. for 1 h. The mixture was poured into water (20.0 mL) and extracted with ethyl acetate (3×10.0 mL). The organic phase was washed by saturated sodium chloride aqueous solution (20.0 mL) and brine (20.0 ml), dried over anhydrous sodium sulfate, filtered and concentrated under reduced pressure to give a residue. The residue was purified by Prep-HPLC (column: Phenomenex Synergi C18 150*25 mm*10 um; mobile phase: [water (formic acid)-acetonitrile]; B %: 31%-61%, 10 min) to afford (2-(2,6-dioxopiperidin-3-yl)-3-oxoisoindolin-5-yl)methyl(5-(1,1-difluoroethyl)-2-fluorophenyl)carbamate #234 (54.0 mg, 112 umol, 97% yield, 99% purity, formate) as a white solid. $^1$H NMR (400 MHz, DMSO-d$_6$) δ=10.99 (s, 1H), 9.75 (s, 1H), 7.97-7.89 (m, 1H), 7.81 (s, 1H), 7.71-7.61 (m, 2H), 7.38-7.30 (m, 2H), 5.29 (s, 2H), 5.13 (dd, J=5.2, 13.6 Hz, 1H), 4.51-4.49 (m, 2H), 4.35-4.31 (m, 1H), 2.97-2.85 (m, 1H), 2.68-2.56 (m, 1H), 2.43-2.36 (m, 1H), 2.04-2.01 (m, 1H), 1.94 (t, J=18.8 Hz, 3H). MS (ESI-NEG) m/z 474.1 [M−H]$^+$ Compound #235: To a mixture of 4-tert-butyl-1-chloro-2-nitro-benzene (2.00 g, 9.36 mmol, 1.00 eq) in sulfolane (40.0 mL) was added cesium fluoride (7.11 g, 46.8 mmol, 5.00 eq). The mixture was stirred at 180° C. for 3 h under microwave. The reaction mixture was poured into water (200 mL) and extracted with ethyl acetate (3×30 mL). The organic phase was concentrated under reduced pressure to give a residue. The residue was purified by column chromatography (SiO$_2$, petroleum ether/ethyl acetate=1/0) and concentrated to afford 4-tert-butyl-1-fluoro-2-nitro-benzene (600 mg, 1.83 mmol, 19% yield, 60% purity) as red oil. $^1$H NMR (400 MHz, CDCl$_3$) δ=8.06-8.04 (m, 1H), 7.66-7.62 (m, 1H), 7.24-7.19 (m, 1H), 1.36 (s, 9H).

To a mixture of 4-tert-butyl-1-fluoro-2-nitro-benzene (500 mg, 1.52 mmol, 60% purity, 1.00 eq) in methanol (10.0 mL) was added palladium on carbon (50.0 mg, 10% purity) under nitrogen atmosphere. After addition, the mixture was purged with hydrogen for 3 times and stirred at 25° C. for 2 h under hydrogen atmosphere (15 psi). The reaction mixture was filtered and the filter cake was washed with methanol (3×30 mL). The filtrate was concentrated under reduced pressure to give a residue. The residue was purified by column chromatography (petroleum ether/ethyl acetate=1/0-50/1) to afford 5-tert-butyl-2-fluoro-aniline (200 mg, 956 umol, 62% yield, 80% purity) as red oil. $^1$H NMR (400 MHz, CDCl$_3$) δ=6.97-6.89 (m, 2H), 6.82-6.77 (m, 1H), 1.28 (s, 9H).

To a mixture of 5-tert-butyl-2-fluoro-aniline (180 mg, 861 umol, 80% purity, 1.00 eq) and pyridine (102 mg, 1.29 mmol, 1.50 eq) in tetrahydrofuran (5.00 mL) was added phenyl carbonochloridate (141 mg, 904 umol, 1.05 eq) at 0° C. After stirring at 25° C. for 0.5 h, the reaction mixture was poured into saturated ammonium chloride aqueous (20 mL) and extracted with ethyl acetate (3×10 mL). The organic phase was concentrated under reduced pressure to give a residue. The residue was purified by column chromatography (petroleum ether/ethyl acetate=1/0-30/1) to afford phenyl N-(5-tert-butyl-2-fluoro-phenyl)carbamate (230 mg, 680 umol, 79% yield, 85% purity) as red oil. MS (ESI) m/z 288.0 [M+H]$^+$ To a mixture of phenyl (5-(tert-butyl)-2-fluorophenyl)carbamate (100 mg, 296 umol, 85% purity, 1.20 eq) and 3-(6-(hydroxymethyl)-1-oxoisoindolin-2-yl)piperidine-2,6-dione I (67.6 mg, 247 umol, 1.00 eq) in N,N-dimethylformamide (2.00 mL) was added sodium hydride (14.8 mg, 370 umol, 60% purity, 1.50 eq) at 0° C. The mixture was stirred at 25° C. for 1.5 h. The mixture was quenched with hydrochloric acid (1 M, 1.00 mL), then diluted with ethyl acetate (1.00 mL). The aqueous phase was extracted with ethyl acetate (3×2 mL). The combined extracts were washed with brine, dried over anhydrous sodium sulfate, filtered and concentrated under vacuum to give a residue. The residue was purified by Prep-HPLC (column: Phenomenex Synergi C18 150*25 mm*10 um; mobile phase: [water (formic acid)-acetonitrile]; B %: 35%-68%, 11 min) to afford (2-(2,6-dioxopiperidin-3-yl)-3-oxoisoindolin-5-yl)methyl(5-(tert-butyl)-2-fluorophenyl)carbamate #235 (75.86 mg, 145 umol, 59% yield, 98% purity) as a white solid. $^1$H NMR (400 MHz, DMSO-d$_6$) δ=10.99 (s, 1H), 9.44 (s, 1H), 8.50-8.43 (m, 1H), 7.81 (s, 1H), 7.73-7.60 (m, 3H), 7.20-7.07 (m, 2H), 5.27 (s, 2H), 5.19-5.09 (dd, J=5.2, 13.6 Hz, 1H), 4.52-4.44 (m, 1H), 4.39-4.31 (m, 1H), 2.98-2.87 (m, 1H), 2.69-2.57 (m, 1H), 2.42-2.32 (m, 1H), 2.09-1.95 (m, 1H), 1.25 (s, 9H). MS (ESI) m/z 468.2 [M+H]$^+$ Compound #236: To a solution of dimethyl 2-methylmalonate (915 mg, 6.27 mmol, 832 uL, 1.10 eq) in dimethyl formamide (3.00 mL) was added sodium hydrogen (273 mg, 6.84 mmol, 60% purity, 1.20 eq) and the mixture was stirred at 0° C. for 0.5 h. Then to the mixture was added 2-chloro-1-fluoro-4-nitrobenzene (1.00 g, 5.70 mmol, 1.00 eq). The mixture was stirred at 25° C. for 2 h. The reaction was quenched by saturated ammonium chloride solution (50 mL), extracted with ethyl acetate (3×30 mL). The combined organic layers were concentrated to give a residue. The residue was purified by silica gel column chromatography (petroleum ether/ethyl acetate=10/1) to afford dimethyl 2-(2-chloro-4-nitrophenyl)-2-methylmalonate (5.00 g, 16.57 mmol, 97% yield) as yellow oil. $^1$H NMR (400 MHz, DMSO-d$_6$) δ=8.32 (d, J=2.4 Hz, 1H), 8.18 (dd, J=2.5, 8.8 Hz, 1H), 7.60 (d, J=8.8 Hz, 1H), 3.74 (s, 6H), 1.86 (s, 3H).

To a mixture of dimethyl 2-(2-chloro-4-nitrophenyl)-2-methylmalonate (3.00 g, 9.94 mmol, 1.00 eq) in tetrahydrofuran (30.0 mL) were added lithium aluminium tetrahydride (400 mg, 10.5 mmol, 1.06 eq). The reaction mixture was stirred at 0° C. for 2 h under nitrogen atmosphere. The mixture was quenched with sodium sulfate decahydrate at 0° C. The mixture was filtered. The filtrate was concentrated to give a residue. The reaction was purified by silica gel column chromatography (petroleum ether/ethyl acetate=1/1) to afford 2-(2-chloro-4-nitro-phenyl)-2-methyl-propane-1,3-diol (500 mg, 2.04 mmol, 21% yield) as a yellow solid.

To a solution of 2-(2-chloro-4-nitrophenyl)-2-methylpropane-1,3-diol (500 mg, 2.04 mmol, 1.00 eq) in tetrahydrofuran (5.00 mL) was added n-butyllithium (2.50 M, 985 uL, 1.21 eq) and p-toluenesulfonyl chloride (582 mg, 3.05 mmol, 1.50 eq) at 0° C. The mixture was stirred at 25° C. for 1 h. After being cooled to 0° C., n-butyllithium (2.50 M, 985 uL, 1.21 eq) was added to the mixture. The mixture was stirred at 65° C. for 2 h. The reaction mixture was quenched by addition saturated ammonium chloride solution (10.0 mL), diluted with water (10.0 mL) and extracted with ethyl acetate (3×30.0 mL). The combined organic layers were dried over anhydrous sodium sulfate, filtered and concentrated under reduced pressure to give a residue. The residue was purified by chromatography on silica gel (petroleum ether/ethyl acetate=10/1 to dichloromethane/methanol=10/1) to afford 3-(2-chloro-4-nitro-phenyl)-3-methyloxetane (140 mg, 615 umol, 30% yield) as yellow oil. $^1$H NMR (400 MHz, DMSO-d$_6$) δ=8.26 (d, J=2.4 Hz, 1H), 8.18 (dd, J=2.4, 8.5 Hz, 1H), 7.45 (d, J=8.4 Hz, 1H), 4.95 (d, J=6.0 Hz, 2H), 4.52 (d, J=6.4 Hz, 2H), 1.72 (s, 3H).

To a solution of 3-(2-chloro-4-nitrophenyl)-3-methyloxetane (140 mg, 615 umol, 1.00 eq) in methanol (2.00 mL) and water (1.00 mL) were added iron powder (103 mg, 1.84 mmol, 3.00 eq) and ammonium chloride (164 mg, 3.07 mmol, 5.00 eq). The mixture was stirred at 80° C. for 2 h. The mixture was diluted with water (20.0 mL) and extracted with ethyl acetate (3×20.0 mL). The combined organic layers were washed with brine (20.0 mL), dried over sodium sulfate, filtered and concentrated under reduced pressure to give a residue. The residue was purified by silica gel column chromatography (petroleum ether/ethyl acetate=1/1) to afford 3-chloro-4-(3-methyloxetan-3-yl)aniline (120 mg, 607 umol, 98% yield) as yellow oil. MS (ESI) m/z 198.1 [M+H]$^+$ To a mixture of 3-chloro-4-(3-methyloxetan-3-yl)aniline (120 mg, 607 umol, 1.00 eq) and pyridine (144 mg, 1.82 mmol, 147 uL, 3.00 eq) in acetonitrile (1.00 mL) was added phenyl carbonochloridate (104 mg, 667 umol, 83.6 uL, 1.10 eq). The reaction was stirred at 25° C. for 2 h. The residue was diluted with water (20.0 mL) and extracted with ethyl acetate (3×20.0 mL). The combined organic layers were washed with brine (20.0 mL), dried over sodium sulfate, filtered and concentrated under reduced pressure to give a residue. The residue was purified by silica gel column chromatography (petroleum ether/ethyl acetate=10/1) to give phenyl (3-chloro-4-(3-methyloxetan-3-yl)phenyl)carbamate (80.0 mg, 251.7 umol, 42% yield) as yellow oil. $^1$H NMR (400 MHz, DMSO-d$_6$) δ=10.40 (br s, 1H), 7.59 (d, J=2.0 Hz, 1H), 7.47-7.39 (m, 3H), 7.30-7.19 (m, 3H), 7.09 (d, J=8.4 Hz, 1H), 4.89 (d, J=5.6 Hz, 2H), 4.45 (d, J=6.0 Hz, 2H), 1.66 (s, 3H).

To a mixture of 3-(6-(hydroxymethyl)-1-oxoisoindolin-2-yl)piperidine-2,6-dione I (34.5 mg, 125 umol, 1.00 eq) and sodium hydrogen (10.0 mg, 251 umol, 60% purity, 2.00 eq) in dimethyl formamide (500 uL) was added phenyl (3-chloro-4-(3-methyloxetan-3-yl)phenyl)carbamate (40.0 mg, 126 umol, 1.00 eq). The reaction was stirred at 20° C. for 1 h. The pH of the mixture was adjusted to 7 with formic acid, then the mixture was diluted with dimethyl formamide (1.00 mL). The mixture was purified by Prep-HPLC (column: Phenomenex Luna C18 150*25 mm*10 um; mobile phase: [water (formic acid)-acetonitrile]; B %: 32%-62%, 10 min) to afford (2-(2,6-dioxopiperidin-3-yl)-3-oxoisoindolin-5-yl)methyl (3-chloro-4-(3-methyloxetan-3-yl)phenyl)carbamate #236 (27.58 mg, 54.8 umol, 44% yield, 99% purity, formate) as a white solid. $^1$H NMR (400 MHz, DMSO-d$_6$) δ=10.98 (br s, 1H), 10.01 (s, 1H), 8.47 (s, 1H), 7.79 (s, 1H), 7.71-7.62 (m, 2H), 7.56 (d, J=1.6 Hz, 1H), 7.37 (dd, J=2.0, 8.4 Hz, 1H), 7.04 (d, J=8.4 Hz, 1H), 5.28 (s, 2H), 5.12 (dd, J=5.2, 13.3 Hz, 1H), 4.87 (d, J=5.6 Hz, 2H), 4.50-4.42 (m, 3H), 4.37-4.30 (m, 1H), 2.99-2.84 (m, 1H), 2.65-2.56 (m, 1H), 2.40 (dq, J=4.4, 13.2 Hz, 1H), 2.07-1.96 (m, 1H), 1.65 (s, 3H). MS (ESI) m/z 498.2 [M+H]$^+$ Compound #237: To a solution of 5-chloro-4-methylpyridin-2-amine (2.00 g, 14.0 mmol, 1.00 eq) in sulfuric acid (30.0 mL) was added hydrogen peroxide (15.9 g, 140 mmol, 13.5 mL, 30% purity, 10.0 eq) dropwise at 0° C. After stirring at 25° C. for 12 h, the mixture was poured into ice water (60.0 mL), yellow solid was precipitate out. The mixture was filtered and the filter cake was dried under reduced pressure to afford 5-chloro-4-methyl-2-nitropyridine (2.00 g, 11.6 mmol, 83% yield) as a yellow solid. $^1$H NMR (400 MHz, DMSO-d$_6$) δ=8.69 (s, 1H), 8.43 (s, 1H), 2.53 (s, 3H).

To a solution of 5-chloro-4-methyl-2-nitropyridine (1.00 g, 5.79 mmol, 1.00 eq) and (R)-2-methylpyrrolidine (1.97 g, 23.2 mmol, 4.00 eq) in N,N-dimethylformamide (10.0 mL) was added potassium carbonate (2.40 g, 17.4 mmol, 3.00 eq). After stirring at 80° C. for 12 h, the mixture was diluted with water (30.0 mL) and extracted with ethyl acetate (3×30 mL). The organic phase was washed with brine (100 mL), dried over anhydrous sodium sulfate, filtered and the filtrate was concentrated to give a residue. The residue was purified by flash silica gel chromatography (petroleum ether/ethylacetate=1/0 to 3/2) to afford (R)-4-methyl-5-(2-methylpyrrolidin-1-yl)-2-nitropyridine (340 mg, 1.38 mmol, 24% yield, 90% purity) as yellow oil. MS (ESI) m/z 222.0 [M+H]$^+$ To a solution of (R)-4-methyl-5-(2-methylpyrrolidin-1-yl)-2-nitropyridine (340 mg, 1.54 mmol, 1.00 eq) in methanol (5.00 mL) was added palladium on carbon (34.0 mg, 10% purity) under nitrogen atmosphere. The suspension was degassed and purged with hydrogen atmosphere for 3 times. After stirring under hydrogen atmosphere (15 Psi) at 25° C.

for 4 h, the reaction mixture was filtered and the filtrate was concentrated under reduced pressure to afford (R)-4-methyl-5-(2-methylpyrrolidin-1-yl)pyridin-2-amine (250 mg, 1.11 mmol, 72% yield, 85% purity) as yellow oil. MS (ESI) m/z 192.2 [M+H]$^+$ To a mixture of (R)-4-methyl-5-(2-methylpyrrolidin-1-yl)pyridin-2-amine (150 mg, 784 umol, 1.00 eq) and pyridine (186 mg, 2.35 mmol, 190 uL, 3.00 eq) in acetonitrile (2.00 mL) was added phenyl carbonochloridate (111 mg, 706 umol, 88.4 uL, 0.900 eq) dropwise at 0° C. After stirring at 25° C. for 1 h, the mixture was concentrated under vacuum to give a residue. The residue was purified by Prep-TLC (SiO$_2$, petroleum ether/ethyl acetate=2/1) to afford (R)-phenyl (4-methyl-5-(2-methylpyrrolidin-1-yl)pyridin-2-yl)carbamate (65.0 mg, 188 umol, 24% yield, 90% purity) as yellow oil. MS (ESI) m/z 311.8 [M+H]$^+$ To a mixture of (R)-phenyl (4-methyl-5-(2-methylpyrrolidin-1-yl)pyridin-2-yl)carbamate (60.0 mg, 193 umol, 1.00 eq) and 3-(6-(hydroxymethyl)-1-oxoisoindolin-2-yl)piperidine-2,6-dione I (52.9 mg, 193 umol, 1.00 eq) in dioxane (1.00 mL) were added 4-dimethylaminopyridine (23.5 mg, 193 umol, 1.00 eq) and N,N-diisopropylethylamine (29.9 mg, 231 umol, 40.3 uL, 1.20 eq) at 25° C. After stirring at 90° C. for 2 h, the reaction mixture was concentrated under reduced pressure to give a residue. The residue was purified by Prep-HPLC (column: Unisil 3-100 C18 Ultra 150*50 mm*3 um; mobile phase: [water (formic acid)-acetonitrile]; B %: 7%-37%, 10 min) to afford (2-(2,6-dioxopiperidin-3-yl)-3-oxoisoindolin-5-yl)methyl (4-methyl-5-((R)-2-methylpyrrolidin-1-yl)pyridin-2-yl)carbamate #237 (18.74 mg, 36.98 umol, 19% yield, 97% purity) as a white solid. $^1$H NMR (400 MHz, DMSO-d$_6$) δ=10.98 (s, 1H), 10.01 (s, 1H), 8.49 (s, 1H), 7.87 (s, 1H), 7.79 (s, 1H), 7.68-7.61 (m, 2H), 7.59 (s, 1H), 5.27 (s, 2H), 5.12 (dd, J=5.2 Hz, 13.2 Hz, 1H), 4.49-4.44 (m, 1H), 4.36-4.31 (m, 1H), 3.70-3.64 (m, 1H), 3.50-3.40 (m, 1H), 2.95-2.86 (m, 1H), 2.75-2.66 (m, 1H), 2.62-2.61 (m, 1H), 2.42-2.37 (m, 1H), 2.21 (s, 3H), 2.13-2.01 (m, 2H), 1.88-1.73 (m, 2H), 1.51-1.46 (m, 1H), 0.91 (d, J=6.0 Hz, 3H). MS (ESI) m/z 492.0 [M+H]$^+$ Compound #238:

To a solution of 5-bromopicolinaldehyde (5.00 g, 26.9 mmol, 1.00 eq) in N,N-dimethylformamide (50.0 mL) was added trimethyl(trifluoromethyl)silane (4.59 g, 32.3 mmol, 1.20 eq) and potassium carbonate (7.43 g, 53.8 mmol, 2.00 eq) at 25° C. After stirring at 25° C. for 4 h, the reaction mixture was poured into water (50.0 mL) and then extracted with ethyl acetate (3×50.0 mL). The combined organic phase was washed with brine (3×20.0 mL), dried with anhydrous sodium sulfate, filtered and the filtrate was concentrated under reduced pressure to give a residue. The residue was purified by flash silica gel chromatography (petroleum ether/ethylacetate=1/0 to 5/1) to afford 1-(5-bromopyridin-2-yl)-2,2,2-trifluoroethanol (5.10 g, 19.7 mmol, 73% yield, 99% purity) as a yellow solid. $^1$H NMR (400 MHz, DMSO-d$_6$) δ=8.73-8.72 (m, 1H), 8.18-8.15 (m, 1H), 7.61-7.58 (m, 1H), 7.15-7.13 (m, 1H), 5.18-5.11 (m, 1H).

To a mixture of 1-(5-bromopyridin-2-yl)-2,2,2-trifluoroethanol (5.10 g, 19.7 mmol, 99% purity, 1.00 eq), tert-butyl carbamate (3.47 g, 29.6 mmol, 1.50 eq), [2-(2-aminophenyl)phenyl]-methylsulfonyloxy-palladium; ditert-butyl-[2-(2,4,6-triisopropylphenyl)phenyl]phosphane (2.82 g, 3.55 mmol, 0.180 eq) in dioxane (60.0 mL) was added sodium tert-butoxide (5.69 g, 59.2 mmol, 3.00 eq) at 25° C., the mixture was degassed and purged with nitrogen atmosphere for 3 times. After stirring at 100° C. for 12 h, the reaction mixture was poured into water (60.0 mL) and then extracted with ethyl acetate (3×60.0 mL), the combined organic phase was washed with brine (3×30.0 mL), dried over anhydrous sodium sulfate, filtered and the filtrate was concentrated under reduced pressure to give a residue. The residue was purified by flash silica gel chromatography (petroleum ether/ethylacetate=1/0 to 2/3) to afford tert-butyl (6-(2,2,2-trifluoro-1-hydroxyethyl)pyridin-3-yl)carbamate (1.50 g, 4.77 mmol, 24% yield, 93% purity) as yellow oil. MS (ESI) m/z 293.0 [M+H]$^+$.

A mixture of tert-butyl (6-(2,2,2-trifluoro-1-hydroxyethyl)pyridin-3-yl)carbamate (1.50 g, 4.77 mmol, 93% purity, 1.00 eq) in hydrochloric acid/ethyl acetate (4 M, 40.0 mL) was stirred at 25° C. for 2 h. The reaction mixture was filtered and the filter cake was dried under reduced pressure to give a residue, the residue was poured into saturated sodium bicarbonate solution (20.0 mL). The mixture was extracted with ethyl acetate (3×20.0 mL), the combined organic phase was washed with brine (3×10.0 mL), dried over anhydrous sodium sulfate, filtered and the filtrate was concentrated under reduced pressure to afford 1-(5-aminopyridin-2-yl)-2,2,2-trifluoroethanol (900 mg, 4.64 mmol, 97% yield, 99% purity) as a yellow solid. $^1$H NMR (400 MHz, DMSO-d$_6$) δ=7.89-7.87 (m, 1H), 7.23-7.21 (m, 1H), 6.97-6.96 (m, 1H), 6.59-6.57 (m, 1H), 5.45 (s, 2H), 4.90-4.86 (m, 1H). MS (ESI) m/z 193.0 [M+H]$^+$.

To a solution of 1-(5-aminopyridin-2-yl)-2,2,2-trifluoroethanol (400 mg, 2.06 mmol, 99% purity, 1.00 eq) in dichloromethane (8.00 mL) was added 2,6-dimethylpyridine (331 mg, 3.09 mmol, 360 uL, 1.50 eq) and tert-butyldimethylsilyl trifluoromethanesulfonate (654 mg, 2.47 mmol, 569 uL, 1.20 eq) at 0° C. After stirring at 25° C. for 12 h, the reaction mixture was concentrated under reduced pressure to give a residue. The residue was purified by flash silica gel chromatography (petroleum ether/ethylacetate=1/0 to 2/3) to afford 6-(1-((tert-butyldimethylsilyl)oxy)-2,2,2-trifluoroethyl)pyridin-3-amine (300 mg, 950 umol, 46% yield, 97% purity) as yellow oil. MS (ESI) m/z 307.1 [M+H]$^+$.

To a solution of 6-(1-((tert-butyldimethylsilyl)oxy)-2,2,2-trifluoroethyl)pyridin-3-amine (250 mg, 791 umol, 97% purity, 1.00 eq) in tetrahydrofuran (3.00 mL) was added pyridine (125 mg, 1.58 mmol, 128 uL, 2.00 eq) and phenyl carbonochloridate (136 mg, 871 umol, 109 uL, 1.10 eq) at 25° C. After stirring at 25° C. for 2 h, the reaction mixture was concentrated under reduced pressure to give a residue. The residue was purified by flash silica gel chromatography (petroleum ether/ethylacetate=1/0 to 4/1) to afford phenyl (6-(1-((tert-butyldimethylsilyl)oxy)-2,2,2-trifluoroethyl)pyridin-3-yl)carbamate (360 mg, 777 umol, 98% yield, 92% purity) as a yellow solid. MS (ESI) m/z 427.2 [M+H]$^+$.

To a solution of 3-(6-(hydroxymethyl)-1-oxoisoindolin-2-yl)piperidine-2,6-dione (300 mg, 1.09 mmol, 1.33 eq) in tetrahydrofuran (5.00 mL) was added sodium hydride (100 mg, 2.50 mmol, 60% purity, 3.05 eq) at 0° C. under nitrogen atmosphere. After stirring at 25° C. for 1 h under nitrogen atmosphere, the mixture was cooled to 0° C. A solution of phenyl (6-(1-((tert-butyldimethylsilyl)oxy)-2,2,2-trifluoroethyl)pyridin-3-yl) carbamate (350 mg, 821 umol, 1.00 eq) in tetrahydrofuran (5.00 mL) was added to the mixture at 0° C. under nitrogen atmosphere, then the resulting mixture was stirred at 25° C. for another 1 h. The residue was quenched by water (10.0 mL) and partitioned between ethyl acetate (40.0 mL) and brine (20.0 mL). The aqueous layer was extracted with ethyl acetate (2×40.0 mL). The combined organic layers were dried over sodium sulfate and evaporated to afford (2-(2,6-dioxopiperidin-3-yl)-3-oxoisoindolin-5-yl)methyl (6-(1-((tert-butyldimethylsilyl)oxy)-2,2,2-trifluoroethyl)pyridin-3-yl)carbamate (200 mg, crude) as yellow gum. MS (ESI) m/z 607.1 [M+H]$^+$.

To a solution of (2-(2,6-dioxopiperidin-3-yl)-3-oxoisoindolin-5-yl)methyl(6-(1-((tert-butyldimethylsilyl)oxy)-2,2,2-trifluoroethyl)pyridin-3-yl)carbamate (180 mg, 297 umol, 1.00 eq) in tetrahydrofuran (5.00 mL) was added tetrabutylammonium fluoride (4 M, 2.00 mL, 27.0 eq), the reaction solution was degassed and purged under nitrogen atmosphere for three times. After stirring at 25° C. for 12 h, the mixture was extracted between ethyl acetate (50.0 mL) and brine (4×20.0 mL). The combined organic layers were dried over sodium sulfate, filtered and the filtrate was evaporated to give a residue, which was purified by prep-HPLC (column: Unisil 3-100 C18 Ultra 150*50 mm*3 um; mobile phase: [water (FA)-ACN]; B %: 14%-44%, 10 min) for three times and lyophilized to afford (2-(2,6-dioxopiperidin-3-yl)-3-oxoisoindolin-5-yl)methyl(6-(2,2,2-trifluoro-1-hydroxyethyl)pyridin-3-yl)carbamate #238: (60 mg, 122 umol, 41% yield, 99% purity) as a white solid. $^1$H NMR (400 MHz, DMSO-d$_6$) δ=10.98 (s, 1H), 10.16 (s, 1H), 8.62-8.61 (m, 1H), 7.98-7.70 (m, 1H), 7.68 (s, 1H), 7.63-7.53 (m, 2H), 7.55-7.53 (m, 1H), 6.95 (s, 1H), 5.30 (s, 2H), 5.12 (dd, J=5.2 Hz, 13.2 Hz, 1H), 5.05 (d, J=7.2 Hz, 1H), 4.47 (d, J=17.2 Hz, 1H), 4.47 (d, J=17.6 Hz, 1H), 2.91-2.86 (m, 1H), 2.63-2.58 (m, 1H), 2.46-2.40 (m, 1H), 2.03-2.01 (m, 1H). MS (ESI) m/z 493.2 [M+H]$^+$.

Compound #239: To a mixture of 3-chloroaniline (500 mg, 3.92 mmol, 416 uL, 1.00 eq) and pyridine (930 mg, 11.7 mmol, 949 uL, 3.00 eq) in acetonitrile (5.00 mL) was added phenyl carbonochloridate (797 mg, 5.10 mmol, 638 uL, 1.30 eq) dropwise. The mixture was stirred at 15° C. for 2 h. The mixture was concentrated to give crude product. The crude product was purified by reversed-phase HPLC (column: spherical C18, 20-45 um, 100 Å, SW 80, mobile phase: [water (0.1% Formic Acid)-ACN]). The desired fraction was collected and lyophilized to give phenyl (3-chlorophenyl)carbamate (900 mg, 3.63 mmol, 92% yield) as a white solid. $^1$H NMR (400 MHz, DMSO-d$_6$) δ=10.46 (br s, 1H), 7.51-7.45 (m, 2H), 7.45-7.41 (m, 2H), 7.40-7.37 (m, 1H), 7.36-7.32 (m, 1H), 7.28 (br d, J=7.5 Hz, 1H), 7.26-7.21 (m, 2H).

To a mixture of 3-(6-(hydroxymethyl)-1-oxoisoindolin-2-yl)piperidine-2,6-dione I (80.0 mg, 291 umol, 1.00 eq) and phenyl (3-chlorophenyl)carbamate (86.6 mg, 350 umol, 1.20 eq) in dimethyl formamide (1.00 mL) was added sodium hydride (17.5 mg, 437 umol, 60% purity, 1.50 eq) in one portion at 0° C. The mixture was stirred at 15° C. for 1 h. The mixture was quenched with 1 M hydrochloric acid (0.500 mL) and filtered. The filtrate was purified by prep-HPLC (column: 3_Phenomenex Luna C18 75*30 mm*3 um; mobile phase: [water (0.05% HCl)-ACN]; B %: 35%-55%, 6.5 min) and lyophilization to give (2-(2,6-dioxopiperidin-3-yl)-3-oxoisoindolin-5-yl)methyl (3-chlorophenyl)carbamate #239 (10.72 mg, 24.8 umol, 8% yield, 99% purity) as an off-white solid. $^1$H NMR (400 MHz, DMSO-d$_6$) δ=11.00 (s, 1H), 10.05 (s, 1H), 7.80 (s, 1H), 7.70-7.67 (m, 1H), 7.66-7.59 (m, 2H), 7.41-7.36 (m, 1H), 7.33-7.27 (m, 1H), 7.07-7.03 (m, 1H), 5.28 (s, 2H), 5.13 (dd, J=5.1, 13.4 Hz, 1H), 4.51-4.43 (m, 1H), 4.38-4.30 (m, 1H), 2.97-2.85 (m, 1H), 2.60 (br d, J=17.7 Hz, 1H), 2.40-2.28 (m, 1H), 2.06-1.96 (m, 1H). MS (ESI) m/z 428.1 [M+H]$^+$ Compound #240: To a solution of 1,2-difluoro-4-nitrobenzene (3.00 g, 18.9 mmol, 2.08 mL, 1.00 eq) in tetrahydrofuran (30.0 mL) was added sodium hydride (1.51 g, 37.7 mmol, 60% purity, 2.00 eq) slowly at 0° C., then stirred at 0° C. for 0.5 h. Dimethyl 2-methylmalonate (4.13 g, 28.3 mmol, 3.76 mL, 1.50 eq) was added to the mixture, the mixture was stirred at 25° C. for 3 h. The reaction mixture was poured into water (200 mL) slowly, then extracted with ethyl acetate (3×100 mL). The combined organic phase was washed with brine (100 mL), dried over anhydrous sodium sulfate, filtered and concentrated in vacuum to give a residue. The residue was purified by silica gel chromatography (Petroleum ether/Ethyl acetate=1/0 to 10/1) to afford dimethyl 2-(2-fluoro-4-nitrophenyl)-2-methylmalonate (3.80 g, 13.3 mmol, 71% yield) as yellow oil. $^1$H NMR (400 MHz, DMSO-d$_6$) δ=8.16 (dd, J=2.3, 11.2 Hz, 1H), 8.08 (dd, J=2.3, 8.8 Hz, 1H), 7.65 (t, J=8.4 Hz, 1H), 3.74 (s, 6H), 1.83 (s, 3H).

To a solution of dimethyl 2-(2-fluoro-4-nitrophenyl)-2-methylmalonate (2.80 g, 9.82 mmol, 1.00 eq) in tetrahydrofuran (30.0 mL) was added lithium aluminum hydride (559 mg, 14.7 mmol, 1.50 eq) slowly at 0° C. under nitrogen atmosphere. Then the mixture was stirred at 0° C. for 3 h. The reaction mixture was added sodium sulfate decahydrate (10.0 g) slowly, then filtered to give a filtrate, the filtrate was concentrated to give a residue. The residue was purified by silica gel chromatography (Petroleum ether/Ethyl acetate=1/0 to 2/1) to afford 2-(2-fluoro-4-nitrophenyl)-2-methylpropane-1,3-diol (300 mg, 1.31 mmol, 13% yield) as yellow oil. $^1$H NMR (400 MHz, DMSO-d$_6$) δ=8.12-7.95 (m, 2H), 7.68 (t, J=8.4 Hz, 1H), 4.76 (t, J=5.2 Hz, 2H), 3.82-3.70 (m, 2H), 3.67-3.58 (m, 2H), 1.30 (d, J=1.2 Hz, 3H).

To a solution of 2-(2-fluoro-4-nitrophenyl)-2-methylpropane-1,3-diol (500 mg, 2.18 mmol, 1.00 eq) in tetrahydrofuran (2.00 mL) was added n-butyllithium (2.50 M, 1.31 mL, 1.50 eq) and paratoluensulfonyl chloride (624 mg, 3.27 mmol, 1.50 eq) in 0° C. The mixture was stirred at 25° C. for 1 h and then stirred at 65° C. for 2 h. The reaction mixture was cooled to 25° C., then quenched with ammonium chloride (30.0 mL), then poured into water (80.0 mL). The aqueous phase was extracted with ethyl acetate (3×60.0 mL). The combined organic phase was washed with brine (60.0 mL), dried with anhydrous sodium sulfate, filtered and concentrated in vacuum to give a residue. The residue was purified by silica gel chromatography (Petroleum ether/Ethyl acetate=1/0 to 3/1) to afford 3-(2-fluoro-4-nitrophenyl)-3-methyloxetane (200 mg, 947 umol, 43% yield) as a yellow solid. $^1$H NMR (400 MHz, CDCl$_3$) δ=8.13-8.02 (m, 1H), 7.94 (dd, J=2.3, 10.4 Hz, 1H), 7.19 (t, J=8.0 Hz, 1H), 5.05 (d, J=5.6 Hz, 2H), 4.65 (d, J=6.0 Hz, 2H), 1.79 (s, 3H).

To a solution of 3-(2-fluoro-4-nitrophenyl)-3-methyloxetane (200 mg, 947 umol, 1.00 eq) in methanol (2.00 mL) and water (1.00 mL) was added iron powder (159 mg, 2.84 mmol, 3.00 eq) and ammonium chloride (253 mg, 4.74 mmol, 5.00 eq). Then the mixture was stirred at 80° C. for 2 h. The mixture was filtered to give a filtrate. The filtrate was diluted with water (100 mL) and extracted with ethyl acetate (3×100 mL), washed with brine (200 mL), dried over anhydrous sodium sulfate, filtered and concentrated under reduced pressure to give 3-fluoro-4-(3-methyloxetan-3-yl)aniline (100 mg, 552 umol, 58% yield) as yellow oil. MS (ESI) m/z 182.2 [M+H]

To a solution of 3-fluoro-4-(3-methyloxetan-3-yl)aniline (100 mg, 551 umol, 1.00 eq) and pyridine (218 mg, 2.76 mmol, 222 uL, 5.00 eq) in acetonitrile (2.00 mL) was added phenyl carbonochloridate (95.0 mg, 607 umol, 76.0 uL, 1.10 eq) at 25° C. for 2 h. The reaction was concentrated under reduced pressure to give a residue. The crude product was purified by reversed-phase HPLC (0.1% formic acid condition) to afford phenyl (3-fluoro-4-(3-methyloxetan-3-yl)phenyl)carbamate as a white solid. $^1$H NMR (400 MHz, DMSO-d$_6$) δ=10.53-10.33 (m, 1H), 7.50-7.38 (m, 2H), 7.31-7.21 (m, 3H), 7.19-7.13 (m, 2H), 6.38-6.29 (m, 1H), 4.86 (d, J=5.6 Hz, 2H), 4.48 (d, J=5.6 Hz, 2H), 1.62 (s, 3H). MS (ESI) m/z 302.0 [M+H]

To a solution of 3-(6-(hydroxymethyl)-1-oxoisoindolin-2-yl)piperidine-2,6-dione I (20.0 mg, 72.9 umol, 1.00 eq) and phenyl(3-fluoro-4-(3-methyloxetan-3-yl)phenyl)carbamate (32.9 mg, 109 umol, 1.50 eq) in dimethylformamide (1.00 mL) was added sodium hydride (5.83 mg, 145 umol, 60% purity, 2.00 eq) at 0° C., The reaction mixture was stirred at 25° C. for 1 h. The reaction mixture quenched with 1M hydrochloric acid (500 uL) and filtered to give a filtrate. The residue was purified by Prep-HPLC (column: Shimpack C18 150*25*10 um; mobile phase: [water (formic acid)-acetonitrile]; B %: 28%-58%, 10 min) to afford (2-(2, 6-dioxopiperidin-3-yl)-3-oxoisoindolin-5-yl)methyl (3-fluoro-4-(3-methyloxetan-3-yl)phenyl)carbamate #240 (37.21 mg, 76.5 umol, 49% yield, 99% purity) as a white solid. $^1$H NMR (400 MHz, DMSO-$d_6$) δ=10.99 (br d, J=2.4 Hz, 1H), 10.03 (s, 1H), 7.80 (s, 1H), 7.74-7.60 (m, 2H), 7.35 (br d, J=13.2 Hz, 1H), 7.22 (dd, J=1.6, 8.4 Hz, 1H), 7.13-7.02 (m, 1H), 5.29 (s, 2H), 5.13 (dd, J=5.0, 13.2 Hz, 1H), 4.85 (d, J=5.6 Hz, 2H), 4.51-4.47 (m, 1H), 4.46 (s, 2H), 4.41-4.29 (m, 1H), 3.00-2.85 (m, 1H), 2.65-2.59 (m, 1H), 2.44-2.35 (m, 1H), 2.09-1.95 (m, 1H), 1.61 (s, 3H). MS (ESI) m/z 482.1 [M+H]

Example 3: Compound Activity by Fluorescent Polarization Assay

Compound activity was monitored in a fluorescence polarization (FP) homogeneous assay using 1-[5-({2-[2-(2-{[2-(2,6-dioxopiperidin-3-yl)-1,3-dioxo-2,3-dihydro-1H-isoindol-4-yl]oxy}acetamido)ethoxy]ethyl}carbamoyl)pentyl]-3,3-dimethyl-2-[(1E,3E)-5-[(2E)-1,3,3-trimethyl-5-sulfo-2,3-dihydro-1H-indol-2-ylidene]penta-1,3-dien-1-yl]-3H-indol-1-ium-5-sulfonate as a fluorescent probe. Unless otherwise stated, all reagents were purchased from Sigma Aldrich. Enzymatic reactions were conducted in Perkin-Elmer Black 384 well ProxiPlate Plus (catalogue no. 6008269) in 10 μL total volume. Full length wild-type cereblon CRBN (80.0 nM, L) was incubated in assay buffer containing 20 mM HEPES (pH 8.0), 150 NaCl, 0.5 mM TCEP and 0.05% Tween 20 in the presence or absence of compound (300 nL). Inhibitors were stored as 10 mM DMSO stocks in an inert environment (low humidity, dark, low oxygen, room temperature) using the Storage Pod System. Compounds and DMSO were dispensed using the Echo E5XX (Labcyte Inc. USA) to give concentrations from 300 to 0.937 or 3000 to 9.3 nM in a 12 data point curve. Mutant YWAA CRBN (80.0 nM, 10 μL) which does not interact with the fluorescent probe was used as a negative control for the assay. Following incubation at room temperature for 30 min, the assay was initiated by dispensing the probe to a final concentration of 5 nM (2.5 nL of a 20 μM stock) using the Echo E5XX. FP was measured after a period of 12 hours using a Pherastar plate reader (BMG Labtech, Germany) exciting at 590 nm and measuring the amount of parallel and perpendicular light at 675 nm. The FP signal was subsequently normalized to the no-compound control (i.e., DMSO). Analysis and IC50 values were derived using Dotmatics (Dotmatics UK) software.

TABLE 2

IC50 values determined in the fluorescence polarization assay indicating the cereblon binding

| Compound | rFP IC50 [nM] |
| --- | --- |
| 1 | C |
| 2 | B |
| 3 | C |
| 4 | B |
| 5 | C |
| 6 | B |
| 7 | B |
| 8 | B |
| 9 | C |
| 10 | C |
| 11 | D |
| 12 | C |
| 13 | B |
| 14 | C |
| 15 | B |
| 16 | A |
| 17 | D |
| 18 | B |
| 19 | D |
| 20 | C |
| 21 | D |
| 22 | D |
| 23 | A |
| 24 | B |
| 25 | B |
| 26 | B |
| 27 | D |
| 28 | C |
| 29 | B |
| 30 | A |
| 31 | D |
| 32 | D |
| 33 | B |
| 34 | D |
| 35 | A |
| 36 | A |
| 37 | D |
| 38 | B |
| 39 | B |
| 40 | A |
| 41 | B |
| 42 | D |
| 43 | D |
| 44 | B |
| 45 | D |
| 46 | A |
| 47 | C |
| 48 | C |
| 49 | C |
| 50 | D |
| 51 | B |
| 52 | B |
| 53 | B |
| 54 | A |
| 55 | B |
| 56 | C |
| 57 | D |
| 58 | B |
| 59 | A |
| 60 | A |
| 61 | D |
| 62 | B |
| 63 | A |
| 64 | B |
| 65 | A |
| 66 | A |
| 67 | B |
| 68 | B |
| 69 | A |
| 70 | A |
| 71 | C |
| 72 | B |
| 73 | A |
| 74 | A |
| 75 | A |
| 76 | B |

TABLE 2-continued

IC50 values determined in the fluorescence polarization assay indicating the cereblon binding

| Compound | rFP IC50 [nM] |
|---|---|
| 77 | B |
| 78 | A |
| 79 | C |
| 80 | A |
| 81 | A |
| 82 | A |
| 83 | B |
| 84 | A |
| 85 | D |
| 86 | B |
| 87 | B |
| 88 | B |
| 89 | B |
| 90 | C |
| 91 | B |
| 92 | B |
| 93 | B |
| 94 | A |
| 95 | C |
| 96 | C |
| 97 | B |
| 98 | B |
| 99 | C |
| 100 | B |
| 101 | D |
| 102 | B |
| 103 | B |
| 104 | D |
| 105 | B |
| 106 | B |
| 107 | A |
| 108 | A |
| 110 | A |
| 111 | A |
| 112 | A |
| 113 | A |
| 114 | A |
| 115 | A |
| 116 | D |
| 117 | B |
| 118 | B |
| 119 | B |
| 120 | B |
| 121 | D |
| 122 | A |
| 123 | B |
| 124 | A |
| 125 | D |
| 126 | A |
| 127 | C |
| 128 | B |
| 129 | A |
| 130 | B |
| 131 | B |
| 132 | B |
| 133 | B |
| 134 | D |
| 135 | A |
| 136 | D |
| 137 | D |
| 139 | B |
| 140 | B |
| 141 | B |
| 142 | B |
| 143 | D |
| 144 | C |
| 145 | B |
| 146 | C |
| 147 | B |
| 148 | D |
| 149 | A |
| 150 | C |
| 151 | A |
| 152 | A |
| 153 | B |
| 154 | D |
| 155 | D |
| 156 | A |
| 157 | A |

Table 2 assigns each compound a code indicating the ability for cereblon binding by measn of their IC50 values: A, B, C or D. According to the code, A represents an IC50 value of ≤500 nM, B represents an IC50 value >500 nM and ≤1100 nM, C represents an IC50 value of >1100 nM and ≤1700 nM and D represents an IC50 value of >1700 nM.

In some embodiments, the disclosure is directed to compounds with an IC50 value of less than 1700 nM, i.e. directed to compounds 1, 2, 3, 4, 5, 6, 7, 8, 9, 10, 12, 13, 14, 15, 16, 18, 20, 23, 24, 25, 26, 28, 29, 30, 33, 35, 36, 38, 39, 40, 41, 44, 46, 47, 48, 49, 51, 52, 53, 54, 55, 56, 58, 59, 60, 62, 63, 64, 65, 66, 67, 68, 69, 70, 71, 72, 73, 74, 75, 76, 77, 78, 79, 80, 81, 82, 83, 84, 86, 87, 88, 89, 90, 91, 92, 93, 94, 95, 96, 97, 98, 99, 100, 102, 103, 105, 106, 107, 108, 110, 111, 112, 113, 114, 115, 117, 118, 119, 120, 122, 123, 124, 126, 127, 128, 129, 130, 131, 132, 133, 135, 138, 139, 140, 141, 142, 144, 145, 146, 147, 149, 150, 151, 152, 153, 156 and 157.

In some embodiments, the disclosure is directed to compounds with an IC50 value of less than 1100 nM, i.e. directed to compounds 2, 4, 6, 7, 8, 13, 15, 16, 18, 23, 24, 25, 26, 29, 30, 33, 35, 36, 38, 39, 40, 41, 44, 46, 51, 52, 53, 54, 55, 58, 59, 60, 62, 63, 64, 65, 66, 67, 68, 69, 70, 72, 73, 74, 75, 76, 77, 78, 80, 81, 82, 83, 84, 86, 87, 88, 89, 91, 92, 93, 94, 97, 98, 100, 102, 103, 105, 106, 107, 108, 110, 111, 112, 113, 114, 115, 117, 118, 119, 120, 122, 123, 124, 126, 128, 129, 130, 131, 132, 133, 135, 138, 139, 140, 141, 142, 145, 147, 149, 151, 152, 153, 156 and 157.

In some embodiments, the disclosure is directed to compounds with an IC50 value of less than 500 nM, i.e. directed to compounds 16, 23, 30, 33, 35, 36, 46, 54, 59, 60, 63, 65, 66, 69, 70, 73, 74, 75, 78, 80, 81, 82, 84, 94, 107, 108, 110, 111, 112, 113, 114, 115, 122, 124, 126, 129, 135, 149, 151, 152, 156 and 157.

Example 4: Compound Binding by Immunofluorescence Assay

The representative compounds were tested in an immunofluorescence assay for their activity to bind to degrade GSPT1. CAL-51 cells were purchased from DSMZ (cat. Number ACC302), sub-cultured in 90% Dulbecco's MEM (4.5 g/L glucose, Gibco 11965)+10% heat inactivated FBS (BioConcept, 2-01F136I) and incubated at 37° C., 5% $CO_2$. For the assay, imaging microtiterplate Cell Carrier 96 Ultra (Perkin Elmer 6055302) were pre-coated with Fibronectin (Sigma F085, 30 µl at 0.2 µg/ml) in PBS (100 µl, Gibco 14190) for 45 min at room temperature, rinsed with PBS and CAL-51 cells (30K cells/well) were plated and let to adhere overnight. Cells were treated with compounds typically using a serial dilution ranging from 30 µM to 0.1 nM for 6 hours. Compounds were stored at 10 mM DMSO stocks. Vehicle (DMSO), positive (CC-885, 10 µM) and rescue controls (positive control plus 0.2 µM bortezomib) were also included at this stage. Cells were subsequently rinsed with PBS and fixed in 10% Formalin solution (50 µl, Sigma HT5011)) for 20 mins at room temperature. Following three consecutive PBS washes (100 µl), cells were permeabilized in 0.1% Triton X-100 in PBS (Sigma 93443, 50 µl) for 15 mins at room temperature. Following three further PBS washes, 50µ blocking buffer (1% BSA, Sigma A4503, in PBS) was added for 45 min for signal-to-noise reduction.

Primary antibody (human GSPT1, Sigma HPA052488) was diluted in blocking buffer (dil. 1/300, 35 µl/well) and incubated with the cells overnight at 4° C. After three PBS washes, Alexa-fluor 488 coupled secondary antibodies (Invitrogen, A32731, dil. 1/1000), Alexa-fluor 647-Phalloidin (Invitrogen, A22287, dil. 1/200) and DAPI (Thermo, #62248, dil. 1/1000) were diluted in blocking buffer and incubated with the samples for 2 hours at room temperature. After three final PBS washes, samples were conserved in 100 µl PBS in the dark, until measurement. Image acquisition was performed on the Operetta High-Content Imager (Perkin-Elmer). Fluorescence intensity of Alexa-Fluor 488 (GSPT1), Alexa-Fluor 647 (Actin) and DAPI (Nucleus) were measured. For the determination of GSPT1 $DC_{50}$ values, a custom algorithm implemented in the PerkinElmer image analysis software Harmony-Acapella® was developed. After user-defined setting of adjustment parameters, the analysis was run identically without human intervention for all image fields. DAPI staining of the nuclei was used to determine the location of cells using standard nuclei detection modules. Segmentation artifacts were removed by threshold-based filters for area, roundness and intensity. The outline of the cells was determined analogously from the sum of the normalized, smoothed DAPI and Actin channel, starting from each nucleus. The Alexa-Fluor 488 (GSPT1) signal intensity in each cell was finally measured, in order to obtain a Mean intensity per cell. GSPT1 degradation ($DC_{50}$) was calculated after normalization to controls and data import in CDD vault Database, using non-linear regression.

TABLE 3

Activity for GSPT1 degradation
Table 3 assigns each compound a code indicating the ability for GSPT1 degradation: A, B or C. According to the code, A represents a DC50 value of ≤30 nM, B represents a DC50 value >30 nM and ≤30 nM and C represents a DC50 value of >300 nM.

| Compound | Code | Compound | Code | Compound | Code |
|---|---|---|---|---|---|
| 1 | A | 2 | A | 3 | A |
| 4 | A | 5 | A | 6 | A |
| 7 | B | 8 | A | 9 | B |
| 10 | A | 11 | A | 12 | B |
| 13 | A | 14 | C | 15 | A |
| 16 | C | 17 | C | 18 | B |
| 19 | B | 20 | C | 21 | A |
| 22 | C | 23 | C | 24 | A |
| 25 | A | 26 | C | 27 | C |
| 28 | C | 29 | C | 30 | C |
| 31 | B | 32 | B | 33 | B |
| 34 | A | 35 | C | 36 | C |
| 37 | B | 38 | C | 39 | A |
| 40 | B | 41 | A | 42 | A |
| 43 | A | 44 | B | 45 | B |
| 46 | A | 47 | A | 48 | A |
| 49 | A | 50 | A | 51 | B |
| 52 | C | 53 | B | 54 | C |
| 55 | A | 56 | B | 57 | A |
| 58 | A | 59 | B | 60 | B |
| 61 | A | 62 | B | 63 | C |
| 64 | B | 65 | C | 66 | B |
| 67 | B | 68 | A | 69 | A |
| 70 | B | 71 | B | 72 | B |
| 73 | B | 74 | A | 75 | B |
| 76 | B | 77 | A | 78 | B |
| 79 | A | 80 | B | 81 | B |
| 82 | C | 83 | A | 84 | A |
| 85 | A | 86 | A | 87 | A |
| 88 | A | 89 | C | 90 | A |
| 91 | A | 92 | A | 93 | B |
| 94 | B | 95 | A | 96 | A |
| 97 | C | 98 | C | 99 | B |
| 100 | B | 101 | B | 102 | C |
| 103 | B | 104 | B | 105 | B |
| 106 | B | 107 | C | | |
| 108 | B | 109 | A | | |
| 110 | A | 111 | B | 112 | B |
| 113 | B | 114 | A | 115 | B |
| 116 | B | 117 | B | 118 | A |
| 119 | C | 120 | B | 121 | C |
| 122 | B | 123 | C | 124 | B |
| 125 | C | 126 | A | 127 | B |
| 128 | C | 129 | B | 130 | C |
| 131 | B | 132 | B | 133 | B |
| 134 | B | 135 | A | 136 | B |
| 137 | A | 138 | C | 139 | B |
| 140 | A | 141 | B | 142 | B |
| 143 | B | 144 | B | 145 | B |
| 146 | B | 147 | C | 148 | C |
| 149 | C | 150 | A | 151 | B |
| 152 | A | 153 | A | 154 | B |
| 155 | B | 156 | A | 157 | A |

In some embodiments, the compounds of any of formula I to VIII exhibits a DC50 value of 30 nM or less, i.e. compounds with code A. In some embodiments the compound is selected from the group consisting of 1, 2, 3, 4, 5, 6, 8, 10, 11, 13, 15, 21, 24, 25, 34, 39, 41, 42, 43, 46, 47, 48, 49, 50, 55, 57, 58, 61, 68, 69, 74, 77, 79, 83, 84, 85, 86, 87, 88, 90, 91, 92, 95, 96, 109, 110, 118, 126, 135, 137, 140, 150, 152, 153, 156, and 157.

Example 5: CK1alpha/Ikaros/Aiolos/ZFP91 Selectivity Determination by Western Blot Assay MM1S cells were purchased from ATCC (cat. Number CRL-2974), sub-cultured in 90% RPMI 1640 with 10% FBS, supplemented with 1×P/S and incubated at 37° C., 500 CO2. Compounds were stored as 10 mM DMSO stock. For the assay, MM1S cells (3 million cells/well) were plated in 6-well plates and incubated over night. Cells were treated with respective compounds using a serial dilution: 0.3 µM, 3 µM and 30 µM as well as a vehicle only (DMSO) control for 6 hours. Media with suspension cells was subsequently transferred to 15 mL conical tubes, wells rinsed twice with ice-cold PBS and merged with cell suspension in respective 15 mL conical tube. Cells were spinned down, supernatant aspirated, pellets resuspended in ice-cold PBS and transferred to microtubes. Cells were spinned down, supernatant aspirated and pellets resuspended in 120 µL RIPA lysis buffer supplemented with protease and phosphatase inhibitors. Cell lysates were incubated on ice for 20 minutes followed by centrifugation at >20,000×g for 5 min. Supernatants were transferred to fresh microtubes and stored at −80° C. Total protein concentration was determined using a BCA assay with a BSA standard curve and concentration of all samples was adjusted to 1 mg/mL. 25 µL 4×LDS sample buffer supplemented with 100 mM DTT was added to 75 µL sample. Samples were centrifuged (8,000×g, 1 min) and incubated at 95° C. for 5 min followed by another centrifugation step (8,000×g, 1 min). 20 µL of each sample was loaded on a 4-12% gel alongside a protein molecular weight marker. Gels were run in the presence of MOPS buffer at 80

Volts for 30 min, followed by 120 Volts for 1.5 h and proteins subsequently transferred onto nitrocellulose membranes at 20 Volts for 7 min using an iBlot2 Gel Transfer Device. Membranes were then cut horizontally into two pieces, covering 80-50 kDa and 50-25 kDa. Blocking the membranes was performed by gently shaking in 5% (w/v) skim milk in TSB-T for 1 hr at room temperature. All primary antibodies were used at a 1/1000 in 5% (w/v) BSA dissolved in TBST and incubated with membranes over night at 4° C. Anti-IKZF1 (Ikaros; D6N9Y; 14859S), anti-IKZF3 (Aiolos; D1C1E; 15103S) antibodies were purchased from Cell Signalling Technology, anti-ZFP91 antibody from Bethyl laboratories, anti-GSPT1 from Sigma Aldrich (HPA052488) and anti CK1alpha from AbCam (ab206652). After three washes with 1×TBST for 5 min, HRP-coupled secondary antibodies diluted in 5% (w/v) BSA/TBST (Goat Anti-Rb IgG, dil. 1/10,000; Goat Anti-Mouse IgG, dil. 1/5000) were added for 1 hr at room temperature. After three washes with 1×TBST (5 minutes each), membranes were incubated with ECL reagent for 1 min at room temperature. Chemiluminescence signals were then detected using a LAS-4000 system with default settings and signals quantified using Image Studio Lite software (version 5.2). Membrane parts previously incubated with antibody against CK1alpha were stripped off antibodies by incubating with stripping buffer for 30 minutes followed by three washed with TBST (5 min each), blocking with 5% (w/v) skim milk for 1 hr, and incubation with primary antibody against GAPDH overnight at 4° C. Subsequent washes, incubation with secondary antibody and signal acquisition were performed as described above.

Quantitative Proteomics Analysis: ABC1 cells were treated with either DMSO (2 replicates) or compound 10 at 100 nM (2 replicates) for 6 hr. Proteins were extracted with the PreOmics iST-NHS lysis buffer (#P.O. 00030). The samples were then processed using the PreOmics kit following their recommended protocol with minor modifications. In brief, the proteins were reduced, alkylated and digested for 2h at 37° C. The peptides were then labelled with TMT reagent (1:4; peptide:TMT label) (Thermo Fisher Scientific). After quenching, the peptides were purified, and the 16 samples were combined to a 1:1 ratio. Mixed and labeled peptides were subjected to high-pH reversed-phase HPLC fractionation on an Agilent X-bridge C18 column (2.1 mm ID, 3.5 µm particles and 15 cm in length). Using an Agilent 1260 Infinity II LC system, a 60 min linear gradient from 0% to 45% 10 mM ammonium formate in 90% acetonitrile separated the peptide mixture into a total of 60 fractions, which were then consolidated into 24 fractions. The dried 24 fractions were reconstituted in 0.1% formic acid for LC-MS3 analysis. Labelled peptides were loaded onto an Aurora column from Ionopticks (75 µm ID, 1.6 µm particles, 25 cm in length) in an EASY-nLC 1200 system. The peptides were separated using a 168 min gradient from 4% to 30% buffer B (80% acetonitrile in 0.1% formic acid) equilibrated with buffer A (0.1% formic acid) at a flow rate of 400 nl/min. Eluted TMT peptides were analyzed on an Orbitrap Eclipse mass spectrometer (Thermo Fisher Scientific). MS1 scans were acquired at resolution 120,000 with 400-1400 m/z scan range, AGC target $4\times10^5$, maximum injection time 50 ms. Then, MS2 precursors were isolated using the quadrupole (0.7 m/z window) with AGC $1\times10^4$ and maximum injection time 50 ms. Precursors were fragmented by CID at a normalized collision energy (NCE) of 35% and analyzed in the ion trap. Following MS2, synchronous precursor selection (SPS) MS3 scans were collected by using high energy collision-induced dissociation (HCD) and fragments were analyzed using the Orbitrap (NCE 55%, AGC target $1\times10^5$, maximum injection time 120 ms, resolution 60,000). Protein identification and quantification were performed using Proteome Discoverer 2.4.0.305 with the SEQUEST algorithm and Uniprot human database (2021-01-29, 20614 protein sequences). Mass tolerance was set at 10 ppm for precursors and at 0.6 Da for fragment. Maximum of 3 missed cleavages were allowed. Methionine oxidation was set as dynamic modification, while TMT tags on peptide N termini/lysine residues and cysteine alkylation (+113.084) were set as static modifications. The list of identified peptide spectrum matches (PSMs) was filtered to respect a 1% False Discovery Rate (FDR) after excluding PSMs with TMT reporter ion signal-to-noise value lower than 10 and a precursor interference level value higher than 50%. Subsequently, protein identifications were inferred from protein specific peptides, i.e. peptides matching multiple protein entries were excluded. Protein relative quantification was performed using an in-house developed java notebook. This analysis included multiple steps; adjustment of reporter ion intensities for isotopic impurities according to the manufacturer's instructions, global data normalization by equalizing the total reporter ion intensity across all channels, summation of reporter ion intensities per protein and channel, calculation of protein abundance log 2 fold changes (L2FC) and testing for differential abundance using moderated t-statistics where the resulting p-values reflect the probability of detecting a given L2FC across sample conditions by chance alone.

TABLE 4

Selectivity for relevant Zincfinger proteins:
Table 4 assigns each compound a code indicating the ability for the degradation of IKZF1, IKZF3, CK1alpha and ZFP91 in comparison to GSPT1: A, B, C, D, E or F.
According to the code, A represents a no degradation observed at 30 µM, B represents trace degradation at 30 µM (below 20%), C represents weak degradation at 30 µM (below 50%), D represents degradation at 30 µM (>90%), E represents degradation at 3 µM (>90%) and F represents degradation at 0.3 µM (>90%).

| Compound | IKZF1 | IKZF3 | CK1alpha | ZFP91 | GSPT1 |
|---|---|---|---|---|---|
| 1 | A | B | B | A | F |
| 3 | A | A | B | B | F |
| 6 | A | B | A |   | F |
| 10 | A | B | B |   | D |
| 15 | A | B | C |   | F |
| 42 | A | A | B |   | F |
| 43 | A | B | C |   | F |
| 47 | A | A | B | B | F |
| 48 | A | B | B |   | F |
| 49 | A | A | B | B | F |

Figure 1B:
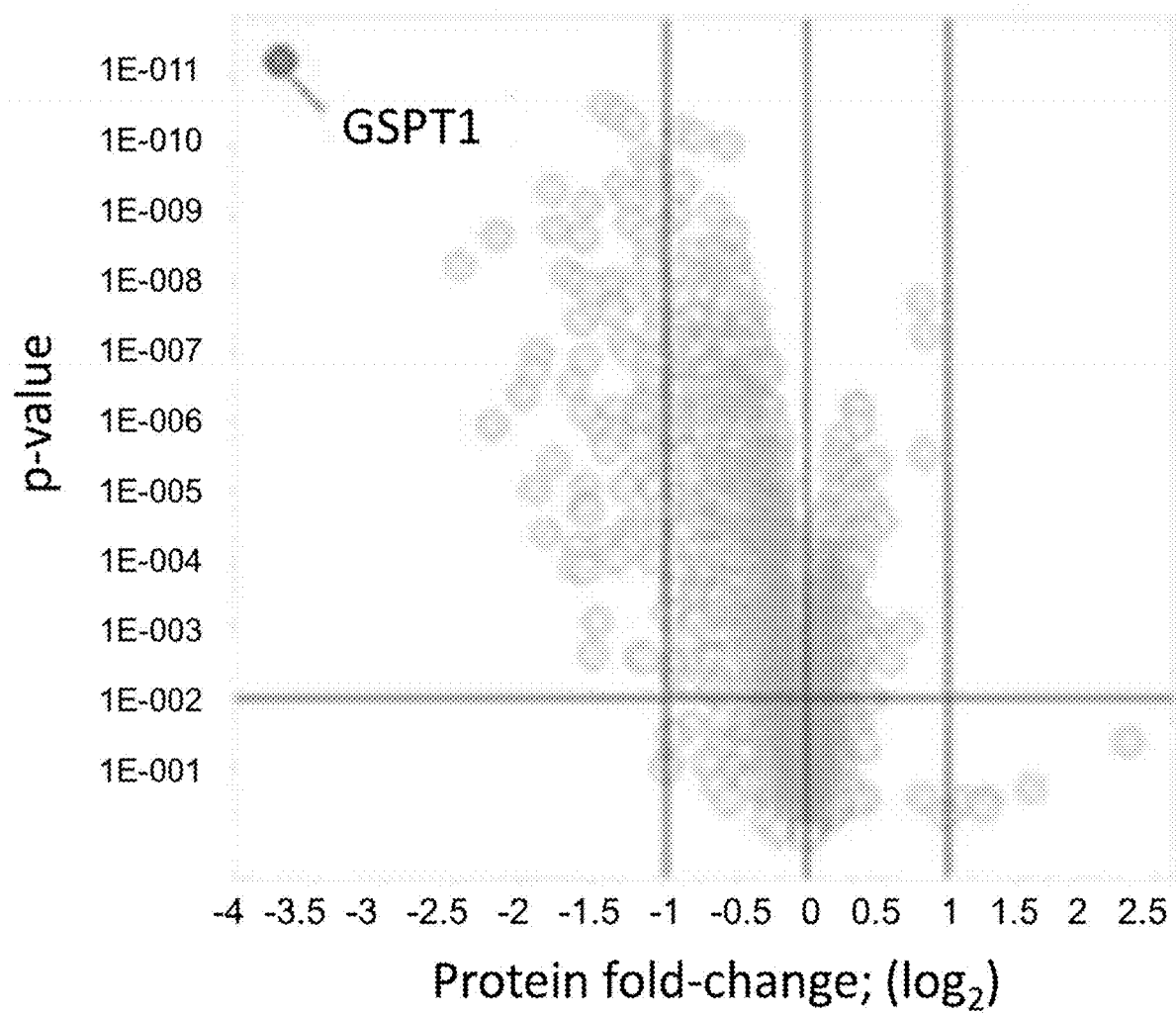
FIG. 1B shows that based on a mass spectrometry-based proteomics analysis of a cancer cell line treated with compound 10, GSPT1 was the most statistically significant downregulated protein (x-axis represents the protein fold-change ($\log_2$); y-axis represents the p-value, which is an assessment of whether the observation is a result of change or the result of a random occurrence, with smaller p-values suggesting stronger evidence of an actual change).

FIG. 1A shows that compound 10 induced complete GSPT1 degradation in cells treated at a concentration of 0.3 µM. In contrast, none of the known the substrates IKZF1, IKZF3, SALL4, CK1alpha was degraded at the highest concentration tested of 30 µM. In addition, mass spectrometry-based proteomics analysis of a cancer cell line treated with compound 10 demonstrated that GSPT1 was the most statistically significant downregulated protein (FIG. 1).

Example 6: Viability Assay and GSPT1 Degradation in Representative in NSCLC Cell Lines The anti-proliferative activity of compound 10 was tested on representative N-Myc high and N-Myc low cell lines (NCI-H1155, ABC-1 and EBC-1, NCI-H2023, respectively)

following treatment with compound for 72 hours. Cells were sub-cultures as recommended by the providers (ATCC, DSMZ) and incubated at 37° C., 5% $CO_2$. All cells were authenticated and confirmed by Short Tandem Repeat (STR) profiling. Briefly, cells were seeded to the appropriate density to allow logarithmic growth over the assay period in 96-well opaque-walled clear bottom plates (from Corning, Cat. No. 3903, Lot. No. 16419061; 100 µL total volume) and incubated overnight. Compound 10 and DMSO control were subsequently dispensed to the plates using HPD300 and a 9 data-point titration curve with concentrations ranging from 30 µM to 0.1 nM. Dilutions were prepared fresh prior to the assay using a 10 mM DMSO stock. Final DMSO concentration was 0.5%. The plates were incubated for 3 days at 5% $CO_2$, 37° C. Cell viability was assessed using the CellTiter-Glo assay kit as recommended by the Manufacturer (Promega, Cat. No. G7558, Lot. No. 0000385738) and measurements performed on the EnSpire multimode plate reader (Perkin Elmer). EC50 values were determined using Prism8 (GraphPad) and the asymmetric (five-parameter) equation and least squares fit. GSPT1 levels were assessed in the NCI-H1155 and ABC-1 cell lines by densitometry analysis following treatment with compound 10 for 6 hours and western blotting analysis. Briefly, cells were rinsed with PBS and lysed using 50 µL RIPA lysis buffer (Pierce 8990) supplemented with protease and phosphate inhibitors (Sigma P8340, Sigma 5726, and Sigma 0044). Primary antibody (human GSPT1, Sigma HPA052488) was diluted in blocking buffer (dil. 1/5000) and incubated with the membranes overnight at 4° C. After two rinses with 1×TBST and two washes with 1×TBST (10 minutes each with shaking at room temperature), HRP-coupled secondary antibody (Invitrogen, A16110, dil. 1/5000) and DyLight680-coupled GAPDH antibody (Invitrogen, MA5-15738-D680, dil. 1/2500) were diluted in blocking buffer, added to membranes and incubated with shaking for at least 45 minutes at room temperature protected from light. Membranes were then transferred between two clean sheets of plastic and chemiluminescence (GSPT1), Dylight680 fluorescence (GAPDH) as well as colorimetric (molecular weight standard) signals were detected using a Chemidoc MP imaging system (BioRad 17001402). For chemiluminescence and colorimetric signals "optimal automatic exposure" settings (3×3 binning) were employed while fluorescence was detected using 1-4 seconds exposure time to achieve best GAPDH signals and avoid overexposure. For image analysis "Image Lab" software (BioRad version 6.0.1) was used. If automatic lane and band detection failed, lanes and bands were indicated manually. Default background correction settings were used. Relative GSPT1 protein levels were calculated by setting GSPT1 levels in vehicle (DMSO)-treated control samples to 100% and normalized to the GAPDH singlas. Dose response data was visualized and a four-parameter non-linear regression curve fitting algorithm (Graphpad Prism version 8.3.0) was used to calculate $DC_{50}$ (value corresponding to 50% reduction in GSPT1 total levels).

Figure 2A:
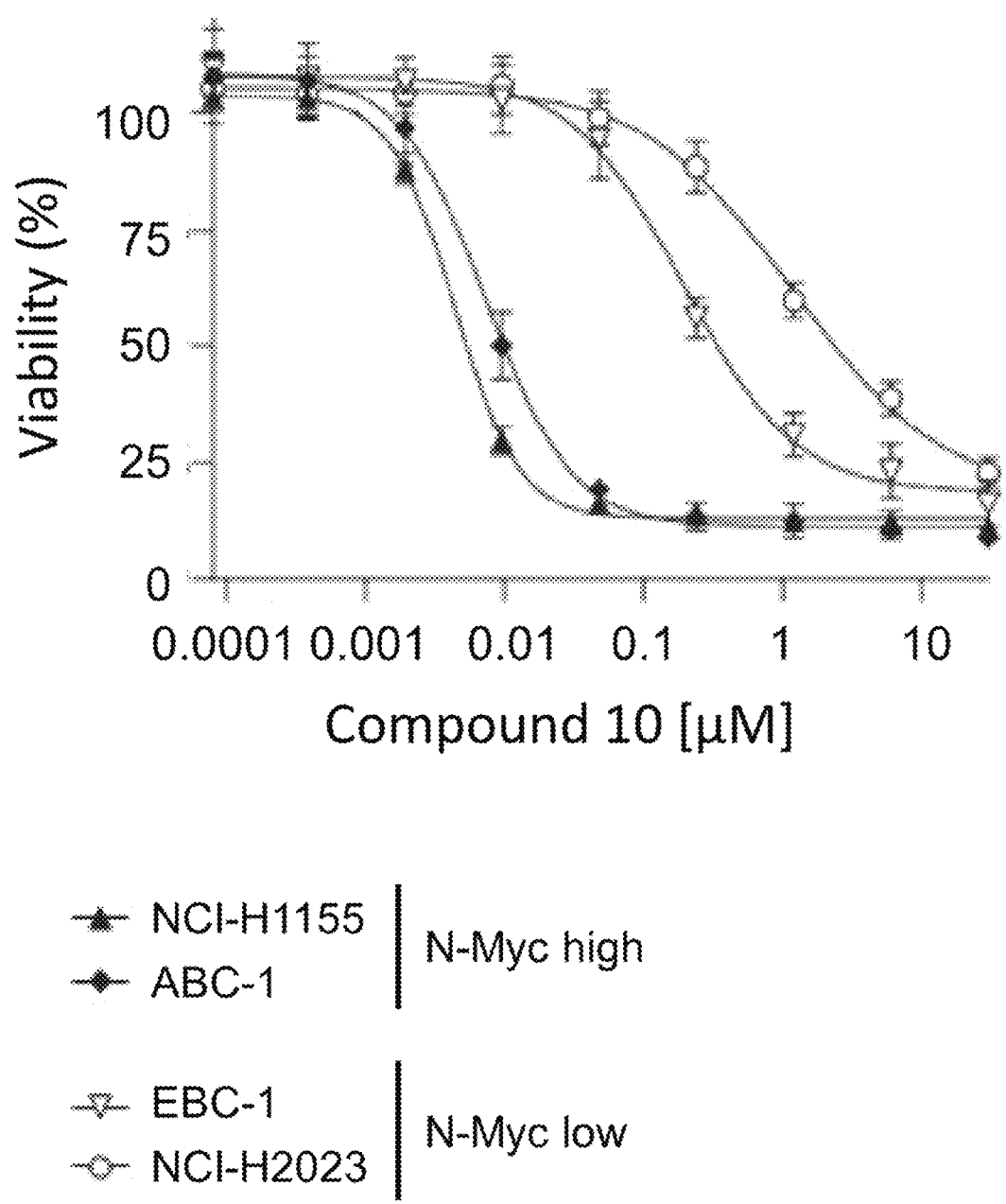
FIG. 2A shows that NSCLC cell lines expressing high levels of N-Myc (NCI-H1155 represented as filled triangles, ABC-1 represented as filled rhombi) were highly sensitive to treatment with compound 10, when compared to the cell lines expressing low levels of N-Myc (EBC-1 represented as empty triangles, NCI-H2023 represented as empty circles). GSPT1 was degraded by compound 10 after six hours of treatment in high N-Myc NCI-H1155 and ABC-1 cells with a DC50 of 3 nM and 22 nM, respectively (x-axis represents □M concentration of compound 10; y-axis represents the viability in %). In both cell lines, we observed complete degradation of GSPT1.
Figure 2B:
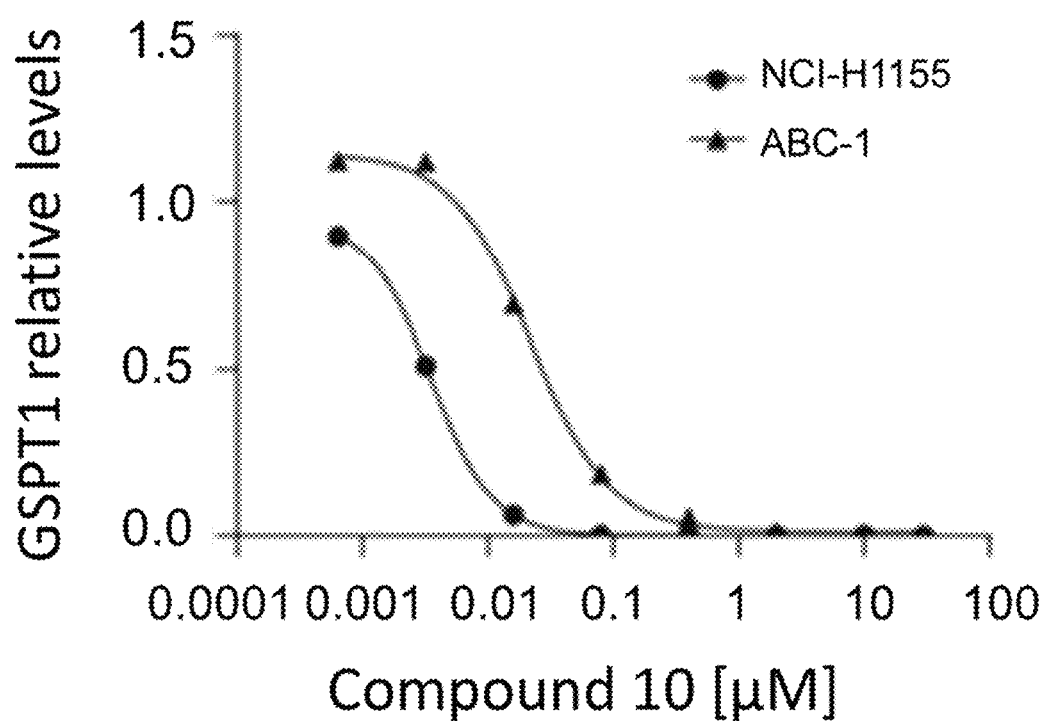
FIG. 2B illustrates that compound 10 degrades GSPT1 in a concentration dependent manner (x-axis represents □M concentration of compound 10; y-axis represents relative levels of GSPT1)

Complete degradation of GSPT1 by compound 10 was observed after six hours of treatment in high N-Myc NCI-H1155 and ABC-1 cells with a DC50 of 3 nM and 22 nM, respectively. Compound 10 sensitivity correlated with the expression of N-Myc in the NSCLC cell line (FIG. 2A). Degradation took place in a concentration dependent manner (FIG. 2B).

Example 7: Representative In Vivo Efficacy Study—Tumor Growth Inhibition in MDA-MB-213 Model MDA-MB-231 cells (human breast adenocarcinoma) were maintained in vitro in DMEM medium supplemented with 20% heat inactivated FBS at 37° C. in an atmosphere of 5% $CO_2$ in air. Cells (10 millions) resuspended in 0.2 mL of PBS with Matrigel (50:50) were inoculated into female BALB/c nude mice and allowed to grow to 150 $mm^3$ in size. Mice were dosed daily i.p. with vehicle or a representative compound of the disclosure (0.3, 1 and 3 mg per kilogram p.o.). Compound formulations were prepared fresh daily in 5% DMSO/95% (30% HP-β-CD in purified water). Mice were dosed for 21 days and tumor volumes measured every 3 days. Highest tumor growth was observed in mice having received administration of vehicle only. Tumor growth was reduced by administration of increasing amounts of a representative compound of the disclosure. No tumor growth or a reduction in tumor size was observed when administering 1 mg/kg or less of a representative compound of the disclosure.

Example 8 In Vivo Efficacy Studies in N-Myc High NSCLC and SCLC Cell Lines

Figure 3A:
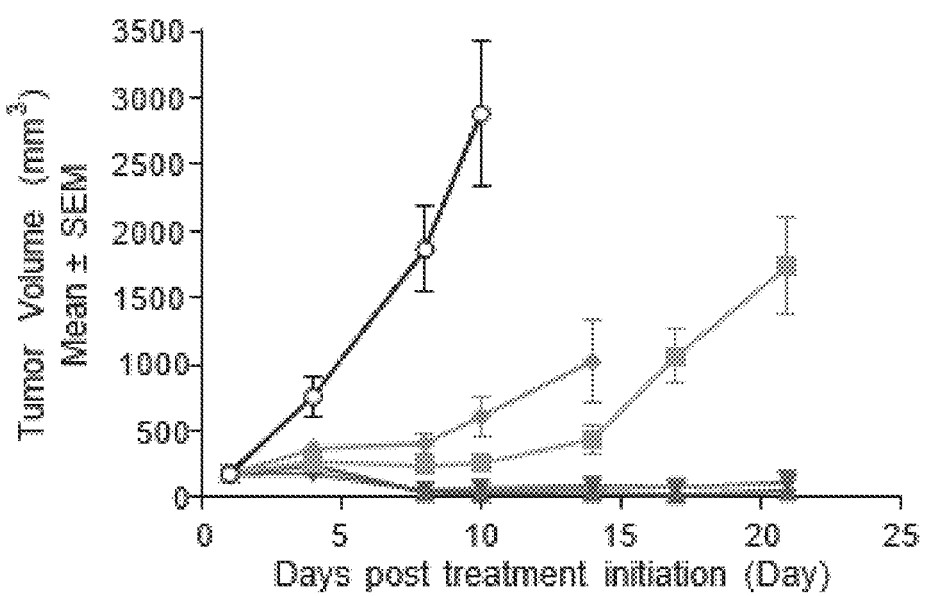
FIG. 3A shows that oral administration of compound 10 in a N-Myc-driven mouse xenograft model using the human cell line NCI-H1155 led to tumor growth inhibition (with no body weight loss observed). At a dose of 1 mg/kg once daily, tumor growth was suppressed for two weeks. At a dose of 3 mg/kg once daily or 6 mg/kg dosed for five days on and nine days off, tumor size decreased, became undetectable by day eight and remained so until the end of the study at day 21 (x-axis represents days post treatment initiation [days]; y-axis represents tumor volume [mm$^3$], mean±SEM; empty circles O: vehicle, PO, QD; filled squares, 1 mg/kg, PO, QD; filled triangles, 3 mg/kg PO, QD; filled triangles inverted, 6 mg/kg, PO, 5 on-9 off; filled rhombi, gemcitabine 40 mg/kg IP, Q4D×5).

For the NCI-H1155 xenograft study, cells (human non small cell lung cancer, ATCC CRL-5818) were maintained in vitro as suspension culture in ATCC-formulated DMEM: F12 Medium supplemented as recommended by the provider and kept at 37° C. in an atmosphere of 5% $CO_2$ in air. Cells (0.5 millions) were resuspended in 0.2 mL of PBS with Matrigel (50:50) and inoculated into female BALB/c nude mice, 6-8 weeks old, and allowed to grow to 150 $mm^3$ in size. Mice were dosed orally with either vehicle or compound 10 at 1 or 3 mg per kilogram daily (filled squares and filled triangles, respectively) or 6 mg per kilogram for 5 continuous days followed by 9 days treatment holidays (5 On—9 off) (filled inverted triangles). Compound formulations were prepared fresh daily in 5% vDMSO/95%(30% w/v HP-β-CD in water). Gemcitabine dosed at 40 mg per kilogram, IP, Q4D×5 was used as a positive control (filled rhombi). For this study, mice were dosed for 21 days with tumor volumes measured every 3 days. Results are shown in FIG. 3A for compound 10 (x-axis: days; y-axis: tumor volume in $mm^3$) and indicate that oral administration of compound 10 in a N-Myc-driven mouse xenograft model using the human cell line NCI-H1155 led to tumor growth inhibition (with no body weight loss observed). At a dose of 1 mg/kg once daily, tumor growth was suppressed for two weeks. At a dose of 3 mg/kg once daily or 6 mg/kg dosed for five days on and nine days off, tumor size decreased, became undetectable by day eight and remained so until the end of the study at day 21.

Figure 3B:
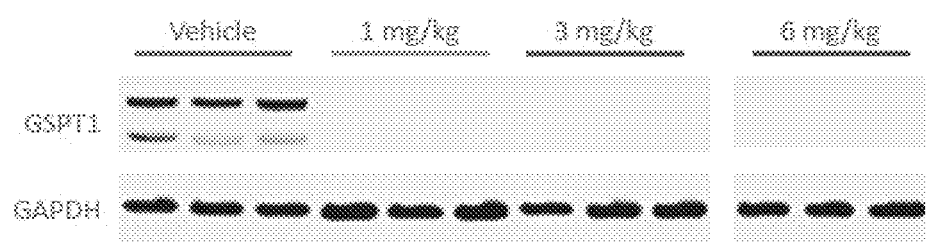
FIG. 3B shows complete degradation of GSPT1 in tumors of mice treated with compound 10 at all three dose levels as compared to mice treated with vehicle control (from left to right: vehicle, 1 mg/kg, 3 mg/kg, 6 mg/kg).

GSPT1 levels in tumors were determined by western blotting 6 hours after the third dose. Western blotting was performed as described previously using GAPDH as loading control. Complete degradation of GSPT1 was observed in tumors of mice treated with compound 10 at all three dose levels as compared to mice treated with vehicle control (FIG. 3B).

Figure 3C:
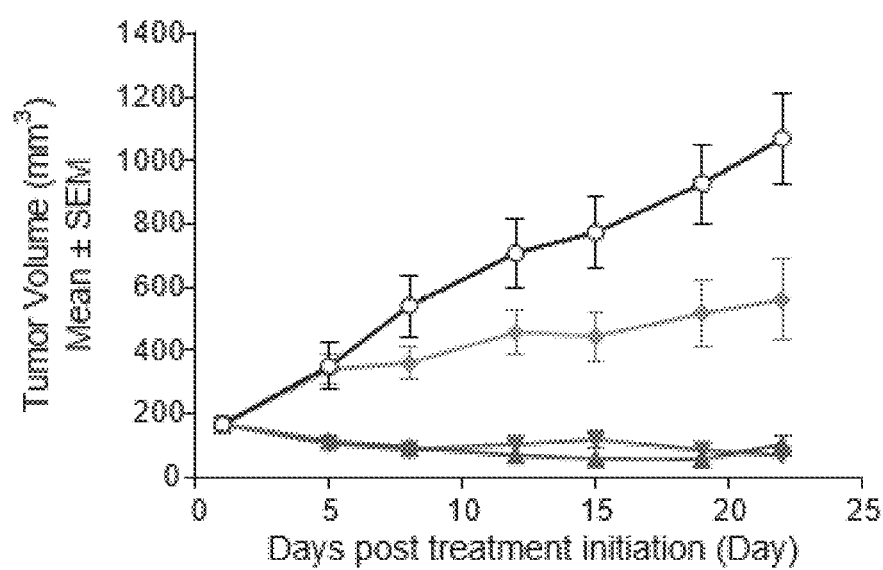
FIGS. 3C and 3D show that oral administration of compound 10 in a N-Myc-driven mouse xenograft model using the human cell line NCI-H1770 and NCI-H526, respectively, led to tumor growth inhibition (with no body weight loss observed). At a dose of 3 mg/kg once daily or 6 mg/kg dosed for five days on and nine days off, tumor size decreased and remained so until the end of the study (x-axis represents days post treatment initiation [days]; y-axis represents tumor volume [mm$^3$], mean±SEM; empty circle O: vehicle, PO, QD; filled triangles, 3 mg/kg PO, QD; filled triangles inverted, 6 mg/kg, PO, 5 on-9 off; filled rhombi, cisplatine 6 mg/kg IP, QW×3).

For the NCI-H1770 study, cells (human non small cell lung cancer, ATCC CRL-5893, Lot No. 5188933) were maintained in vitro as suspension culture in ATCC-formulated RPMI-1640 Medium supplemented by 10% FBS and cultured at 37° C. in an atmosphere of 5% $CO_2$ in air. Cells (10.0 millions) were resuspended in 0.2 mL of PBS with Matrigel (50:50) and inoculated into female BALB/c nude mice, 6-8 weeks old, and allowed to grow to 150 mm$^3$ in size. Mice were dosed orally with either vehicle (empty circles) or compound 10 at 3 mg per kilogram daily or 6 mg per kilogram for 5 continuous days followed by 9 days treatment holidays (5 On—9 off) (filled triangles and filled inverted triangles, respectively). Compound formulations were prepared fresh daily in 5% vDMSO/95%(30% w/v HP-β-CD in water). Cisplatin dosed at 6 mg per kilogram, IP, QW×3 was used as a positive for this model (filled rhombi). Mice were dosed for 21 days with tumor volumes measured every 3 days. Similar results were observed as for NCI-H1155 as shown in FIG. 3C for compound 10 (x-axis: days; y-axis: tumor volume in mm$^3$).

Figure 3D:
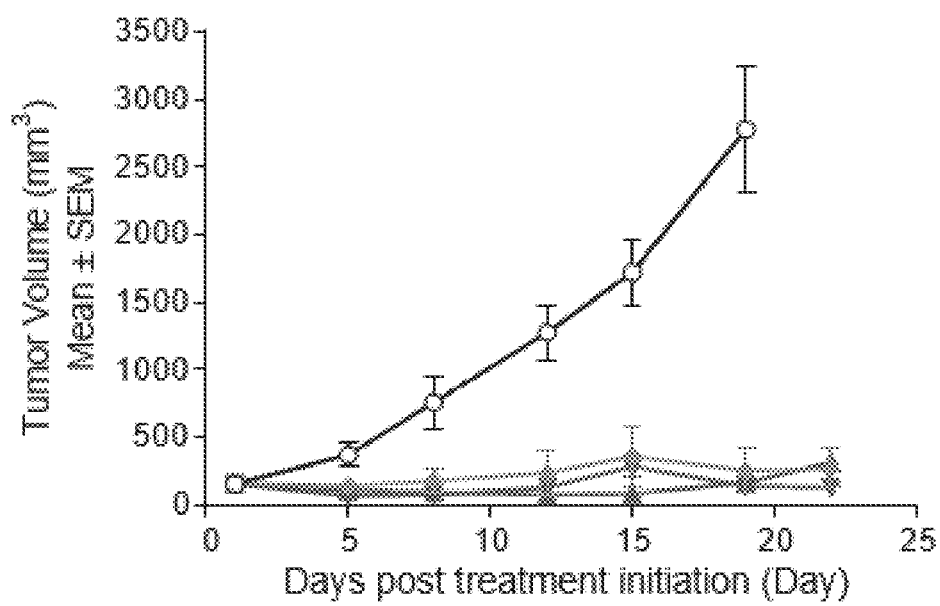

For the NCI-H526 study, cells (human small cell lung cancer, ATCC CRL-5811) were maintained in vitro as suspension culture in ATCC-formulated RPMI-1640 Medium supplemented with 10% FBS and cultured at 37° C. in an atmosphere of 5% $CO_2$ in air. Cells (2.5 millions) were resuspended in 0.2 mL of PBS with Matrigel (50:50) and inoculated into female BALB/c nude mice, 6-8 weeks old, and allowed to grow to 150 mm$^3$ in size. Mice were dosed orally with either vehicle (empty circles) or compound 10 at 3 mg per kilogram daily or 6 mg per kilogram for 5 continuous days followed by 9 days treatment holidays (5 On—9 off) (filled triangles and filled inverted triangles, respectively). Compound formulations were prepared fresh daily in 5% vDMSO/95%(30% w/v HP-β-CD in water). Cisplatin dosed at 6 mg per kilogram, IP, QW×3 was used as a positive for this model (filled rhombi). Mice were dosed for 21 days with tumor volumes measured every 3 days. Similar results were observed as for NCI-H1155 as shown in FIG. 3D for compound 10 (x-axis: days; y-axis: tumor volume in mm$^3$).

Example 9: HTRF Binding of Compounds to CRBN and Activity for GSPT1 Degradation

Compound activity was monitored in a Homogenous Time-Resolved Fluorescence (HTRF) assay using 1-[5-({2-[2-(2-{[2-(2,6-dioxopiperidin-3-yl)-1,3-dioxo-2,3-dihydro-1H-isoindol-4-yl]oxy}acetamido)ethoxy]ethyl}carbamoyl)pentyl]-3,3-dimethyl-2-[(1E,3E)-5-[(2E)-1,3,3-trimethyl-5-sulfo-2,3-dihydro-1H-indol-2-ylidene]penta-1,3-dien-1-yl]-3H-indol-1-ium-5-sulfonate as a fluorescent probe. Biochemical assays were conducted in Greiner white 384 well HiBase plates (Cat. No 784075-25) in 10 μL total volume. A one pot detection solution of CRBN-DDB1 (2.5 nM), Anti-His Terbium Cryptate Gold (1×, PerkinElmer Cat. #: 61HI2TLB), and Cy5-Thalidomide (100 nM, Tenova Cat.: T52461) was prepared in 20 mM HEPES, 20 mM NaCl, 0.2 mM TCEP, 0.2 mM EDTA, and 0.005% Tween20 was dispensed to each assay plate. Compounds were stored in dry, ambient temperatures at 10 mM. A 10-point, 1:3 dilution series was prepared from 10 mM stock concentrations in Echo-compatible LDV plates. 10 nL of each compound dilution series was dispensed into assays wells using an Echo 650 (Labcyte inc. USA). 10 nL of 10 mM Lenalidomide was transferred into the active-control wells for the assay and 10 nL of DMSO was transferred into the neutral-control wells. The assay was then allowed to incubate for 30 min at ambient temperature after transferring compound. Plate measurements were taken on a Pherastar FSX (BMG Labtech, Germany) using the HTRF Red filter (Ex. 337 nm, em1: 620 nm, em2: 665 nm) (Flashes: 50, Integration time: 60-400 us, Z-height: 10 mm, Ratio-multiplier: 10,000). The HTRF signal was then subsequently normalized to the neutral and active controls. Analysis and IC50 values were derived using KNIME analytics (KNIME Zurich) transformation and fitting within Collaborative Drug Discovery (Collaborative Drug Discovery USA). Ki was derived from the geometric mean of the IC50 values using the Cheng-Prustoff transformation.

Example 10: Compound Activity by Immunofluorescence Assay

The representative compounds were tested in an immunofluorescence assay for their activity to degrade GSPT1. CAL-51 cells were purchased from DSMZ (cat. Number ACC302), sub-cultured in 90% Dulbecco's MEM (4.5 g/L glucose, Gibco 11965)+10% heat inactivated FBS (BioConcept, 2-01F136I) and incubated at 37° C., 5% $CO_2$. For the assay imaging microtiter plate Cell Carrier 96 Ultra (Perkin Elmer 6055302) were pre-coated with Fibronectin (Sigma F085, 30 μl at 0.2 g/ml) in PBS (100 μL, Gibco 14190) for 45 min at room temperature, rinsed with PBS and CAL-51 cells (30K cells/well) were plated and let to adhere overnight. Cells were treated with compounds typically using a serial dilution ranging from 30 μM to 0.1 nM for 6 h. Compounds were stored at 10 mM DMSO stocks. Vehicle (DMSO), positive (CC-885, 10 μM) and rescue controls (positive control plus 0.2 μM bortezomib) were also included at this stage. Cells were subsequently rinsed with PBS and fixed in 10% Formalin solution (50 μl, Sigma HT5011)) for 20 mins at room temperature. Following three consecutive PBS washes (100 μL), cells were permeabilized in 0.1% Triton X-100 in PBS (Sigma 93443, 50 μL) for 15 min. at room temperature. Following three further PBS washes, 50 μL blocking buffer (1% BSA, Sigma A4503, in PBS) was added for 45 min for signal-to noise reduction. Primary antibody (human GSPT1, Sigma HPA052488) was diluted in blocking buffer (dil. 1/300, 35 L/well) and incubated with the cells overnight at 4° C. After three PBS washes, Alexa-fluor 488 coupled secondary antibodies (Invitrogen, A32731, dil. 1/1000), Alexa-fluor 647-Phalloidin (Invitrogen, A22287, dil. 1/200) and DAPI (Thermo, #62248, dil. 1/1000) were diluted in blocking buffer and incubated with the samples for 2 h at room temperature. After three final PBS washes, samples were conserved in 100 μL PBS in the dark, until measurement. Image acquisition was performed on the Operetta High-Content Imager (Perkin-Elmer). Fluorescence intensity of Alexa-F 5 luor 488 (GSPT1), Alexa-Fluor 647 (Actin) and DAPI (Nucleus) were measured. For the determination of GSPT1 DC50 values, a custom algorithm implemented in the PerkinElmer image analysis software Harmony-Acapella® was developed. After user-defined setting of adjustment parameters, the analysis was run identically without human intervention for all image fields. DAPI staining of the nuclei was used to determine the location of cells using standard nuclei detection modules. Segmentation artifacts were removed by threshold-based filters for area, roundness and intensity. The outline of the cells was determined analogously from the sum of the normalized, smoothed DAPI and Actin channel, starting from each nucleus. The Alexa-Fluor 488 (GSPT1) signal intensity in each cell was finally measured, in order to obtain a Mean intensity per cell. GSPT1 degradation (DC50) was calculated after normalization to controls and data import in CDD vault Database, using non-linear regression.

In Table 5 each compound is assigned a class (HTRF class) indicating the ability for Cereblon binding by means of their HTRF IC50 values according to Example 9: A, B, C or D. According to the code, A represents an IC50 value of 100 nM, B represents an IC50 value>100 nM and ≤1000 nM, C represents an IC50 value>1000 nM. IF Class assigns each compound a code indicating the ability for GSPT1 degradation: A, B or C. According to the code, A represents a DC50 value of ≤30 nM, B represents a DC50 value>30 nM and ≤300 nM and C represents a DC50 value of >300 nM. The IF data were obtained according to Example 10.

TABLE 5

HTRF Binding of compounds to CRBN and Activity for GSPT1 degradation.

| Compound | HTRF Class | IF Class |
|---|---|---|
| 158 | A | C |
| 159 | B | B |
| 160 | B | C |
| 161 | B | C |
| 162 | B | C |
| 163 | B | C |
| 164 | B | C |
| 165 | B | A |
| 166 | A | C |
| 167 | A | C |
| 168 | B | C |
| 169 | B | B |
| 170 | B | B |
| 171 | B | C |
| 172 | B | C |
| 173 | B | C |
| 174 | A | A |
| 175 | C | A |
| 176 | A | A |
| 177 | B | B |
| 178 | B | C |
| 179 | B | A |
| 180 | B | B |
| 181 | B | B |
| 182 | B | C |
| 183 | B | B |
| 184 | B | C |
| 185 | B | C |
| 186 | B | A |
| 187 | A | C |
| 188 | B | A |
| 189 | A | B |
| 190 | B | C |
| 191 | B | B |
| 192 | A | B |
| 193 | B | C |
| 194 | B | C |
| 195 | B | C |
| 196 | A | C |
| 197 | A | B |
| 198 | B | C |
| 199 | B | C |
| 200 | B | B |
| 201 | B | B |
| 202 | B | C |
| 203 | B | C |
| 204 | B | B |
| 205 | B | B |
| 206 | B | B |
| 207 | A | B |
| 208 | B | C |
| 209 | B | C |
| 210 | A | C |
| 211 | A | B |
| 212 | A | A |
| 213 | A | C |
| 214 | A | B |
| 215 | B | C |
| 216 | B | A |
| 217 | B | A |
| 218 | A | C |
| 219 | A | C |
| 220 | B | A |
| 221 | A | B |
| 222 | B | B |
| 223 | A | C |

TABLE 5-continued

HTRF Binding of compounds to CRBN and Activity for GSPT1 degradation.

| Compound | HTRF Class | IF Class |
|---|---|---|
| 224 | B | B |
| 225 | A | C |
| 226 | B | B |
| 227 | B | C |
| 228 | A | A |
| 229 | A | B |
| 230 | A | A |
| 231 | A | A |
| 232 | A | B |
| 233 | B | B |
| 234 | A | C |
| 235 | B | B |
| 236 | A | A |
| 237 | A | B |
| 238 | B | C |
| 239 | B | A |
| 240 | B | B |

The invention claimed is:

1. A compound or pharmaceutically acceptable salts or stereoisomers thereof of formula I:

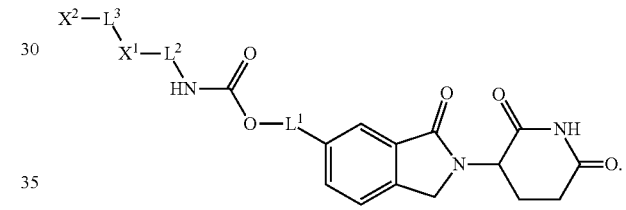

wherein $X^1$ is linear or branched $C_{1-6}$ alkyl, $C_{3-8}$ cycloalkyl, $C_{6-10}$ aryl, 5-10 membered heteroaryl, 4-8 membered heterocycloalkyl, wherein $X^1$ is unsubstituted or substituted with one or more of halogen, linear or branched $C_{1-6}$ alkyl, linear or branched $C_{1-6}$ heteroalkyl, $CF_3$, $CHF_2$, $CMeF_2$, —O—$CHF_2$, —O—$(CH_2)_2$—OMe, $OCF_3$, $C_{1-6}$ alkylamino, —CN, —N(H)C(O)—$C_{1-6}$alkyl, —OC(O)—$C_{1-6}$alkyl, —OC(O)—$C_{1-4}$alkylamino, —C(O)O-$C_{1-6}$alkyl, —COOH, —$C_{1-6}$alkylC(O) OH, —$C_{1-6}$alkylC(O)O-$C_{1-6}$alkyl, $NH_2$, $C_{1-4}$ alkoxy, $C_{1-4}$ alkylhydroxy, —$CH_2F$, —N(H) C(O)—O-$C_{1-6}$ alkyl, and $C(OH)(CF_3)$;

or $X^1$ together with the N atom of the carbamate forms a 4-8 membered heterocycloalkyl, which is unsubstituted or substituted with one or more of halogen, linear or branched —$C_{1-6}$ alkyl, $CF_3$, $CHF_2$, $CMeF_2$, —O—$(CH_2)_2$—OMe, $OCF_3$, $OCHF_2$, $C_{1-6}$ alkylamino, —CN, —N(H)C(O)—$C_{1-6}$alkyl, —OC(O)—$C_{1-6}$alkyl, —C(O)O-$C_{1-6}$alkyl, —COOH, —$C_{1-6}$alkylC(O) OH, —$C_{1-6}$alkylC(O)O-$C_{1-6}$alkyl, $NH_2$, $C_{1-4}$ alkylhydroxy, and $C_{1-4}$ alkoxy;

$X^2$ is H, $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and $C_{1-4}$ alkylhydroxy;

$L^1$ is a covalent bond, linear or branched $C_{1-6}$ alkyl;

$L^2$ is a covalent bond, linear or branched $C_{1-6}$ alkyl; and

L³ is a covalent bond, linear or branched $C_{1-6}$ alkyl, —O—, or —$C_{1-4}$ alkoxy, wherein linear or branched $C_{1-6}$ alkyl is unsubstituted or substituted with one or more of halogen.

2. The compound of claim 1, or pharmaceutically acceptable salts or stereoisomers thereof, wherein $X^1$ is linear or branched —$C_{1-6}$ alkyl, —$C_{3-6}$ cycloalkyl, —$C_{6-10}$ aryl, 5-10 membered heteroaryl, 5-6 membered heterocycloalkyl, wherein $X^1$ is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy; or $X^1$ together with the N atom of the carbamate forms a 5-6 membered heterocycloalkyl, which is unsubstituted or substituted with one or more of halogen, linear or branched —$C_{1-4}$ alkyl, $CF_3$, $CHF_2$, $CMeF_2$, —O—$(CH_2)_2$—OMe, $OCF_3$, $OCHF_2$, $C_{1-6}$ alkylamino, —CN, $NH_2$, $C_{1-4}$ alkylhydroxy, and $C_{1-4}$ alkoxy.

3. The compound of claim 1, wherein $X^2$ is H, $C_{3-6}$ cycloalkyl, $C_6$ aryl, 5-6 membered heteroaryl, 4-8 membered heterocycloalkyl, wherein $X^2$ is unsubstituted or substituted with one or more of linear or branched $C_{1-4}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and —$C_{1-4}$ alkylhydroxy.

4. The compound of claim 1, wherein $L^1$ is —$CH_2$— or —$CH(CH_3)$— and/or $L^2$ is a covalent bond, —$CH_2$— or —$CH(CH_3)$— and/or $L^3$ is a —$CH_2$—, —O—, —$CH_2$—O—, —$CH_2$—$CH_2$—O—.

5. The compound of claim 1, or pharmaceutically acceptable salts or stereoisomers thereof of formula II:

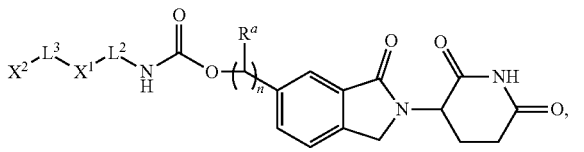

II wherein
$X^1$ is linear or branched $C_{1-6}$ alkyl, $C_{3-6}$ cycloalkyl, $C_{6-10}$ aryl, 5-10 membered heteroaryl, 4-8 membered heterocycloalkyl, wherein $X^1$ is unsubstituted or substituted with one or more of halogen, linear or branched $C_{1-6}$ alkyl, linear or branched $C_{1-6}$ heteroalkyl, $CF_3$, $CHF_2$, $CMeF_2$, —O—$CHF_2$, —O—$(CH_2)_2$—OMe, $OCF_3$, $C_{1-6}$ alkylamino, —CN, —N(H) C(O)—$C_{1-6}$alkyl, —OC(O)—$C_{1-6}$alkyl, —OC(O)—$C_{1-4}$alkylamino, —C(O)O-$C_{1-6}$alkyl, —COOH, —$C_{1-6}$alkylC(O) OH, —$C_{1-6}$alkylC(O)O-$C_{1-6}$alkyl, $NH_2$, $C_{1-4}$ alkoxy and $C_{1-4}$ alkylhydroxy;

or $X^1$ together with the N atom of the carbamate forms a 4-8 membered heterocycloalkyl, which is unsubstituted or substituted with one or more of halogen, linear or branched —$C_{1-6}$ alkyl, $CF_3$, $CHF_2$, $CMeF_2$, —O—$(CH_2)_2$—OMe, $OCF_3$, $OCHF_2$, $C_{1-6}$ alkylamino, —CN, —N(H)C(O)—$C_{1-6}$alkyl, —OC(O)—$C_{1-6}$alkyl, —C(O)O-$C_{1-6}$alkyl, —COOH, —$C_{1-6}$alkylC(O) OH, —$C_{1-6}$alkylC(O)O-$C_{1-6}$alkyl, $NH_2$, $C_{1-4}$ alkylhydroxy, and $C_{1-4}$ alkoxy;

$X^2$ is H, $C_{3-6}$ cycloalkyl, $C_{6-10}$ aryl, 5-10 membered heteroaryl, 4-8 membered heterocycloalkyl, wherein $X^2$ is unsubstituted or substituted with one or more of linear or branched $C_{1-6}$ alkyl, —$C_{1-4}$ alkoxy, $NH_2$, $NMe_2$, halogen, $CF_3$, $CHF_2$, $CMeF_2$, —O—$(CH_2)_2$—OMe, $OCF_3$, $OCHF_2$, and $C_{1-4}$ alkylhydroxy;

$L^2$ is a covalent bond, linear or branched $C_{1-6}$ alkyl;

$L^3$ is a covalent bond, linear or branched $C_{1-6}$ alkyl, —O—, —$C_{1-4}$ alkoxy;

$R^a$ is H or linear or branched $C_{1-4}$ alkyl, such as methyl or ethyl, n is 1 or 2.

6. The compound of claim 5, or pharmaceutically acceptable salts or stereoisomers thereof, wherein n is 1 and $R^a$ is H or methyl.

7. The compound of claim 5, or pharmaceutically acceptable salts or stereoisomers thereof, wherein p is 0.

8. The compound of claim 5, or pharmaceutically acceptable salts or stereoisomers thereof, wherein p is 1 and $R^b$, $R^c$ are H or wherein p is 1, $R^b$ is methyl and $R^c$ is H.

9. The compound of claim 5, wherein $L^2$ is a covalent bond, —$CH_2$— or —$CH(CH_3)$— and/or $L^3$ is a —$CH_2$—, —O—, —$CH_2$—O—, —$CH_2$—$CH_2$—O—.

10. The compound of claim 1, or pharmaceutically acceptable salts or stereoisomers thereof, of formula III, such as IVa or IVb:

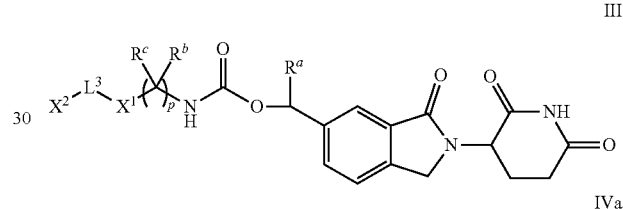

III

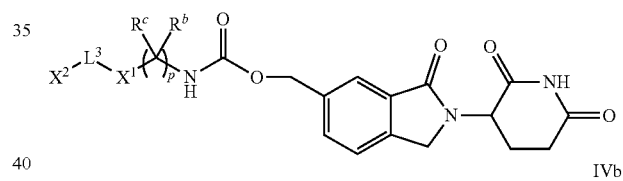

IVa

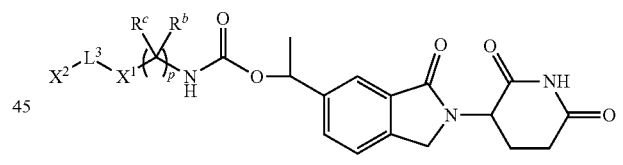

IVb wherein
$X^1$ is linear or branched $C_{1-6}$ alkyl, $C_{3-6}$ cycloalkyl, $C_{6-10}$ aryl, 5-10 membered heteroaryl, 4-8 membered heterocycloalkyl, wherein $X^1$ is unsubstituted or substituted with one or more of halogen, linear or branched $C_{1-6}$ alkyl, linear or branched $C_{1-6}$ heteroalkyl, $CF_3$, $CHF_2$, $CMeF_2$, —O—$CHF_2$, —O—$(CH_2)_2$—OMe, $OCF_3$, $C_{1-6}$ alkylamino, —CN, —N(H) C(O)—$C_{1-6}$alkyl, —OC(O)—$C_{1-6}$alkyl, —OC(O)—$C_{1-4}$alkylamino, —C(O)O-$C_{1-6}$alkyl, —COOH, —$C_{1-6}$alkylC(O) OH, —$C_{1-6}$alkylC(O)O-$C_{1-6}$alkyl, $NH_2$, $C_{1-4}$ alkoxy and $C_{1-4}$ alkylhydroxy;

or $X^1$ together with the N atom of the carbamate forms a 4-8 membered heterocycloalkyl, which is unsubstituted or substituted with one or more of halogen, linear or branched —$C_{1-6}$ alkyl, $CF_3$, $CHF_2$, $CMeF_2$, —O—$(CH_2)_2$—OMe, $OCF_3$, $OCHF_2$, $C_{1-6}$ alkylamino, —CN, —N(H)C(O)—$C_{1-6}$alkyl, —OC(O)—$C_{1-6}$alkyl, —C(O)O-$C_{1-6}$alkyl, —COOH, —C$_{1-6}$alkylC(O) OH, —C$_{1-6}$alkylC(O)O-C$_{1-6}$alkyl, NH$_2$, C$_{1-4}$ alkylhydroxy, and C$_{1-4}$ alkoxy;

X$^2$ is H, C$_{3-6}$ cycloalkyl, C$_{6-10}$ aryl, 5-10 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and C$_{1-4}$ alkylhydroxy;

L$^3$ is a covalent bond, linear or branched C$_{1-6}$ alkyl, —O—, —C$_{1-4}$ alkoxy;

R$^a$, R$^b$, R$^c$ are independently of each other H, linear or branched C$_{1-4}$ alkyl, such as methyl;

p is 0 or 1.

11. The compound of claim 10, or pharmaceutically acceptable salts or stereoisomers thereof, wherein p is 0.

12. The compound of claim 10, or pharmaceutically acceptable salts or stereoisomers thereof, wherein p is 1 and R$^b$, R$^c$ are H or wherein p is 1, R$^b$ is methyl and R$^c$ is H.

13. The compound of claim 1, or pharmaceutically acceptable salts or stereoisomers thereof, of formula V, VI or VII:

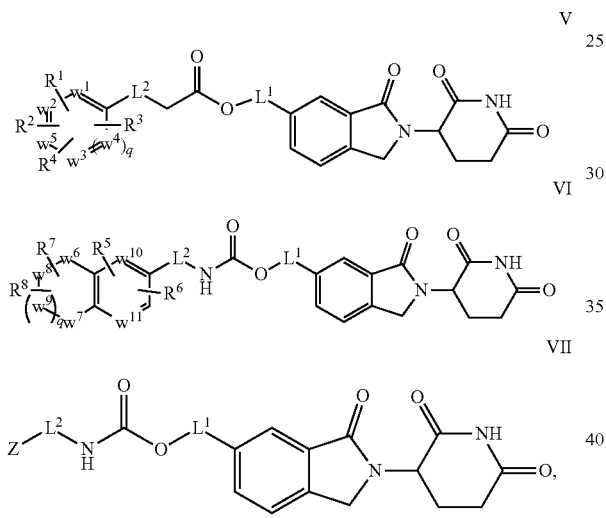

wherein
one or two of w$^1$, w$^2$, w$^3$, w$^4$, w$^5$ are independently of each other selected from C, N, S, and O, and the remaining of w$^1$, w$^2$, w$^3$, w$^4$, w$^5$ are C;
one or two of w$^6$, w$^7$, w$^8$, w$^9$ are selected from C and O and the remaining of w$^6$, w$^7$, w$^8$, w$^9$ are C;
w$^{10}$, w$^{11}$ are independently of each other selected from C and N;
L$^1$ is a covalent bond, linear or branched C$_{1-6}$ alkyl;
L$^2$ is a covalent bond, linear or branched C$_{1-6}$ alkyl;
R$^1$, R$^2$, R$^3$, R$^4$ are independently of each other selected from H, linear or branched —C$_{1-6}$ alkyl, linear or branched C$_{1-6}$ heteroalkyl, —C$_{1-4}$ alkoxy, CF$_3$, CHF$_2$, CMeF$_2$, —O—(CH$_2$)$_2$—OMe, OCF$_3$, OCHF$_2$, —C$_{1-6}$ alkylamino, —CN, —OC(O)—C$_{1-6}$alkyl, —N(H)C(O)—C$_{1-6}$alkyl, —C(O)O—C$_{1-6}$alkyl, —COOH, —C$_{1-6}$alkylC(O) OH, —C$_{1-6}$alkylC(O)O-C$_{1-6}$alkyl, NH$_2$, —C$_{1-4}$ alkylhydroxy, and halogen, such as F, Cl or Br, e.g. F or Cl, or a group of formula -L$^3$-X$^2$, wherein L$^3$ is a covalent bond, linear or branched C$_{1-6}$ alkyl, —O—, —C$_{1-4}$ alkoxy and X$^2$ is C$_{3-6}$ cycloalkyl, C$_{6-10}$ aryl, 5-10 membered heteroaryl, 4-8 membered heterocycloalkyl, wherein X$^2$ is unsubstituted or substituted with one or more of linear or branched C$_{1-6}$ alkyl, —C$_{1-4}$ alkoxy, NH$_2$, NMe$_2$, halogen, CF$_3$, CHF$_2$, CMeF$_2$, —O—(CH$_2$)$_2$—OMe, OCF$_3$, OCHF$_2$, and —C$_{1-4}$ alkylhydroxy;

R$^5$, R$^6$, R$^7$ R$^8$ are independently of each other selected from H, linear or branched C$_{1-4}$ alkyl, such as methyl, and halogen, such as F or Cl, e.g. F;

Z is linear or branched —C$_{1-6}$ alkyl, —C$_{3-6}$ cycloalkyl, 4-8 membered heterocycloalkyl, wherein Z is unsubstituted or substituted with C$_{1-4}$ alkyl, C$_6$ aryl, C$_6$ aryloxy, 6 membered heteroaryl or CF$_3$; or Z together with the N atom of the carbamate forms a 4-8 membered heterocycloalkyl, which is unsubstituted or substituted with C$_{1-4}$ alkyl, C$_6$ aryl, C$_6$ aryloxy, 6 membered heteroaryl or CF$_3$;

q is 0, 1.

14. The compound of claim 1, or pharmaceutically acceptable salts or stereoisomers thereof, of formula VIII or VIIIa

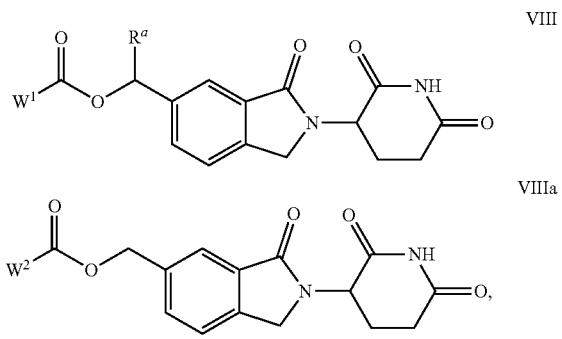

wherein R$^a$ is H or methyl and W$^1$ and W$^2$ are selected from

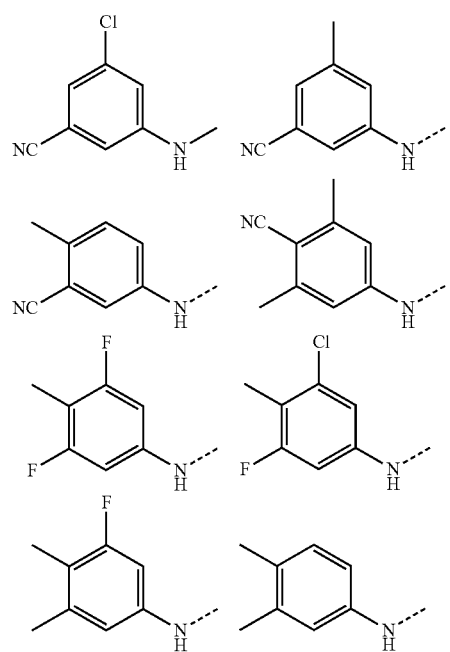

491
-continued
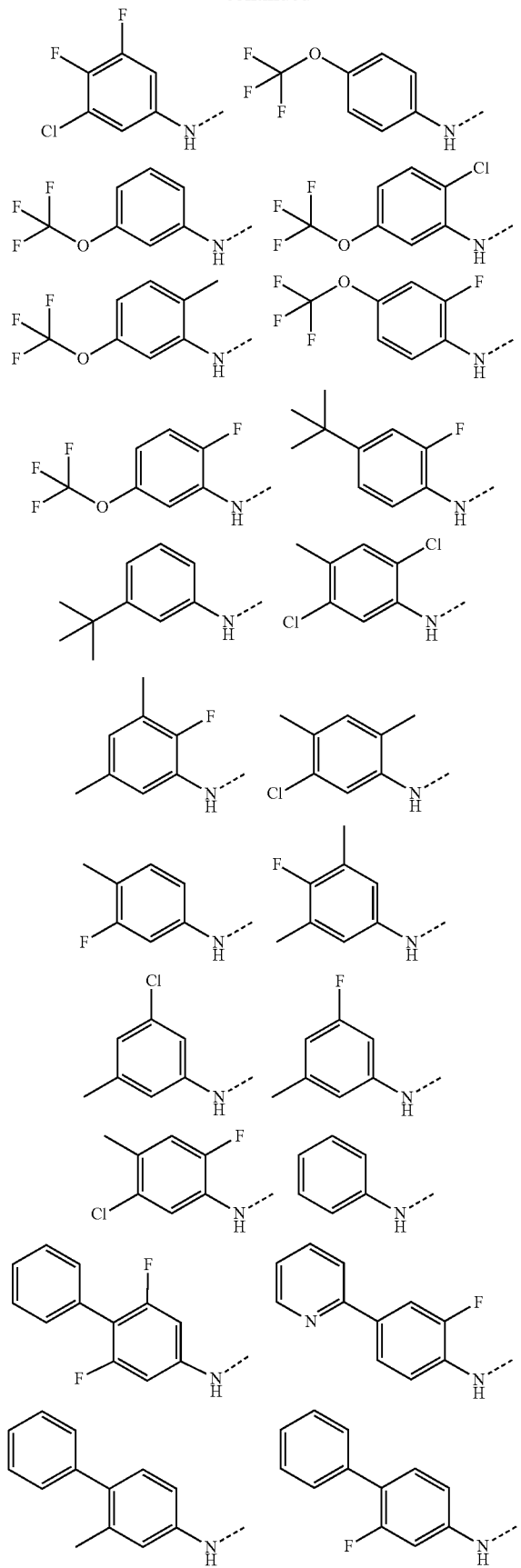
492
-continued
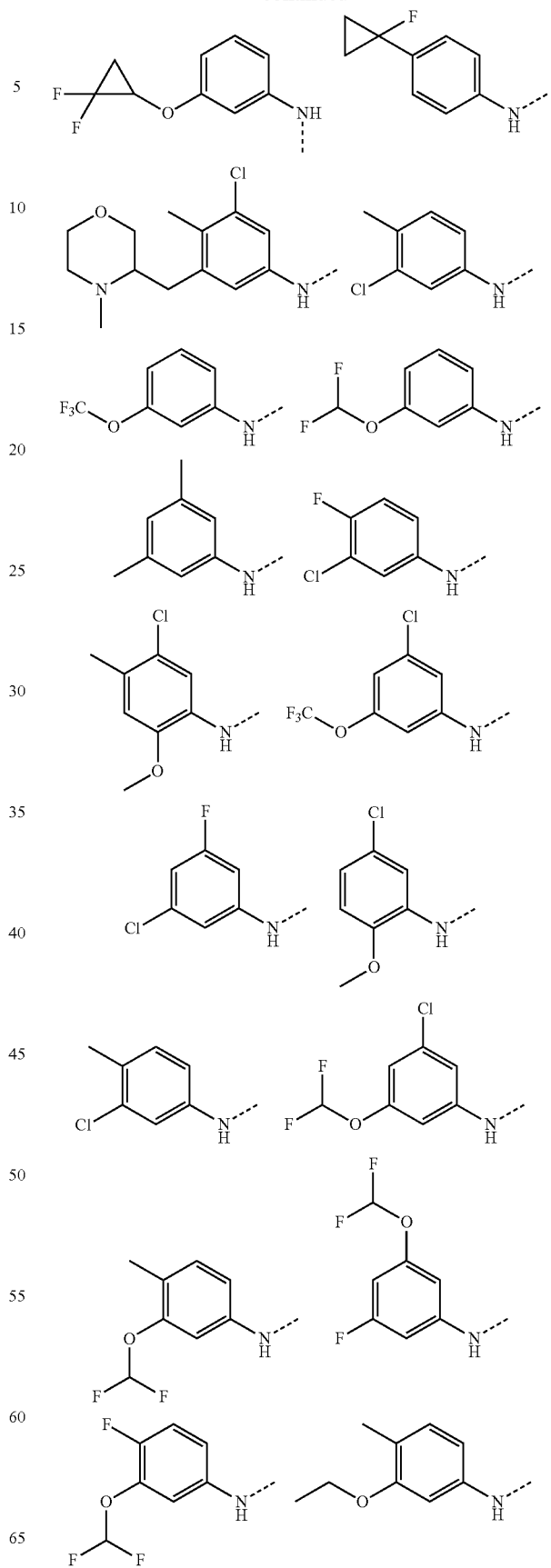

493
-continued
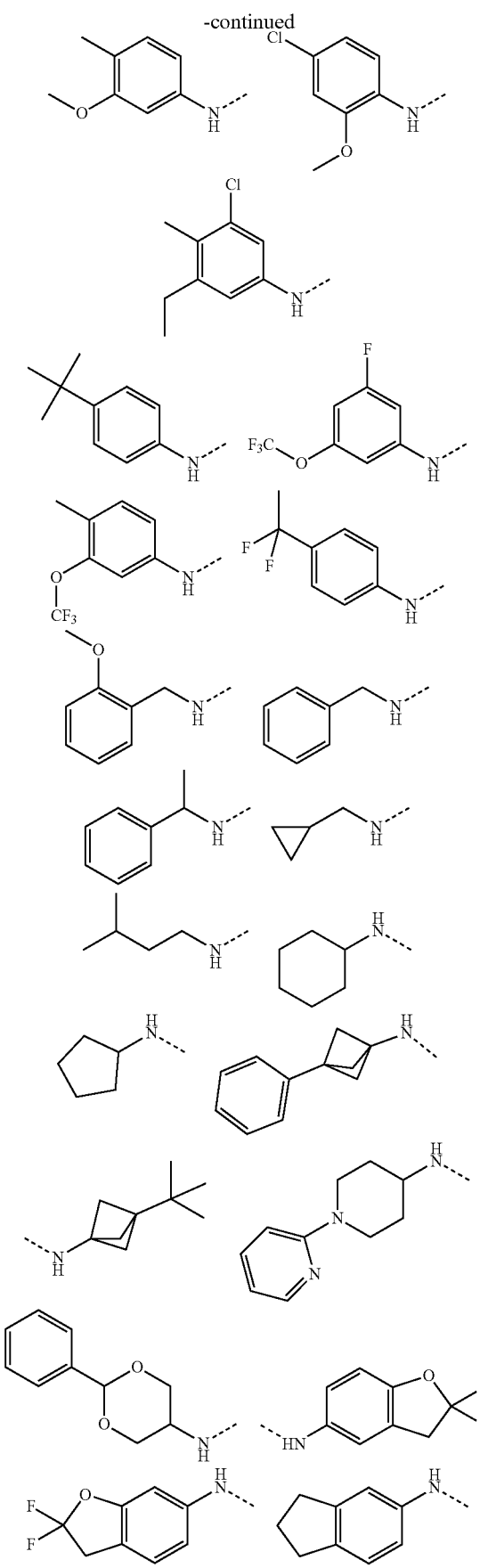
494
-continued
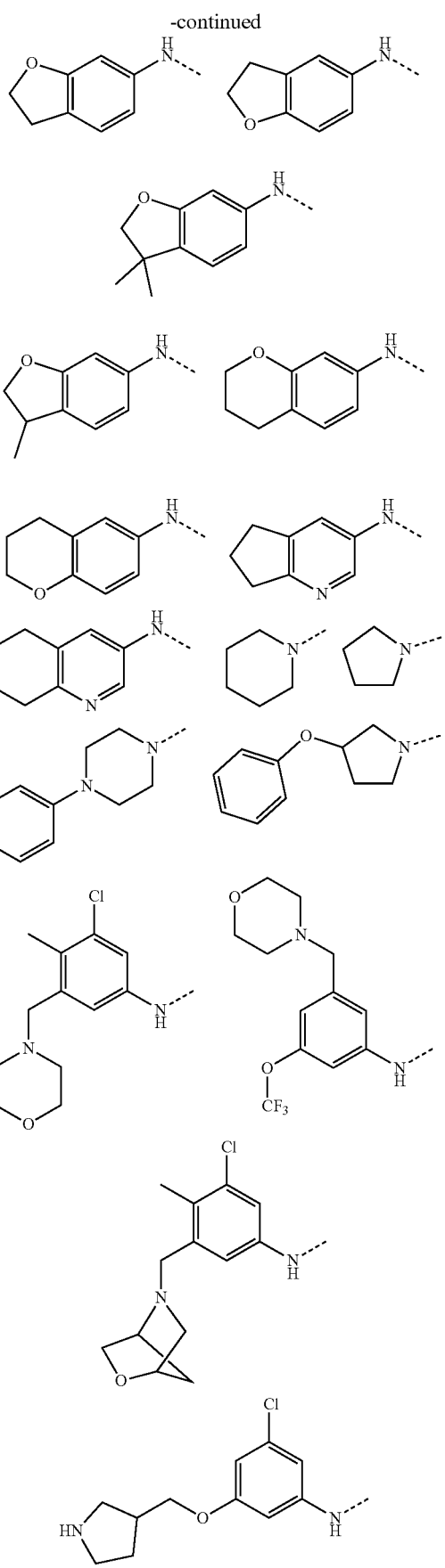

495
-continued
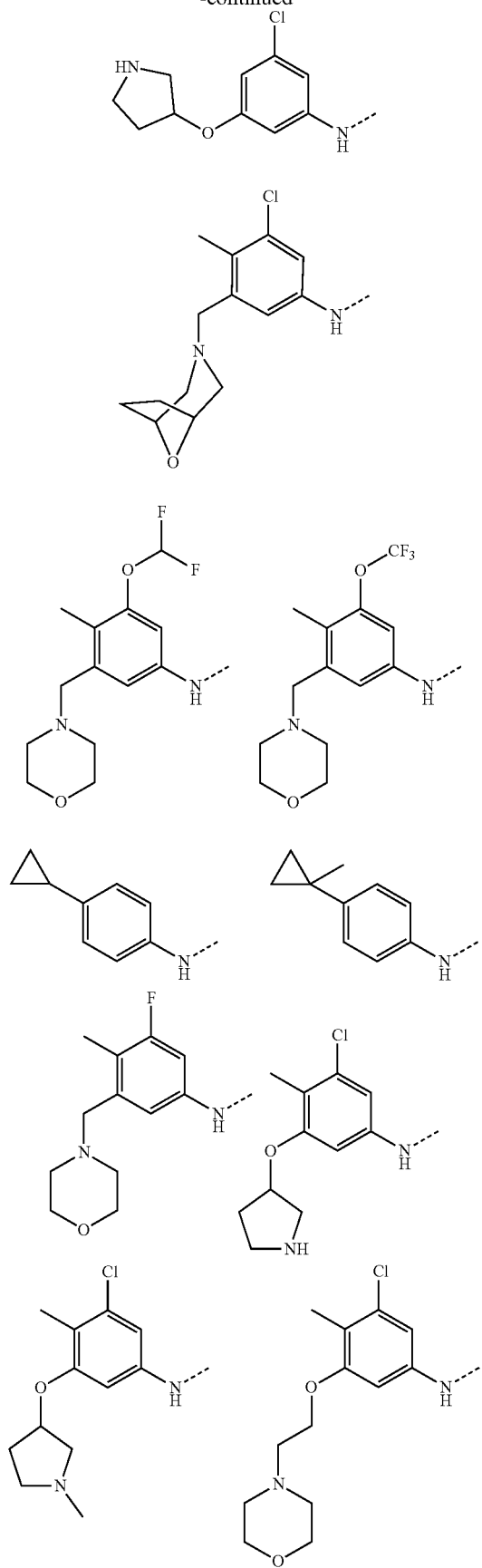
496
-continued
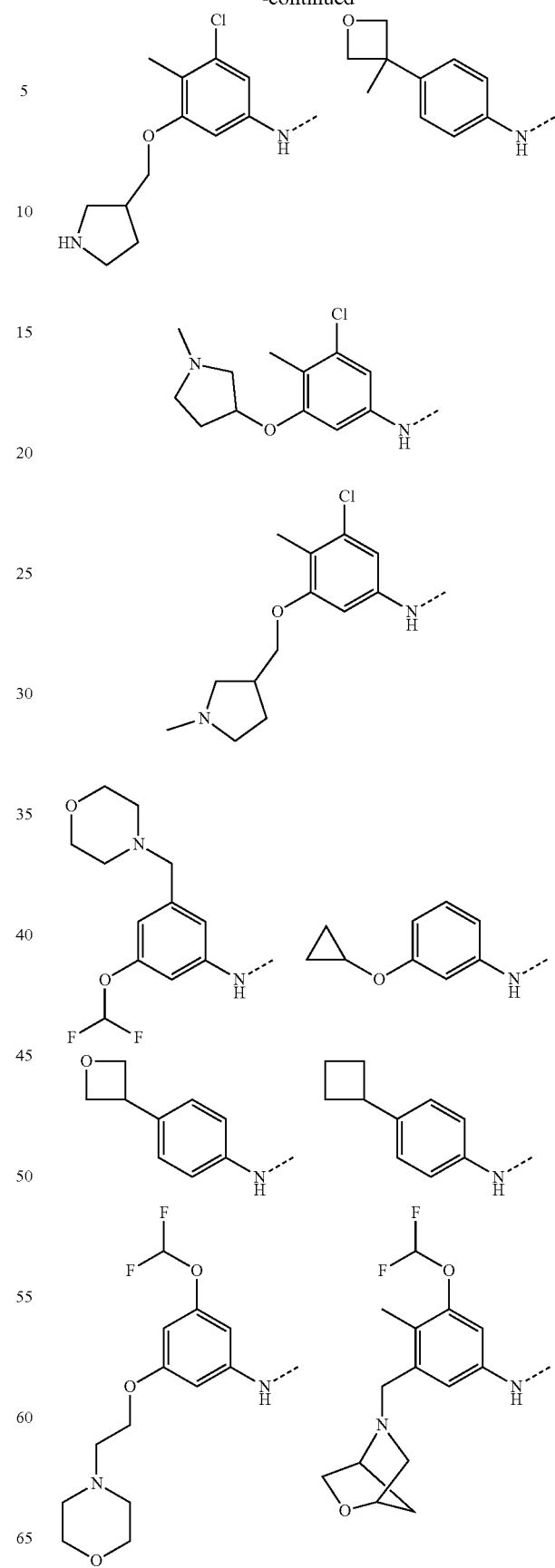

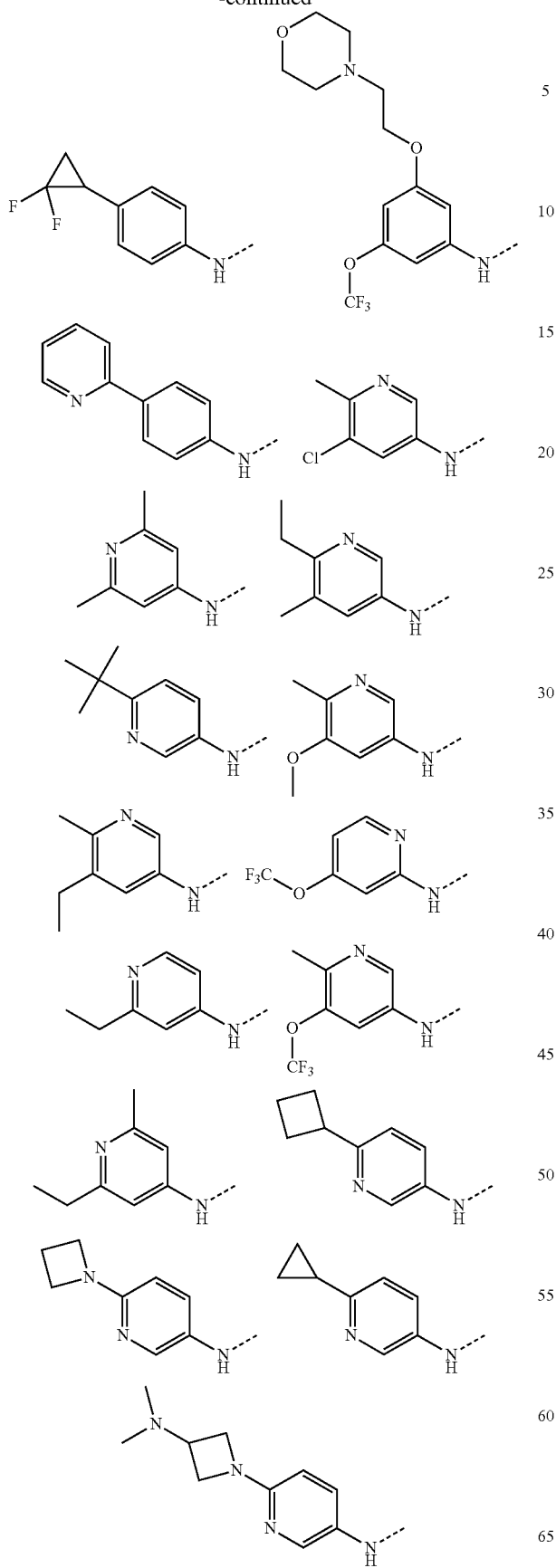
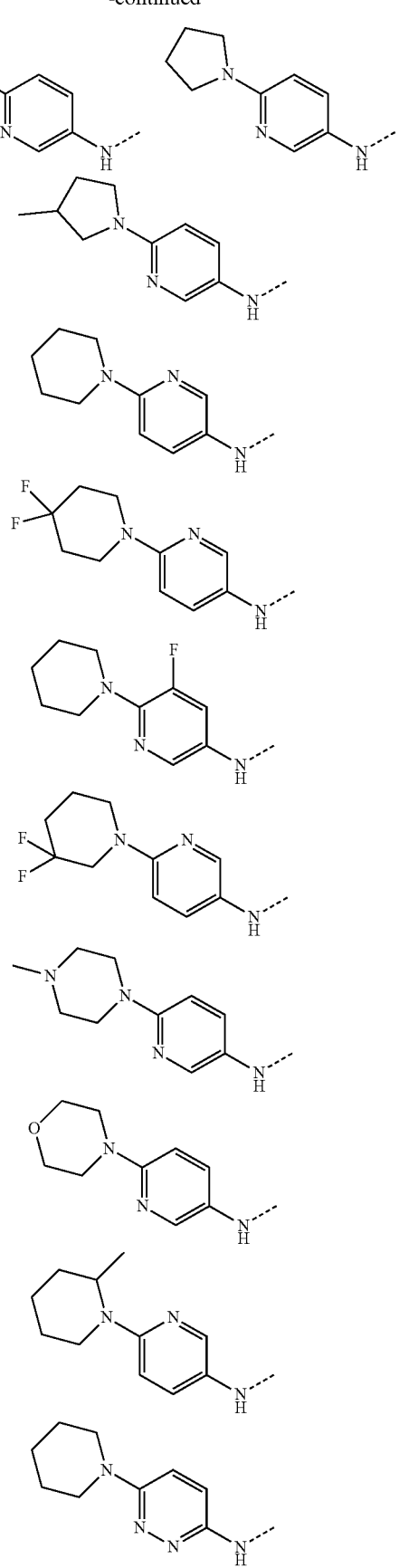

499
-continued

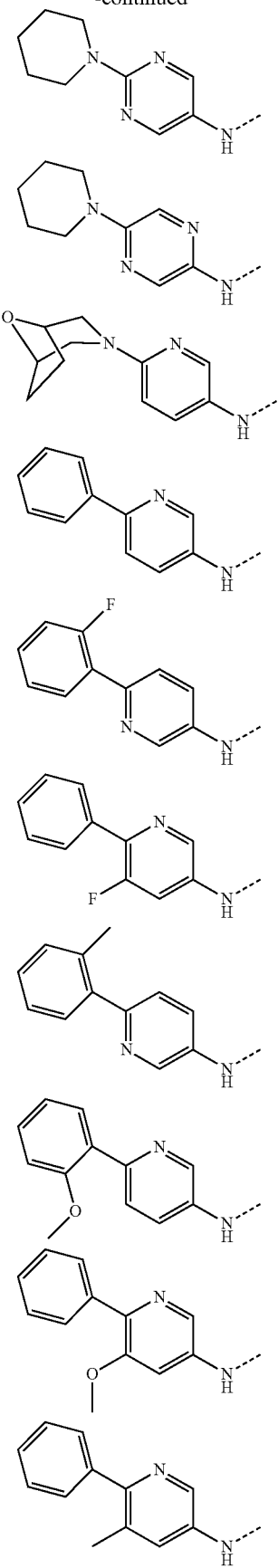

500
-continued

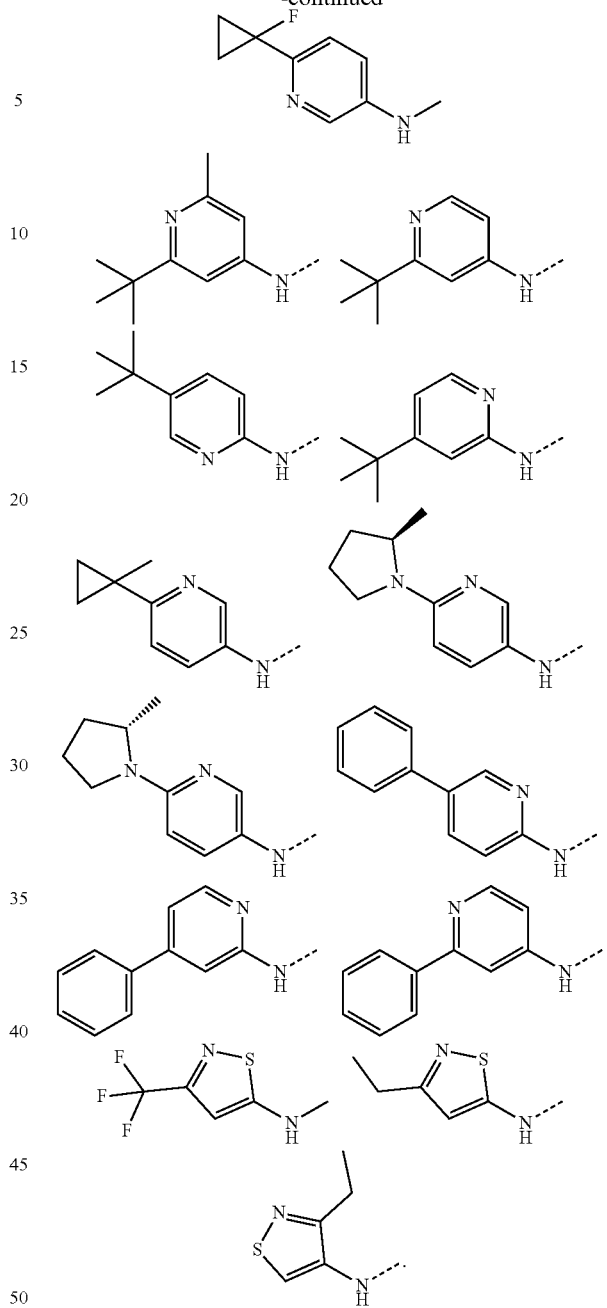

15. A pharmaceutical composition comprising the compound of claim 1, or a pharmaceutically acceptable salt or stereoisomer thereof, and a pharmaceutically acceptable excipient.

16. A method of treating lung cancer, breast cancer, or neuroendocrine cancer in a subject in need thereof, comprising administering to the subject a therapeutically effective amount of the compound of claim 1, or a pharmaceutically acceptable salt or stereoisomer thereof.

17. The method of claim 16, wherein the lung cancer is a non-small cell lung cancer.

18. The method of claim 16, wherein the non-small cell lung cancer is squamous cell lung cancer.

19. A method of degrading GSPT1 in a subject suffering from cancer, comprising administering to the subject an effective amount of the compound of claim 1, or a pharmaceutically acceptable salt or stereoisomer thereof.

20. A method of reducing the level of GSPT1 in a subject suffering from cancer, comprising administering to the subject an effective amount of the compound of claim 1, or a pharmaceutically acceptable salt or stereoisomer thereof.

* * * * *